United States Patent
Jin et al.

(10) Patent No.: US 12,060,343 B2
(45) Date of Patent: *Aug. 13, 2024

(54) SUBSTITUTED 1,2,4-TRIAZOLES AS INTERMEDIATES IN THE SYNTHESIS OF TYK2 INHIBITORS

(71) Applicant: Alumis Inc., San Francisco, CA (US)

(72) Inventors: Bohan Jin, San Francisco, CA (US); Qing Dong, San Francisco, CA (US); Gene Hung, San Francisco, CA (US); Stephen W. Kaldor, San Francisco, CA (US)

(73) Assignee: Alumis Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/713,646

(22) Filed: Apr. 5, 2022

(65) Prior Publication Data
US 2022/0235035 A1    Jul. 28, 2022

Related U.S. Application Data

(63) Continuation of application No. 17/243,508, filed on Apr. 28, 2021, which is a continuation of application No. 16/938,183, filed on Jul. 24, 2020, now Pat. No. 11,053,219, which is a continuation of application No. PCT/US2019/057485, filed on Oct. 22, 2019.

(60) Provisional application No. 62/907,354, filed on Sep. 27, 2019, provisional application No. 62/893,721, filed on Aug. 29, 2019, provisional application No. 62/875,449, filed on Jul. 17, 2019, provisional application No. 62/839,459, filed on Apr. 26, 2019, provisional application No. 62/756,942, filed on Nov. 7, 2018, provisional application No. 62/749,003, filed on Oct. 22, 2018.

(51) Int. Cl.
| | |
|---|---|
| *C07D 213/72* | (2006.01) |
| *C07D 249/08* | (2006.01) |
| *C07D 401/12* | (2006.01) |
| *C07D 401/14* | (2006.01) |
| *C07D 403/12* | (2006.01) |

(52) U.S. Cl.
CPC ......... *C07D 401/14* (2013.01); *C07D 401/12* (2013.01); *C07D 403/12* (2013.01)

(58) Field of Classification Search
CPC ............................ C07D 213/72; C07D 249/08
USPC ........................................ 546/314; 548/269.4
See application file for complete search history.

*Primary Examiner* — Douglas M Willis
(74) *Attorney, Agent, or Firm* — Goodwin Procter LLP

(57) ABSTRACT

Described herein are compounds, for example, 1,2,4-triazole-substituted N-heteroaryl amines, that are useful in treating a TYK2-mediated disorder. In some embodiments, the TYK2-mediated disorder is an autoimmune disorder, an inflammatory disorder, a proliferative disorder, an endocrine disorder, a neurological disorder, or a disorder associated with transplantation.

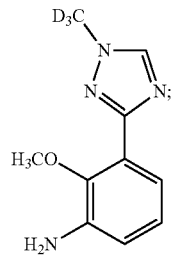

6 Claims, No Drawings

SUBSTITUTED 1,2,4-TRIAZOLES AS INTERMEDIATES IN THE SYNTHESIS OF TYK2 INHIBITORS

CROSS-REFERENCE

This patent application is a continuation of U.S. patent application Ser. No. 17/713,646, filed Apr. 5, 2022; which is a continuation of U.S. patent application Ser. No. 17/243,508, filed Apr. 28, 2021; which is a continuation of U.S. patent application Ser. No. 16/938,183, filed Jul. 24, 2020; which is a continuation of International Patent Application No. PCT/US2019/057485, filed Oct. 22, 2019; which claims the benefit of, and priority to, U.S. Provisional Application No. 62/749,003, filed Oct. 22, 2018; U.S. Provisional Application No. 62/756,942, filed Nov. 7, 2018; U.S. Provisional Application No. 62/839,459, filed Apr. 26, 2019; U.S. Provisional Application No. 62/875,449, filed Jul. 17, 2019; U.S. Provisional Application No. 62/893,721, filed Aug. 29, 2019; and U.S. Provisional Application No. 62/907,354, filed Sep. 27, 2019 each of which is incorporated herein by reference in their entirety.

FIELD OF THE INVENTION

Described herein are compounds, methods of making such compounds, pharmaceutical compositions and medicaments comprising such compounds, and methods of using such compounds for inhibiting nonreceptor tyrosine-protein kinase 2 ("TYK2"), also known as Tyrosine kinase 2.

BACKGROUND OF THE INVENTION

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-$\alpha$, IFN-$\beta$, IFN-$\kappa$, IFN-$\delta$, IFN-$\epsilon$, IFN-$\tau$, IFN-$\omega$, and IFN-$\zeta$ also known as limitin), and interleukins (e.g. IL-4, IL-6, IL-10, IL-11, IL-12, IL-13, L-22, IL-23, IL-27, IL-31, oncostatin M, ciliary neurotrophic factor, cardiotrophin 1, cardiotrophin-like cytokine, and LIF). The activated TYK2 then goes on to phosphorylate further signaling proteins such as members of the STAT family, including STAT1, STAT2, STAT4, and STAT6.

TYK2 activation by IL-23, has been linked to inflammatory bowel disease (IBD), Crohn's disease, and ulcerative colitis. A genome-wide association study of 2,622 individuals with psoriasis identified associations between disease susceptibility and TYK2. Knockout or tyrphostin inhibition of TYK2 significantly reduces both IL-23 and IL-22-induced dermatitis.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6. Decreased TYK2 activity leads to protection of joints from collagen antibody-induced arthritis, a model of human rheumatoid arthritis. Mechanistically, decreased Tyk2 activity reduced the production of Th1/Th17-related cytokines and matrix metalloproteases, and other key markers of inflammation.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4-mediated disease development in MS. This corroborates earlier studies linking increased TYK2 expression with MS susceptibility. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Genome-wide association studies of individuals with SLE versus an unaffected cohort showed highly significant correlation between the TYK2 locus and SLE.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects.

Studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V731I), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform.

Thus, selective inhibition of TYK2 has been suggested as a suitable target for patients with IL-10 and/or BCL2-addicted tumors, such as 70% of adult T-cell leukemia cases. TYK2 mediated STAT3 signaling has also been shown to mediate neuronal cell death caused by amyloid-$\beta$ (A$\beta$) peptide. Decreased TYK2 phosphorylation of STAT3 following A$\beta$ administration lead to decreased neuronal cell death, and increased phosphorylation of STAT3 has been observed in postmortem brains of Alzheimer's patients.

Inhibition of JAK-STAT signaling pathways is also implicated in hair growth, and the reversal of the hair loss associated with alopecia areata.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Accordingly there is a need to provide novel inhibitors having more effective or advantageous pharmaceutically relevant properties, like selectivity over other JAK kinases (especially JAK2).

BRIEF SUMMARY OF THE INVENTION

Disclosed herein is a compound of Formula (XII), or a pharmaceutically acceptable salt, solvate, or stereoisomer thereof:

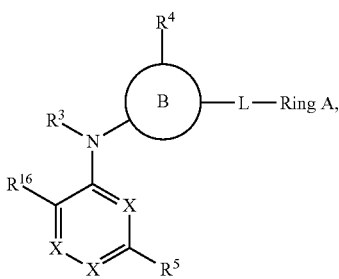

Formula (XII)

wherein:
Ring B is cycloalkyl, heterocycloalkyl, aryl, heteroaryl;
$R^{16}$ is —C(=O)NR$^1$R$^2$, —C(=N—CN)NR$^1$R$^2$, —P(=O)R$^1$R$^2$, or —C(=O)R$^{11}$;
$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
$R^3$ is hydrogen, $C_1$-$C_6$alkyl, $C_1$-$C_6$haloalkyl, or $C_1$-$C_6$deuteroalkyl;
$R^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, —P(=O)R$^b$R$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
or $R^3$ and $R^4$ are taken together to form an optionally substituted ring;
L is a bond or —C(=O)—;
Ring A is cycloalkyl, heterocycloalkyl, aryl, or heteroaryl; each optionally substituted with one or more $R^A$;
each $R^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;
or two $R^A$ on the same carbon are taken together to form an oxo;
or -L-Ring A is absent;
each X is independently —CR$^x$— or —N—;
each $R^x$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
$R^5$ is halogen, —CN, —OR$^8$, —SR$^8$, —S(=O)R$^7$, —S(=O)$_2$R$^7$, —NO$_2$, —NR$^9$R$^{10}$, —NR$^8$S(=O)R$^7$, —NR$^8$S(=O)$_2$R$^7$, —S(=O)$_2$NR$^9$R$^{10}$, —C(=N—CN)R$^7$, —C(=O)R$^7$, —OC(=N—CN)R$^7$, —OC(=O)R$^7$, —C(=N—CN)OR$^8$, —C(=O)OR$^8$, —OC(=N—CN)OR$^8$, —OC(=O)OR$^8$, —C(=N—CN)NR$^9$R$^{10}$, —C(=O)NR$^9$R$^{10}$, —OC(=N—CN) NR$^9$R$^{10}$, —OC(=O)NR$^9$R$^{10}$, —NR$^8$C(=N—CN) NR$^9$R$^{10}$, —NR$^8$C(=O)NR$^9$R$^{10}$, —NR$^8$C(=N—CN) R$^7$, —NR$^8$C(=N—OH)R$^7$, —NR$^8$C(=N—CN)OR$^8$, —NR$^8$C(=O)OR$^8$, —NR$^8$S(=O)(=NR$^8$)R$^7$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;
$R^7$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;
each $R^8$ is independently hydrogen, CN, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

$R^9$ and $R^{10}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, $C_1$-$C_6$deuteroalkyl, $C_1$-$C_6$haloalkyl, $C_1$-$C_6$hydroxyalkyl, $C_1$-$C_6$hydroxydeuteroalkyl, cycloalkyl, or heterocycloalkyl;

or $R^9$ and $R^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or $R^8$ and $R^9$ are taken together with the atoms to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

$R^{11}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more $R^{11a}$;

each $R^{11a}$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^c$ and $R^d$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

Also disclosed herein is a compound of Formula (XIII), or a pharmaceutically acceptable salt, stereoisomer, or solvate thereof:

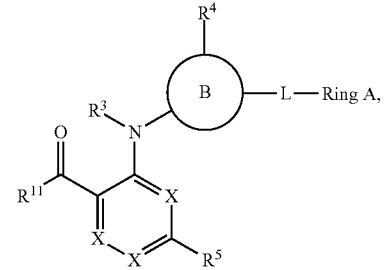

Formula (XIII)

wherein:

Ring B is cycloalkyl, heterocycloalkyl, aryl, or heteroaryl;

$R^3$ is hydrogen, $C_1$-$C_6$alkyl, $C_1$-$C_6$haloalkyl, or $C_1$-$C_6$deuteroalkyl;

$R^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, —P(=O)R$^b$R$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

or $R^3$ and $R^4$ are taken together to form an optionally substituted ring;

L is a bond or —C(=O)—;

Ring A is cycloalkyl, heterocycloalkyl, aryl, or heteroaryl; each optionally substituted with one or more $R^A$;

each $R^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

or two $R^A$ on the same carbon are taken together to form an oxo;

or -L-Ring A is absent;

each X is independently —CR$^x$— or —N—;

each $R^x$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

R$^5$ is halogen, —CN, —OR$^8$, —SR$^8$, —S(=O)R$^7$, —S(=O)$_2$R$^7$, —NO$_2$, —NR$^9$R$^{10}$, —NR$^8$S(=O)R$^7$, —NR$^8$S(=O)$_2$R$^7$, —S(=O)$_2$NR$^9$R$^{10}$, —C(=N—CN)R$^7$, —C(=O)R$^7$, —OC(=N—CN)R$^7$, —OC(=O)R$^7$, —C(=N—CN)OR$^8$, —C(=O)OR$^8$, —OC(=N—CN)OR$^8$, —OC(=O)OR$^8$, —C(=N—CN)NR$^9$R$^{10}$, —C(=O)NR$^9$R$^{10}$, —OC(=N—CN)NR$^9$R$^{10}$, —OC(=O)NR$^9$R$^{10}$, —NR$^8$C(=N—CN)NR$^9$R$^{10}$, —NR$^8$C(=O)NR$^9$R$^{10}$, —NR$^8$C(=N—CN)R$^7$, —NR$^8$C(=N—OH)R$^7$, —NR$^8$C(=O)R$^7$, —NR$^8$C(=N—CN)OR$^8$, —NR$^8$C(=O)OR$^8$, —NR$^8$S(=O)(=NR$^8$)R$^7$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

R$^7$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^8$ is independently hydrogen, CN, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

R$^9$ and R$^{10}$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, C$_1$-C$_6$haloalkyl, C$_1$-C$_6$hydroxyalkyl, C$_1$-C$_6$hydroxydeuteroalkyl, cycloalkyl, or heterocycloalkyl;

or R$^9$ and R$^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^8$ and R$^9$ are taken together with the atoms to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

R$^{11}$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R$^{11a}$;

each R$^{11a}$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^c$ and R$^d$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^c$ and R$^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

Also disclosed herein is a pharmaceutical composition comprising a therapeutically effective amount of the compound disclosed herein, or a pharmaceutically acceptable salt, stereoisomer, or solvate thereof, and a pharmaceutically acceptable excipient.

Also disclosed herein is a method of inhibiting a TYK2 enzyme in a patient or biological sample comprising contacting said patient or biological sample with a compound disclosed herein, or a pharmaceutically acceptable salt, stereoisomer, or solvate thereof.

Also disclosed herein is a method of treating a TYK2-mediated disorder comprising administering to a patient in need thereof a compound disclosed herein, or a pharmaceutically acceptable salt, stereoisomer, or solvate thereof. In some embodiments, the TYK2-mediated disorder is an autoimmune disorder, an inflammatory disorder, a proliferative disorder, an endocrine disorder, a neurological disorder, or a disorder associated with transplantation. In some embodiments, the disorder is associated with type I interferon, IL-10, IL-12, or IL-23 signaling.

DETAILED DESCRIPTION OF THE INVENTION

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Aliphatic chain" refers to a linear chemical moiety that is composed of only carbons and hydrogens. In some embodiments, the aliphatic chain is saturated. In some embodiments, the aliphatic chain is unsaturated. In some embodiments, the unsaturated aliphatic chain contains one unsaturation. In some embodiments, the unsaturated aliphatic chain contains more than one unsaturation. In some embodiments, the unsaturated aliphatic chain contains two unsaturations. In some embodiments, the unsaturated aliphatic chain contains one double bond. In some embodiments, the unsaturated aliphatic chain contains two double bonds.

"Alkyl" refers to an optionally substituted straight-chain, or optionally substituted branched-chain saturated hydrocarbon monoradical having from one to about ten carbon atoms, or from one to six carbon atoms. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_8$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —CF$_3$, —OH, —OMe, —NH$_2$, or —NO$_2$. In some embodiments, the alkyl is optionally substituted with oxo, halogen, —CN, —CF$_3$, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to, ethenyl (—CH═CH$_2$), 1-propenyl (—CH$_2$CH═CH$_2$), isopropenyl [—C(CH$_3$)═CH$_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_5$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —CF$_3$, —OH, —OMe, —NH$_2$, or —NO$_2$. In some embodiments, an alkenyl is optionally substituted with oxo, halogen, —CN, —CF$_3$, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to, ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —$CF_3$, —OH, —OMe, —$NH_2$, or —$NO_2$. In some embodiments, an alkynyl is optionally substituted with oxo, halogen, —CN, —$CF_3$, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —$CF_3$, —OH, —OMe, —$NH_2$, or —$NO_2$. In some embodiments, an alkylene is optionally substituted with oxo, halogen, —CN, —$CF_3$, —OH, or —OMe. In some embodiments, the alkylene is optionally substituted with halogen.

"Alkoxy" refers to a radical of the formula —$OR_a$ where $R_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —$CF_3$, —OH, —OMe, —$NH_2$, or —$NO_2$. In some embodiments, an alkoxy is optionally substituted with oxo, halogen, —CN, —$CF_3$, —OH, or —OMe. In some embodiments, the alkoxy is optionally substituted with halogen.

"Aminoalkyl" refers to an alkyl radical, as defined above, that is substituted by one or more amines. In some embodiments, the alkyl is substituted with one amine. In some embodiments, the alkyl is substituted with one, two, or three amines. Hydroxyalkyl include, for example, aminomethyl, aminoethyl, aminopropyl, aminobutyl, or aminopentyl. In some embodiments, the hydroxyalkyl is aminomethyl.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —$CF_3$, —OH, —OMe, —$NH_2$, or —$NO_2$. In some embodiments, an aryl is optionally substituted with halogen, methyl, ethyl, —CN, —$CF_3$, —OH, or —OMe. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_5$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —$CF_3$, —OH, —OMe, —$NH_2$, or —$NO_2$. In some embodiments, a cycloalkyl is optionally substituted with oxo, halogen, methyl, ethyl, —CN, —$CF_3$, —OH, or —OMe. In some embodiments, the cycloalkyl is optionally substituted with halogen.

"Deuteroalkyl" refers to an alkyl radical, as defined above, that is substituted by one or more deuterium atoms. In some embodiments, the alkyl is substituted with one deuterium atom. In some embodiments, the alkyl is substituted with one, two, or three deuterium atoms. In some embodiments, the alkyl is substituted with one, two, three, four, five, or six deuterium atoms. Deuteroalkyl includes, for example, $CD_3$, $CH_2D$, $CHD_2$, $CH_2CD_3$, $CD_2CD_3$, $CHDCD_3$, $CH_2CH_2D$, or $CH_2CHD_2$. In some embodiments, the deuteroalkyl is $CD_3$.

"Haloalkyl" refers to an alkyl radical, as defined above, that is substituted by one or more halogen atoms. In some embodiments, the alkyl is substituted with one, two, or three halogen atoms. In some embodiments, the alkyl is substituted with one, two, three, four, five, or six halogen halogens. Haloalkyl includes, for example, trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. In some embodiments, the haloalkyl is trifluoromethyl.

"Halo" or "halogen" refers to bromo, chloro, fluoro or iodo. In some embodiments, halogen is fluoro or chloro. In some embodiments, halogen is fluoro.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, or —CH(CH$_3$)OCH$_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl comprises 1 or 2 heteroatoms selected from nitrogen and oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (C$_2$-C$_{15}$ heterocycloalkyl), from two to ten carbon atoms (C$_2$-C$_{10}$ heterocycloalkyl), from two to eight carbon atoms (C$_2$-C$_{15}$ heterocycloalkyl), from two to six carbon atoms (C$_2$-C$_6$ heterocycloalkyl), from two to five carbon atoms (C$_2$-C$_5$ heterocycloalkyl), or two to four carbon atoms (C$_2$-C$_4$ heterocycloalkyl). In some embodiments, the heterocycloalkyl is a 3- to 6-membered heterocycloalkyl. In some embodiments, the cycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a C$_1$-C$_6$heteroalkyl. Unless stated otherwise specifically in the specification, a Heteroalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, about 100%, about 90%, about 80%, about 70%, about 60%, about 50%, about 40%, about 30%, about 20%, or about 10%. Furthermore, the treatment, prevention, amelioration, or inhibition provided by the methods disclosed herein can include treatment, prevention, amelioration, or inhibition of one or more conditions or symptoms of the disorder, e.g., cancer or an inflammatory disease. Also, for purposes herein, "treatment," "prevention," "amelioration," or "inhibition" encompass delaying the onset of the disorder, or a symptom or condition thereof.

The terms "effective amount" or "therapeutically effective amount," as used herein, refer to a sufficient amount of a compound disclosed herein being administered which will relieve to some extent one or more of the symptoms of the disease or condition being treated, e.g., cancer or an inflammatory disease. In some embodiments, the result is a reduction and/or alleviation of the signs, symptoms, or causes of a disease, or any other desired alteration of a biological system. For example, an "effective amount" for therapeutic uses is the amount of the composition comprising a compound disclosed herein required to provide a clinically significant decrease in disease symptoms. In some embodiments, an appropriate "effective" amount in any individual case is determined using techniques, such as a dose escalation study.

As used herein, the term "TYK2-mediated" disorders, diseases, and/or conditions as used herein means any disease or other deleterious condition in which TYK2 or a mutant thereof is known to play a role. Accordingly, another embodiment relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

Compounds

Described herein are compounds that are useful in treating a TYK2-mediated disorder. In some embodiments, the TYK2-mediated disorder is an autoimmune disorder, an inflammatory disorder, a proliferative disorder, an endocrine disorder, a neurological disorder, or a disorder associated with transplantation.

Disclosed herein is a compound of Formula (I), or a pharmaceutically acceptable salt, solvate, or stereoisomer thereof:

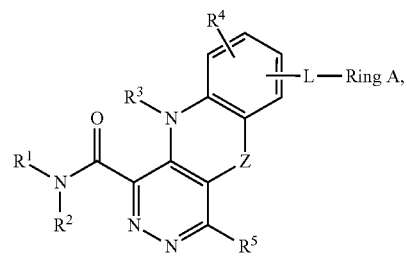

Formula (I)

wherein:
Z is a bond, —CR$^Z$$_2$—, or —(CR$^Z$$_2$—.
each R$^Z$ is independently hydrogen, deuterium, halogen, —CN, —OR$^b$, —NR$^c$R$^d$, C$_1$-C$_6$alkyl, C$_1$-C$_6$haloalkyl, or C$_1$-C$_6$deuteroalkyl;
R$^1$ and R$^2$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;
R$^3$ is hydrogen, C$_1$-C$_6$alkyl, C$_1$-C$_6$haloalkyl, or C$_1$-C$_6$deuteroalkyl;
R$^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O) NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;
or R$^3$ and R$^4$ are taken together to form an optionally substituted ring;
L is a bond or —C(=O)—;
Ring A is cycloalkyl, heterocycloalkyl, aryl, or heteroaryl; each optionally substituted with one or more R$^A$;
each R$^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC (=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C (=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;
or two R$^A$ on the same carbon are taken together to form an oxo;
R$^5$ is halogen, —CN, —OR$^8$, —SR$^8$, —S(=O)R$^7$, —S(=O)$_2$R$^7$, —NO$_2$, —NR$^9$R$^{10}$, —NHS(=O)$_2$R$^7$, —S(=O)$_2$NR$^9$R$^{10}$, —C(=O)R$^7$, —OC(=O)R$^7$, —C(=O)OR$^8$, —OC(=O)OR$^8$, —C(=O)NR$^9$R$^{10}$, —OC(=O)NR$^9$R$^{10}$, —NR$^8$C(=O)NR$^9$R$^{10}$, —NR$^8$C (=O)R$^7$, —NR$^8$C(=O)OR$^8$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

R$^7$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^8$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

R$^9$ and R$^{10}$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^9$ and R$^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^c$ and R$^d$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^c$ and R$^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (I), L is a bond. In some embodiments of a compound of Formula (I), L is —C(=O)—.

In some embodiments of a compound of Formula (I), Ring A is heterocycloalkyl or heteroaryl; each optionally substituted with one or more R$^A$. In some embodiments of a compound of Formula (I), Ring A is a 5-membered heterocycloalkyl or a 5-membered heteroaryl; each optionally substituted with one or more R$^A$. In some embodiments of a compound of Formula (I), Ring A is heteroaryl optionally substituted with one or more R$^A$.

In some embodiments of a compound of Formula (I), each R$^A$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (I), each R$^A$ is independently deuterium, halogen, C$_1$-C$_6$alkyl, C$_1$-C$_6$haloalkyl, or C$_1$-C$_6$deuteroalkyl. In some embodiments of a compound of Formula (I), each R$^A$ is independently halogen or C$_1$-C$_6$alkyl. In some embodiments of a compound of Formula (I), each R$^A$ is independently C$_1$-C$_6$alkyl.

In some embodiments of a compound of Formula (I), R$^4$ is hydrogen, deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (I), R$^4$ is hydrogen or —OR$^b$. In some embodiments of a compound of Formula (I), R$^4$ is —OR$^b$. In some embodiments of a compound of Formula (I), R$^4$ is hydrogen.

In some embodiments of a compound of Formula (I), the compound is of Formula (Ia):

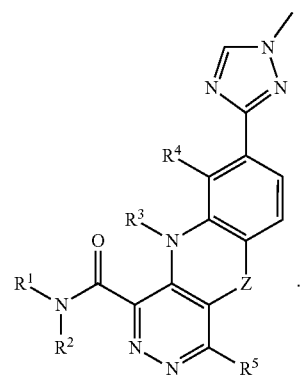

Formula (Ia)

In some embodiments of a compound of Formula (I), the compound is of Formula (Ib):

Formula (Ib)

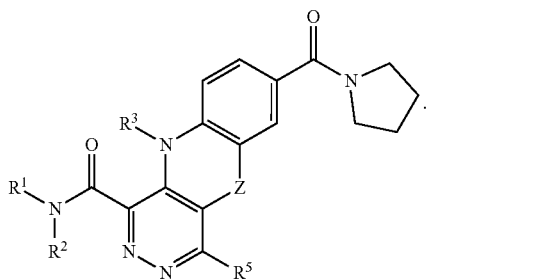

In some embodiments of a compound of Formula (I), (Ia), or (Ib), $R^3$ is hydrogen or $C_1$-$C_6$alkyl. In some embodiments of a compound of Formula (I), (Ia), or (Ib), $R^3$ is hydrogen.

In some embodiments of a compound of Formula (I), (Ia), or (Ib), Z is a bond or —$CH_2$—. In some embodiments of a compound of Formula (I), (Ia), or (Ib), Z is —$CH_2$—. In some embodiments of a compound of Formula (I), (Ia), or (Ib), Z is a bond.

In some embodiments of a compound of Formula (I), (Ia), or (Ib), $R^1$ and $R^2$ are independently hydrogen, $C_1$-$C_6$alkyl, $C_1$-$C_6$haloalkyl, or $C_1$-$C_6$deuteroalkyl. In some embodiments of a compound of Formula (I), (Ia), or (Ib), $R^1$ and $R^2$ are independently hydrogen or $C_1$-$C_6$deuteroalkyl. In some embodiments of a compound of Formula (I), (Ia), or (Ib), $R^8$ is hydrogen. In some embodiments of a compound of Formula (I), (Ia), or (Ib), $R^2$ is $C_1$-$C_6$alkyl or $C_1$-$C_6$deuteroalkyl. In some embodiments of a compound of Formula (I), (Ia), or (Ib), $R^2$ is $C_1$-$C_6$deuteroalkyl.

In some embodiments of a compound of Formula (I), (Ia), or (Ib), $R^5$ is halogen, —CN, —$OR^8$, —$NR^9R^{10}$, —C(=O)$R^7$, —C(=O)$OR^8$, —C(=O)$NR^9R^{10}$, —$NR^8$C(=O)$NR^9R^{10}$, —$NR^8$C(=O)$R^7$, —$NR^8$C(=O)$OR^8$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl.

In some embodiments of a compound of Formula (I), (Ia), or (Ib), $R^5$ is —$OR^8$, —$NR^9R^{10}$, —C(=O)$R^7$, —C(=O)$OR^8$, —C(=O)$NR^9R^{10}$, —$NR^8$C(=O)$NR^9R^{10}$, —$NR^8$C(=O)$R^7$, —$NR^8$C(=O)$OR^8$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl.

In some embodiments of a compound of Formula (I), (Ia), or (Ib), $R^5$ is —$OR^8$, —$NR^9R^{10}$, —$NR^8$C(=O)$R^7$, or aryl optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl.

In some embodiments of a compound of Formula (I), (Ia), or (Ib), $R^5$ is —$OR^8$, —$NR^9R^{10}$, —$NR^8$C(=O)$R^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl. In some embodiments of a compound of Formula (I), (Ia), or (Ib), $R^5$ is —$NR^8$C(=O)$R^7$. In some embodiments of a compound of Formula (I), (Ia), or (Ib), $R^5$ is aryl optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl.

In some embodiments of a compound of Formula (I), (Ia), or (Ib), $R^7$ is $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (I), (Ia), or (Ib), $R^7$ is $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (I), (Ia), or (Ib), $R^7$ is cycloalkyl optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (I), (Ia), or (Ib), $R^7$ is unsubstituted cycloalkyl.

In some embodiments of a compound of Formula (I), (Ia), or (Ib), $R^8$ is hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (I), (Ia), or (Ib), $R^8$ is hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl.

In some embodiments of a compound of Formula (I), (Ia), or (Ib), $R^9$ and $R^{10}$ are independently hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (I), (Ia), or (Ib), $R^9$ and $R^{10}$ are independently hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl.

Also disclosed herein is a compound of Formula (II) or (II'), or a pharmaceutically acceptable salt, stereoisomer, or solvate thereof:

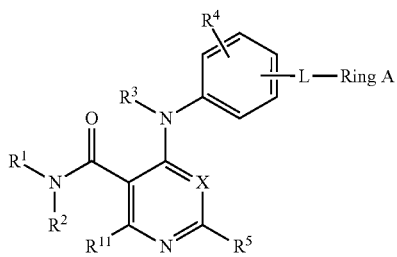

Formula (II)

Formula (II')

wherein:
R¹¹ is deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

R¹ and R² are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

R³ is hydrogen, C$_1$-C$_6$alkyl, C$_1$-C$_6$haloalkyl, or C$_1$-C$_6$deuteroalkyl;

R⁴ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

or R³ and R⁴ are taken together to form an optionally substituted ring;

L is a bond or —C(=O)—;

Ring A is cycloalkyl, heterocycloalkyl, aryl, or heteroaryl; each optionally substituted with one or more R$^A$;

each R$^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or two R$^A$ on the same carbon are taken together to form an oxo;

X is —CR$^x$— or —N—;

R$^x$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

R⁵ is halogen, —CN, —OR⁸, —SR⁸, —S(=O)R⁷, —S(=O)$_2$R⁷, —NO$_2$, —NR⁹R¹⁰, —NHS(=O)$_2$R⁷, —S(=O)$_2$NR⁹R¹⁰, —C(=O)R⁷, —OC(=O)R⁷, —C(=O)OR⁸, —OC(=O)OR⁸, —C(=O)NR⁹R¹⁰, —OC(=O)NR⁹R¹⁰, —NR⁸C(=O)NR⁹R¹⁰, —NR⁸C(=O)R⁷, —NR⁸C(=O)OR⁸, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or R$^x$ and R⁵ are taken together to form ring D optionally substituted with one or more R$^D$;

Ring D is a cycloalkyl, heterocycloalkyl, aryl, or heteroaryl;

each R$^D$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or two R$^D$ on the same carbon are taken together to form an oxo;

R⁷ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R⁸ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

R$^9$ and R$^{10}$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^9$ and R$^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^c$ and R$^d$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^c$ and R$^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (II) or (II'), L is a bond. In some embodiments of a compound of Formula (II) or (II'), L is —C(=O)—.

In some embodiments of a compound of Formula (II) or (II'), Ring A is heterocycloalkyl or heteroaryl; each optionally substituted with one or more R$^A$. In some embodiments of a compound of Formula (II) or (II'), Ring A is a 5-membered heterocycloalkyl or a 5-membered heteroaryl; each optionally substituted with one or more R$^A$. In some embodiments of a compound of Formula (II) or (II'), Ring A is heteroaryl optionally substituted with one or more R$^A$.

In some embodiments of a compound of Formula (II) or (II'), each R$^A$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (II) or (II'), each R$^A$ is independently deuterium, halogen, C$_1$-C$_6$alkyl, C$_1$-C$_6$haloalkyl, or C$_1$-C$_6$deuteroalkyl. In some embodiments of a compound of Formula (II) or (II'), each R$^A$ is independently halogen or C$_1$-C$_6$alkyl. In some embodiments of a compound of Formula (II) or (II'), each R$^A$ is independently C$_1$-C$_6$alkyl.

In some embodiments of a compound of Formula (II) or (II'), R$^4$ is hydrogen, deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (II) or (II'), R$^4$ is hydrogen or —OR$^b$. In some embodiments of a compound of Formula (II) or (II'), R$^4$ is —OR$^b$. In some embodiments of a compound of Formula (II) or (II'), R$^4$ is hydrogen.

In some embodiments of a compound of Formula (II) or (II'), X is —CH—. In some embodiments of a compound of Formula (II) or (II'), X is —N—.

In some embodiments of a compound of Formula (II) or (II'), the compound is of Formula (IIa) or (II'a):

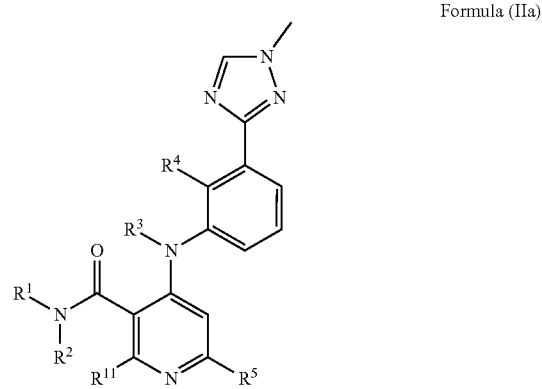

Formula (IIa)

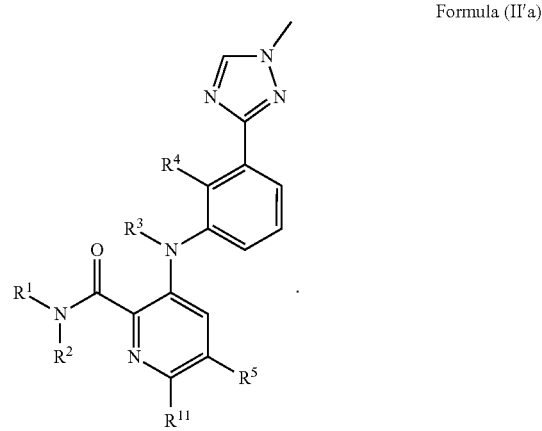

Formula (II'a)

In some embodiments of a compound of Formula (II) or (II'), the compound is of Formula (IIb) or (II'b):

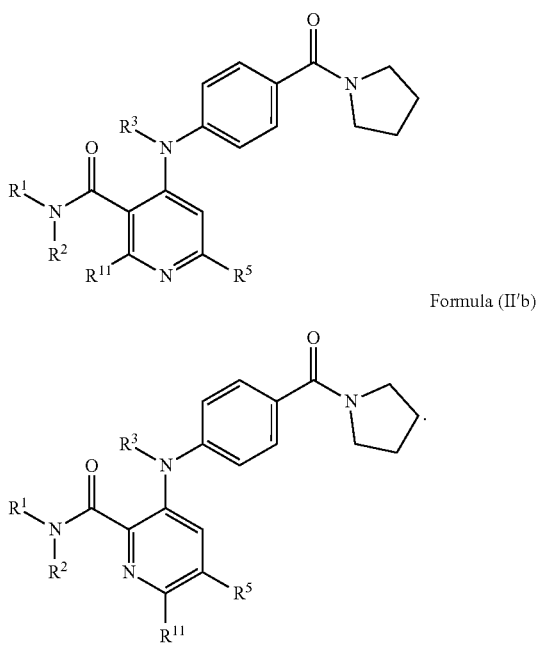

Formula (IIb)

Formula (II'b)

In some embodiments of a compound of Formula (II), (II'), (IIa), (II'a), (IIb), or (II'b), $R^3$ is hydrogen or $C_1$-$C_6$alkyl. In some embodiments of a compound of Formula (II), (II'), (IIa), (II'a), (IIb), or (II'b), $R^3$ is hydrogen.

In some embodiments of a compound of Formula (II), (II'), (IIa), (II'a), (IIb), or (II'b), $R^1$ and $R^2$ are independently hydrogen, $C_1$-$C_6$alkyl, $C_1$-$C_6$haloalkyl, or $C_1$-$C_6$deuteroalkyl. In some embodiments of a compound of Formula (II), (II'), (IIa), (II'a), (IIb), or (II'b), $R^1$ and $R^2$ are independently hydrogen or $C_1$-$C_6$deuteroalkyl. In some embodiments of a compound of Formula (II), (II'), (IIa), (II'a), (IIb), or (II'b), $R^1$ is hydrogen. In some embodiments of a compound of Formula (II), (II'), (IIa), (II'a), (IIb), or (II'b), $R^2$ is $C_1$-$C_6$alkyl or $C_1$-$C_6$deuteroalkyl. In some embodiments of a compound of Formula (II), (II'), (IIa), (II'a), (IIb), or (II'b), $R^2$ is $C_1$-$C_6$deuteroalkyl.

In some embodiments of a compound of Formula (II), (II'), (IIa), (II'a), (IIb), or (II'b), $R^5$ is halogen, —CN, —$OR^8$, —$NR^9R^{10}$, —C(=O)$R^7$, —C(=O)$OR^8$, —C(=O)$NR^9R^{10}$, —$NR^8$C(=O)$NR^9R^{10}$, —$NR^8$C(=O)$R^7$, —$NR^8$C(=O)$OR^8$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl.

In some embodiments of a compound of Formula (II), (II'), (IIa), (II'a), (IIb), or (II'b), $R^5$ is —$OR^8$, —$NR^9R^{10}$, —C(=O)$R^7$, —C(=O)$OR^8$, —C(=O)$NR^9R^{10}$, —$NR^8$C(=O)$NR^9R^{10}$, —$NR^8$C(=O)$R^7$, —$NR^8$C(=O)$OR^8$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl.

In some embodiments of a compound of Formula (II), (II'), (IIa), (II'a), (IIb), or (II'b), $R^5$ is —$OR^8$, —$NR^9R^{10}$, —$NR^8$C(=O)$R^7$, or aryl optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl.

In some embodiments of a compound of Formula (II), (II'), (IIa), (II'a), (IIb), or (II'b), $R^5$ is —$OR^8$, —$NR^9R^{10}$, —$NR^8$C(=O)$R^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl. In some embodiments of a compound of Formula (II), (II'), (IIa), (II'a), (IIb), or (II'b), $R^5$ is —$NR^8$C(=O)$R^7$. In some embodiments of a compound of Formula (II), (II'), (IIa), (II'a), (IIb), or (II'b), $R^5$ is aryl optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl.

In some embodiments of a compound of Formula (II), (II'), (IIa), (II'a), (IIb), or (II'b), $R^7$ is $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (II), (II'), (IIa), (II'a), (IIb), or (II'b), $R^7$ is $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (II), (II'), (IIa), (II'a), (IIb), or (II'b), $R^7$ is cycloalkyl optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (II), (II'), (IIa), (II'a), (IIb), or (II'b), $R^7$ is unsubstituted cycloalkyl.

In some embodiments of a compound of Formula (II), (II'), (IIa), (II'a), (IIb), or (II'b), $R^8$ is hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (II), (II'), (IIa), (II'a), (IIb), or (II'b), $R^8$ is hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl.

In some embodiments of a compound of Formula (II), (II'), (IIa), (II'a), (IIb), or (II'b), $R^9$ and $R^{10}$ are independently hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (II), (II'), (IIa), (II'a), (IIb), or (II'b), $R^9$ and $R^{10}$ are independently hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (II), (II'), (IIa), (II'a), (IIb), or (II'b), $R^{11}$ is deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, or $C_1$-$C_6$deuteroalkyl. In some embodiments of a compound of Formula (II), (II'), (IIa), (II'a), (IIb), or (II'b), $R^{11}$ is deuterium, halogen, $C_1$-$C_6$alkyl, $C_1$-$C_6$haloalkyl, or $C_1$-$C_6$deuteroalkyl. In some embodiments of a compound of Formula (II), (II'), (IIa), (II'a), (IIb), or (II'b), $R^1$ is halogen. In some embodiments of a compound of Formula (II), (II'), (IIa), (II'a), (IIb), or (II'b), $R^{11}$ is hydrogen.

Also disclosed herein is a compound of Formula (III), or a pharmaceutically acceptable salt, stereoisomer, or solvate thereof:

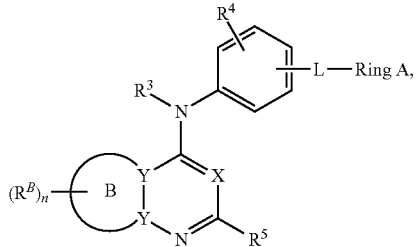

Formula (III)

wherein:
Ring B is a cycloalkyl, heterocycloalkyl, aryl, or heteroaryl; provided that

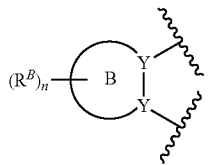

is not

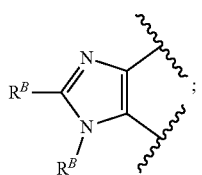

;

each $R^B$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

or two $R^B$ on the same carbon are taken together to form an oxo;
or two $R^B$ on adjacent atoms are taken together to form a cycloalkyl, heterocycloalkyl, aryl, or heteroaryl; each optionally substituted with one or more deuterium, oxo, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$deuteroalkyl, or $C_1$-$C_6$haloalkyl;

n is 0-4;
each Y is independently C or N;
$R^3$ is hydrogen, $C_1$-$C_6$alkyl, $C_1$-$C_6$haloalkyl, or $C_1$-$C_6$deuteroalkyl;
$R^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

or $R^3$ and $R^4$ are taken together to form an optionally substituted ring;
L is a bond or —C(=O)—;
Ring A is cycloalkyl, heterocycloalkyl, aryl, or heteroaryl; each optionally substituted with one or more $R^A$;
each $R^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

or two $R^A$ on the same carbon are taken together to form an oxo;
X is —CR$^x$— or —N—;
$R^x$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
$R^5$ is halogen, —CN, —OR$^8$, —SR$^8$, —S(=O)R$^7$, —S(=O)$_2$R$^7$, —NO$_2$, —NR$^9$R$^{10}$, —NHS(=O)$_2$R$^7$, —S(=O)$_2$NR$^9$R$^{10}$, —C(=O)R$^7$, —OC(=O)R$^7$, —C(=O)OR$^8$, —OC(=O)OR$^8$, —C(=O)NR$^9$R$^{10}$, —OC(=O)NR$^9$R$^{10}$, —NR$^8$C(=O)NR$^9$R$^{10}$, —NR$^8$C(=O)R$^7$, —NR$^8$C(=O)OR$^8$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or R$^x$ and R$^5$ are taken together to form ring D optionally substituted with one or more R$^D$;

Ring D is a cycloalkyl, heterocycloalkyl, aryl, or heteroaryl;

each R$^D$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or two R$^D$ on the same carbon are taken together to form an oxo;

R$^7$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^8$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

R$^9$ and R$^{10}$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^9$ and R$^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^c$ and R$^d$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^c$ and R$^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (III), L is a bond. In some embodiments of a compound of Formula (III), L is —C(=O)—.

In some embodiments of a compound of Formula (III), Ring A is heterocycloalkyl or heteroaryl; each optionally substituted with one or more R$^A$. In some embodiments of a compound of Formula (III), Ring A is a 5-membered heterocycloalkyl or a 5-membered heteroaryl; each optionally substituted with one or more R$^A$. In some embodiments of a compound of Formula (III), Ring A is heteroaryl optionally substituted with one or more R$^A$.

In some embodiments of a compound of Formula (III), each R$^A$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (III), each R$^A$ is independently deuterium, halogen, C$_1$-C$_6$alkyl, C$_1$-C$_6$haloalkyl, or C$_1$-C$_6$deuteroalkyl. In some embodiments of a compound of Formula (III), each R$^A$ is independently halogen or C$_1$-C$_6$alkyl. In some embodiments of a compound of Formula (III), each R$^A$ is independently C$_1$-C$_6$alkyl.

In some embodiments of a compound of Formula (III), R$^4$ is hydrogen, deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (III), R$^4$ is hydrogen or —OR$^b$. In some embodiments of a compound of Formula (III), R$^4$ is —OR$^b$. In some embodiments of a compound of Formula (III), R$^4$ is hydrogen.

In some embodiments of a compound of Formula (III), X is —CH—. In some embodiments of a compound of Formula (III), X is —N—.

In some embodiments of a compound of Formula (III), the compound is of Formula (IIIa):

Formula (IIIa)

In some embodiments of a compound of Formula (III), the compound is of Formula (IIIb):

Formula (IIIb)

In some embodiments of a compound of Formula (III), (IIIa), or (IIIb), $R^3$ is hydrogen or $C_1$-$C_6$alkyl. In some embodiments of a compound of Formula (III), (IIIa), or (IIIb), $R^3$ is hydrogen.

In some embodiments of a compound of Formula (III), (IIIa), or (IIIb), $R^5$ is halogen, —CN, —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (III), (IIIa), or (IIIb), $R^5$ is —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (III), (IIIa), or (IIIb), $R^8$ is —OR$^8$, —NR$^9$R$^{10}$, —NR$^8$C(=O)R$^7$, or aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (III), (IIIa), or (IIIb), $R^8$ is —OR$^8$, —NR$^9$R$^{10}$, —NR$^8$C(=O)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl. In some embodiments of a compound of Formula (III), (IIIa), or (IIIb), $R^8$ is —NR$^8$C(=O)R$^7$. In some embodiments of a compound of Formula (III), (IIIa), or (IIIb), $R^5$ is aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (III), (IIIa), or (IIIb), $R^7$ is $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (III), (IIIa), or (IIIb), $R^7$ is $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (III), (IIIa), or (IIIb), $R^7$ is cycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (III), (IIIa), or (IIIb), $R^7$ is unsubstituted cycloalkyl.

In some embodiments of a compound of Formula (III), (IIIa), or (IIIb), $R^8$ is hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (III), (IIIa), or (IIIb), $R^8$ is hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (III), (IIIa), or (IIIb), $R^9$ and $R^{10}$ are independently hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (III), (IIIa), or (IIIb), $R^9$ and $R^{10}$ are independently hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (III), (IIIa), or (IIIb), Ring B is a heterocycloalkyl or heteroaryl.

In some embodiments of a compound of Formula (III), (IIIa), or (IIIb),

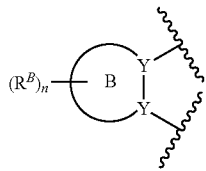

is

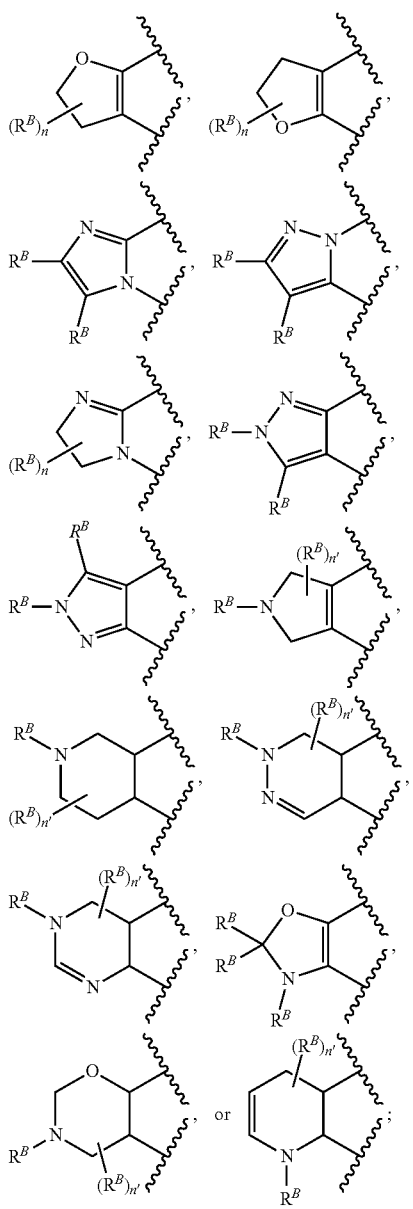

and n' is 0-3.

In some embodiments of a compound of Formula (III), (IIIa), or (IIIb), each $R^B$ is independently hydrogen, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, or $C_1$-$C_6$deuteroalkyl; or two $R^B$ on the same carbon are taken together to form an oxo. In some embodiments of a compound of Formula (III), (IIIa), or (IIIb), each $R^B$ is independently hydrogen, deuterium, halogen, $C_1$-$C_6$alkyl, $C_1$-$C_6$haloalkyl, or $C_1$-$C_6$deuteroalkyl; two $R^B$ on the same carbon are taken together to form an oxo.

In some embodiments of a compound of Formula (III), (IIIa), or (IIIb), two $R^B$ on adjacent atoms are taken together to form a cycloalkyl, heterocycloalkyl, aryl, or heteroaryl; each optionally substituted with one or more deuterium, oxo, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$deuteroalkyl, or $C_1$-$C_6$haloalkyl. In some embodiments of a compound of Formula (III), (IIIa), or (IIIb), two $R^B$ on adjacent atoms are taken together to form a heterocycloalkyl or heteroaryl; each optionally substituted with one or more deuterium, oxo, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$deuteroalkyl, or $C_1$-$C_6$haloalkyl.

In some embodiments of a compound of Formula (III), (IIIa), or (IIIb), n is 0. In some embodiments of a compound of Formula (III), (IIIa), or (IIIb), n is 1. In some embodiments of a compound of Formula (III), (IIIa), or (IIIb), n is 2. In some embodiments of a compound of Formula (III), (IIIa), or (IIIb), n is 0-2. In some embodiments of a compound of Formula (III), (IIIa), or (IIIb), n is 0 or 1. In some embodiments of a compound of Formula (III), (IIIa), or (IIIb), n is 1 or 2. In some embodiments of a compound of Formula (III), (IIIa), or (IIIb), n is 1-3.

In some embodiments of a compound of Formula (III), (IIIa), or (IIIb), n' is 0. In some embodiments of a compound of Formula (III), (IIIa), or (IIIb), n' is 1. In some embodiments of a compound of Formula (III), (IIIa), or (IIIb), n' is 2. In some embodiments of a compound of Formula (III), (IIIa), or (IIIb), n' is 0-2. In some embodiments of a compound of Formula (III), (IIIa), or (IIIb), n' is 0 or 1. In some embodiments of a compound of Formula (III), (IIIa), or (IIIb), n' is 1 or 2.

Also disclosed herein is a compound of Formula (IV), or a pharmaceutically acceptable salt, stereoisomer, or solvate thereof:

Formula (IV)

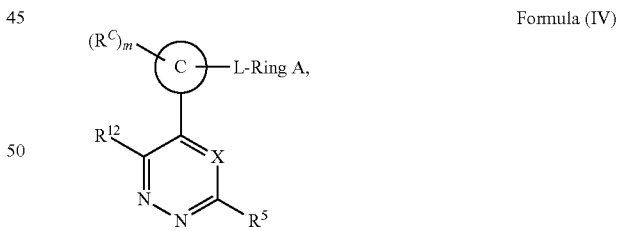

wherein:
Ring C is a bicyclic ring system;
each $R^C$ is independently hydrogen, oxo, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
m is 0-4;
$R^{12}$ is —C(=O)NR$^1$R$^2$ or -L$^1$-R$^{13}$ $R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

$L^1$ is —O—, —NH—, or —N(CH$_3$)—;

$R^{13}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

L is a bond or —C(=O)—;

Ring A is cycloalkyl, heterocycloalkyl, aryl, or heteroaryl; each optionally substituted with one or more $R^A$;

each $R^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

or two $R^A$ on the same carbon are taken together to form an oxo;

X is —CR$^x$— or —N—;

$R^x$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

$R^5$ is halogen, —CN, —OR$^8$, —SR$^8$, —S(=O)R$^7$, —S(=O)$_2$R$^7$, —NO$_2$, —NR$^9$R$^{10}$, —NHS(=O)$_2$R$^7$, —S(=O)$_2$NR$^9$R$^{10}$, —C(=O)R$^7$, —OC(=O)R$^7$, —C(=O)OR$^8$, —OC(=O)OR$^8$, —C(=O)NR$^9$R$^{10}$, —OC(=O)NR$^9$R$^{10}$, —NR$^8$C(=O)NR$^9$R$^{10}$, —NR$^8$C(=O)R$^7$, —NR$^8$C(=O)OR$^8$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

or $R^x$ and $R^5$ are taken together to form ring D optionally substituted with one or more $R^D$;

Ring D is a cycloalkyl, heterocycloalkyl, aryl, or heteroaryl;

each $R^D$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

or two $R^D$ on the same carbon are taken together to form an oxo;

$R^7$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^8$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

$R^9$ and $R^{10}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or $R^9$ and $R^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^c$ and R$^d$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^c$ and R$^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (IV), L is a bond. In some embodiments of a compound of Formula (IV), L is —C(=O)—.

In some embodiments of a compound of Formula (IV), Ring A is heterocycloalkyl or heteroaryl; each optionally substituted with one or more R$^4$. In some embodiments of a compound of Formula (IV), Ring A is a 5-membered heterocycloalkyl or a 5-membered heteroaryl; each optionally substituted with one or more R$^4$. In some embodiments of a compound of Formula (IV), Ring A is heteroaryl optionally substituted with one or more R$^4$.

In some embodiments of a compound of Formula (IV), each R$^4$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (IV), each R$^4$ is independently deuterium, halogen, C$_1$-C$_6$alkyl, C$_1$-C$_6$haloalkyl, or C$_1$-C$_6$deuteroalkyl. In some embodiments of a compound of Formula (IV), each R$^4$ is independently halogen or C$_1$-C$_6$alkyl. In some embodiments of a compound of Formula (IV), each R$^4$ is independently C$_1$-C$_6$alkyl.

In some embodiments of a compound of Formula (IV), R$^4$ is hydrogen, deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (IV), R$^4$ is hydrogen or —OR$^b$. In some embodiments of a compound of Formula (IV), R$^4$ is —OR$^b$. In some embodiments of a compound of Formula (IV), R$^4$ is hydrogen.

In some embodiments of a compound of Formula (IV), X is —CH—. In some embodiments of a compound of Formula (IV), X is —N—.

In some embodiments of a compound of Formula (IV), the compound is of Formula (IVa):

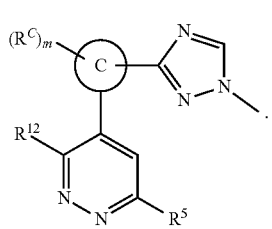

Formula (IVa)

In some embodiments of a compound of Formula (IV), the compound is of Formula (IVb):

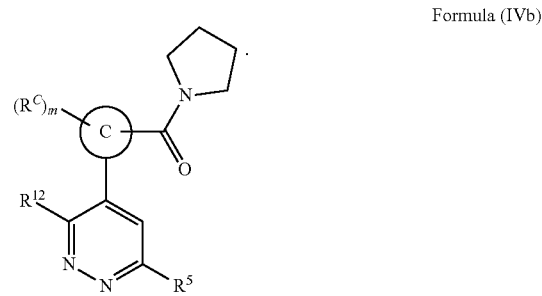

Formula (IVb)

In some embodiments of a compound of Formula (IV), (IVa), or (IVb), R$^{12}$ is —C(=O)NR$^1$R$^2$.

In some embodiments of a compound of Formula (IV), (IVa), or (IVb), R$^1$ and R$^2$ are independently hydrogen, C$_1$-C$_6$alkyl, C$_1$-C$_6$haloalkyl, or C$_1$-C$_6$deuteroalkyl. In some embodiments of a compound of Formula (IV), (IVa), or (IVb), R$^1$ and R$^2$ are independently hydrogen or C$_1$-C$_6$deuteroalkyl. In some embodiments of a compound of Formula (IV), (IVa), or (IVb), R$^1$ is hydrogen. In some embodiments of a compound of Formula (IV), (IVa), or (IVb), R$^2$ is C$_1$-C$_6$alkyl or C$_1$-C$_6$deuteroalkyl. In some embodiments of a compound of Formula (IV), (IVa), or (IVb), R$^2$ is C$_1$-C$_6$deuteroalkyl.

In some embodiments of a compound of Formula (IV), (IVa), or (IVb), R$^{12}$ is -L$^1$-R$^{13}$.

In some embodiments of a compound of Formula (IV), (IVa), or (IVb), L$^1$ is —NH—. In some embodiments of a compound of Formula (IV), (IVa), or (IVb), L$^1$ is —O— or —NH—.

In some embodiments of a compound of Formula (IV), (IVa), or (IVb), R$^{13}$ is C$_1$-C$_6$alkyl, C$_1$-C$_6$haloalkyl, or C$_1$-C$_6$deuteroalkyl.

In some embodiments of a compound of Formula (IV), (IVa), or (IVb), R$^5$ is halogen, —CN, —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, C$_1$-C$_6$alkyl, C$_1$-C$_6$haloalkyl, C$_1$-C$_6$deuteroalkyl, C$_2$-C$_6$alkenyl, C$_2$-C$_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (IV), (IVa), or (IVb), R$^5$ is —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (IV), (IVa), or (IVb), R$^5$ is —OR$^8$, —NR$^9$R$^{10}$, —NR$^8$C(=O)R$^7$, or aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (IV), (IVa), or (IVb), R$^5$ is —OR$^8$, —NR$^9$R$^{10}$, —NR$^8$C(=O)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl. In some embodiments of a compound of Formula (IV), (IVa), or (IVb), $R^5$ is —NR$^8$C(=O)R$^7$. In some embodiments of a compound of Formula (IV), (IVa), or (IVb), $R^5$ is aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (IV), (IVa), or (IVb), $R^7$ is $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (IV), (IVa), or (IVb), $R^7$ is $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (IV), (IVa), or (IVb), $R^7$ is cycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (IV), (IVa), or (IVb), $R^7$ is unsubstituted cycloalkyl.

In some embodiments of a compound of Formula (IV), (IVa), or (IVb), $R^8$ is hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (IV), (IVa), or (IVb), $R^8$ is hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (IV), (IVa), or (IVb), $R^9$ and $R^{10}$ are independently hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (IV), (IVa), or (IVb), $R^9$ and $R^{10}$ are independently hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (IV), (IVa), or (IVb), Ring C is indole or benzimidazole.

In some embodiments of a compound of Formula (IV), (IVa), or (IVb), each $R^C$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, $C_1$-$C_6$alkyl, $C_1$-$C_6$haloalkyl, or $C_1$-$C_6$deuteroalkyl.

In some embodiments of a compound of Formula (IV), (IVa), or (IVb), each $R^C$ is independently deuterium, halogen, $C_1$-$C_6$alkyl, $C_1$-$C_6$haloalkyl, or $C_1$-$C_6$deuteroalkyl. In some embodiments of a compound of Formula (IV), (IVa), or (IVb), each $R^C$ is independently halogen or $C_1$-$C_6$alkyl.

In some embodiments of a compound of Formula (IV), (IVa), or (IVb), m is 0. In some embodiments of a compound of Formula (IV), (IVa), or (IVb), m is 1. In some embodiments of a compound of Formula (IV), (IVa), or (IVb), m is 2. In some embodiments of a compound of Formula (IV), (IVa), or (IVb), m is 0 or 1. In some embodiments of a compound of Formula (IV), (IVa), or (IVb), m is 0-2. In some embodiments of a compound of Formula (IV), (IVa), or (IVb), m is 1 or 2. In some embodiments of a compound of Formula (IV), (IVa), or (IVb), m is 1-3.

Also disclosed herein is a compound of Formula (V), or a pharmaceutically acceptable salt, stereoisomer, or solvate thereof:

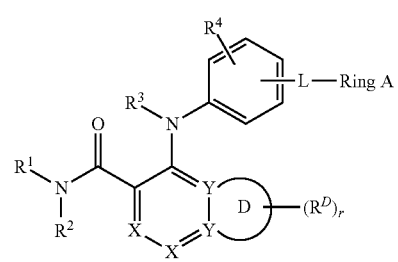

Formula (V)

wherein:

Ring D is a cycloalkyl, heterocycloalkyl, aryl, or heteroaryl;

each $R^D$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

or two $R^D$ on the same carbon are taken together to form an oxo;

or two $R^D$ on adjacent atoms are taken together to form a cycloalkyl, heterocycloalkyl, aryl, or heteroaryl; each optionally substituted with one or more deuterium, oxo, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$deuteroalkyl, or $C_1$-$C_6$haloalkyl;

r is 0-4;

each Y is independently C or N;

$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

$R^3$ is hydrogen, $C_1$-$C_6$alkyl, $C_1$-$C_6$haloalkyl, or $C_1$-$C_6$deuteroalkyl;

$R^4$ is hydrogen, deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

or $R^3$ and $R^4$ are taken together to form an optionally substituted ring;

L is a bond or —C(=O)—;

Ring A is cycloalkyl, heterocycloalkyl, aryl, or heteroaryl; each optionally substituted with one or more $R^A$;

each $R^A$ is independently deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl;

or two $R^A$ on the same carbon are taken together to form an oxo;

each X is independently —$CR^x$— or —N—;

each $R^x$ is independently hydrogen, deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, —C(=O)OMe, $C_1$-$C_6$alkyl, or $C_1$-$C_6$haloalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

each $R^c$ and $R^d$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl.

In some embodiments of a compound of Formula (V), L is a bond. In some embodiments of a compound of Formula (V), L is —C(=O)—.

In some embodiments of a compound of Formula (V), Ring A is heterocycloalkyl or heteroaryl; each optionally substituted with one or more $R^A$. In some embodiments of a compound of Formula (V), Ring A is a 5-membered heterocycloalkyl or a 5-membered heteroaryl; each optionally substituted with one or more $R^A$. In some embodiments of a compound of Formula (V), Ring A is heteroaryl optionally substituted with one or more $R^A$.

In some embodiments of a compound of Formula (V), each $R^A$ is independently deuterium, halogen, —CN, —$OR^b$, —$NR^cR^d$, —C(=O)$R^a$, —C(=O)$OR^b$, —C(=O)$NR^cR^d$, —OC(=O)$NR^cR^d$, $C_1$-$C_6$alkyl, $C_1$-$C_6$haloalkyl, or $C_1$-$C_6$deuteroalkyl. In some embodiments of a compound of Formula (V), each $R^A$ is independently deuterium, halogen, $C_1$-$C_6$alkyl, $C_1$-$C_6$haloalkyl, or $C_1$-$C_6$deuteroalkyl. In some embodiments of a compound of Formula (V), each $R^A$ is independently halogen or $C_1$-$C_6$alkyl. In some embodiments of a compound of Formula (V), each $R^A$ is independently $C_1$-$C_6$alkyl.

In some embodiments of a compound of Formula (V), $R^4$ is hydrogen, deuterium, halogen, —CN, —$OR^b$, —$NR^cR^d$, —C(=O)$R^a$, —C(=O)$OR^b$, —C(=O)$NR^cR^d$, —OC(=O)$NR^cR^d$, $C_1$-$C_6$alkyl, $C_1$-$C_6$haloalkyl, or $C_1$-$C_6$deuteroalkyl. In some embodiments of a compound of Formula (V), $R^4$ is hydrogen or —$OR^b$. In some embodiments of a compound of Formula (V), $R^4$ is —$OR^b$. In some embodiments of a compound of Formula (V), $R^4$ is hydrogen.

In some embodiments of a compound of Formula (V), each X is —N—. In some embodiments of a compound of Formula (V), each X is —CH—. In some embodiments of a compound of Formula (V), one X is —N— and the other is —CH—.

In some embodiments of a compound of Formula (V), the compound is of Formula (Va):

Formula (Va)

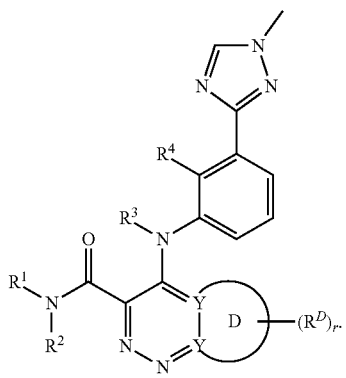

In some embodiments of a compound of Formula (V), the compound is of Formula (Vb):

Formula (Vb)

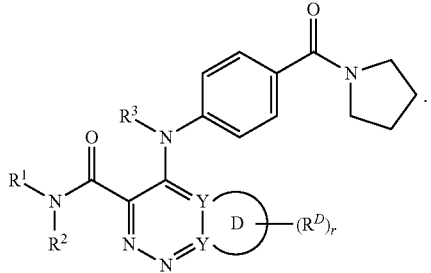

In some embodiments of a compound of Formula (V), (Va), or (Vb), $R^3$ is hydrogen or $C_1$-$C_6$alkyl. In some embodiments of a compound of Formula (V), (Va), or (Vb), $R^3$ is hydrogen.

In some embodiments of a compound of Formula (V), (Va), or (Vb), $R^1$ and $R^2$ are independently hydrogen, $C_1$-$C_6$alkyl, $C_1$-$C_6$haloalkyl, or $C_1$-$C_6$deuteroalkyl. In some embodiments of a compound of Formula (V), (Va), or (Vb), $R^1$ and $R^2$ are independently hydrogen or $C_1$-$C_6$deuteroalkyl. In some embodiments of a compound of Formula (V), (Va), or (Vb), $R^8$ is hydrogen. In some embodiments of a compound of Formula (V), (Va), or (Vb), $R^2$ is $C_1$-$C_6$alkyl or $C_1$-$C_6$deuteroalkyl. In some embodiments of a compound of Formula (V), (Va), or (Vb), $R^2$ is $C_1$-$C_6$deuteroalkyl.

In some embodiments of a compound of Formula (V), (Va), or (Vb), Ring D is a heterocycloalkyl or heteroaryl.

In some embodiments of a compound of Formula (V), (Va), or (Vb)

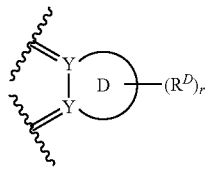

is

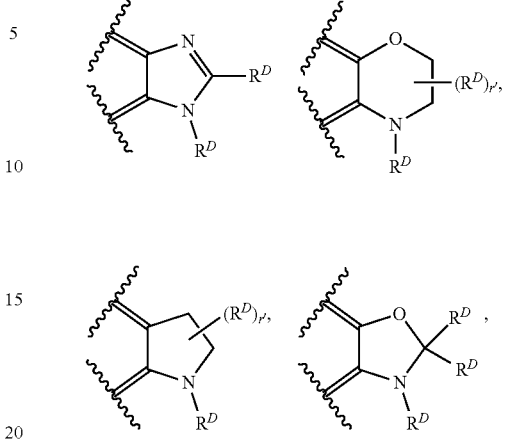

and r' is 0-3.

In some embodiments of a compound of Formula (V), (Va), or (Vb), each $R^D$ is independently hydrogen, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, cycloalkyl, or heterocycloalkyl. In some embodiments of a compound of Formula (V), (Va), or (Vb), each $R^D$ is independently hydrogen, deuterium, halogen, $C_1$-$C_6$alkyl, $C_1$-$C_6$haloalkyl, $C_1$-$C_6$deuteroalkyl, or cycloalkyl. In some embodiments of a compound of Formula (V), (Va), or (Vb), each $R^D$ is independently hydrogen or cycloalkyl.

In some embodiments of a compound of Formula (V), (Va), or (Vb), r is 0. In some embodiments of a compound of Formula (V), (Va), or (Vb), r is 1. In some embodiments of a compound of Formula (V), (Va), or (Vb), r is 2. In some embodiments of a compound of Formula (V), (Va), or (Vb), r is 0-2. In some embodiments of a compound of Formula (V), (Va), or (Vb), r is 0 or 1. In some embodiments of a compound of Formula (V), (Va), or (Vb), r is 1 or 2. In some embodiments of a compound of Formula (V), (Va), or (Vb), r is 1-3.

In some embodiments of a compound of Formula (V), (Va), or (Vb), r' is 0. In some embodiments of a compound of Formula (V), (Va), or (Vb), r' is 1. In some embodiments of a compound of Formula (V), (Va), or (Vb), r' is 2. In some embodiments of a compound of Formula (V), (Va), or (Vb), r' is 0-2. In some embodiments of a compound of Formula (V), (Va), or (Vb), r' is 0 or 1. In some embodiments of a compound of Formula (V), (Va), or (Vb), r' is 1 or 2. In some embodiments of a compound of Formula (V), (Va), or (Vb), r' is 1-3.

Also disclosed herein is a compound of Formula (VI), or a pharmaceutically acceptable salt, stereoisomer, or solvate thereof:

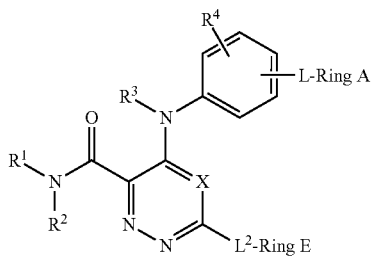

Formula (VI)

wherein:

Ring E is cycloalkyl, heterocycloalkyl, aryl, or heteroaryl; each optionally substituted with one or more $R^E$;

each $R^E$ is independently deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl;

or two $R^E$ on the same carbon are taken together to form an oxo;

$L^2$ is a bond, —O—, or

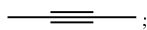;

$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

$R^3$ is hydrogen, $C_1$-$C_6$alkyl, $C_1$-$C_6$haloalkyl, or $C_1$-$C_6$deuteroalkyl;

$R^4$ is hydrogen, deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

or $R^3$ and $R^4$ are taken together to form an optionally substituted ring;

L is a bond or —C(=O)—;

Ring A is cycloalkyl, heterocycloalkyl, aryl, or heteroaryl; each optionally substituted with one or more $R^A$;

each $R^A$ is independently deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl;

or two $R^A$ on the same carbon are taken together to form an oxo;

X is —$CR^x$— or —N—;

$R^x$ is hydrogen, deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

each $R^c$ and $R^d$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl.

In some embodiments of a compound of Formula (VI), L is a bond. In some embodiments of a compound of Formula (VI), L is —C(=O)—.

In some embodiments of a compound of Formula (VI), Ring A is heterocycloalkyl or heteroaryl; each optionally substituted with one or more $R^A$. In some embodiments of a compound of Formula (VI), Ring A is a 5-membered heterocycloalkyl or a 5-membered heteroaryl; each optionally substituted with one or more $R^A$. In some embodiments of a compound of Formula (VI), Ring A is heteroaryl optionally substituted with one or more $R^A$.

In some embodiments of a compound of Formula (VI), each $R^A$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, $C_1$-$C_6$alkyl, $C_1$-$C_6$haloalkyl, or $C_1$-$C_6$deuteroalkyl. In some embodiments of a compound of Formula (VI), each $R^A$ is independently deuterium, halogen, $C_1$-$C_6$alkyl, $C_1$-$C_6$haloalkyl, or $C_1$-$C_6$deuteroalkyl. In some embodiments of a compound of Formula (VI), each $R^A$ is independently halogen or $C_1$-$C_6$alkyl. In some embodiments of a compound of Formula (VI), each $R^A$ is independently $C_1$-$C_6$alkyl.

In some embodiments of a compound of Formula (VI), $R^4$ is hydrogen, deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, $C_1$-$C_6$alkyl, $C_1$-$C_6$haloalkyl, or $C_1$-$C_6$deuteroalkyl. In some embodiments of a compound of Formula (VI), $R^4$ is hydrogen or —OR$^b$. In some embodiments of a compound of Formula (VI), $R^4$ is —OR$^b$. In some embodiments of a compound of Formula (VI), $R^4$ is hydrogen.

In some embodiments of a compound of Formula (VI), X is —CH—. In some embodiments of a compound of Formula (VI), X is —N—.

In some embodiments of a compound of Formula (VI), the compound is of Formula (VIa):

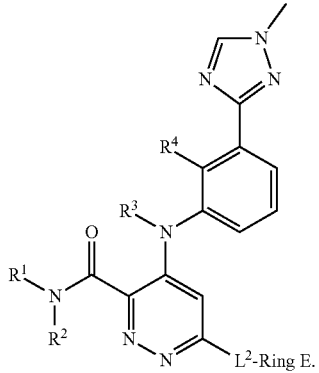

Formula (VIa)

In some embodiments of a compound of Formula (VI), the compound is of Formula (VIb):

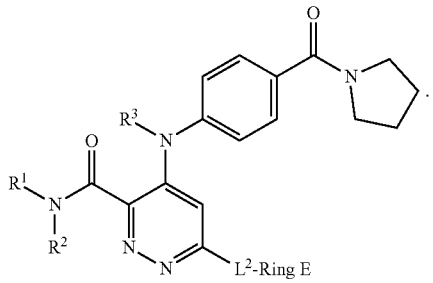

Formula (VIb)

In some embodiments of a compound of Formula (VI), (VIa), or (VIb), $R^3$ is hydrogen or $C_1$-$C_6$alkyl. In some embodiments of a compound of Formula (VI), (VIa), or (VIb), $R^3$ is hydrogen.

In some embodiments of a compound of Formula (VI), (VIa), or (VIb), $R^1$ and $R^2$ are independently hydrogen, $C_1$-$C_6$alkyl, $C_1$-$C_6$haloalkyl, or $C_1$-$C_6$deuteroalkyl. In some embodiments of a compound of Formula (VI), (VIa), or (VIb), $R^1$ and $R^2$ are independently hydrogen or $C_1$-$C_6$deuteroalkyl. In some embodiments of a compound of Formula (VI), (VIa), or (VIb), $R^8$ is hydrogen. In some embodiments of a compound of Formula (VI), (VIa), or (VIb), $R^2$ is $C_1$-$C_6$alkyl or $C_1$-$C_6$deuteroalkyl. In some embodiments of a compound of Formula (VI), (VIa), or (VIb), $R^2$ is $C_1$-$C_6$deuteroalkyl.

In some embodiments of a compound of Formula (VI), (VIa), or (VIb), $L^2$ is a bond.

In some embodiments of a compound of Formula (VI), (VIa), or (VIb), Ring E is cycloalkyl, heterocycloalkyl, or aryl; each optionally substituted with one or more $R^E$.

In some embodiments of a compound of Formula (VI), (VIa), or (VIb), Ring E is aryl optionally substituted with one or more $R^E$.

In some embodiments of a compound of Formula (VI), (VIa), or (VIb), each $R^E$ is independently deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, or $C_1$-$C_6$deuteroalkyl.

In some embodiments of a compound of Formula (VI), (VIa), or (VIb), each $R^E$ is independently deuterium, halogen, $C_1$-$C_6$alkyl, $C_1$-$C_6$haloalkyl, or $C_1$-$C_6$deuteroalkyl.

In some embodiments of a compound of Formula (VI), (VIa), or (VIb), each $R^E$ is independently halogen.

Also disclosed herein is a compound of Formula (VII), or a pharmaceutically acceptable salt, stereoisomer, or solvate thereof:

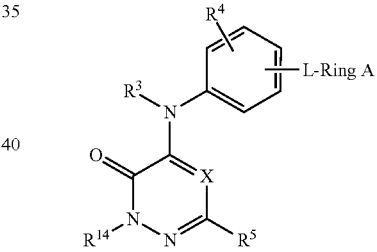

Formula (VII)

wherein:
$R^{14}$ is hydrogen, —S(=O)R$^a$, —S(=O)$_2$R$^a$, —S(=O)$_2$NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, $C_1$-$C_6$alkyl(cycloalkyl), $C_1$-$C_6$alkyl(heterocycloalkyl), $C_1$-$C_6$alkyl(aryl), $C_1$-$C_6$alkyl(heteroaryl), cycloalkyl, or heterocycloalkyl;

$R^3$ is hydrogen, $C_1$-$C_6$alkyl, $C_1$-$C_6$haloalkyl, or $C_1$-$C_6$deuteroalkyl;

$R^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

or $R^3$ and $R^4$ are taken together to form an optionally substituted ring;

L is a bond or —C(=O)—;

Ring A is cycloalkyl, heterocycloalkyl, aryl, or heteroaryl; each optionally substituted with one or more $R^A$;

each $R^A$ is independently deuterium, halogen, —CN, —$OR^b$, —$SR^b$, —S(=O)$R^a$, —S(=O)$_2R^a$, —NO$_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl;

or two $R^A$ on the same carbon are taken together to form an oxo;

X is —$CR^x$— or —N—;

$R^x$ is hydrogen, deuterium, halogen, —CN, —$OR^b$, —$SR^b$, —S(=O)$R^a$, —S(=O)$_2R^a$, —NO$_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

$R^5$ is halogen, —CN, —$OR^8$, —$SR^8$, —S(=O)$R^7$, —S(=O)$_2R^7$, —NO$_2$, —$NR^9R^{10}$, —NHS(=O)$_2R^7$, —S(=O)$_2NR^9R^{10}$, —C(=O)$R^7$, —OC(=O)$R^7$, —C(=O)$OR^8$, —OC(=O)$OR^8$, —C(=O)$NR^9R^{10}$, —OC(=O)$NR^9R^{10}$, —$NR^8C$(=O)$NR^9R^{10}$, —$NR^8C$(=O)$R^7$, —$NR^8C$(=O)$OR^8$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl;

or $R^x$ and $R^5$ are taken together to form ring D optionally substituted with one or more $R^D$;

Ring D is a cycloalkyl, heterocycloalkyl, aryl, or heteroaryl;

each $R^D$ is independently hydrogen, deuterium, halogen, —CN, —$OR^b$, —$SR^b$, —S(=O)$R^a$, —S(=O)$_2R^a$, —NO$_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl;

or two $R^D$ on the same carbon are taken together to form an oxo;

$R^7$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^8$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

$R^9$ and $R^{10}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or $R^9$ and $R^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^c$ and $R^d$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (VII), L is a bond. In some embodiments of a compound of Formula (VII), L is —C(=O)—.

In some embodiments of a compound of Formula (VII), Ring A is heterocycloalkyl or heteroaryl; each optionally substituted with one or more $R^A$. In some embodiments of a compound of Formula (VII), Ring A is a 5-membered heterocycloalkyl or a 5-membered heteroaryl; each optionally substituted with one or more $R^A$. In some embodiments of a compound of Formula (VII), Ring A is heteroaryl optionally substituted with one or more $R^A$.

In some embodiments of a compound of Formula (VII), each $R^A$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, $C_1$-$C_6$alkyl, $C_1$-$C_6$haloalkyl, or $C_1$-$C_6$deuteroalkyl. In some embodiments of a compound of Formula (VII), each $R^A$ is independently deuterium, halogen, $C_1$-$C_6$alkyl, $C_1$-$C_6$haloalkyl, or $C_1$-$C_6$deuteroalkyl. In some embodiments of a compound of Formula (VII), each $R^A$ is independently halogen or $C_1$-$C_6$alkyl. In some embodiments of a compound of Formula (VII), each $R^A$ is independently $C_1$-$C_6$alkyl.

In some embodiments of a compound of Formula (VII), $R^4$ is hydrogen, deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, $C_1$-$C_6$alkyl, $C_1$-$C_6$haloalkyl, or $C_1$-$C_6$deuteroalkyl. In some embodiments of a compound of Formula (VII), $R^4$ is hydrogen or —OR$^b$. In some embodiments of a compound of Formula (VII), $R^4$ is —OR$^b$. In some embodiments of a compound of Formula (VII), $R^4$ is hydrogen.

In some embodiments of a compound of Formula (VII), X is —CH—. In some embodiments of a compound of Formula (VII), X is —N—.

In some embodiments of a compound of Formula (VII), the compound is of Formula (VIIa):

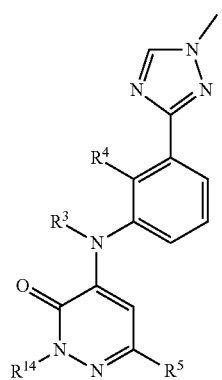

Formula (VIIa)

In some embodiments of a compound of Formula (VII), the compound is of Formula (VIIb):

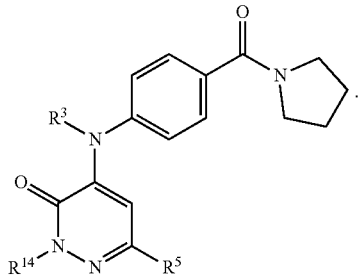

Formula (VIIb)

In some embodiments of a compound of Formula (VII), (VIIa), or (VIIb), $R^3$ is hydrogen or $C_1$-$C_6$alkyl. In some embodiments of a compound of Formula (VII), (VIIa), or (VIIb), $R^3$ is hydrogen.

In some embodiments of a compound of Formula (VII), (VIIa), or (VIIb), $R^5$ is halogen, —CN, —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (VII), (VIIa), or (VIIb), $R^5$ is —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (VII), (VIIa), or (VIIb), $R^5$ is —OR$^8$, —NR$^9$R$^{10}$, —NR$^8$C(=O)R$^7$, or aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (VII), (VIIa), or (VIIb), $R^5$ is —OR$^8$, —NR$^9$R$^{10}$, —NR$^8$C(=O)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl. In some embodiments of a compound of Formula (VII), (VIIa), or (VIIb), $R^5$ is —NR$^8$C(=O)R$^7$. In some embodiments of a compound of Formula (VII), (VIIa), or (VIIb), $R^5$ is aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (VII), (VIIa), or (VIIb), $R^7$ is $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (VII), (VIIa), or (VIIb), R$^7$ is C$_1$-C$_6$alkyl, C$_1$-C$_6$haloalkyl, C$_1$-C$_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (VII), (VIIa), or (VIIb), R$^7$ is cycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (VII), (VIIa), or (VIIb), R$^7$ is unsubstituted cycloalkyl.

In some embodiments of a compound of Formula (VII), (VIIa), or (VIIb), R$^8$ is hydrogen, C$_1$-C$_6$alkyl, C$_1$-C$_6$haloalkyl, C$_1$-C$_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (VII), (VIIa), or (VIIb), R$^8$ is hydrogen, C$_1$-C$_6$alkyl, C$_1$-C$_6$haloalkyl, C$_1$-C$_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (VII), (VIIa), or (VIIb), R$^9$ and R$^{10}$ are independently hydrogen, C$_1$-C$_6$alkyl, C$_1$-C$_6$haloalkyl, C$_1$-C$_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (VII), (VIIa), or (VIIb), R$^9$ and R$^{10}$ are independently hydrogen, C$_1$-C$_6$alkyl, C$_1$-C$_6$haloalkyl, C$_1$-C$_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (VII), (VIIa), or (VIIb), R$^{14}$ is hydrogen, C$_1$-C$_6$alkyl, C$_1$-C$_6$haloalkyl, C$_1$-C$_6$deuteroalkyl, or C$_1$-C$_6$alkyl(cycloalkyl). In some embodiments of a compound of Formula (VII), (VIIa), or (VIIb), R$^{14}$ is C$_1$-C$_6$alkyl or C$_1$-C$_6$alkyl(cycloalkyl).

Also disclosed herein is a compound of Formula (VIII), or a pharmaceutically acceptable salt, stereoisomer, or solvate thereof:

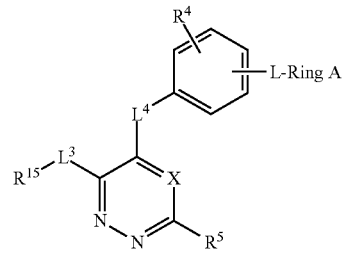

Formula (VIII)

wherein:
R$^{15}$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;
L$^3$ is —O—, —NH—, or —N(CH$_3$)—;
L$^4$ is —NR$^3$— or —C(=O)—;
R$^3$ is hydrogen, C$_1$-C$_6$alkyl, C$_1$-C$_6$haloalkyl, or C$_1$-C$_6$deuteroalkyl;
R$^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;
or R$^3$ and R$^4$ are taken together to form an optionally substituted ring;
L is a bond or —C(=O)—;
Ring A is cycloalkyl, heterocycloalkyl, aryl, or heteroaryl; each optionally substituted with one or more R$^A$;
each R$^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;
or two R$^A$ on the same carbon are taken together to form an oxo;
X is —CR$^x$— or —N—;
R$^x$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

$R^5$ is halogen, —CN, —OR$^8$, —SR$^8$, —S(=O)R$^7$, —S(=O)$_2$R$^7$, —NO$_2$, —NR$^9$R$^{10}$, —NHS(=O)$_2$R$^7$, —S(=O)$_2$NR$^9$R$^{10}$, —C(=O)R$^7$, —OC(=O)R$^7$, —C(=O)OR$^8$, —OC(=O)OR$^8$, —C(=O)NR$^9$R$^{10}$, —OC(=O)NR$^9$R$^{10}$, —NR$^8$C(=O)NR$^9$R$^{10}$, —NR$^8$C(=O)R$^7$, —NR$^8$C(=O)OR$^8$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

or $R^x$ and $R^5$ are taken together to form ring D optionally substituted with one or more $R^D$;

Ring D is a cycloalkyl, heterocycloalkyl, aryl, or heteroaryl;

each $R^D$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

or two $R^D$ on the same carbon are taken together to form an oxo;

$R^7$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^8$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

$R^9$ and $R^{10}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or $R^9$ and $R^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^c$ and $R^d$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (VIII), L is a bond. In some embodiments of a compound of Formula (VIII), L is —C(=O)—.

In some embodiments of a compound of Formula (VIII), Ring A is heterocycloalkyl or heteroaryl; each optionally substituted with one or more $R^A$. In some embodiments of a compound of Formula (VIII), Ring A is a 5-membered heterocycloalkyl or a 5-membered heteroaryl; each optionally substituted with one or more $R^A$. In some embodiments of a compound of Formula (VIII), Ring A is heteroaryl optionally substituted with one or more $R^A$.

In some embodiments of a compound of Formula (VIII), each $R^A$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, $C_1$-$C_6$alkyl, $C_1$-$C_6$haloalkyl, or $C_1$-$C_6$deuteroalkyl. In some embodiments of a compound of Formula (VIII), each $R^A$ is independently deuterium, halogen, $C_1$-$C_6$alkyl, $C_1$-$C_6$haloalkyl, or $C_1$-$C_6$deuteroalkyl. In some embodiments of a compound of Formula (VIII), each $R^A$ is independently halogen or $C_1$-$C_6$alkyl. In some embodiments of a compound of Formula (VIII), each $R^A$ is independently $C_1$-$C_6$alkyl.

In some embodiments of a compound of Formula (VIII), $R^4$ is hydrogen, deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (VIII), $R^4$ is hydrogen or —OR$^b$. In some embodiments of a compound of Formula (VIII), $R^4$ is —OR$^b$. In some embodiments of a compound of Formula (VIII), $R^4$ is hydrogen.

In some embodiments of a compound of Formula (VIII), X is —CH—. In some embodiments of a compound of Formula (VIII), X is —N—.

In some embodiments of a compound of Formula (VIII), the compound is of Formula (VIIIa):

Formula (VIIIa)

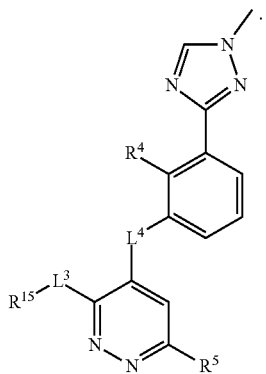

In some embodiments of a compound of Formula (VIII), the compound is of Formula (VIIIb):

Formula (VIIIb)

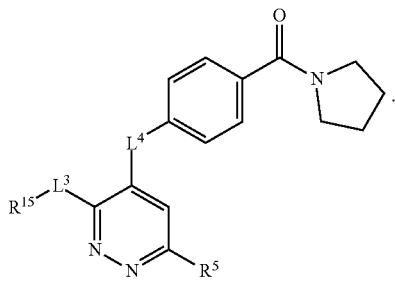

In some embodiments of a compound of Formula (VIII), (VIIIa), or (VIIIb), $R^5$ is halogen, —CN, —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, C$_1$-C$_6$alkyl, C$_1$-C$_6$haloalkyl, C$_1$-C$_6$deuteroalkyl, C$_2$-C$_6$alkenyl, C$_2$-C$_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (VIII), (VIIIa), or (VIIIb), $R^5$ is —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (VIII), (VIIIa), or (VIIIb), $R^5$ is —OR$^8$, —NR$^9$R$^{10}$, —NR$^8$C(=O)R$^7$, or aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (VIII), (VIIIa), or (VIIIb), $R^5$ is —OR$^8$, —NR$^9$R$^{10}$, —NR$^8$C(=O)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl. In some embodiments of a compound of Formula (VIII), (VIIIa), or (VIIIb), $R^5$ is —NR$^8$C(=O)R$^7$. In some embodiments of a compound of Formula (VIII), (VIIIa), or (VIIIb), $R^5$ is aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (VIII), (VIIIa), or (VIIIb), $R^7$ is C$_1$-C$_6$alkyl, C$_1$-C$_6$haloalkyl, C$_1$-C$_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (VIII), (VIIIa), or (VIIIb), $R^7$ is C$_1$-C$_6$alkyl, C$_1$-C$_6$haloalkyl, C$_1$-C$_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (VIII), (VIIIa), or (VIIIb), $R^7$ is cycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (VIII), (VIIIa), or (VIIIb), $R^7$ is unsubstituted cycloalkyl.

In some embodiments of a compound of Formula (VIII), (VIIIa), or (VIIIb), $R^8$ is hydrogen, C$_1$-C$_6$alkyl, C$_1$-C$_6$haloalkyl, C$_1$-C$_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (VIII), (VIIIa), or (VIIIb), $R^8$ is hydrogen, C$_1$-C$_6$alkyl, C$_1$-C$_6$haloalkyl, C$_1$-C$_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (VIII), (VIIIa), or (VIIIb), $R^9$ and $R^{10}$ are independently hydrogen, C$_1$-C$_6$alkyl, C$_1$-C$_6$haloalkyl, C$_1$-C$_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (VIII), (VIIIa), or (VIIIb), $R^9$ and $R^{10}$ are independently hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (VIII), (VIIIa), or (VIIIb), $L^3$ is —O—. In some embodiments of a compound of Formula (VIII), (VIIIa), or (VIIIb), $L^3$ is —NH—.

In some embodiments of a compound of Formula (VIII), (VIIIa), or (VIIIb), $R^{15}$ is $C_1$-$C_6$alkyl, $C_1$-$C_6$haloalkyl, $C_1$-$C_6$deuteroalkyl, or cycloalkyl.

In some embodiments of a compound of Formula (VIII), (VIIIa), or (VIIIb), $L^4$ is —NR$^3$—.

In some embodiments of a compound of Formula (VIII), (VIIIa), or (VIIIb), $R^3$ is hydrogen or $C_1$-$C_6$alkyl. In some embodiments of a compound of Formula (VIII), (VIIIa), or (VIIIb), $R^3$ is hydrogen.

In some embodiments of a compound of Formula (VIII), (VIIIa), or (VIIIb), $L^4$ is —C(=O)—.

A compound of Formula (IX), or a pharmaceutically acceptable salt, stereoisomer, or solvate thereof:

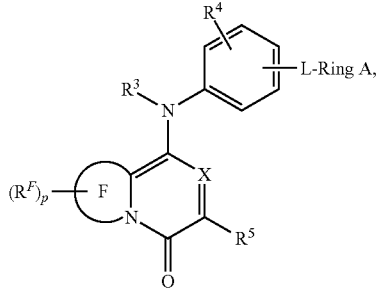

Formula (IX)

wherein:
Ring F is a heterocycloalkyl or heteroaryl;
each $R^F$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
or two $R^F$ on the same carbon are taken together to form an oxo;
or two $R^F$ on adjacent atoms are taken together to form a cycloalkyl, heterocycloalkyl, aryl, or heteroaryl; each optionally substituted with one or more deuterium, oxo, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$deuteroalkyl, or $C_1$-$C_6$haloalkyl;
p is 0-4;
$R^3$ is hydrogen, $C_1$-$C_6$alkyl, $C_1$-$C_6$haloalkyl, or $C_1$-$C_6$deuteroalkyl;
$R^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
or $R^3$ and $R^4$ are taken together to form an optionally substituted ring;
L is a bond or —C(=O)—;
Ring A is cycloalkyl, heterocycloalkyl, aryl, or heteroaryl; each optionally substituted with one or more $R^A$;
each $R^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;
or two $R^A$ on the same carbon are taken together to form an oxo;
X is —CR$^x$— or —N—;
$R^x$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
$R^5$ is halogen, —CN, —OR$^8$, —SR$^8$, —S(=O)R$^7$, —S(=O)$_2$R$^7$, —NO$_2$, —NR$^9$R$^{10}$, —NHS(=O)$_2$R$^7$, —S(=O)$_2$NR$^9$R$^{10}$, —C(=O)R$^7$, —OC(=O)R$^7$, —C(=O)OR$^8$, —OC(=O)OR$^8$, —C(=O)NR$^9$R$^{10}$, —OC(=O)NR$^9$R$^{10}$, —NR$^8$C(=O)NR$^9$R$^{10}$, —NR$^8$C(=O)R$^7$, —NR$^8$C(=O)OR$^8$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;
or $R^x$ and $R^5$ are taken together to form ring D optionally substituted with one or more $R^D$;
Ring D is a cycloalkyl, heterocycloalkyl, aryl, or heteroaryl;
each $R^D$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C₁-C₆alkyl, or C₁-C₆haloalkyl;

or two R$^D$ on the same carbon are taken together to form an oxo;

R⁷ is C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

each R⁸ is independently hydrogen, C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

R⁹ and R¹⁰ are independently hydrogen, C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

or R⁹ and R¹⁰ are taken together with the nitrogen atom to which they are attached to form a heterocycloalkyl optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

each R$^a$ is independently C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

each R$^b$ is independently hydrogen, C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

each R$^c$ and R$^d$ is independently hydrogen, C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

or R$^c$ and R$^d$ are taken together with the nitrogen atom to which they are attached to form a heterocycloalkyl optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl.

In some embodiments of a compound of Formula (IX), L is a bond. In some embodiments of a compound of Formula (IX), L is —C(=O)—.

In some embodiments of a compound of Formula (IX), Ring A is heterocycloalkyl or heteroaryl; each optionally substituted with one or more R$^A$. In some embodiments of a compound of Formula (IX), Ring A is a 5-membered heterocycloalkyl or a 5-membered heteroaryl; each optionally substituted with one or more R$^A$. In some embodiments of a compound of Formula (IX), Ring A is heteroaryl optionally substituted with one or more R$^A$.

In some embodiments of a compound of Formula (IX), each R$^A$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C₁-C₆alkyl, C₁-C₆haloalkyl, or C₁-C₆deuteroalkyl. In some embodiments of a compound of Formula (IX), each R$^A$ is independently deuterium, halogen, C₁-C₆alkyl, C₁-C₆haloalkyl, or C₁-C₆deuteroalkyl. In some embodiments of a compound of Formula (IX), each R$^A$ is independently halogen or C₁-C₆alkyl. In some embodiments of a compound of Formula (IX), each R$^A$ is independently C₁-C₆alkyl.

In some embodiments of a compound of Formula (IX), R⁴ is hydrogen, deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C₁-C₆alkyl, C₁-C₆haloalkyl, or C₁-C₆deuteroalkyl. In some embodiments of a compound of Formula (IX), R⁴ is hydrogen or —OR$^b$. In some embodiments of a compound of Formula (IX), R⁴ is —OR$^b$. In some embodiments of a compound of Formula (IX), R⁴ is hydrogen.

In some embodiments of a compound of Formula (IX), X is —CH—. In some embodiments of a compound of Formula (IX), X is —N—.

In some embodiments of a compound of Formula (IX), the compound is of Formula (IXa):

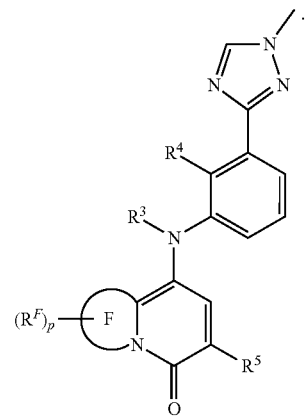

Formula (IXa)

In some embodiments of a compound of Formula (IX), the compound is of Formula (IXb):

Formula (IXb)

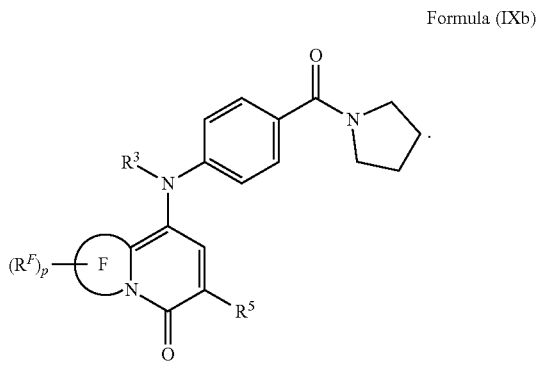

In some embodiments of a compound of Formula (IX), (IXa), or (IXb), $R^3$ is hydrogen or $C_1$-$C_6$alkyl. In some embodiments of a compound of Formula (IX), (IXa), or (IXb), $R^3$ is hydrogen.

In some embodiments of a compound of Formula (IX), (IXa), or (IXb), $R^5$ is halogen, —CN, —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (IX), (IXa), or (IXb), $R^5$ is —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (IX), (IXa), or (IXb), $R^5$ is —OR$^8$, —NR$^9$R$^{10}$, —NR$^8$C(=O)R$^7$, or aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (IX), (IXa), or (IXb), $R^8$ is —OR$^8$, —NR$^9$R$^{10}$, —NR$^8$C(=O)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl. In some embodiments of a compound of Formula (IX), (IXa), or (IXb), $R^8$ is —NR$^8$C(=O)R$^7$. In some embodiments of a compound of Formula (IX), (IXa), or (IXb), $R^8$ is aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (IX), (IXa), or (IXb), $R^7$ is $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (IX), (IXa), or (IXb), $R^7$ is $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (IX), (IXa), or (IXb), $R^7$ is cycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (IX), (IXa), or (IXb), $R^7$ is unsubstituted cycloalkyl.

In some embodiments of a compound of Formula (IX), (IXa), or (IXb), $R^8$ is hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (IX), (IXa), or (IXb), $R^8$ is hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (IX), (IXa), or (IXb), $R^9$ and $R^{10}$ are independently hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (IX), (IXa), or (IXb), $R^9$ and $R^{10}$ are independently hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (IX), (IXa), or (IXb), Ring F is a heterocycloalkyl.

In some embodiments of a compound of Formula (IX), (IXa), or (IXb),

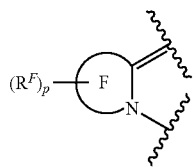

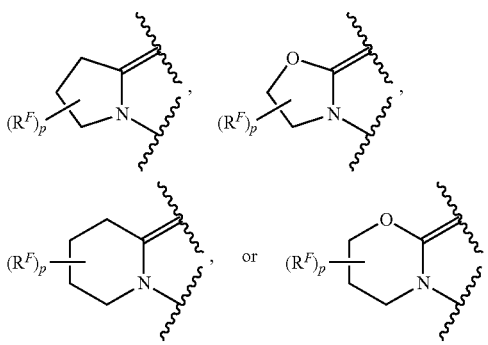

In some embodiments of a compound of Formula (IX), (IXa), or (IXb), each RF is independently hydrogen, deuterium, halogen, —CN, —OR$^b$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, or $C_1$-$C_6$deuteroalkyl. In some embodiments of a compound of Formula (IX), (IXa), or (IXb), each R$^F$ is independently hydrogen, deuterium, halogen, $C_1$-$C_6$alkyl, $C_1$-$C_6$haloalkyl, or $C_1$-$C_6$deuteroalkyl.

In some embodiments of a compound of Formula (IX), (IXa), or (IXb), p is 0. In some embodiments of a compound of Formula (IX), (IXa), or (IXb), p is 1. In some embodiments of a compound of Formula (IX), (IXa), or (IXb), p is 2. In some embodiments of a compound of Formula (IX), (IXa), or (IXb), p is 0-2. In some embodiments of a compound of Formula (IX), (IXa), or (IXb), p is 0 or 1. In some embodiments of a compound of Formula (IX), (IXa), or (IXb), p is 1 or 2. In some embodiments of a compound of Formula (IX), (IXa), or (IXb), p is 1-3.

Also disclosed herein is a compound of Formula (X), or a pharmaceutically acceptable salt, solvate, or stereoisomer thereof:

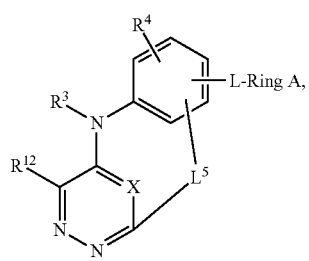

Formula (X)

wherein:
- $L^5$ is a saturated or unsaturated linear aliphatic chain having 1-10 carbon atoms optionally substituted with one or more $R^{L5}$, wherein 1-5 carbon atoms are optionally replaced with —NH—, —N(CH$_3$)—, —O—, —S—, —S(═O)—, —S(═O)$_2$—, or —P(═O)—;
- each $R^{L5}$ is independently deuterium, halogen, —CN, —OR$^b$, —SR$^b$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
- or two $R^{L5}$ on the same carbon atom are taken together to form an oxo;
- $R^{12}$ is —C(═O)NR$^1$R$^2$ or -L$^1$-R$^{13}$;
- $R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
- $L^1$ is —O—, —NH—, or —N(CH$_3$)—;
- $R^{13}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(═O)R$^a$, —C(═O)OR$^b$, —C(═O)NR$^c$R$^d$, $C_1$-$C_6$alkyl, or $C_1$-$C_6$haloalkyl;
- $R^3$ is hydrogen, $C_1$-$C_6$alkyl, $C_1$-$C_6$haloalkyl, or $C_1$-$C_6$deuteroalkyl;
- $R^4$ is hydrogen, deuterium, halogen, —CN, —OR$^b$, —SR$^b$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
- or $R^3$ and $R^4$ are taken together to form an optionally substituted ring;
- L is a bond or —C(═O)—;
- Ring A is cycloalkyl, heterocycloalkyl, aryl, or heteroaryl; each optionally substituted with one or more $R^A$;
- each $R^A$ is independently deuterium, halogen, —CN, —OR$^b$, —SR$^b$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(═O)R$^a$, —C(═O)OR$^b$, —C(═O)NR$^c$R$^d$, $C_1$-$C_6$alkyl, or $C_1$-$C_6$haloalkyl;
- or two $R^A$ on the same carbon are taken together to form an oxo;
- X is —CR$^x$— or —N—;
- $R^x$ is hydrogen, deuterium, halogen, —CN, —OR$^b$, —SR$^b$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
- each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

each R$^b$ is independently hydrogen, C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

each R$^c$ and R$^d$ is independently hydrogen, C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

or R$^c$ and R$^d$ are taken together with the nitrogen atom to which they are attached to form a heterocycloalkyl optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl.

In some embodiments of a compound of Formula (X), L is a bond. In some embodiments of a compound of Formula (X), L is —C(=O)—.

In some embodiments of a compound of Formula (X), Ring A is heterocycloalkyl or heteroaryl; each optionally substituted with one or more R$^A$. In some embodiments of a compound of Formula (X), Ring A is a 5-membered heterocycloalkyl or a 5-membered heteroaryl; each optionally substituted with one or more R$^A$. In some embodiments of a compound of Formula (X), Ring A is heteroaryl optionally substituted with one or more R$^A$.

In some embodiments of a compound of Formula (X), each R$^A$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C₁-C₆alkyl, C₁-C₆haloalkyl, or C₁-C₆deuteroalkyl. In some embodiments of a compound of Formula (X), each R$^A$ is independently deuterium, halogen, C₁-C₆alkyl, C₁-C₆haloalkyl, or C₁-C₆deuteroalkyl. In some embodiments of a compound of Formula (X), each R$^A$ is independently halogen or C₁-C₆alkyl. In some embodiments of a compound of Formula (X), each R$^A$ is independently C₁-C₆alkyl.

In some embodiments of a compound of Formula (X), R$^4$ is hydrogen, deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C₁-C₆alkyl, C₁-C₆haloalkyl, or C₁-C₆deuteroalkyl. In some embodiments of a compound of Formula (X), R$^4$ is hydrogen or —OR$^b$. In some embodiments of a compound of Formula (X), R$^4$ is —OR$^b$. In some embodiments of a compound of Formula (X), R$^4$ is hydrogen.

In some embodiments of a compound of Formula (X), X is —CH—. In some embodiments of a compound of Formula (X), X is —N—.

In some embodiments of a compound of Formula (X), the compound is of Formula

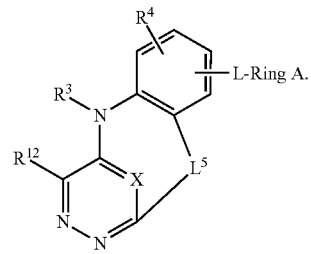

In some embodiments of a compound of Formula (X), the compound is of Formula

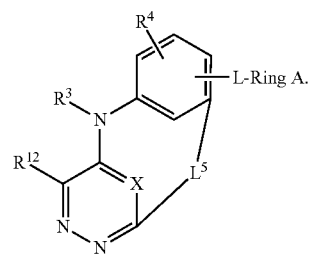

In some embodiments of a compound of Formula (X), the compound is of Formula (Xa):

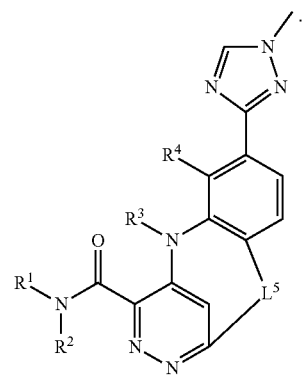

Formula (Xa)

In some embodiments of a compound of Formula (X), the compound is of Formula (Xb):

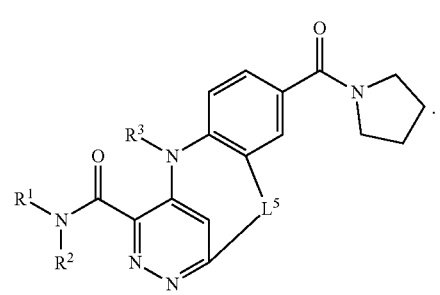

Formula (Xb)

In some embodiments of a compound of Formula (X), the compound is of Formula (Xa-1):

Formula (Xa-1)

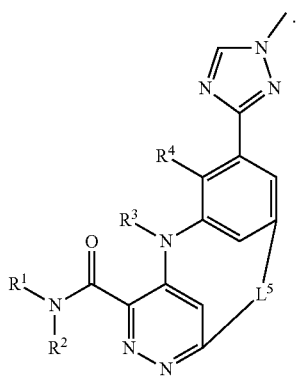

In some embodiments of a compound of Formula (X), the compound is of Formula (Xb-1):

Formula (Xb-1)

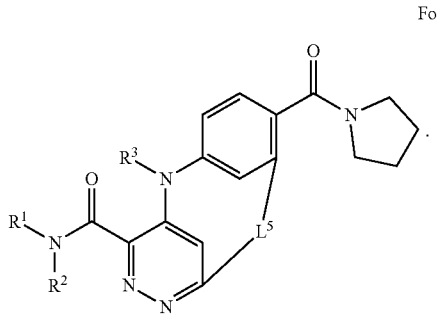

In some embodiments of a compound of Formula (X), (Xa), (Xa-1), (Xb), or (Xb-1), $R^3$ is hydrogen or $C_1$-$C_6$alkyl. In some embodiments of a compound of Formula (X), (Xa), (Xa-1), (Xb), or (Xb-1), $R^3$ is hydrogen.

In some embodiments of a compound of Formula (X), (Xa), (Xa-1), (Xb), or (Xb-1), $R^{12}$ is —C(=O)NR$^1$R$^2$.

In some embodiments of a compound of Formula (X), (Xa), (Xa-1), (Xb), or (Xb-1), $R^1$ and $R^2$ are independently hydrogen, $C_1$-$C_6$alkyl, $C_1$-$C_6$haloalkyl, or $C_1$-$C_6$deuteroalkyl. In some embodiments of a compound of Formula (X), (Xa), (Xa-1), (Xb), or (Xb-1), $R^1$ and $R^2$ are independently hydrogen or $C_1$-$C_6$deuteroalkyl. In some embodiments of a compound of Formula (X), (Xa), (Xa-1), (Xb), or (Xb-1), $R^8$ is hydrogen. In some embodiments of a compound of Formula (X), (Xa), (Xa-1), (Xb), or (Xb-1), $R^2$ is $C_1$-$C_6$alkyl or $C_1$-$C_6$deuteroalkyl. In some embodiments of a compound of Formula (X), (Xa), (Xa-1), (Xb), or (Xb-1), $R^2$ is $C_1$-$C_6$deuteroalkyl.

In some embodiments of a compound of Formula (X), (Xa), (Xa-1), (Xb), or (Xb-1), $R^{12}$ is -L$^1$-R$^{13}$.

In some embodiments of a compound of Formula (X), (Xa), (Xa-1), (Xb), or (Xb-1), $L^1$ is —NH—. In some embodiments of a compound of Formula (X), (Xa), (Xa-1), (Xb), or (Xb-1), $L^1$ is —O— or —NH—.

In some embodiments of a compound of Formula (X), (Xa), (Xa-1), (Xb), or (Xb-1), $R^{13}$ is $C_1$-$C_6$alkyl, $C_1$-$C_6$haloalkyl, or $C_1$-$C_6$deuteroalkyl.

In some embodiments of a compound of Formula (X), (Xa), (Xa-1), (Xb), or (Xb-1), $L^5$ is a saturated linear aliphatic chain having 1-8 carbon atoms optionally substituted with one or more R$^L$, wherein 1, 2, or 3 carbon atoms are optionally replaced with —NH—, —N(CH$_3$)—, —O—, —S—, —S(=O)—, —S(=O)$_2$—, or —P(=O)—. In some embodiments of a compound of Formula (X), (Xa), (Xa-1), (Xb), or (Xb-1), $L^5$ is a saturated linear aliphatic chain having 1-8 carbon atoms optionally substituted with one or more R$^L$, wherein 1, 2, or 3 carbon atoms are optionally replaced with —NH—, —N(CH$_3$)—, or —O—. In some embodiments of a compound of Formula (X), (Xa), (Xa-1), (Xb), or (Xb-1), $L^5$ is a saturated linear aliphatic chain having 1-8 carbon atoms optionally substituted with one or more R$^{L5}$, wherein 1, 2, or 3 carbon atoms are optionally replaced with —NH— or —O—.

In some embodiments of a compound of Formula (X), (Xa), (Xa-1), (Xb), or (Xb-1), $L^5$ is a saturated linear aliphatic chain having 1-8 carbon atoms, wherein 1, 2, or 3 carbon atoms are optionally replaced with —NH—, —N(CH$_3$)—, —O—, —S—, —S(=O)—, or —S(=O)$_2$—. In some embodiments of a compound of Formula (X), (Xa), (Xa-1), (Xb), or (Xb-1), $L^5$ is a saturated linear aliphatic chain having 1-8 carbon atoms, wherein 1, 2, or 3 carbon atoms are optionally replaced with —NH—, —N(CH$_3$)—, or —O—. In some embodiments of a compound of Formula (X), (Xa), (Xa-1), (Xb), or (Xb-1), $L^5$ is a saturated linear aliphatic chain having 1-8 carbon atoms, wherein 1, 2, or 3 carbon atoms are optionally replaced with —NH— or —O—.

In some embodiments of a compound of Formula (X), (Xa), (Xa-1), (Xb), or (Xb-1), $L^5$ is an unsaturated linear aliphatic chain having 1-8 carbon atoms optionally substituted with one or more R$^L$, wherein 1, 2, or 3 carbon atoms are optionally replaced with —NH—, —N(CH$_3$)—, —O—, —S—, —S(=O)—, or —S(=O)$_2$—. In some embodiments of a compound of Formula (X), (Xa), (Xa-1), (Xb), or (Xb-1), $L^5$ is an unsaturated linear aliphatic chain having 1-8 carbon atoms optionally substituted with one or more R$^L$, wherein 1, 2, or 3 carbon atoms are optionally replaced with —NH—, —N(CH$_3$)—, or —O—. In some embodiments of a compound of Formula (X), (Xa), (Xa-1), (Xb), or (Xb-1), $L^5$ is an unsaturated linear aliphatic chain having 1-8 carbon atoms optionally substituted with one or more R$^{L5}$, wherein 1, 2, or 3 carbon atoms are optionally replaced with —NH— or —O—.

In some embodiments of a compound of Formula (X), (Xa), (Xa-1), (Xb), or (Xb-1), $L^5$ is an unsaturated linear aliphatic chain having 1-8 carbon atoms, wherein 1, 2, or 3 carbon atoms are optionally replaced with —NH—, —N(CH$_3$)—, —O—, —S—, —S(=O)—, —S(=O)$_2$—, or —P(=O)—. In some embodiments of a compound of Formula (X), (Xa), (Xa-1), (Xb), or (Xb-1), $L^5$ is an unsaturated linear aliphatic chain having 1-8 carbon atoms, wherein 1, 2, or 3 carbon atoms are optionally replaced with —NH—, —N(CH$_3$)—, or —O—. In some embodiments of a compound of Formula (X), (Xa), (Xa-1), (Xb), or (Xb-1), $L^5$ is an unsaturated linear aliphatic chain having 1-8 carbon atoms, wherein 1, 2, or 3 carbon atoms are optionally replaced with —NH— or —O—.

In some embodiments of a compound of Formula (X), (Xa), (Xa-1), (Xb), or (Xb-1), each $R^{L5}$ is independently deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, or $C_1$-$C_6$deuteroalkyl. In some embodiments of a compound of Formula (X), (Xa), (Xa-1), (Xb), or (Xb-1), each $R^{15}$ is independently deuterium, halogen, $C_1$-$C_6$alkyl, $C_1$-$C_6$haloalkyl, or $C_1$-$C_6$deuteroalkyl. In some embodiments of a compound of Formula (X), (Xa), (Xa-1), (Xb), or (Xb-1), each $R^{15}$ is independently deuterium or halogen.

In some embodiments of a compound of Formula (X), (Xa), (Xa-1), (Xb), or (Xb-1), two $R^{15}$ on the same carbon atom are taken together to form an oxo.

In some embodiments of a compound of Formula (X), (Xa), (Xa-1), (Xb), or (Xb-1), $L^5$ is

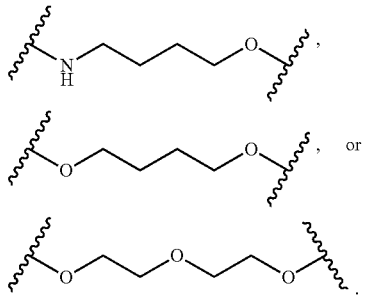

Also disclosed herein is a compound of Formula (XI), or a pharmaceutically acceptable salt, solvate, or stereoisomer thereof:

Formula (XI)

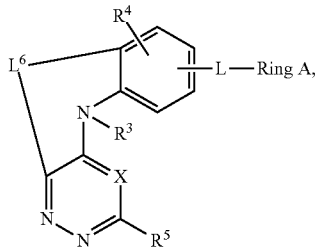

wherein:
- $L^6$ is a saturated or unsaturated linear aliphatic chain having 1-10 carbon atoms optionally substituted with one or more $R^{L6}$, wherein 1-5 carbon atoms are optionally replaced with —NH—, —N(CH$_3$)—, —O—, —S—, —S(=O)—, —S(=O)$_2$—, or —P(=O)—;
- each $R^{L6}$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
- or two $R^{L6}$ on the same carbon atom are taken together to form an oxo;
- $R^3$ is hydrogen, $C_1$-$C_6$alkyl, $C_1$-$C_6$haloalkyl, or $C_1$-$C_6$deuteroalkyl;
- $R^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
- or $R^3$ and $R^4$ are taken together to form an optionally substituted ring;
- L is a bond or —C(=O)—;
- Ring A is cycloalkyl, heterocycloalkyl, aryl, or heteroaryl; each optionally substituted with one or more $R^A$;
- each $R^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;
- or two $R^A$ on the same carbon are taken together to form an oxo;
- X is —CR$^x$— or —N—;
- $R^x$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
- $R^5$ is hydrogen, halogen, —CN, —OR$^8$, —SR$^8$, —S(=O)R$^7$, —S(=O)$_2$R$^7$, —NO$_2$, —NR$^9$R$^{10}$, —NHS(=O)$_2$R$^7$, —S(=O)$_2$NR$^9$R$^{10}$, —C(=O)R$^7$, —OC(=O)R$^7$, —C(=O)OR$^8$, —OC(=O)OR$^8$, —C(=O)NR$^9$R$^{10}$, —OC(=O)NR$^9$R$^{10}$, —NR$^8$C(=O)NR$^9$R$^{10}$, —NR$^8$C(=O)R$^7$, —NR$^8$C(=O)OR$^8$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;
- or $R^x$ and $R^5$ are taken together to form ring D optionally substituted with one or more $R^D$;
- Ring D is a cycloalkyl, heterocycloalkyl, aryl, or heteroaryl;
- each $R^D$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

or two R$^D$ on the same carbon are taken together to form an oxo;

R$^7$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^8$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

R$^9$ and R$^{10}$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^9$ and R$^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^c$ and R$^d$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^c$ and R$^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (XI), L is a bond. In some embodiments of a compound of Formula (XI), L is —C(=O)—.

In some embodiments of a compound of Formula (XI), Ring A is heterocycloalkyl or heteroaryl; each optionally substituted with one or more R$^A$. In some embodiments of a compound of Formula (XI), Ring A is a 5-membered heterocycloalkyl or a 5-membered heteroaryl; each optionally substituted with one or more R$^A$. In some embodiments of a compound of Formula (XI), Ring A is heteroaryl optionally substituted with one or more R$^A$.

In some embodiments of a compound of Formula (XI), each R$^A$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (XI), each R$^A$ is independently deuterium, halogen, C$_1$-C$_6$alkyl, C$_1$-C$_6$haloalkyl, or C$_1$-C$_6$deuteroalkyl. In some embodiments of a compound of Formula (XI), each R$^A$ is independently halogen or C$_1$-C$_6$alkyl. In some embodiments of a compound of Formula (XI), each R$^A$ is independently C$_1$-C$_6$alkyl.

In some embodiments of a compound of Formula (XI), R$^4$ is hydrogen, deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (XI), R$^4$ is hydrogen or —OR$^b$. In some embodiments of a compound of Formula (XI), R$^4$ is —OR$^b$. In some embodiments of a compound of Formula (XI), R$^4$ is hydrogen.

In some embodiments of a compound of Formula (XI), X is —CH—. In some embodiments of a compound of Formula (XI), X is —N—.

In some embodiments of a compound of Formula (XI), the compound is of Formula (XIa):

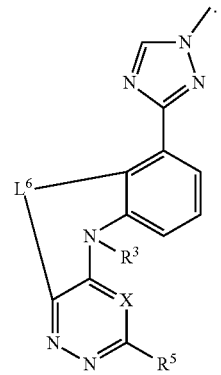

Formula (XIa)

In some embodiments of a compound of Formula (XI), the compound is of Formula (XIb):

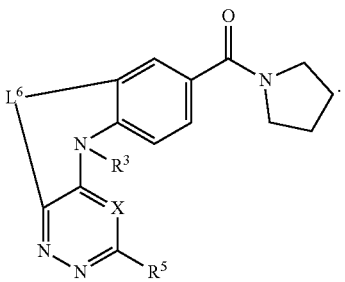

Formula (XIb)

In some embodiments of a compound of Formula (XI), (XIa), or (XIb), $R^3$ is hydrogen or $C_1$-$C_6$alkyl. In some embodiments of a compound of Formula (XI), (XIa), or (XIb), $R^3$ is hydrogen.

In some embodiments of a compound of Formula (XI), (XIa), or (XIb), $R^5$ is halogen, —CN, —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XI), (XIa), or (XIb), $R^5$ is —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=O)R$^7$, —NR$^8$C(=O)OR$^8$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XI), (XIa), or (XIb), $R^5$ is —OR$^8$, —NR$^9$R$^{10}$, —NR$^8$C(=O)R$^7$, or aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XI), (XIa), or (XIb), $R^5$ is —OR$^8$, —NR$^9$R$^{10}$, —NR$^8$C(=O)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl. In some embodiments of a compound of Formula (XI), (XIa), or (XIb), $R^8$ is —NR$^8$C(=O)R$^7$. In some embodiments of a compound of Formula (XI), (XIa), or (XIb), $R^8$ is aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XI), (XIa), or (XIb), $R^7$ is $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (XI), (XIa), or (XIb), $R^7$ is $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (XI), (XIa), or (XIb), $R^7$ is cycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (XI), (XIa), or (XIb), $R^7$ is unsubstituted cycloalkyl.

In some embodiments of a compound of Formula (XI), (XIa), or (XIb), $R^8$ is hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (XI), (XIa), or (XIb), $R^8$ is hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (XI), (XIa), or (XIb), $R^9$ and $R^{10}$ are independently hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl. In some embodiments of a compound of Formula (XI), (XIa), or (XIb), $R^9$ and $R^{10}$ are independently hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (XI), (XIa), or (XIb), $L^6$ is a saturated linear aliphatic chain having 1-8 carbon atoms optionally substituted with one or more $R^{L6}$, wherein 1, 2, or 3 carbon atoms are optionally replaced with —NH—, —N(CH$_3$)—, —O—, —S—, —S(=O)—, or —S(=O)$_2$—. In some embodiments of a compound of Formula (XI), (XIa), or (XIb), $L^6$ is a saturated linear aliphatic chain having 1-8 carbon atoms optionally substituted with one or more $R^{L6}$, wherein 1, 2, or 3 carbon atoms are optionally replaced with —NH—, —N(CH$_3$)—, or —O—. In some embodiments of a compound of Formula (XI), (XIa), or (XIb), $L^6$ is a saturated linear aliphatic chain having 1-8 carbon atoms optionally substituted with one or more $R^{L6}$, wherein 1, 2, or 3 carbon atoms are optionally replaced with —NH— or —O—.

In some embodiments of a compound of Formula (XI), (XIa), or (XIb), $L^6$ is a saturated linear aliphatic chain having 1-8 carbon atoms, wherein 1, 2, or 3 carbon atoms are optionally replaced with —NH—, —N(CH$_3$)—, —O—, —S—, —S(=O)—, or —S(=O)$_2$—. In some embodiments of a compound of Formula (XI), (XIa), or (XIb), $L^6$ is a saturated linear aliphatic chain having 1-8 carbon atoms, wherein 1, 2, or 3 carbon atoms are optionally replaced with —NH—, —N(CH$_3$)—, or —O—. In some embodiments of a compound of Formula (XI), (XIa), or (XIb), $L^6$ is a saturated linear aliphatic chain having 1-8 carbon atoms, wherein 1, 2, or 3 carbon atoms are optionally replaced with —NH— or —O—.

In some embodiments of a compound of Formula (XI), (XIa), or (XIb), $L^6$ is an unsaturated linear aliphatic chain having 1-8 carbon atoms optionally substituted with one or more $R^{L6}$, wherein 1, 2, or 3 carbon atoms are optionally replaced with —NH—, —N(CH$_3$)—, —O—, —S—, —S(=O)—, —S(=O)$_2$—, or —P(=O)—. In some embodiments of a compound of Formula (XI), (XIa), or (XIb), $L^6$ is an unsaturated linear aliphatic chain having 1-8 carbon atoms optionally substituted with one or more $R^{L6}$, wherein 1, 2, or 3 carbon atoms are optionally replaced with —NH—, —N(CH$_3$)—, or —O—. In some embodiments of a compound of Formula (XI), (XIa), or (XIb), $L^6$ is an unsaturated linear aliphatic chain having 1-8 carbon atoms optionally substituted with one or more $R^{L6}$, wherein 1, 2, or 3 carbon atoms are optionally replaced with —NH— or —O—.

In some embodiments of a compound of Formula (XI), (XIa), or (XIb), $L^6$ is an unsaturated linear aliphatic chain having 1-8 carbon atoms, wherein 1, 2, or 3 carbon atoms are optionally replaced with —NH—, —N(CH$_3$)—, —O—, —S—, —S(=O)—, —S(=O)$_2$—, or —P(=O)—. In some embodiments of a compound of Formula (XI), (XIa), or (XIb), $L^6$ is an unsaturated linear aliphatic chain having 1-8 carbon atoms, wherein 1, 2, or 3 carbon atoms are optionally replaced with —NH—, —N(CH$_3$)—, or —O—. In some embodiments of a compound of Formula (XI), (XIa), or (XIb), $L^6$ is an unsaturated linear aliphatic chain having 1-8 carbon atoms, wherein 1, 2, or 3 carbon atoms are optionally replaced with —NH— or —O—.

In some embodiments of a compound of Formula (XI), (XIa), or (XIb), each $R^{L6}$ is independently deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, or C$_1$-C$_6$deuteroalkyl. In some embodiments of a compound of Formula (XI), (XIa), or (XIb), each $R^{L6}$ is independently deuterium, halogen, C$_1$-C$_6$alkyl, C$_1$-C$_6$haloalkyl, or C$_1$-C$_6$deuteroalkyl. In some embodiments of a compound of Formula (XI), (XIa), or (XIb), each $R^{L6}$ is independently deuterium or halogen.

In some embodiments of a compound of Formula (XI), (XIa), or (XIb), two $R^{L6}$ on the same carbon atom are taken together to form an oxo.

In some embodiments of a compound of Formula (XI), (XIa), or (XIb), $L^6$ is

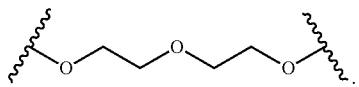 [SMILES: *OCCOCCO*]

Also disclosed herein is a compound of Formula (XII), or a pharmaceutically acceptable salt, solvate, or stereoisomer thereof:

Formula (XII)

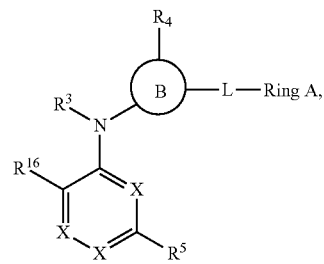

wherein:
Ring B is cycloalkyl, heterocycloalkyl, aryl, heteroaryl;
$R^{16}$ is —C(=O)NR$^1$R$^2$, —C(=N—CN)NR$^1$R$^2$, —P(=O)R$^1$R$^2$, or —C(=O)R$^{11}$;
$R^1$ and $R^2$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;
$R^3$ is hydrogen, C$_1$-C$_6$alkyl, C$_1$-C$_6$haloalkyl, or C$_1$-C$_6$deuteroalkyl;
$R^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, —P(=O)R$^b$R$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;
or $R^3$ and $R^4$ are taken together to form an optionally substituted ring;
L is a bond or —C(=O)—;
Ring A is cycloalkyl, heterocycloalkyl, aryl, or heteroaryl; each optionally substituted with one or more $R^A$;
each $R^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;
or two $R^A$ on the same carbon are taken together to form an oxo;
or -L-Ring A is absent;
each X is independently —CR$^x$— or —N—;
each $R^x$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

$R^5$ is halogen, —CN, —OR$^8$, —SR$^8$, —S(=O)R$^7$, —S(=O)$_2$R$^7$, —NO$_2$, —NR$^9$R$^{10}$, —NR$^8$S(=O)R$^7$, —NR$^8$S(=O)$_2$R$^7$, —S(=O)$_2$NR$^9$R$^{10}$, —C(=N—CN)R$^7$, —OC(=O)R$^7$, —OC(=N—CN)R$^7$, —OC(=N—CN)R$^7$, —C(=N—CN)OR$^8$, —C(=O)OR$^8$, —OC(=N—CN)OR$^8$, —OC(=O)OR$^8$, —C(=N—CN)NR$^9$R$^{10}$, —C(=O)NR$^9$R$^{10}$, —OC(=N—CN)NR$^9$R$^{10}$, —OC(=O)NR$^9$R$^{10}$, —NR$^8$C(=N—CN)NR$^9$R$^{10}$, —NR$^8$C(=O)NR$^9$R$^{10}$, —NR$^8$C(=N—CN)R$^7$, —NR$^8$C(=N—OH)R$^7$, —NR$^8$C(=O)R$^7$, —NR$^8$C(=N—CN)OR$^8$, —NR$^8$C(=O)OR$^8$, —NR$^8$S(=O)(=NR$^8$)R$^7$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or $R^x$ and $R^5$ are taken together to form ring D optionally substituted with one or more $R^D$;

Ring D is a cycloalkyl, heterocycloalkyl, aryl, or heteroaryl;

each $R^D$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or two $R^D$ on the same carbon are taken together to form an oxo;

$R^7$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each $R^8$ is independently hydrogen, CN, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

$R^9$ and $R^{10}$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, C$_1$-C$_6$haloalkyl, C$_1$-C$_6$hydroxyalkyl, C$_1$-C$_6$hydroxydeuteroalkyl, cycloalkyl, or heterocycloalkyl;

or $R^9$ and $R^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or $R^8$ and $R^9$ are taken together with the atoms to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

$R^{11}$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more $R^{11a}$;

each $R^{11a}$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

each $R^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each $R^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each $R^c$ and $R^d$ is independently hydrogen, C$_1$-C$_6$alkyl, C$_1$-C$_6$haloalkyl, C$_1$-C$_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

Also disclosed herein is a compound of Formula (XII), or a pharmaceutically acceptable salt, stereoisomer, or solvate thereof:

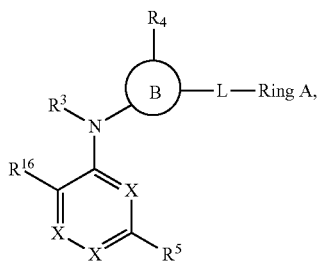

Formula (XII)

wherein:
Ring B is cycloalkyl, heterocycloalkyl, aryl, heteroaryl;
$R^{16}$ is —C(=O)NR$^1$R$^2$, —C(=N—CN)NR$^1$R$^2$, —P(=O)R$^1$R$^2$, or —C(=O)R$^{11}$;
$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
$R^3$ is hydrogen, $C_1$-$C_6$alkyl, $C_1$-$C_6$haloalkyl, or $C_1$-$C_6$deuteroalkyl;
$R^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, —P(=O)R$^b$R$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
or $R^3$ and $R^4$ are taken together to form an optionally substituted ring;
L is a bond or —C(=O)—;
Ring A is cycloalkyl, heterocycloalkyl, aryl, or heteroaryl; each optionally substituted with one or more $R^A$;
each $R^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

or two $R^A$ on the same carbon are taken together to form an oxo;
or -L-Ring A is absent;
each X is independently —CR$^x$— or —N—;
each $R^x$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
$R^5$ is halogen, —CN, —OR$^8$, —SR$^8$, —S(=O)R$^7$, —S(=O)$_2$R$^7$, —NO$_2$, —NR$^9$R$^{10}$, —NR$^8$S(=O)R$^7$, —NR$^8$S(=O)$_2$R$^7$, —S(=O)$_2$NR$^9$R$^{10}$, —C(=N—CN)R$^7$, —C(=O)R$^7$, —OC(=N—CN)R$^7$, —OC(=O)R$^7$, —C(=N—CN)OR$^8$, —C(=O)OR$^8$, —OC(=N—CN)OR$^8$, —OC(=O)OR$^8$, —C(=N—CN)NR$^9$R$^{10}$, —C(=O)NR$^9$R$^{10}$, —OC(=N—CN)NR$^9$R$^{10}$, —OC(=O)NR$^9$R$^{10}$, —NR$^8$C(=N—CN)NR$^9$R$^{10}$, —NR$^8$C(=O)NR$^9$R$^{10}$, —NR$^8$C(=N—CN)R$^7$, —NR$^8$C(=N—OH)R$^7$, —NR$^8$C(=N—CN)OR$^8$, —NR$^8$C(=O)OR$^8$, —NR$^8$S(=O)(=NR$^8$)R$^7$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;
$R^7$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;
each $R^8$ is independently hydrogen, CN, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

R$^9$ and R$^{10}$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, C$_1$-C$_6$haloalkyl, C$_1$-C$_6$hydroxyalkyl, C$_1$-C$_6$hydroxydeuteroalkyl, cycloalkyl, or heterocycloalkyl;

or R$^9$ and R$^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^8$ and R$^9$ are taken together with the atoms to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

R$^{11}$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R$^{11a}$;

each R$^{11a}$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^c$ and R$^d$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^c$ and R$^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

Also disclosed herein is a compound of Formula (XII), or a pharmaceutically acceptable salt, solvate, or stereoisomer thereof:

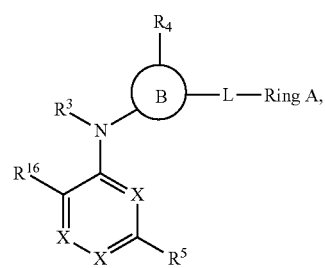

Formula (XII)

wherein:
Ring B is cycloalkyl, heterocycloalkyl, aryl, heteroaryl;
R$^{16}$ is —C(=O)NR$^1$R$^2$, —C(=N—CN)NR$^1$R$^2$, —P(=O)R$^1$R$^2$, or —C(=O)R$^{11}$;
R$^1$ and R$^2$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;
R$^3$ is hydrogen, C$_1$-C$_6$alkyl, C$_1$-C$_6$haloalkyl, or C$_1$-C$_6$deuteroalkyl;
R$^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, —P(=O)R$^b$R$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;
or R$^3$ and R$^4$ are taken together to form an optionally substituted ring;
L is a bond or —C(=O)—;
Ring A is cycloalkyl, heterocycloalkyl, aryl, or heteroaryl; each optionally substituted with one or more R$^A$;
each R$^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or two $R^A$ on the same carbon are taken together to form an oxo;

each X is independently $-CR^x-$ or $-N-$;

each $R^x$ is independently hydrogen, deuterium, halogen, $-CN$, $-OR^b$, $-SR^b$, $-S(=O)R^a$, $-S(=O)_2R^a$, $-NO_2$, $-NR^cR^d$, $-NHS(=O)_2R^a$, $-S(=O)_2NR^cR^d$, $-C(=O)R^a$, $-OC(=O)R^a$, $-C(=O)OR^b$, $-OC(=O)OR^b$, $-C(=O)NR^cR^d$, $-OC(=O)NR^cR^d$, $-NR^bC(=O)NR^cR^d$, $-NR^bC(=O)R^a$, $-NR^bC(=O)OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

$R^5$ is halogen, $-CN$, $-OR^8$, $-SR^8$, $-S(=O)R^7$, $-S(=O)_2R^7$, $-NO_2$, $-NR^9R^{10}$, $-NR^8S(=O)R^7$, $-NR^8S(=O)_2R^7$, $-S(=O)_2NR^9R^{10}$, $-C(=N-CN)R^7$, $-C(=O)R^7$, $-OC(=N-CN)R^7$, $-OC(=O)R^7$, $-C(=N-CN)OR^8$, $-C(=O)OR^8$, $-OC(=N-CN)OR^8$, $-OC(=O)OR^8$, $-C(=N-CN)NR^9R^{10}$, $-C(=O)NR^9R^{10}$, $-OC(=N-CN)NR^9R^{10}$, $-OC(=O)NR^9R^{10}$, $-NR^8C(=N-CN)NR^9R^{10}$, $-NR^8C(=O)NR^9R^{10}$, $-NR^8C(=N-CN)R^7$, $-NR^8C(=N-OH)R^7$, $-NR^8C(=O)R^7$, $-NR^8C(=N-CN)OR^8$, $-NR^8C(=O)OR^8$, $-NR^8S(=O)(=NR^8)R^7$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, $-CN$, $-OR^b$, $-NR^cR^d$, $-C(=O)R^a$, $-C(=O)OR^b$, $-C(=O)NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, $-CN$, $-OR^b$, $-NR^cR^d$, $-C(=O)R^a$, $-C(=O)OR^b$, $-C(=O)NR^cR^d$, $C_1$-$C_6$alkyl, or $C_1$-$C_6$haloalkyl;

or $R^x$ and $R^5$ are taken together to form ring D optionally substituted with one or more $R^D$;

Ring D is a cycloalkyl, heterocycloalkyl, aryl, or heteroaryl;

each $R^D$ is independently hydrogen, deuterium, halogen, $-CN$, $-OR^b$, $-SR^b$, $-S(=O)R^a$, $-S(=O)_2R^a$, $-NO_2$, $-NR^cR^d$, $-NHS(=O)_2R^a$, $-S(=O)_2NR^cR^d$, $-C(=O)R^a$, $-OC(=O)R^a$, $-C(=O)OR^b$, $-OC(=O)OR^b$, $-C(=O)NR^cR^d$, $-OC(=O)NR^cR^d$, $-NR^bC(=O)NR^cR^d$, $-NR^bC(=O)R^a$, $-NR^bC(=O)OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, $-CN$, $-OR^b$, $-NR^cR^d$, $-C(=O)R^a$, $-C(=O)OR^b$, $-C(=O)NR^cR^d$, $C_1$-$C_6$alkyl, or $C_1$-$C_6$haloalkyl;

or two $R^D$ on the same carbon are taken together to form an oxo;

$R^7$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, $-CN$, $-OH$, $-OMe$, $-NH_2$, $-C(=O)Me$, $-C(=O)OH$, $-C(=O)OMe$, $C_1$-$C_6$alkyl, or $C_1$-$C_6$haloalkyl;

each $R^8$ is independently hydrogen, CN, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, $-CN$, $-OH$, $-OMe$, $-NH_2$, $-C(=O)Me$, $-C(=O)OH$, $-C(=O)OMe$, $C_1$-$C_6$alkyl, or $C_1$-$C_6$haloalkyl;

$R^9$ and $R^{10}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, $-CN$, $-OH$, $-OMe$, $-NH_2$, $-C(=O)Me$, $-C(=O)OH$, $-C(=O)OMe$, $C_1$-$C_6$alkyl, $C_1$-$C_6$deuteroalkyl, $C_1$-$C_6$haloalkyl, $C_1$-$C_6$hydroxyalkyl, $C_1$-$C_6$hydroxydeuteroalkyl, cycloalkyl, or heterocycloalkyl;

or $R^9$ and $R^{10}$ are taken together with the nitrogen atom to which they are attached to form a heterocycloalkyl optionally substituted with one or more oxo, deuterium, halogen, $-CN$, $-OH$, $-OMe$, $-NH_2$, $-C(=O)Me$, $-C(=O)OH$, $-C(=O)OMe$, $C_1$-$C_6$alkyl, or $C_1$-$C_6$haloalkyl;

or $R^8$ and $R^9$ are taken together with the atoms to which they are attached to form a heterocycloalkyl optionally substituted with one or more oxo, deuterium, halogen, $-CN$, $-OH$, $-OMe$, $-NH_2$, $-C(=O)Me$, $-C(=O)OH$, $-C(=O)OMe$, $C_1$-$C_6$alkyl, or $C_1$-$C_6$haloalkyl;

$R^{11}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more $R^{11a}$;

each $R^{11a}$ is independently deuterium, halogen, $-CN$, $-OR^b$, $-SR^b$, $-S(=O)R^a$, $-S(=O)_2R^a$, $-NO_2$, $-NR^cR^d$, $-NHS(=O)_2R^a$, $-S(=O)_2NR^cR^d$, $-C(=O)R^a$, $-OC(=O)R^a$, $-C(=O)OR^b$, $-OC(=O)OR^b$, $-C(=O)NR^cR^d$, $-OC(=O)NR^cR^d$, $-NR^bC(=O)NR^cR^d$, $-NR^bC(=O)R^a$, $-NR^bC(=O)OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, $-CN$, $-OH$, $-OMe$, $-NH_2$, $-C(=O)Me$, $-C(=O)OH$, $-C(=O)OMe$, $C_1$-$C_6$alkyl, or $C_1$-$C_6$haloalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^c$ and $R^d$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

Also disclosed herein is a compound of Formula (XII), or a pharmaceutically acceptable salt, solvate, or stereoisomer thereof:

Formula (XII)

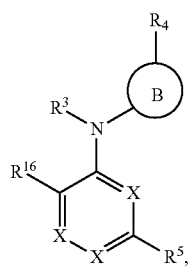

wherein:
Ring B is cycloalkyl, heterocycloalkyl, aryl, heteroaryl;
$R^{16}$ is —C(=O)NR$^1$R$^2$, —C(=N—CN)NR$^1$R$^2$, —P(=O)R$^1$R$^2$, or —C(=O)R$^{11}$;
$R^1$ and $R^2$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
$R^3$ is hydrogen, $C_1$-$C_6$alkyl, $C_1$-$C_6$haloalkyl, or $C_1$-$C_6$deuteroalkyl;
$R^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, —P(=O)R$^b$R$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;
or $R^3$ and $R^4$ are taken together to form an optionally substituted ring;
each X is independently —CR$^x$— or —N—;
each $R^x$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

$R^5$ is halogen, —CN, —OR$^8$, —SR$^8$, —S(=O)R$^7$, —S(=O)$_2$R$^7$, —NO$_2$, —NR$^9$R$^{10}$, —NR$^8$S(=O)R$^7$, —NR$^8$S(=O)$_2$R$^7$, —S(=O)$_2$NR$^9$R$^{10}$, —C(=N—CN)R$^7$, —C(=O)R$^7$, —C(=N—CN)R$^7$, —OC(=O)R$^7$, —C(=N—CN)OR$^8$, —C(=O)OR$^8$, —OC(=N—CN)OR$^8$, —OC(=O)OR$^8$, —C(=N—CN)NR$^9$R$^{10}$, —C(=O)NR$^9$R$^{10}$, —OC(=N—CN)NR$^9$R$^{10}$, —OC(=O)NR$^9$R$^{10}$, —NR$^8$C(=N—CN)NR$^9$R$^{10}$, —NR$^8$C(=O)NR$^9$R$^{10}$, —NR$^8$C(=N—CN)R$^7$, —NR$^8$C(=N—OH)R$^7$, —NR$^8$C(=O)R$^7$, —NR$^8$C(=N—CN)OR$^8$, —NR$^8$C(=O)OR$^8$, —NR$^8$S(=O)(=NR$^8$)R$^7$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;

or $R^x$ and $R^5$ are taken together to form ring D optionally substituted with one or more $R^D$;
Ring D is a cycloalkyl, heterocycloalkyl, aryl, or heteroaryl;
each $R^D$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl;
or two $R^D$ on the same carbon are taken together to form an oxo;
$R^7$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl;

each R$^8$ is independently hydrogen, CN, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl;

R$^9$ and R$^{10}$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, C$_1$-C$_6$deuteroalkyl, C$_1$-C$_6$haloalkyl, C$_1$-C$_6$hydroxyalkyl, C$_1$-C$_6$hydroxydeuteroalkyl, cycloalkyl, or heterocycloalkyl;

or R$^9$ and R$^{10}$ are taken together with the nitrogen atom to which they are attached to form a heterocycloalkyl optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl;

or R$^8$ and R$^9$ are taken together with the atoms to which they are attached to form a heterocycloalkyl optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl;

R$^{11}$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R$^{11a}$;

each R$^{11a}$ is independently deuterium, halogen, —CN, —OR$^b$, —SR$^b$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl;

each R$^c$ and R$^d$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl;

or R$^c$ and R$^d$ are taken together with the nitrogen atom to which they are attached to form a heterocycloalkyl optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl.

In some embodiments of a compound of Formula (XII), Ring B is aryl or heteroaryl. In some embodiments of a compound of Formula (XII), Ring B is aryl. In some embodiments of a compound of Formula (XII), Ring B is phenyl. In some embodiments of a compound of Formula (XII), Ring B is heteroaryl. In some embodiments of a compound of Formula (XII), Ring B is 5- or 6-membered heteroaryl. In some embodiments of a compound of Formula (XII), Ring B is 6-membered heteroaryl. In some embodiments of a compound of Formula (XII), Ring B is pyridyl.

Also disclosed herein is a compound of Formula (XII'), or a pharmaceutically acceptable salt, solvate, or stereoisomer thereof:

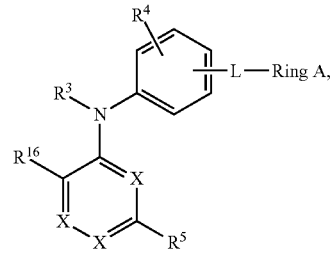

Formula (XII')

wherein:
R$^{16}$ is —C(═O)NR$^1$R$^2$, —C(═N—CN)NR$^1$R$^2$, —P(═O)R$^1$R$^2$, or —C(═O)R$^{11}$;

R$^1$ and R$^2$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

R$^3$ is hydrogen, C$_1$-C$_6$alkyl, C$_1$-C$_6$haloalkyl, or C$_1$-C$_6$deuteroalkyl;

R$^4$ is hydrogen, deuterium, halogen, —CN, —OR$^b$, —SR$^b$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, —P(═O)R$^b$R$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

or $R^3$ and $R^4$ are taken together to form an optionally substituted ring;

L is a bond or —C(=O)—;

Ring A is cycloalkyl, heterocycloalkyl, aryl, or heteroaryl; each optionally substituted with one or more $R^A$;

each $R^A$ is independently deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl;

or two $R^A$ on the same carbon are taken together to form an oxo;

each X is independently —$CR^x$— or —N—;

each $R^x$ is independently hydrogen, deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

$R^5$ is halogen, —CN, —$OR^8$, —$SR^8$, —S(=O)$R^7$, —S(=O)$_2R^7$, —$NO_2$, —$NR^9R^{10}$, —$NR^8S$(=O)$R^7$, —$NR^8S$(=O)$_2R^7$, —S(=O)$_2NR^9R^{10}$, —C(=N—CN)$R^7$, —C(=O)$R^7$, —OC(=N—CN)$R^7$, —OC(=O)$R^7$, —C(=N—CN)$OR^8$, —C(=O)$OR^8$, —OC(=N—CN)$OR^8$, —OC(=O)$OR^8$, —C(=N—CN)$NR^9R^{10}$, —C(=O)$NR^9R^{10}$, —OC(=N—CN)$NR^9R^{10}$, —OC(=O)$NR^9R^{10}$, —$NR^8C$(=N—CN)$NR^9R^{10}$, —$NR^8C$(=N—CN)$NR^9R^{10}$, —$NR^8C$(=N—CN)$R^7$, —$NR^8C$(=N—OH)$R^7$, —$NR^8C$(=O)$R^7$, —$NR^8C$(=N—CN)$OR^8$, —$NR^8C$(=O)$OR^8$, —$NR^8S$(=O)(=$NR^8$)$R^7$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl;

or $R^x$ and $R^5$ are taken together to form ring D optionally substituted with one or more $R^D$;

Ring D is a cycloalkyl, heterocycloalkyl, aryl, or heteroaryl;

each $R^D$ is independently hydrogen, deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl;

or two $R^D$ on the same carbon are taken together to form an oxo;

$R^7$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

each $R^8$ is independently hydrogen, CN, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

$R^9$ and $R^{10}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, $C_1$-$C_6$deuteroalkyl, $C_1$-$C_6$haloalkyl, $C_1$-$C_6$hydroxyalkyl, $C_1$-$C_6$hydroxydeuteroalkyl, cycloalkyl, or heterocycloalkyl;

or $R^9$ and $R^{10}$ are taken together with the nitrogen atom to which they are attached to form a heterocycloalkyl optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

or $R^8$ and $R^9$ are taken together with the atoms to which they are attached to form a heterocycloalkyl optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

$R^{11}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more $R^{11a}$;

each $R^{11a}$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

each $R^c$ and $R^d$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (XII) or (XII'), L is a bond. In some embodiments of a compound of Formula (XII) or (XII'), L is —C(=O)—.

In some embodiments of a compound of Formula (XII) or (XII'), -L-Ring A is absent.

In some embodiments of a compound of Formula (XII) or (XII'), Ring A is heterocycloalkyl or heteroaryl; each optionally substituted with one or more $R^A$. In some embodiments of a compound of Formula (XII) or (XII'), Ring A is a 5-membered heterocycloalkyl or a 5-membered heteroaryl; each optionally substituted with one or more $R^A$. In some embodiments of a compound of Formula (XII) or (XII'), Ring A is heteroaryl optionally substituted with one or more $R^A$.

In some embodiments of a compound of Formula (XII) or (XII'), each $R^A$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, $C_1$-$C_6$alkyl, $C_1$-$C_6$haloalkyl, or $C_1$-$C_6$deuteroalkyl. In some embodiments of Formula (XII) or (XII'), each $R^A$ is independently deuterium, halogen, $C_1$-$C_6$alkyl, $C_1$-$C_6$haloalkyl, or $C_1$-$C_6$deuteroalkyl. In some embodiments of a compound of Formula (XII) or (XII'), each $R^A$ is independently halogen or $C_1$-$C_6$alkyl. In some embodiments of a compound of Formula (XII) or (XII'), each $R^A$ is independently $C_1$-$C_6$alkyl.

In some embodiments of a compound of Formula (XII), the compound is of Formula (XIIa):

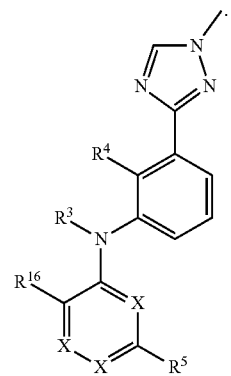

Formula (XIIa)

In some embodiments of a compound of Formula (XII), the compound is of Formula (XIIb):

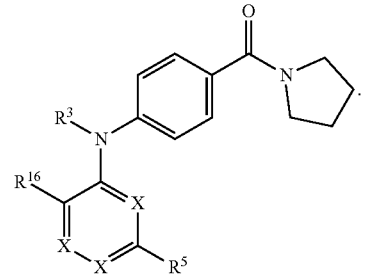

Formula (XIIb)

In some embodiments of a compound of Formula (XII), (XII'), (XIIa), (XIIb), or (XIIc), $R^4$ is hydrogen, deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, $C_1$-$C_6$alkyl, $C_1$-$C_6$haloalkyl, or $C_1$-$C_6$deuteroalkyl. In some embodiments of a compound of Formula (XII), (XII'), (XIIa), (XIIb), or (XIIc), $R^4$ is hydrogen or —OR$^b$. In some embodiments of a compound of Formula (XII), (XII'), (XIIa), (XIIb), or (XIIc), $R^4$ is —OR$^b$. In some embodiments of a compound of Formula (XII), (XII'), (XIIa), (XIIb), or (XIIc), $R^4$ is hydrogen. In some embodiments of a compound of Formula (XII), $R^4$ is —P(=O)R$^b$R$^b$. In some embodiments of a compound of Formula (XII), (XII'), (XIIa), (XIIb), or (XIIc), $R^4$ is —S(=O)$_2$R$^a$.

In some embodiments of a compound of Formula (XII), (XII'), (XIIa), (XIIb), or (XIIc), each X is —N—. In some embodiments of a compound of Formula (XII), (XII'), (XIIa), (XIIb), or (XIIc) each X is —CR$^X$—. In some embodiments of a compound of Formula (XII), (XII'), (XIIa), (XIIb), or (XIIc), two X are —N— and the other is —CR$^X$—. In some embodiments of a compound of Formula (XII), (XII'), (XIIa), (XIIb), or (XIIc), one X is —N— and the others are —CR$^X$—. In some embodiments of a compound of Formula (XII), (XII'), (XIIa), (XIIb), or (XIIc), each X is —CH—. In some embodiments of a compound of Formula (XII), (XII'), (XIIa), (XIIb), or (XIIc), two X are —N— and the other is —CH—. In some embodiments of a compound of Formula (XII), (XII'), (XIIa), (XIIb), or (XIIc), one X is —N— and the others are —CH—. In some embodiments of a compound of Formula (XII), (XII'), (XIIa), (XIIb), or (XIIc),

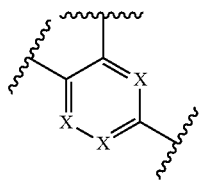

is

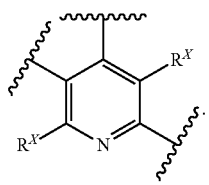

In some embodiments of a compound of Formula (XII), (XII'), (XIIa), (XIIb), or (XIIc),

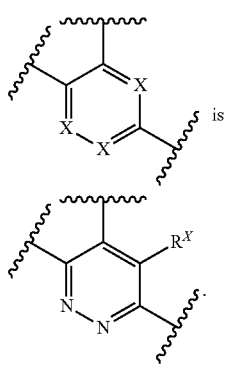

In some embodiments of a compound of Formula (XII), (XII'), (XIIa), (XIIb), or (XIIc),

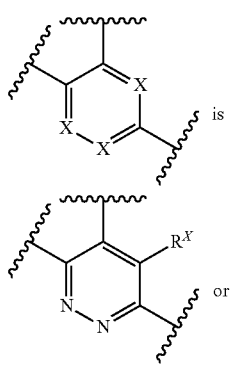

or

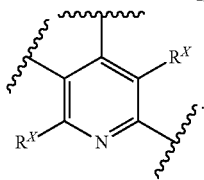

In some embodiments of a compound of Formula (XII), (XII'), (XIIa), (XIIb), or (XIIc), each $R^X$ is independently hydrogen, deuterium, halogen, —CN, —OR$^b$, —NR$^c$R$^d$, —C(=O)R$^a$, —C(=O)OR$^b$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound of Formula (XII), (XII'), (XIIa), (XIIb), or (XIIc), each RX is independently hydrogen, deuterium, halogen, $C_1$-$C_6$alkyl, $C_1$-$C_6$haloalkyl, or $C_1$-$C_6$deuteroalkyl. In some embodiments of a compound of Formula (XII), (XII'), (XIIa), (XIIb), or (XIIc), each RX is independently hydrogen, deuterium, or halogen.

In some embodiments of a compound of Formula (XII), (XII'), (XIIa), (XIIb), or (XIIc),

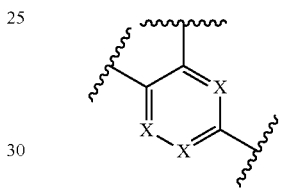

is

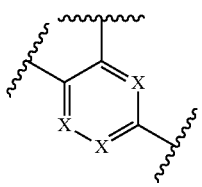

In some embodiments of a compound of Formula (XII), (XII'), (XIIa), (XIIb), or (XIIc),

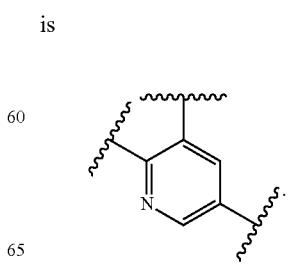

is

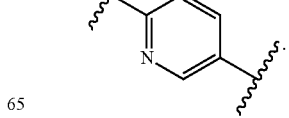

In some embodiments of a compound of Formula (XII), (XII'), (XIIa), (XIIb), or (XIIc),

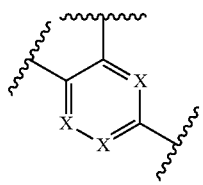

is

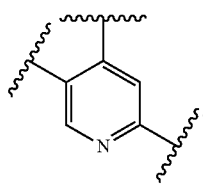

In some embodiments of a compound of Formula (XII), (XII'), (XIIa), (XIIb), or (XIIc), $R^3$ is hydrogen or $C_1$-$C_6$alkyl. In some embodiments of a compound of Formula (XII), (XII'), (XIIa), (XIIb), or (XIIc), $R^3$ is hydrogen.

In some embodiments of a compound of Formula (XII), (XII'), (XIIa), (XIIb), or (XIIc), $R^{16}$ is —C(=O)NR$^1$R$^2$ or —C(=O)R$^{11}$. In some embodiments of a compound of Formula (XII), (XII'), (XIIa), (XIIb), or (XIIc), $R^{16}$ is —C(=O)NR$^1$R$^2$. In some embodiments of a compound of Formula (XII), (XII'), (XIIa), (XIIb), or (XIIc), $R^{16}$ is —C(=N—CN)NR$^1$R$^2$. In some embodiments of a compound of Formula (XII), (XII'), (XIIa), (XIIb), or (XIIc), $R^{16}$ is —P(=O)R$^1$R$^2$. In some embodiments of a compound of Formula (XII), (XII'), (XIIa), (XIIb), or (XIIc), $R^{16}$ is —C(=O)R$^{11}$.

In some embodiments of a compound of Formula (XII), (XII'), (XIIa), (XIIb), or (XIIc), $R^1$ and $R^2$ are independently hydrogen, $C_1$-$C_6$alkyl, $C_1$-$C_6$haloalkyl, or $C_1$-$C_6$deuteroalkyl. In some embodiments of a compound of Formula (XII), (XII'), (XIIa), (XIIb), or (XIIc), $R^1$ and $R^2$ are independently hydrogen or $C_1$-$C_6$deuteroalkyl. In some embodiments of a compound of Formula (XII), (XII'), (XIIa), (XIIb), or (XIIc), $R^1$ and $R^2$ are independently $C_1$-$C_6$alkyl. In some embodiments of a compound of Formula (XII), (XII'), (XIIa), (XIIb), or (XIIc), $R^1$ is hydrogen. In some embodiments of a compound of Formula (XII), (XII'), (XIIa), (XIIb), or (XIIc), $R^2$ is $C_1$-$C_6$alkyl or $C_1$-$C_6$deuteroalkyl. In some embodiments of a compound of Formula (XII), (XII'), (XIIa), (XIIb), or (XIIc), $R^2$ is $C_1$-$C_6$deuteroalkyl. In some embodiments of a compound of Formula (XII), (XII'), (XIIa), (XIIb), or (XIIc), $R^2$ is $C_1$-$C_6$alkyl.

In some embodiments of a compound of Formula (XII), (XII'), (XIIa), (XIIb), or (XIIc), $R^{11}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, or heteroaryl; wherein each alkyl, cycloalkyl, heterocycloalkyl, aryl, and heteroaryl is independently optionally substituted with one or more $R^{11a}$. In some embodiments of a compound of Formula (XII), (XII'), (XIIa), (XIIb), or (XIIc), $R^{11}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one or more $R^{11a}$. In some embodiments of a compound of Formula (XII), (XII'), (XIIa), (XIIb), or (XIIc), $R^{11}$ is $C_1$-$C_6$alkyl, $C_1$-$C_6$haloalkyl, $C_1$-$C_6$deuteroalkyl, cycloalkyl, or heterocycloalkyl; wherein each alkyl, cycloalkyl, and heterocycloalkyl is independently optionally substituted with one or more $R^{11a}$. In some embodiments of a compound of Formula (XII), (XII'), (XIIa), (XIIb), or (XIIc), $R^{11}$ is $C_1$-$C_6$alkyl, $C_1$-$C_6$haloalkyl, or cycloalkyl; wherein each alkyl and cycloalkyl is independently optionally substituted with one or more $R^{11a}$. In some embodiments of a compound of Formula (XII), (XII'), (XIIa), (XIIb), or (XIIc), $R^{11}$ is $C_1$-$C_6$alkyl or cycloalkyl; wherein each alkyl and cycloalkyl is independently optionally substituted with one or more $R^{11a}$. In some embodiments of a compound of Formula (XII), (XII'), (XIIa), (XIIb), or (XIIc), $R^{11}$ is $C_1$-$C_6$alkyl, $C_1$-$C_6$deuteroalkyl, $C_1$-$C_6$haloalkyl, or cycloalkyl. In some embodiments of a compound of Formula (XII), (XII'), (XIIa), (XIIb), or (XIIc), $R^{11}$ is $C_1$-$C_6$alkyl, $C_1$-$C_6$haloalkyl, or cycloalkyl. In some embodiments of a compound of Formula (XII), (XII'), (XIIa), (XIIb), or (XIIc), $R^{11}$ is $C_1$-$C_6$deuteroalkyl. In some embodiments of a compound of Formula (XII), (XII'), (XIIa), (XIIb), or (XIIc), $R^{11}$ is $C_1$-$C_6$alkyl. In some embodiments of a compound of Formula (XII), (XII'), (XIIa), (XIIb), or (XIIc), $R^{11}$ is cycloalkyl. In some embodiments of a compound of Formula (XII), (XII'), (XIIa), (XIIb), or (XIIc), $R^{11}$ is $C_1$-$C_6$deuteroalkyl, or cycloalkyl.

In some embodiments of a compound of Formula (XII), (XII'), (XIIa), (XIIb), or (XIIc), each $R^{11a}$ is independently deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound of Formula (XII), (XII'), (XIIa), (XIIb), or (XIIc), each $R^{11a}$ is independently deuterium, halogen, —CN, —OR$^b$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound of Formula (XII), (XII'), (XIIa), (XIIb), or (XIIc), each $R^{11a}$ is independently deuterium, halogen, —CN, —OR$^b$, —NR$^c$R$^d$, $C_1$-$C_6$alkyl, $C_1$-$C_6$haloalkyl, or $C_1$-$C_6$deuteroalkyl. In some embodiments of a compound of Formula (XII), (XII'), (XIIa), (XIIb), or (XIIc), each $R^{11a}$ is independently deuterium, halogen, —CN, —OR$^b$, —NR$^c$R$^d$, or $C_1$-$C_6$alkyl. In some embodiments of a compound of Formula (XII), (XII'), (XIIa), (XIIb), or (XIIc), each $R^{11a}$ is independently deuterium, halogen, $C_1$-$C_6$alkyl, $C_1$-$C_6$haloalkyl, or $C_1$-$C_6$deuteroalkyl. In some embodiments of a compound of Formula (XII), (XII'), (XIIa), (XIIb), or (XIIc), each $R^{11a}$ is independently deuterium, halogen, or $C_1$-$C_6$alkyl.

In some embodiments of a compound of Formula (XII), (XII'), (XIIa), or (XIIb), $R^5$ is halogen, —CN, —OR$^8$, —SR$^8$, —S(=O)R$^7$, —S(=O)$_2$R$^7$, —NO$_2$, —NR$^9$R$^{10}$, —NHS(=O)$_2$R$^7$, —S(=O)$_2$NR$^9$R$^{10}$, —C(=N—CN)R$^7$, —C(=O)R$^7$, —OC(=N—CN)R$^7$, —OC(=O)R$^7$, —C(=N—CN)OR$^8$, —C(=O)OR$^8$, —OC(=N—CN) OR$^8$, —OC(=O)OR$^8$, —C(=N—CN)NR$^9$R$^{10}$, —C(=O) NR$^9$R$^{10}$, —OC(=N—CN)NR$^9$R$^{10}$, —OC(=O)NR$^9$R$^{10}$, —NR$^8$C(=N—CN)NR$^9$R$^{10}$, —NR$^8$C(=O)NR$^9$R$^{10}$, —NR$^8$C(=N—CN)R$^7$, —NR$^8$C(=N—OH)R$^7$, —NR$^8$C (=N—CN)OR$^8$, —NR$^8$C(=O)OR$^8$, —NR$^8$S(=O) (=NR$^8$)R$^7$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XII), (XII'), (XIIa), or (XIIb), R$^5$ is halogen, —CN, —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=N—CN)R$^7$, —NR$^8$C(=O)R$^7$, —NR$^8$C(=O)OR$^8$, —NR'S(=O)(=NR$^8$)R$^7$, C$_1$-C$_6$alkyl, C$_1$-C$_6$haloalkyl, C$_1$-C$_6$deuteroalkyl, C$_2$-C$_6$alkenyl, C$_2$-C$_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XII), (XII'), (XIIa), or (XIIb), R$^5$ is halogen, —CN, —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=N—CN)R$^7$, —NR$^8$C(=O)OR$^8$, —NR'S(=O)(=NR$^8$)R$^7$, C$_1$-C$_6$alkyl, C$_1$-C$_6$haloalkyl, C$_1$-C$_6$deuteroalkyl, C$_2$-C$_6$alkenyl, C$_2$-C$_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XII), (XII'), (XIIa), or (XIIb), R$^5$ is halogen, —CN, —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=N—CN)R$^7$, —NR$^8$C(=O)OR$^8$, —NR'S(=O)(=NR$^8$)R$^7$, C$_1$-C$_6$alkyl, C$_1$-C$_6$haloalkyl, C$_1$-C$_6$deuteroalkyl, C$_2$-C$_6$alkenyl, C$_2$-C$_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XII), (XII'), (XIIa), or (XIIb), R$^5$ is —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=N—CN)R$^7$, —NR$^8$C(=O)R$^7$, —NR$^8$C(=O)OR$^8$, —NR'S(=O)(=NR$^8$)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XII), (XII'), (XIIa), or (XIIb), R$^5$ is —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=N—CN)R$^7$, —NR$^8$C(=O)OR$^8$, —NR'S(=O)(=NR$^8$)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XII), (XII'), (XIIa), or (XIIb), R$^5$ is —OR$^8$, —NR$^9$R$^{10}$, —NR$^8$C(=N—CN)R$^7$, —NR$^8$S(=O)(=NR$^8$)R$^7$, or aryl optionally substituted with one or more deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XII), (XII'), (XIIa), or (XIIb), R$^5$ is —OR$^8$, —NR$^9$R$^{10}$, —NR$^8$C(=N—CN)R$^7$, —NR$^8$S(=O)(=NR$^8$)R$^7$, or aryl optionally substituted with one or more deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XII), (XII'), (XIIa), or (XIIb), R$^5$ is —OR$^8$, —NR$^9$R$^{10}$, —NR$^8$C(=O)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl. In some embodiments of a compound of Formula (XII), (XII'), (XIIa), or (XIIb), R$^5$ is aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XII), (XII'), (XIIa), or (XIIb), R$^5$ is —NR$^9$R$^{10}$, —NR$^8$C(=O)NR$^9$R$^{10}$, or —NR$^8$C(=N—CN)R$^7$.

In some embodiments of a compound of Formula (XII), (XII'), (XIIa), or (XIIb), R$^5$ is —NR$^9$R$^{10}$.

In some embodiments of a compound of Formula (XII), (XII'), (XIIa), or (XIIb), R$^5$ is —NR$^9$R$^{10}$ or —NR$^8$C(=O)NR$^9$R$^{10}$.

In some embodiments of a compound of Formula (XII), (XII'), (XIIa), or (XIIb), R$^5$ is —NR$^8$C(=N—CN)R$^7$.

In some embodiments of a compound of Formula (XII), (XII'), (XIIa), or (XIIb), R$^5$ is —NR$^8$S(=O)(=NR$^8$)R$^7$.

In some embodiments of a compound of Formula (XII), (XII'), (XIIa), or (XIIb), R$^5$ is —NR$^8$C(=O)NR$^9$R$^{10}$ or —NR$^8$C(=O)R$^7$.

In some embodiments of a compound of Formula (XII), (XII'), (XIIa), or (XIIb), R$^5$ is —NR$^8$C(=O)NR$^9$R$^{10}$.

In some embodiments of a compound of Formula (XII), (XII'), (XIIa), or (XIIb), R$^5$ is —NR$^8$C(=O)R$^7$.

In some embodiments of a compound of Formula (XII), (XII'), (XIIa), or (XIIb), R$^5$ is not—NR$^8$C(=O)R$^7$.

In some embodiments of a compound of Formula (XII), (XII'), (XIIa), or (XIIb), R$^5$ is —NR$^8$C(=O)NR$^9$R$^{10}$ or heterocycloalkyl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XII), (XII'), (XIIa), or (XIIb), R$^5$ is heterocycloalkyl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), $C_1$-$C_6$alkyl (heteroaryl); wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl.

In some embodiments of a compound of Formula (XII), (XII'), (XIIa), or (XIIb), $R^5$ is heterocycloalkyl optionally substituted with one or more oxo, deuterium, halogen, —CN, —$OR^b$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), or $C_1$-$C_6$alkyl(heterocycloalkyl); wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl.

In some embodiments of a compound of Formula (XII), (XII'), (XIIa), or (XIIb), $R^5$ is heterocycloalkyl optionally substituted with one or more oxo, halogen, —$OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, cycloalkyl, heterocycloalkyl, aryl, $C_1$-$C_6$alkyl(cycloalkyl), or $C_1$-$C_6$alkyl(heterocycloalkyl); wherein each alkyl, alkynyl, cycloalkyl, heterocycloalkyl, and aryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl.

In some embodiments of a compound of Formula (XII), (XII'), (XIIa), or (XIIb), the heterocycloalkyl of $R^5$ is

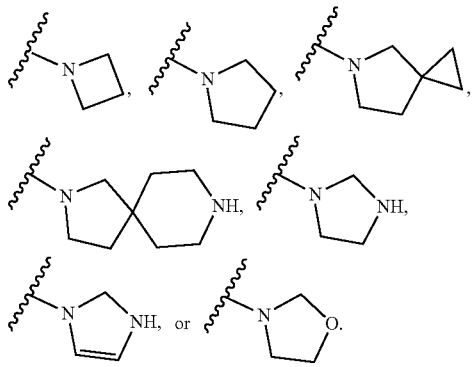

In some embodiments of a compound of Formula (XII), (XII'), (XIIa), or (XIIb), the heterocycloalkyl of $R^5$ is

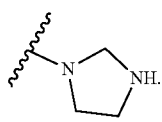

In some embodiments of a compound of Formula (XII), (XII'), (XIIa), or (XIIb), $R^7$ is $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (XII), (XII'), (XIIa), or (XIIb), $R^7$ is $C_1$-$C_6$alkyl, cycloalkyl, or heterocycloalkyl; wherein each alkyl, cycloalkyl, or heterocycloalkyl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (XII), (XII'), (XIIa), or (XIIb), $R^7$ is $C_1$-$C_6$alkyl, $C_1$-$C_6$haloalkyl, $C_1$-$C_6$deuteroalkyl, or cycloalkyl; wherein each alkyl and cycloalkyl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (XII), (XII'), (XIIa), or (XIIb), $R^7$ is $C_1$-$C_6$alkyl or cycloalkyl; wherein each alkyl and cycloalkyl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (XII), (XII'), (XIIa), or (XIIb), $R^7$ is cycloalkyl optionally substituted with one or more oxo, deuterium, halogen, —CN, —OH, —OMe, —$NH_2$, —C(=O)Me, —C(=O)OH, —C(=O) OMe, $C_1$-$C_6$alkyl, or $C_1$-$C_6$haloalkyl. In some embodiments of a compound of Formula (XII), (XII'), (XIIa), or (XIIb), $R^7$ is unsubstituted cycloalkyl. In some embodiments of a compound of Formula (XII), (XII'), (XIIa), or (XIIb), $R^7$ is heterocycloalkyl optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (XII), (XII'), (XIIa), or (XIIb), $R^7$ is unsubstituted heterocycloalkyl.

In some embodiments of a compound of Formula (XII), (XII'), (XIIa), or (XIIb), $R^8$ is hydrogen, CN, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl. In some embodiments of a compound of Formula (XII), (XII'), (XIIa), or (XIIb), $R^8$ is hydrogen, CN, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl.

In some embodiments of a compound of Formula (XII), (XII'), (XIIa), or (XIIb), $R^9$ and $R^{10}$ are independently hydrogen, $C_1$-$C_6$alkyl, $C_1$-$C_6$haloalkyl, $C_1$-$C_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, $C_1$-$C_6$deuteroalkyl, $C_1$-$C_6$haloalkyl, or $C_1$-$C_6$hydroxyalkyl. In some embodiments of a compound of Formula (XII), (XII'), (XIIa), or (XIIb), $R^9$ and $R^{10}$ are independently hydrogen, $C_1$-$C_6$alkyl, $C_1$-$C_6$haloalkyl, $C_1$-$C_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, C$_1$-C$_6$haloalkyl, or C$_1$-C$_6$hydroxyalkyl.

In some embodiments of a compound of Formula (XII), (XII'), (XIIa), or (XIIb), R$^9$ and R$^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (XII), (XII'), (XIIa), or (XIIb), R$^9$ and R$^{10}$ are taken together with the nitrogen atom to which they are attached to form a C$_2$-C$_8$heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (XII), (XII'), (XIIa), or (XIIb), R$^9$ and R$^{10}$ are taken together with the nitrogen atom to which they are attached to form a bicyclic heterocycloalkyl or a spiro heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (XII), (XII'), (XIIa), or (XIIb), R$^9$ and R$^{10}$ are taken together with the nitrogen atom to which they are attached to form a heterocycloalkyl selected from aziridinyl, azetidinyl, pyrrolidinyl, piperidinyl, 2-azabicyclo[1.1.1]pentanyl, or 2-azaspiro[3.3]heptanyl, each optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (XII), the compound is of Formula (XIIc):

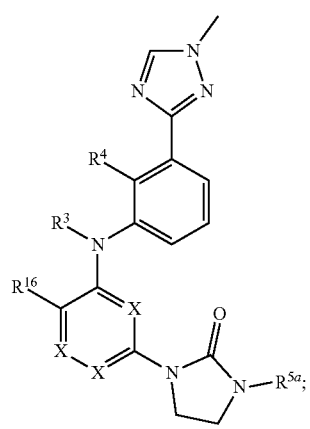

Formula (XIIc)

wherein R$^{5a}$ is deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XIIc); R$^{5a}$ is deuterium, halogen, —CN, —OR$^b$, —NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl.

In some embodiments of a compound of Formula (XIIc); R$^{5a}$ is halogen, —OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkynyl, cycloalkyl, heterocycloalkyl, aryl, C$_1$-C$_6$alkyl(cycloalkyl), or C$_1$-C$_6$alkyl(heterocycloalkyl); wherein each alkyl, alkenyl, alkynyl, cycloalkyl, heterocycloalkyl, and aryl is independently optionally substituted with one or more oxo, deuterium, halogen, —CN, —OR$^b$, —NR$^c$R$^d$, —C(=O)R$^a$, —C(=O)OR$^b$, —C(=O) NR$^c$R$^d$, C$_1$-C$_6$alkyl, or C$_1$-C$_6$haloalkyl.

Also disclosed herein is a compound of Formula (XIII), or a pharmaceutically acceptable salt, solvate, or stereoisomer thereof:

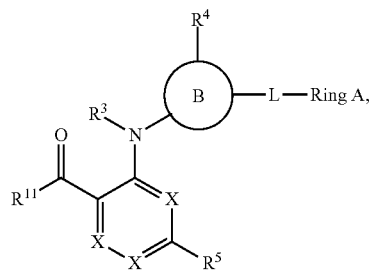

Formula (XIII)

wherein:
Ring B is cycloalkyl, heterocycloalkyl, aryl, or heteroaryl;
R$^3$ is hydrogen, C$_1$-C$_6$alkyl, C$_1$-C$_6$haloalkyl, or C$_1$-C$_6$deuteroalkyl;
R$^4$ is hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O) NR$^c$R$^d$, —NR$^b$C(=O)R$^a$, —NR$^b$C(=O)OR$^b$, —P(=O)R$^b$R$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;
or R$^3$ and R$^4$ are taken together to form an optionally substituted ring;
L is a bond or —C(=O)—;
Ring A is cycloalkyl, heterocycloalkyl, aryl, or heteroaryl; each optionally substituted with one or more R$^A$;
each R$^A$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC (=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C (=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or two R$^A$ on the same carbon are taken together to form an oxo;

or -L-Ring A is absent;

each X is independently —CR$^x$— or —N—;

each R$^x$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

R$^5$ is halogen, —CN, —OR$^8$, —SR$^8$, —S(=O)R$^7$, —S(=O)$_2$R$^7$, —NO$_2$, —NR$^9$R$^{10}$, —NR$^8$S(=O)R$^7$, —NR$^8$S(=O)$_2$R$^7$, —S(=O)$_2$NR$^9$R$^{10}$, —C(=N—CN)R$^7$, —C(=O)R$^7$, —OC(=N—CN)R$^7$, —OC(=O)R$^7$, —C(=N—CN)OR$^8$, —C(=O)OR$^8$, —OC(=N—CN)OR$^8$, —OC(=O)OR$^8$, —C(=N—CN)NR$^9$R$^{10}$, —C(=O)NR$^9$R$^{10}$, —OC(=N—CN)NR$^9$R$^{10}$, —OC(=O)NR$^9$R$^{10}$, —NR$^8$C(=N—CN)NR$^9$R$^{10}$, —NR$^8$C(=O)NR$^9$R$^{10}$, —NR$^8$C(=N—CN)R$^7$, —NR$^8$C(=N—OH)R$^7$, —NR$^8$C(=O)R$^7$, —NR$^8$C(=N—CN)OR$^8$, —NR$^8$C(=O)OR$^8$, —NR$^8$S(=O)(=NR$^8$)R$^7$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkyl(cycloalkyl), C$_1$-C$_6$alkyl(heterocycloalkyl), C$_1$-C$_6$alkyl(aryl), or C$_1$-C$_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or R$^x$ and R$^5$ are taken together to form ring D optionally substituted with one or more R$^D$;

Ring D is a cycloalkyl, heterocycloalkyl, aryl, or heteroaryl;

each R$^D$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or two R$^D$ on the same carbon are taken together to form an oxo;

R$^7$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^8$ is independently hydrogen, CN, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

R$^9$ and R$^{10}$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, C$_1$-C$_6$haloalkyl, C$_1$-C$_6$hydroxyalkyl, C$_1$-C$_6$hydroxydeuteroalkyl, cycloalkyl, or heterocycloalkyl;

or R$^9$ and R$^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^8$ and R$^9$ are taken together with the atoms to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

R$^{11}$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more R$^{11a}$;

each R$^{11a}$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

each R$^a$ is independently C$_1$-C$_6$alkyl, C$_1$-C$_6$haloalkyl, C$_1$-C$_6$deuteroalkyl, C$_1$-C$_6$hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

each $R^b$ is independently hydrogen, C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

each $R^c$ and $R^d$ is independently hydrogen, C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —NH₂, —C(=O)Me, —C(=O)OH, —C(=O)OMe, C₁-C₆alkyl, or C₁-C₆haloalkyl.

Also disclosed herein is a compound of Formula (XIII), or a pharmaceutically acceptable salt, solvate, or stereoisomer thereof:

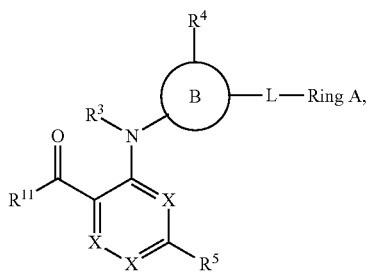

Formula (XIII)

wherein:
Ring B is cycloalkyl, heterocycloalkyl, aryl, or heteroaryl;
$R^3$ is hydrogen, C₁-C₆alkyl, C₁-C₆haloalkyl, or C₁-C₆deuteroalkyl;
$R^4$ is hydrogen, deuterium, halogen, —CN, —OR$^b$, —SR$^b$, —S(=O)R$^a$, —S(=O)₂R$^a$, —NO₂, —NR$^c$R$^d$, —NHS(=O)₂R$^a$, —S(=O)₂NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, —P(=O)R$^b$R$^b$, C₁-C₆alkyl, C₁-C₆haloalkyl, C₁-C₆deuteroalkyl, C₁-C₆hydroxyalkyl, C₁-C₆aminoalkyl, C₂-C₆alkenyl, or C₂-C₆alkynyl;
or $R^3$ and $R^4$ are taken together to form an optionally substituted ring;

L is a bond or —C(=O)—;
Ring A is cycloalkyl, heterocycloalkyl, aryl, or heteroaryl; each optionally substituted with one or more $R^A$;
each $R^A$ is independently deuterium, halogen, —CN, —OR$^b$, —SR$^b$, —S(=O)R$^a$, —S(=O)₂R$^a$, —NO₂, —NR$^c$R$^d$, —NHS(=O)₂R$^a$, —S(=O)₂NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C₁-C₆alkyl, or C₁-C₆haloalkyl;

or two $R^A$ on the same carbon are taken together to form an oxo;

each X is independently —CR$^x$— or —N—;
each $R^x$ is independently hydrogen, deuterium, halogen, —CN, —OR$^b$, —SR$^b$, —S(=O)R$^a$, —S(=O)₂R$^a$, —NO₂, —NR$^c$R$^d$, —NHS(=O)₂R$^a$, —S(=O)₂NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C₁-C₆alkyl, C₁-C₆haloalkyl, C₁-C₆deuteroalkyl, C₁-C₆hydroxyalkyl, C₁-C₆aminoalkyl, C₂-C₆alkenyl, or C₂-C₆alkynyl;

$R^5$ is halogen, —CN, —OR$^8$, —SR$^8$, —S(=O)R$^7$, —S(=O)₂R$^7$, —NO₂, —NR$^9$R$^{10}$, —NR$^8$S(=O)R$^7$, —NR$^8$S(=O)₂R$^7$, —S(=O)₂NR$^9$R$^{10}$, —C(=N—CN)R$^7$, —C(=O)R$^7$, —OC(=N—CN)R$^7$, —OC(=O)R$^7$, —C(=N—CN)OR$^8$, —C(=O)OR$^8$, —OC(=N—CN)OR$^8$, —OC(=O)OR$^8$, —C(=N—CN)NR$^9$R$^{10}$, —C(=O)NR$^9$R$^{10}$, —OC(=N—CN)NR$^9$R$^{10}$, —OC(=O)NR$^9$R$^{10}$, —NR$^8$C(=N—CN)NR$^9$R$^{10}$, —NR$^8$C(=N—CN)R$^7$, —NR$^8$C(=N—OH)R$^7$, —NR$^8$C(=O)R$^7$, —NR$^8$C(=N—CN)OR$^8$, —NR$^8$C(=O)OR$^8$, —NR$^8$S(=O)(=NR$^8$)R$^7$, C₁-C₆alkyl, C₁-C₆haloalkyl, C₁-C₆deuteroalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C₁-C₆alkyl, C₁-C₆haloalkyl, C₁-C₆deuteroalkyl, C₁-C₆hydroxyalkyl, C₁-C₆aminoalkyl, C₁-C₆heteroalkyl, C₂-C₆alkenyl, C₂-C₆alkynyl, cycloalkyl, heterocycloalkyl, aryl, heteroaryl, C₁-C₆alkyl(cycloalkyl), C₁-C₆alkyl(heterocycloalkyl), C₁-C₆alkyl(aryl), or C₁-C₆alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C₁-C₆alkyl, or C₁-C₆haloalkyl;

or $R^x$ and $R^5$ are taken together to form ring D optionally substituted with one or more $R^D$;
Ring D is a cycloalkyl, heterocycloalkyl, aryl, or heteroaryl;

each $R^D$ is independently hydrogen, deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl;

or two $R^D$ on the same carbon are taken together to form an oxo;

$R^7$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each $R^8$ is independently hydrogen, CN, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

$R^9$ and $R^{10}$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, C$_1$-C$_6$haloalkyl, C$_1$-C$_6$hydroxyalkyl, C$_1$-C$_6$hydroxydeuteroalkyl, cycloalkyl, or heterocycloalkyl;

or $R^9$ and $R^{10}$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or $R^8$ and $R^9$ are taken together with the atoms to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

$R^{11}$ is C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more $R^{11a}$;

each $R^{11a}$ is independently deuterium, halogen, —CN, —OR$^b$, —SR$^b$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

each $R^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each $R^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each $R^c$ and $R^d$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or $R^c$ and $R^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

Also disclosed herein is a compound of Formula (XIII), or a pharmaceutically acceptable salt, solvate, or stereoisomer thereof:

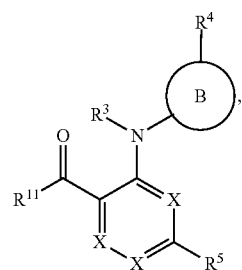

Formula (XIII)

wherein:

Ring B is cycloalkyl, heterocycloalkyl, aryl, or heteroaryl;

$R^3$ is hydrogen, $C_1$-$C_6$alkyl, $C_1$-$C_6$haloalkyl, or $C_1$-$C_6$deuteroalkyl;

$R^4$ is hydrogen, deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)OR^b$, —P(=O)$R^bR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

or $R^3$ and $R^4$ are taken together to form an optionally substituted ring;

each X is independently —$CR^x$— or —N—;

each $R^x$ is independently hydrogen, deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, or $C_2$-$C_6$alkynyl;

$R^5$ is halogen, —CN, —$OR^8$, —$SR^8$, —S(=O)$R^7$, —S(=O)$_2R^7$, —$NO_2$, —$NR^9R^{10}$, —$NR^8S(=O)R^7$, —$NR^8S(=O)_2R^7$, —S(=O)$_2NR^9R^{10}$, —C(=N—CN)$R^7$, —C(=O)$R^7$, —OC(=N—CN)$R^7$, —OC(=O)$R^7$, —C(=N—CN)$OR^8$, —C(=O)$OR^8$, —OC(=N—CN)$OR^8$, —OC(=O)$OR^8$, —C(=N—CN)$NR^9R^{10}$, —C(=O)$NR^9R^{10}$, —OC(=N—CN)$NR^9R^{10}$, —OC(=O)$NR^9R^{10}$, —$NR^8C(=N—CN)NR^9R^{10}$, —$NR^8C(=O)NR^9R^{10}$, —$NR^8C(=N—CN)R^7$, —$NR^8C(=N—OH)R^7$, —$NR^8C(=O)R^7$, —$NR^8C(=N—CN)OR^8$, —$NR^8C(=O)OR^8$, —$NR^8S(=O)(=NR^8)R^7$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl;

or $R^x$ and $R^5$ are taken together to form ring D optionally substituted with one or more $R^D$;

Ring D is a cycloalkyl, heterocycloalkyl, aryl, or heteroaryl;

each $R^D$ is independently hydrogen, deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)OR^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl;

or two $R^D$ on the same carbon are taken together to form an oxo;

$R^7$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

each $R^8$ is independently hydrogen, CN, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

$R^9$ and $R^{10}$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —$NH_2$, —C(=O)Me, —C(=O)OH, —C(=O)OMe, $C_1$-$C_6$alkyl, $C_1$-$C_6$deuteroalkyl, $C_1$-$C_6$haloalkyl, $C_1$-$C_6$hydroxyalkyl, $C_1$-$C_6$hydroxydeuteroalkyl, cycloalkyl, or heterocycloalkyl;

or $R^9$ and $R^{10}$ are taken together with the nitrogen atom to which they are attached to form a heterocycloalkyl optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

or $R^8$ and $R^9$ are taken together with the atoms to which they are attached to form a heterocycloalkyl optionally substituted with one or more oxo, deuterium, halogen, —CN, —OH, —OMe, —$NH_2$, —C(=O)Me, —C(=O)OH, —C(=O)OMe, $C_1$-$C_6$alkyl, or $C_1$-$C_6$haloalkyl;

$R^{11}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more $R^{11a}$;

each $R^{11a}$ is independently deuterium, halogen, —CN, —$OR^b$, —$SR^b$, —S(=O)$R^a$, —S(=O)$_2R^a$, —$NO_2$, —$NR^cR^d$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC$ (=O)OR$^b$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, or C$_2$-C$_6$alkynyl;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

each R$^c$ and R$^d$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^c$ and R$^d$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (XIII), Ring B is aryl or heteroaryl. In some embodiments of a compound of Formula (XIII), Ring B is aryl. In some embodiments of a compound of Formula (XIII), Ring B is phenyl. In some embodiments of a compound of Formula (XIII), Ring B is heteroaryl. In some embodiments of a compound of Formula (XIII), Ring B is 5- or 6-membered heteroaryl. In some embodiments of a compound of Formula (XIII), Ring B is 6-membered heteroaryl. In some embodiments of a compound of Formula (XIII), Ring B is 6-membered pyridyl.

In some embodiments of a compound of Formula (XIII), L is a bond. In some embodiments of a compound of Formula (XIII), L is —C(=O)—.

In some embodiments of a compound of Formula (XIII), L-Ring A is absent.

In some embodiments of a compound of Formula (XIII), Ring A is heterocycloalkyl or heteroaryl; each optionally substituted with one or more R$^A$. In some embodiments of a compound of Formula (XIII), Ring A is a 5-membered heterocycloalkyl or a 5-membered heteroaryl; each optionally substituted with one or more R$^A$. In some embodiments of a compound of Formula (XIII), Ring A is heteroaryl optionally substituted with one or more R$^A$.

In some embodiments of a compound of Formula (XIII), each R$^A$ is independently deuterium, halogen, —CN, —OR$^b$, —NR$^c$R$^d$, —C(=O)R$^a$, —C(=O)OR$^b$, —C(=O)NR$^c$R$^d$, —OC(=O)NR$^c$R$^d$, C$_1$-C$_6$alkyl, C$_1$-C$_6$haloalkyl, or C$_1$-C$_6$deuteroalkyl. In some embodiments of a compound of Formula (XIII), each R$^A$ is independently deuterium, halogen, C$_1$-C$_6$alkyl, C$_1$-C$_6$haloalkyl, or C$_1$-C$_6$deuteroalkyl. In some embodiments of a compound of Formula (XIII), each R$^A$ is independently halogen or C$_1$-C$_6$alkyl. In some embodiments of a compound of Formula (XIII), each R$^A$ is independently C$_1$-C$_6$alkyl.

In some embodiments of a compound of Formula (XIII), the compound is of Formula (XIIIa):

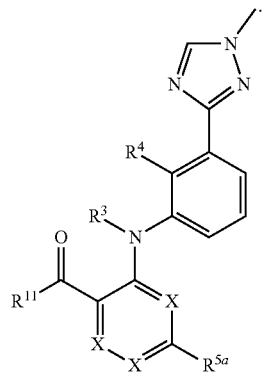

Formula (XIIIa)

In some embodiments of a compound of Formula (XIII), the compound is of Formula (XIIIb):

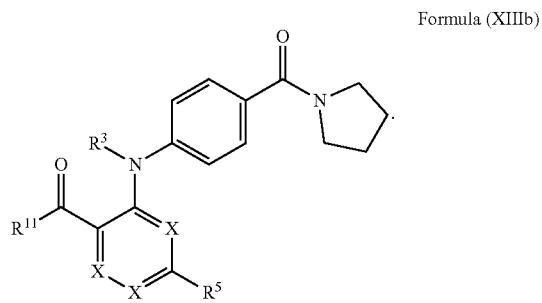

Formula (XIIIb)

In some embodiments of a compound of Formula (XIII), the compound is of Formula (XIIIc):

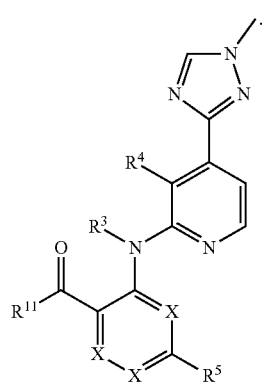

Formula (XIIIc)

In some embodiments of a compound of Formula (XIII), the compound is of Formula (XIIId):

Formula (XIIId)

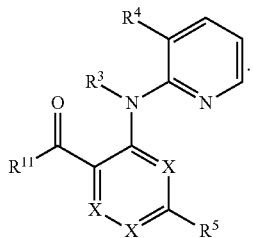

In some embodiments of a compound of Formula (XIII) or (XIIIa)-(XIIId), $R^4$ is hydrogen, deuterium, halogen, —CN, —$OR^b$, —$S(=O)_2R^a$, —$NR^cR^d$, —$C(=O)R^a$, —$C(=O)OR^b$, —$C(=O)NR^cR^d$, $C_1$-$C_6$alkyl, $C_1$-$C_6$haloalkyl, or $C_1$-$C_6$deuteroalkyl. In some embodiments of a compound of Formula (XIII) or (XIIIa)-(XIIId), $R^4$ is hydrogen, deuterium, halogen, —CN, —$OR^b$, —$NR^cR^d$, —$C(=O)R^a$, —$C(=O)OR^b$, —$C(=O)NR^cR^d$, —$OC(=O)NR^cR^d$, $C_1$-$C_6$alkyl, $C_1$-$C_6$haloalkyl, or $C_1$-$C_6$deuteroalkyl. In some embodiments of a compound of Formula (XIII) or (XIIIa)-(XIIId), $R^4$ is hydrogen or —$OR^b$. In some embodiments of a compound of Formula (XIII) or (XIIIa)-(XIIId), $R^4$ is —$OR^b$. In some embodiments of a compound of Formula (XIII) or (XIIIa)-(XIIId), $R^4$ is hydrogen. In some embodiments of a compound of Formula (XIII) or (XIIIa)-(XIIId), $R^4$ is —$P(=O)R^bR^b$. In some embodiments of a compound of Formula (XIII) or (XIIIa)-(XIIId), $R^4$ is —$S(=O)_2R^a$.

In some embodiments of a compound of Formula (XIII) or (XIIIa)-(XIIId), each X is —N—. In some embodiments of a compound of Formula (XIII) or (XIIIa)-(XIIId) each X is —$CR^X$—. In some embodiments of a compound of Formula (XIII) or (XIIIa)-(XIIId), two X are —N— and the other is —$CR^x$—. In some embodiments of a compound of Formula (XIII) or (XIIIa)-(XIIId), one X is —N— and the others are —$CR^X$—. In some embodiments of a compound of Formula (XIII) or (XIIIa)-(XIIId), each X is —CH—. In some embodiments of a compound of Formula (XIII) or (XIIIa)-(XIIId), two X are —N— and the other is —CH—. In some embodiments of a compound of Formula (XIII) or (XIIIa)-(XIIId), one X is —N— and the others are —CH—. In some embodiments of a compound of Formula (XIII) or (XIIIa)-(XIIId),

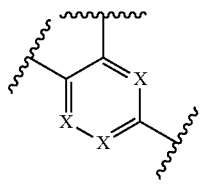

is

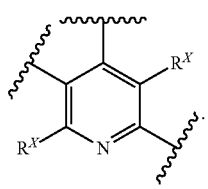

In some embodiments of a compound of Formula (XIII) or (XIIIa)-(XIIId),

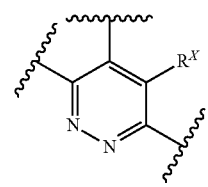

is

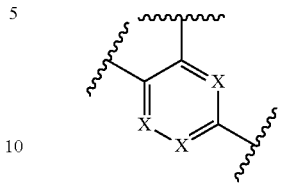

In some embodiments of a compound of Formula (XIII) or (XIIIa)-(XIIId),

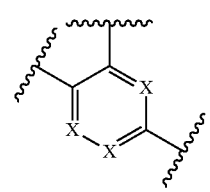

is

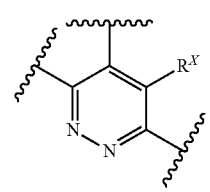 or 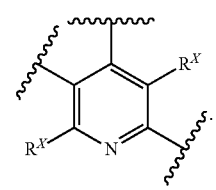

In some embodiments of a compound of Formula (XIII) or (XIIIa)-(XIIId), each $R^X$ is independently hydrogen, deuterium, halogen, —CN, —$OR^b$, —$NR^cR^d$, —$C(=O)R^a$, —$C(=O)OR^b$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound of Formula (XIII) or (XIIIa)-(XIIId), each $R^x$ is independently hydrogen, deuterium, halogen, $C_1$-$C_6$alkyl, $C_1$-$C_6$haloalkyl, or $C_1$-$C_6$deuteroalkyl. In some embodiments of a compound of Formula (XIII) or (XIIIa)-(XIIId), each $R^x$ is independently hydrogen, deuterium, or halogen.

In some embodiments of a compound of Formula (XIII) or (XIIIa)-(XIIId),

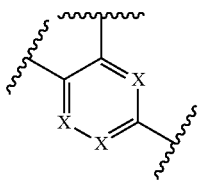

is

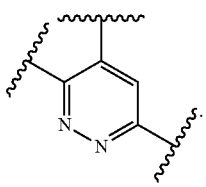

In some embodiments of a compound of Formula (XIII) or (XIIIa)-(XIIId),

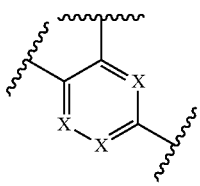

is

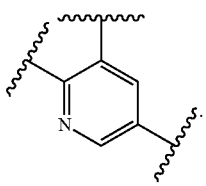 [SMILES: *c1cnc(*)c(*)c1]

In some embodiments of a compound of Formula (XIII) or (XIIIa)-(XIIId),

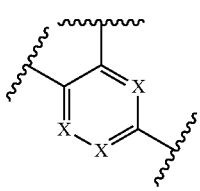

is

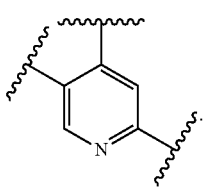 [SMILES: *c1cc(*)c(*)cn1]

In some embodiments of a compound of Formula (XIII) or (XIIIa)-(XIIId), $R^3$ is hydrogen or $C_1$-$C_6$alkyl. In some embodiments of a compound of Formula (XIII) or (XIIIa)-(XIIId), $R^3$ is hydrogen.

In some embodiments of a compound of Formula (XIII) or (XIIIa)-(XIIId), $R^{11}$ is $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, or heteroaryl; wherein each alkyl, cycloalkyl, heterocycloalkyl, aryl, and heteroaryl is independently optionally substituted with one or more $R^{11a}$. In some embodiments of a compound of Formula (XIII) or (XIIIa)-(XIIId), $R^{11}$ is $C_1$-$C_6$alkyl, $C_1$-$C_8$haloalkyl, $C_1$-$C_6$deuteroalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one or more $R^{11a}$. In some embodiments of a compound of Formula (XIII) or (XIIIa)-(XIIId), $R^{11}$ is $C_1$-$C_6$alkyl, $C_1$-$C_8$haloalkyl, $C_1$-$C_6$deuteroalkyl, cycloalkyl, or heterocycloalkyl; wherein each alkyl, cycloalkyl, and heterocycloalkyl is independently optionally substituted with one or more $R^{11a}$. In some embodiments of a compound of Formula (XIII) or (XIIIa)-(XIIId), $R^{11}$ is $C_1$-$C_6$alkyl, $C_1$-$C_6$haloalkyl, or cycloalkyl; wherein each alkyl and cycloalkyl is independently optionally substituted with one or more $R^{11a}$. In some embodiments of a compound of Formula (XIII) or (XIIIa)-(XIIId), $R^{11}$ is $C_1$-$C_6$alkyl or cycloalkyl; wherein each alkyl and cycloalkyl is independently optionally substituted with one or more $R^{11a}$. In some embodiments of a compound of Formula (XIII) or (XIIIa)-(XIIId), $R^{11}$ is $C_1$-$C_6$alkyl, $C_1$-$C_6$deuteroalkyl, $C_1$-$C_6$haloalkyl, or cycloalkyl. In some embodiments of a compound of Formula (XIII) or (XIIIa)-(XIIId), $R^{11}$ is $C_1$-$C_6$alkyl, $C_1$-$C_6$haloalkyl, or cycloalkyl. In some embodiments of a compound of Formula (XIII) or (XIIIa)-(XIIId), $R^{11}$ is $C_1$-$C_6$deuteroalkyl. In some embodiments of a compound of Formula (XIII) or (XIIIa)-(XIIId), $R^{11}$ is $C_1$-$C_6$alkyl. In some embodiments of a compound of Formula (XIII) or (XIIIa)-(XIIId), $R^{11}$ is cycloalkyl.

In some embodiments of a compound of Formula (XIII) or (XIIIa)-(XIIId), each $R^{1a}$ is independently deuterium, halogen, —CN, —$OR^b$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound of Formula (XIII) or (XIIIa)-(XIIId), each $R^{11a}$ is independently deuterium, halogen, —CN, —$OR^b$, —$NR^cR^d$, $C_1$-$C_6$alkyl, $C_1$-$C_6$haloalkyl, $C_1$-$C_6$deuteroalkyl, $C_1$-$C_6$hydroxyalkyl, or $C_1$-$C_6$aminoalkyl. In some embodiments of a compound of Formula (XIII) or (XIIIa)-(XIIId), each $R^{11a}$ is independently deuterium, halogen, —CN, —$OR^b$, —$NR^cR^d$, $C_1$-$C_6$alkyl, $C_1$-$C_6$haloalkyl, or $C_1$-$C_6$deuteroalkyl. In some embodiments of a compound of Formula (XIII) or (XIIIa)-(XIIId), each $R^{11a}$ is independently deuterium, halogen, —CN, —$OR^b$, —$NR^cR^d$, or $C_1$-$C_6$alkyl. In some embodiments of a compound of Formula (XIII) or (XIIIa)-(XIIId), each $R^{11a}$ is independently deuterium, halogen, $C_1$-$C_6$alkyl, $C_1$-$C_6$haloalkyl, or $C_1$-$C_6$deuteroalkyl. In some embodiments of a compound of Formula (XIII) or (XIIIa)-(XIIId), each $R^{11a}$ is independently deuterium, halogen, or $C_1$-$C_6$alkyl.

In some embodiments of a compound of Formula (XIII) or (XIIIa)-(XIIId), $R^5$ is halogen, —CN, —$OR^8$, —$NR^9R^{10}$, —C(=O)$R^7$, —C(=O)$OR^8$, —C(=O)$NR^9R^{10}$, —$NR^8$C(=O)$NR^9R^{10}$, —$NR^8$C(=N—CN)$R^7$, —$NR^8$C(=O)$R^7$, —$NR^8$C(=O)$OR^8$, —NR'S(=O)(=$NR^8$)$R^7$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XIII) or (XIIIa)-(XIIId), R$^5$ is halogen, —CN, —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=N—CN)R$^7$, —NR$^8$C(=O)OR$^8$, —NR'S(=O)(=NR$^8$)R$^7$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XIII) or (XIIIa)-(XIIId), R$^5$ is halogen, —CN, —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=N—CN)R$^7$, —NR$^8$C(=O)OR$^8$, —NR'S(=O)(=NR$^8$)R$^7$, $C_1$-$C_6$alkyl, $C_1$-$C_6$haloalkyl, $C_1$-$C_6$deuteroalkyl, $C_2$-$C_6$alkenyl, $C_2$-$C_6$alkynyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XIII) or (XIIIa)-(XIIId), R$^5$ is —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=N—CN)R$^7$, —NR$^8$C(=O)R$^7$, —NR$^8$C(=O)OR$^8$, —NR'S(=O)(=NR$^8$)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XIII) or (XIIIa)-(XIIId), R$^5$ is —OR$^8$, —NR$^9$R$^{10}$, —C(=O)R$^7$, —C(=O)OR$^8$, —C(=O)NR$^9$R$^{10}$, —NR$^8$C(=O)NR$^9$R$^{10}$, —NR$^8$C(=N—CN)R$^7$, —NR$^8$C(=O)OR$^8$, —NR'S(=O)(=NR$^8$)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl. In some embodiments of a compound of Formula (XIII) or (XIIIa)-(XIIId), R$^5$ is —OR$^8$, —NR$^9$R$^{10}$, —NR$^8$C(=O)R$^7$, —NR$^8$C(=N—CN)R$^7$, —NR'S(=O)(=NR$^8$)R$^7$, or aryl optionally substituted with one or more deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XIII) or (XIIIa)-(XIIId), R$^5$ is —OR$^8$, —NR$^9$R$^{10}$, —NR$^8$C(=N—CN)R$^7$, —NR'S(=O)(=NR$^8$)R$^7$, or aryl optionally substituted with one or more deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XIII) or (XIIIa)-(XIIId), R$^5$ is —OR$^8$, —NR$^9$R$^{10}$, —NR$^8$C(=O)R$^7$, cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl. In some embodiments of a compound of Formula (XIII) or (XIIIa)-(XIIId), R$^5$ is —NR$^8$C(=O)R$^7$. In some embodiments of a compound of Formula (XIII) or (XIIIa)-(XIIId), R$^5$ is aryl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XIII) or (XIIIa)-(XIIId), R$^5$ is —NR$^9$R$^{10}$, —NR$^8$C(=O)NR$^9$R$^{10}$, or —NR$^8$C(=N—CN)R$^7$.

In some embodiments of a compound of Formula (XIII) or (XIIIa)-(XIIId), R$^5$ is —NR$^9$R$^{10}$.

In some embodiments of a compound of Formula (XIII) or (XIIIa)-(XIIId), R$^5$ is —NR$^9$R$^{10}$ or —NR$^8$C(=O)NR$^9$R$^{10}$.

In some embodiments of a compound of Formula (XIII) or (XIIIa)-(XIIId), R$^8$ is —NR$^8$C(=N—CN)R$^7$.

In some embodiments of a compound of Formula (XIII) or (XIIIa)-(XIIId), R$^5$ is —NR'S(=O)(=NR$^8$)R$^7$.

In some embodiments of a compound of Formula (XIII) or (XIIIa)-(XIIId), R$^5$ is —NR$^8$C(=O)NR$^9$R$^{10}$ or —NR$^8$C(=O)R$^7$.

In some embodiments of a compound of Formula (XIII) or (XIIIa)-(XIIId), R$^5$ is —NR$^8$C(=O)NR$^9$R$^{10}$.

In some embodiments of a compound of Formula (XIII) or (XIIIa)-(XIIId), R$^8$ is —NR$^8$C(=O)R$^7$.

In some embodiments of a compound of Formula (XIII) or (XIIIa)-(XIIId), R$^5$ is —NR$^8$C(=O)NR$^9$R$^{10}$ or heterocycloalkyl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XIII) or (XIIIa)-(XIIId), R$^5$ is heterocycloalkyl optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), $C_1$-$C_6$alkyl(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(=O)R$^a$, —C(=O)OR$^b$, —C(=O)NR$^c$R$^d$, $C_1$-$C_6$alkyl, or $C_1$-$C_6$haloalkyl.

In some embodiments of a compound of Formula (XIII) or (XIIIa)-(XIIId), R$^5$ is heterocycloalkyl optionally substituted with one or more oxo, deuterium, halogen, —CN, —OR$^b$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), or $C_1$-$C_6$alkyl(heterocycloalkyl); wherein each alkyl, alkenyl, alkynyl, cycloalkyl, heterocycloalkyl, aryl, and heteroaryl is independently optionally substituted with one or more oxo, deuterium, halogen, —CN, —OR$^b$, —NR$^c$R$^d$, —C(═O)R$^a$, —C(═O)OR$^b$, —C(═O)NR$^c$R$^d$, C$_1$-C$_6$alkyl, or C$_1$-C$_6$haloalkyl.

In some embodiments of a compound of Formula (XIII) or (XIIIa)-(XIIId), R$^5$ is heterocycloalkyl optionally substituted with one or more oxo, halogen, —OR$^b$, C$_1$-C$_6$alkyl, C$_1$-C$_6$haloalkyl, C$_1$-C$_6$deuteroalkyl, C$_1$-C$_6$heteroalkyl, C$_1$-C$_6$hydroxyalkyl, C$_1$-C$_6$aminoalkyl, C$_1$-C$_6$heteroalkyl, C$_2$-C$_8$alkynyl, cycloalkyl, heterocycloalkyl, aryl, C$_1$-C$_6$alkyl(cycloalkyl), or C$_1$-C$_6$alkyl(heterocycloalkyl); wherein each alkyl, alkynyl, cycloalkyl, heterocycloalkyl, and aryl is independently optionally substituted with one or more oxo, deuterium, halogen, —CN, —OR$^b$, —NR$^c$R$^d$, —C(═O)R$^a$, —C(═O)OR$^b$, —C(═O)NR$^c$R$^d$, C$_1$-C$_6$alkyl, or C$_1$-C$_6$haloalkyl.

In some embodiments of a compound of Formula (XIII) or (XIIIa)-(XIIId), the heterocycloalkyl of R$^5$ is

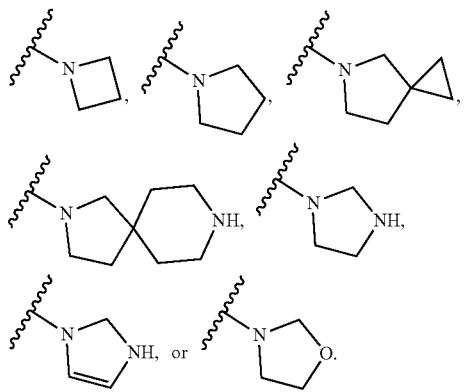

In some embodiments of a compound of Formula (XIII) or (XIIIa)-(XIIId), the heterocycloalkyl of R$^5$ is

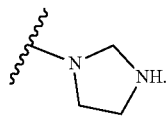 [SMILES: *N1CCNC1]

In some embodiments of a compound of Formula (XIII) or (XIIIa)-(XIIId), R$^7$ is C$_1$-C$_6$alkyl, C$_1$-C$_6$haloalkyl, C$_1$-C$_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl. In some embodiments of a compound of Formula (XIII) or (XIIIa)-(XIIId), R$^7$ is C$_1$-C$_6$alkyl, cycloalkyl, or heterocycloalkyl; wherein each alkyl, cycloalkyl, or heterocycloalkyl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl. In some embodiments of a compound of Formula (XIII) or (XIIIa)-(XIIId), R$^7$ is C$_1$-C$_6$alkyl, C$_1$-C$_6$haloalkyl, C$_1$-C$_6$deuteroalkyl, or cycloalkyl; wherein each alkyl and cycloalkyl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl. In some embodiments of a compound of Formula (XIII) or (XIIIa)-(XIIId), R$^7$ is C$_1$-C$_6$alkyl or cycloalkyl; wherein each alkyl and cycloalkyl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl. In some embodiments of a compound of Formula (XIII) or (XIIIa)-(XIIId), R$^7$ is cycloalkyl optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl. In some embodiments of a compound of Formula (XIII) or (XIIIa)-(XIIId), R$^7$ is unsubstituted cycloalkyl. In some embodiments of a compound of Formula (XIII) or (XIIIa)-(XIIId), R$^7$ is heterocycloalkyl optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl. In some embodiments of a compound of Formula (XIII) or (XIIIa)-(XIIId), R$^7$ is unsubstituted heterocycloalkyl.

In some embodiments of a compound of Formula (XIII) or (XIIIa)-(XIIId), R$^8$ is hydrogen, CN, C$_1$-C$_6$alkyl, C$_1$-C$_6$haloalkyl, C$_1$-C$_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl. In some embodiments of a compound of Formula (XIII) or (XIIIa)-(XIIId), R$^8$ is hydrogen, CN, C$_1$-C$_6$alkyl, C$_1$-C$_6$haloalkyl, C$_1$-C$_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl.

In some embodiments of a compound of Formula (XIII) or (XIIIa)-(XIIId), R$^9$ and R$^{10}$ are independently hydrogen, C$_1$-C$_6$alkyl, C$_1$-C$_6$haloalkyl, C$_1$-C$_6$deuteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, C$_1$-C$_6$deuteroalkyl, C$_1$-C$_6$haloalkyl, or C$_1$-C$_6$hydroxyalkyl. In some embodiments of a compound of Formula (XIII) or (XIIIa)-(XIIId), R$^9$ and R$^{10}$ are independently hydrogen, C$_1$-C$_6$alkyl, C$_1$-C$_6$haloalkyl, C$_1$-C$_6$deuteroalkyl, or cycloalkyl; wherein each alkyl, cycloalkyl, and heterocycloalkyl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, C$_1$-C$_6$deuteroalkyl, C$_1$-C$_6$haloalkyl, or C$_1$-C$_6$hydroxyalkyl.

In some embodiments of a compound of Formula (XIII) or (XIIIa)-(XIIId), R$^9$ and R$^{10}$ are taken together with the nitrogen atom to which they are attached to form a heterocycloalkyl optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl. In some embodiments of a compound of Formula (XIII) or (XIIIa)-(XIIId), R$^9$ and R$^{10}$ are taken together with the nitrogen atom to which they are attached to form a C$_2$-C$_8$heterocycloalkyl optionally substituted with one or more oxo, deuterium, halogen, —CN, —OH,—OMe, —NH$_2$, —C(═O)Me, —C(═O)OH, —C(═O)OMe, C$_1$-C$_6$alkyl, or C$_1$-C$_6$haloalkyl. In some embodiments of a compound of Formula (XIII) or (XIIIa)-(XIIId), R$^9$ and R$^{10}$ are taken together with the nitrogen atom to which they are attached to form a bicyclic heterocycloalkyl or a spiro heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound of Formula (XIII) or (XIIIa)-(XIIId), R$^9$ and R$^{10}$ are taken together with the nitrogen atom to which they are attached to form a heterocycloalkyl selected from aziridinyl, azetidinyl, pyrrolidinyl, piperidinyl, 2-azabicyclo[1.1.1]pentanyl, or 2-azaspiro[3.3]heptanyl, each optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound described above, each R$^a$ is independently C$_1$-C$_6$alkyl, C$_1$-C$_6$haloalkyl, C$_1$-C$_6$deuteroalkyl, or cycloalkyl; wherein each alkyl and cycloalkyl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound described above, each R$^a$ is independently C$_1$-C$_6$alkyl, C$_1$-C$_6$haloalkyl, or C$_1$-C$_6$deuteroalkyl. In some embodiments of a compound described above, each R$^a$ is independently C$_1$-C$_6$alkyl.

In some embodiments of a compound described above, each R$^b$ is independently hydrogen, C$_1$-C$_6$alkyl, C$_1$-C$_6$haloalkyl, C$_1$-C$_6$deuteroalkyl, or cycloalkyl; wherein each alkyl and cycloalkyl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound described above, each R$^b$ is independently hydrogen, C$_1$-C$_6$alkyl, C$_1$-C$_6$haloalkyl, or C$_1$-C$_6$deuteroalkyl. In some embodiments of a compound described above, each R$^b$ is independently C$_1$-C$_6$alkyl or C$_1$-C$_6$deuteroalkyl. In some embodiments of a compound described above, each R$^b$ is independently hydrogen or C$_1$-C$_6$alkyl. In some embodiments of a compound described above, each R$^b$ is hydrogen. In some embodiments of a compound described above, each R$^b$ is independently C$_1$-C$_6$alkyl.

In some embodiments of a compound described above, each R$^c$ and R$^d$ is independently hydrogen, C$_1$-C$_6$alkyl, C$_1$-C$_6$haloalkyl, C$_1$-C$_6$deuteroalkyl, or cycloalkyl; wherein each alkyl and cycloalkyl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl. In some embodiments of a compound described above, each R$^c$ and R$^d$ is independently hydrogen, C$_1$-C$_6$alkyl, C$_1$-C$_6$haloalkyl, or C$_1$-C$_6$deuteroalkyl. In some embodiments of a compound described above, each R$^c$ and R$^d$ is independently hydrogen or C$_1$-C$_6$alkyl. In some embodiments of a compound described above, each R$^c$ and R$^d$ is hydrogen. In some embodiments of a compound described above, each R$^c$ and R$^d$ is independently C$_1$-C$_6$alkyl.

Disclosed herein is a compound, or a pharmaceutically acceptable salt, solvate, or stereoisomer thereof, selected from the group consisting of:

| Ex. | Structure |
|---|---|
| 1 | 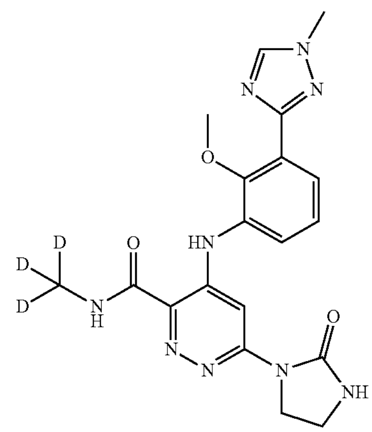 [SMILES: [2H]C([2H])([2H])NC(=O)c1nnc(N2CCNC2=O)cc1Nc1cccc(-c2ncn(C)n2)c1OC] |
| 2 | 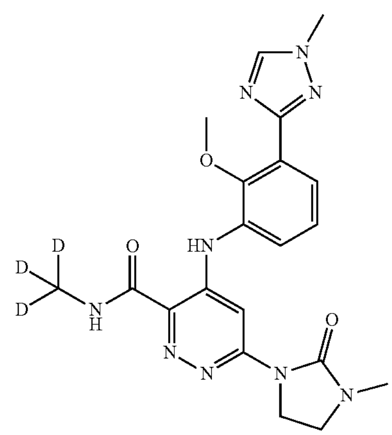 [SMILES: [2H]C([2H])([2H])NC(=O)c1nnc(N2CCN(C)C2=O)cc1Nc1cccc(-c2ncn(C)n2)c1OC] |
| 3 | 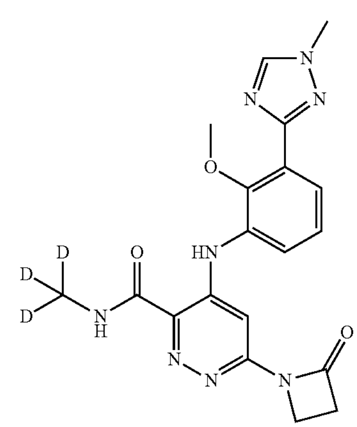 [SMILES: [2H]C([2H])([2H])NC(=O)c1nnc(N2CCC2=O)cc1Nc1cccc(-c2ncn(C)n2)c1OC] |

-continued
| Ex. | Structure |
|---|---|
| 4 | 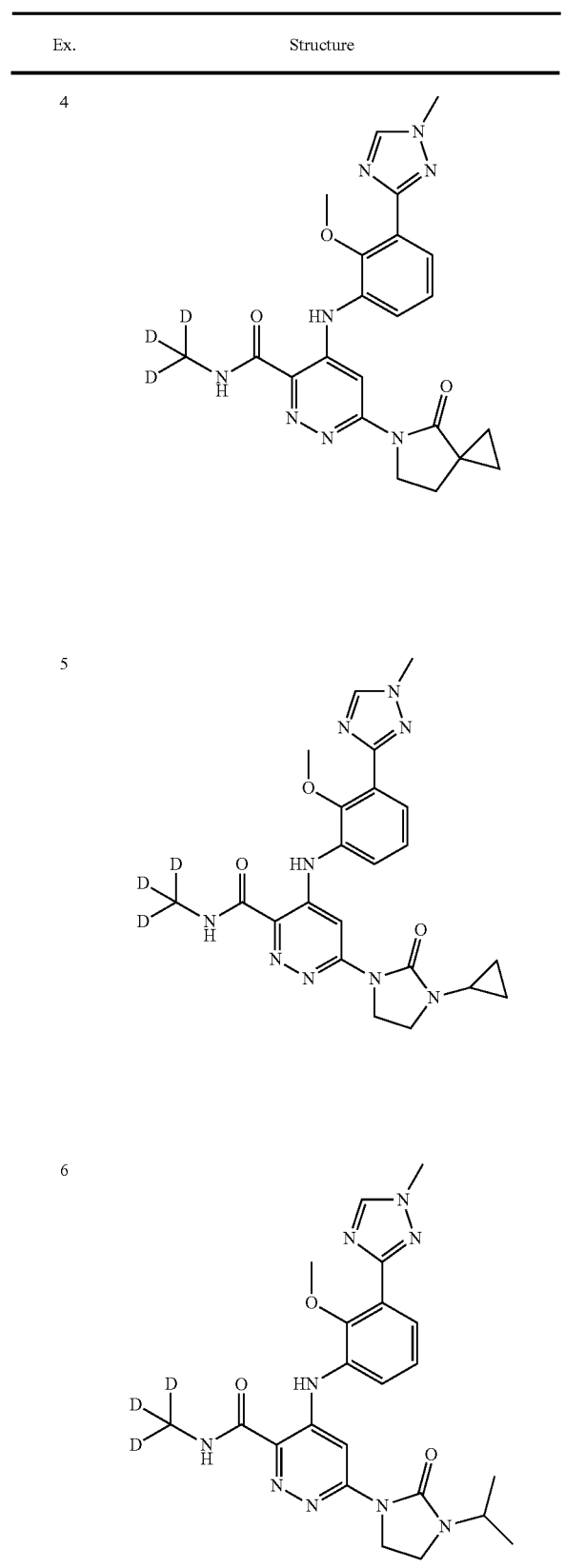 |
| 5 | 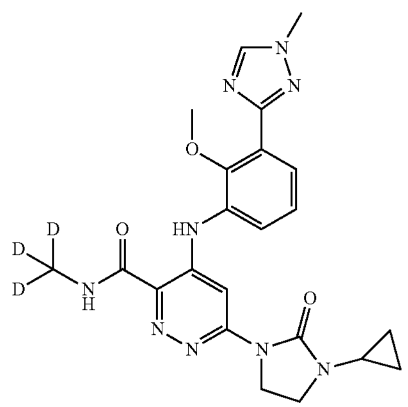 [SMILES: [2H]C([2H])([2H])NC(=O)c1nnc(N2CCN(C3CC3)C2=O)cc1Nc1cccc(-c2ncn(C)n2)c1OC] |
| 6 | 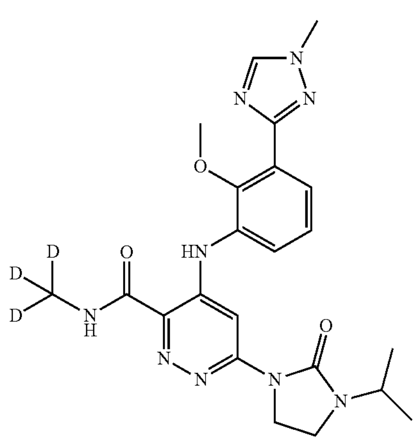 [SMILES: [2H]C([2H])([2H])NC(=O)c1nnc(N2CCN(C(C)C)C2=O)cc1Nc1cccc(-c2ncn(C)n2)c1OC] |
-continued
| Ex. | Structure |
|---|---|
| 7 | 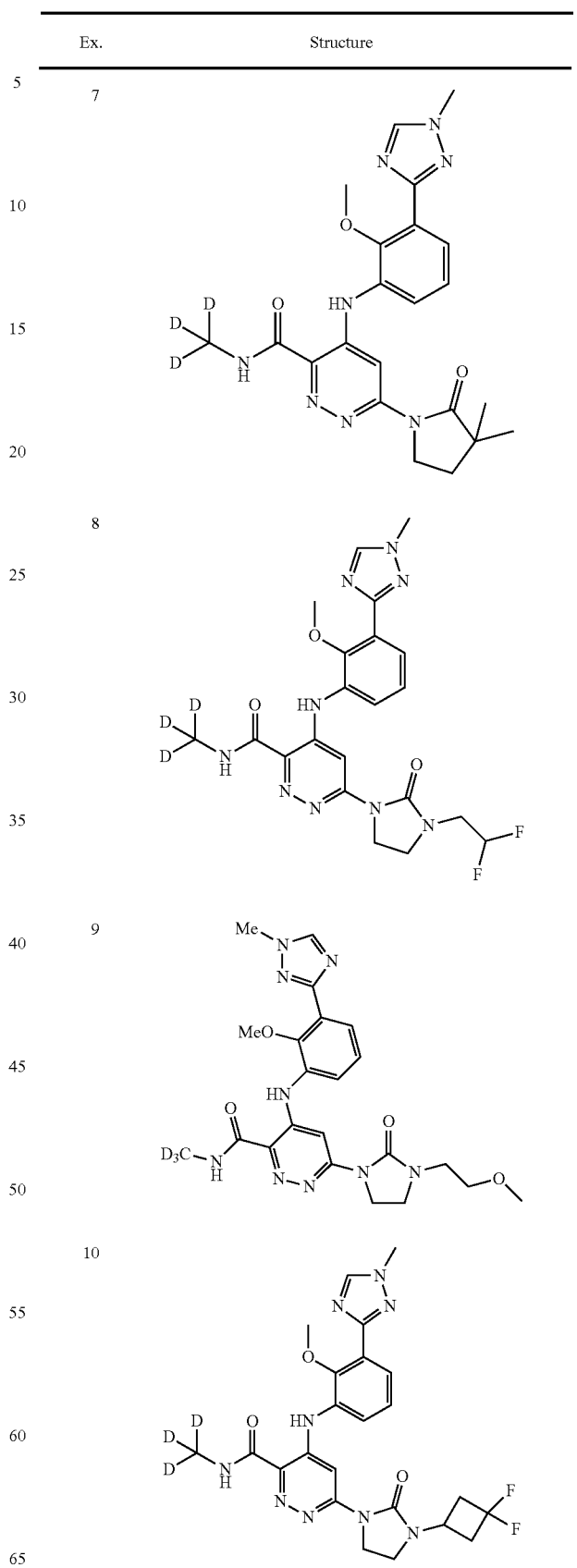 |
| 8 | 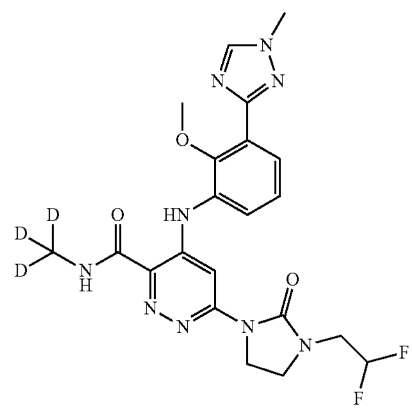 [SMILES: [2H]C([2H])([2H])NC(=O)c1nnc(N2CCN(CC(F)F)C2=O)cc1Nc1cccc(-c2ncn(C)n2)c1OC] |
| 9 | 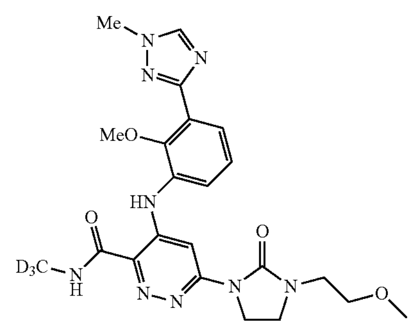 [SMILES: [2H]C([2H])([2H])NC(=O)c1nnc(N2CCN(CCOC)C2=O)cc1Nc1cccc(-c2ncn(C)n2)c1OC] |
| 10 | 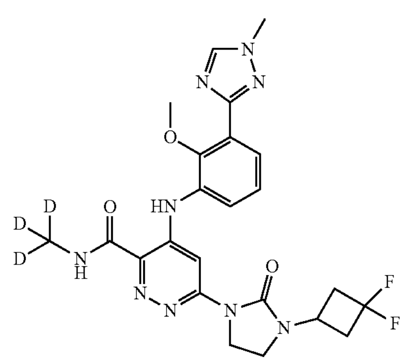 [SMILES: [2H]C([2H])([2H])NC(=O)c1nnc(N2CCN(C3CC(F)(F)C3)C2=O)cc1Nc1cccc(-c2ncn(C)n2)c1OC] |

| Ex. | Structure |
|---|---|
| 11 | (structure) |
| 12 | (structure) |
| 13 | (structure) |
| 14 | (structure) |
| 15 | (structure) |
| 16 | (structure) |

| Ex. | Structure |
|---|---|
| 17 | (structure) |
| 18 | (structure) |
| 19 | (structure) |
| 20 | (structure) |
| 21 | (structure) |
| 22 | (structure) |
| 23 | (structure) |

-continued
| Ex. | Structure |
|---|---|
| 24 | 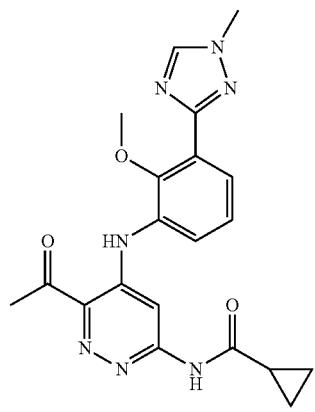 [SMILES: COc1c(Nc2cc(NC(=O)C3CC3)nnc2C(C)=O)cccc1-c1ncn(C)n1] |
| 25 | 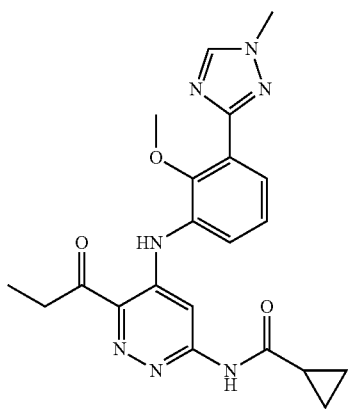 [SMILES: CCC(=O)c1nnc(NC(=O)C2CC2)cc1Nc1cccc(-c2ncn(C)n2)c1OC] |
| 26 | 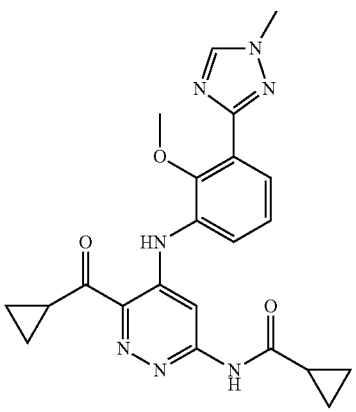 [SMILES: COc1c(Nc2cc(NC(=O)C3CC3)nnc2C(=O)C2CC2)cccc1-c1ncn(C)n1] |
-continued
| Ex. | Structure |
|---|---|
| 27 | 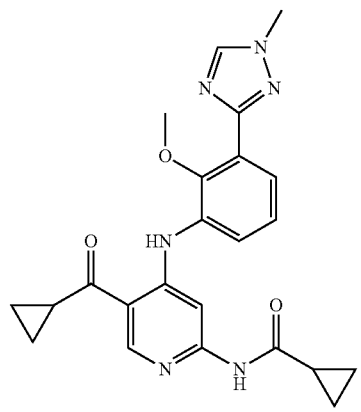 [SMILES: COc1c(Nc2cc(NC(=O)C3CC3)ncc2C(=O)C2CC2)cccc1-c1ncn(C)n1] |
| 28 | 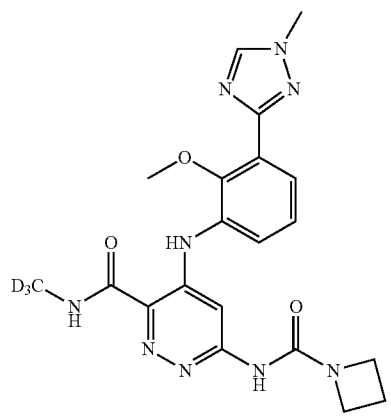 [SMILES: [2H]C([2H])([2H])NC(=O)c1nnc(NC(=O)N2CCC2)cc1Nc1cccc(-c2ncn(C)n2)c1OC] |
| 29 | 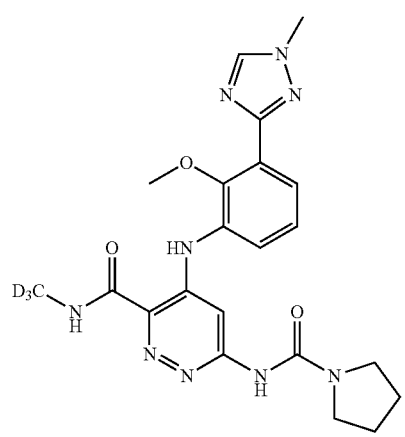 [SMILES: [2H]C([2H])([2H])NC(=O)c1nnc(NC(=O)N2CCCC2)cc1Nc1cccc(-c2ncn(C)n2)c1OC] |

| Ex. | Structure |
|---|---|
| 30 | 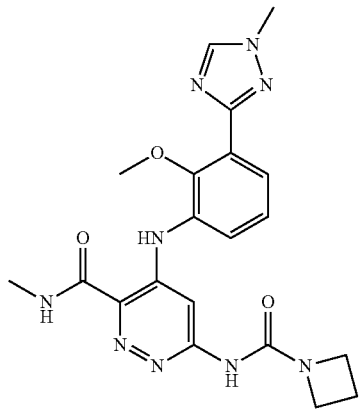 [SMILES: CNC(=O)c1nnc(NC(=O)N2CCC2)cc1Nc1cccc(-c2ncn(C)n2)c1OC] |
| 31 | 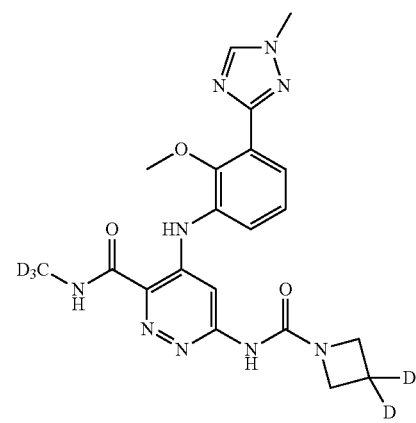 [SMILES: [2H]C1([2H])CN(C(=O)Nc2cc(Nc3cccc(-c4ncn(C)n4)c3OC)c(C(=O)NC([2H])([2H])[2H])nn2)C1] |
| 32 | 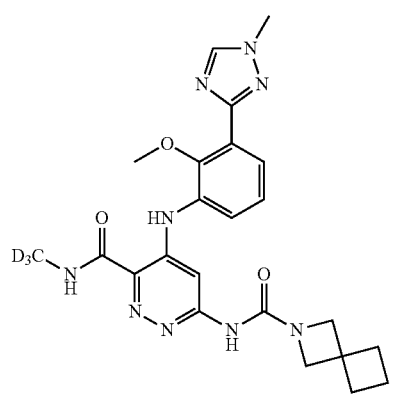 [SMILES: [2H]C([2H])([2H])NC(=O)c1nnc(NC(=O)N2CC3(CCC3)C2)cc1Nc1cccc(-c2ncn(C)n2)c1OC] |
| Ex. | Structure |
|---|---|
| 33 | 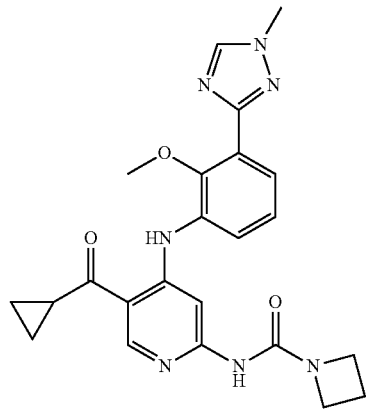 [SMILES: COc1c(Nc2cc(NC(=O)N3CCC3)ncc2C(=O)C2CC2)cccc1-c1ncn(C)n1] |
| 34 | 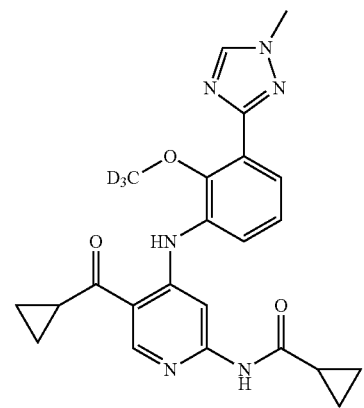 [SMILES: [2H]C([2H])([2H])Oc1c(Nc2cc(NC(=O)C3CC3)ncc2C(=O)C2CC2)cccc1-c1ncn(C)n1] |
| 35 | 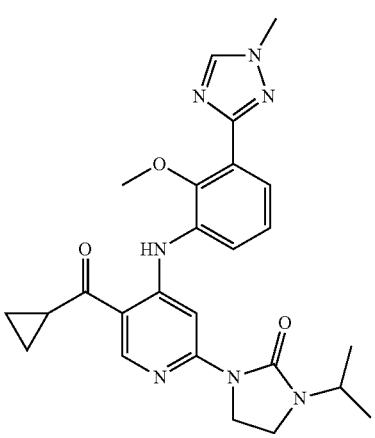 [SMILES: COc1c(Nc2cc(N3CCN(C(C)C)C3=O)ncc2C(=O)C2CC2)cccc1-c1ncn(C)n1] |

| Ex. | Structure |
|---|---|
| 36 | 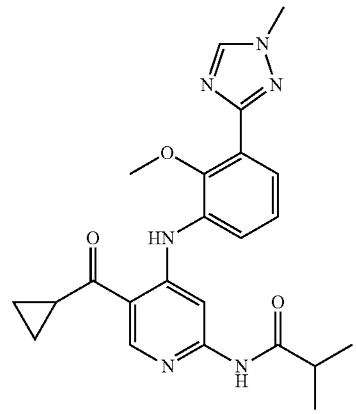 [SMILES: COc1c(Nc2cc(NC(=O)C(C)C)ncc2C(=O)C2CC2)cccc1-c1ncn(C)n1] |
| 37 | 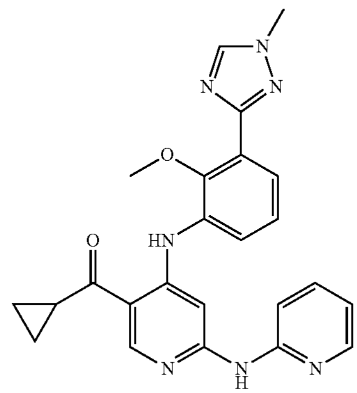 [SMILES: COc1c(Nc2cc(Nc3ccccn3)ncc2C(=O)C2CC2)cccc1-c1ncn(C)n1] |
| 38 | 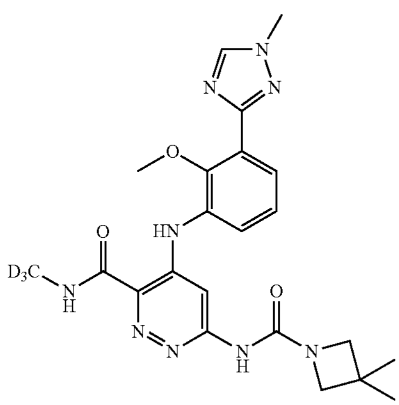 [SMILES: [2H]C([2H])([2H])NC(=O)c1nnc(NC(=O)N2CC(C)(C)C2)cc1Nc1cccc(-c2ncn(C)n2)c1OC] |
| 39 | 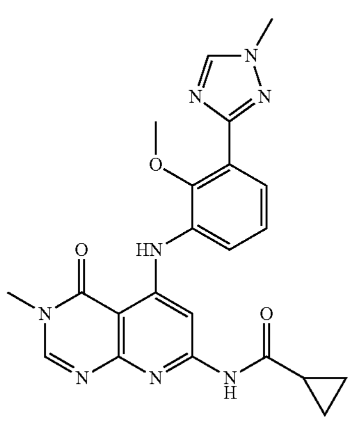 [SMILES: COc1c(Nc2cc(NC(=O)C3CC3)nc3ncn(C)c(=O)c23)cccc1-c1ncn(C)n1] |
| 40 | |
| 41 | |
| 42 | |

| Ex. | Structure |
|---|---|
| 43 | 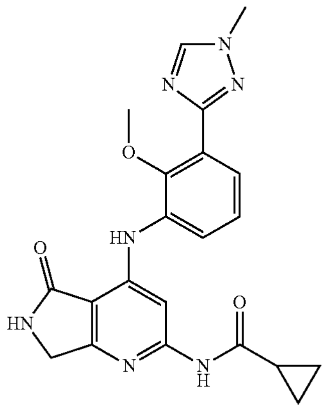 [SMILES: COc1c(Nc2cc(NC(=O)C3CC3)nc3c2C(=O)NC3)cccc1-c1ncn(C)n1] |
| 44 | 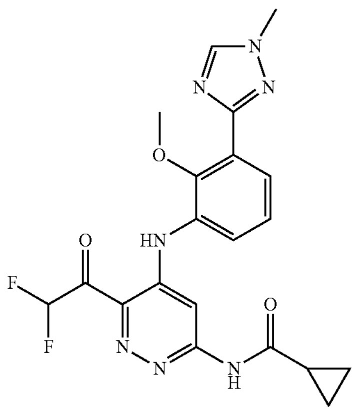 [SMILES: COc1c(Nc2cc(NC(=O)C3CC3)nnc2C(=O)C(F)F)cccc1-c1ncn(C)n1] |
| 45 | 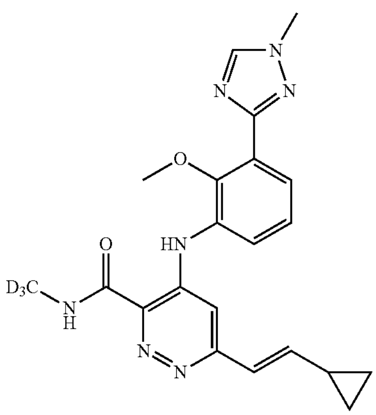 [SMILES: [2H]C([2H])([2H])NC(=O)c1nnc(/C=C/C2CC2)cc1Nc1cccc(-c2ncn(C)n2)c1OC] |
| 46 | 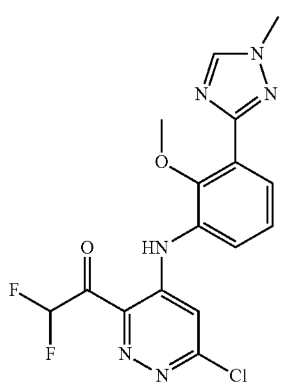 [SMILES: COc1c(Nc2cc(Cl)nnc2C(=O)C(F)F)cccc1-c1ncn(C)n1] |
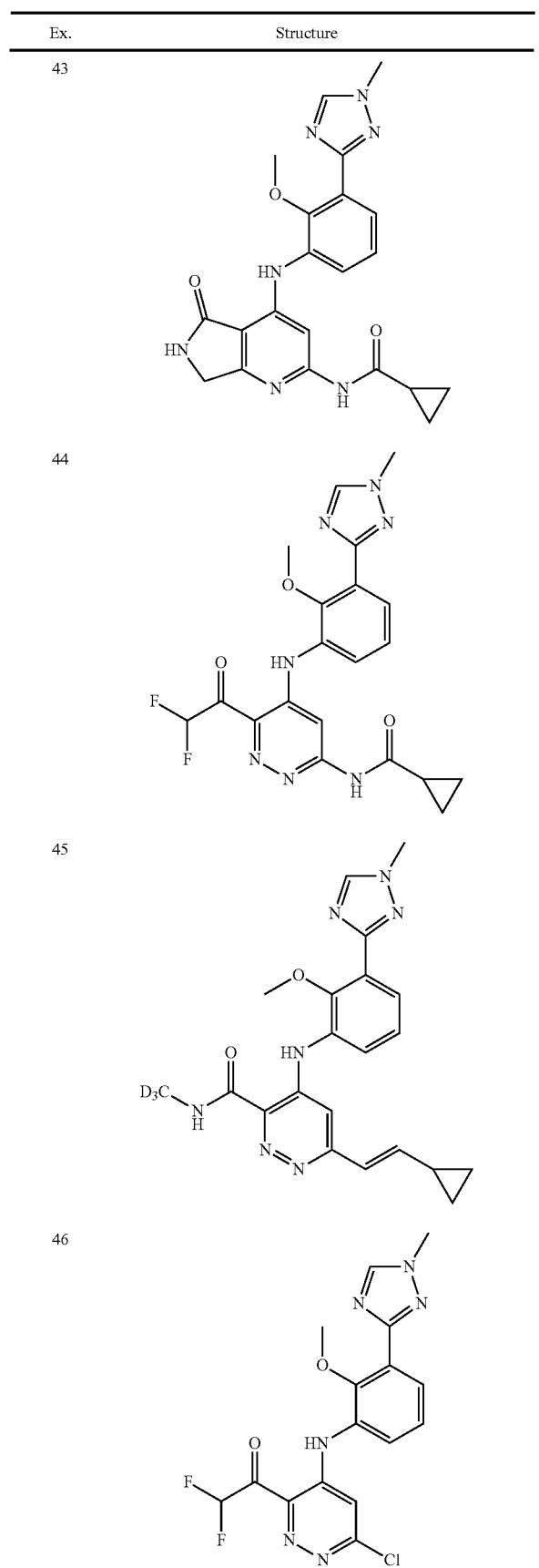
| Ex. | Structure |
|---|---|
| 47 | 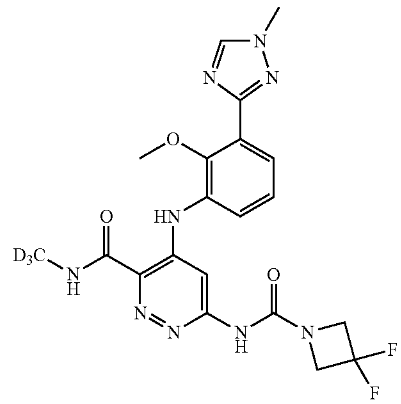 [SMILES: [2H]C([2H])([2H])NC(=O)c1nnc(NC(=O)N2CC(F)(F)C2)cc1Nc1cccc(-c2ncn(C)n2)c1OC] |
| 48 | 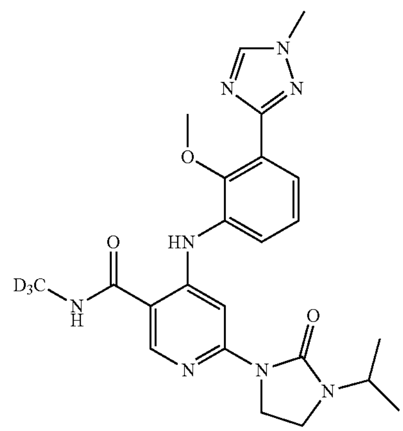 [SMILES: [2H]C([2H])([2H])NC(=O)c1cnc(N2CCN(C(C)C)C2=O)cc1Nc1cccc(-c2ncn(C)n2)c1OC] |
| 49 | 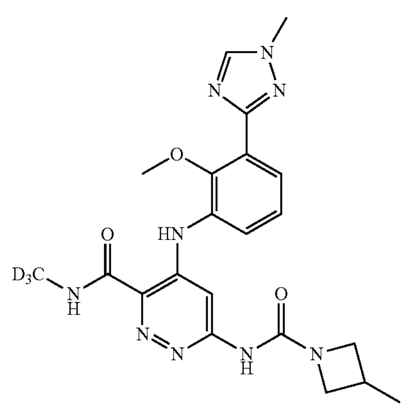 [SMILES: [2H]C([2H])([2H])NC(=O)c1nnc(NC(=O)N2CC(C)C2)cc1Nc1cccc(-c2ncn(C)n2)c1OC] |
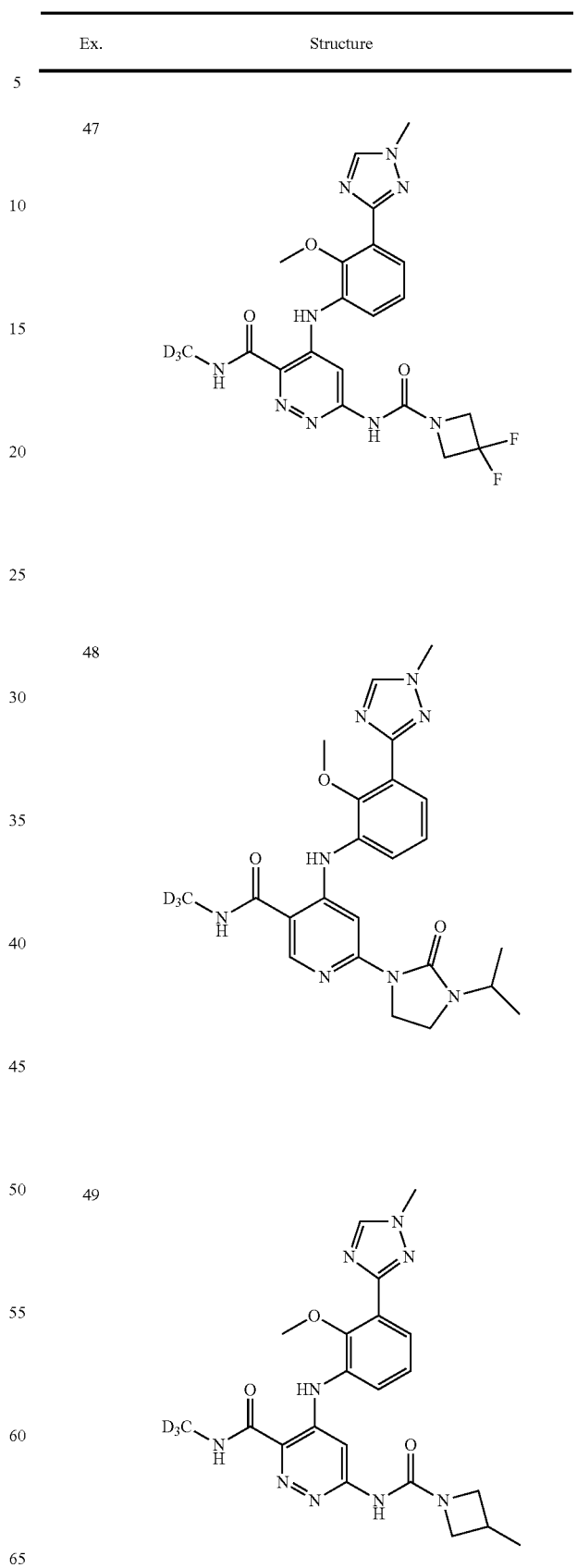

| Ex. | Structure |
|---|---|
| 50 | 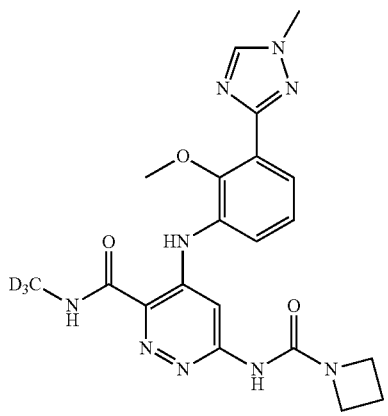 [SMILES: [2H]C([2H])([2H])NC(=O)c1nnc(NC(=O)N2CCC2)cc1Nc1cccc(-c2ncn(C)n2)c1OC] |
| 51 | 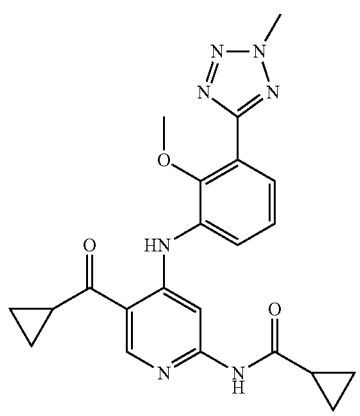 [SMILES: COc1c(Nc2cc(NC(=O)C3CC3)ncc2C(=O)C2CC2)cccc1-c1nnn(C)n1] |
| 52 | 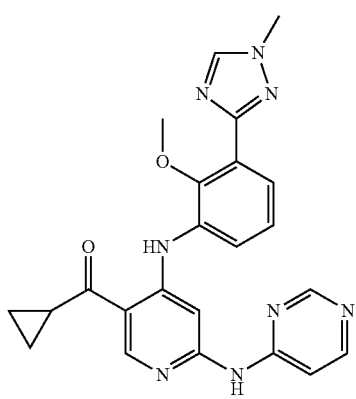 [SMILES: COc1c(Nc2cc(Nc3ccncn3)ncc2C(=O)C2CC2)cccc1-c1ncn(C)n1] |
| 53 | 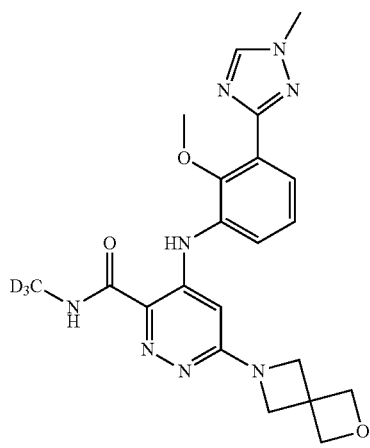 [SMILES: [2H]C([2H])([2H])NC(=O)c1nnc(N2CC3(COC3)C2)cc1Nc1cccc(-c2ncn(C)n2)c1OC] |
| 54 | 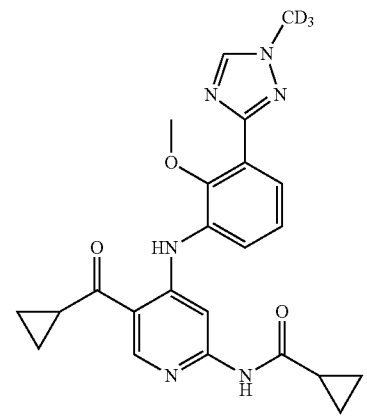 [SMILES: [2H]C([2H])([2H])n1cnc(-c2cccc(Nc3cc(NC(=O)C4CC4)ncc3C(=O)C3CC3)c2OC)n1] |
| 55 | 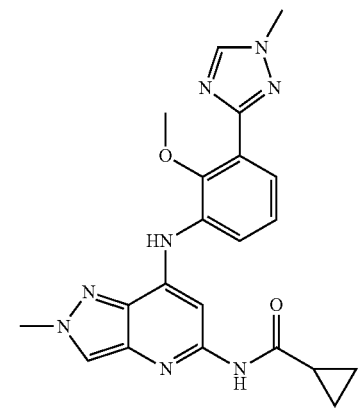 [SMILES: COc1c(Nc2cc(NC(=O)C3CC3)nc3cn(C)nc23)cccc1-c1ncn(C)n1] |

| Ex. | Structure |
|---|---|
| 56 | 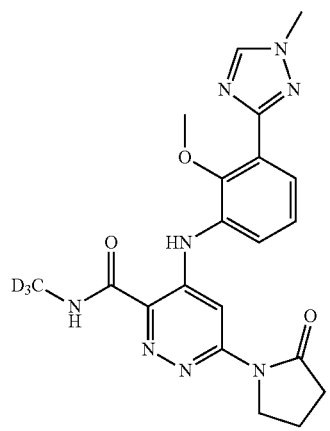 [SMILES: [2H]C([2H])([2H])NC(=O)c1nnc(N2CCCC2=O)cc1Nc1cccc(-c2ncn(C)n2)c1OC] |
| 57 | 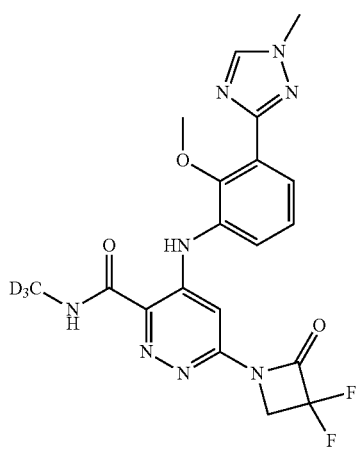 [SMILES: [2H]C([2H])([2H])NC(=O)c1nnc(N2CC(F)(F)C2=O)cc1Nc1cccc(-c2ncn(C)n2)c1OC] |
| 58 | 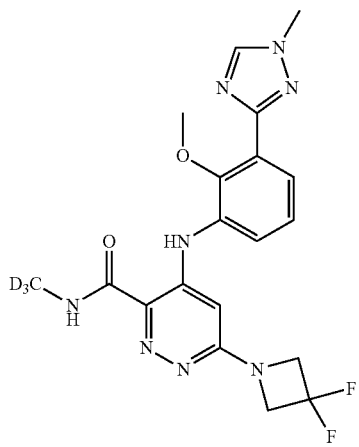 [SMILES: [2H]C([2H])([2H])NC(=O)c1nnc(N2CC(F)(F)C2)cc1Nc1cccc(-c2ncn(C)n2)c1OC] |
| Ex. | Structure |
|---|---|
| 59 | 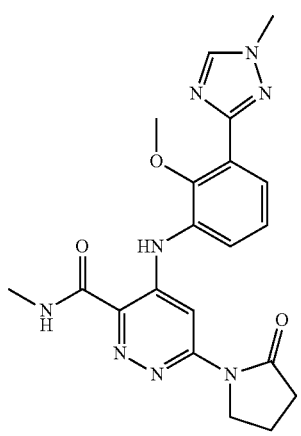 [SMILES: CNC(=O)c1nnc(N2CCCC2=O)cc1Nc1cccc(-c2ncn(C)n2)c1OC] |
| 60 | 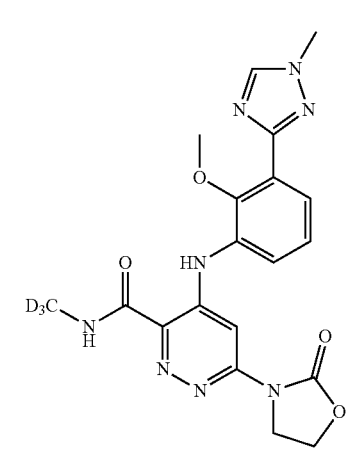 [SMILES: [2H]C([2H])([2H])NC(=O)c1nnc(N2CCOC2=O)cc1Nc1cccc(-c2ncn(C)n2)c1OC] |
| 61 | 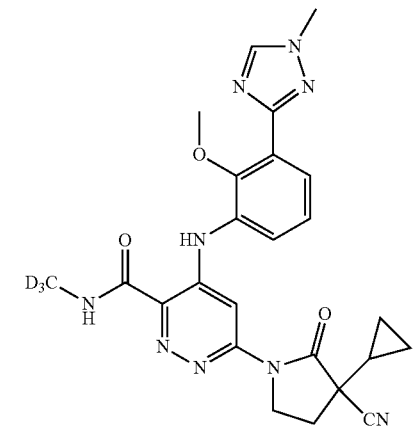 [SMILES: [2H]C([2H])([2H])NC(=O)c1nnc(N2CCC(C#N)(C3CC3)C2=O)cc1Nc1cccc(-c2ncn(C)n2)c1OC] |

-continued

| Ex. | Structure |
|---|---|
| 62 | 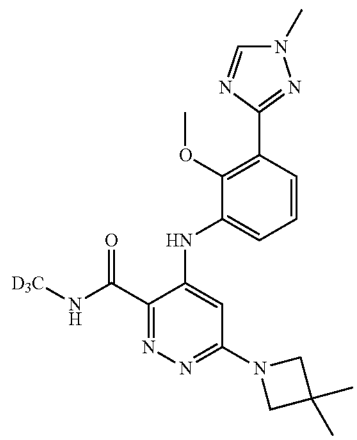 [SMILES: [2H]C([2H])([2H])NC(=O)c1nnc(N2CC(C)(C)C2)cc1Nc1cccc(-c2ncn(C)n2)c1OC] |
| 63 | 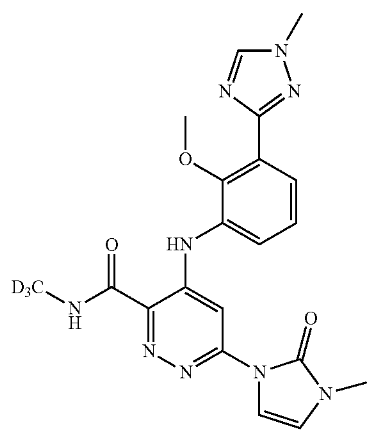 [SMILES: [2H]C([2H])([2H])NC(=O)c1nnc(-n2ccn(C)c2=O)cc1Nc1cccc(-c2ncn(C)n2)c1OC] |
| 64 | 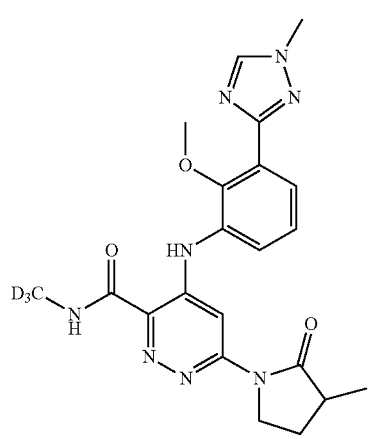 [SMILES: [2H]C([2H])([2H])NC(=O)c1nnc(N2CCC(C)C2=O)cc1Nc1cccc(-c2ncn(C)n2)c1OC] |

-continued

| Ex. | Structure |
|---|---|
| 65 | 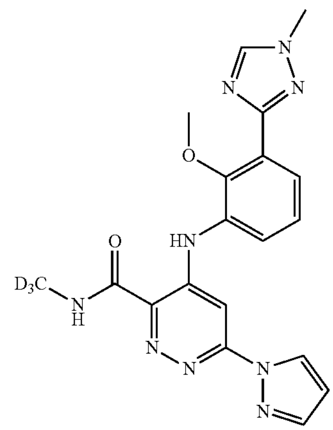 [SMILES: [2H]C([2H])([2H])NC(=O)c1nnc(-n2cccn2)cc1Nc1cccc(-c2ncn(C)n2)c1OC] |
| 66 | 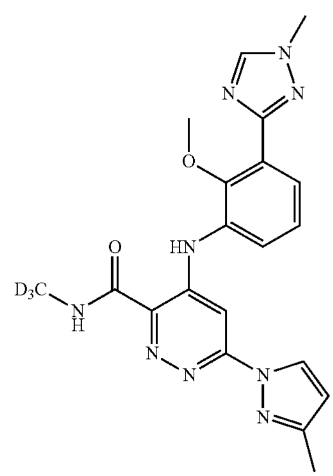 [SMILES: [2H]C([2H])([2H])NC(=O)c1nnc(-n2ccc(C)n2)cc1Nc1cccc(-c2ncn(C)n2)c1OC] |
| 67 | 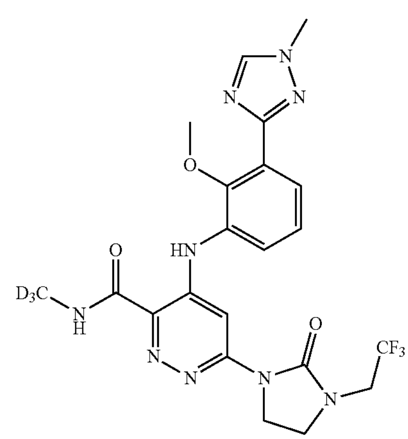 [SMILES: [2H]C([2H])([2H])NC(=O)c1nnc(N2CCN(CC(F)(F)F)C2=O)cc1Nc1cccc(-c2ncn(C)n2)c1OC] |

| Ex. | Structure |
|---|---|
| 68 | |
| 69 | |
| 70 | |
| 71 | 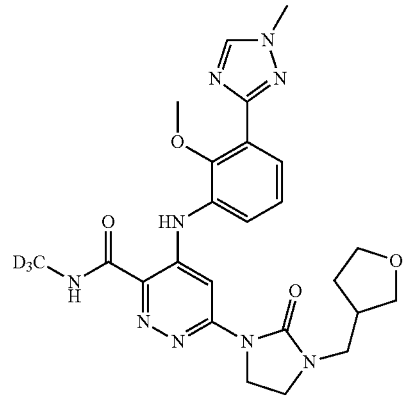 [SMILES: [2H]C([2H])([2H])NC(=O)c1nnc(N2CCN(CC3CCOC3)C2=O)cc1Nc1cccc(-c2ncn(C)n2)c1OC] |
| 72 | 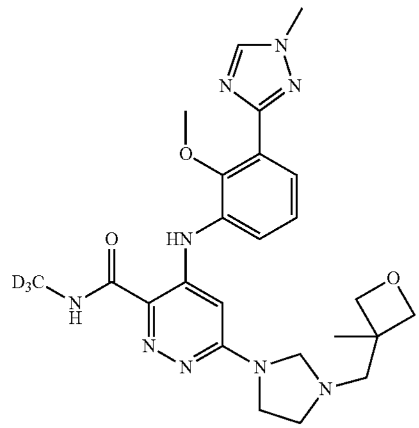 [SMILES: [2H]C([2H])([2H])NC(=O)c1nnc(N2CCN(CC3(C)COC3)C2)cc1Nc1cccc(-c2ncn(C)n2)c1OC] |
| 73 | 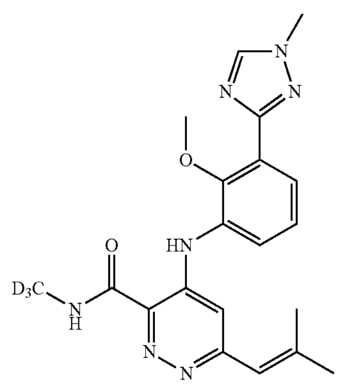 [SMILES: [2H]C([2H])([2H])NC(=O)c1nnc(C=C(C)C)cc1Nc1cccc(-c2ncn(C)n2)c1OC] |
| 74 | 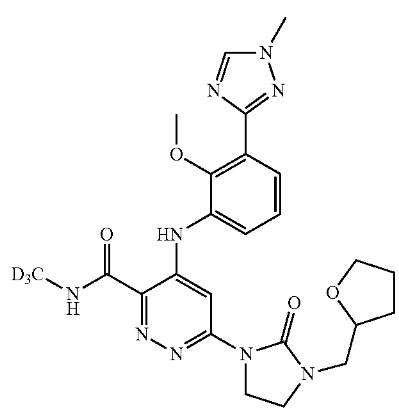 [SMILES: [2H]C([2H])([2H])NC(=O)c1nnc(N2CCN(CC3CCCO3)C2=O)cc1Nc1cccc(-c2ncn(C)n2)c1OC] |

| Ex. | Structure |
|---|---|
| 75 | 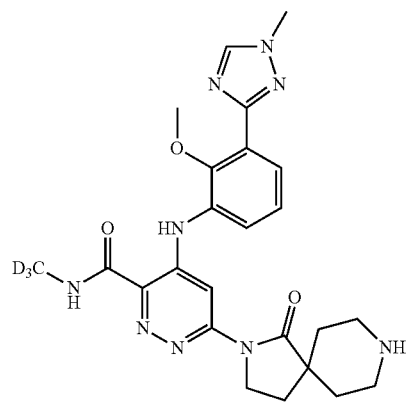 [SMILES: [2H]C([2H])([2H])NC(=O)c1nnc(N2CCC3(CCNCC3)C2=O)cc1Nc1cccc(-c2ncn(C)n2)c1OC] |
| 76 | 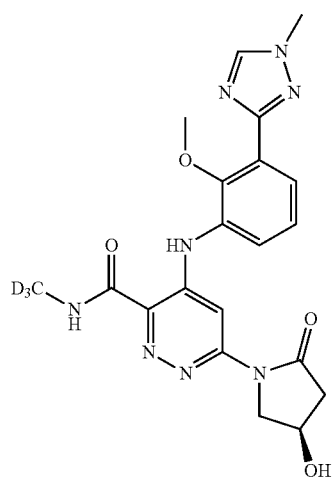 [SMILES: [2H]C([2H])([2H])NC(=O)c1nnc(N2C[C@H](O)CC2=O)cc1Nc1cccc(-c2ncn(C)n2)c1OC] |
| 77 | 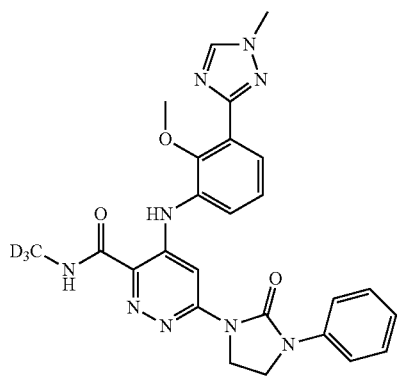 [SMILES: [2H]C([2H])([2H])NC(=O)c1nnc(N2CCN(c3ccccc3)C2=O)cc1Nc1cccc(-c2ncn(C)n2)c1OC] |
| 78 | 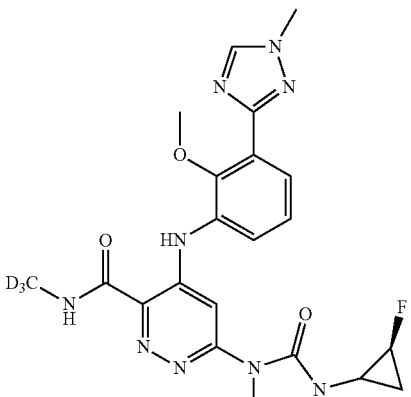 |
| 79 | 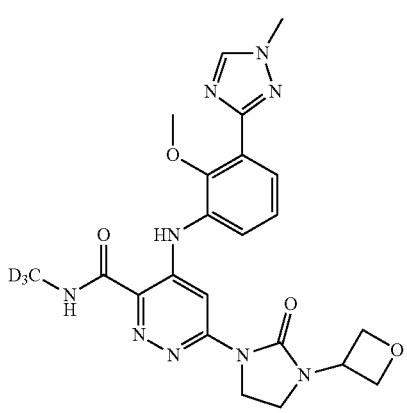 [SMILES: [2H]C([2H])([2H])NC(=O)c1nnc(N2CCN(C3COC3)C2=O)cc1Nc1cccc(-c2ncn(C)n2)c1OC] |
| 80 | 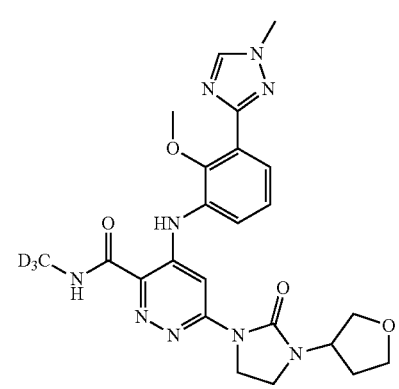 [SMILES: [2H]C([2H])([2H])NC(=O)c1nnc(N2CCN(C3CCOC3)C2=O)cc1Nc1cccc(-c2ncn(C)n2)c1OC] |
| 81 | 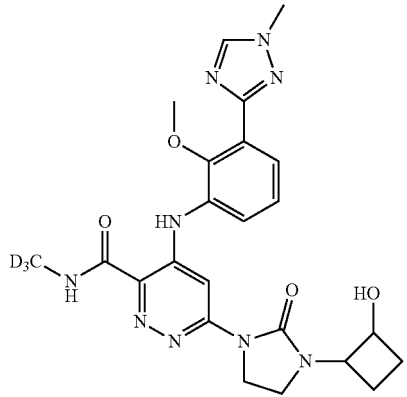 [SMILES: [2H]C([2H])([2H])NC(=O)c1nnc(N2CCN(C3CCC3O)C2=O)cc1Nc1cccc(-c2ncn(C)n2)c1OC] |

| Ex. | Structure |
|---|---|
| 82 | 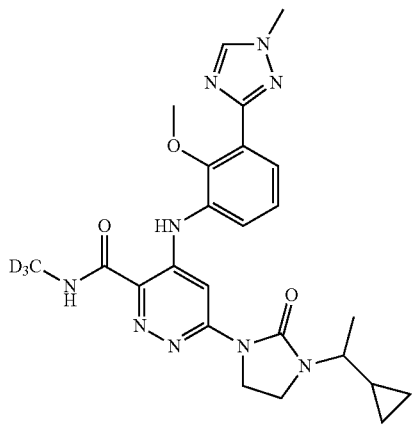 [SMILES: [2H]C([2H])([2H])NC(=O)c1nnc(N2CCN(C(C)C3CC3)C2=O)cc1Nc1cccc(-c2ncn(C)n2)c1OC] |
| 83 | 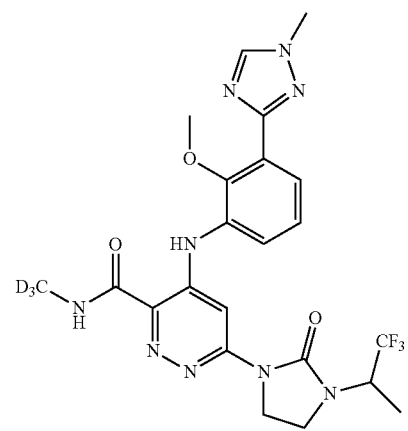 [SMILES: [2H]C([2H])([2H])NC(=O)c1nnc(N2CCN(C(C)C(F)(F)F)C2=O)cc1Nc1cccc(-c2ncn(C)n2)c1OC] |
| 84 | 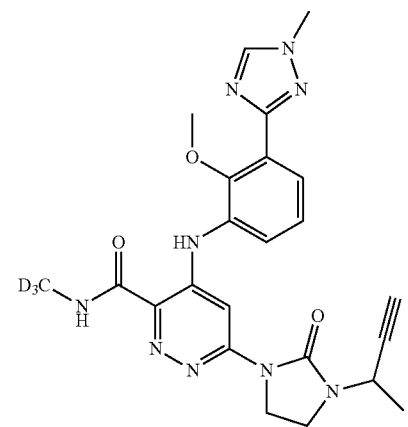 [SMILES: [2H]C([2H])([2H])NC(=O)c1nnc(N2CCN(C(C)C#C)C2=O)cc1Nc1cccc(-c2ncn(C)n2)c1OC] |
| Ex. | Structure |
|---|---|
| 85 | 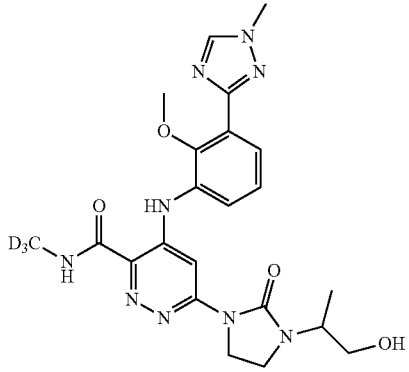 [SMILES: [2H]C([2H])([2H])NC(=O)c1nnc(N2CCN(C(C)CO)C2=O)cc1Nc1cccc(-c2ncn(C)n2)c1OC] |
| 86 | 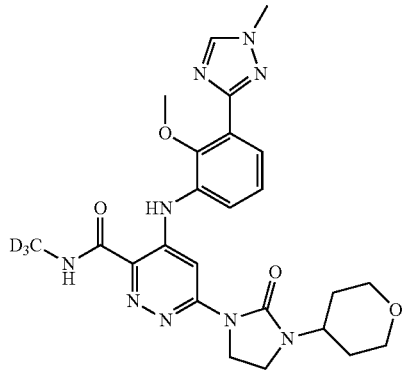 |
| 87 | 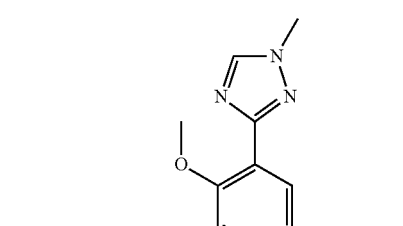 |
| 88 | 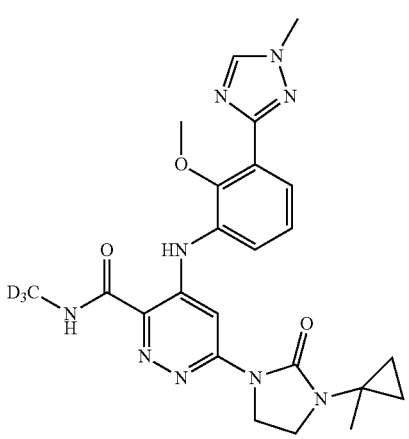 [SMILES: [2H]C([2H])([2H])NC(=O)c1nnc(N2CCN(C3(C)CC3)C2=O)cc1Nc1cccc(-c2ncn(C)n2)c1OC] |

-continued

| Ex. | Structure |
|---|---|
| 89 | 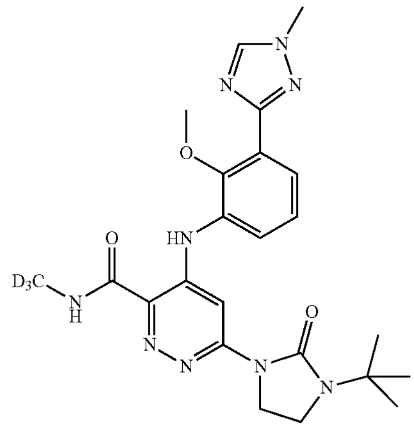 [SMILES: [2H]C([2H])([2H])NC(=O)c1nnc(N2CCN(C(C)(C)C)C2=O)cc1Nc1cccc(-c2ncn(C)n2)c1OC] |
| 90 | 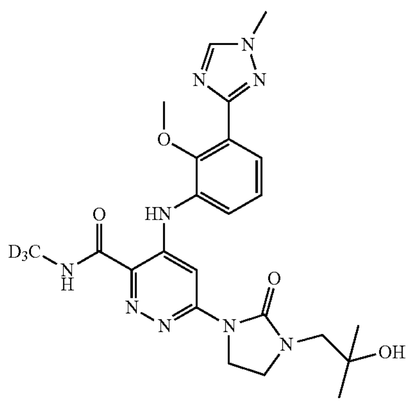 [SMILES: [2H]C([2H])([2H])NC(=O)c1nnc(N2CCN(CC(C)(C)O)C2=O)cc1Nc1cccc(-c2ncn(C)n2)c1OC] |
| 91 | 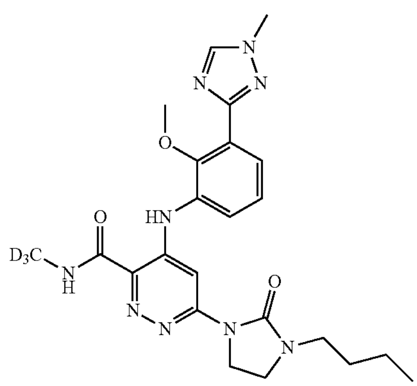 [SMILES: [2H]C([2H])([2H])NC(=O)c1nnc(N2CCN(CCCC)C2=O)cc1Nc1cccc(-c2ncn(C)n2)c1OC] |
| 92 | 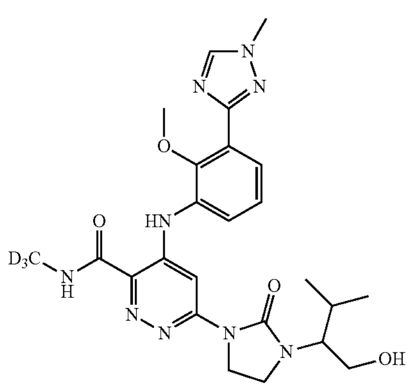 [SMILES: [2H]C([2H])([2H])NC(=O)c1nnc(N2CCN(C(CO)C(C)C)C2=O)cc1Nc1cccc(-c2ncn(C)n2)c1OC] |

-continued

| Ex. | Structure |
|---|---|
| 93 | |
| 94 | |
| 95 | |
| 96 | |

| Ex. | Structure |
|---|---|
| 97 | 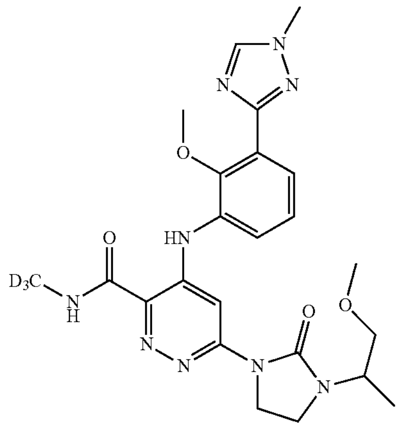 [SMILES: [2H]C([2H])([2H])NC(=O)c1nnc(N2CCN(C(C)COC)C2=O)cc1Nc1cccc(-c2ncn(C)n2)c1OC] |
| 98 | 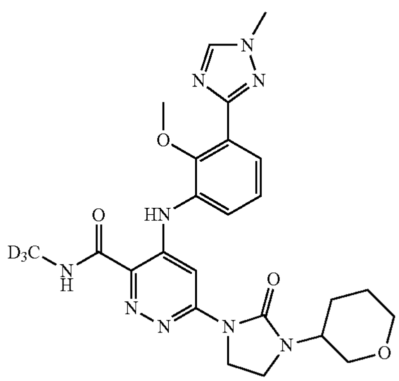 [SMILES: [2H]C([2H])([2H])NC(=O)c1nnc(N2CCN(C3CCCOC3)C2=O)cc1Nc1cccc(-c2ncn(C)n2)c1OC] |
| 99 | 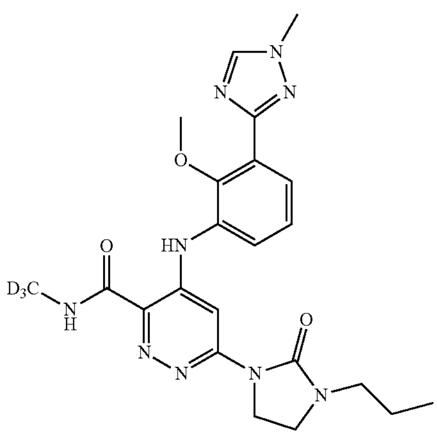 [SMILES: [2H]C([2H])([2H])NC(=O)c1nnc(N2CCN(CCC)C2=O)cc1Nc1cccc(-c2ncn(C)n2)c1OC] |
| 100 | 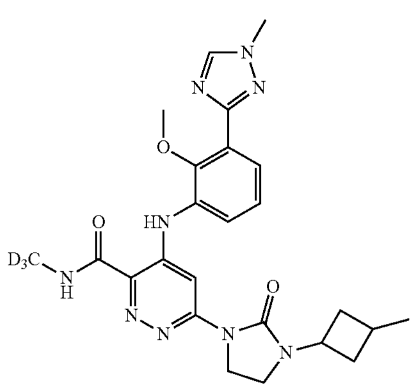 [SMILES: [2H]C([2H])([2H])NC(=O)c1nnc(N2CCN(C3CC(C)C3)C2=O)cc1Nc1cccc(-c2ncn(C)n2)c1OC] |

| Ex. | Structure |
|---|---|
| 101 | 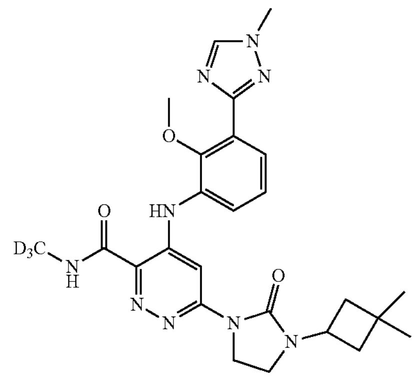 [SMILES: [2H]C([2H])([2H])NC(=O)c1nnc(N2CCN(C3CC(C)(C)C3)C2=O)cc1Nc1cccc(-c2ncn(C)n2)c1OC] |
| 102 | 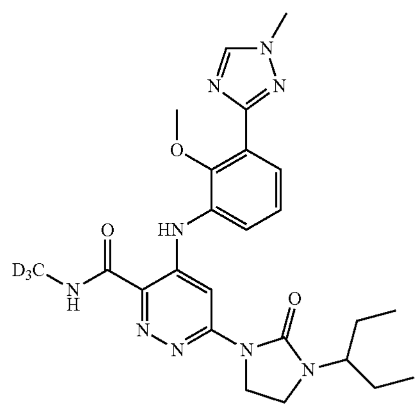 [SMILES: [2H]C([2H])([2H])NC(=O)c1nnc(N2CCN(C(CC)CC)C2=O)cc1Nc1cccc(-c2ncn(C)n2)c1OC] |
| 103 | 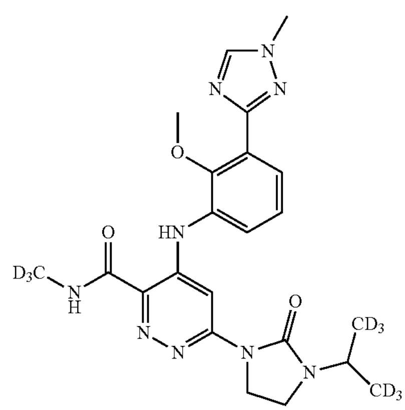 [SMILES: [2H]C([2H])([2H])NC(=O)c1nnc(N2CCN(C(C([2H])([2H])[2H])C([2H])([2H])[2H])C2=O)cc1Nc1cccc(-c2ncn(C)n2)c1OC] |
| 104 | 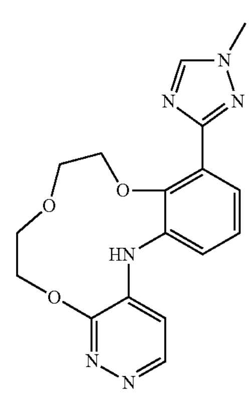 [SMILES: Cn1cnc(-c2cccc3c2OCCOCCOc2nnccc2N3)n1] |

-continued
| Ex. | Structure |
|---|---|
| 105 | 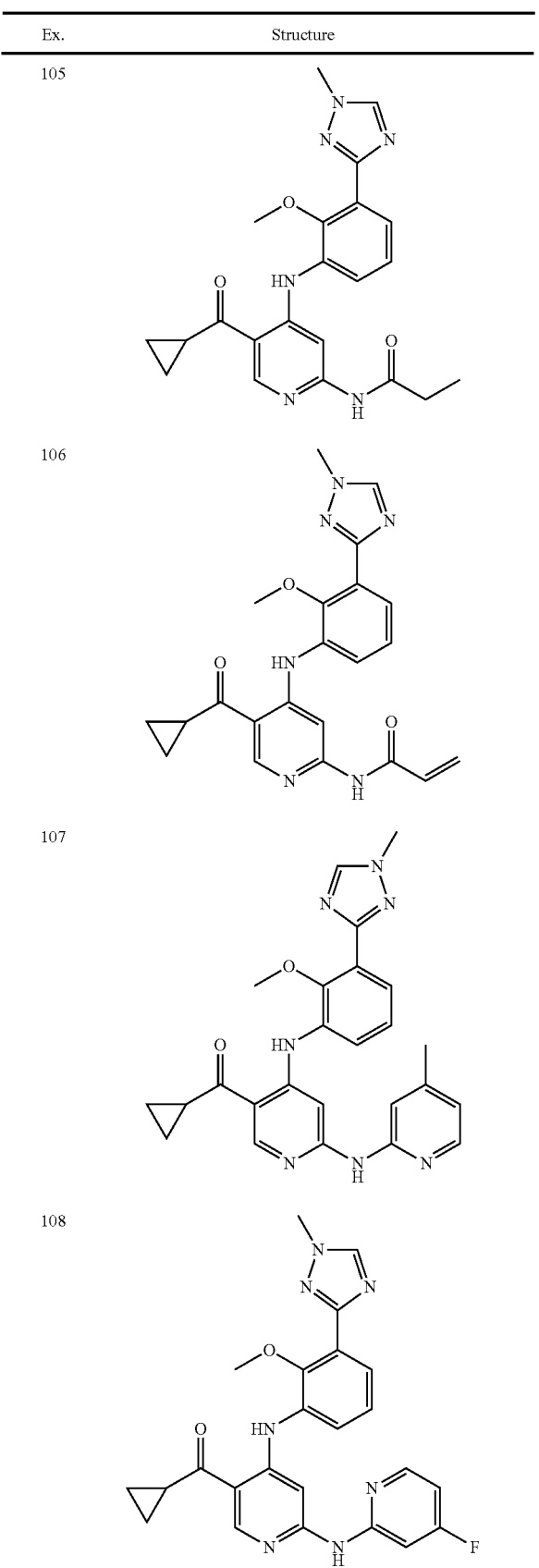 |
| 106 | 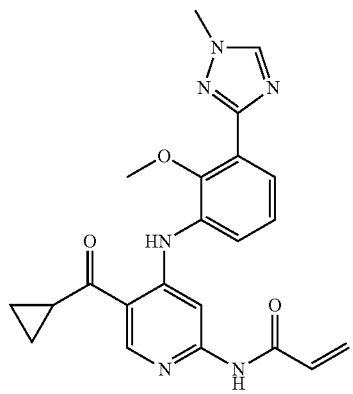 [SMILES: C=CC(=O)Nc1cc(Nc2cccc(-c3ncn(C)n3)c2OC)c(C(=O)C2CC2)cn1] |
| 107 | 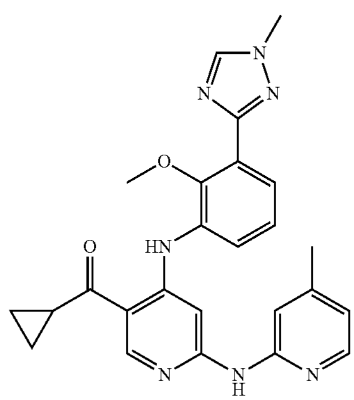 [SMILES: COc1c(Nc2cc(Nc3cc(C)ccn3)ncc2C(=O)C2CC2)cccc1-c1ncn(C)n1] |
| 108 | 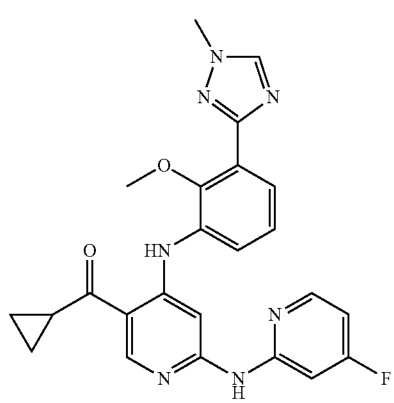 [SMILES: COc1c(Nc2cc(Nc3cc(F)ccn3)ncc2C(=O)C2CC2)cccc1-c1ncn(C)n1] |
-continued
| Ex. | Structure |
|---|---|
| 109 | 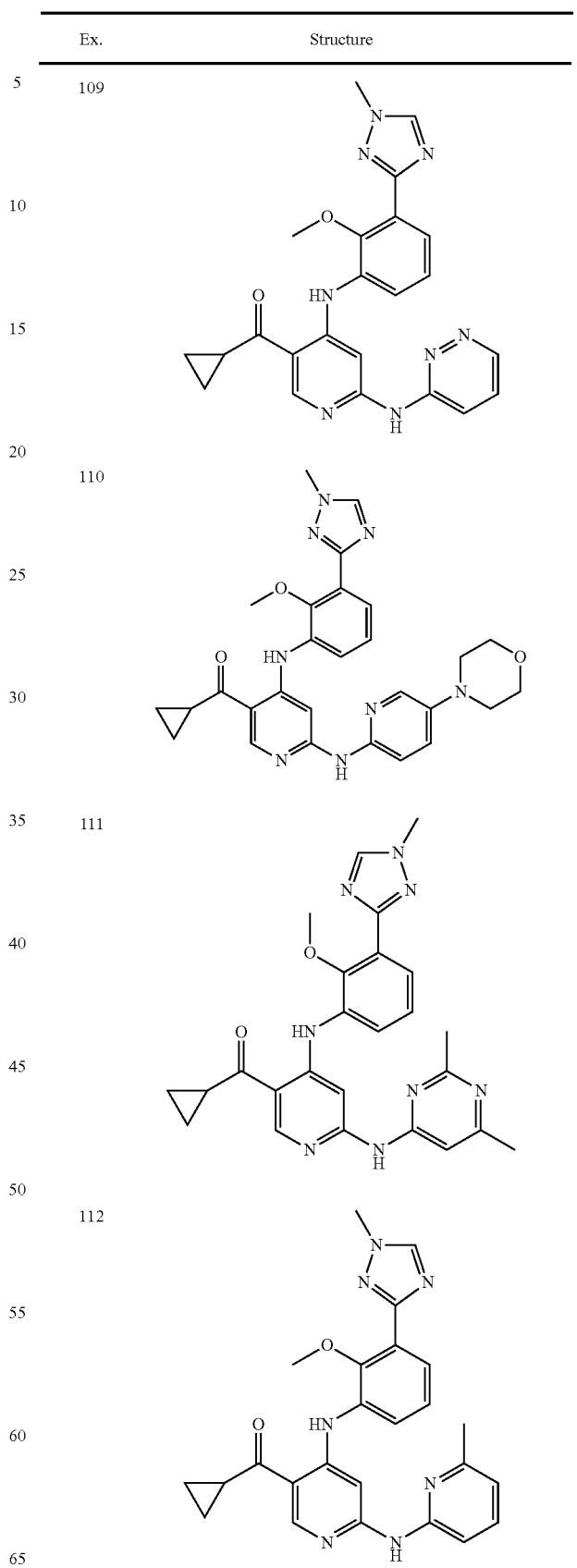 |
| 110 | 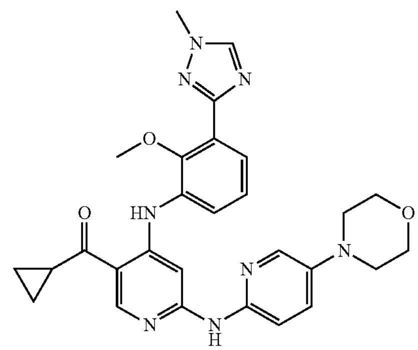 [SMILES: COc1c(Nc2cc(Nc3ccc(N4CCOCC4)cn3)ncc2C(=O)C2CC2)cccc1-c1ncn(C)n1] |
| 111 | 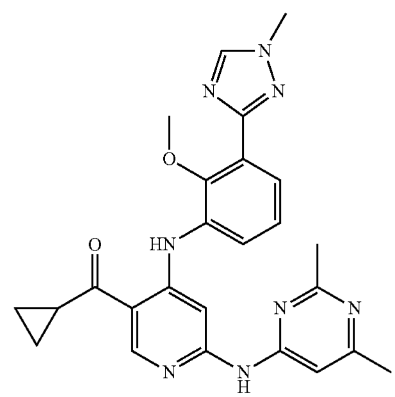 [SMILES: COc1c(Nc2cc(Nc3cc(C)nc(C)n3)ncc2C(=O)C2CC2)cccc1-c1ncn(C)n1] |
| 112 | 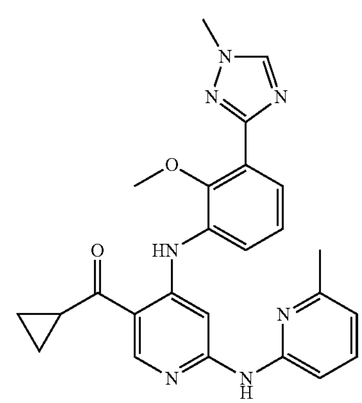 [SMILES: COc1c(Nc2cc(Nc3cccc(C)n3)ncc2C(=O)C2CC2)cccc1-c1ncn(C)n1] |

| Ex. | Structure | Ex. | Structure |
|---|---|---|---|
| 113 | 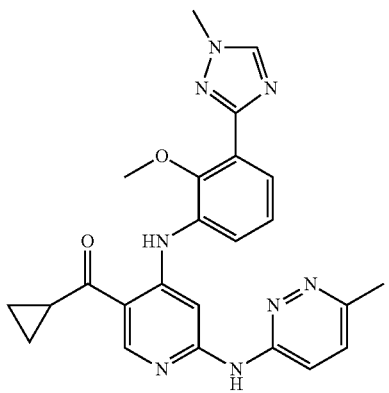 [SMILES: COc1c(Nc2cc(Nc3ccc(C)nn3)ncc2C(=O)C2CC2)cccc1-c1ncn(C)n1] | 116 | 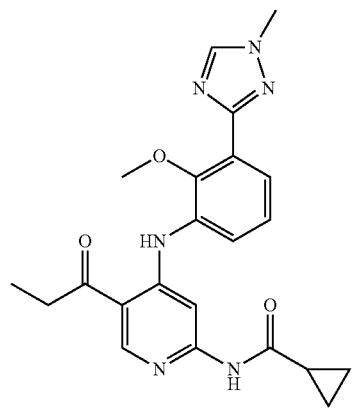 |
| 114 | 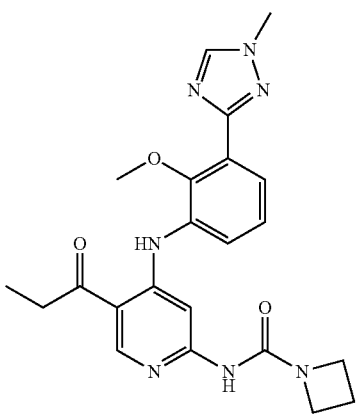 [SMILES: CCC(=O)c1cnc(NC(=O)N2CCC2)cc1Nc1cccc(-c2ncn(C)n2)c1OC] | 117 | 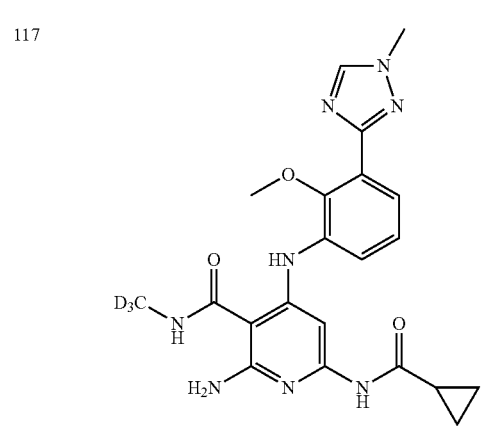 |
| 115 | 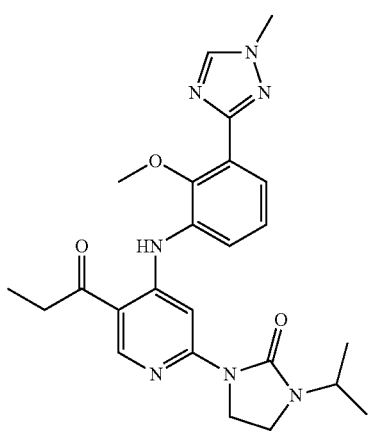 [SMILES: CCC(=O)c1cnc(N2CCN(C(C)C)C2=O)cc1Nc1cccc(-c2ncn(C)n2)c1OC] | 118 | 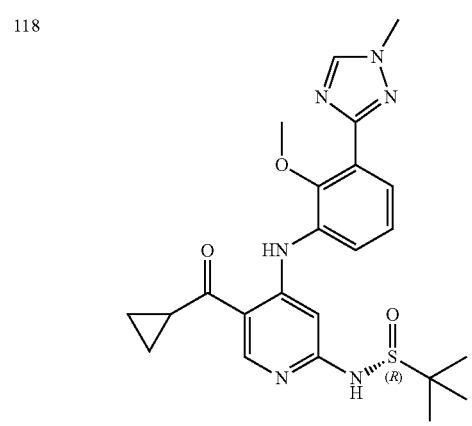 |

| Ex. | Structure |
|---|---|
| 119 | 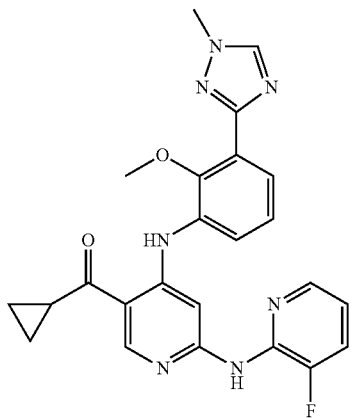 [SMILES: COc1c(Nc2cc(Nc3ncccc3F)ncc2C(=O)C2CC2)cccc1-c1ncn(C)n1] |
| 120 | 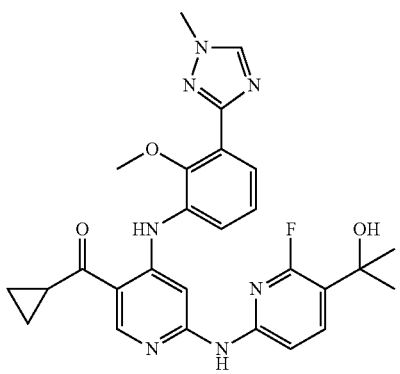 [SMILES: COc1c(Nc2cc(Nc3ccc(C(C)(C)O)c(F)n3)ncc2C(=O)C2CC2)cccc1-c1ncn(C)n1] |
| 121 | 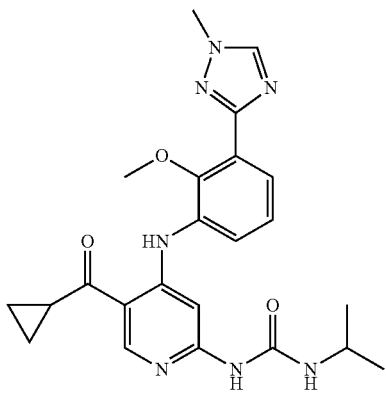 [SMILES: COc1c(Nc2cc(NC(=O)NC(C)C)ncc2C(=O)C2CC2)cccc1-c1ncn(C)n1] |
| 122 | 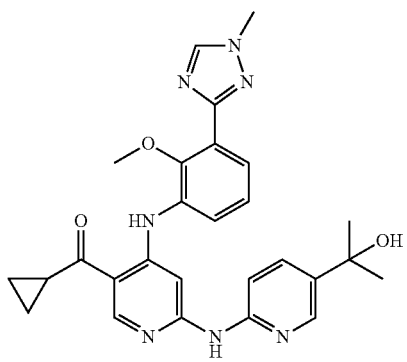 [SMILES: COc1c(Nc2cc(Nc3ccc(C(C)(C)O)cn3)ncc2C(=O)C2CC2)cccc1-c1ncn(C)n1] |
| Ex. | Structure |
|---|---|
| 123 | 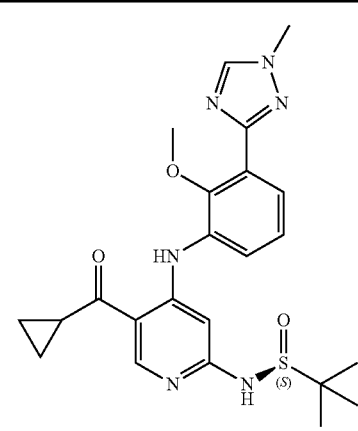 |
| 124 | 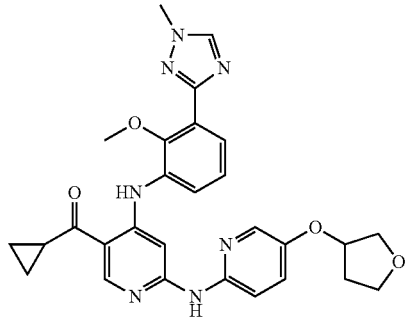 [SMILES: COc1c(Nc2cc(Nc3ccc(OC4CCOC4)cn3)ncc2C(=O)C2CC2)cccc1-c1ncn(C)n1] |
| 125 | 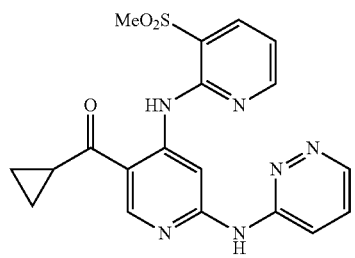 [SMILES: CS(=O)(=O)c1cccnc1Nc1cc(Nc2cccnn2)ncc1C(=O)C1CC1] |
| 126 | 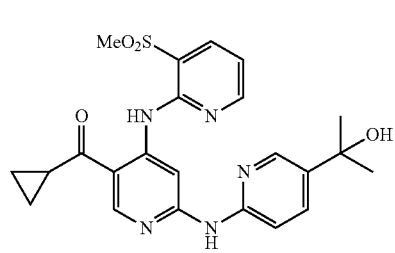 [SMILES: CC(C)(O)c1ccc(Nc2cc(Nc3ncccc3S(C)(=O)=O)c(C(=O)C3CC3)cn2)nc1] |

-continued
| Ex. | Structure |
|---|---|
| 127 | 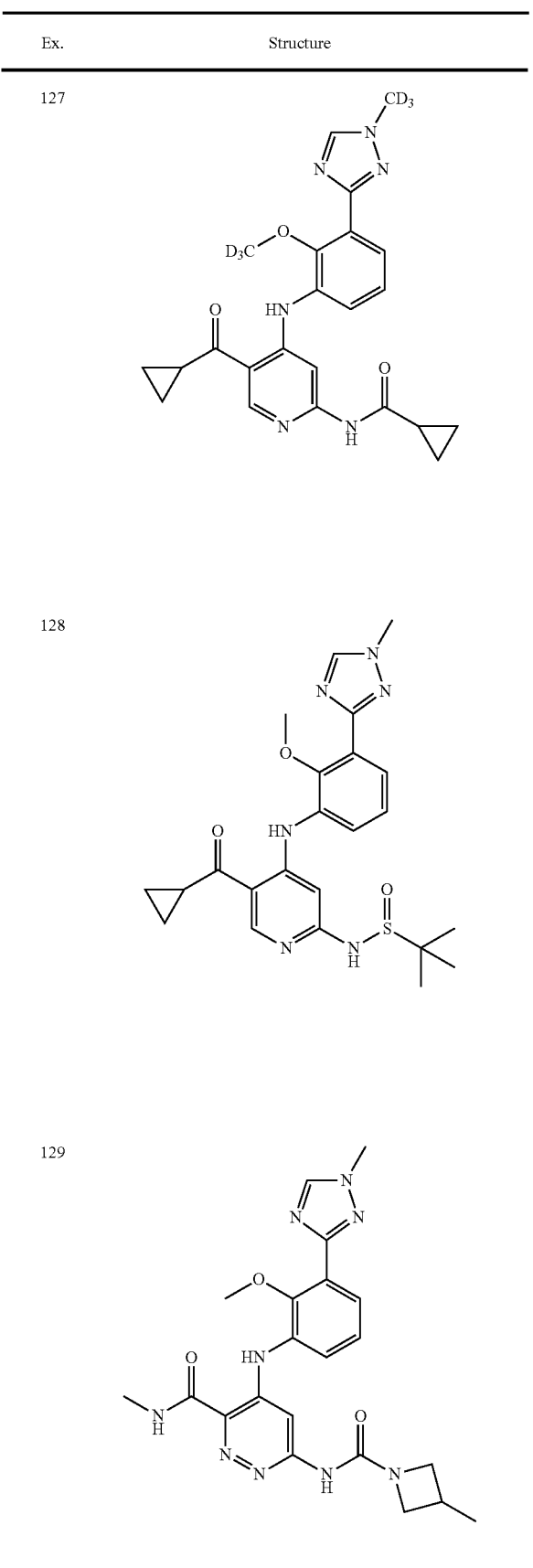 |
| 128 | 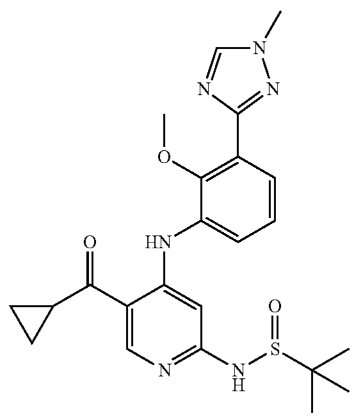 [SMILES: COc1c(Nc2cc(NS(=O)C(C)(C)C)ncc2C(=O)C2CC2)cccc1-c1ncn(C)n1] |
| 129 | 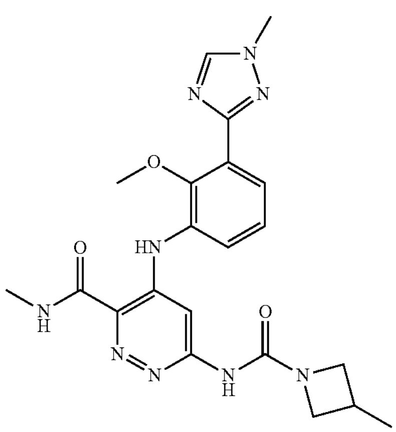 |
-continued
| Ex. | Structure |
|---|---|
| 130 | 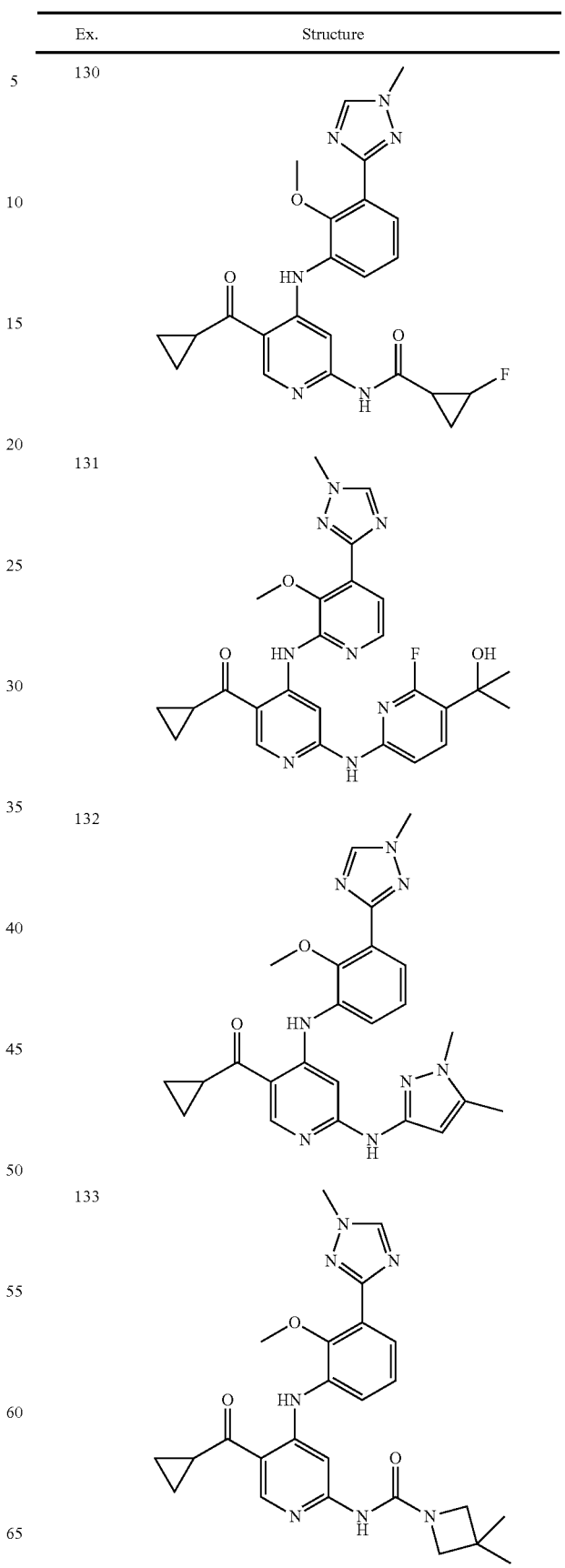 |
| 131 | 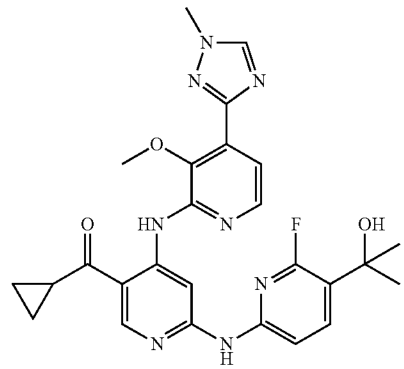 |
| 132 | 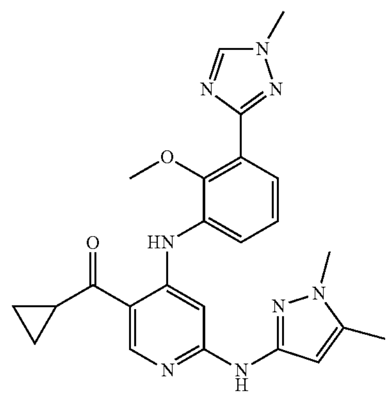 [SMILES: COc1c(Nc2cc(Nc3cc(C)n(C)n3)ncc2C(=O)C2CC2)cccc1-c1ncn(C)n1] |
| 133 | 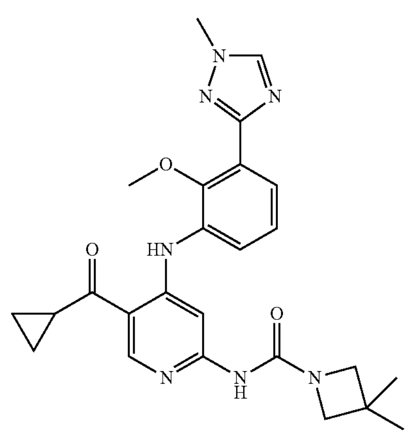 [SMILES: COc1c(Nc2cc(NC(=O)N3CC(C)(C)C3)ncc2C(=O)C2CC2)cccc1-c1ncn(C)n1] |

| Ex. | Structure |
|---|---|
| 134 | 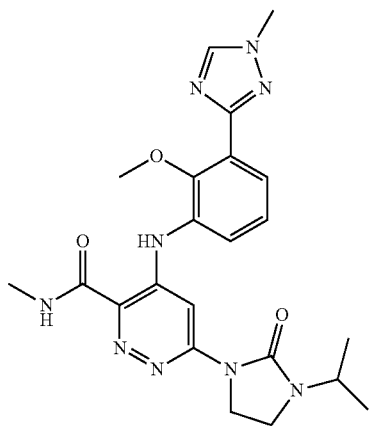 [SMILES: CNC(=O)c1nnc(N2CCN(C(C)C)C2=O)cc1Nc1cccc(-c2ncn(C)n2)c1OC] |
| 135 | 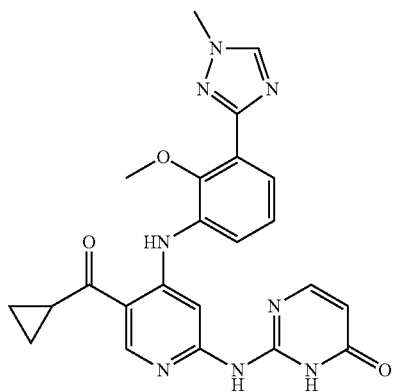 [SMILES: COc1c(Nc2cc(Nc3nccc(=O)[nH]3)ncc2C(=O)C2CC2)cccc1-c1ncn(C)n1] |
| 136 | 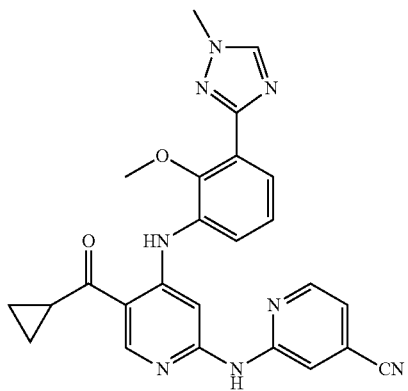 [SMILES: COc1c(Nc2cc(Nc3cc(C#N)ccn3)ncc2C(=O)C2CC2)cccc1-c1ncn(C)n1] |
| 137 | 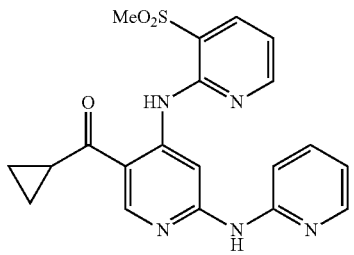 [SMILES: CS(=O)(=O)c1cccnc1Nc1cc(Nc2ccccn2)ncc1C(=O)C1CC1] |
| 138 | 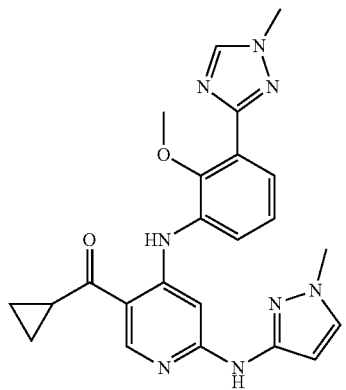 [SMILES: COc1c(Nc2cc(Nc3ccn(C)n3)ncc2C(=O)C2CC2)cccc1-c1ncn(C)n1] |
| 139 | 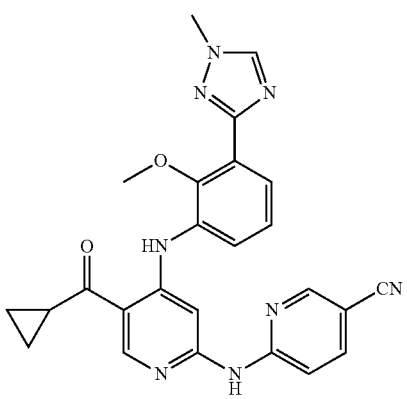 [SMILES: COc1c(Nc2cc(Nc3ccc(C#N)cn3)ncc2C(=O)C2CC2)cccc1-c1ncn(C)n1] |
| 140 | 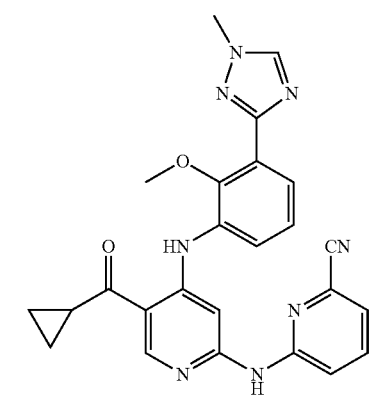 [SMILES: COc1c(Nc2cc(Nc3cccc(C#N)n3)ncc2C(=O)C2CC2)cccc1-c1ncn(C)n1] |
| 141 | 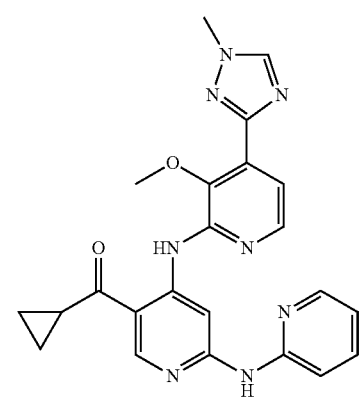 [SMILES: COc1c(-c2ncn(C)n2)ccnc1Nc1cc(Nc2ccccn2)ncc1C(=O)C1CC1] |

-continued
| Ex. | Structure |
|---|---|
| 142 | 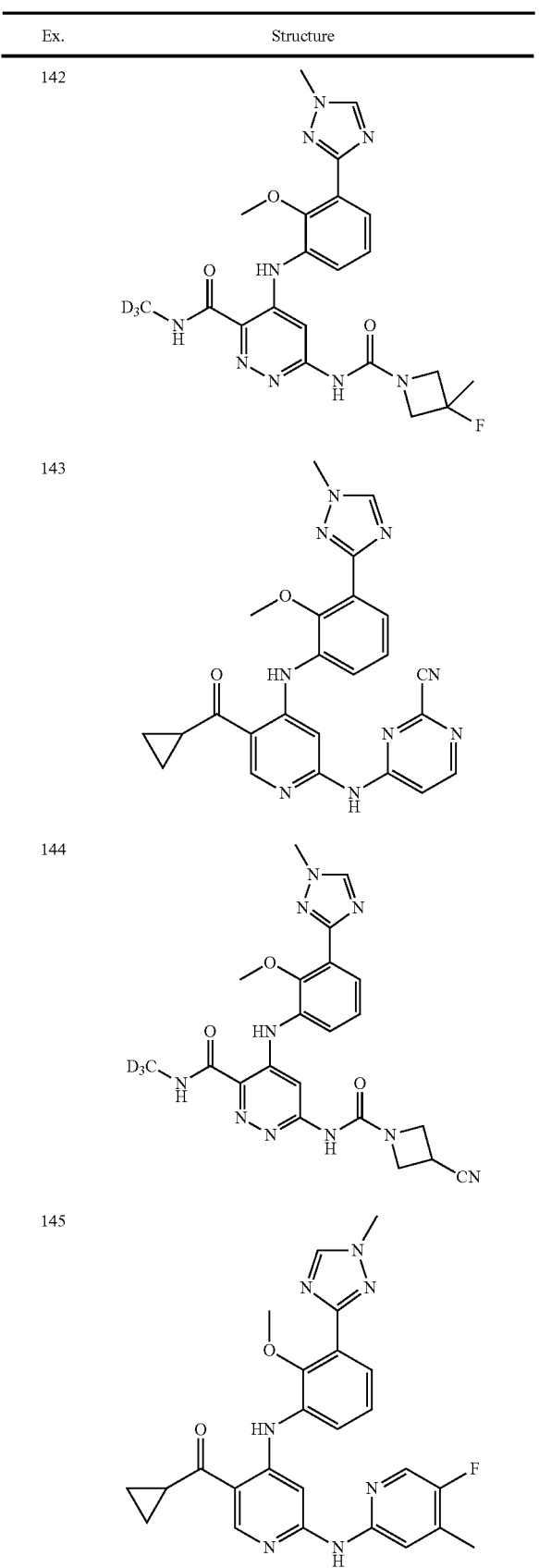 |
| 143 | 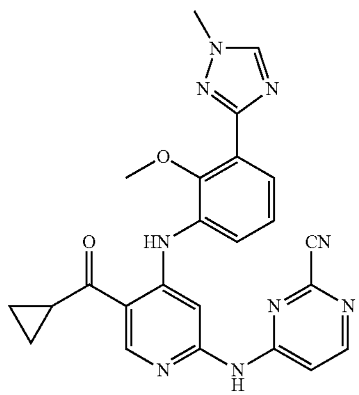 [SMILES: COc1c(Nc2cc(Nc3ccnc(C#N)n3)ncc2C(=O)C2CC2)cccc1-c1ncn(C)n1] |
| 144 | 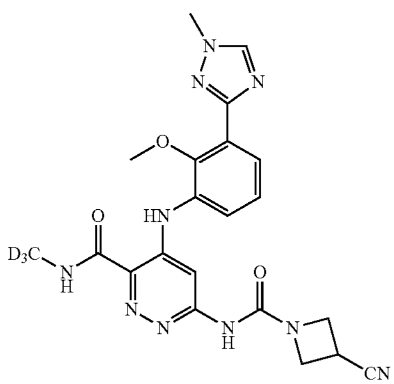 [SMILES: [2H]C([2H])([2H])NC(=O)c1nnc(NC(=O)N2CC(C#N)C2)cc1Nc1cccc(-c2ncn(C)n2)c1OC] |
| 145 | 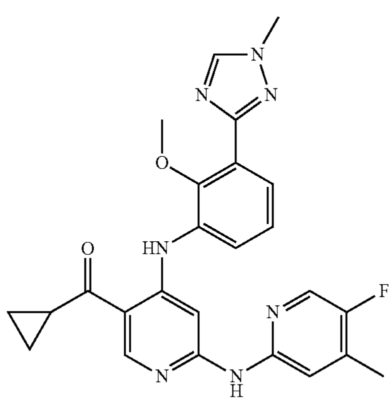 [SMILES: COc1c(Nc2cc(Nc3cc(C)c(F)cn3)ncc2C(=O)C2CC2)cccc1-c1ncn(C)n1] |
-continued
| Ex. | Structure |
|---|---|
| 146 | 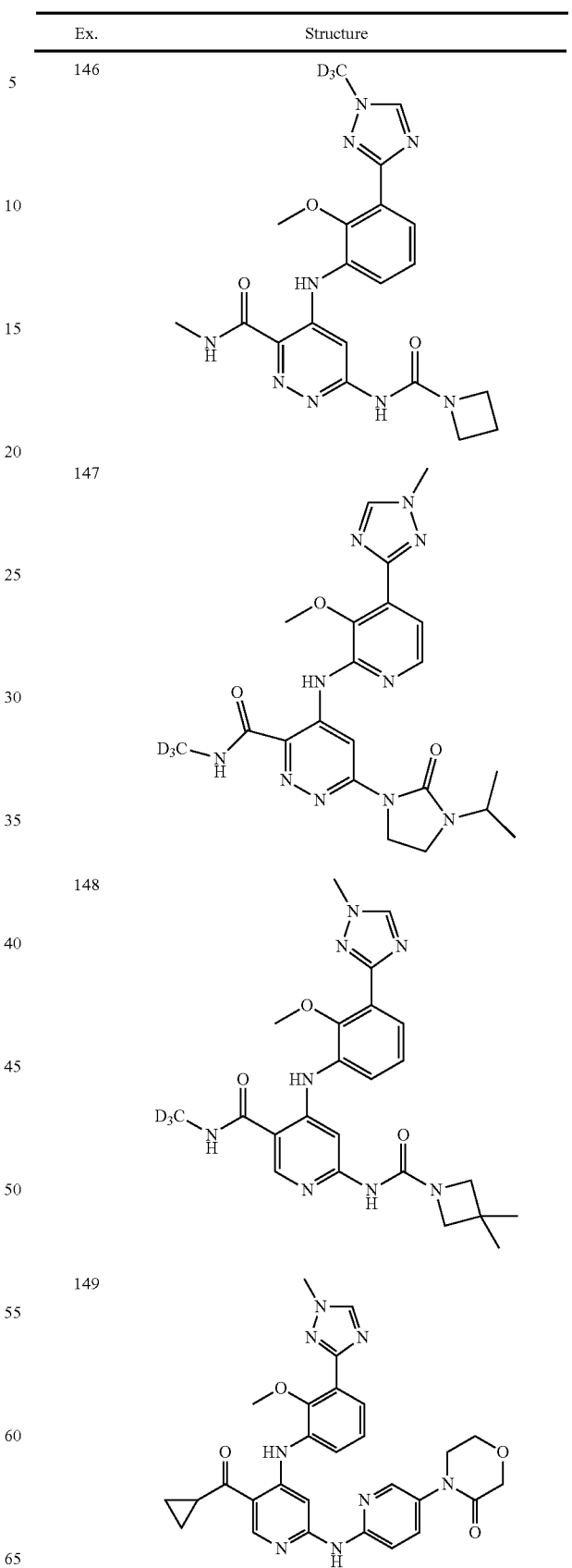 |
| 147 | 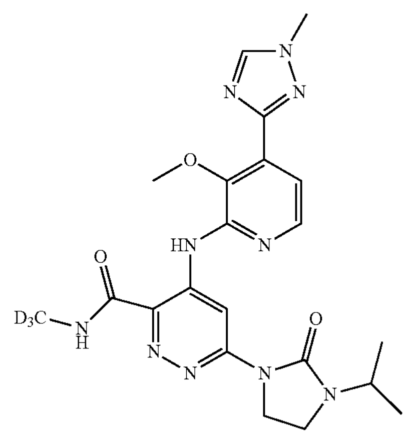 [SMILES: [2H]C([2H])([2H])NC(=O)c1nnc(N2CCN(C(C)C)C2=O)cc1Nc1nccc(-c2ncn(C)n2)c1OC] |
| 148 | 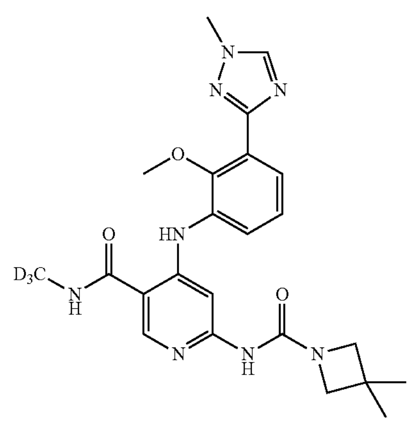 [SMILES: [2H]C([2H])([2H])NC(=O)c1cnc(NC(=O)N2CC(C)(C)C2)cc1Nc1cccc(-c2ncn(C)n2)c1OC] |
| 149 | 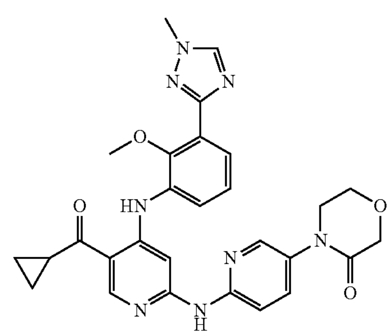 [SMILES: COc1c(Nc2cc(Nc3ccc(N4CCOCC4=O)cn3)ncc2C(=O)C2CC2)cccc1-c1ncn(C)n1] |

| Ex. | Structure |
|---|---|
| 150 | 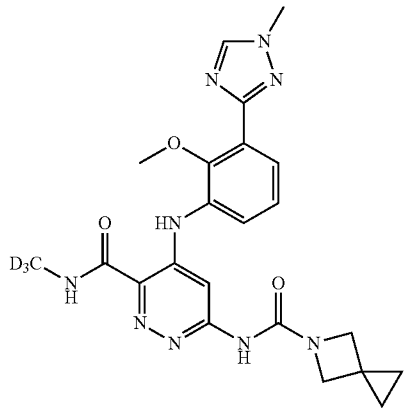 [SMILES: [2H]C([2H])([2H])NC(=O)c1nnc(NC(=O)N2CC3(CC3)C2)cc1Nc1cccc(-c2ncn(C)n2)c1OC] |
| 151 | 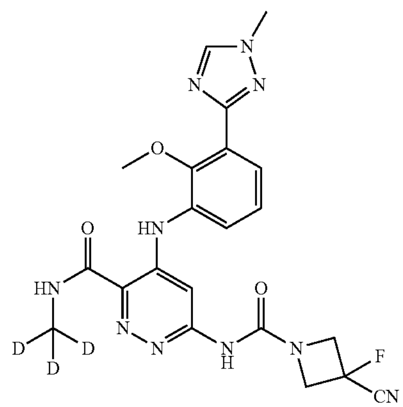 [SMILES: [2H]C([2H])([2H])NC(=O)c1nnc(NC(=O)N2CC(F)(C#N)C2)cc1Nc1cccc(-c2ncn(C)n2)c1OC] |
| 152 | 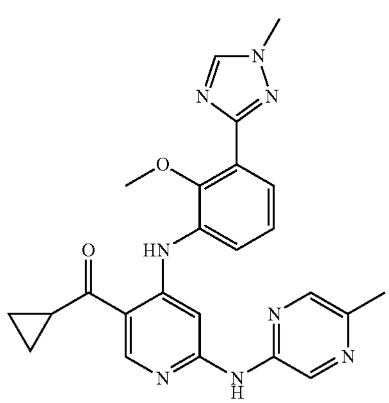 [SMILES: COc1c(Nc2cc(Nc3cnc(C)cn3)ncc2C(=O)C2CC2)cccc1-c1ncn(C)n1] |
| 153 | 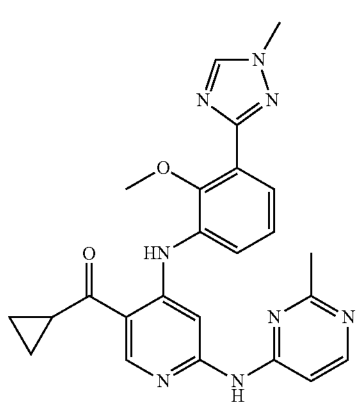 [SMILES: COc1c(Nc2cc(Nc3ccnc(C)n3)ncc2C(=O)C2CC2)cccc1-c1ncn(C)n1] |

| Ex. | Structure |
|---|---|
| 154 | 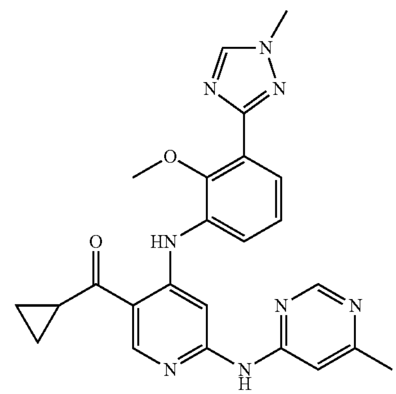 [SMILES: COc1c(Nc2cc(Nc3cc(C)ncn3)ncc2C(=O)C2CC2)cccc1-c1ncn(C)n1] |
| 155 | 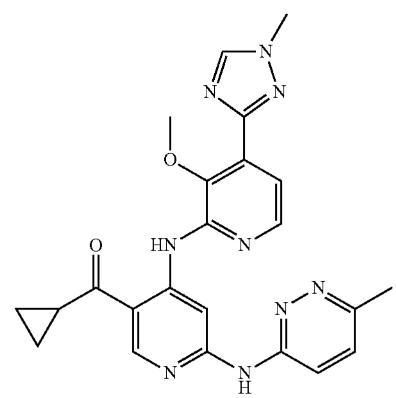 [SMILES: COc1c(-c2ncn(C)n2)ccnc1Nc1cc(Nc2ccc(C)nn2)ncc1C(=O)C1CC1] |
| 156 | 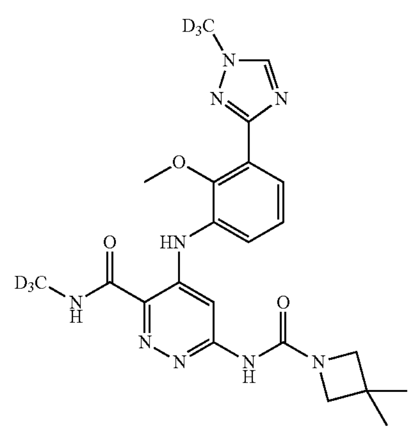 [SMILES: [2H]C([2H])([2H])NC(=O)c1nnc(NC(=O)N2CC(C)(C)C2)cc1Nc1cccc(-c2ncn(C([2H])([2H])[2H])n2)c1OC] |

| Ex. | Structure |
|---|---|
| 157 | 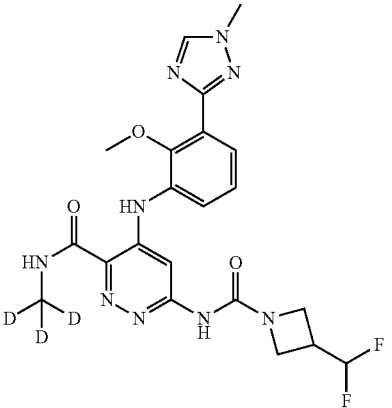 [SMILES: [2H]C([2H])([2H])NC(=O)c1nnc(NC(=O)N2CC(C(F)F)C2)cc1Nc1cccc(-c2ncn(C)n2)c1OC] |
| 158 | 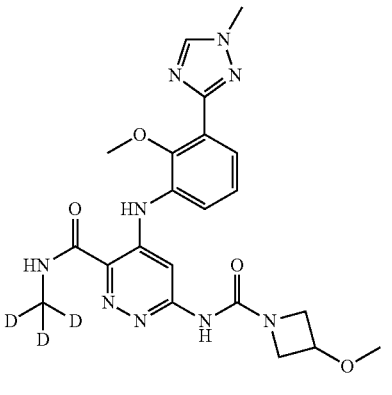 [SMILES: [2H]C([2H])([2H])NC(=O)c1nnc(NC(=O)N2CC(OC)C2)cc1Nc1cccc(-c2ncn(C)n2)c1OC] |
| 159 | 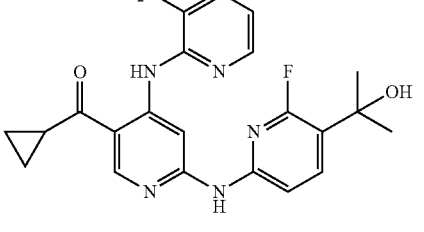 |
| 160 | 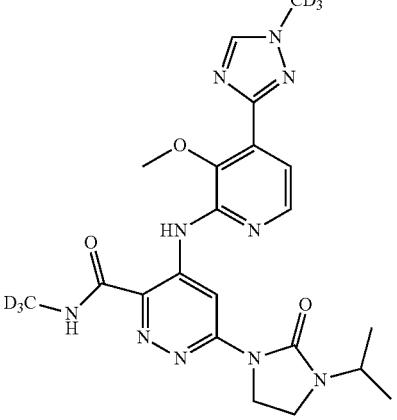 |
| 161 | 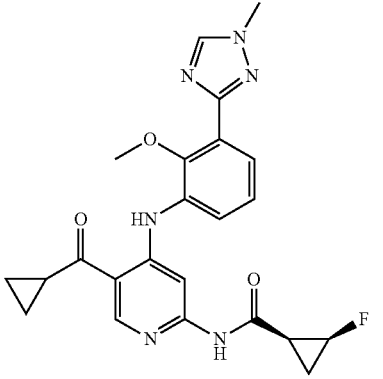 [SMILES: COc1c(Nc2cc(NC(=O)[C@@H]3C[C@@H]3F)ncc2C(=O)C2CC2)cccc1-c1ncn(C)n1] |
| 162 | 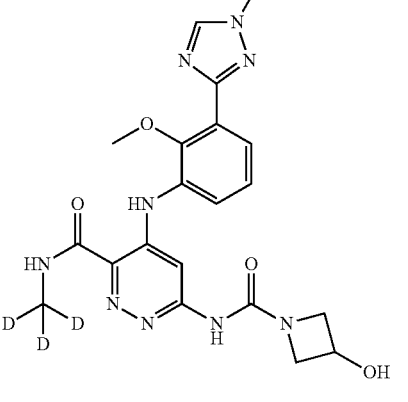 |
| 163 | 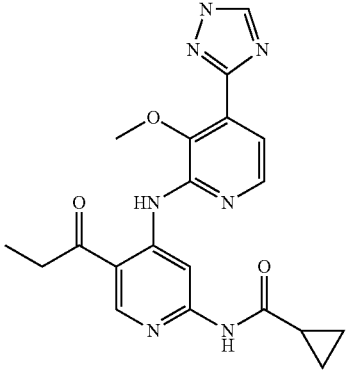 |
| 164 | 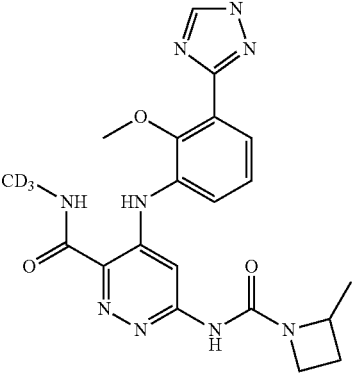 |

-continued

| Ex. | Structure |
|---|---|
| 165 | 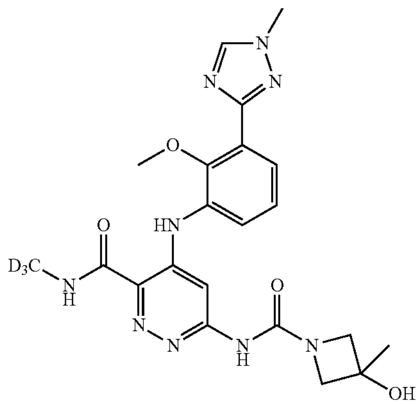 [SMILES: [2H]C([2H])([2H])NC(=O)c1nnc(NC(=O)N2CC(C)(O)C2)cc1Nc1cccc(-c2ncn(C)n2)c1OC] |
| 166 | 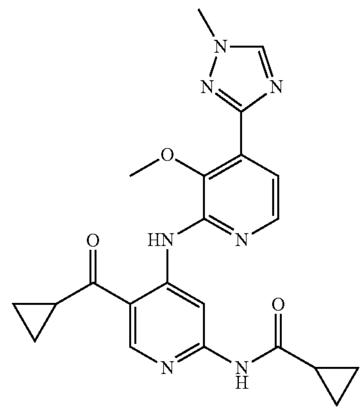 [SMILES: COc1c(-c2ncn(C)n2)ccnc1Nc1cc(NC(=O)C2CC2)ncc1C(=O)C1CC1] |
| 169 | 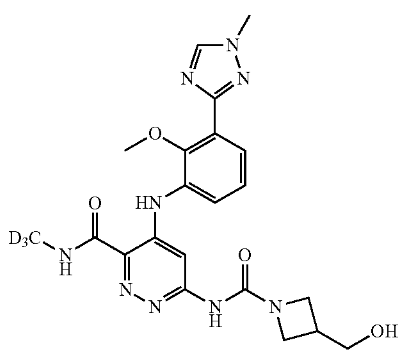 [SMILES: [2H]C([2H])([2H])NC(=O)c1nnc(NC(=O)N2CC(CO)C2)cc1Nc1cccc(-c2ncn(C)n2)c1OC] |
| 171 | 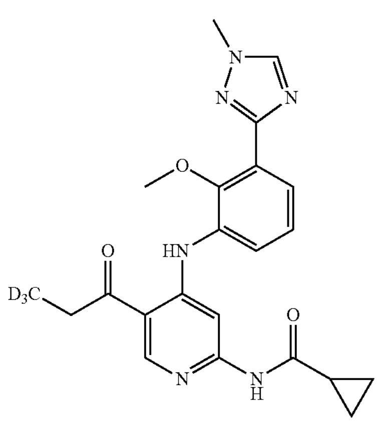 [SMILES: [2H]C([2H])([2H])CC(=O)c1cnc(NC(=O)C2CC2)cc1Nc1cccc(-c2ncn(C)n2)c1OC] |

-continued

| Ex. | Structure |
|---|---|
| 172 | 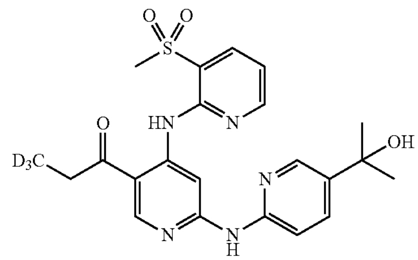 [SMILES: [2H]C([2H])([2H])CC(=O)c1cnc(Nc2ccc(C(C)(C)O)cn2)cc1Nc1ncccc1S(C)(=O)=O] |
| 173 | 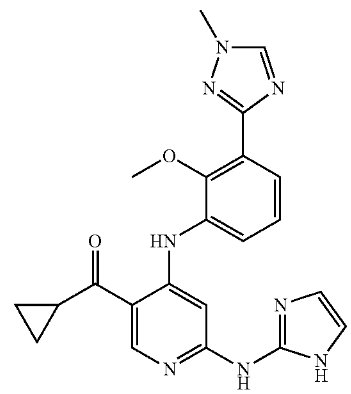 [SMILES: COc1c(Nc2cc(Nc3ncc[nH]3)ncc2C(=O)C2CC2)cccc1-c1ncn(C)n1] |
| 174 | 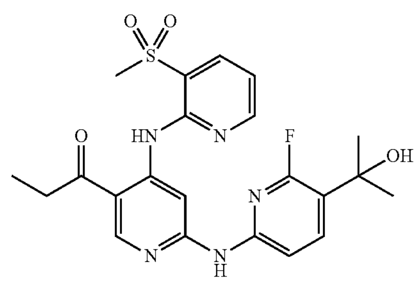 [SMILES: CCC(=O)c1cnc(Nc2ccc(C(C)(C)O)c(F)n2)cc1Nc1ncccc1S(C)(=O)=O] |
| 175 | 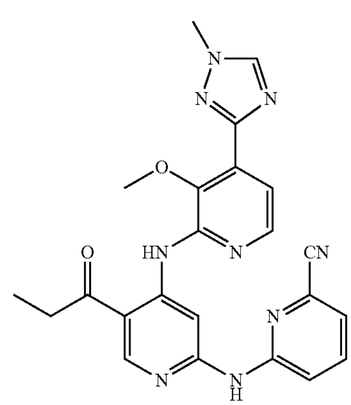 [SMILES: CCC(=O)c1cnc(Nc2cccc(C#N)n2)cc1Nc1nccc(-c2ncn(C)n2)c1OC] |

-continued

| Ex. | Structure |
|-----|-----------|
| 176 | 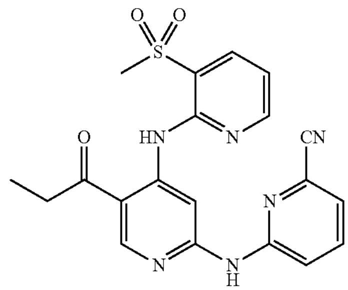 [SMILES: CCC(=O)c1cnc(Nc2cccc(C#N)n2)cc1Nc1ncccc1S(C)(=O)=O] |
| 177 | 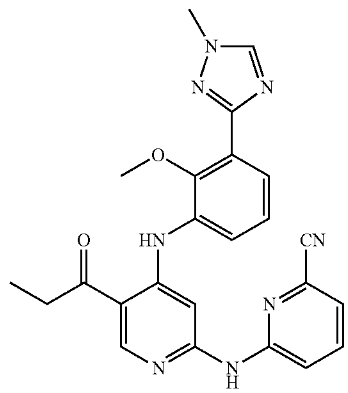 [SMILES: CCC(=O)c1cnc(Nc2cccc(C#N)n2)cc1Nc1cccc(-c2ncn(C)n2)c1OC] |
| 178 | 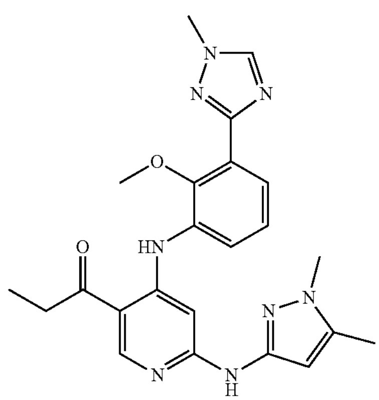 [SMILES: CCC(=O)c1cnc(Nc2cc(C)n(C)n2)cc1Nc1cccc(-c2ncn(C)n2)c1OC] |
| 179 | 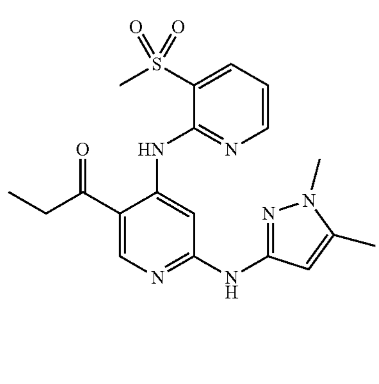 [SMILES: CCC(=O)c1cnc(Nc2cc(C)n(C)n2)cc1Nc1ncccc1S(C)(=O)=O] |

-continued

| Ex. | Structure |
|-----|-----------|
| 180 | 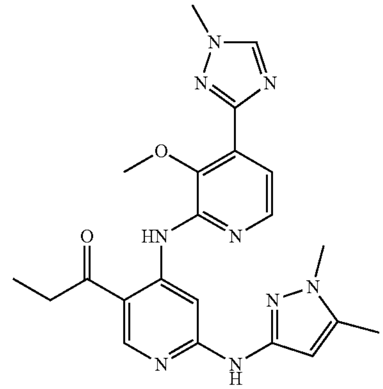 [SMILES: CCC(=O)c1cnc(Nc2cc(C)n(C)n2)cc1Nc1nccc(-c2ncn(C)n2)c1OC] |
| 181 | 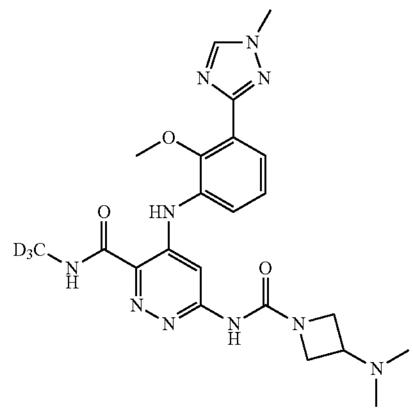 [SMILES: [2H]C([2H])([2H])NC(=O)c1nnc(NC(=O)N2CC(N(C)C)C2)cc1Nc1cccc(-c2ncn(C)n2)c1OC] |
| 182 | 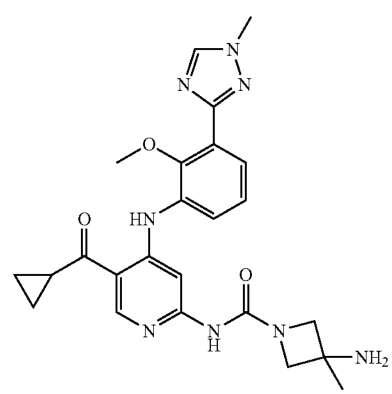 [SMILES: COc1c(Nc2cc(NC(=O)N3CC(C)(N)C3)ncc2C(=O)C2CC2)cccc1-c1ncn(C)n1] |
| 183 | 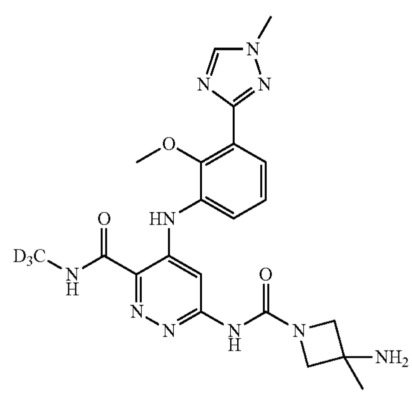 [SMILES: [2H]C([2H])([2H])NC(=O)c1nnc(NC(=O)N2CC(C)(N)C2)cc1Nc1cccc(-c2ncn(C)n2)c1OC] |

-continued
| Ex. | Structure |
|---|---|
| 184 | 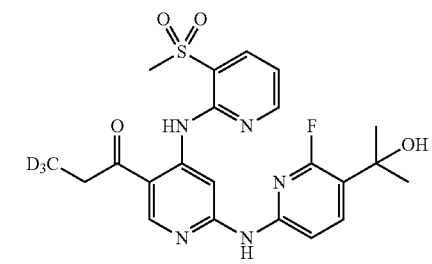 [SMILES: [2H]C([2H])([2H])CC(=O)c1cnc(Nc2ccc(C(C)(C)O)c(F)n2)cc1Nc1ncccc1S(C)(=O)=O] |
| 185 | 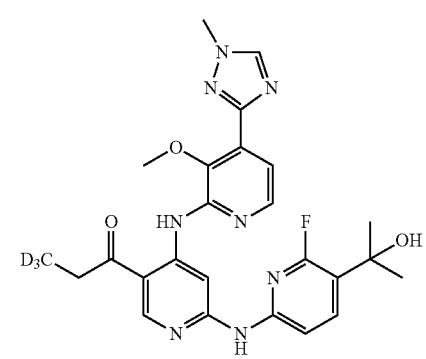 [SMILES: [2H]C([2H])([2H])CC(=O)c1cnc(Nc2ccc(C(C)(C)O)c(F)n2)cc1Nc1nccc(-c2ncn(C)n2)c1OC] |
| 188 | 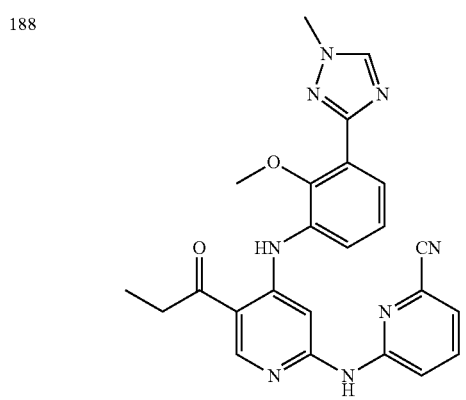 |
| 189 | 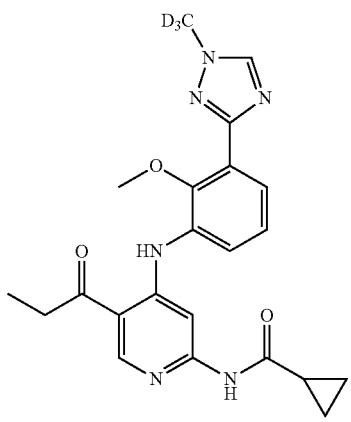 [SMILES: [2H]C([2H])([2H])n1cnc(-c2cccc(Nc3cc(NC(=O)C4CC4)ncc3C(=O)CC)c2OC)n1] |
-continued
| Ex. | Structure |
|---|---|
| 190 | 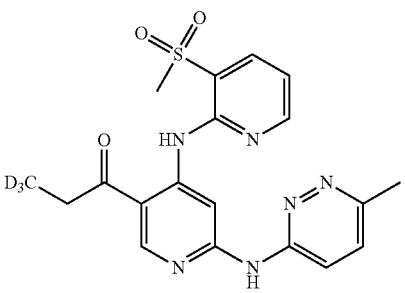 [SMILES: [2H]C([2H])([2H])CC(=O)c1cnc(Nc2ccc(C)nn2)cc1Nc1ncccc1S(C)(=O)=O] |
| 191 | 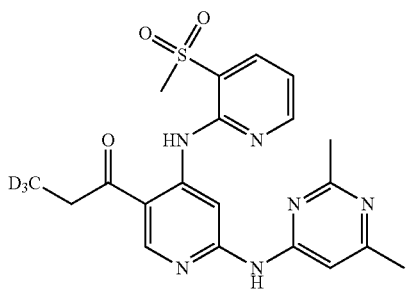 [SMILES: [2H]C([2H])([2H])CC(=O)c1cnc(Nc2cc(C)nc(C)n2)cc1Nc1ncccc1S(C)(=O)=O] |
| 193 | 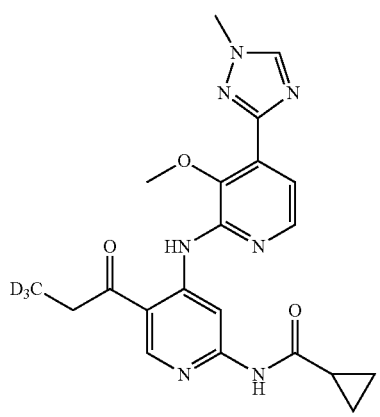 [SMILES: [2H]C([2H])([2H])CC(=O)c1cnc(NC(=O)C2CC2)cc1Nc1nccc(-c2ncn(C)n2)c1OC] |
| 195 | 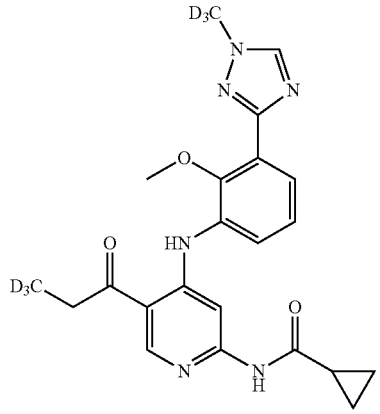 [SMILES: [2H]C([2H])([2H])CC(=O)c1cnc(NC(=O)C2CC2)cc1Nc1cccc(-c2ncn(C([2H])([2H])[2H])n2)c1OC] |

177
-continued
| Ex. | Structure |
|---|---|
| 196 | 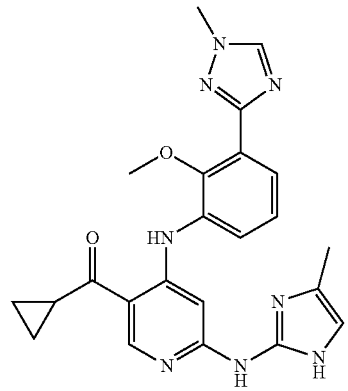 [SMILES: COc1c(Nc2cc(Nc3nc(C)c[nH]3)ncc2C(=O)C2CC2)cccc1-c1ncn(C)n1] |
| 198 | 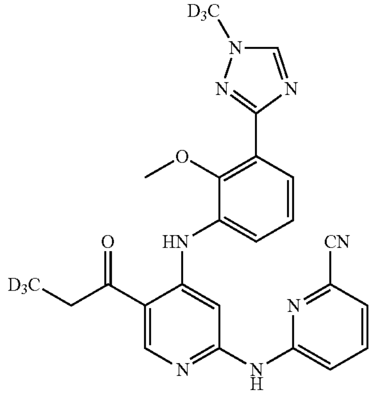 [SMILES: [2H]C([2H])([2H])CC(=O)c1cnc(Nc2cccc(C#N)n2)cc1Nc1cccc(-c2ncn(C([2H])([2H])[2H])n2)c1OC] |
| 199 | 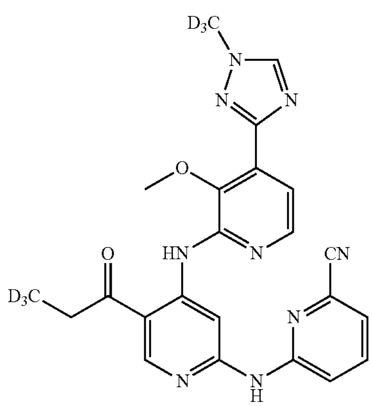 [SMILES: [2H]C([2H])([2H])CC(=O)c1cnc(Nc2cccc(C#N)n2)cc1Nc1nccc(-c2ncn(C([2H])([2H])[2H])n2)c1OC] |
| 200 | 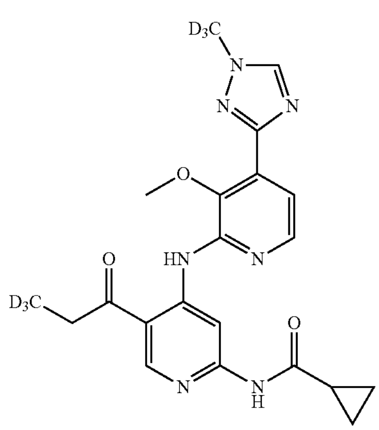 [SMILES: [2H]C([2H])([2H])CC(=O)c1cnc(NC(=O)C2CC2)cc1Nc1nccc(-c2ncn(C([2H])([2H])[2H])n2)c1OC] |
178
-continued
| Ex. | Structure |
|---|---|
| 201 | 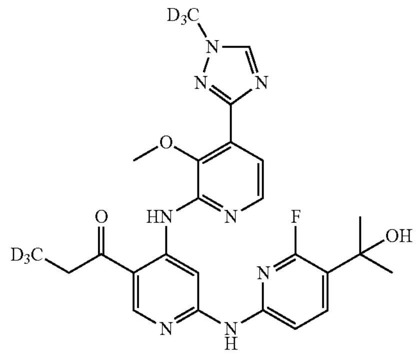 [SMILES: [2H]C([2H])([2H])CC(=O)c1cnc(Nc2ccc(C(C)(C)O)c(F)n2)cc1Nc1nccc(-c2ncn(C([2H])([2H])[2H])n2)c1OC] |
| 202 | 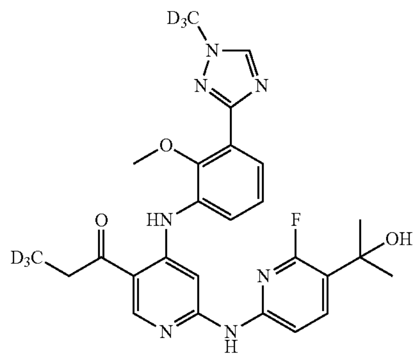 [SMILES: [2H]C([2H])([2H])CC(=O)c1cnc(Nc2ccc(C(C)(C)O)c(F)n2)cc1Nc1cccc(-c2ncn(C([2H])([2H])[2H])n2)c1OC] |
| 203 | 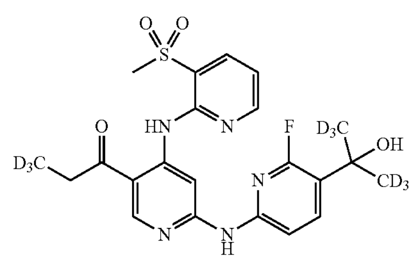 [SMILES: [2H]C([2H])([2H])CC(=O)c1cnc(Nc2ccc(C(O)(C([2H])([2H])[2H])C([2H])([2H])[2H])c(F)n2)cc1Nc1ncccc1S(C)(=O)=O] |
Disclosed herein is a compound, or a pharmaceutically acceptable salt, solvate, or stereoisomer thereof, selected from the group consisting of:
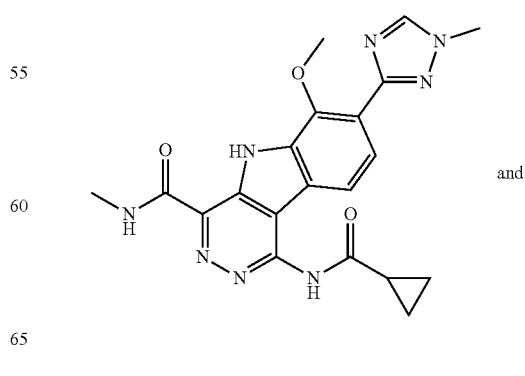
and 179
-continued
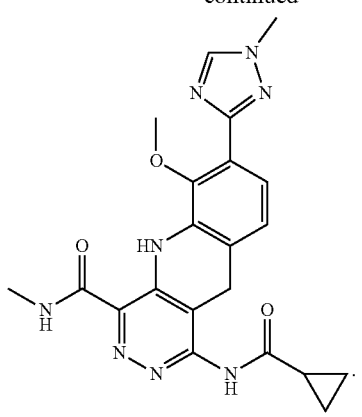
Disclosed herein is a compound, or a pharmaceutically acceptable salt, solvate, or stereoisomer thereof, selected from the group consisting of:
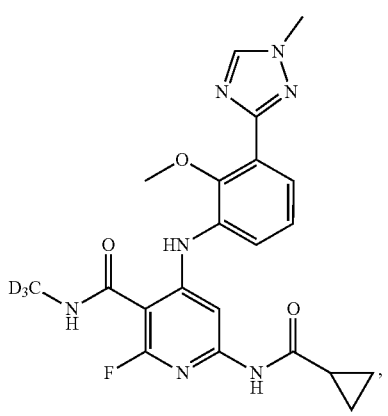
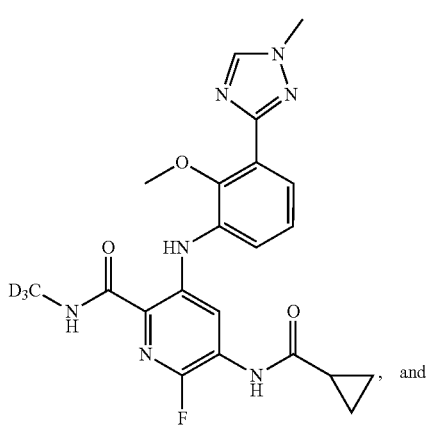
, and
180
-continued
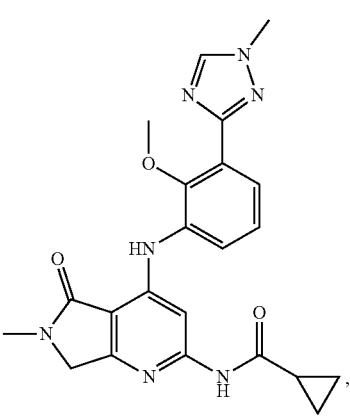
Disclosed herein is a compound, or a pharmaceutically acceptable salt, solvate, or stereoisomer thereof, selected from the group consisting of:
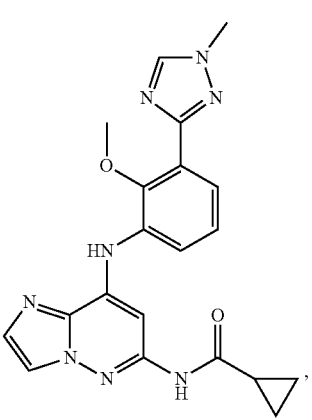
, -continued
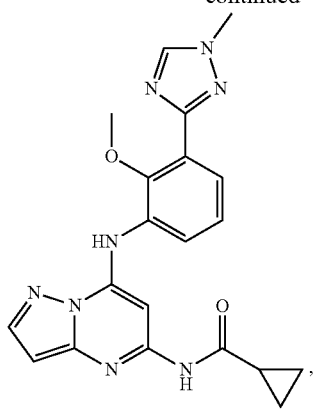
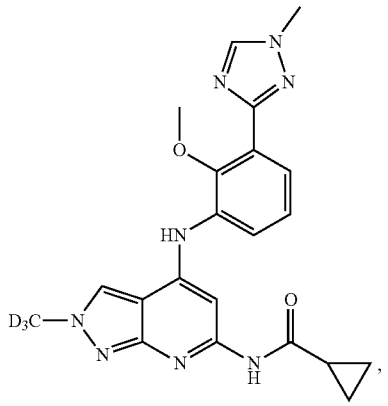
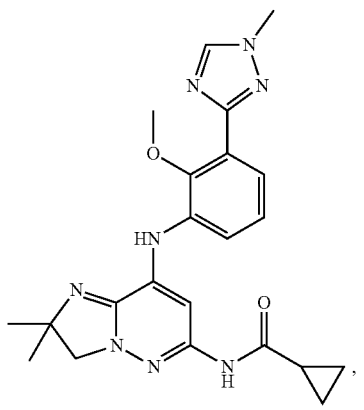
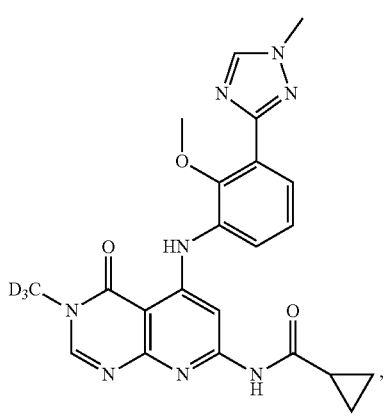
-continued
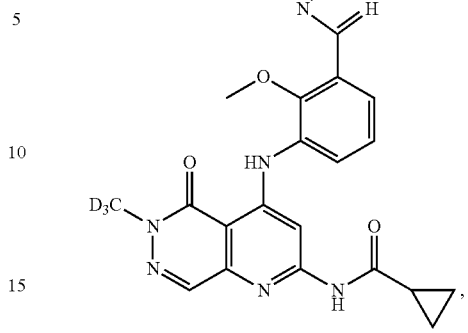
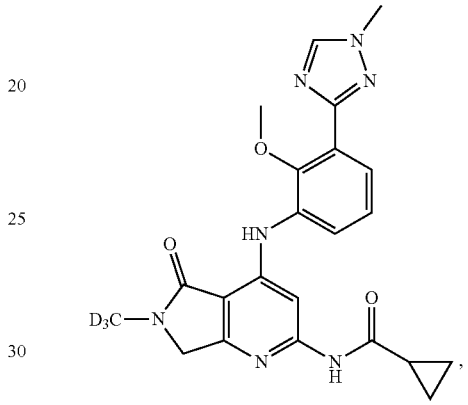
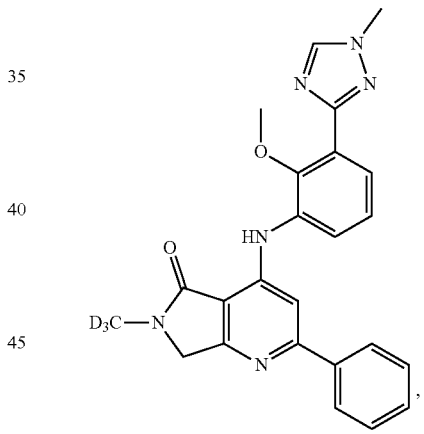
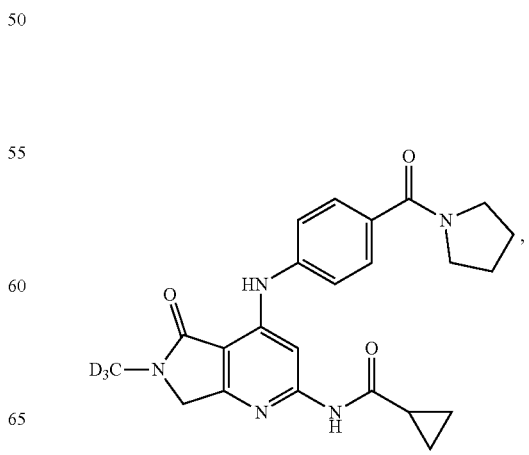

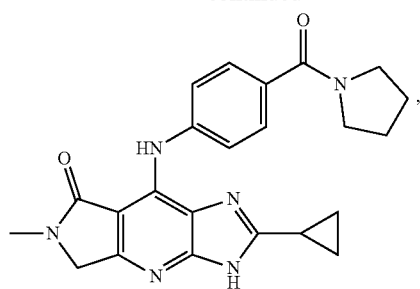
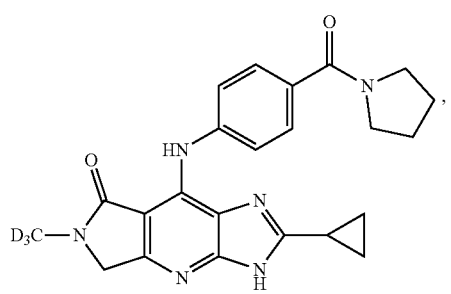
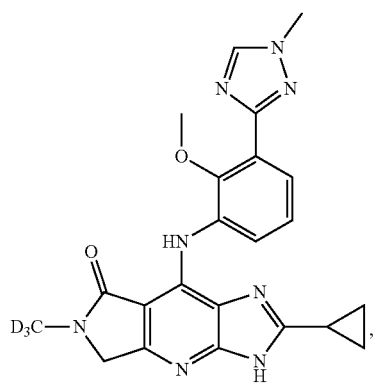
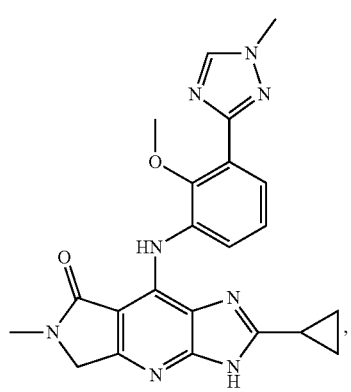
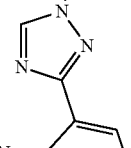
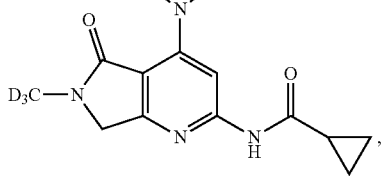
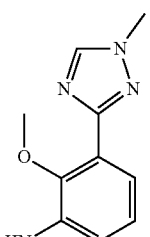
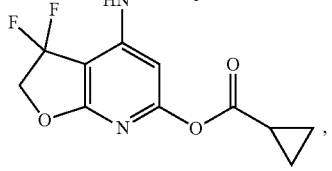
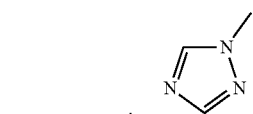
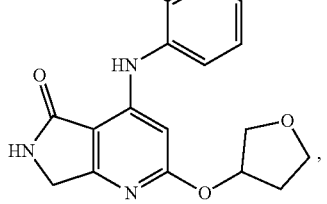
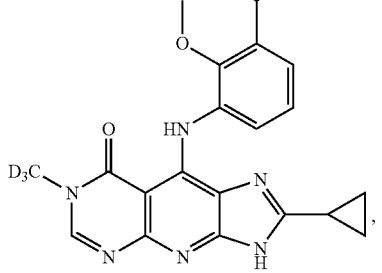

185
-continued
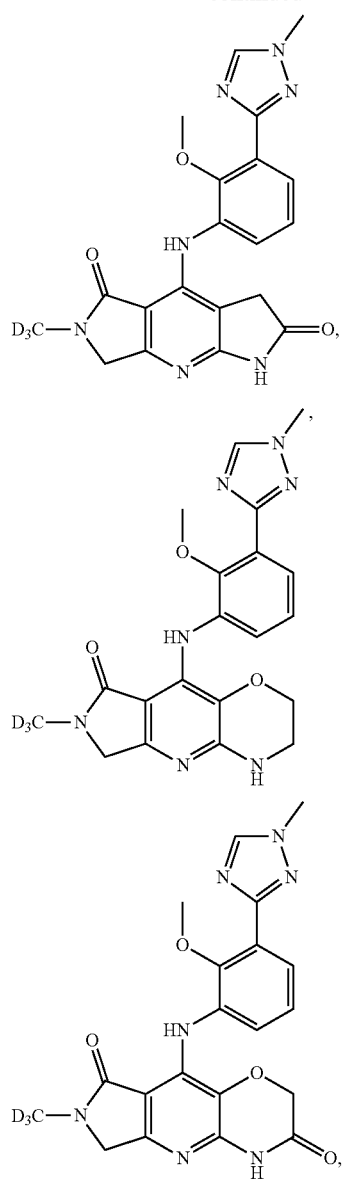
186
-continued
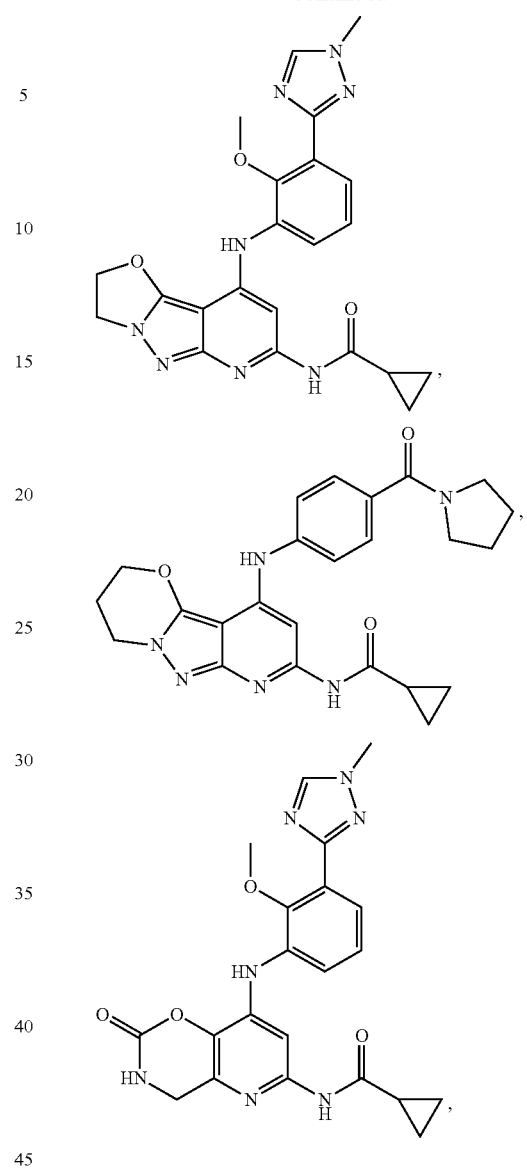
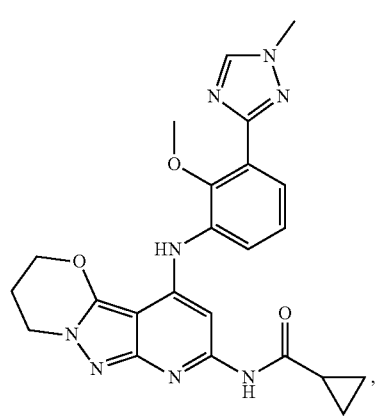
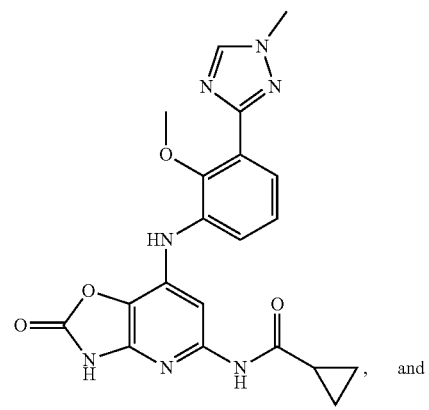, and -continued
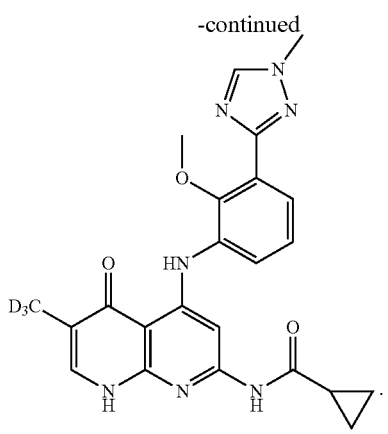
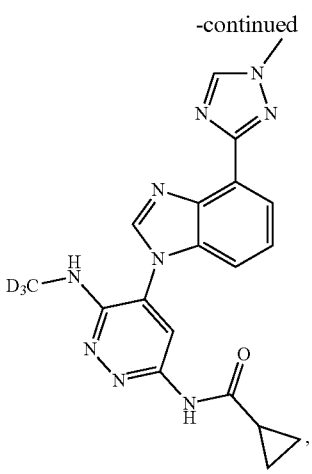
Disclosed herein is a compound, or a pharmaceutically acceptable salt, solvate, or stereoisomer thereof, selected from the group consisting of:
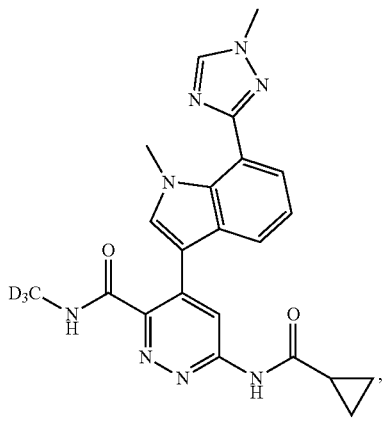
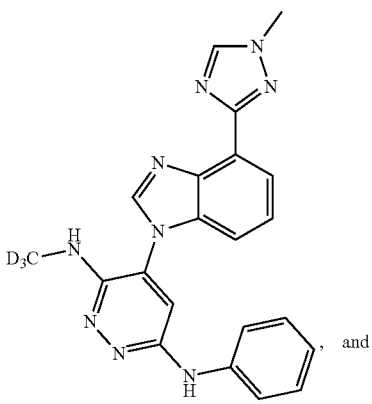
, and
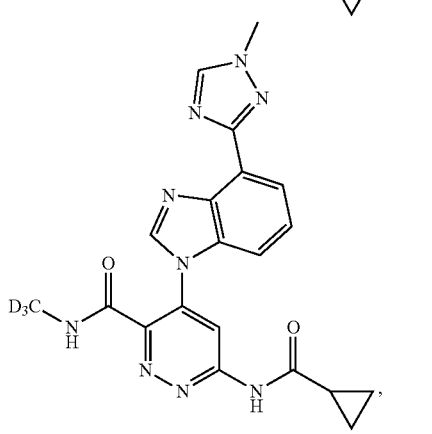
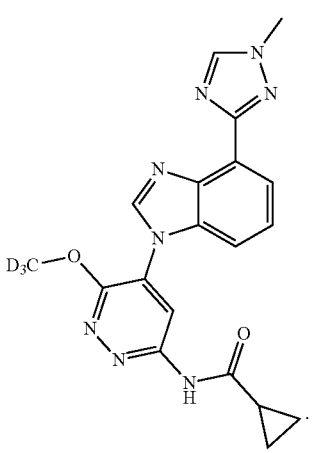
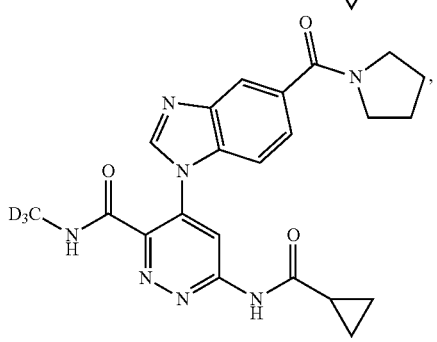
Disclosed herein is a compound, or a pharmaceutically acceptable salt, solvate, or stereoisomer thereof, selected from the group consisting of:

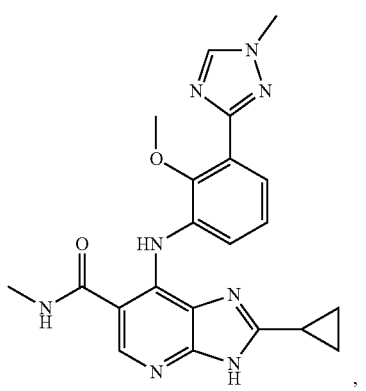
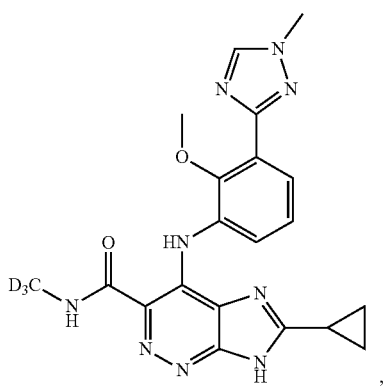
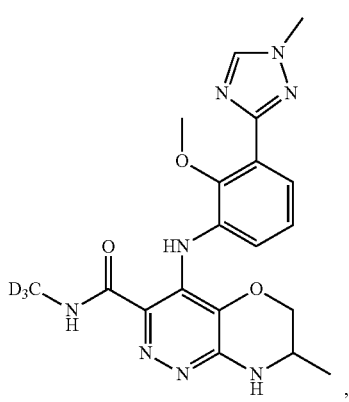
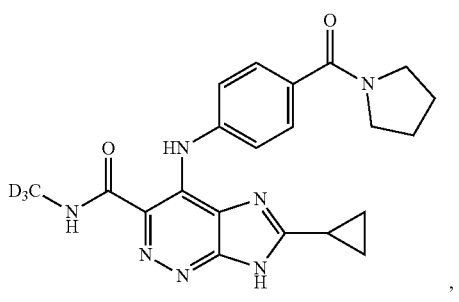
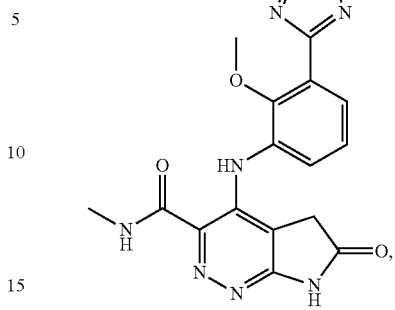
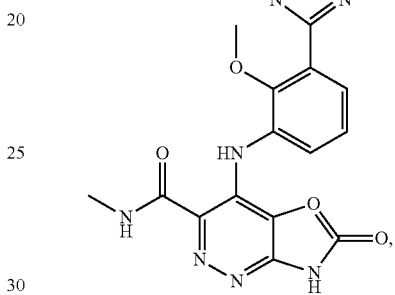
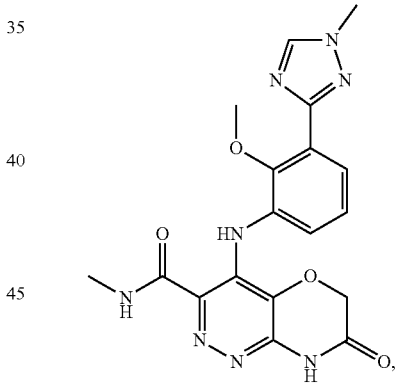

191
-continued
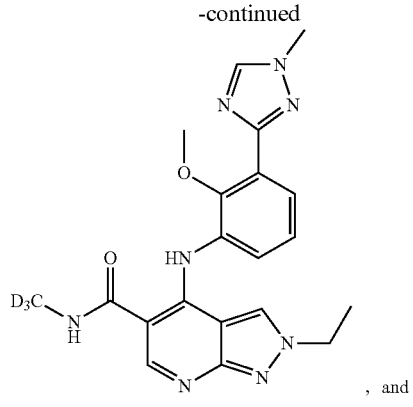
, and
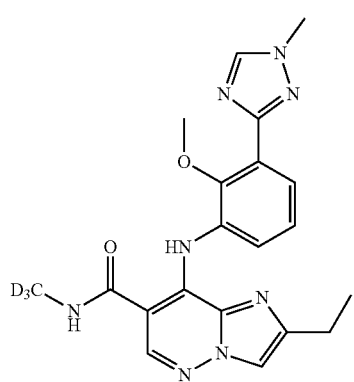
.
Disclosed herein is a compound, or a pharmaceutically acceptable salt, solvate, or stereoisomer thereof, selected from the group consisting of:
,
192
-continued
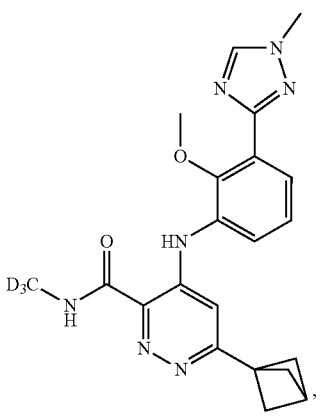
,
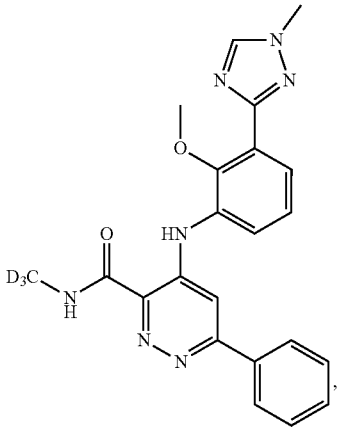
,
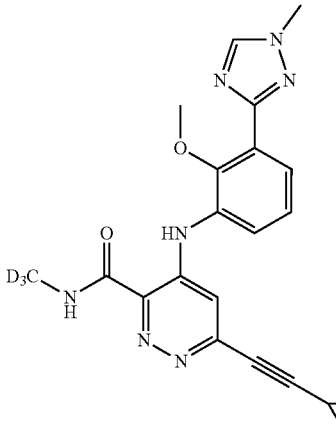
, and
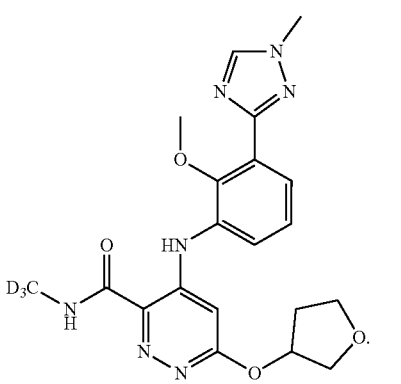 [SMILES: [2H]C([2H])([2H])NC(=O)c1nnc(OC2CCOC2)cc1Nc1cccc(-c2ncn(C)n2)c1OC]
.

Disclosed herein is a compound, or a pharmaceutically acceptable salt, solvate, or stereoisomer thereof, selected from the group consisting of:

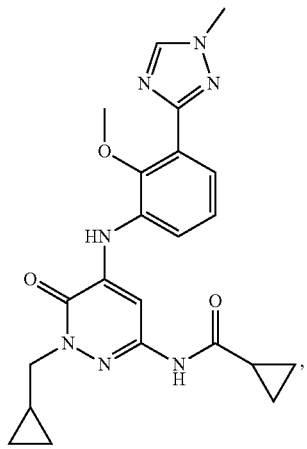

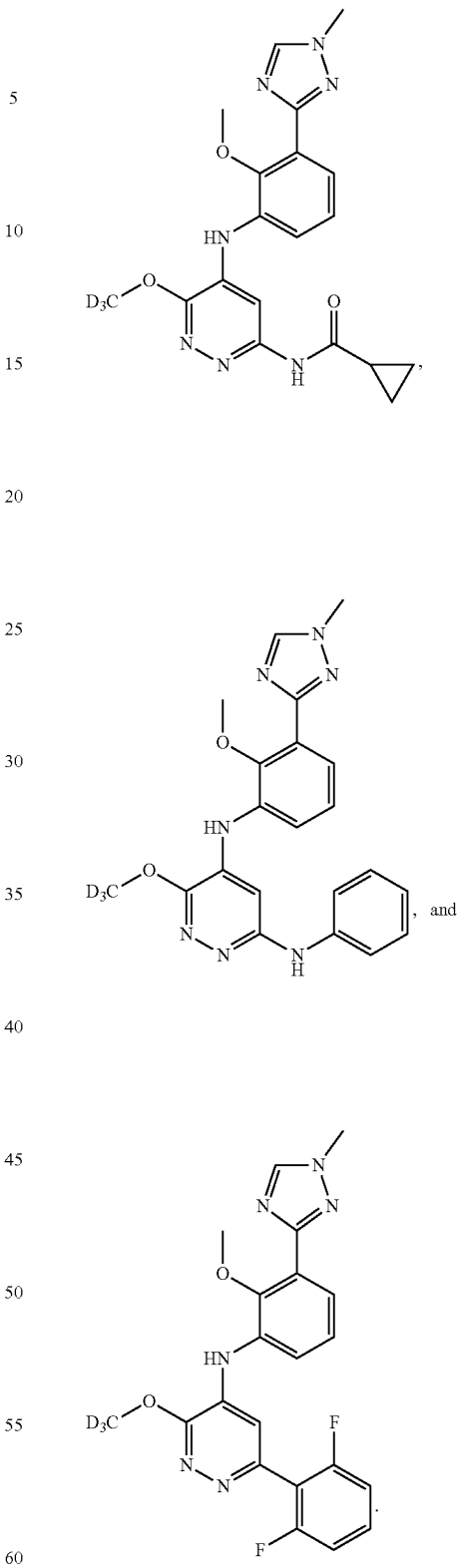

Disclosed herein is a compound, or a pharmaceutically acceptable salt, solvate, or stereoisomer thereof, selected from the group consisting of:

Disclosed herein is a compound, or a pharmaceutically acceptable salt, solvate, or stereoisomer thereof, selected from the group consisting of:

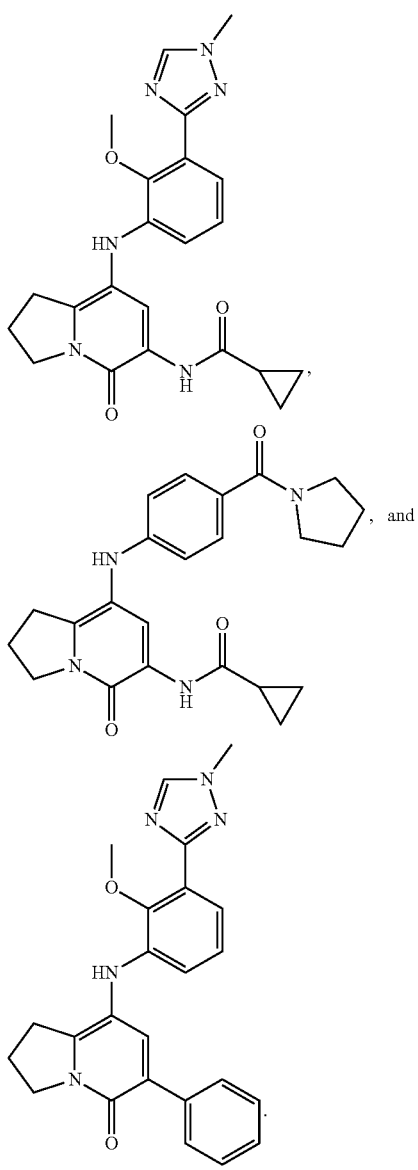
Disclosed herein is a compound, or a pharmaceutically acceptable salt, solvate, or stereoisomer thereof, selected from the group consisting of:
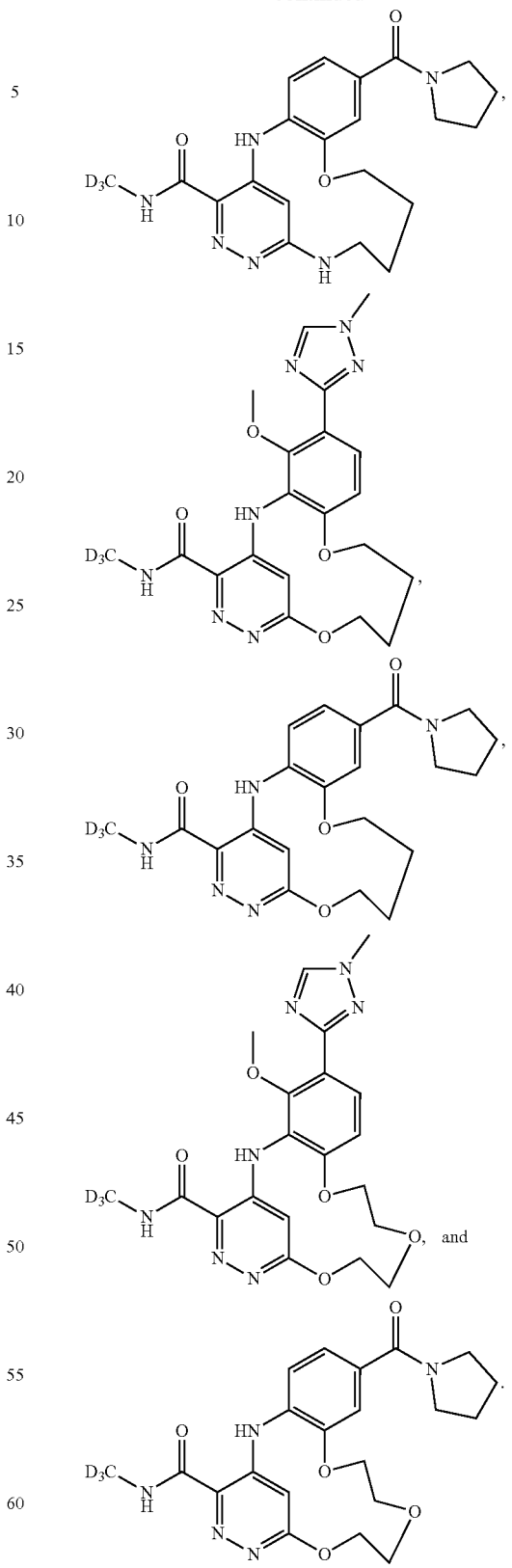
Disclosed herein is a compound, or a pharmaceutically acceptable salt, solvate, or stereoisomer thereof, selected from the group consisting of:

197
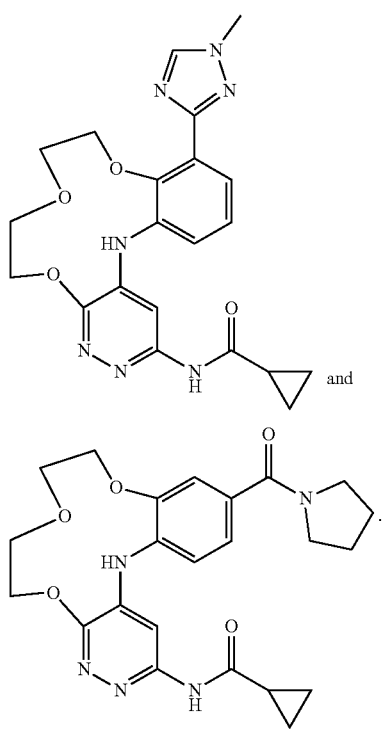
and
Disclosed herein is a compound, or a pharmaceutically acceptable salt, solvate, or stereoisomer thereof, selected from the group consisting of:
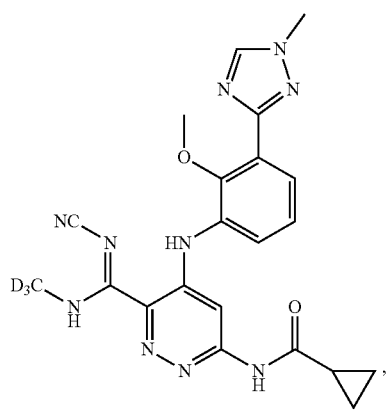
,
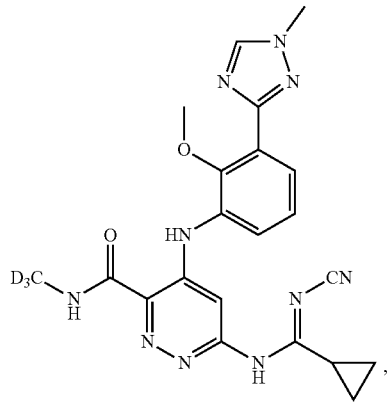
,
198
-continued
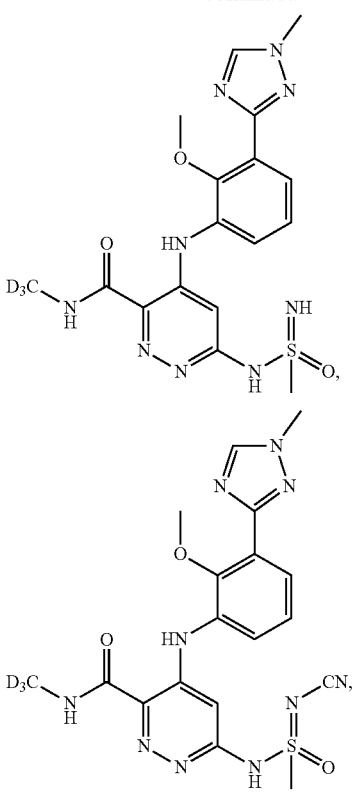
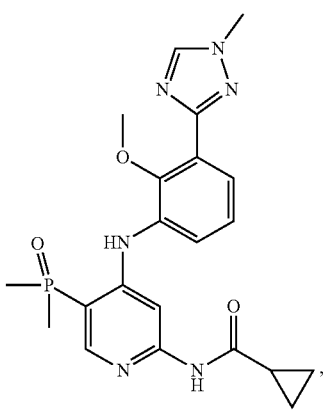
,

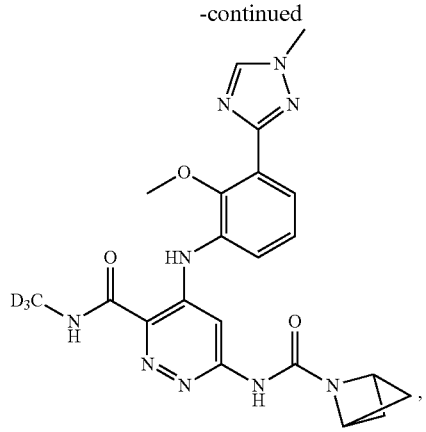
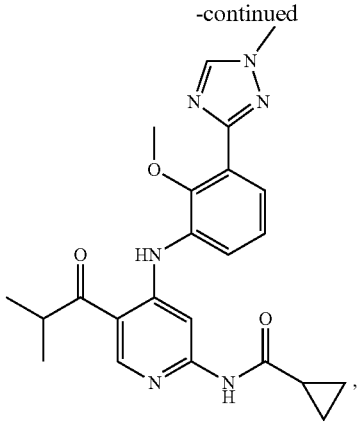
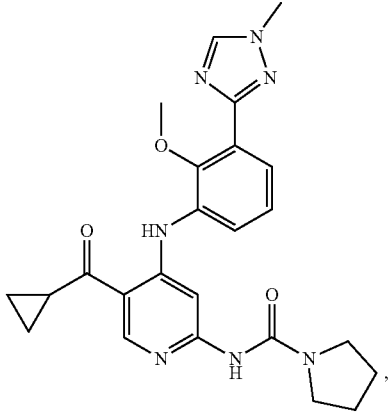
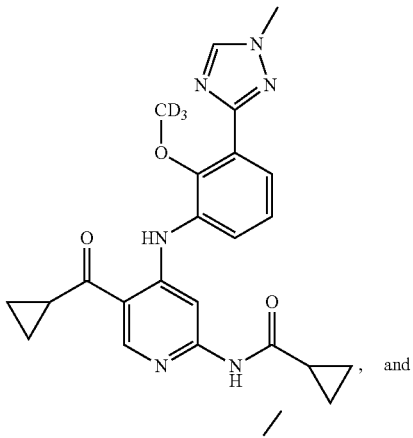, and
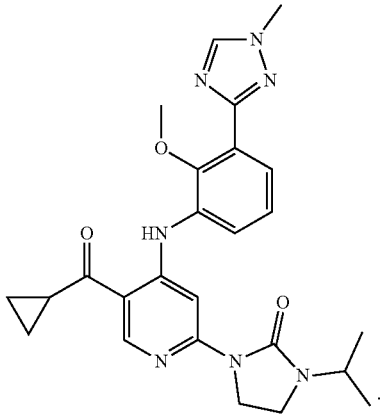
Disclosed herein is a compound, or a pharmaceutically acceptable salt, solvate, or stereoisomer thereof, selected from the group consisting of:

201
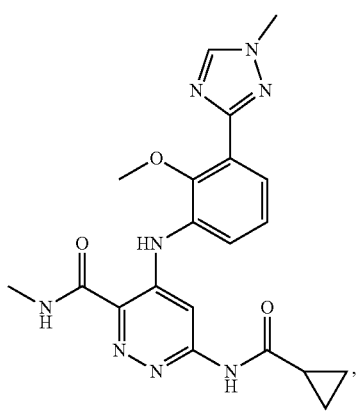
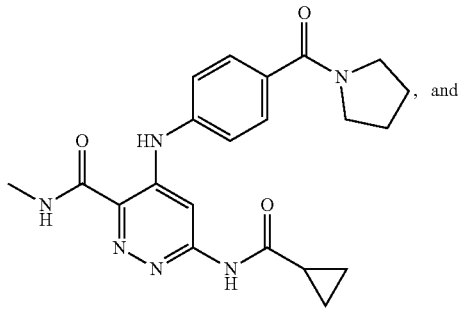, and
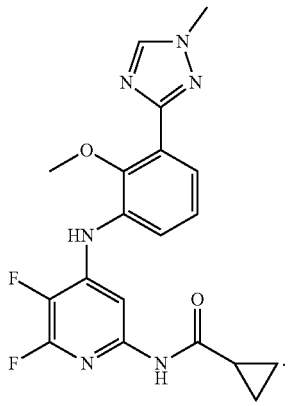.
Disclosed herein is a compound, or a pharmaceutically acceptable salt, solvate, or stereoisomer thereof, selected from the group consisting of:
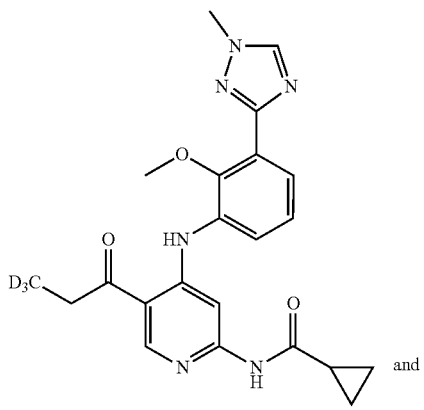 and
202
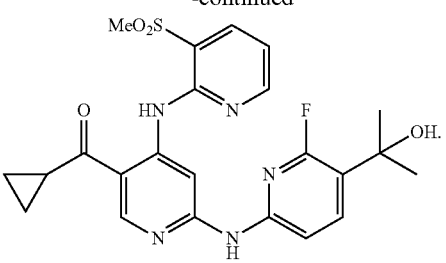
Disclosed herein is a compound, or a pharmaceutically acceptable salt, solvate, or stereoisomer thereof, selected from the group consisting of:
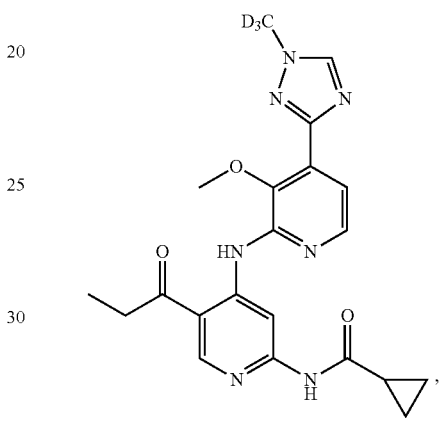, 203
-continued
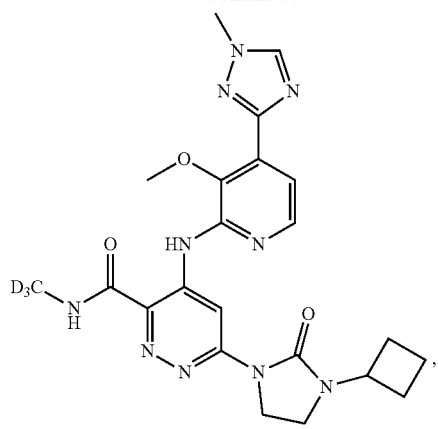
204
-continued
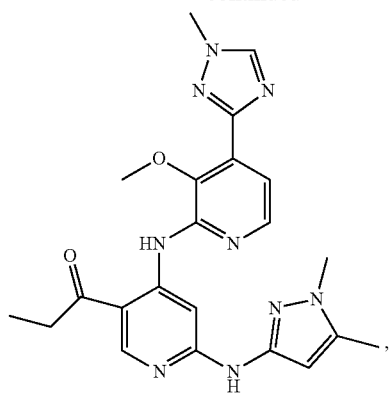
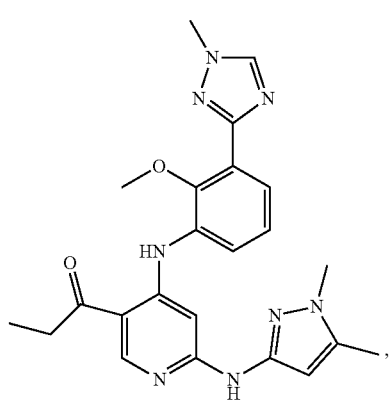
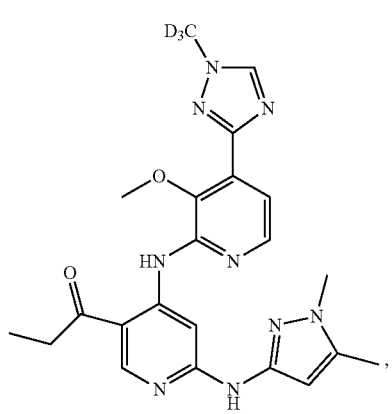
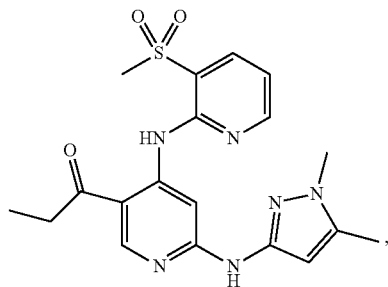

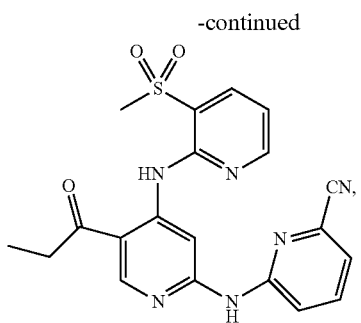
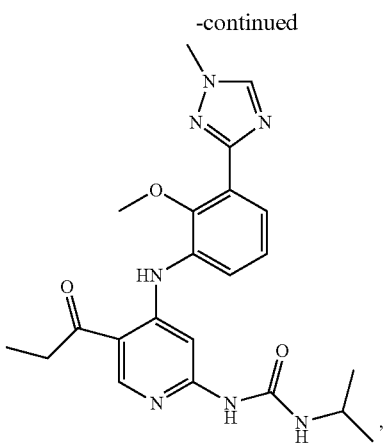
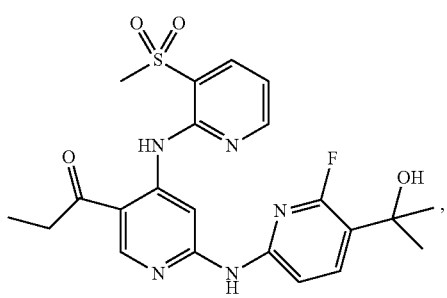
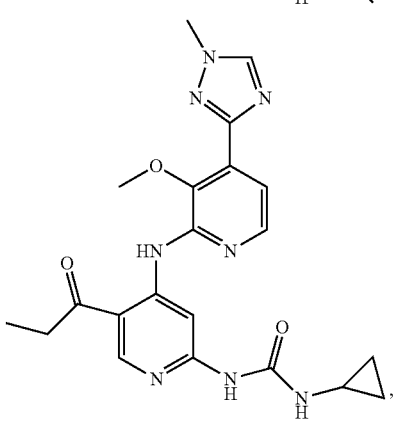
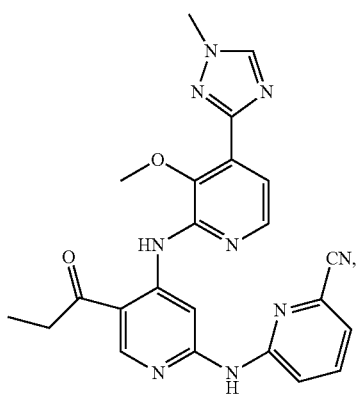
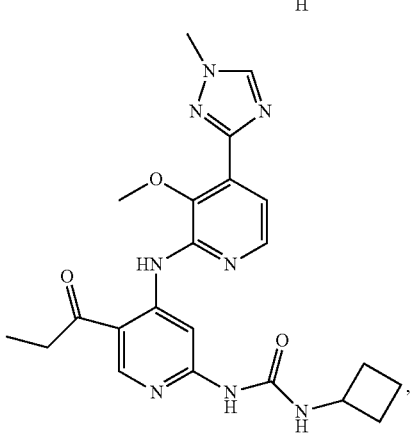
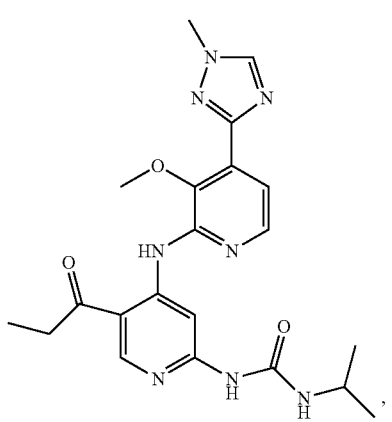
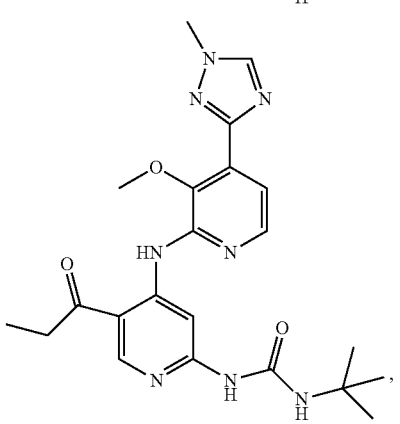

207
-continued
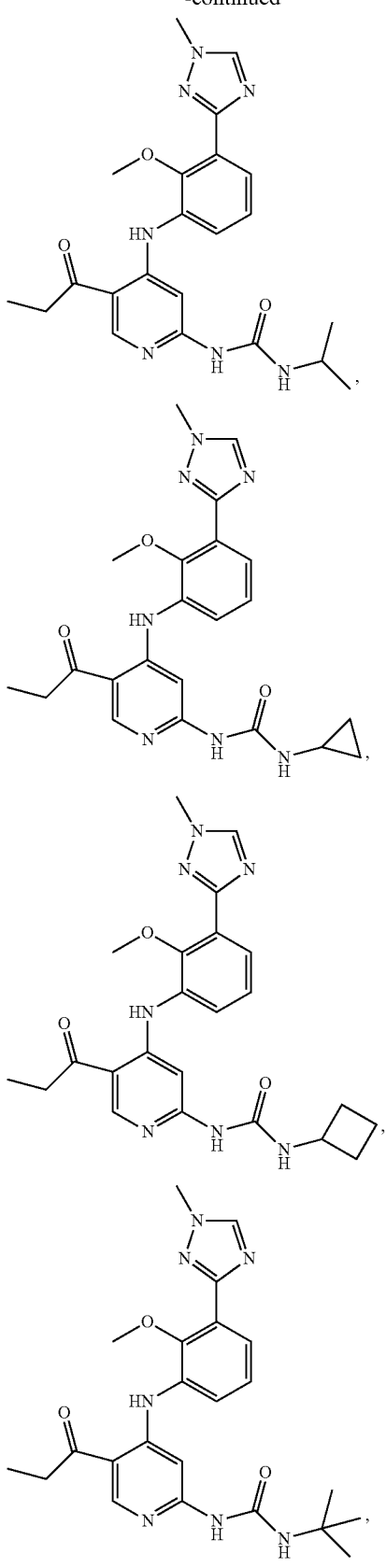
208
-continued
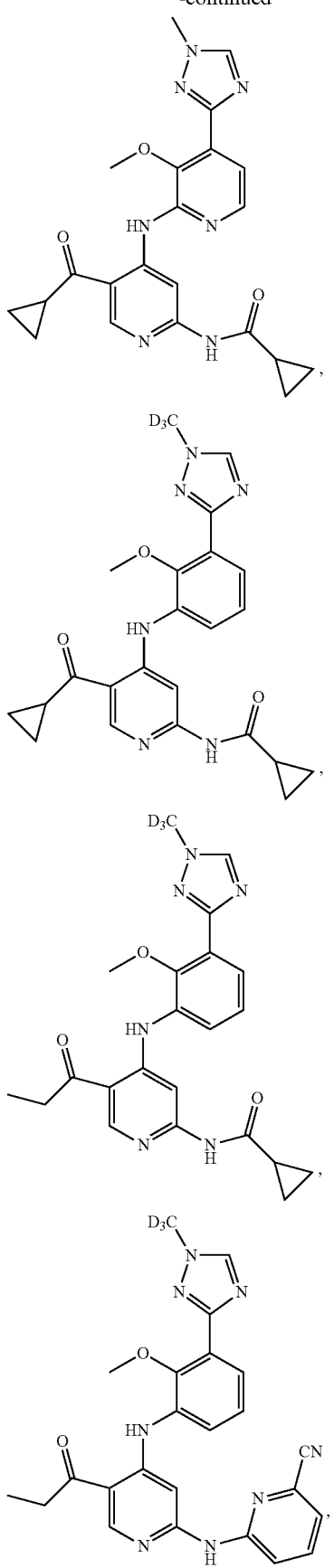

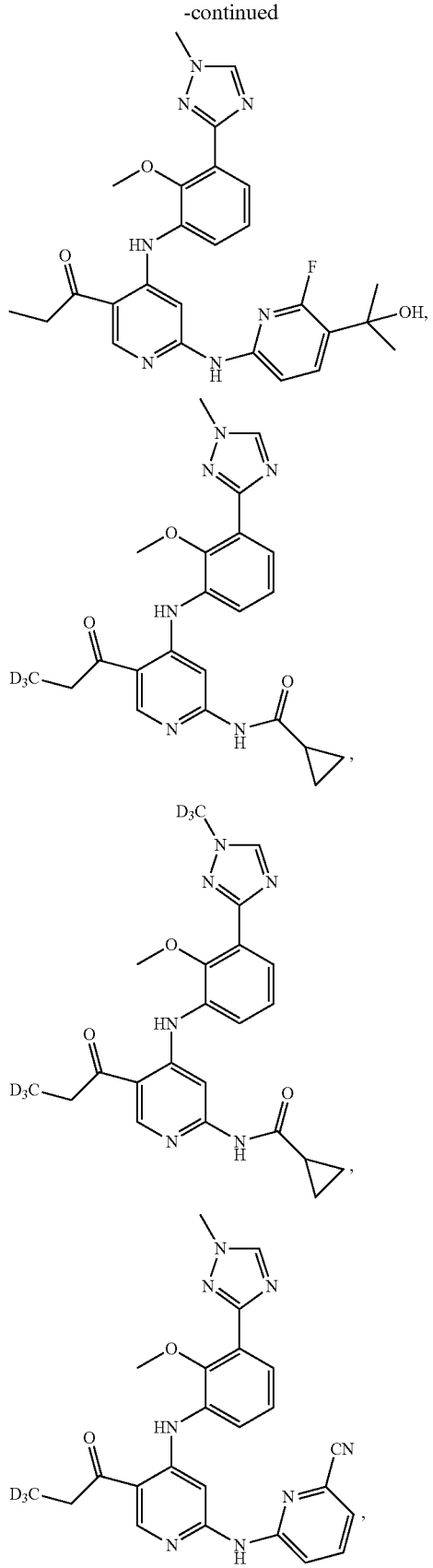
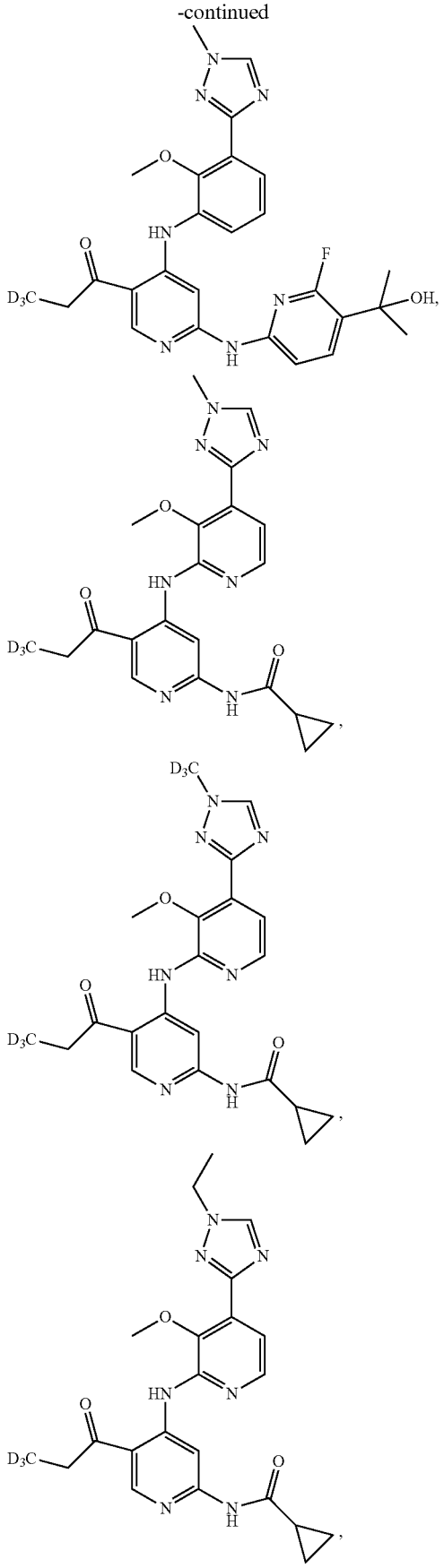

211
-continued
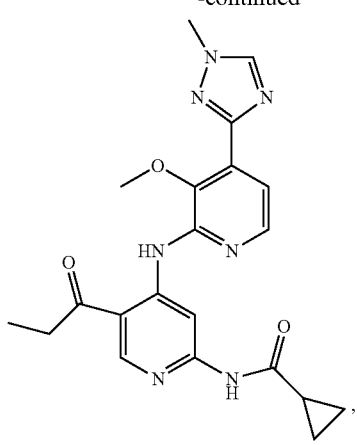
,
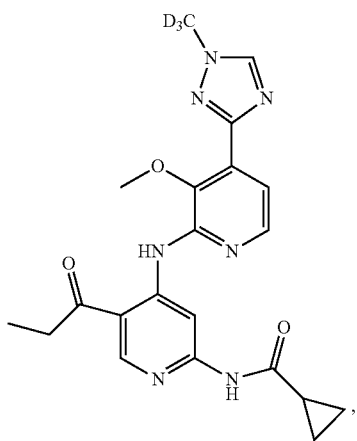 [SMILES: [2H]C([2H])([2H])n1cnc(-c2cccc(Nc3cc(NC(=O)C4CC4)ncc3C(=O)C3CC3)c2OC)n1]
,
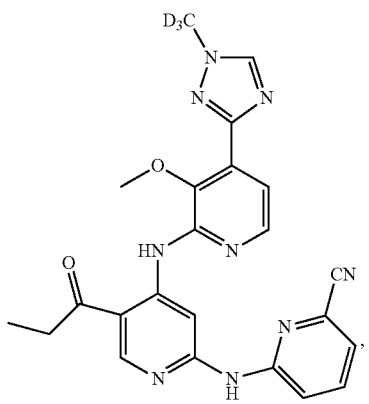
,
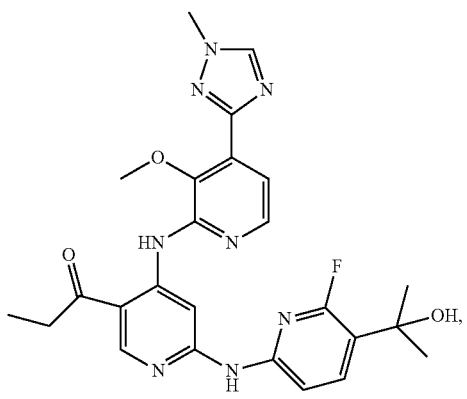
,
212
-continued
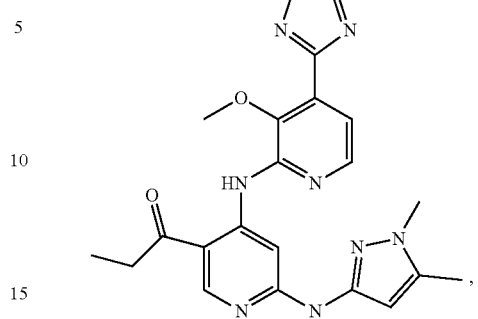
,
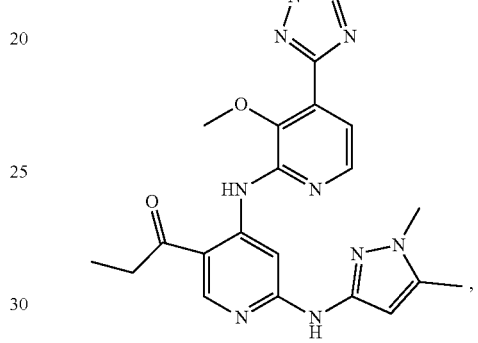
,
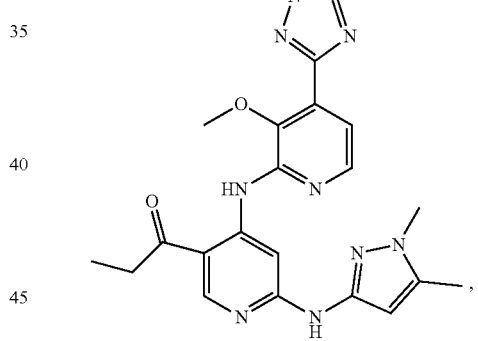
,
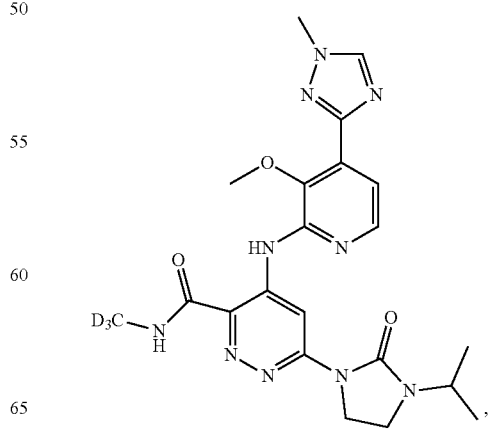
, 213
-continued
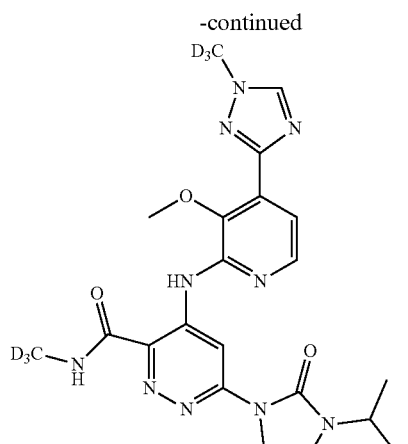
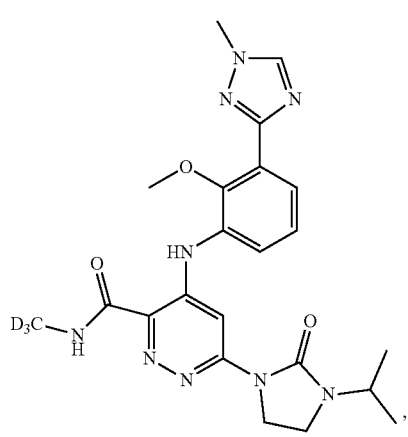
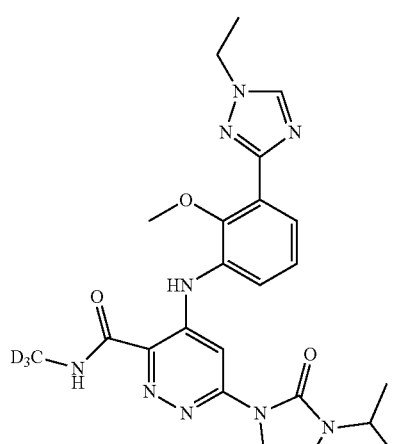
214
-continued
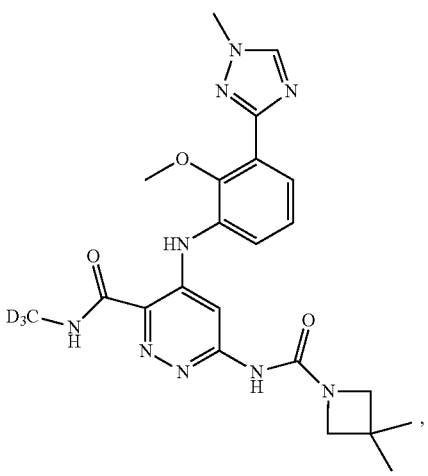
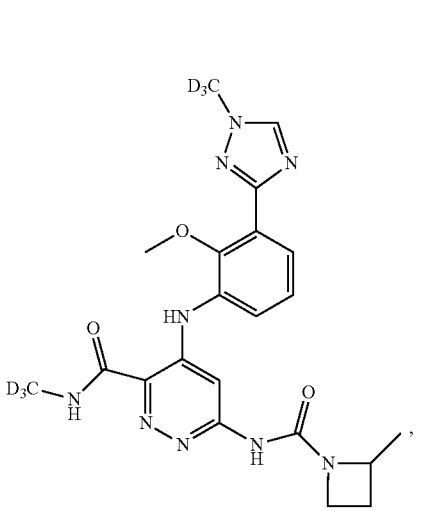

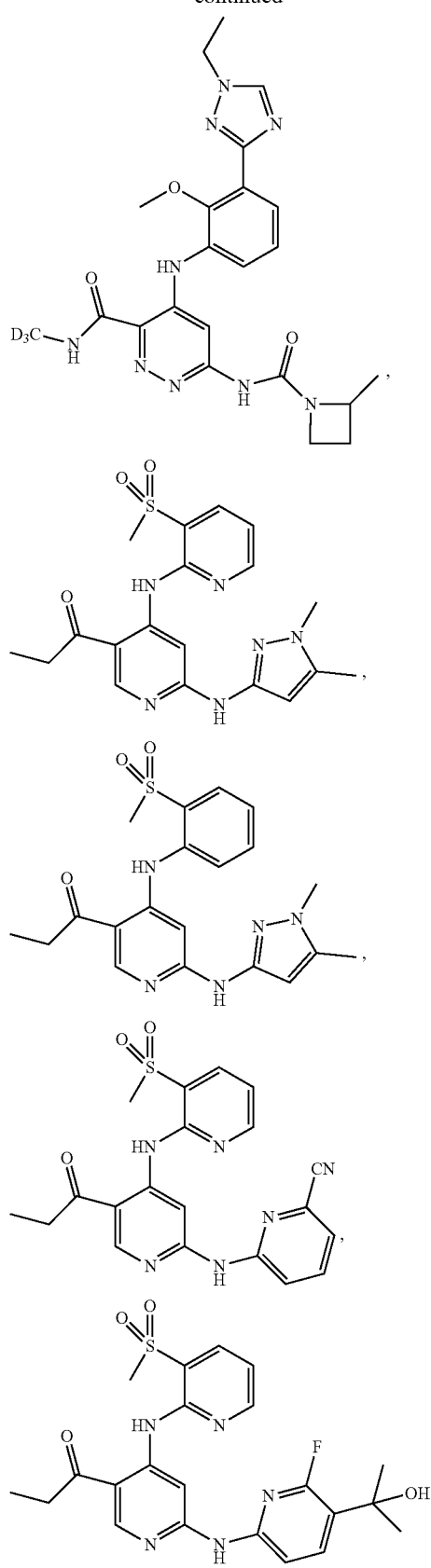
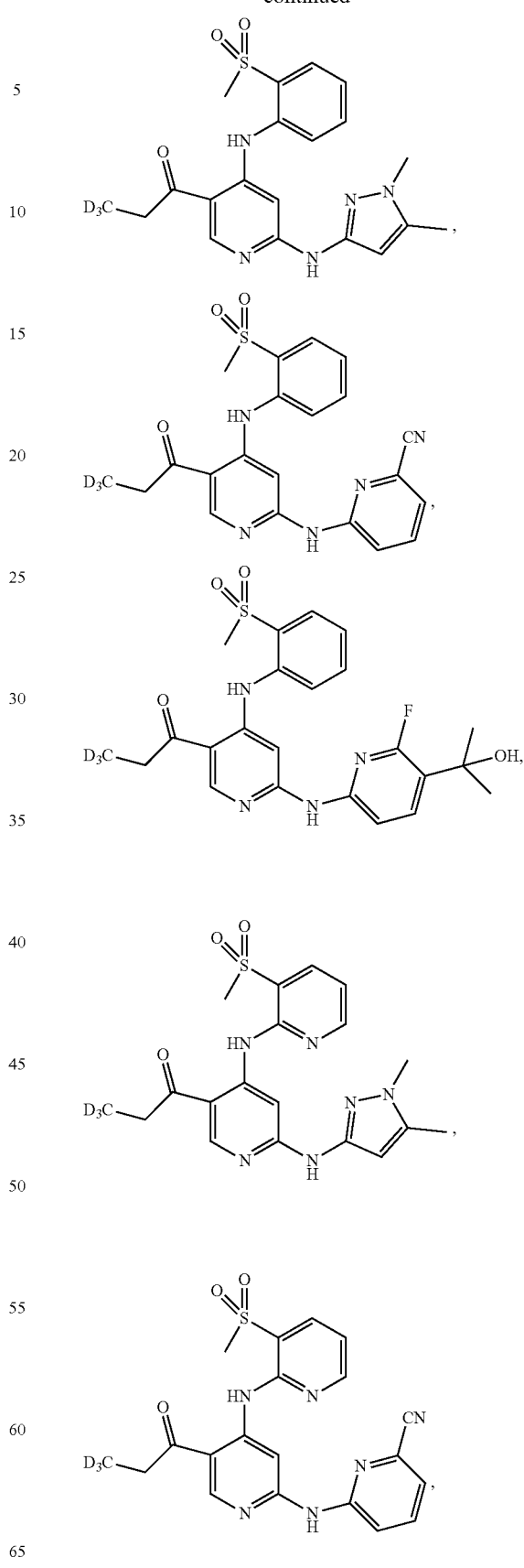

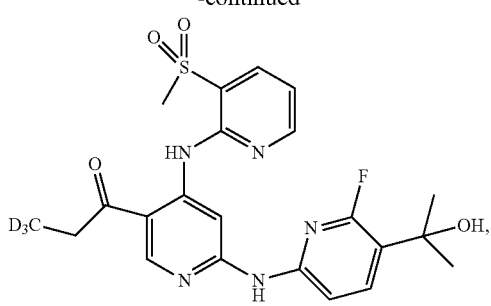
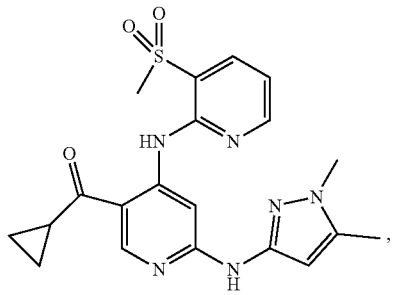
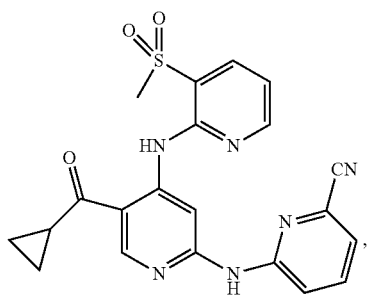
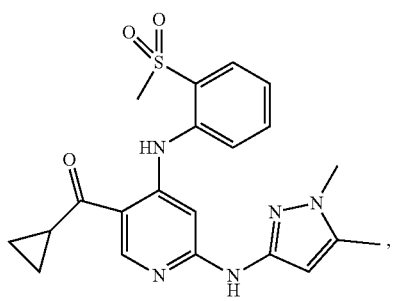
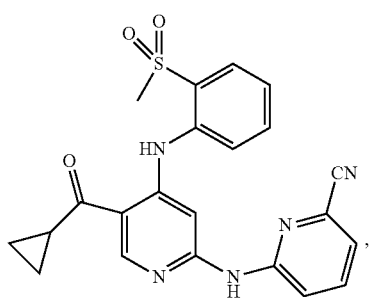
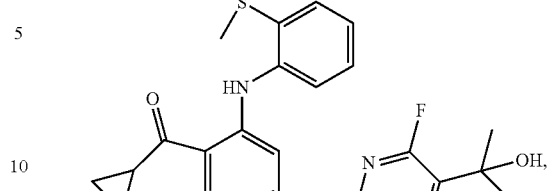
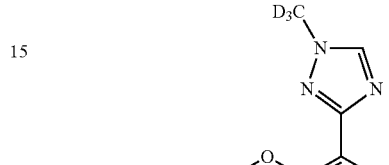
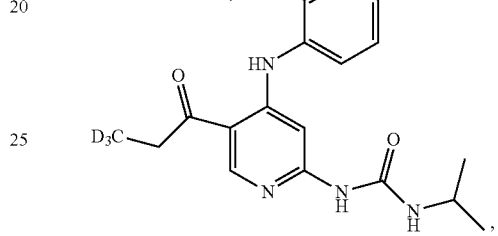
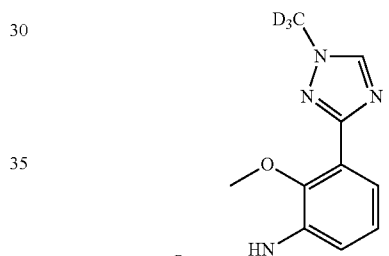
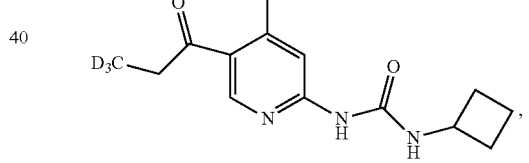
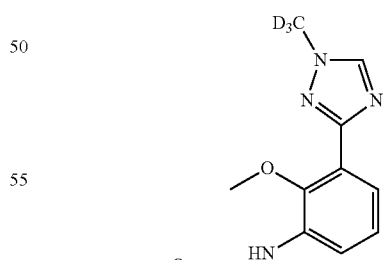
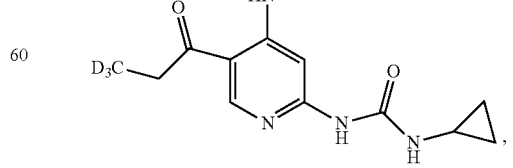

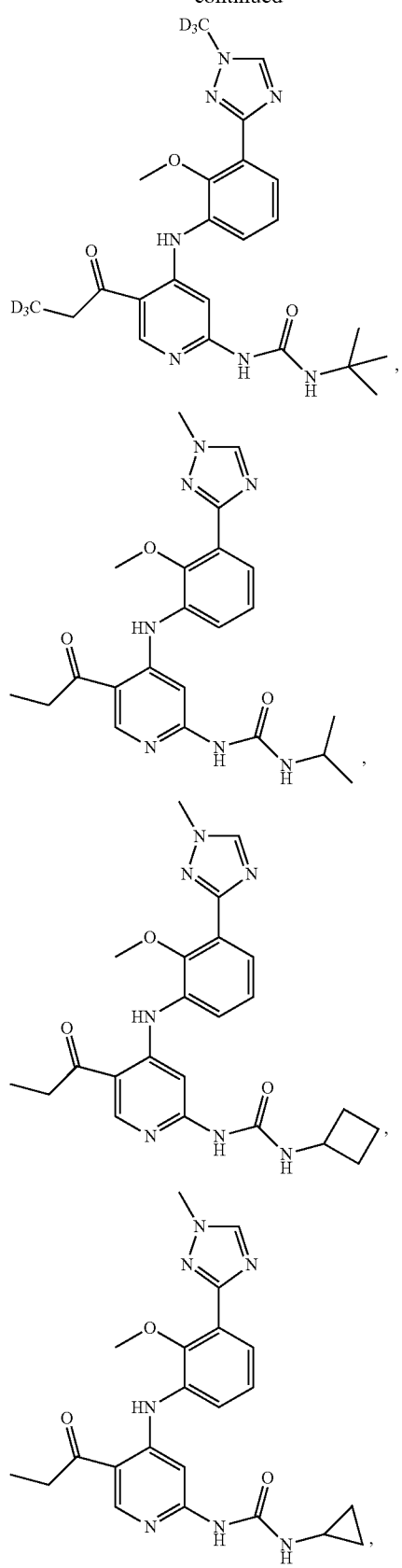
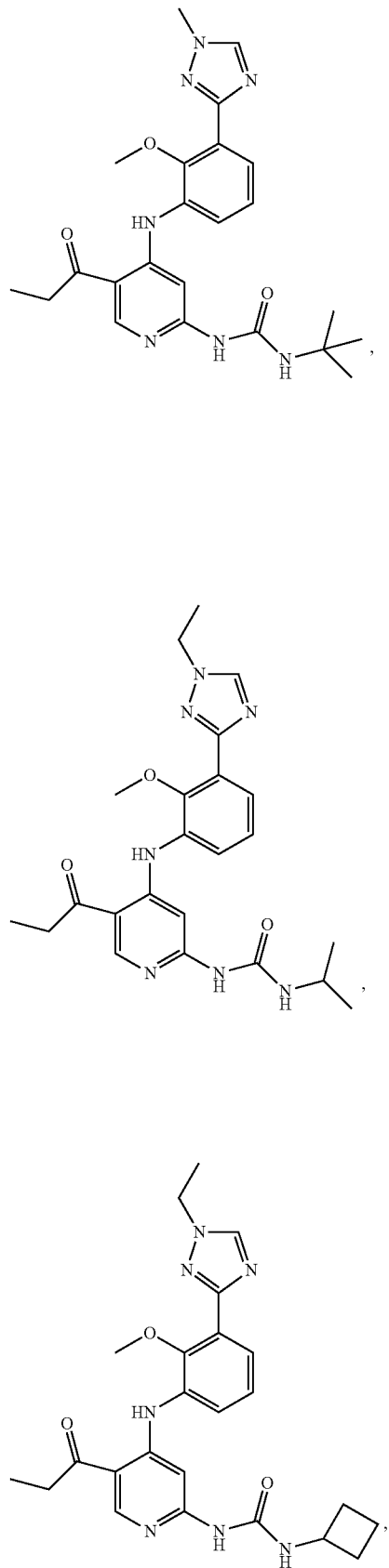

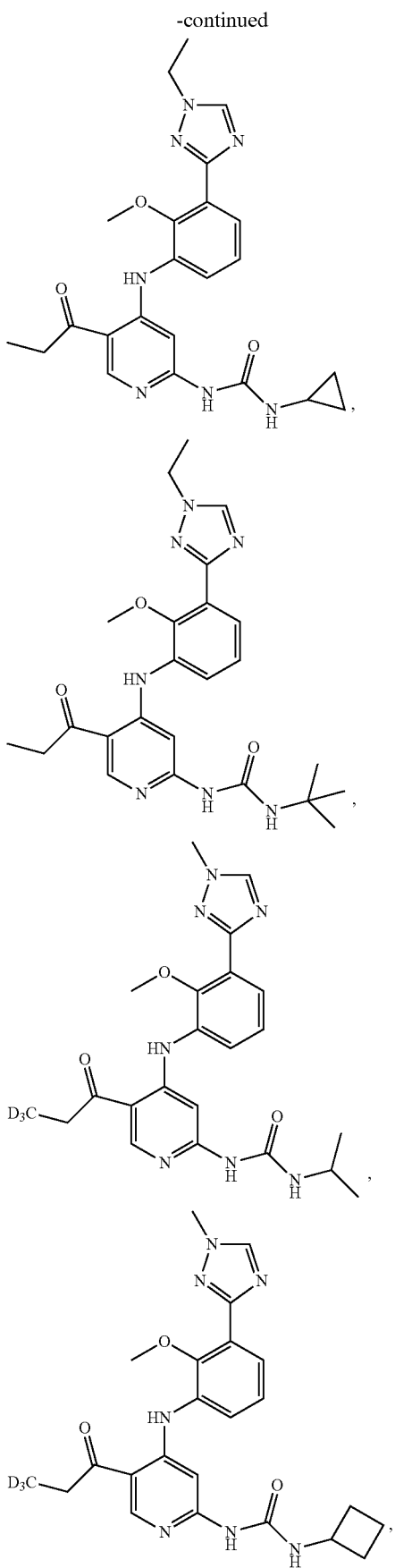
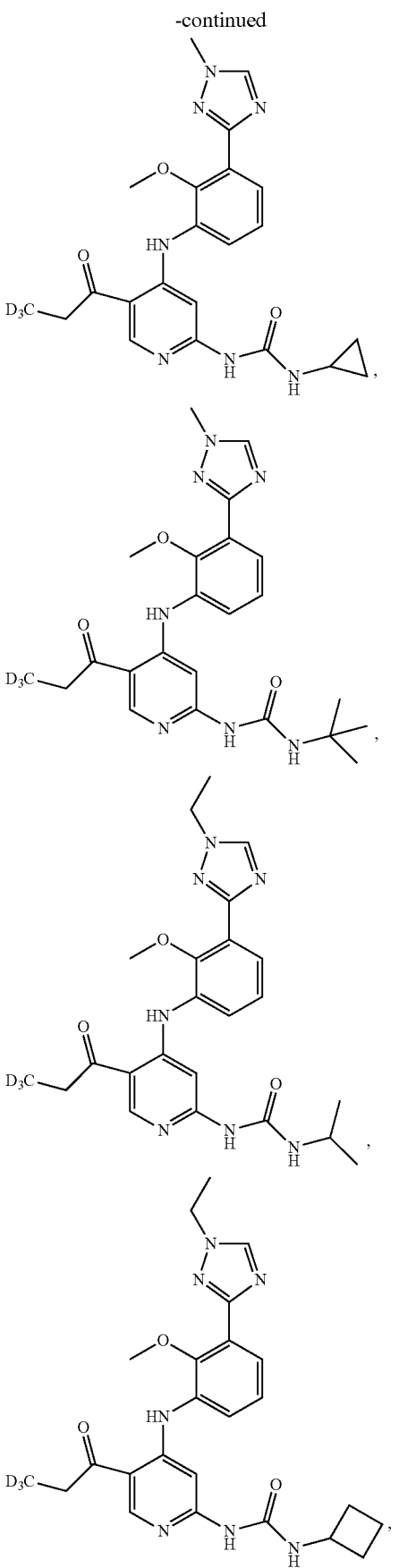

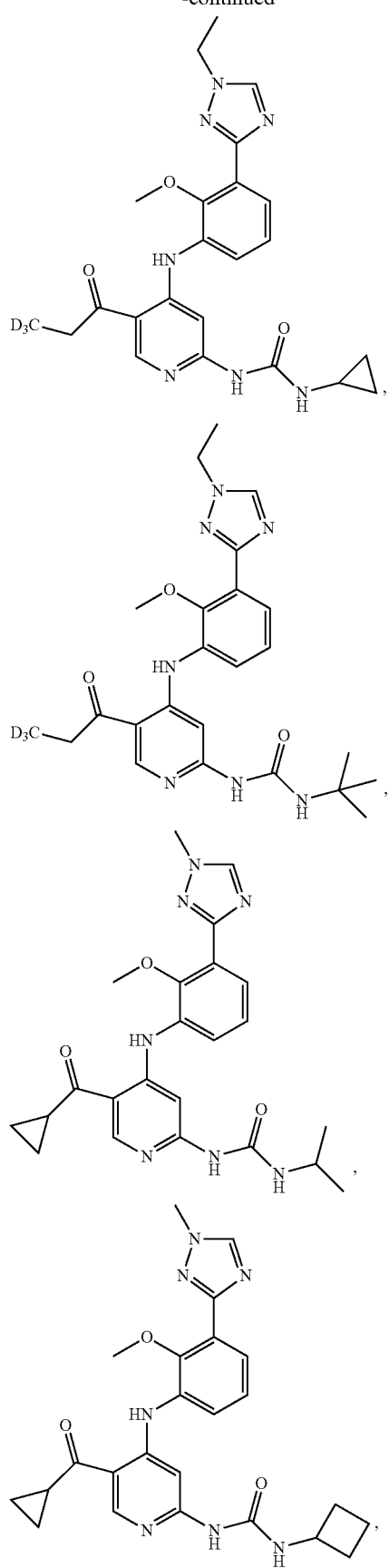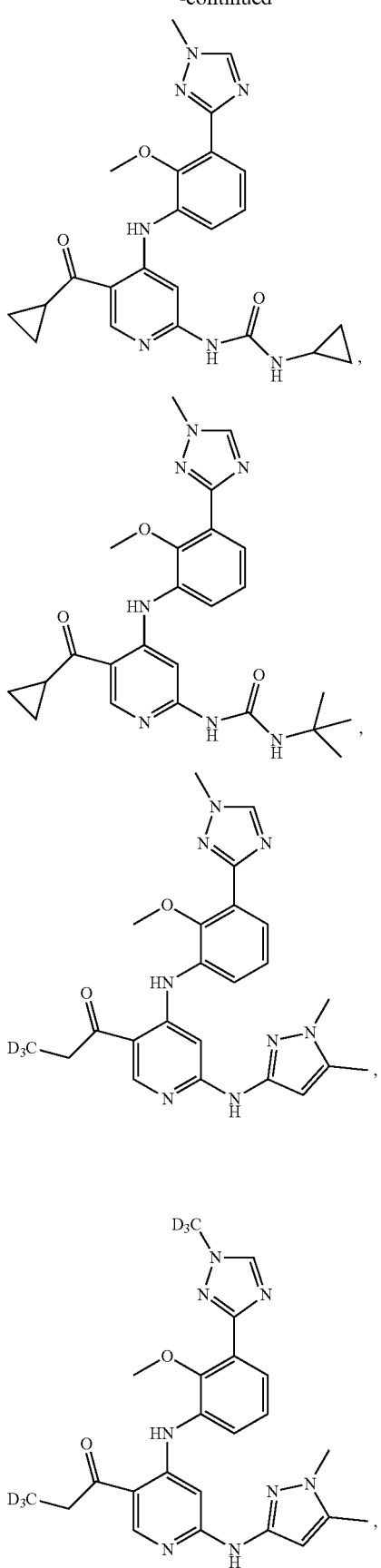

-continued

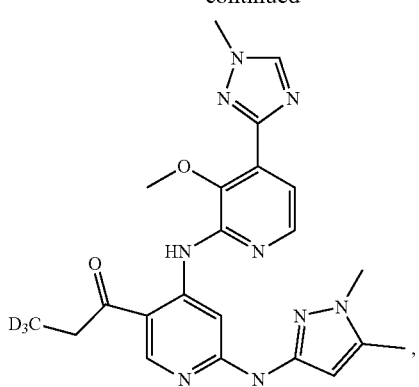

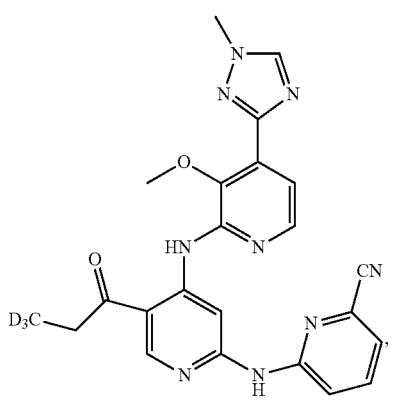

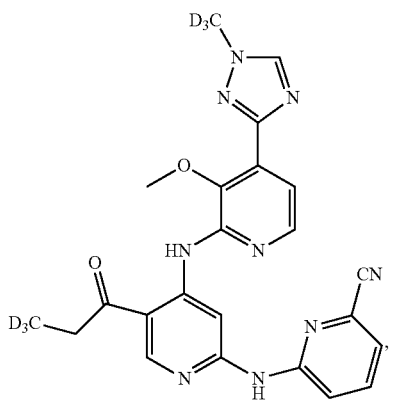

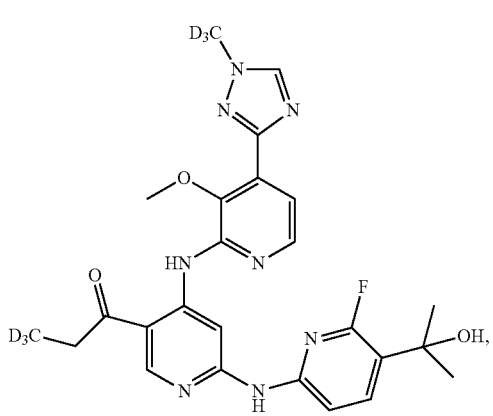

-continued

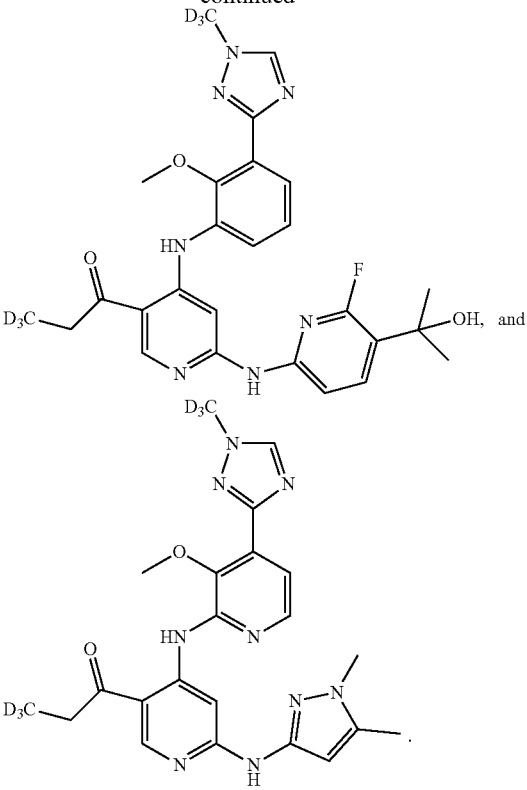

Disclosed herein is a compound, or a pharmaceutically acceptable salt, solvate, or stereoisomer thereof, selected from the group consisting of:

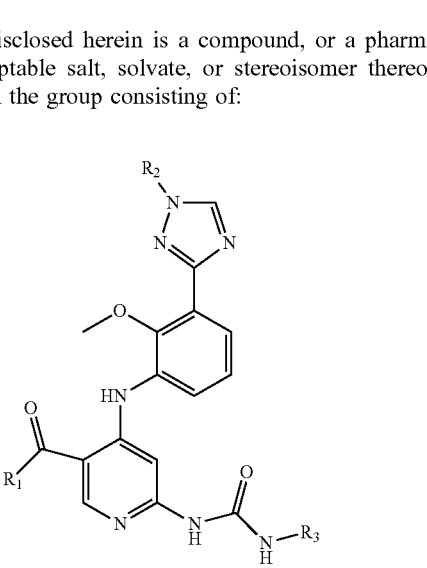

wherein:
R₁=-Et, —CH₂—CD₃, or cyclopropyl;
R₂=Me, CD₃, or Et
R₃=Isopropyl, cyclobutyl, cyclopropyl, or t-butyl.

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this disclosure. Certain isotopically-labeled compounds, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, or sulfate of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\ alkyl)_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH, Inc. (Toronto, Canada), Bionet (Cornwall, U.K.), Chem Service Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line. Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the compound described herein is administered as a pure chemical. In some embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, $21^{st}$ Ed. Mack Pub. Co., Easton, PA (2005)).

Accordingly, provided herein is a pharmaceutical composition comprising a compound described herein, or a pharmaceutically acceptable salt, solvate, or stereoisomer thereof, and a pharmaceutically acceptable excipient.

In certain embodiments, the compound provided herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

In some embodiments, the pharmaceutical composition is formulated for oral, topical (including buccal and sublingual), rectal, vaginal, transdermal, parenteral, intrapulmonary, intradermal, intrathecal and epidural and intranasal administration. Parenteral administration includes intramuscular, intravenous, intraarterial, intraperitoneal, or subcutaneous administration. In some embodiments, the pharmaceutical composition is formulated for intravenous injection, oral administration, inhalation, nasal administration, topical administration, or ophthalmic administration. In some embodiments, the pharmaceutical composition is formulated for oral administration. In some embodiments, the pharmaceutical composition is formulated for intravenous injection. In some embodiments, the pharmaceutical composition is formulated as a tablet, a pill, a capsule, a liquid, an inhalant, a nasal spray solution, a suppository, a suspension, a gel, a colloid, a dispersion, a suspension, a solution, an emulsion, an ointment, a lotion, an eye drop, or an ear drop. In some embodiments, the pharmaceutical composition is formulated as a tablet.

Suitable doses and dosage regimens are determined by conventional range-finding techniques known to those of ordinary skill in the art. Generally, treatment is initiated with smaller dosages that are less than the optimum dose of the compound disclosed herein. Thereafter, the dosage is increased by small increments until the optimum effect under the circumstances is reached. In some embodiments, the present method involve the administration of about 0.1 µg to about 50 mg of at least one compound described herein per kg body weight of the subject. For a 70 kg patient, dosages of from about 10 µg to about 200 mg of the compound disclosed herein would be more commonly used, depending on a subject's physiological response.

By way of example only, the dose of the compound described herein for methods of treating a disease as described herein is about 0.001 to about 1 mg/kg body weight of the subject per day, for example, about 0.001 mg, about 0.002 mg, about 0.005 mg, about 0.010 mg, 0.015 mg, about 0.020 mg, about 0.025 mg, about 0.050 mg, about 0.075 mg, about 0.1 mg, about 0.15 mg, about 0.2 mg, about 0.25 mg, about 0.5 mg, about 0.75 mg, or about 1 mg/kg body weight per day. In some embodiments, the dose of compound described herein for the described methods is about 1 to about 1000 mg/kg body weight of the subject being treated per day, for example, about 1 mg, about 2 mg, about 5 mg, about 10 mg, about 15 mg, about 20 mg, about 25 mg, about 50 mg, about 75 mg, about 100 mg, about 150 mg, about 200 mg, about 250 mg, about 500 mg, about 750 mg, or about 1000 mg per day.

Methods of Treatment

The compounds disclosed herein, or pharmaceutically acceptable salts, solvates, or stereoisomers thereof, are useful for the inhibition of kinase activity of one or more enzymes. In some embodiments the kinase inhibited by the compounds and methods is TYK2.

Provided herein are compounds that are inhibitors of TYK2 and are therefore useful for treating one or more disorders associated with activity of TYK2 or mutants thereof.

Provided herein are methods for treating a disease or disorder, wherein the disease or disorder is an autoimmune disorders, inflammatory disorders, proliferative disorders, endocrine disorders, neurological disorders, or disorders associated with transplantation, said method comprising administering to a patient in need thereof, a pharmaceutical composition comprising an effective amount of a compound described herein, or a pharmaceutically acceptable salt, solvate, or stereoisomer thereof.

In some embodiments, the disease or disorder is an autoimmune disorder. In some embodiments the disease or disorder is selected from type 1 diabetes, systemic lupus erythematosus, multiple sclerosis, psoriasis, Behçet's disease, POEMS syndrome, Crohn's disease, ulcerative colitis, and inflammatory bowel disease.

In some embodiments, the disease or disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, inflammatory bowel disease.

In some embodiments, the disease or disorder is a proliferative disorder. In some embodiments, the proliferative disorder is a hematological cancer. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments the proliferative disorder is polycythemia vera, myelofibrosis, essential or thrombocytosis.

In some embodiments, the disease or disorder is an endocrine disorder. In some embodiments, the endocrine disorder is polycystic ovary syndrome, Crouzon's syndrome, or type 1 diabetes.

In some embodiments, the disease or disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH2 domain, or the kinase domain. In some embodiments the activating mutation in TYK2 is selected from G36D, S47N, R425H, V731I, E957D, and R1027H.

In some embodiments, the disease or disorder is associated with transplantation. In some embodiments the disease or disorder associated with transplantation is transplant rejection, or graft versus host disease.

In some embodiments the disease or disorder is associated with type I interferon, IL-10, IL-12, or IL-23 signaling. In some embodiments the disease or disorder is associated with type I interferon signaling. In some embodiments the disease or disorder is associated with IL-10 signaling. In some embodiments the disorder is associated with IL-12 signaling. In some embodiments the disease or disorder is associated with IL-23 signaling.

Provided herein are methods for treating an inflammatory or allergic condition of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Provided herein are methods for treating other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease is acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), or osteoarthritis.

In some embodiments the inflammatory disease is a Th1 or Th17 mediated disease. In some embodiments the Th17 mediated disease is selected from Systemic lupus erythematosus, Multiple sclerosis, and inflammatory bowel disease (including Crohn's disease or ulcerative colitis).

In some embodiments the inflammatory disease is Sjogren's syndrome, allergic disorders, osteoarthritis, conditions of the eye such as ocular allergy, conjunctivitis, keratoconjunctivitis sicca, vernal conjunctivitis, or diseases affecting the nose such as allergic rhinitis.

Combination Therapy

In certain instances, the compound described herein, or a pharmaceutically acceptable salt, solvate, or stereoisomer thereof, is administered in combination with a second therapeutic agent.

In some embodiments, the benefit experienced by a patient is increased by administering one of the compounds described herein with a second therapeutic agent (which also includes a therapeutic regimen) that also has therapeutic benefit.

In one specific embodiment, a compound described herein, or a pharmaceutically acceptable salt, solvate, or stereoisomer thereof, is co-administered with a second therapeutic agent, wherein the compound described herein, or a pharmaceutically acceptable salt, solvate, or stereoisomer thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply additive of the two therapeutic agents or the patient experiences a synergistic benefit.

In certain embodiments, different therapeutically-effective dosages of the compounds disclosed herein will be utilized in formulating a pharmaceutical composition and/or in treatment regimens when the compounds disclosed herein are administered in combination with a second therapeutic agent. Therapeutically-effective dosages of drugs and other agents for use in combination treatment regimens are optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt, solvate, or stereoisomer thereof, is initiated prior to, during, or after treatment with a second agent described herein, and continues until any time during treatment with the second agent or after termination of treatment with the second agent. It also includes treatments in which a compound described herein, or a pharmaceutically acceptable salt, solvate, or stereoisomer thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated, and so forth. In additional embodiments, when co-administered with a second therapeutic agent, the compound provided herein is administered either simultaneously with the second therapeutic agent, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt, solvate, or stereoisomer thereof, as well as combination therapies, are administered before, during, or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, the compound of described herein, or a pharmaceutically acceptable salt, solvate, or stereoisomer thereof, is administered in combination with an adjuvant. In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced).

EXAMPLES

Intermediate A:

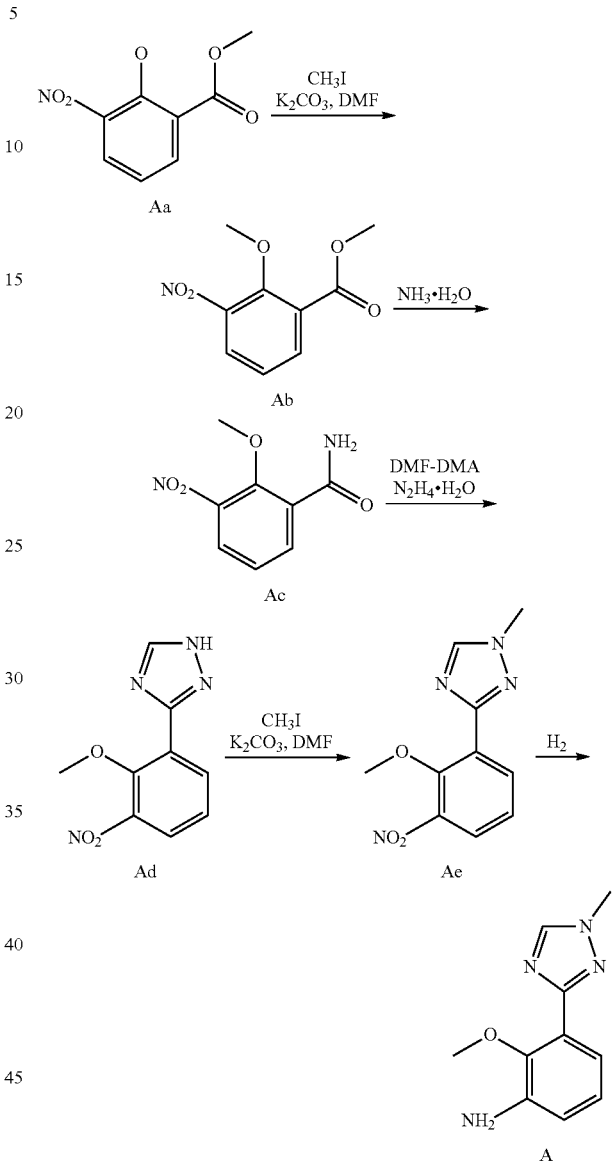

Step 1: Synthesis of Compound Ab

To a solution of methyl 2-hydroxy-3-nitrobenzoate (10 g, 50.7 mmol) in DMF (100 mL) at room temperature was added potassium carbonate (14.02 g, 101 mmol) followed by addition of methyl iodide (6.34 mL, 101 mmol) and the resulting orange mixture was heated to 60° C. for 1 h. The reaction was cooled to room temperature and then crushed ice (~100 mL) was added, followed by water to a total volume of ~400 mL 10 causing a yellow solid to crystallize from solution. The slurry was stirred for a few minutes and then collected by vacuum filtration and the resulting initially yellow solid was rinsed with additional water (~100 mL) until all of the yellow color was rinsed into the filtrate giving a near white solid in the funnel. Partially air-dried solid in funnel then transferred to a flask and further dried under vacuum over night to afford Ab (10.5 g, 98%) of a yellow solid as the desired product. LCMS [M+1]⁺=197.1.

Step 2: Synthesis of Compound Ac

Methyl 2-methoxy-3-nitrobenzoate (11 g, 52.1 mmol) was dissolved in a cold solution of ammonia in methanol (7 N, 250 mL) and conc. aqueous ammonium hydroxide (100 mL) was added. The flask was sealed and the resulting solution was allowed to gently stir at room temperature overnight (~17 h). The reaction mixture was concentrated to afford Ac (1.67 g, 86%) as a yellow solid. LCMS [M+1]+=196.1.

Step 3: Synthesis of Compound Ad 2-methoxy-3-nitrobenzamide (6.5 g, 33.1 mmol) was slurried in dimethyl formamide dimethyl acetal (39.5 g, 331 mmol) and the mixture was heated to 95° C. giving a clear, pale yellow solution. After heating for ~30 min at 95° C., the reaction was cooled and was concentrated on the rotovap and the resulting yellow oil was azeotroped twice with 1,2-dichloroethane (40 mL portions) to ensure complete removal of any residual dimethyl formamide dimethyl acetal. The crude oil thus obtained was immediately dissolved in 35 mL of ethanol and was immediately used in the following step.

In a separate flask was prepared a mixture of ethanol (150 mL) and acetic acid (AcOH, 35 mL) and the resulting solution was cooled in an ice bath. Once cooled, hydrazine hydrate (16.1 mL, 331 mmol) was added dropwise. At this time, the solution containing the crude dimethyl formamide dimethyl acetal adduct as prepared above was transferred dropwise over ~15 min by cannula into the previously prepared well-stirred ice-cold mixture containing the hydrazine. During the addition, a pale yellow solid formed in the solution. After the addition was complete, the resulting cloudy yellow mixture was allowed to warm to room temperature and stir for ~4 h. The reaction mixture at this time was concentrated on the rotovap to remove some of the ethanol, diluted with additional water and filtered to collect the solid. The solid was washed with additional portions of water, air dried in the funnel then under vacuum to afford Ad (4.0 g, 54.8%) of a pale yellow solid as the desired product. LCMS [M+1]⁺=221.1.

Step 4: Synthesis of Compound Ae

A solution of 3-(2-methoxy-3-nitrophenyl)-4H-1,2,4-triazole (5.00 g, 22.71 mmol) in DMF (20 mL) was treated with potassium carbonate (4.20 g, 30.4 mmol). After cooling the resulting mixture in an ice bath, a solution of iodomethane (4.20 g, 29.59 mmol) in DMF (5 mL) was slowly added dropwise by syringe over 2 min. After the addition was complete, the ice bath was removed and the reaction mixture was allowed to warm to rt. After stirring at room temperature for ~4 h, LCMS analysis indicated complete and clean conversion to the region-isomeric mixture of products in ~2:1 ratio, respectively. The reaction was cooled in an ice bath and was diluted with water (~50 mL) and the solution was extracted with EtOAc (3×40 mL) and the combined extracts were washed with 10% aq. LiCl (2×20 mL), water (20 mL) then brine (20 mL), concentrated and purified by CC to afford Ae (2.0 g, 38%) of the major isomer as a pale yellow solid. LCMS [M+1]⁺=235.1. ¹H NMR (400 MHz, methanol-d₆) δ 8.50 (s, 1H), 8.11 (dd, J=7.9, 1.8 Hz, 1H), 7.85 (dd, J=8.1, 1.8 Hz, 1H), 7.38 (t, J=8.0 Hz, 1H), 4.03 (s, 3H), 3.83 (s, 3H).

Step 5: Synthesis of Intermediate A

A solution of 3-(2-methoxy-3-nitrophenyl)-1-methyl-1H-1,2,4-triazole (2.20 g, 10.77 mmol) in EtOH (50 mL) was sparged with nitrogen for a few minutes before adding 10% Pd-C (0.90 g, 0.43 mmol) followed by sparging with hydrogen from a balloon for a few minutes then allowing the mixture to stir under a balloon of hydrogen for 1.5 h at rt. The mixture was then sparged with nitrogen to deactivate the catalyst and the mixture was filtered through a pad of celite washing with additional amounts of EtOH and the resulting clear, colorless filtrate containing the product was concentrated and purified by CC to afford an off-white solid Intermediate A (1.5 g, 68%). LCMS [M+1]⁺=205.2. ¹H NMR (400 MHz, chloroform-d) δ 8.09 (s, 1H), 7.35 (dd, J=7.8, 1.7 Hz, 1H), 7.00 (t, J=7.8 Hz, 1H), 6.82 (dd, J=7.8, 1.7 Hz, 1H), 4.00 (s, 3H), 3.94 (s, 2H), 3.78 (s, 3H).

Intermediate 1:

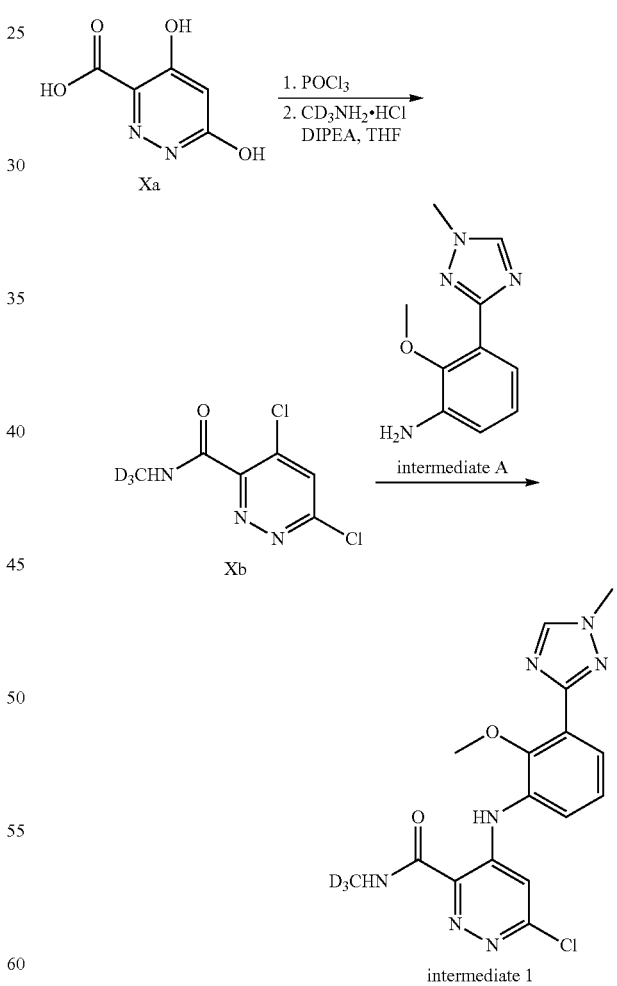

Step 1: Synthesis of Compound Xb

Xa (10 g, 64.1 mmol) was placed in a 1 L flask and triethylamine (8.9 mL, 64.1 mmol) was added, followed by phosphorus oxychloride (50 mL, 546 mmol). the mixture was heated to 110° C. and stirred for 120 minutes, then concentrated under reduced pressure. 200 mL of anhydrous 1,2-dichloroethane was added to the residue and the mixture sonicated and then concentrated. the residue was dissolved in THF (200 mL), deuteromethylamine (HCl salt, 2.26 g, 32 mmol) was then added, followed by N, N-diisopropylethylamine (18 mL, 103 mmol). After 1 hour the reaction was concentrated and the residue adsorbed onto celite using dichloromethane, The filtrate was re-concentrated and purified by CC to afford a yellow solid Xb (5.1 g, 37%).

Step 2: Synthesis of Intermediate 1

To a solution of Xb (5.00 g, 23.92 mmol) and intermediate A (4.88 g, 23.92 mmol) in THF (50 mL) under $N_2$ was added LiHMDS (1 M, 71.80 mL, 71.80 mmol) at 0° C. resulting a mild exotherm. The reaction was stirred at r.t. for 3h. The reaction mixture was cooled to 0° C., quenched by adding satd. $NH_4Cl$ (aq.), diluted with water (100 mL) and extracted by EtOAc (50 mL×3). The combined organic layers were washed by brine (50 mL), dried over $Na_2SO_4$, filtered and concentrated under reduced pressure to afford the crude product which was purified by column chromatography (DCM/EtOAc=3/1) to give the desired product Intermediate 1 (6.5 g, yield: 72.2%) as a yellow solid. LCMS $[M+1]^+=377.1$.

Intermediate 2:

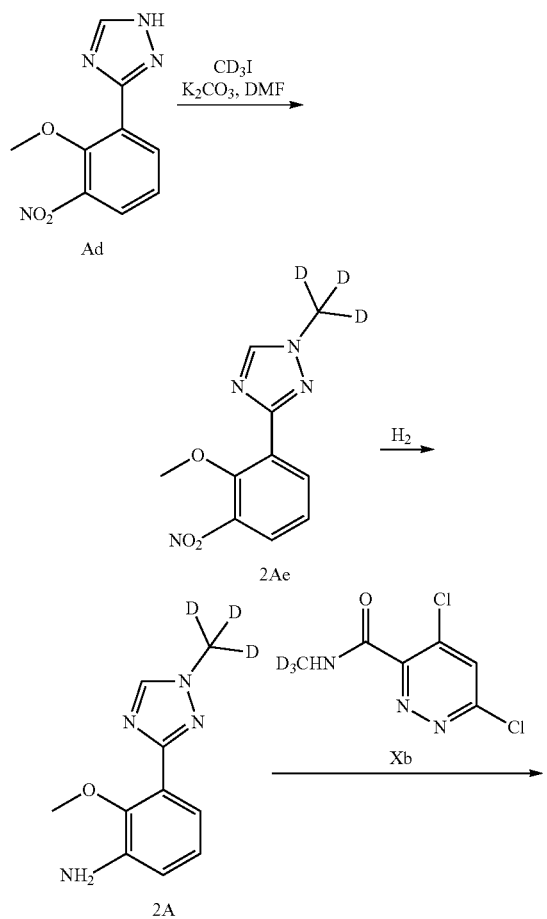

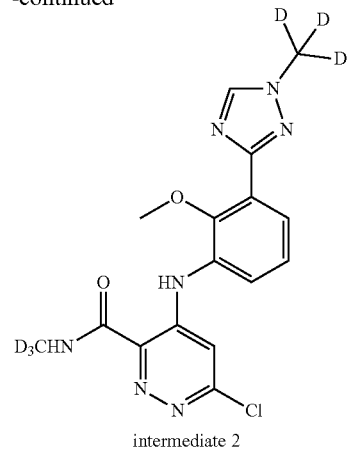

intermediate 2

Step 1: Synthesis of Compound 2Ae

A solution of 3-(2-methoxy-3-nitrophenyl)-4H-1,2,4-triazole (Ad) (5.00 g, 22.71 mmol) in DMF (20 mL) was treated with potassium carbonate (4.20 g, 30.4 mmol). After cooling the resulting mixture in an ice bath, a solution of iodomethane-$d_3$ (4.20 g, 29.59 mmol) in DMF (5 mL) was slowly added dropwise by syringe over 2 min. After the addition was complete, the ice bath was removed and the reaction mixture was allowed to warm to rt. After stirring at room temperature for ~4 h, LCMS analysis indicated complete and clean conversion to the regioisomeric mixture of products in ~2:1 ratio, respectively. The reaction was cooled in an ice bath and was diluted with water (~50 mL) and the solution was extracted with EtOAc (3×40 mL) and the combined extracts were washed with 10% aq. LiCl (2×20 mL), water (20 mL) then brine (20 mL), concentrated and purified by CC to afford 2Ae (2.0 g, 38%) of the major isomer as a pale yellow solid. LCMS $[M+1]^+=238.1$.

Step 2: Synthesis of Compound 2A

A solution of 3-(2-methoxy-3-nitrophenyl)-1-(methyl-d3)-1H-1,2,4-triazole (2.20 g, 10.77 mmol) in EtOH (50 mL) was sparged with nitrogen for a few minutes before adding 10% Pd-C (0.90 g, 0.43 mmol) followed by sparging with hydrogen from a balloon for a few minutes then allowing the mixture to stir under a balloon of hydrogen for 1.5 h at rt. The mixture was then sparged with nitrogen to deactivate the catalyst and the mixture was filtered through a pad of CELITE® washing with additional amounts of EtOH and the resulting clear, colorless filtrate containing the product was concentrated and purified by CC to afford an off-white solid 2A (1.5 g, 68%). LCMS $[M+1]^+=208.2$.

Step 3: Synthesis of Intermediate 2

To a solution of Xb (5.00 g, 23.92 mmol) and Example 2A (4.88 g, 23.92 mmol) in THF (50 mL) under $N_2$ was added LiHMDS (1 M, 71.80 mL, 71.80 mmol) at 0° C. resulting a mild exotherm. The reaction was stirred at r.t. When completed, The reaction mixture was cooled to 0° C., quenched by adding satd. $NH_4Cl$ (aq.), diluted with water (100 mL) and extracted by EtOAc (50 mL*3). The combined organic layers were washed by brine (50 mL), dried over $Na_2SO_4$, filtered and concentrated under reduced pressure to afford the crude product which was purified by column chromatography (DCM/EtOAc=3/1) to give the desired product intermediate 2 (6.5 g, yield: 72.2%) as a yellow solid. LCMS [M+1]⁺=380.1.

Intermediate 3A:

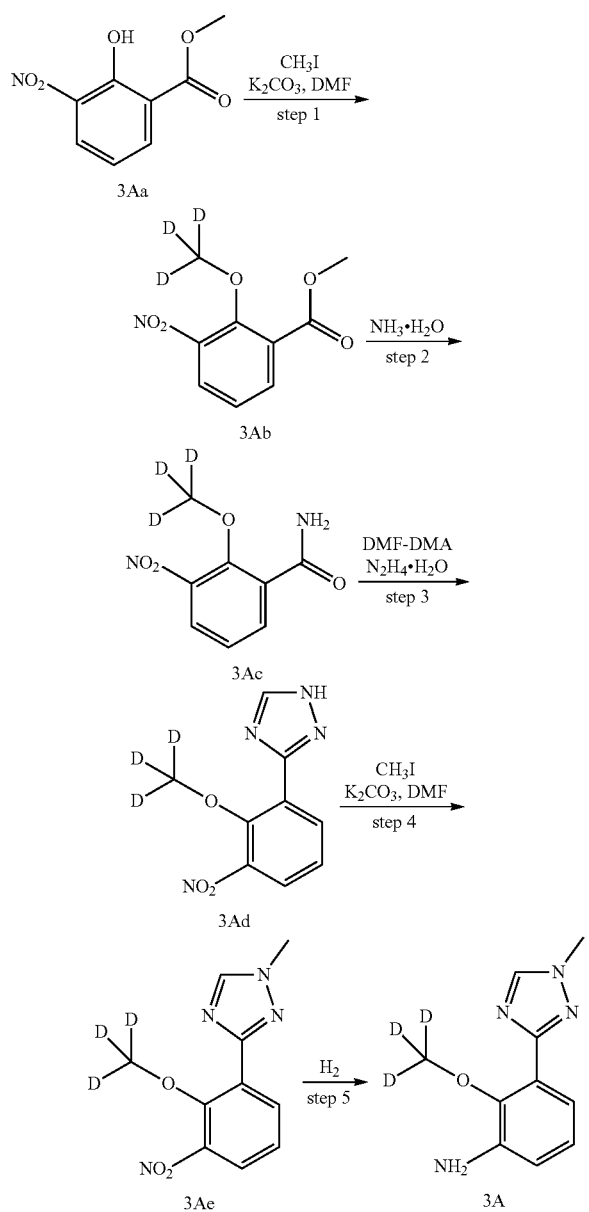

Step 1: Synthesis of Compound 3Ab

To a solution of methyl 2-hydroxy-3-nitrobenzoate (7 g, 35.5 mmol) in DMF (70 mL) at room temperature was added potassium carbonate (9.8 g, 71.0 mmol) followed by addition of iodomethane-d₃ (4.42 mL, 71.0 mmol) and the resulting orange mixture was heated to 60° C. for 1 h. The reaction was cooled to room temperature and then crushed ice (~100 mL) was added, followed by water to a total volume of ~400 mL causing a yellow solid to crystallize from solution. The slurry was stirred for a few minutes and then collected by vacuum filtration and the resulting initially yellow solid was rinsed with additional water (~100 mL) until all of the yellow color was rinsed into the filtrate giving a near white solid in the funnel. Partially air-dried solid in funnel then transferred to a flask and further dried under vacuum overnight to afford 3Ab (6.5 g, 86%) of a yellow solid as the desired product. LCMS [M+1]⁺=215.1.

Step 2: Synthesis of Compound 3Ac methyl 2-(methoxy-d3)-3-nitrobenzoate 3Ab (6.5 g, 30.3 mmol) was dissolved in a cold solution of ammonia in methanol (7N, 140 mL) and conc. aqueous ammonium hydroxide (60 mL) was added. The flask was sealed and the resulting solution was allowed to gently stir at room temperature overnight (~17 h). The reaction mixture was concentrated to afford 3Ac (5.8 g, 96%) as a yellow solid. LCMS [M+1]⁺=200.1

Step 3: Synthesis of Compound 3Ad 2-(methoxy-d3)-3-nitrobenzamide 3Ac (5.8 g, 29.1 mmol) was slurried in dimethyl formamide dimethyl acetal (38.6 mL, 291 mmol) and the mixture was heated to 95° C. giving a clear, pale yellow solution. After heating for ~30 min at this temp the reaction was cooled and was concentrated on the rotovap and the resulting yellow oil was azeotroped twice with 1,2-dichloroethane (40 mL portions) to ensure complete removal of any residual dimethyl formamide dimethyl acetal. The crude oil thus obtained was immediately dissolved in 35 mL of ethanol and was immediately used in the following step.

In a separate flask was prepared a mixture of ethanol (150 mL) and acetic acid (AcOH, 35 mL) and the resulting solution was cooled in an ice bath. Once cooled, hydrazine hydrate (14.1 mL, 291 mmol) was added dropwise. At this time, the solution containing the crude dimethyl formamide dimethyl acetal adduct as prepared above was transferred dropwise over ~15 min by cannula into the previously prepared well-stirred ice-cold mixture containing the hydrazine. During the addition, a pale yellow solid formed in the solution. After the addition was complete, the resulting cloudy yellow mixture was allowed to warm to room temperature and stir for ~4 h. The reaction mixture at this time was concentrated on the rotovap to remove some of the ethanol, diluted with additional water and filtered to collect the solid. The solid was washed with additional portions of water, air dried in the funnel then under vacuum to afford 3Ad (5.0 g, 77.0%) of a pale yellow solid as the desired product. LCMS [M+1]⁺=224.1

Step 4: Synthesis of Compound 3Ae

A solution of 3-(2-(methoxy-d3)-3-nitrophenyl)-1H-1,2,4-triazole 3Ad (5.00 g, 22.4 mmol) in DMF (20 mL) was treated with potassium carbonate (9.28 g, 67.2 mmol). After cooling the resulting mixture in an ice bath, a solution of iodomethane (1.9 mL, 30.2 mmol) in DMF (5 mL) was slowly added dropwise by syringe over 2 min. After the addition was complete, the ice bath was removed and the reaction mixture was allowed to warm to rt. After stirring at room temperature for ~4 h, LCMS analysis indicated complete and clean conversion to the regioisomeric mixture of products in ~2:1 ratio, respectively. The reaction was cooled in an ice bath and was diluted with water (~50 mL) and the solution was extracted with EtOAc (3×40 mL) and the combined extracts were washed with 10% aq. LiCl (2×20 mL), water (20 mL) then brine (20 mL), concentrated and purified by CC to afford 3Ae (2.1 g, 39.54%) of the major isomer as a pale yellow solid. LCMS [M+1]$^+$=238.2.

Step 5: Synthesis of Compound 3A

A solution of 3-(2-(methoxy-d3)-3-nitrophenyl)-1-methyl-1H-1,2,4-triazole 3Ae (1.6 g, 6.75 mmol) in EtOH (50 mL) was sparged with nitrogen for a few minutes before adding 10% Pd-C (0.8 g) followed by sparging with hydrogen from a balloon for a few minutes then allowing the mixture to stir under a balloon of hydrogen for 1.5h at rt. The mixture was then sparged with nitrogen to deactivate the catalyst and the mixture was filtered through a pad of CELITE® washing with additional amounts of EtOH and the resulting clear, colorless filtrate containing the product was concentrated and purified by CC to afford an off-white solid 3A (1.1 g, 68%).

LCMS [M+1]$^+$=208.2. $^1$H NMR (400 MHz, CDCl$_3$) δ 8.09 (s, 1H), 7.35 (dd, 1H), 6.99 (t, 1H), 6.83 (dd, 1H), 3.99 (s, 3H), 3.80-3.45 (m, 2H).
Intermediate 3:

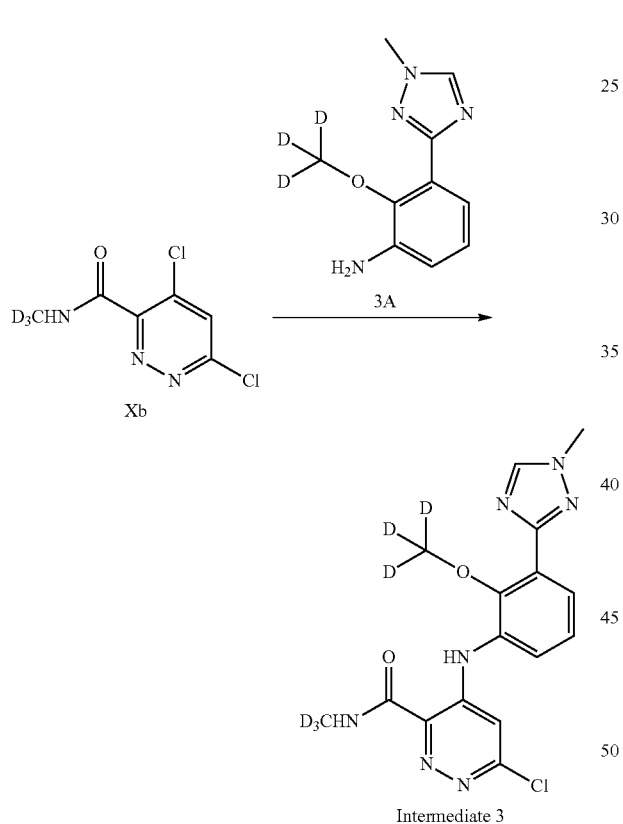

To a solution of Xb (0.9 g, 4.32 mmol) and 3A (0.9 g, 4.32 mmol) in THF (15 mL) under N$_2$ was added LiHMDS (1 M, 13 mL, 13 mmol) at 0° C. resulting a mild exotherm. The reaction was stirred at r.t. When completed, The reaction mixture was cooled to 0° C., quenched by adding satd. NH$_4$Cl (aq.), diluted with water (100 mL) and extracted by EtOAc (50 mL×3). The combined organic layers were washed by brine (50 mL), dried over Na$_2$SO$_4$, filtered and concentrated under reduced pressure to afford the crude product which was purified by column chromatography (DCM/EtOAc=3/1) to give the desired product intermediate 3 (1.3 g, yield: 79.26%) as a yellow solid. LCMS [M+1]$^+$=380.2.

Example 1: 4-[2-methoxy-3-(1-methyl-1,2,4-triazol-3-yl)anilino]-6-(2-oxoimidazolidin-1-yl)-N-(trideuteriomethyl)pyridazine-3-carboxamide

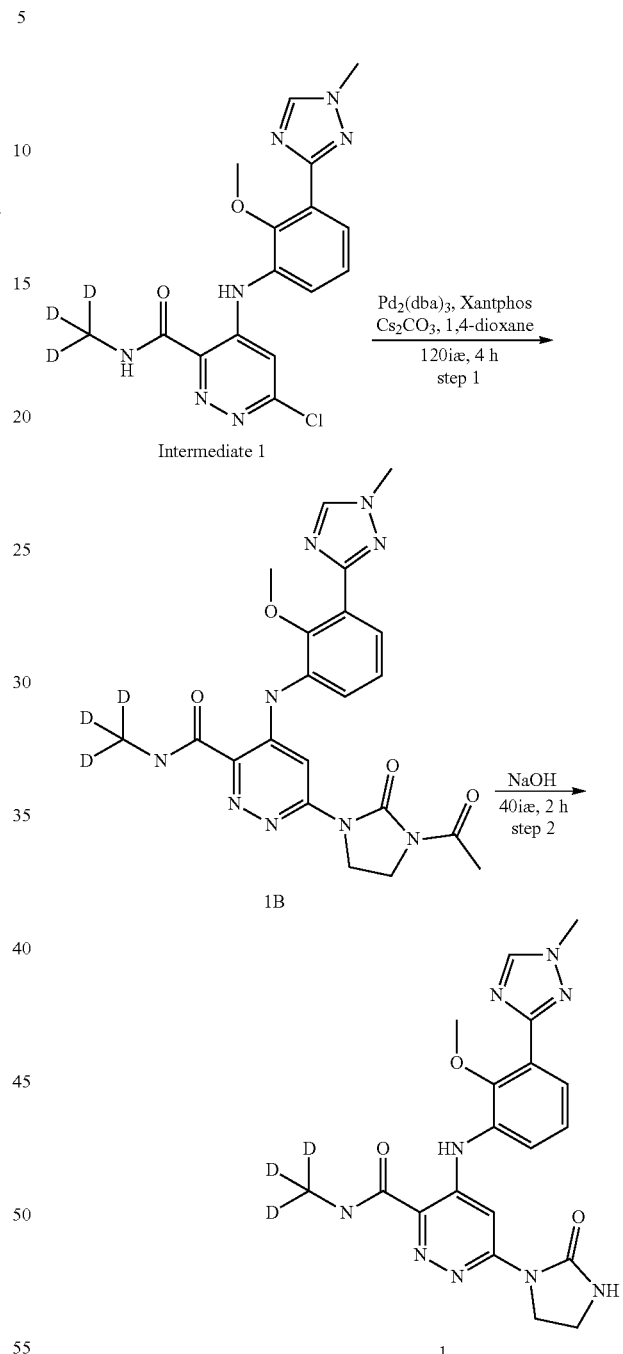

Step 1: 6-(3-acetyl-2-oxo-imidazolidin-1-yl)-4-[2-methoxy-3-(1-methyl-1,2,4-triazol-3-yl)anilino]-N-(trideuteriomethyl)pyridazine-3-carboxamide To a solution of intermediate 1 (60m g, 0.16 mmol) and 1A (41 mg, 0.32 mmol) in 1,4-dioxane (8 mL) was added Cesium carbonate (100 mg, 0.32 mmol), Pd$_2$(dba)$_3$ (43 mg, 0.048 mmol), and xantphos (46 mg, 0.08 mmol). The mixture degassed by N$_2$ for 3 times and heated to 120° C. for 4 hrs. When reaction completed, filtered, filtrate was removed in vacuo, chromatography (PE/EtOAc=50/50 then DCM/MeOH=97/3) to give the desired product Example 1 (6 mg, yield: 8%) as a yellow solid. LM-MS: m/z=469.2 [M+H]$^+$ Step 2: 4-[2-methoxy-3-(1-methyl-1,2,4-triazol-3-yl) anilino]-6-(2-oxoimidazolidin-1-yl)-N-(trideuteriomethyl)pyridazine-3-carboxamide To a solution of 1B (6 mg, 0.013 mmol) in methanol (3 mL) was added NaOH (1.04 mg, 0.026 mmol) The mixture was heated to 40° C. for 2 hrs. When reaction completed, filtered, filtrate was removed in vacuo, chromatography (PE/EtOAc=50/50 then DCM/MeOH=97/3) to give the desired product Example 1 (3 mg, yield: 50%) as a yellow solid. LM-MS: m/z=428.2[M+H]$^+$. 1H NMR (400 MHz, DMSO) δ 10.91 (s, 1H), 9.14 (s, 1H), 8.56 (s, 1H), 8.29 (s, 1H), 7.63 (dd, 1H), 7.53 (dd, 1H), 7.43 (s, 1H), 7.25 (t, 1H), 4.17-4.12 (m, 2H), 3.95 (s, 3H), 3.74 (s, 3H), 3.49-3.37 (m, 2H).

Example 2: 4-[2-methoxy-3-(1-methyl-1,2,4-triazol-3-yl)anilino]-6-(3-methyl-2-oxo-imidazolidin-1-yl)-N-(trideuteriomethyl)pyridazine-3-carboxamide

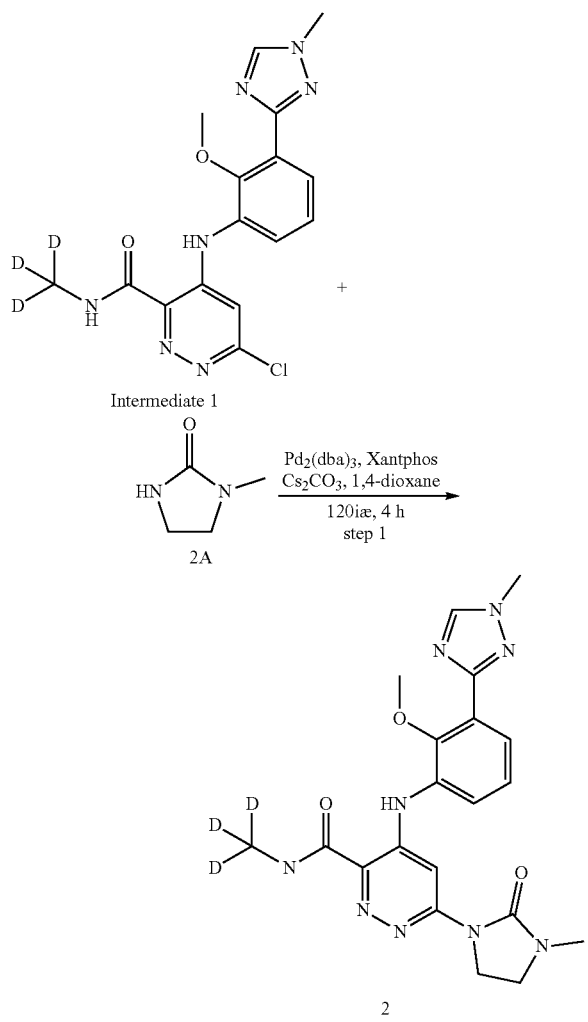

To a solution of intermediate 1 (60 mg, 0.16 mmol) and 2A (32 mg, 0.32 mmol) in 1,4-dioxane (8 mL) was added Cesium carbonate (100 mg, 0.32 mmol), Pd$_2$(dba)$_3$ (43 mg, 0.048 mmol), and xantphos (46 mg, 0.08 mmol). The mixture degassed by N$_2$ for 3 times and heated to 120° C. for 4 hrs. When reaction completed, filtered, filtrate was removed in vacuo, chromatography (PE/EtOAc=50/50 then DCM/MeOH=97/3) to give the desired product 2. (6 mg, yield: 9%) as a yellow solid. LM-MS: m/z=441.2 [M+H]$^+$. $^1$H NMR (400 MHz, CDCl$_3$) δ 11.60 (s, 1H), 8.39 (s, 1H), 8.22 (s, 1H), 8.06-7.88 (m, 2H), 7.50 (d, 1H), 7.32 (t, 1H), 4.62-4.49 (m, 2H), 4.03 (s, 3H), 3.81 (s, 3H), 3.65-3.54 (m, 2H), 2.91 (s, 3H).

Example 3: 4-[2-methoxy-3-(1-methyl-1,2,4-triazol-3-yl)anilino]-N-methyl-6-(2-oxoazetidin-1-yl)pyridazine-3-carboxamide

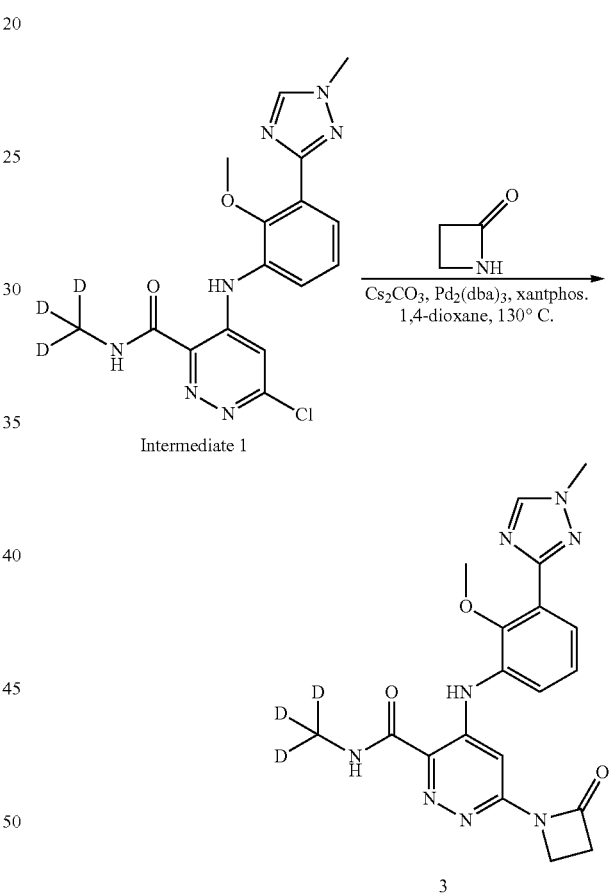

Intermediate 1 (0.05 g, 0.133 mmol), azetidin-2-one (0.02 g, 0.282 mmol), cesium carbonate (0.086 g, 0.264 mmol), tris(dibenzylideneacetone)dipalladium (0.012 g, 0.013 mmoL) and xantphos (0.012 g, 0.021 mmol) were added to 45 mL sealed tube. 10 mL 1,4-dioxane was added to the mixture. The resulting solution was stirred at 130° C. for 1 h under N$_2$ atmosphere. The mixture solution was evaporated to dryness, residues was purified by flash chromatography to afford 3 (0.0121 g, 20%) as a light yellow solid. $^1$H NMR (400 MHz, CD$_3$OD) δ 8.70 (s, 1H), 7.77 (d, J=7.6 Hz, 1H), 7.64-7.55 (m, 2H), 7.34 (t, J=8.0 Hz, 1H), 4.05 (s, 3H), 3.92 (t, J=4.9 Hz, 2H), 3.75 (s, 3H), 3.25 (t, J=4.8 Hz, 2H). LC-MS (ESI): m/z=412.2 [M+H]$^+$.

Example 4: 4-[2-methoxy-3-(1-methyl-1,2,4-triazol-3-yl)anilino]-6-(4-oxo-5-azaspiro[2.4]heptan-5-yl)-N-(trideuteriomethyl)pyridazine-3-carboxamide

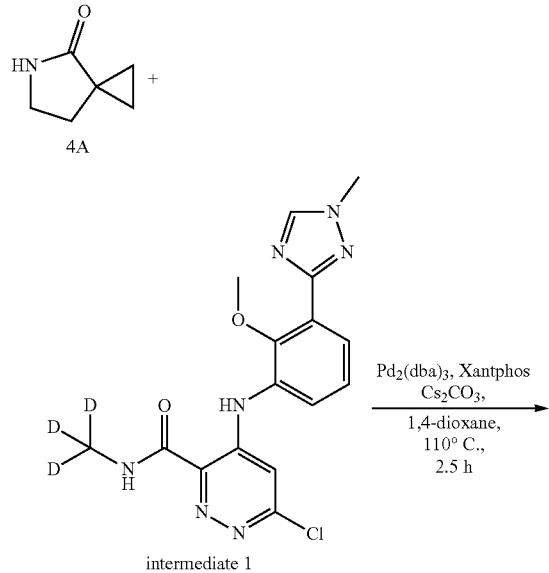

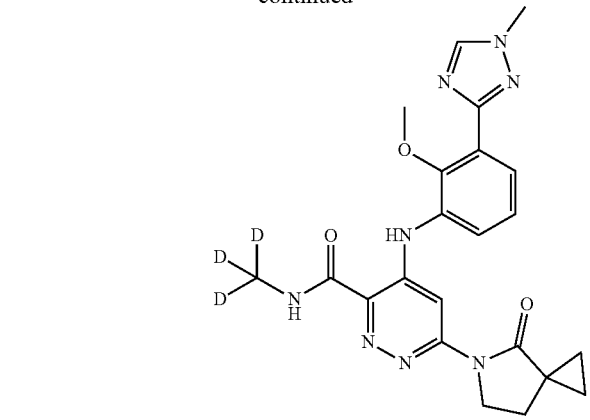

To a solution of intermediate 1 (60 mg, 0.16 mmol) and 4A (35 mg, 0.32 mmol) in 1,4-dioxane (8 mL) was added Cesium carbonate (100 mg, 0.32 mmol), Pd$_2$(dba)$_3$ (43 mg, 0.048 mmol), and xantphos (46 mg, 0.08 mmol). The mixture degassed by N$_2$ for 3 times and heated to 110° C. for 4 hrs. When reaction completed, filtered, filtrate was removed in vacuo, The residue was purified by flash Chromatography (PE/EtOAc=50/50 then DCM/MeOH=97/3) to afford the title compound Example 4 (24 mg, 33.33%) as a white solid. LM-MS: m/z=452.3 [M+H]$^+$. $^1$H NMR (400 MHz, CDCl$_3$) δ 11.22 (s, 1H), 8.53 (s, 1H), 8.32 (s, 1H), 8.16 (s, 1H), 7.78 (d, 1H), 7.55 (d, 1H), 7.31 (t, 1H), 4.34 (t, 2H), 4.05 (s, 3H), 3.78 (s, 3H), 2.26 (t, 2H), 1.28-1.24 (m, 2H), 0.98-0.93 (m, 2H).

Example 5: 6-(3-cyclopropyl-2-oxo-imidazolidin-1-yl)-4-[2-methoxy-3-(1-methyl-1,2,4-triazol-3-yl)anilino]-N-(trideuteriomethyl)pyridazine-3-carboxamide

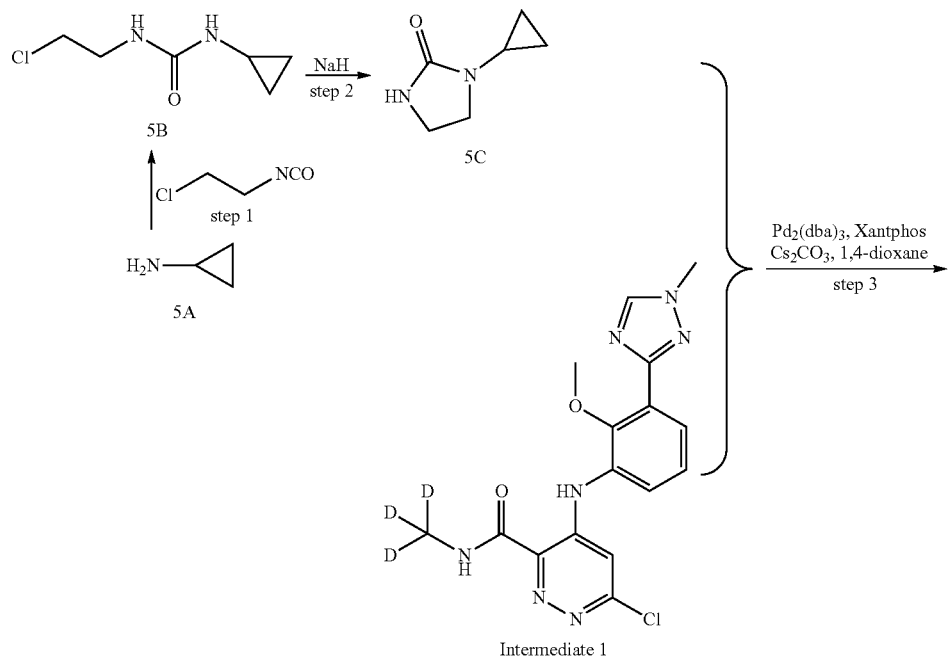

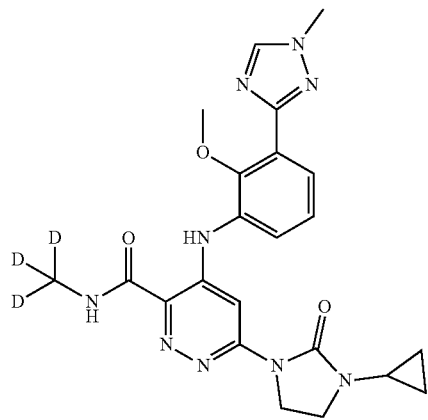

5

Step 1: 1-(2-chloroethyl)-3-cyclopropyl-urea

To a solution of cyclopropanamine (2.0 g, 35.03 mmol) in Acetonitrile (20 mL) was added 1-chloro-2-isocyanato-ethane (3.70 g, 35.03 mmol), then it was stirred at room temperature for 2 h. solid precipitation, filtered, give the desired product 5B (4.05 g, 71.1%) as a white solid, it was used in the next step without further purification. LM-MS: m/z=163.2 [M+H]$^+$

Step 2: 1-cyclopropylimidazolidin-2-one

To a solution of 5B (0.5 g, 3.07 mmol) in THF (30 ml) was added sodium hydride (0.15 g, 6.0 mmol), then it was stirred at room temperature for 2h. Quenched with water (20 mL) and extracted by EtOAc (30 mL×2). The combined organic layers were washed by brine (30 mL), dried over Na$_2$SO$_4$, filtered and concentrated under reduced pressure to afford the crude product which was purified by column chromatography (EtOAc/PE=1/1) to give the desired product 5C (0.17 g, yield: 38.67%) as a white solid. LM-MS: m/z=127.2 [M+H]$^+$

Step 3: 6-(3-cyclopropyl-2-oxo-imidazolidin-1-yl)-4-[2-methoxy-3-(1-methyl-1,2,4-triazol-3-yl)anilino]-N-(trideuteriomethyl)pyridazine-3-carboxamide To a solution of intermediate 1 (70 mg, 0.18 mmol) and 5C (35 mg, 0.28 mmol) in 1,4-dioxane (8 mL) was added Cesium carbonate (100 mg, 0.32 mmol), Pd$_2$(dba)$_3$ (43 mg, 0.048 mmol), and xantphos (46m g, 0.08 mmol). The mixture degassed by N$_2$ for 3 times and heated to 120° C. for 4 hrs. When reaction completed, filtered, filtrate was removed in vacuo, chromatography (PE/EtOAc=50/50 then DCM/MeOH=97/3) to give the desired product Example 5 (10 mg, yield: 10%) as a yellow solid. LM-MS: m/z=467.2 [M+H]$^+$. $^1$H NMR (400 MHz, MeOD) δ 8.46 (s, 1H), 8.39 (s, 1H), 7.66-7.62 (m, 2H), 7.24 (t, 1H), 4.11 (t, 2H), 4.02 (s, 3H), 3.74 (s, 3H), 3.53 (t, 2H), 2.56-2.52 (m, 1H), 0.77-0.72 (m, 4H).

Example 6: 6-(3-isopropyl-2-oxo-imidazolidin-1-yl)-4-[2-methoxy-3-(1-methyl-1,2,4-triazol-3-yl)anilino]-N-(trideuteriomethyl)pyridazine-3-carboxamide

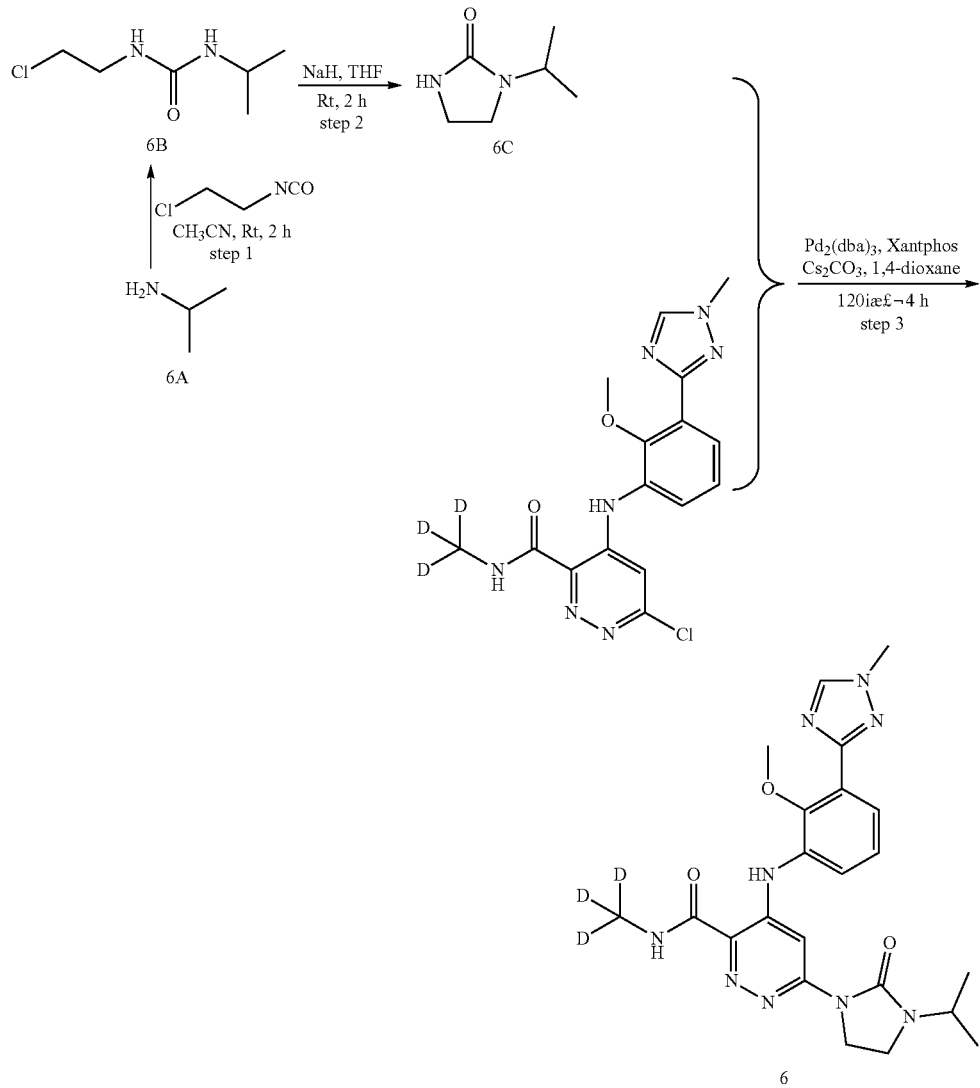

Step 1: 1-(2-chloroethyl)-3-isopropyl-urea

To a solution of propan-2-amine (2.0 g, 33.8 mmol) in Acetonitrile (20 mL) was added 1-chloro-2-isocyanato-ethane (3.57 g, 33.8 mmol), then it was stirred at room temperature for 2h. solid precipitation, filtered, give the desired product Example 6B (4.2 g, 75.4%) as a white solid, it was used in the next step without further purification. LM-MS: m/z=165.2 [M+H]$^+$. 1H NMR (400 MHz, CDCl3) δ 5.39-4.32 (m, 2H), 3.85 (dt, 1H), 3.65-3.58 (m, 2H), 3.58-3.49 (m, 2H), 1.15 (d, 6H).

Step 2: 1-isopropylimidazolidin-2-one

To a solution of 6B (0.5 g, 3.0 mmol) in THF (30 ml) was added sodium hydride (0.15 g, 6.0 mmol), then it was stirred at room temperature for 2h. Quenched with water (20 mL) and extracted by EtOAc (30 mL×2). The combined organic layers were washed by brine (30 mL), dried over Na$_2$SO$_4$, filtered and concentrated under reduced pressure to afford the crude product which was purified by column chromatography (EtOAc/PE=1/1) to give the desired product Example 6C (0.17 g, yield: 44%) as a white solid. LM-MS: m/z=129.2 [M+H]$^+$. 1H NMR (400 MHz, CDCl$_3$) δ 4.36 (s, 1H), 4.14 (dt, 1H), 3.42-3.33 (m, 4H), 1.14 (d, 3H), 1.12 (s, 3H).

Step 3: 6-(3-isopropyl-2-oxo-imidazolidin-1-yl)-4-[2-methoxy-3-(1-methyl-1,2,4-triazol-3-yl)anilino]-N-(trideuteriomethyl)pyridazine-3-carboxamide; 2,2,2-trifluoroacetic acid To a solution of Intermediate 1 (60m g, 0.16 mmol) and 6C (41 mg, 0.32 mmol) in 1,4-dioxane (8 mL) was added Cesium carbonate (100 mg, 0.32 mmol), Pd₂(dba)₃ (43 mg, 0.048 mmol), and xantphos (46m g, 0.08 mmol). The mixture degassed by N₂ for 3 times and heated to 120° C. for 4 hrs. When reaction completed, filtered, filtrate was removed in vacuo, chromatography (PE/EtOAc=50/50 then DCM/MeOH=97/3) to give the desired product Example 6 (5 mg, yield: 5%) as a yellow solid. LM-MS: m/z=469.2 [M+H]⁺. ¹H NMR (400 MHz, CDCl₃) δ 11.47 (s, 1H), 8.54 (s, 1H), 8.02 (s, 1H), 7.89 (s, 1H), 7.83 (d, 1H), 7.54 (d, 1H), 7.34 (t, 1H), 4.21 (dd, 3H), 4.06 (s, 3H), 3.76 (s, 3H), 3.64-3.49 (m, 2H), 1.19 (d, 6H).

Example 7: 6-(3,3-dimethyl-2-oxo-pyrrolidin-1-yl)-4-[2-methoxy-3-(1-methyl-1,2,4-triazol-3-yl)anilino]-N-(trideuteriomethyl)pyridazine-3-carboxamide

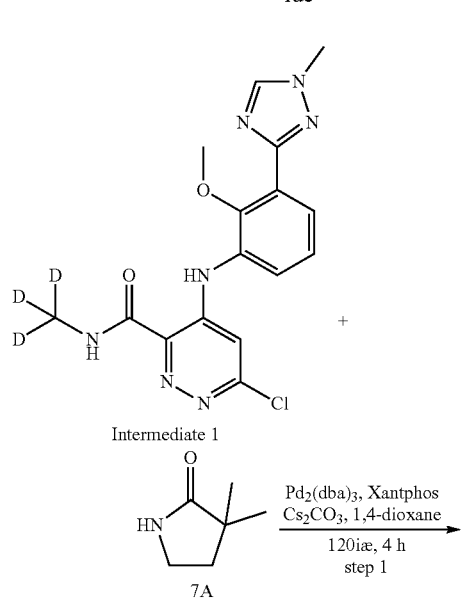

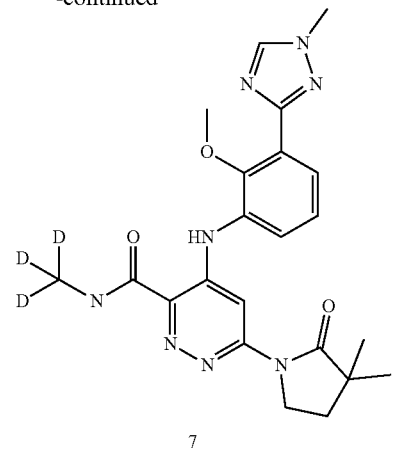

To a solution of intermediate 1 (60 mg, 0.16 mmol) and 7A (36 mg, 0.32 mmol) in 1,4-dioxane (8 mL) was added Cesium carbonate (100 mg, 0.32 mmol), Pd₂(dba)₃ (43 mg, 0.048 mmol), and xantphos (46 mg, 0.08 mmol). The mixture degassed by N₂ for 3 times and heated to 120° C. for 4 hrs. When reaction completed, filtered, filtrate was removed in vacuo, chromatography (PE/EtOAc=50/50 then DCM/MeOH=97/3) to give the desired product Example 7 (24 mg, yield: 30%) as a yellow solid. LM-MS: m/z=455.3 [M+H]⁺. ¹H NMR (400 MHz, CDCl₃) δ 11.08 (s, 1H), 8.42 (d, 2H), 8.17 (s, 1H), 7.77 (d, 1H), 7.58 (d, 1H), 7.31 (t, 1H), 4.17 (t, 2H), 4.04 (s, 3H), 3.80 (s, 3H), 2.02 (t, 2H), 1.25 (s, 6H).

Example 8: 6-[3-(2,2-difluoroethyl)-2-oxo-imidazolidin-1-yl]-4-[2-methoxy-3-(1-methyl-1,2,4-triazol-3-yl)anilino]-N-(trideuteriomethyl)pyridazine-3-carboxamide; 2,2,2-trifluoroacetic acid

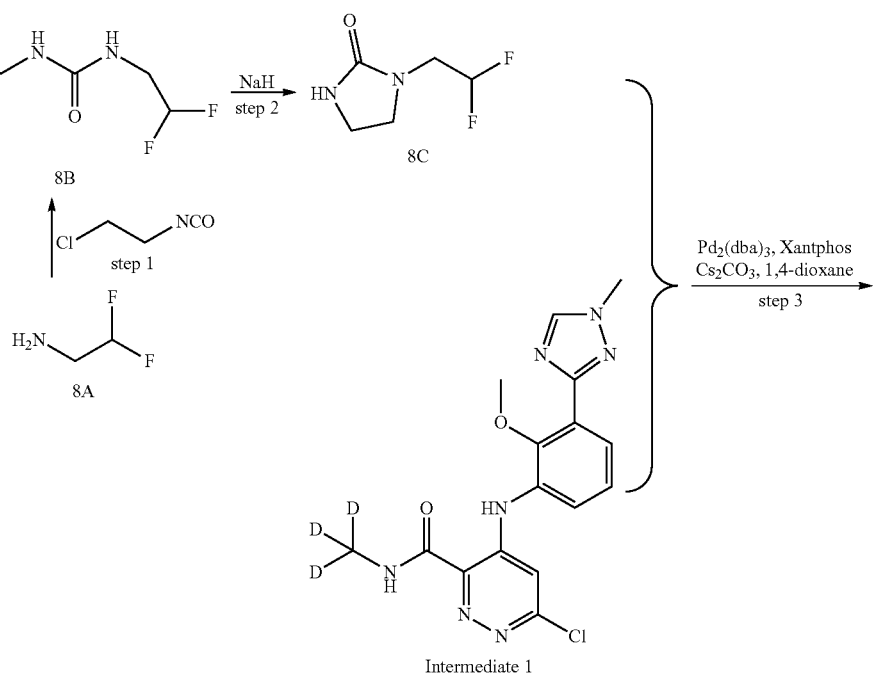

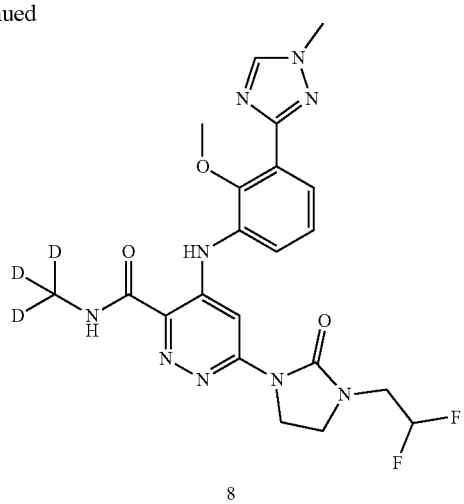

8

Step 1: 1-(2-chloroethyl)-3-(2,2-difluoroethyl)urea

To a solution of 2,2-difluoroethanamine (2.0 g, 24.67 mmol) in Acetonitrile (20 mL) was added 1-chloro-2-iso-cyanato-ethane (2.60 g, 24.67 mmol), then it was stirred at room temperature for 2 h. solid precipitation, filtered, give the desired product 8B (2.80 g, 60.83%) as a white solid, it was used in the next step without further purification. LM-MS: m/z=187.2 [M+H]+

Step 2: 1-(2,2-difluoroethyl)imidazolidin-2-one

To a solution of 8B (0.5 g, 2.68 mmol) in THF (30 ml) was added sodium hydride (0.15 g, 6.0 mmol), then it was stirred at room temperature for 2h. Quenched with water (20 mL) and extracted by EtOAc (30 mL×2). The combined organic layers were washed by brine (30 mL), dried over Na₂SO₄, filtered and concentrated under reduced pressure to afford the crude product which was purified by column chromatography (EtOAc/PE=1/1) to give the desired product 8C (0.15 g, yield: 37.29%) as a white solid. LM-MS: m/z=151.2 [M+H]+

Step 3: 6-[3-(2,2-difluoroethyl)-2-oxo-imidazolidin-1-yl]-4-[2-methoxy-3-(1-methyl-1,2,4-triazol-3-yl)anilino]-N-(trideuteriomethyl)pyridazine-3-carboxamide; 2,2,2-trifluoroacetic acid To a solution of intermediate 1 (80 mg, 0.21 mmol) and 8C (47 mg, 0.32 mmol) in 1,4-dioxane (8 mL) was added Cesium carbonate (100 mg, 0.32 mmol), Pd₂(dba)₃ (43 mg, 0.048 mmol), and xantphos (46 mg, 0.08 mmol). The mixture degassed by N₂ for 3 times and heated to 120° C. for 4 hrs. When reaction completed, filtered, filtrate was removed in vacuo, chromatography (PE/EtOAc=50/50 then DCM/MeOH=97/3) to give the desired product Example 8. (4 mg, yield: 4%) as a yellow solid. LM-MS: m/z=491.2 [M+H]+. ¹H NMR (400 MHz, CD₃OD): δ 7.77-7.71 (m, 2H), 7.64 (d, 1H), 7.33 (t, 1H), 6.18-5.91 (m, 1H), 4.09 (t, 1H), 4.04 (s, 3H), 3.72-3.72 (m, 4H), 3.70-3.65 (m, 2H).

Example 9: 6-[3-(2-methoxyethyl)-2-oxo-imidazolidin-1-yl]-4-[2-methoxy-3-(1-methyl-1,2,4-triazol-3-yl)anilino]-N-(trideuteriomethyl)pyridazine-3-carboxamide

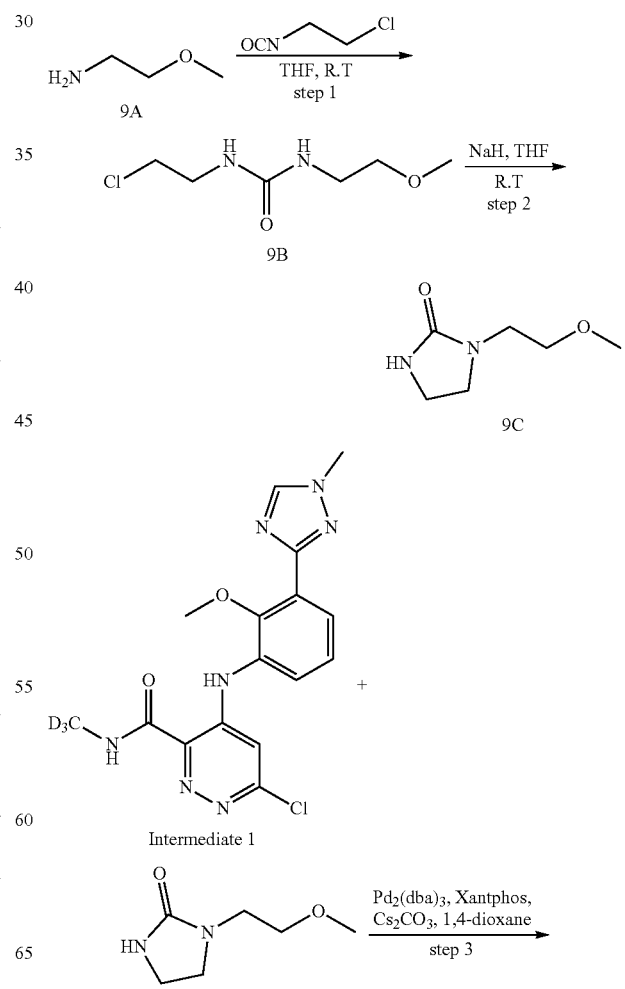

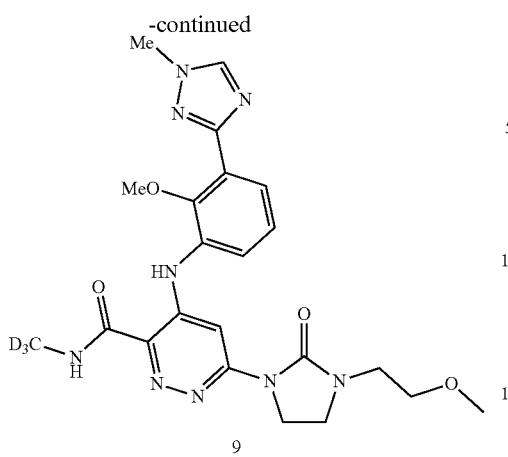

9

Step 1: 1-(2-chloroethyl)-3-(2-methoxyethyl)urea

To a solution of 2-methoxyethanamine (0.38 g, 5 mmol) in THF (10 mL) was added 1-chloro-2-isocyanato-ethane (0.53 g, 5 mmol), then it was stirred at room temperature for 2 h give the desired product 9B (0.81 g, 90%) as a colorless oil, it was used in the next step without further purification. LC-MS: m/z=180.6 [M+H]+

Step 2: 1-(3-methyloxetan-3-yl)imidazolidin-2-one

To a solution of 9 B (0.81 g, 4.5 mmol) in THF (20 ml) was added sodium hydride (0.13 g, 5.4 mmol), then it was stirred at room temperature for 4h. Quenched with water (20 mL) and extracted by EtOAc (40 mL×2). The combined organic layers were washed by brine (60 mL), dried over Na₂SO₄, filtered and concentrated under reduced pressure to afford the crude product which was purified by column chromatography (EtOAc/PE=1/1) to give the desired product 9C (0.25 g, yield: 40%) as a colorless oil. LC-MS: m/z=144.2 [M+H]+

Step 3: 6-[3-(2-methoxyethyl)-2-oxo-imidazolidin-1-yl]-4-[2-methoxy-3-(1-methyl-1,2,4-triazol-3-yl)anilino]-N-(trideuteriomethyl)pyridazine-3-carboxamide To a solution of intermediate 1 (60 mg, 0.16 mmol) and 9C (30 mg, 0.2 mmol) in 1,4-dioxane (8 mL) was added Cesium carbonate (160 mg, 0.5 mmol), Pd₂(dba)₃ (20 mg, 0.02 mmol), and xantphos (24 mg, 0.04 mmol). The mixture degassed by N₂ for 3 times and heated to 130° C. for 2 hrs. When reaction completed, filtered, filtrate was removed in vacuo, chromatography (PE/EtOAc=50/50 then DCM/MeOH=95/5) to give the desired product Example 9 (8.4 mg, yield: 11%) as a white solid. LM-MS: m/z=484.5 [M+H]+. ¹H NMR (400 MHz, CDCl₃): δ 11.03 (s, 1H), 8.36 (s, 1H), 8.13-8.11 (m, 2H), 7.80-7.79 (d, 1H), 7.55-7.53 (d, 1H), 7.25-7.29 (m, 1H), 4.30-4.26 (q, 2H), 4.00 (s, 3H), 3.82 (s, 3H), 3.68-3.64 (q, 2H), 3.56-3.53 (q, 2H), 3.49-3.46 (q, 2H), 3.35 (s, 3H).

Example 10: 6-[3-(3,3-difluorocyclobutyl)-2-oxo-imidazolidin-1-yl]-4-[2-methoxy-3-(1-methyl-1,2,4-triazol-3-yl)anilino]-N-(trideuteriomethyl)pyridazine-3-carboxamide

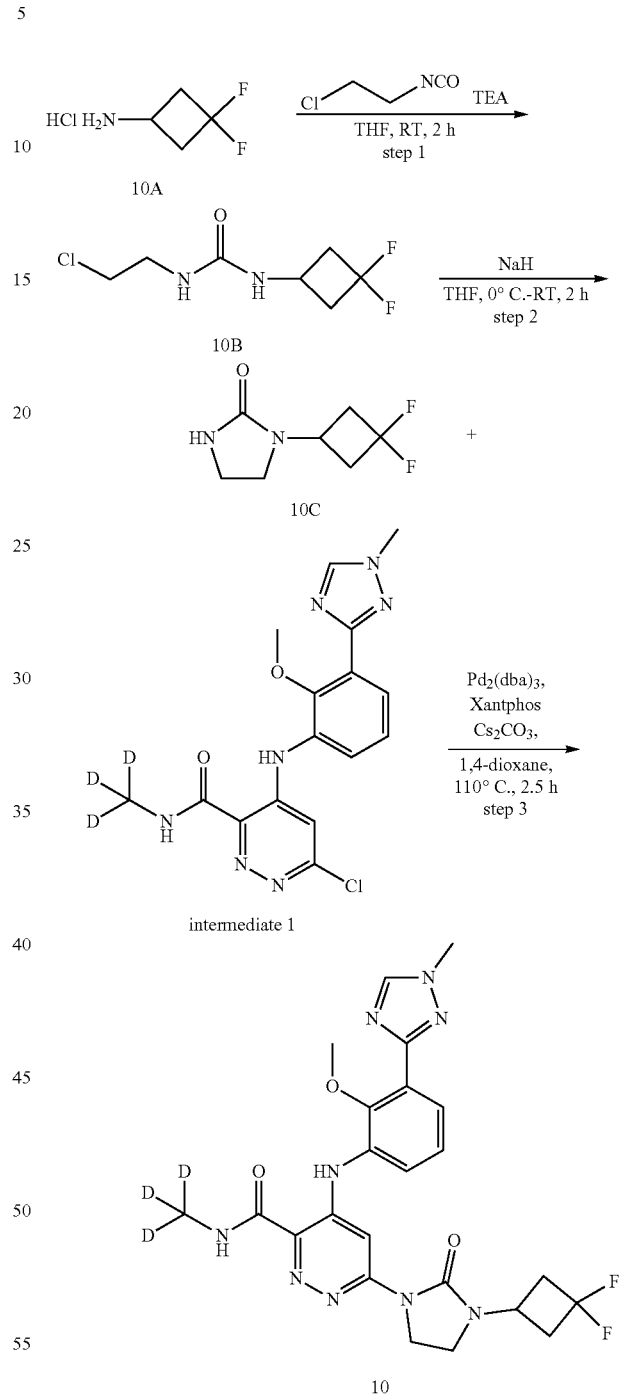

10

Step 1: 1-(2-chloroethyl)-3-(3,3-difluorocyclobutyl)urea

To a solution of 3,3-difluorocyclobutanamine hydrochloride (10A) (1.0 g, 6.96 mmol) and TEA (1.94 mL, 13.93 mmol) in THF (15 mL) was added 1-chloro-2-isocyanato-ethane (0.6 mL, 6.96 mmol) via a syringe, then it was stirred at room temperature for 2 h. The mixture solution was evaporated to dryness, redissolved in EtOAc (80 mL). The organic layer was then washed with NaHCO$_3$ and brine, dried over Na$_2$SO$_4$, filtered and concentrated, then the title compound 10B (550 mg, 37.4%) was obtained as white solid, which was used in the next step without further purification. LM-MS: m/z=213.1 [M+H]$^+$ Step 2: 1-(3,3-difluorocyclobutyl)imidazolidin-2-one To a solution of 10B (0.5 g, 2.35 mmol) in THF (30 mL) was added sodium hydride (0.19 g, 4.7 mmol), then it was stirred at room temperature for 2 h. Quenched with water (20 mL) and extracted by EtOAc (30 mL×2). The combined organic layers were washed by brine (30 mL), dried over Na$_2$SO$_4$, filtered and concentrated under reduced pressure to afford the crude product which was purified by column chromatography (EtOAc/PE=1/1) to give the desired product 10C (0.23 g, yield: 55.4%) as a white solid.

Step 3: 6-[3-(3,3-difluorocyclobutyl)-2-oxo-imidazolidin-1-yl]-4-[2-methoxy-3-(1-methyl-1,2,4-triazol-3-yl)anilino]-N-(trideuteriomethyl)pyridazine-3-carboxamide To a solution of intermediate 1 (60 mg, 0.16 mmol) and 10C (56 mg, 0.32 mmol) in 1,4-dioxane (8 mL) was added Cesium carbonate (100 mg, 0.32 mmol), Pd$_2$(dba)$_3$ (43 mg, 0.048 mmol), and xantphos (46 mg, 0.08 mmol). The mixture degassed by N$_2$ for 3 times and heated to 110° C. for 4 hrs. When reaction completed, filtered, filtrate was removed in vacuo, The residue was purified by flash Chromatography (PE/EtOAc=50/50 then DCM/MeOH=97/3) to afford the title compound Example 10 (12 mg, yield: 13.95%) as a white solid. LM-MS: m/z=517.2 [M+H]$^+$. $^1$H NMR (400 MHz, CDCl$_3$): δ 10.98 (s, 1H), 8.32 (s, 1H), 8.18-8.07 (m, 2H), 7.77 (d, 1H), 7.55-7.49 (d, 1H), 7.30 (d, 1H), 4.51-4.41 (m, 1H), 4.26 (t, 2H), 4.03 (s, 3H), 3.78 (s, 3H), 3.60 (t, 2H), 2.95-2.71 (m, 4H).

Example 11: 6-(3-cyclobutyl-2-oxo-imidazolidin-1-yl)-4-[2-methoxy-3-(1-methyl-1,2,4-triazol-3-yl)anilino]-N-(trideuteriomethyl)pyridazine-3-carboxamide

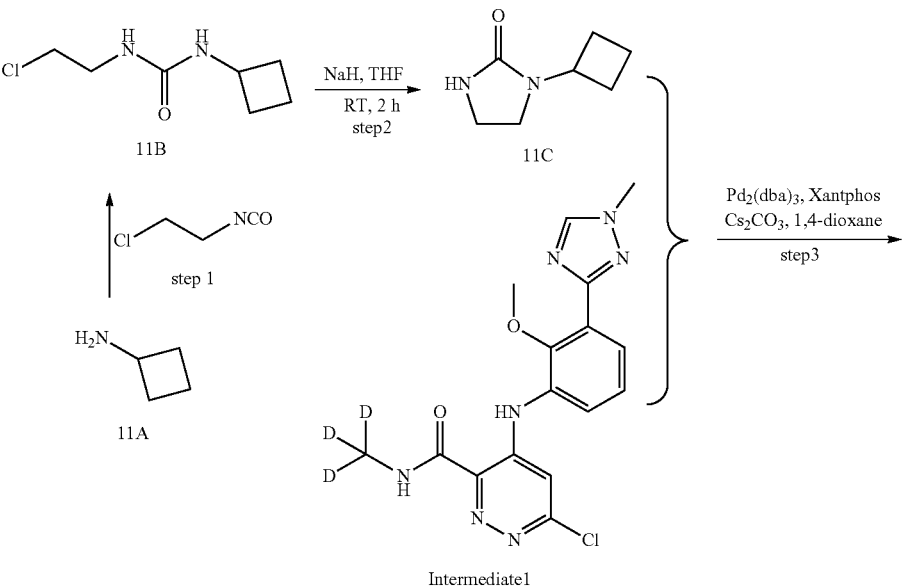

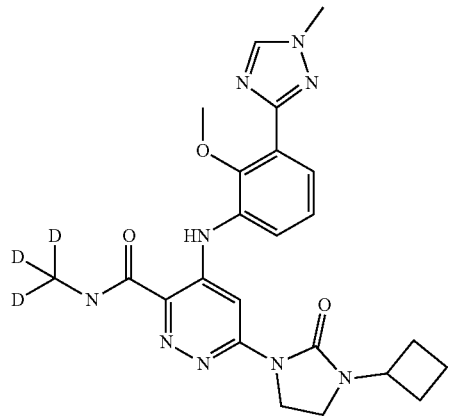

11

Step 1: 1-(2-chloroethyl)-3-cyclobutyl-urea

To a solution of cyclobutanamine (1.0 g, 14.1 mmol) in acetonitrile (20 mL) was added 1-chloro-2-isocyanato-ethane (1.48 g, 14.1 mmol), then it was stirred at room temperature for 2h. solid precipitation, filtered, give the desired product Example 11B (1.5 g, 60.4%) as a white solid, it was used in the next step without further purification. LM-MS: m/z=177.1 [M+H]$^+$. $^1$H NMR (400 MHz, CDCl$_3$): δ 4.57 (s, 2H), 4.16-4.06 (m, 1H), 3.68-3.59 (m, 2H), 3.59-3.51 (m, 2H), 2.40-2.30 (m, 2H), 1.91-1.79 (m, 2H), 1.79-1.60 (m, 2H).

Step 2: 1-cyclobutylimidazolidin-2-one

To a solution of 1-(2-chloroethyl)-3-cyclobutyl-urea (1.0 g, 5.7 mmol) in THF (30 ml) was added sodium hydride (0.27 g, 11 mmol), then it was stirred at room temperature for 2h. Quenched with water (20 mL) and extracted by EtOAc (30 mL×2). The combined organic layers were washed by brine (30 mL), dried over Na$_2$SO$_4$, filtered and concentrated under reduced pressure to afford the crude product which was purified by column chromatography (EtOAc/PE=1/1) to give the desired product Example 11C (0.70 g, yield: 88%) as a white solid. LM-MS: m/z=141.2 [M+H]$^+$. $^1$H NMR (400 MHz, CDCl$_3$) δ 4.43 (t, 1H), 3.50 (dd, 2H), 3.40 (dd, 2H), 2.14-2.05 (m, 4H), 1.68-1.61 (m, 2H).

Step 3: 6-(3-cyclobutyl-2-oxo-imidazolidin-1-yl)-4-[2-methoxy-3-(1-methyl-1,2,4-triazol-3-yl)anilino]-N-(trideuteriomethyl)pyridazine-3-carboxamide To a solution of Intermediate 1 (60 mg, 0.16 mmol) and 11C (45 mg, 0.32 mmol) in 1,4-dioxane (8 mL) was added Cesium carbonate (100 mg, 0.32 mmol), Pd$_2$(dba)$_3$ (43 mg, 0.048 mmol), and xantphos (46 mg, 0.08 mmol). The mixture degassed by N$_2$ for 3 times and heated to 120° C. for 4 hrs. When reaction completed, filtered, filtrate was removed in vacuo, chromatography (PE/EtOAc=50/50 then DCM/MeOH=97/3) to give the desired product 11 (5 mg, yield: 7%) as a yellow solid. LM-MS: m/z=481.2 [M+H]$^+$. $^1$H NMR (400 MHz, CD$_3$OD) δ 8.46 (s, 1H), 8.37 (s, 1H), 7.63 (td, 2H), 7.29 (t, 1H), 4.43 (t, 1H), 4.19-4.09 (m, 2H), 4.01 (s, 3H), 3.74 (s, 3H), 3.70-3.61 (m, 2H), 2.38-2.23 (m, 2H), 2.13 (dd, 2H), 1.77-1.68 (m, 2H).

Example 12: 6-(3-ethyl-2-oxo-imidazolidin-1-yl)-4-[2-methoxy-3-(1-methyl-1,2,4-triazol-3-yl)anilino]-N-(trideuteriomethyl)pyridazine-3-carboxamide

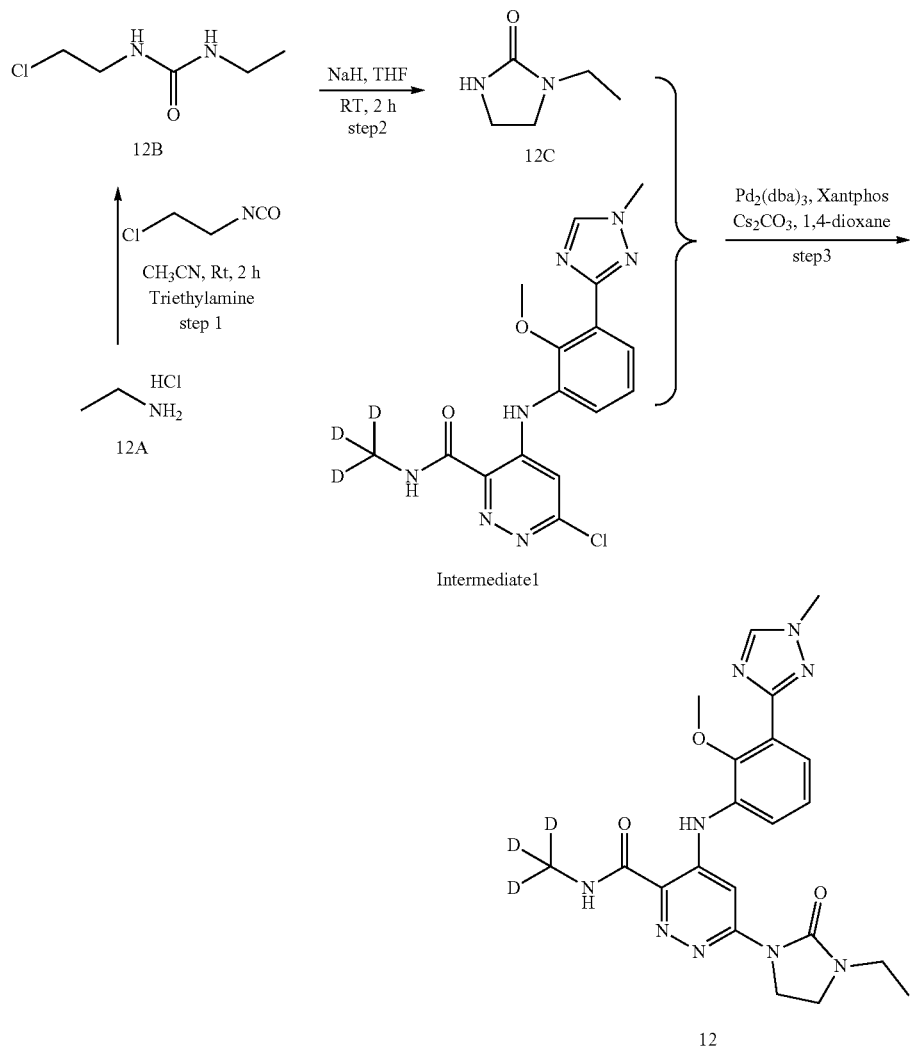

Step 1: 1-(2-chloroethyl)-3-ethyl-urea

To a solution of ethylamine hydrochloride (1.0 g, 12.3 mmol) in Acetonitrile (20 mL) was added Triethylamine (2.48 g, 24.6 mmol) and 1-chloro-2-isocyanato-ethane (1.24 g, 12.3 mmol), then it was stirred at room temperature for 2 h. solid precipitation, filtered, give the desired product Example 12B (1.5 g, 81%) as a white solid, it was used in the next step without further purification.

Step 2: 1-ethylimidazolidin-2-one

To a solution of 12B (1.0 g, 6.6 mmol) in THF (30 ml) was added sodium hydride (0.32 g, 13 mmol), then it was stirred at room temperature for 2 h. Quenched with water (20 mL) and extracted by EtOAc (30 mL×2). The combined organic layers were washed by brine (30 mL), dried over Na$_2$SO$_4$, filtered and concentrated under reduced pressure to afford the crude product which was purified by column chromatography (EtOAc/PE=1/1) to give the desired product Example 12C (0.70 g, yield: 92%) as a white solid.

Step 3: 6-(3-ethyl-2-oxo-imidazolidin-1-yl)-4-[2-methoxy-3-(1-methyl-1,2,4-triazol-3-yl)anilino]-N-(trideuteriomethyl)pyridazine-3-carboxamide To a solution of Intermediate 1 (60 mg, 0.16 mmol) and 12C (36 mg, 0.32 mmol) in 1,4-dioxane (8 mL) was added Cesium carbonate (100 mg, 0.32 mmol), Pd$_2$(dba)$_3$ (43 mg, 0.048 mmol), and xantphos (46 mg, 0.08 mmol). The mixture degassed by N$_2$ for 3 times and heated to 120° C. for 4 hrs. When reaction completed, filtered, filtrate was removed in vacuo, chromatography (PE/EtOAc=50/50 then DCM/MeOH=97/3) to give the desired product Example 12 (5 mg, yield: 6%) as a yellow solid. LM-MS: m/z=455.3 [M+H]$^+$. $^1$H NMR (400 MHz, MeOD): δ 8.53 (s, 1H), 7.76 (dd, 1H), 7.63 (dd, 1H), 7.58 (s, 1H), 7.35 (d, 1H), 4.13-3.94 (m, 5H), 3.74 (s, 3H), 3.69-3.58 (m, 2H), 3.37 (d, 2H), 1.19 (t, 3H).

Example 13: 6-(3-isopropyl-2-oxo-imidazolidin-1-yl)-4-[2-methoxy-3-(1-methyl-1,2,4-triazol-3-yl)anilino]-N-(trideuteriomethyl)pyridazine-3-carboxamide

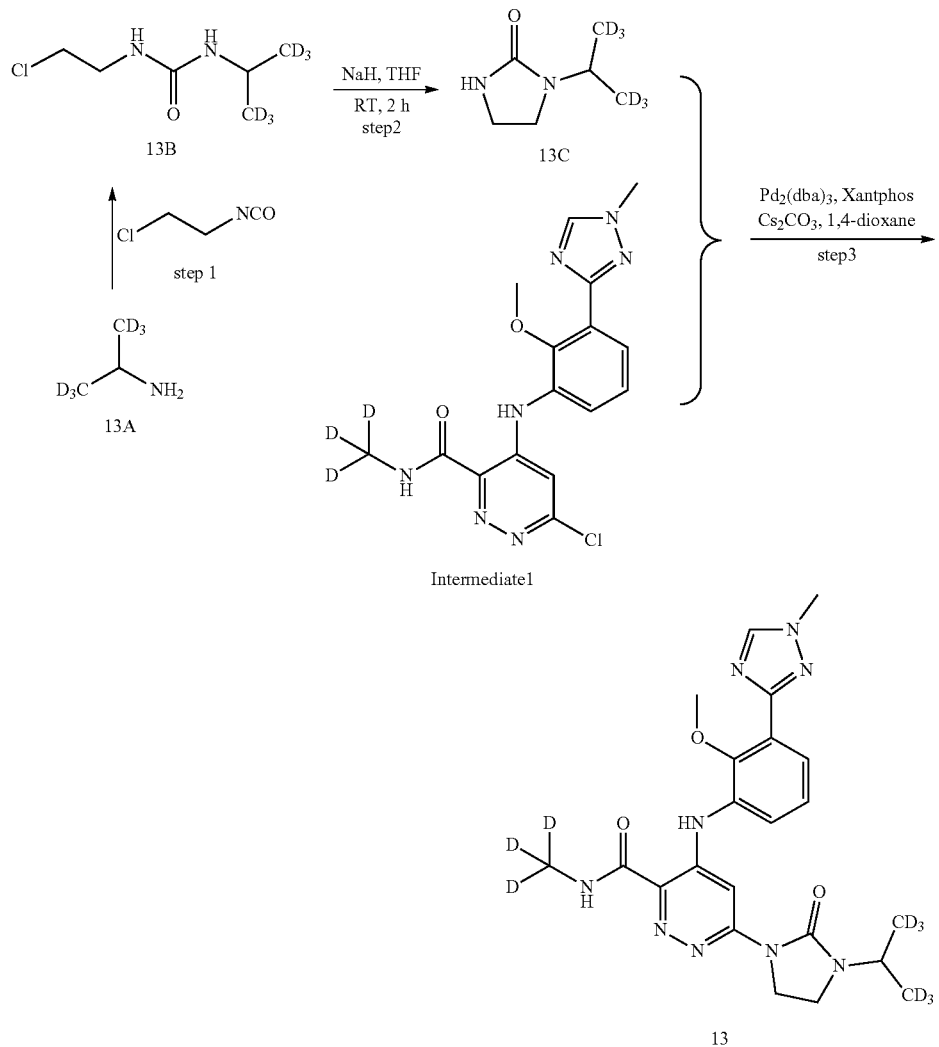

Step 1: 1-(2-chloroethyl)-3-[2,2,2-trideuterio-1-(trideuteriomethyl)ethyl]urea To a solution of 1,1,1,3,3,3-hexadeuteriopropan-2-amine (0.20 g, 3.1 mmol) in acetonitrile (20 mL) was added 1-chloro-2-isocyanato-ethane (0.32 g, 3.1 mmol), then it was stirred at room temperature for 2 h. solid precipitation, filtered, give the desired product 13B (0.4 g, 76%) as a white solid, it was used in the next step without further purification. LM-MS: m/z=171.2 [M+H]$^+$

Step 2: 1-[2,2,2-trideuterio-1-(trideuteriomethyl)ethyl]imidazolidin-2-one

To a solution of 13B (0.2 g, 1.2 mmol) in THF (10 ml) was added sodium hydride (0.056 g, 2.4 mmol), then it was stirred at room temperature for 2 h. Quenched with water (20 mL) and extracted by EtOAc (30 mL×2). The combined organic layers were washed by brine (30 mL), dried over Na$_2$SO$_4$, filtered and concentrated under reduced pressure to afford the crude product which was purified by column chromatography (EtOAc/PE=1/1) to give the desired product Example 13C (0.070 g, yield: 40%) as a white solid.

Step 3: 6-(3-isopropyl-2-oxo-imidazolidin-1-yl)-4-[2-methoxy-3-(1-methyl-1,2,4-triazol-3-yl)anilino]-N-(trideuteriomethyl)pyridazine-3-carboxamide To a solution of intermediate 1 (80 mg, 0.21 mmol) and 13C (57 mg, 0.42 mmol) in 1,4-dioxane (8 mL) was added Cesium carbonate (140 mg, 0.42 mmol), Pd$_2$(dba)$_3$ (57 mg, 0.063 mmol), and xantphos (72 mg, 0.126 mmol). The mixture degassed by N$_2$ for 3 times and heated to 120° C. f or 4 hrs. When reaction completed, filtered, filtrate was removed in vacuo, chromatography (PE/EtOAc=50/50 then DCM/MeOH=97/3) to give the desired product Example 13 (7 mg, yield: 7%) as a yellow solid. LM-MS: m/z=475.3 [M+H]$^+$. $^1$H NMR (400 MHz, MeOD): δ 8.46 (s, 1H), 8.40 (d, 1H), 7.66-7.61 (m, 2H), 7.29 (t, 1H), 4.14 (dd, 3H), 4.01 (s, 3H), 3.74 (s, 3H), 3.58-3.52 (m, 2H).

Example 14: 6-(3-isopropyl-2-oxo-imidazolidin-1-yl)-4-[3-(1-methyl-1,2,4-triazol-3-yl)-2-(trideuteriomethoxy)anilino]-N-(trideuteriomethyl)pyridazine-3-carboxamide Example 15: 6-(3-isopropyl-2-oxo-imidazolidin-1-yl)-4-[2-methoxy-3-[1-(trideuteriomethyl)-1,2,4-triazol-3-yl]anilino]-N-(trideuteriomethyl)pyridazine-3-carboxamide

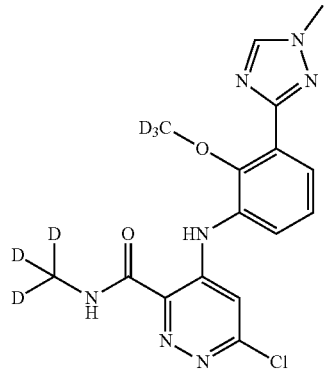

Intermediate 3

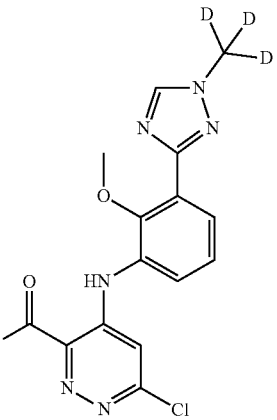

Intermediate 2

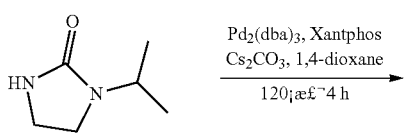

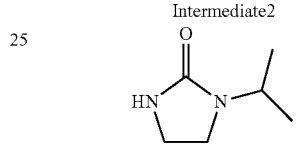

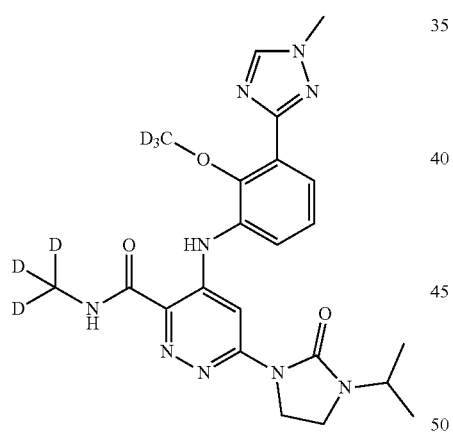

14

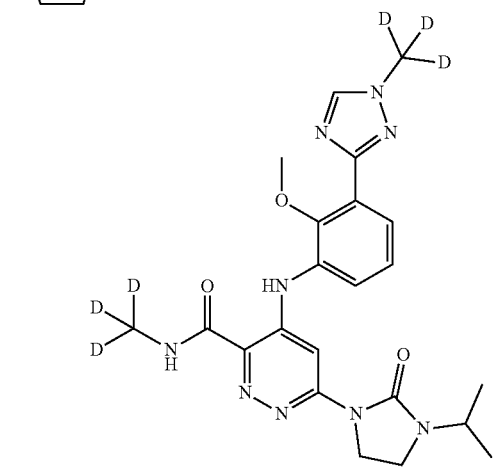

15

To a solution of intermediate 3 (160 mg, 0.42 mmol) and 1-isopropylimidazolidin-2-one (110 mg, 0.84 mmol) in 1,4-dioxane (8 mL) was added Cesium carbonate (270 mg, 0.84 mmol), $Pd_2(dba)_3$ (115.3 mg, 0.126 mmol), and xantphos (145.6 mg, 0.252 mmol). The mixture degassed by $N_2$ for 3 times and heated to 120° C. for 4 hrs. When reaction completed, filtered, filtrate was removed in vacuo, chromatography (PE/EtOAc=50/50 then DCM/MeOH=97/3) to give the desired product Example 14 (60 mg, yield: 24%) as a yellow solid. LM-MS: m/z=472.3 [M+H]$^+$. $^1$H NMR (400 MHz, CDCl$_3$) δ 11.10 (s, 1H), 8.38 (s, 1H), 8.10 (d, 2H), 7.81 (d, 1H), 7.55 (d, 1H), 7.29 (d, 1H), 4.31 (s, 2H), 4.27-4.21 (m, 1H), 4.00 (s, 3H), 3.53-3.46 (m, 2H), 1.18 (d, 6H).

To a solution of Intermediate 2 (60 mg, 0.16 mmol) and 1-isopropylimidazolidin-2-one (41 mg, 0.32 mmol) in 1,4-dioxane (8 mL) was added Cesium carbonate (100 mg, 0.32 mmol), $Pd_2(dba)_3$ (43 mg, 0.048 mmol), and xantphos (46 mg, 0.08 mmol). The mixture degassed by $N_2$ for 3 times and heated to 120° C. for 4 hrs. When reaction completed, filtered, filtrate was removed in vacuo, chromatography (PE/EtOAc=50/50 then DCM/MeOH=97/3) to give the desired product Example 15. (6 mg, yield: 8%) as a yellow solid. LM-MS: m/z=472.3 [M+H]$^+$. $^1$H NMR (400 MHz, CDCl$_3$) δ 10.92 (s, 1H), 8.35 (s, 1H), 8.16 (s, 1H), 8.10 (s, 1H), 7.77 (dd, 1H), 7.55 (dd, 1H), 7.28 (d, 1H), 4.25 (ddd, 1H), 3.81 (s, 3H), 3.51-3.44 (m, 2H), 1.18 (d, 6H).

Example 16. 4-[2-methoxy-3-(1-methyl-1,2,4-triazol-3-yl)anilino]-6-[3-(3-methyloxetan-3-yl)-2-oxo-imidazolidin-1-yl]-N-(trideuteriomethyl)pyridazine-3-carboxamide

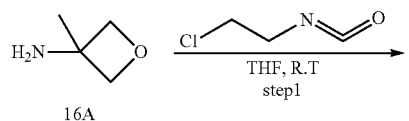

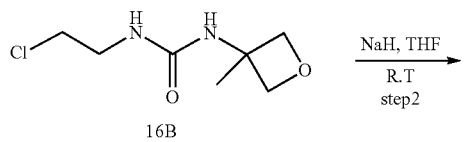

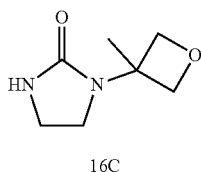

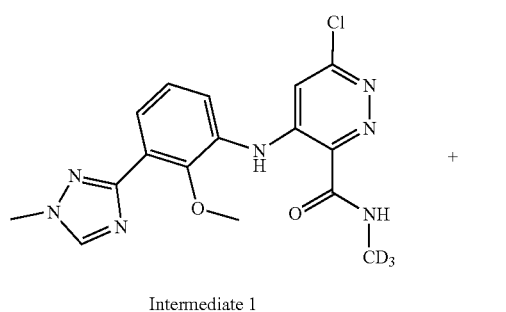

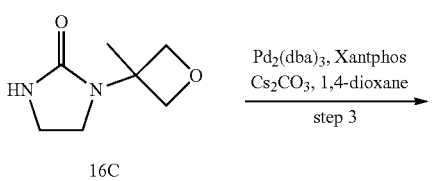

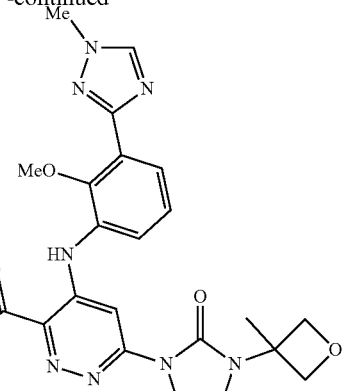

Step 1: 1-(2-chloroethyl)-3-(3-methyloxetan-3-yl)urea

To a solution of 3-methyloxetan-3-amine (0.87 g, 10 mmol) in THF (20 mL) was added 1-chloro-2-isocyanato-ethane (1.06 g, 10 mmol), then it was stirred at room temperature for 2 h give the desired product 16B (1.82 g, 94%) as a colorless oil, it was used in the next step without further purification. LC-MS: m/z=192.6 [M+H]$^+$

Step 2: 1-(3-methyloxetan-3-yl)imidazolidin-2-one

To a solution of 16B (1.82 g, 9.2 mmol) in THF (30 ml) was added sodium hydride (0.29 g, 12 mmol), then it was stirred at room temperature for 4 h. Quenched with water (20 mL) and extracted by EtOAc (40 mL×2). The combined organic layers were washed by brine (60 mL), dried over Na$_2$SO$_4$, filtered and concentrated under reduced pressure to afford the crude product which was purified by column chromatography (EtOAc/PE=1/1) to give the desired product 16C (1.0 g, yield: 69%) as a white solid. LC-MS: m/z=156.2 [M+H]$^+$

Step 3: 4-[2-methoxy-3-(1-methyl-1,2,4-triazol-3-yl)anilino]-6-[3-(3-methyloxetan-3-yl)-2-oxo-imidazolidin-1-yl]-N-(trideuteriomethyl)pyridazine-3-carboxamide To a solution of intermediate 1 (110 mg, 0.3 mmol) and 16C (63 mg, 0.4 mmol) in 1,4-dioxane (8 mL) was added Cesium carbonate (300 mg, 0.9 mmol), Pd$_2$(dba)$_3$ (30 mg, 0.03 mmol), and xantphos (35m g, 0.06 mmol). The mixture degassed by N$_2$ for 3 times and heated to 130° C. for 2 hrs. When reaction completed, filtered, filtrate was removed in vacuo, chromatography (PE/EtOAc=50/50 then DCM/MeOH=95/5) to give the desired product Example 16. (40 mg, yield: 30%) as a white solid. LM-MS: m/z=496.6 [M+H]$^+$. $^1$H NMR (400 MHz, CDCl$_3$): δ 11.09 (s, 1H), 8.13-8.06 (m, 3H), 7.76 (s, 1H), 7.45 (s, 1H), 7.19 (m, 1H), 4.83-4.81 (d, 2H), 4.35-4.30 (m, 4H), 3.94 (s, 3H), 3.75 (s, 3H), 3.39 (m, 2H). 1.57 (s, 3H)

Example 17: 6-(3-isobutyl-2-oxo-imidazolidin-1-yl)-4-[2-methoxy-3-(1-methyl-1,2,4-triazol-3-yl)anilino]-N-(trideuteriomethyl)pyridazine-3-carboxamide

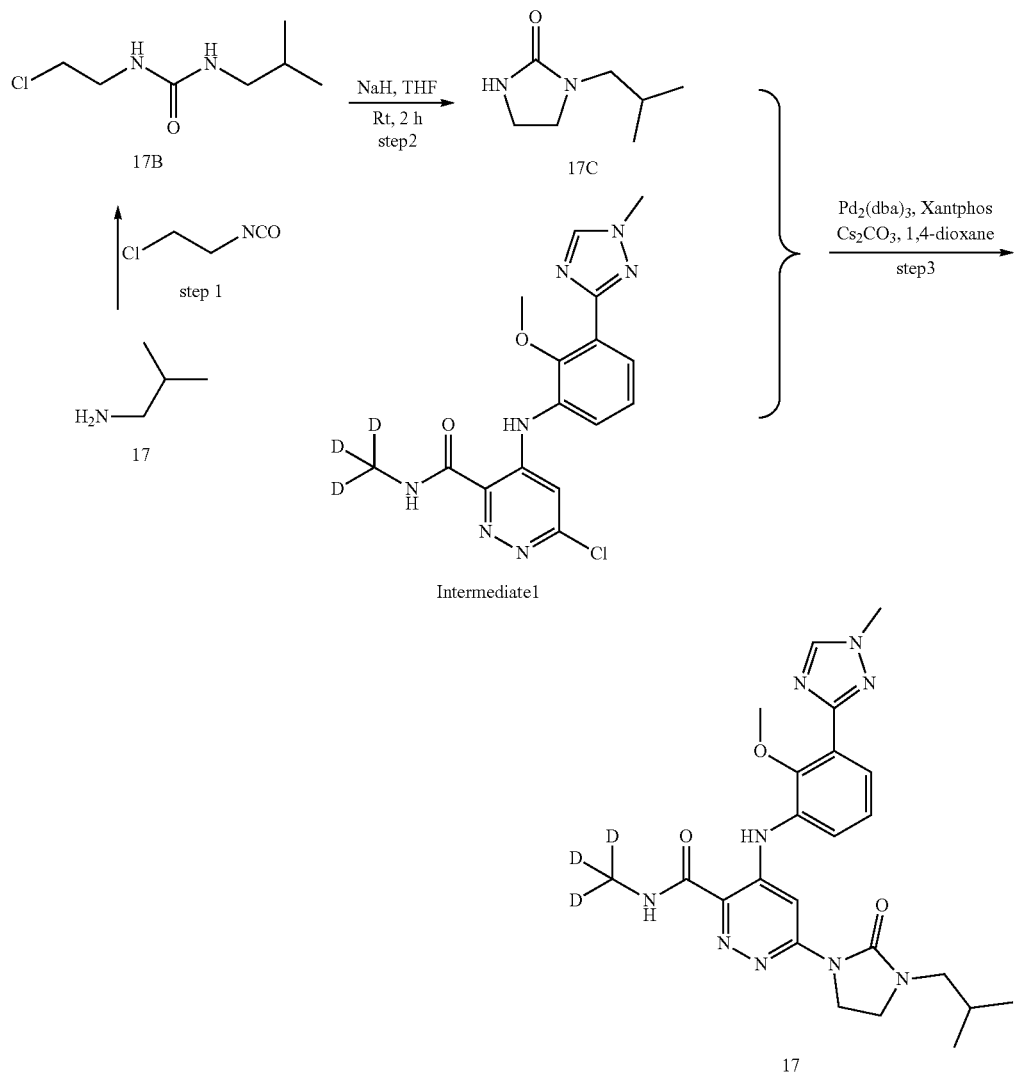

Step 1: 1-(2-chloroethyl)-3-isobutyl-urea

To a solution of 2-methylpropan-1-amine (1.0 g, 14 mmol) in acetonitrile (20 mL) was added 1-chloro-2-isocyanato-ethane (1.4 g, 14 mmol), then it was stirred at room temperature for 2 h. solid precipitation, filtered, give the desired product Example 17B (1.5 g, 61%) as a white solid, it was used in the next step without further purification. LM-MS: m/z=171.2 [M+H]+

Step 2: 1-(2-chloroethyl)-3-isobutyl-urea

To a solution of 1-(2-chloroethyl)-3-isobutyl-urea (1.2 g, 6.7 mmol) in THF (10 ml) was added sodium hydride (0.32 g, 13 mmol), then it was stirred at room temperature for 2 h. Quenched with water (20 mL) and extracted by EtOAc (30 mL×2). The combined organic layers were washed by brine (30 mL), dried over Na$_2$SO$_4$, filtered and concentrated under reduced pressure to afford the crude product which was purified by column chromatography (EtOAc/PE=1/1) to give the desired product Example 17C (0.5 g, yield: 50%) as a white solid.

Step 3: 6-(3-isobutyl-2-oxo-imidazolidin-1-yl)-4-[2-methoxy-3-(1-methyl-1,2,4-triazol-3-yl)anilino]-N-(trideuteriomethyl)pyridazine-3-carboxamide To a solution of intermediate 1 (110 mg, 0.292 mmol) and 1-(2-chloroethyl)-3-isobutyl-urea (83 mg, 0.584 mmol) in 1,4-dioxane (8 mL) was added Cesium carbonate (190 mg, 0.584 mmol), Pd$_2$(dba)$_3$ (80 mg, 0.087 mmol), and xantphos (100.7 mg, 0.175 mmol). The mixture degassed by N$_2$ for 3 times and heated to 120° C. for 4 hrs. When reaction completed, filtered, filtrate was removed in vacuo, chromatography (PE/EtOAc=50/50 then DCM/MeOH=97/3) to give the desired product Example 17 (55 mg, yield: 39%) as a yellow solid. LM-MS: m/z=483.3 [M+H]⁺. 1H NMR (400 MHz, CDCl₃) δ 11.01 (s, 1H), 8.37 (s, 1H), 8.11 (d, 2H), 7.78 (d, 1H), 7.56 (d, 1H), 7.28 (d, 1H), 4.34-4.21 (m, 2H), 4.00 (s, 3H), 3.82 (s, 3H), 3.58-3.48 (m, 2H), 3.09 (d, 2H), 1.95-1.90 (m, 1H), 0.91 (dd, 6H).

Example 18: 6-(3-cyclopentyl-2-oxo-imidazolidin-1-yl)-4-[2-methoxy-3-(1-methyl-1,2,4-triazol-3-yl)anilino]-N-(trideuteriomethyl)pyridazine-3-carboxamide

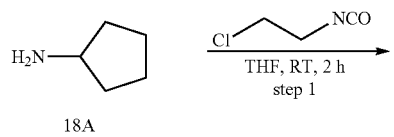

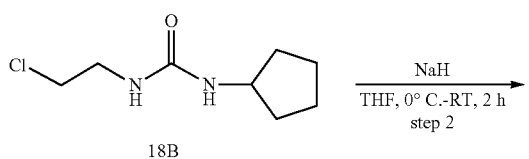

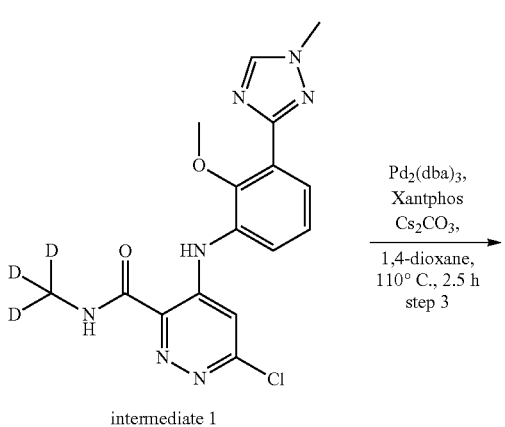

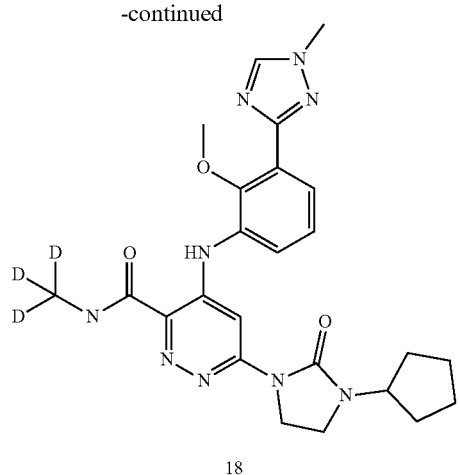

Step 1: 1-(2-chloroethyl)-3-cyclopentyl-urea

To a solution of cyclopentylamine (18A) (1.0 g, 11.7 mmol) and in THF (15 mL) was added 1-chloro-2-isocyanato-ethane (1 mL, 11.7 mmol) via a syringe, then it was stirred at room temperature for 2 h. The mixture solution was evaporated to afford the title compound 18B (780 mg, 34.97%) as a colourless oil, which was used in the next step without further purification. LM-MS: m/z=191.1 [M+H]⁺

Step 2: 1-cyclopentylimidazolidin-2-one

To a solution of T177B (0.5 g, 2.63 mmol) in THF (30 mL) was added sodium hydride (0.21 g, 5.26 mmol), then it was stirred at room temperature for 2 h. Quenched with water (20 mL) and extracted by EtOAc (30 mL×2). The combined organic layers were washed by brine (30 mL), dried over Na₂SO₄, filtered and concentrated under reduced pressure to afford the title product (18C) (310 mg, 76.54%) as colourless oil. LM-MS: m/z=155.2 [M+H]⁺

Step 3: 6-(3-cyclopentyl-2-oxo-imidazolidin-1-yl)-4-[2-methoxy-3-(1-methyl-1,2,4-triazol-3-yl)anilino]-N-(trideuteriomethyl)pyridazine-3-carboxamide To a solution of intermediate 1 (60 mg, 0.16 mmol) and 18C (49 mg, 0.32 mmol) in 1,4-dioxane (8 mL) was added Cesium carbonate (100 mg, 0.32 mmol), Pd₂(dba)₃ (43 mg, 0.048 mmol), and xantphos (46 mg, 0.08 mmol). The mixture degassed by N₂ for 3 times and heated to 110° C. for 4 hrs. When reaction completed, filtered, filtrate was removed in vacuo, The residue was purified by flash Chromatography (PE/EtOAc=50/50 then DCM/MeOH=97/3) to afford the title compound Example 18 (16 mg, 20.3%) as a white solid. LM-MS: m/z=495.3 [M+H]*. ¹H NMR (400 MHz, CDCl₃) δ 11.05 (s, 1H), 8.37 (s, 1H), 8.14-8.08 (m, 2H), 7.80 (d, 1H), 7.55 (d, 1H), 7.29 (d, 1H), 4.41-4.32 (m, 1H), 4.31-4.25 (m, 2H), 4.00 (s, 3H), 3.82 (s, 3H), 3.57-3.45 (m, 2H), 1.88-1.82 (m, 2H), 1.74-1.69 (m, 2H), 1.66-1.50 (m, 4H).

Example 19: 6-[3-(3-bicyclo[1.1.1]pentanyl)-2-oxo-imidazolidin-1-yl]-4-[2-methoxy-3-(1-methyl-1,2,4-triazol-3-yl)anilino]-N-(trideuteriomethyl)pyridazine-3-carboxamide

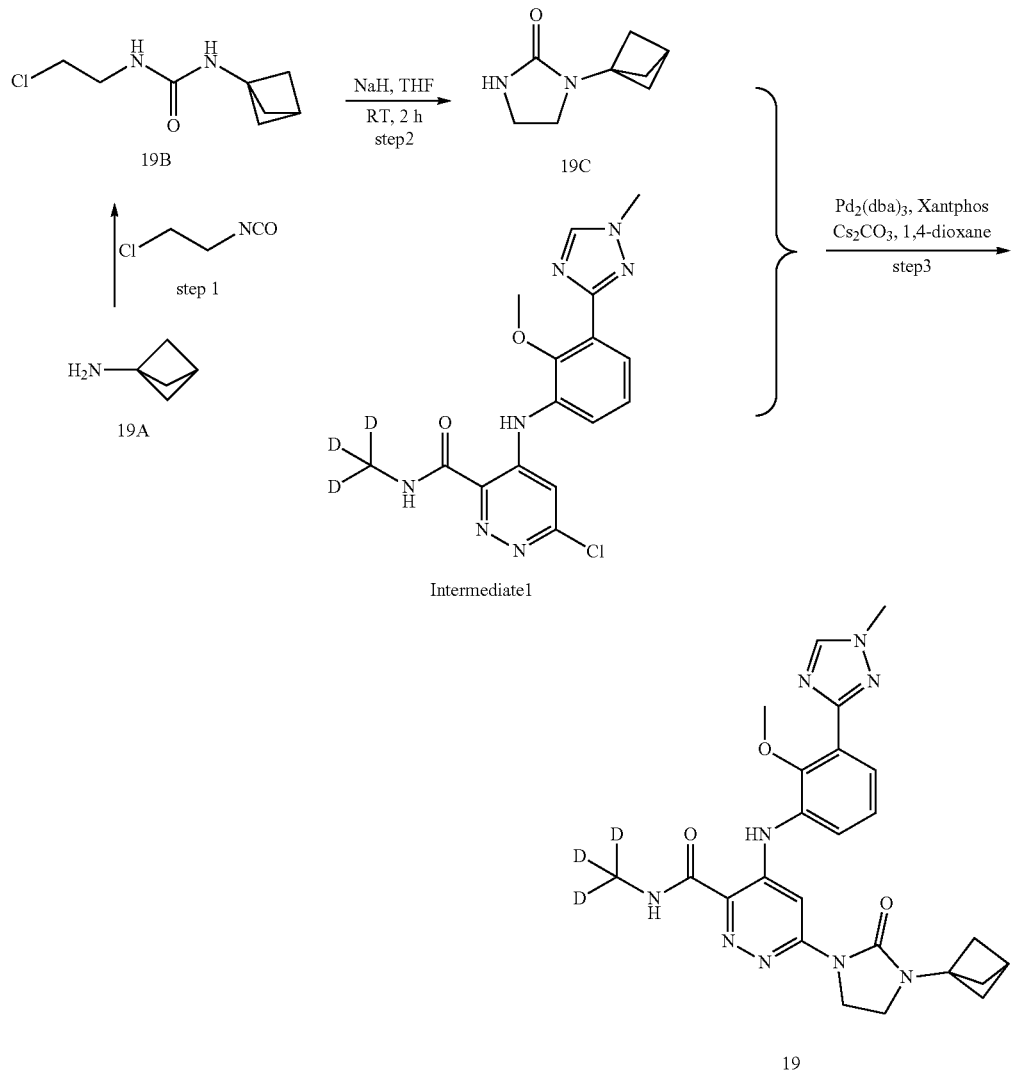

Step 1: 1-(3-bicyclo[1.1.1]pentanyl)-3-(2-chloroethyl)urea

To a solution of bicyclo[1.1.1]pentan-3-amine (0.5 g, 4.2 mmol) in acetonitrile (20 mL) was added 1-chloro-2-isocyanato-ethane (0.44 g, 4.2 mmol), then it was stirred at room temperature for 2 h. solid precipitation, filtered, give the desired product Example 19B (0.5 g, 63%) as a white solid, it was used in the next step without further purification. LM-MS: m/z=189.1 [M+H]$^+$

Step 2: 1-(3-bicyclo[1.1.1]pentanyl)imidazolidin-2-one

To a solution of 19B (0.5 g, 2.7 mmol) in THF (10 ml) was added sodium hydride (0.13 g, 5.3 mmol), then it was stirred at room temperature for 2 h. Quenched with water (20 mL) and extracted by EtOAc (30 mL×2). The combined organic layers were washed by brine (30 mL), dried over Na2SO4, filtered and concentrated under reduced pressure to afford the crude product which was purified by column chromatography (EtOAc/PE=1/1) to give the desired product Example T202C (0.35 g, yield: 87%) as a white solid.

Step 3: 6-[3-(3-bicyclo[1.1.1]pentanyl)-2-oxo-imidazolidin-1-yl]-4-[2-methoxy-3-(1-methyl-1,2,4-triazol-3-yl)anilino]-N-(trideuteriomethyl)pyridazine-3-carboxamide To a solution of intermediate 1 (170 mg, 0.451 mmol) and 19C (103 mg, 0.677 mmol) in 1,4-dioxane (8 mL) was added Cesium carbonate (293 mg, 0.902 mmol), Pd$_2$(dba)$_3$ (123.8 mg, 0.135 mmol), and xantphos (155 mg, 0.27 mmol). The mixture degassed by N$_2$ for 3 times and heated to 120° C. for 4 hrs. When reaction completed, filtered, filtrate was removed in vacuo, chromatography (PE/EtOAc=50/50 then DCM/MeOH=97/3) to give the desired product Example 19 (55 mg, yield: 39%) as a yellow solid. LM-MS: m/z=493.3 [M+H]+. 1H NMR (400 MHz, CDCl3): δ 10.94 (s, 1H), 8.30 (s, 1H), 8.12 (d, 2H), 7.78 (dd, 1H), 7.54 (dd, 1H), 7.28 (d, 1H), 4.24-4.15 (m, 2H), 4.00 (s, 3H), 3.81 (s, 3H), 3.57-3.46 (m, 2H), 2.48 (s, 1H), 2.13 (s, 6H).

Example 20: 6-(3-cyclobutyl-2-oxo-imidazolidin-1-yl)-4-[3-(1-methyl-1,2,4-triazol-3-yl)-2-(trideuteriomethoxy)anilino]-N-(trideuteriomethyl)pyridazine-3-carboxamide Example 21: 6-(3-isopropyl-2-oxo-imidazolidin-1-yl)-4-[2-methoxy-3-(1-methyl-1,2,4-triazol-3-yl)anilino]-N-(trideuteriomethyl)pyridazine-3-carboxamide

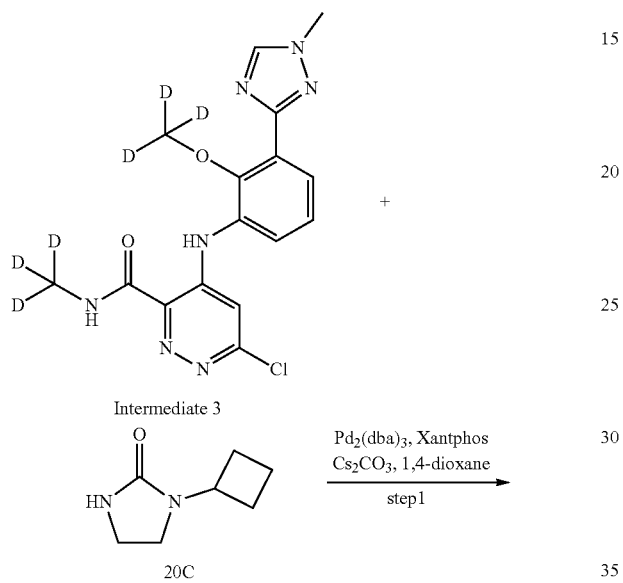

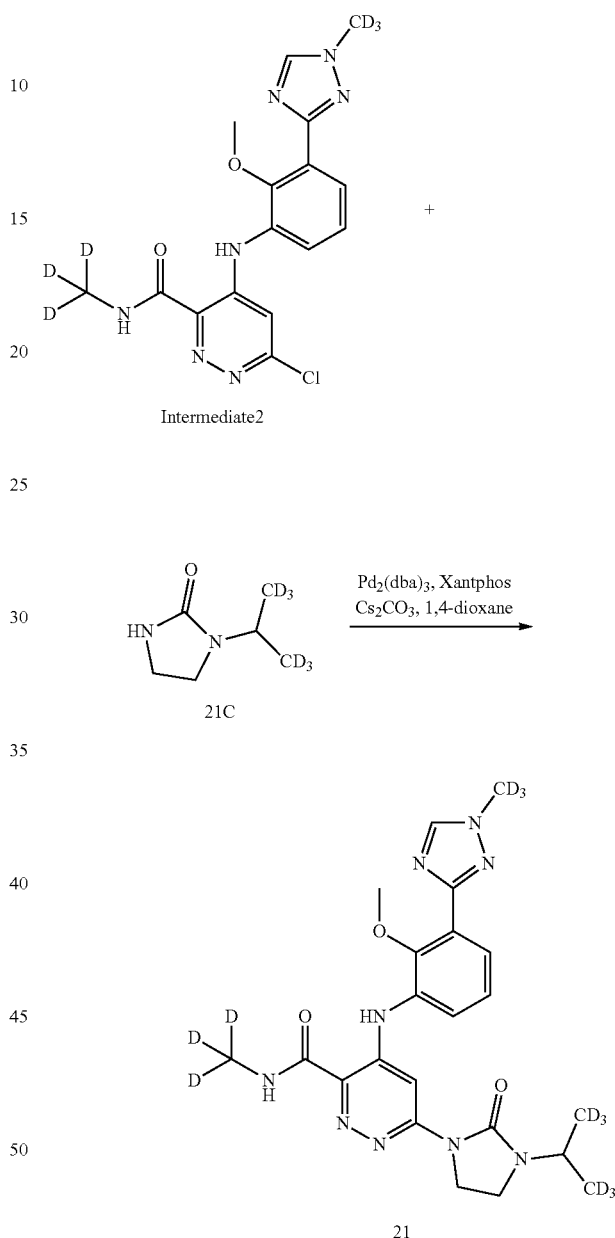

To a solution of intermediate 3 (60 mg, 0.16 mmol) and 20C (45 mg, 0.32 mmol) in 1,4-dioxane (8 mL) was added Cesium carbonate (100 mg, 0.32 mmol), Pd2(dba)3 (43 mg, 0.048 mmol), and xantphos (46 mg, 0.08 mmol). The mixture degassed by N2 for 3 times and heated to 120° C. for 4 hrs. When reaction completed, filtered, filtrate was removed in vacuo, chromatography (PE/EtOAc=50/50 then DCM/MeOH=97/3) to give the desired product Example 20 (6 mg, yield: 8%) as a yellow solid. LM-MS: m/z=484.3 [M+H]+. 1H NMR (400 MHz, CDCl3) δ 10.85 (s, 1H), 8.34 (s, 1H), 8.11 (d, 2H), 7.75 (dd, 1H), 7.55 (dd, 1H), 7.27 (d, 1H), 4.62-4.47 (m, 1H), 4.27-4.11 (m, 2H), 3.99 (s, 3H), 3.65-3.52 (m, 2H), 2.26-2.03 (m, 4H), 1.70 (dt, 2H).

To a solution of intermediate 2 (200 mg, 0.527 mmol) and 21C (141 mg, 1.05 mmol) in 1,4-dioxane (8 mL) was added Cesium carbonate (342 mg, 1.05 mmol), Pd2(dba)3 (144.6 mg, 0.158 mmol), and xantphos (182.6 mg, 0.316 mmol). The mixture degassed by N2 for 3 times and heated to 120° C. for 4 hrs. When reaction completed, filtered, filtrate was removed in vacuo, chromatography (PE/EtOAc=50/50 then DCM/MeOH=97/3) to give the desired product Example 21 (60 mg, yield: 24%) as a yellow solid. LM-MS: m/z=478.3 [M+H]+. 1H NMR (400 MHz, CDCl3): δ 11.04-10.91 (m, 1H), 8.38 (t, 1H), 8.15-8.03 (m, 2H), 7.82-7.75 (m, 1H), 7.60-7.52 (m, 1H), 7.31-7.26 (m, 1H), 4.32-4.18 (m, 3H), 3.86-3.76 (m, 3H), 3.53-3.44 (m, 2H).

Example 22: 6-(3-cyclobutyl-2-oxo-imidazolidin-1-yl)-4-[2-methoxy-3-[1-(trideuteriomethyl)-1,2,4-triazol-3-yl]anilino]-N-(trideuteriomethyl)pyridazine-3-carboxamide

Example 23

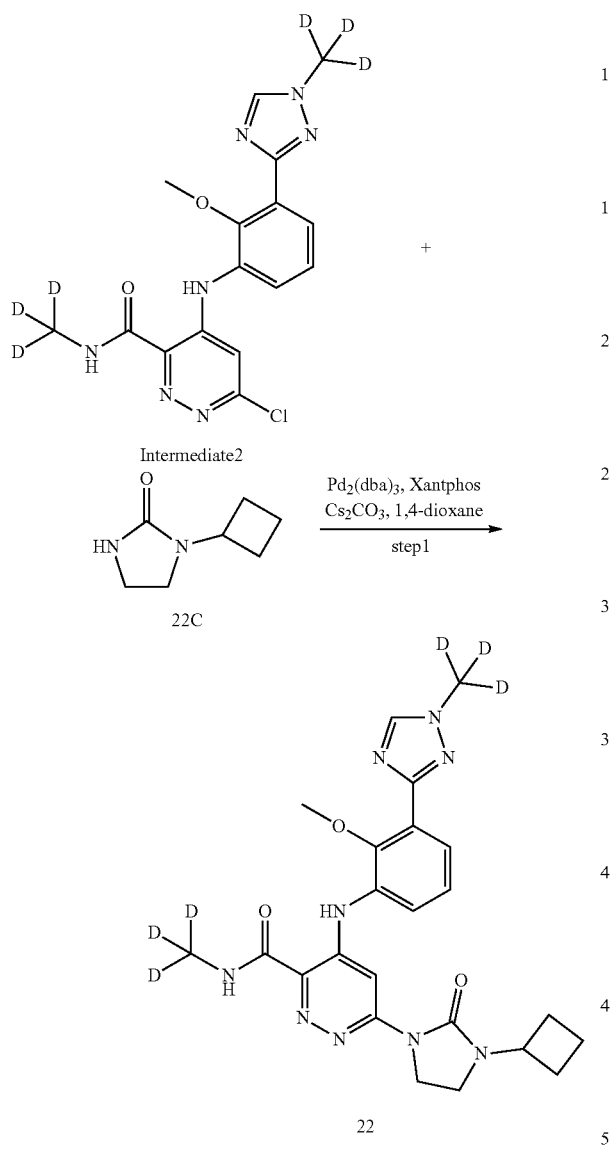

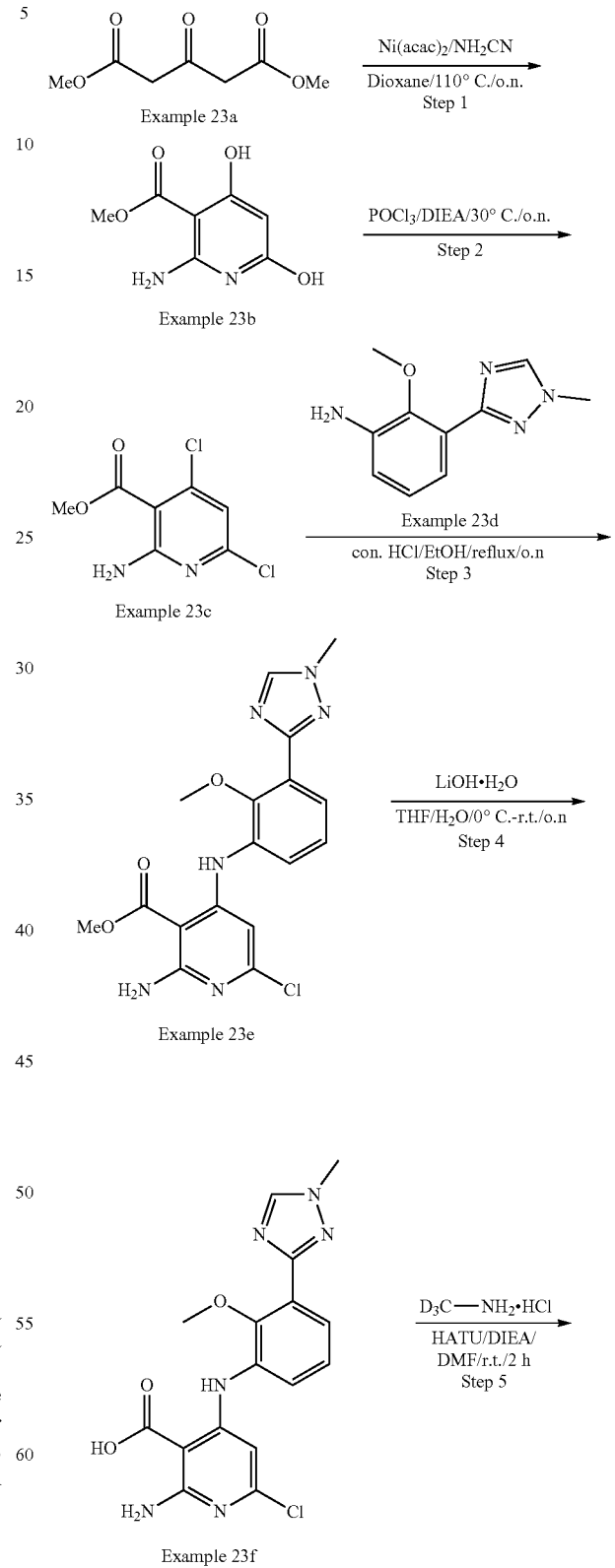

To a solution of intermediate 2 (60 mg, 0.16 mmol) and 22C (45 mg, 0.32 mmol) in 1,4-dioxane (8 mL) was added Cesium carbonate (100 mg, 0.32 mmol), Pd$_2$(dba)$_3$ (43 mg, 0.048 mmol), and xantphos (46 mg, 0.08 mmol). The mixture degassed by N$_2$ for 3 times and heated to 120° C. for 4 hrs. When reaction completed, filtered, filtrate was removed in vacuo, chromatography (PE/EtOAc=50/50 then DCM/MeOH=97/3) to give the desired product Example 22. (6 mg, yield: 8%) as a yellow solid. LM-MS: m/z=484.3 [M+H]$^+$. $^1$H NMR (400 MHz, CDCl$_3$) δ 10.97 (s, 1H), 8.35 (s, 1H), 8.11 (d, 2H), 7.79 (dd, 1H), 7.54 (dt, 1H), 7.28 (d, 1H), 4.53 (t, 1H), 4.29-4.21 (m, 2H), 3.81 (s, 3H), 3.66-3.53 (m, 2H), 2.25-2.07 (m, 4H), 1.74-1.65 (m, 2H).

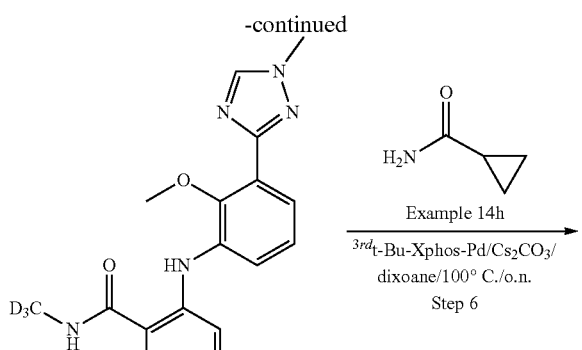

Example 23g

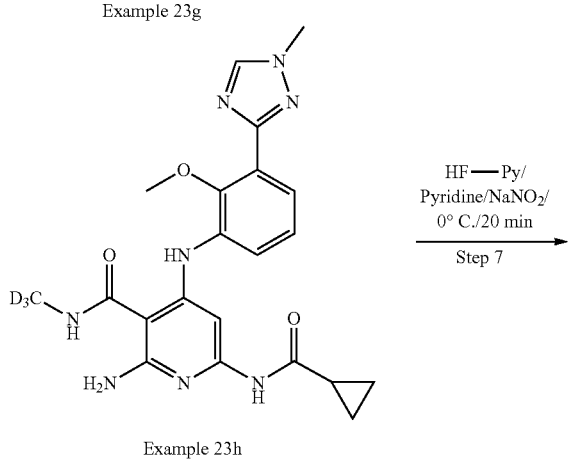

Example 23h

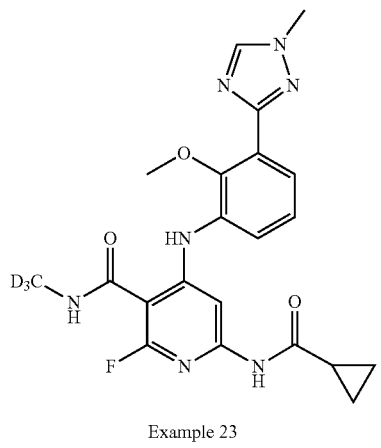 [SMILES: [2H]C([2H])([2H])NC(=O)c1c(Nc2cccc(-c3ncn(C)n3)c2OC)cc(NC(=O)C2CC2)nc1F]

Example 23

Step 1: Example 23b

To a solution of dimethyl 3-oxopentanedioate (5.0 g, 28.7 mmol) and Ni(acac)₂ (738 mg, 2.87 mmol) in dioxane (30 mL) was added NH₂—CN (3.6 g, 86.2 mmol). The mixture was stirred at 110° C. for o.n. The reaction was cooled to r.t. The mixture was filtered and the filter cake was collected, washed with MeOH (20 mL) and concentrated in vacuo to give the desired product Example 23b (3.0 g, 56.6% yield) as a yellow solid. LCMS [M+1]$^+$=185.0

Step 2: Example 23c

To a solution of Example 23b (2.5 g, 13.58 mmol) in POCl₃ (15 mL) was added DIEA (2 mL) at 0° C., which was heated to 30° C. and stirred for o.n. The reaction was concentrated in vacuo. H₂O (15 mL) and MeOH (3 mL) were added at 0° C., which was stirred at r.t. for 1 h. The mixture was filtered and the filtrate cake was collected by filtration to give Example 23c (1.5 g, 50.1% yield) as a yellow solid. LCMS [M+1]$^+$=221.0

Step 3: Example 23e

To a solution of Example 23c (1.2 g, 5.42 mmol) and Example 23d (1.21 g, 5.96 mmol) in EtOH (30 mL) was added conc. HCl (5 mL) and the solution was heated to reflux for o.n. The reaction was concentrated in vacuo. The residue was dissolved in EtOAc (100 mL) and H₂O (50 mL), and the pH was adjusted to ~8 with sat. NaHCO₃. The organic layer was separated and concentrated. The residue was purified by silica gel chromatography (DCM/MeOH=30/1) to afford the product Example 23e (700 mg, 33.1% yield) as a yellow solid. LCMS [M+1]$^+$=389.1

Step 4: Example 23f

To a solution of Example 23e (690 mg, 1.78 mmol) in THF (30 mL) and H₂O (10 mL) cooled at 0° C. was added LiOH·H₂O (112 mg, 2.67 mmol) and the solution was stirred at r.t. for o.n. The reaction was concentrated in vacuo. The residue was dissolved in H₂O (50 mL), adjusted pH ~4 with HCl (2 mol/L), and extracted with EtOAc (100 mL). The organic layer was concentrated to afford the crude product Example 23f (750 mg, 100% crude yield) as a yellow solid. LCMS [M+1]$^+$=375.2

Step 5: Example 23g

To a solution of Example 23f (500 mg, 1.33 mmol) in DMF (10 mL) were added DIEA (515 mg, 3.99 mmol), HATU (610 mg, 1.60 mmol) and CD₃—NH₂·HCl (110 mg, 1.59 mmol) and the solution was stirred at r.t. for 2 h. The reaction was diluted with EtOAc (50 mL), washed with brine (10 mL*3), dried over Na₂SO₄, and concentrated in vacuo. The residue was purified by silica gel chromatography (DCM/MeOH=30/1) to afford the product Example 14g (510 mg, 98% yield) as a light yellow solid. LCMS [M+1]$^+$=391.0

Step 6: Example 23h

To a mixture of Example 23g (500 mg, 1.278 mmol), Example 23h (33 mg, 1.917 mmol) and Cs₂CO₃ (167 mg, 2.55 mmol) in dioxane (5 mL) was added 3$^{rd}$ t-Bu-Xphos-Pd (22.5 mg, 0.128 mmol). The mixture was degassed with N₂ three times, then heated to 100° C. and stirred for overnight. The reaction was concentrated in vacuo. The residue was further purified by prep-HPLC to give the desired product Example 23h (60 mg, 54.2% yield) as a white solid. LCMS [M+1]$^+$=440.1. $^1$H NMR (300 MHz, DMSO-d₆) δ 9.29 (s, 1H), 8.56 (s, 1H), 8.43 (s, 1H), 7.74 (d, J=6.8 Hz, 1H), 7.39 (d, J=7.6 Hz, 1H), 7.29 (t, J=7.8 Hz, 1H), 3.94 (s, 3H), 3.70 (s, 3H), 1.65-1.80 (m, 1H), 0.8-0.94 (m, 4H).

Step 7: Example 23

To a solution of Example 23h (50 mg, 0.11 mmol, 1.0 eq) in pyridine (2.0 mL) was added pyridine hydrofluoride (70% in pyridine, 0.5 mL) followed by NaNO₂ (10 mg, 0.15 mmol, 1.4 eq) at 0° C. very slowly and the resulting mixture was stirred for 20 min. The reaction was concentrated in vacuo. The residue was purified by prep-HPLC to give the desired product Example 23 (13.5 mg, 28.1% yield) as a light yellow solid. LCMS [M+1]$^+$=443.3. $^1$H NMR (300 MHz, DMSO-d$_6$) δ 10.87 (s, 1H), 10.29 (s, 1H), 8.56 (s, 1H), 8.31 (s, 1H), 7.89 (s, 1H), 7.61 (dd, J=7.8 Hz, J=1.8 Hz, 1H), 7.45 (d, J=8.0 Hz, 1H), 7.24 (d, J=7.8 Hz, 1H), 3.95 (s, 3H), 3.72 (s, 3H), 1.95-1.91 (m, 1H), 0.79-0.77 (m, 4H).

Example 24

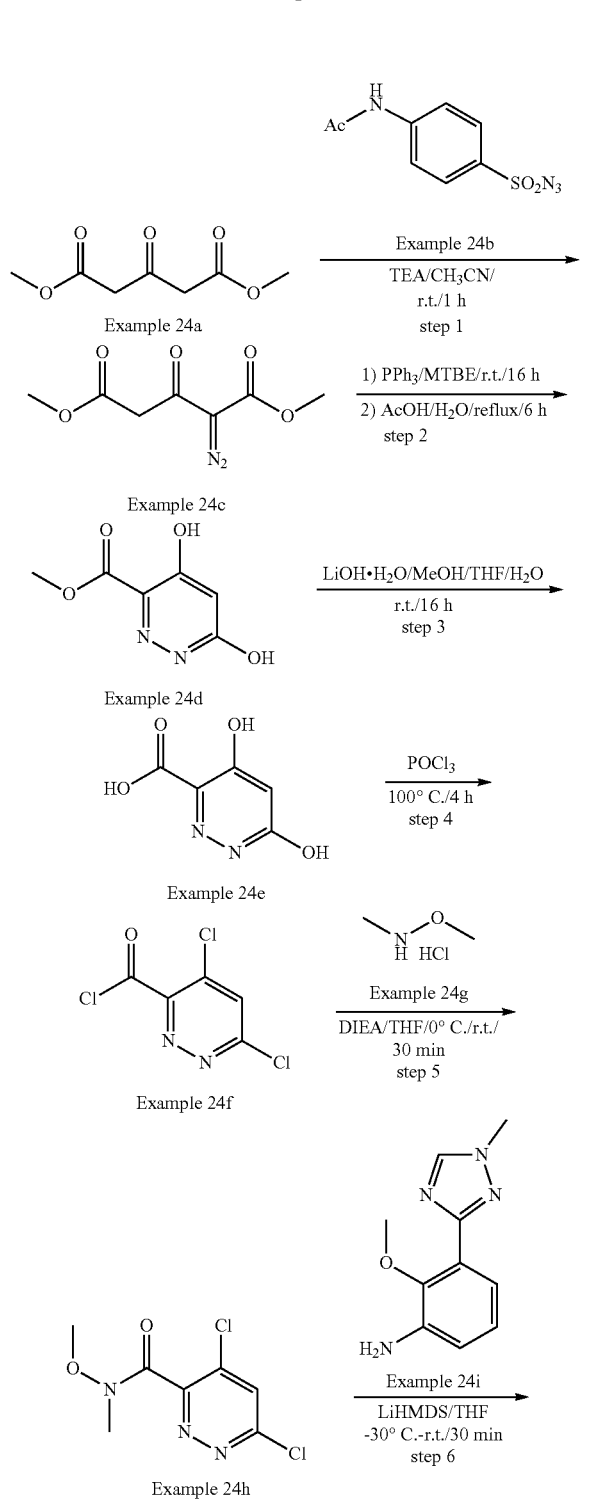

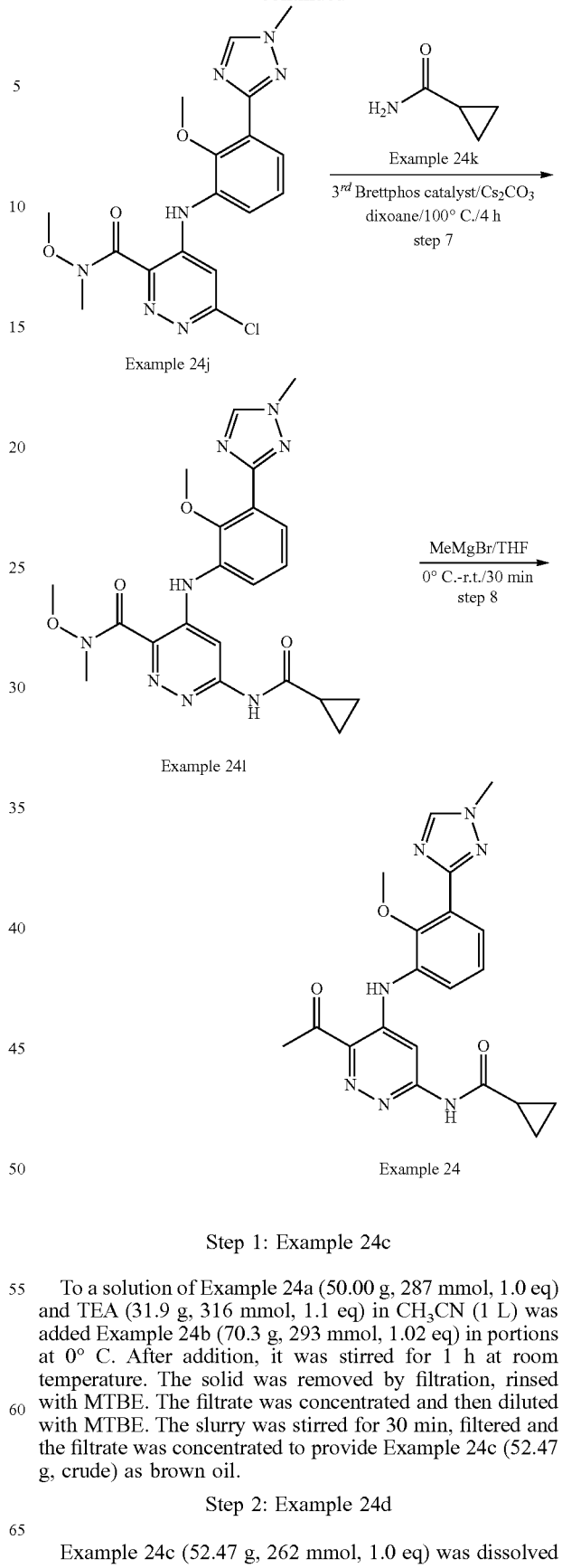

Step 1: Example 24c

To a solution of Example 24a (50.00 g, 287 mmol, 1.0 eq) and TEA (31.9 g, 316 mmol, 1.1 eq) in CH$_3$CN (1 L) was added Example 24b (70.3 g, 293 mmol, 1.02 eq) in portions at 0° C. After addition, it was stirred for 1 h at room temperature. The solid was removed by filtration, rinsed with MTBE. The filtrate was concentrated and then diluted with MTBE. The slurry was stirred for 30 min, filtered and the filtrate was concentrated to provide Example 24c (52.47 g, crude) as brown oil.

Step 2: Example 24d

Example 24c (52.47 g, 262 mmol, 1.0 eq) was dissolved in MTBE (600 mL) and PPh$_3$ (68.74 g, 262 mmol, 1.0 eq)

was added. The reaction solution was stirred 16 h at room temperature and then concentrated in vacuo. To the residual sludge was added AcOH (500 mL) and H$_2$O (50 mL). The vessel was equipped with a condenser and the mixture was heated to reflux for 6 h, and then concentrated in vacuo. The crude product (115.0 g, crude) was used to next step without purification.

Step 3: Example 24e

To last step crude product Example 24d (115.0 g, 32% purity, 216 mmol, 1.0 eq) dissolved in THF (150 mL)/MeOH (50 mL)/H$_2$O (50 mL) was added LiOH·H$_2$O (36.3 g, 864 mmol, 4.0 eq) and the reaction mixture was stirred for 16 at room temperature. After the reaction was completed, MeOH and THF were concentrated. The residue was diluted with H$_2$O (200 mL), and then extracted with EtOAc (300 mL*3). Then pH of the aqueous phase was adjusted to 3 with conc. HCl. Acidification of the water solution afforded a brown precipitate which was collected by filtration and dried in vacuo to afford Example 24e (31.5 g, 93.5% yield) as a yellow solid.

Step 4: Example 24f

The solution of Example 24e (15.0 g, 96.15 mmol, 1.0 eq) in POCl$_3$ (150 mL) was stirred for 4 h at 100° C. After the reaction was completed, it was concentrated in vacuo to give Example 24f (17.4 g, crude), which was used to next step without further purification.

Step 5: Example 24h

To a solution of Example 24g (2.30 g, 23.70 mmol, 2.0 eq) and DIEA (12.23 g, 94.79 mmol, 8.0 eq) in THF (50 mL) was added the solution of Example 24f (2.5 g, 11.85 mmol, 1.0 eq) in DCM (25 mL) dropwise at 0° C. The reaction solution was stirred for 30 min at r.t. The reaction solution was diluted with EtOAc (100 mL), washed with brine (80 mL*3), dried over anhydrous Na$_2$SO$_4$ and concentrated in vacuo. The residue was purified by silica gel chromatography (Petroleum Ether/EtOAc=1/2) to afford the product Example 24h (1.8 g, 64.4% yield) as a yellow solid. LCMS [M+1]$^+$=236.2

Step 6: Example 24j

To a solution of Example 24h (700 mg, 2.98 mmol, 1.0 eq) and Example 24i (611 mg, 2.98 mmol, 1.0 eq) in dry THF (15 mL) was add LiHMDS (5.96 mL, 1M, 2.0 eq) dropwise at ~30° C. under N$_2$. The reaction mixture was stirred for 30 min at r.t. The crude product was concentrated and purified by silica gel chromatography (DCM/MeOH=10/1) to afford the product Example 24j (450 mg, 37.5% yield) as a yellow solid. LCMS [M+1]$^+$=404.2.

Step 7: Example 24l

To the solution of Example 24j (450 mg, 1.12 mmol, 1.0 eq) in dioxane (5 mL) were added Cs$_2$CO$_3$ (728 mg, 2.23 mmol, 2.0 eq), Example 24k (285 mg, 3.35 mmol, 3.0 eq) and 3$^{rd}$ t-Bu-Xphos catalyst (99 mg, 0.11 mmol, 0.1 eq) and the reaction mixture was stirred for 4 h at 110° C. under N$_2$. The reaction solution was concentrated and purified by silica gel chromatography (DCM/MeOH=10/1) to afford the product Example 24l (320 mg, 63.5% yield) as a yellow solid. LCMS [M+1]$^+$=453.2.

Step 5: Example 24

To a solution of Example 24h (120 mg, 0.27 mmol, 1.0 eq) in THF (3 mL) was added CH$_3$MgBr (0.27 mL, 3.0 M, 3.0 eq) dropwise at 0° C. under N$_2$. The reaction solution was stirred for 30 min at r.t. The reaction solution was poured into saturated aqueous NH$_4$Cl (10 mL), and extracted with DCM (10 mL*3). The combined organic layer was washed with brine (30 mL), dried by Na$_2$SO$_4$ and concentrated. The crude product was purified by prep-HPLC to give the desired product Example 24 (8.8 mg, 8.0% yield) as an off white solid. LCMS [M+1]$^+$=408.3. $^1$H NMR (300 MHz, DMSO-d$_6$) δ 11.52 (s, 1H), 10.57 (s, 1H), 8.58 (s, 1H), 8.12 (s, 1H), 7.72 (d, J=7.6 Hz, 1H), 7.53 (d, J=7.2 Hz, 1H), 7.30 (t, J=7.8 Hz, 1H), 3.96 (s, 3H), 3.71 (s, 3H), 2.81 (s, 3H), 1.09-1.03 (m, 1H), 0.86-0.83 (m, 4H).

Example 25

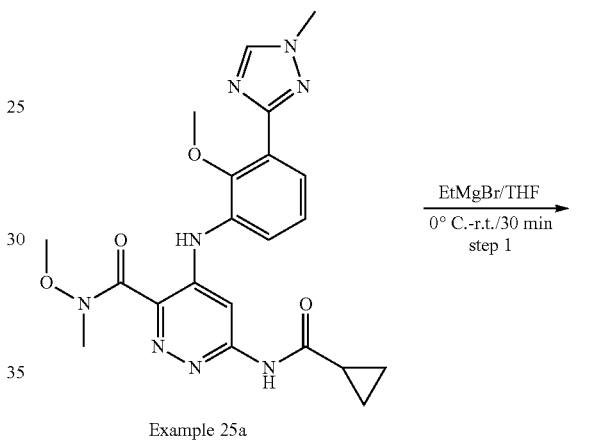

Example 25a

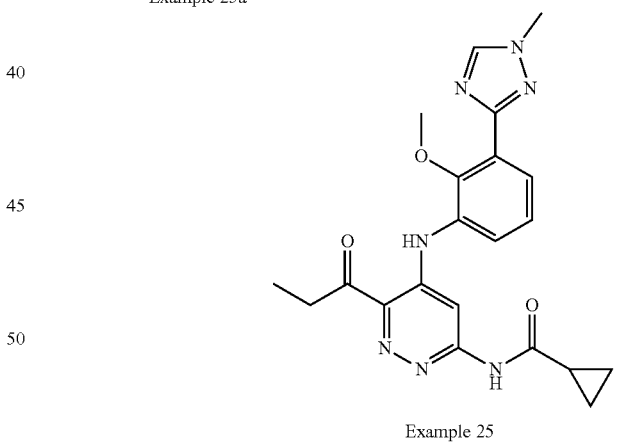

Example 25

Step 1 Example 25

To the solution of Example 25a (50 mg, 0.11 mmol, 1.0 eq) in THF (1 mL) was added CH$_3$MgBr (0.55 mL, 1.0 M, 5.0 eq) dropwise at 0° C. under N$_2$. The reaction solution was stirred for 30 min at r.t. The reaction solution was purified by prep-TLC (DCM/MeOH=12/1) to obtained crude product (27 mg) and further purified by prep-HPLC (Prep-C18, 5 μM XBridge column, 19×150 mm, Waters; gradient elution of 40% MeCN in water to 50% MeCN in water over a 7 min period, where both solvents contain 0.1% formic acid) to give the desired product Example 25 (6.8 mg, 14.6% yield) as a yellow solid (FA salt). LCMS [M+1]⁺=422.3. ¹H NMR (300 MHz, DMSO-d₆) δ 10.55 (s, 1H), 8.58 (s, 1H), 8.48 (br, 2H), 8.10 (s, 1H), 7.71 (dd, J=7.8, 1.6 Hz, 1H), 7.52 (dd, J=7.8, 1.6 Hz, 1H), 7.29 (t, J=7.8 Hz, 1H), 3.95 (s, 3H), 3.72 (s, 3H), 3.36 (q, J=7.2 Hz, 2H), 2.11-2.04 (m, 1H), 1.17 (t, J=7.2 Hz, 3H), 0.85-0.81 (m, 4H).

Example 26

Example 27

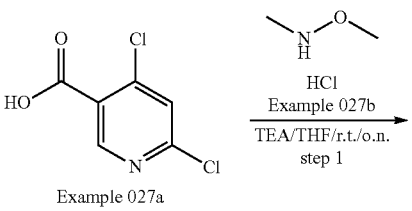

Example 027a

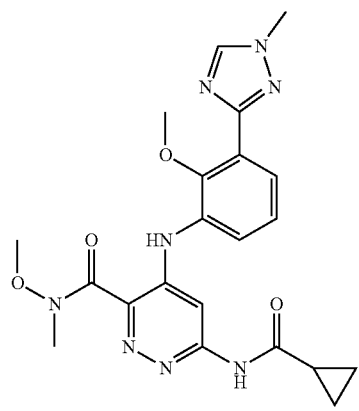

Example 26a

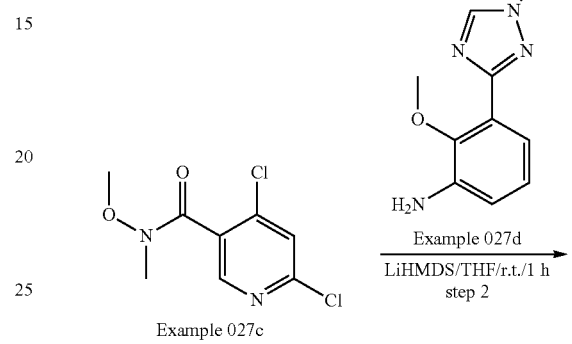

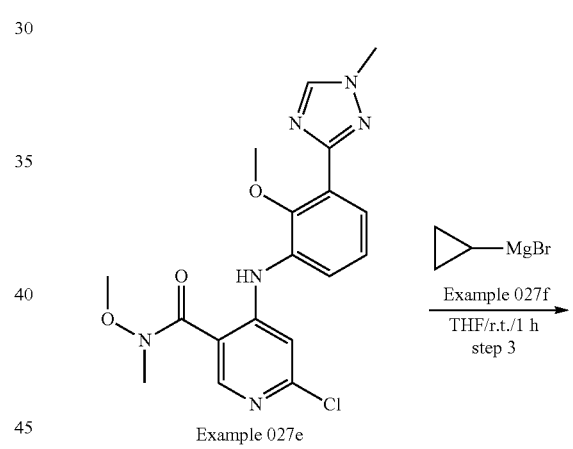

Example 26

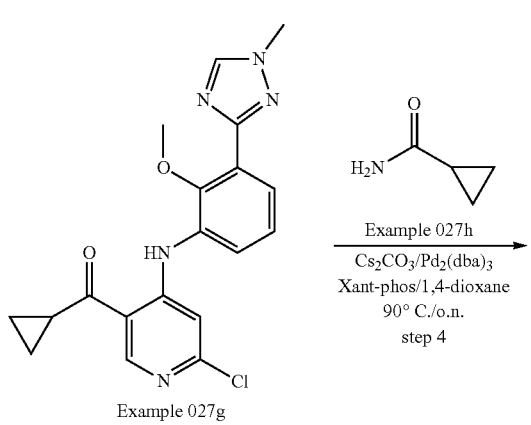

To a solution of Example 26a (135 mg, 0.3 mmol) in dry THF (10 mL) was added Example 26b (1.2 mL, 1M in THF, 1.2 mmol) dropwise at 0° C. under nitrogen. After addition (about 5 min), the reaction mixture was stirred for 1 h at r.t. Then, the reaction was quenched with MeOH (1 mL) and concentrated in vacuo. The residue was purified by prep-TLC (DCM/MeOH=20/1) to afford the product Example 26 (19.5 mg, 15% yield) as an off-white solid. LCMS [M+1]⁺=434.3/. ¹H NMR (400 MHz, DMSO-d₆) δ 11.53 (s, 1H), 10.61 (s, 1H), 8.57 (s, 1H), 8.11 (s, 1H), 7.72 (dd, J=7.8 Hz, 1.6 Hz, 1H), 7.52 (dd, J=7.8 Hz, 1.8 Hz, 1H), 7.29 (t, J=7.8 Hz, 1H), 3.95 (s, 3H), 3.72-3.69 (m, 4H), 2.11-2.05 (m, 1H), 1.24-1.16 (m, 4H), 0.85-0.82 (m, 4H).

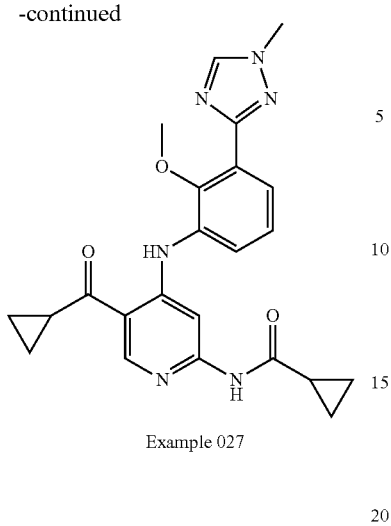

Example 027

Step 1: Example 027c

To a solution of Example 057a (5 g, 21.3 mmol) and Example 027b (2.28 g, 23.4 mmol) in THF (20 mL) were added Et₃N (3.28 g, 31.9 mmol) and EDCI (6 g, 31.9 mmmol). The mixture was stirred at r.t. overnight. The reaction mixture was washed by brine (60 mL), and extracted by DCM (60 mL*3). The combined organic layer was dried over Na₂SO₄, concentrated under reduced pressure, and dried to give Example 027c (4.4 g, 95% yield) as a yellow solid. LCMS [M+1]⁺=234.9/236.9

Step 2: Example 027e

To a solution of Example 027c (4.4 g, 18.7 mmol), Example 027d (CAS: 1609394-10-6, 4.2 g, 20.6 mmol) in THF (20 mL) under N₂ was added LiHMDS (1 mol/L, 28 mL, 28.05 mmol) dropwise. The mixture was stirred at r.t. for 1 h. The reaction mixture was washed by brine (60 mL), extracted by DCM (60 mL*3). The combined organic layer was dried over Na₂SO₄, concentrated under reduced pressure, purified by flash C-18 column (H₂O/CH₃CN=3/1) to give Example 027e (2.4 g, 32% yield) as yellow oil. LCMS [M+1]⁺=403.1

Step 3: Example 027g

To a solution of Example 027e (500 mg, 1.24 mmol) in THF (10 mL) under N₂, was added Example 027f (1 mol/L, 10 mL, 12.4 mmol) in one portion. The mixture was stirred at r.t. for 1 h. The reaction mixture was washed by brine (40 mL), and extracted by EtOAc (40 mL*3). The combined organic layer was dried over Na₂SO₄, concentrated under reduced pressure to get crude product (600 mg, crude) as a yellow solid, which was directly used in next step without further purification. LCMS [M+1]⁺=384.1

Step 4: Example 027

To a solution of Example 027g (100 mg, 0.26 mmol), Example 027h (33.3 mg 0.92 mmol) in 1,4-dioxane (2 mL) were added Cs₂CO₃ (127.3 mg 0.392 mmol), Pd₂(dba)₃ (23.9 mg 0.026 mmol), and Xant-phos (15.1 mg 0.026 mmol). The mixture was degassed by Ar, heated to 90° C. and stirred over night. The reaction mixture was diluted by DCM and filtrated. The filtrate was concentrated under reduced pressure to remove solvent, which was further purified by prep-HPLC to give Example 027 (17.5 mg, 15% yield) as a white solid. LCMS [M+1]⁺=433.2. ¹H NMR (400 MHz, Chloroform-d) δ 11.25 (s, 1H), 8.84 (s, 1H), 8.11 (s, 1H), 8.09 (s, 1H), 7.80 (d, J=8.0, 1.6 Hz, 1H), 7.55 (d, J=8.0, 1.6 Hz, 1H), 7.27-7.29 (m, 1H), 4.00 (s, 3H), 3.76 (s, 3H), 2.54-2.60 (m, 1H), 1.67-1.56 (m, 1H), 1.26-1.29 (m, 2H), 1.04-1.10 (m, 4H), 0.87-0.93 (m, 2H).

Example 28

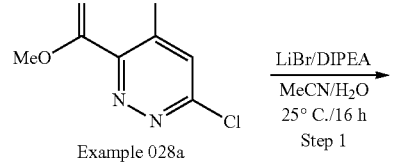

Example 028a

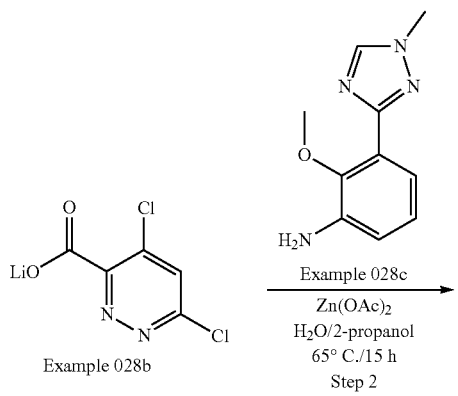

Example 028b

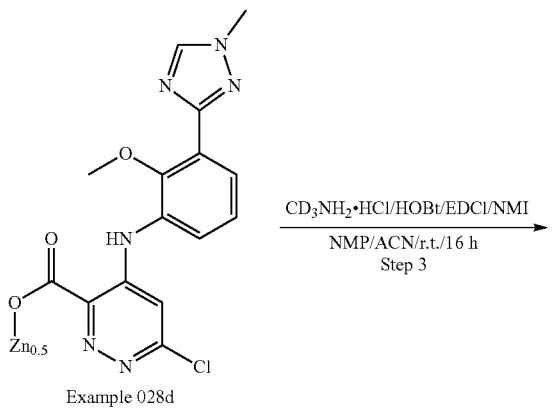

Example 028d

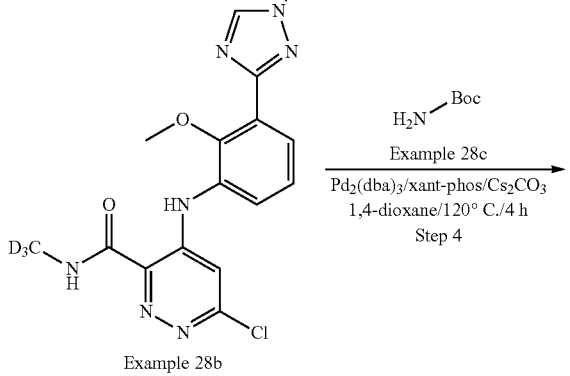

Example 28b

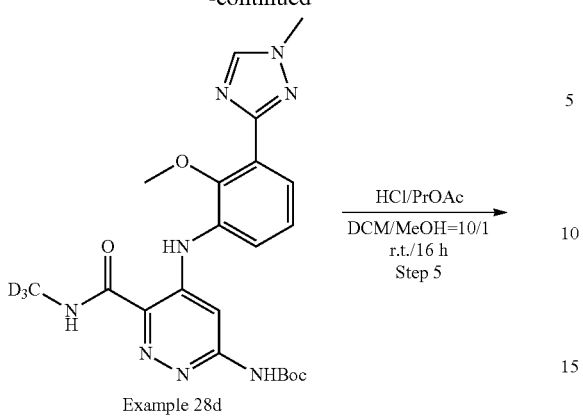

Example 28d

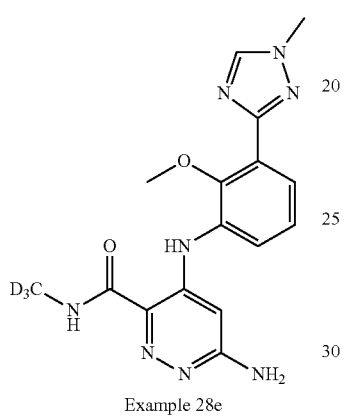

Example 28e

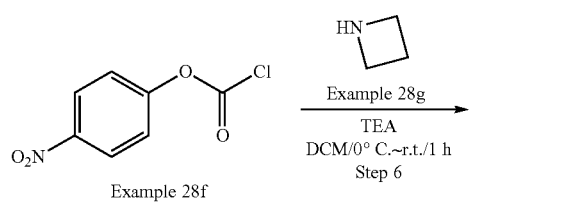

Example 28f

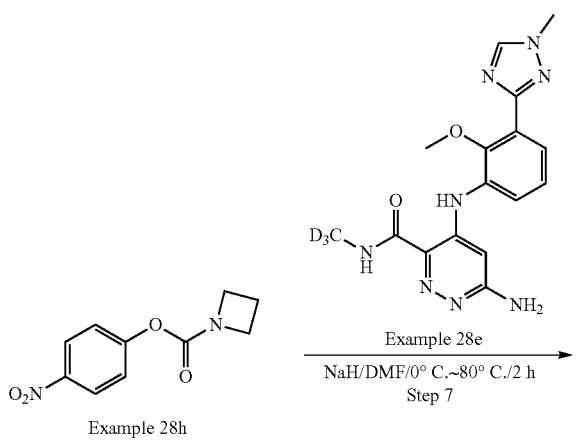

Example 28h

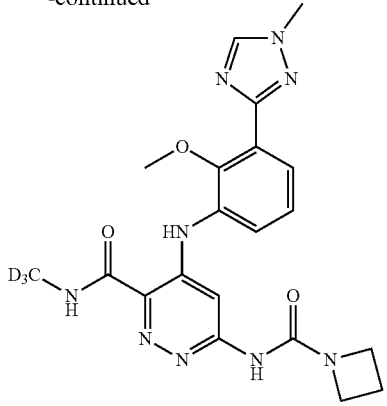

Example 28

Step 1: Example 028b

To a suspension of Example 028a (20 g, 96.6 mmol) in MeCN (100 mL) and H$_2$O (15 mL) was added LiBr (25.2 g, 289.8 mmol), DIPEA (35.4 g, 289.8 mmol). The mixture was stirred at 25° C. for 16 h. The reaction mixture was isolated by filtration. The crude solid was washed with MeCN (25 mL), dried under vacuum at 45° C. to give Example 028b (17.8 g, 93% yield) as a light yellow solid.

Step 2: Example 028d

To a suspension of Example 028b (17.5 g, 88.2 mmol) and Example 028c (15.0 g, 73.5 mmol) in H$_2$O (90 mL) and 2-propanol (15 mL) was added Zn(OAc)$_2$ (13.4 g, 73.5 mmol). The mixture was stirred at 65° C. for 15 h. The reaction mixture was cooled to room temperature and isolated by filtration. The crude solid was washed with water (45 mL) and THF (45 mL). The solid was dried under vacuum at 70° C. to give Example 028d (25.2 g, 61% yield) as a light yellow solid.

Step 3: Example 28b

To a suspension of Example 28d (2.0 g, 5.10 mmol), CD$_3$NH$_2$·HCl (431 mg, 6.12 mmol) and NMI (293 mg, 3.57 mmol) in NMP/ACN (20 mL/20 mL) were added HOBt (344 mg, 2.55 mmol) and EDCI (1.37 g, 7.13 mmol). The mixture was stirred at r.t. for 16 h. After cooling to 0° C., the mixture was aged for 2 h at 0° C. The product was isolated by filtration. The wet cake was washed with H$_2$O (20 mL), and then ACN (20 mL). The solid was collected and dried under vacuum to give Example 28b (1.1 g, 57.3% yield) as a white solid. LCMS [M+1]$^+$=377.0

Step 4: Example 28d

To a solution of Example 28b (1.1 g, 2.92 mmol) and Example 28c (512 mg, 4.38 mmol) in 1,4-dioxane (15 mL) were added Pd$_2$(dba)$_3$ (267 mg, 0.29 mmol), XantPhos (337 mg, 0.58 mmol) and Cs$_2$CO$_3$ (1.9 g, 5.84 mmol). The mixture was degassed by nitrogen for 3 times and stirred at 120° C. for 4 h. The reaction was cooled to r.t. and concentrated. The residue was purified by silica gel chromatography (DCM/MeOH=85/15) to give the desired crude product Example 28d (1.08 g, 81.2% yield, ~35% purity) as a yellow solid, which was used for the next step directly. LCMS [M+1]⁺=458.0

Step 5: Example 28e

To a solution of the crude Example 28d (1.08 g, 2.36 mmol) in DCM/MeOH (10 mL) was added 6N HCl/iPrOAc (20 mL). The mixture was stirred at r.t. for 16 h. The resulting mixture was concentrated, and the residue was purified by silica gel chromatography (EtOAc/MeOH=85/15) to give the desired product Example 28e (240 mg, 28.4% yield) as a yellow solid. CMS [M+1]⁺=358.0

Step 6: Example 28h

To a solution of Example 28g (200 mg, 3.51 mmol) and TEA (709 mg, 7.02 mmol) in DCM (15 mL) was slowly added a solution of Example 28f (707 mg, 3.51 mmol) in DCM (5 mL) at 0° C. The mixture was then stirred at r.t. for 1 h. The solvent was removed in vacuo, and the residue was purified by silica gel chromatography (Petroleum Ether/EtOAc=92/8) to give the desired product Example 28h (470 mg, 60.4% yield) as a yellow solid. LCMS [M+1]⁺=223.0

Step 7: Example 28

To an ice-cooled solution of NaH (14.5 mg, 0.36 mmol, 60% w.t. % in mineral oil) in DMF (1 mL) under nitrogen atmosphere was added (dropwise) a solution of Example 28e (35.7 mg, 0.1 mmol) in DMF (1 mL). After 15 min, a solution of Example 28h (20.2 mg, 0.091 mmol) in DMF (1 mL) was added. After 5 min, the cooling bath was removed and the reaction was warmed to 80° C. and stirred for 2 h. The mixture was quenched by adding water, purified by prep-HPLC to give the desired product Example 28 (1.1 mg, 2.8% yield) as a yellow solid. LCMS [M+1]⁺=441.0. ¹H NMR (400 MHz, DMSO-d) δ 10.89 (s, 1H), 9.60 (s, 1H), 9.00 (s, 1H), 8.54 (s, 1H), 8.00 (s, 1H), 7.61 (dd, J=7.8, 1.6 Hz, 1H), 7.49 (dd, J=8.0, 1.6 Hz, 1H), 7.24 (t, J=7.8 Hz, 1H), 3.99 (t, J=6.4 Hz, 4H), 3.93 (s, 3H), 3.71 (s, 3H), 2.13 (p, J=7.6 Hz, 2H).

Example 29

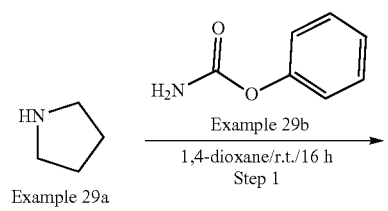

Example 29a

Example 29b 1,4-dioxane/r.t./16 h
Step 1

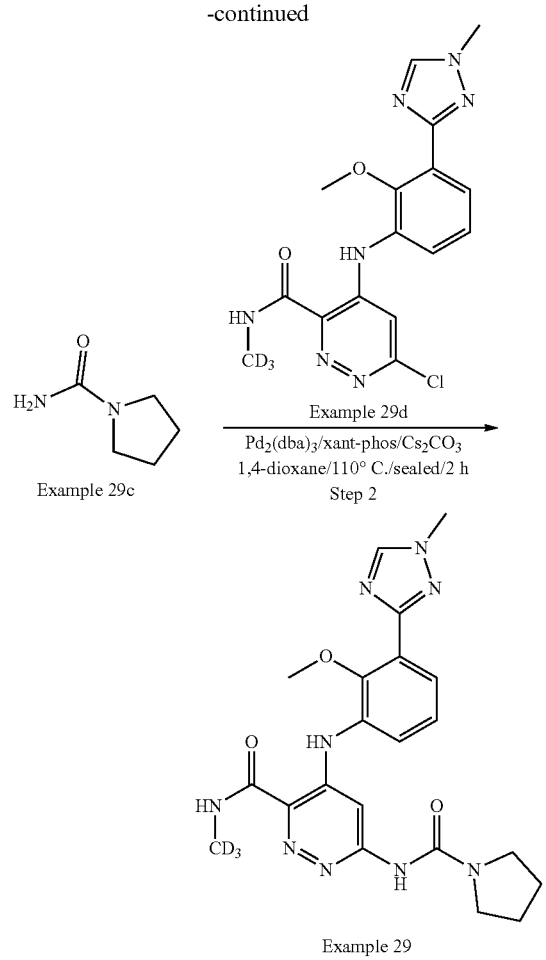

Example 29c

Example 29d

Pd₂(dba)₃/xant-phos/Cs₂CO₃
1,4-dioxane/110° C./sealed/2 h
Step 2

Example 29

Step 1: Example 29c

To a solution of Example 29b (1.0 g, 7.30 mmol) in 1,4-dioxane (15 mL) was treated with Example 29a (2 mL, 24.1 mmol) and stirred at r.t. for 16 h. After the reaction was completed, the solvent was concentrated, and the residue was suspended in DCM (5 mL) and sonicated. The resulting solid was collected via filtration, and dried to afford the desired product Example 29c (665 mg, 80% yield) as a white solid. LCMS [M+1]⁺=115.0. ¹H NMR (400 MHz, DMSO-d₆) δ 5.62 (s, 2H), 3.18-3.12 (m, 4H), 1.80-1.68 (m, 4H).

Step 2: Example 29

To a solution of Example 29d (50 mg, 0.13 mmol) and Example 29c (22.7 mg, 0.20 mmol) in 1,4-dioxane (1 mL) were added Pd₂(dba)₃ (12.1 mg, 0.013 mmol), XantPhos (15.3 mg, 0.026 mmol) and Cs₂CO₃ (86.5 mg, 0.27 mmol). The mixture was sealed, degassed by nitrogen for 3 times and stirred at 110° C. for 2 h. When completed, the reaction was cooled to r.t. and filtered. The filtrate was purified directly by prep-HPLC to give the desired product Example 29 (13 mg, 21.7% yield) as a white solid. LCMS [M+1]⁺=455.0. ¹H NMR (400 MHz, DMSO-d₆) δ 10.88 (s, 1H), 9.21 (s, 1H), 8.99 (s, 1H), 8.54 (s, 1H), 7.96 (s, 1H), 7.62 (dd, J=7.8, 1.6 Hz, 1H), 7.49 (dd, J=8.0, 1.6 Hz, 1H), 7.25 (t, J=8.0 Hz, 1H), 3.93 (s, 3H), 3.71 (s, 3H), 3.42-3.37 (m, 4H), 1.81 (s, 4H).

Example 30

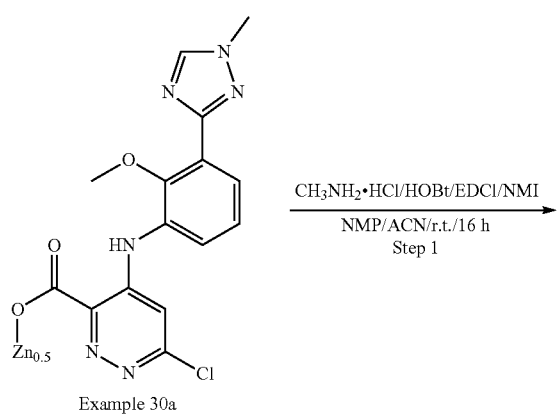

Example 30a

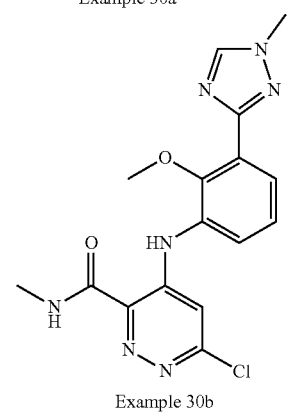

Example 30b

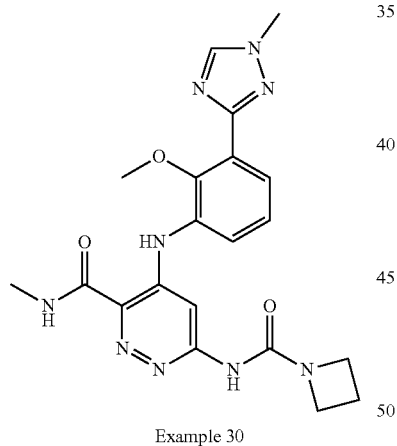

Example 30

Step 1: Example 30b

To a suspension of Example 30a (1.0 g, 2.55 mmol), CH₃NH₂·HCl (206 mg, 3.06 mmol) and NMI (146 mg, 1.78 mmol) in NMP/ACN (7 mL/7 mL) were added HOBt (172 mg, 1.27 mmol) and EDCI (685 mg, 3.57 mmol). The mixture was stirred at r.t. for 16 h. After cooling to 0° C., the mixture was aged for 2 h at 0° C. The product was isolated by filtration. The wet cake was washed with H₂O (10 mL), and then ACN (10 mL). The solid was collected and dried under vacuum to give Example 30b (417 mg, 43.9% yield) as a white solid. LCMS [M+1]⁺=374.0

Step 2: Example 30

To a solution of Example 68b (72 mg, 0.19 mmol) and Example 30c (23 mg, 0.23 mmol) in 1,4-dioxane (2 mL) were added Pd₂(dba)₃ (17.6 mg, 0.019 mmol), XantPhos (22.3 mg, 0.038 mmol) and Cs₂CO₃ (125.5 mg, 0.38 mmol). The mixture was degassed by nitrogen for 3 times and stirred at 110° C. for 3.5 h in a sealed tube. When completed, the reaction was cooled to r.t. and filtered. The filtrate was purified directly by prep-HPLC to give the desired product Example 30 (16 mg, 19.0% yield) as a white solid. LCMS [M+1]⁺=438.0. H NMR (400 MHz, DMSO-d₆) δ 10.88 (s, 1H), 9.59 (s, 1H), 9.02 (d, J=5.4 Hz, 1H), 8.54 (s, 1H), 7.99 (s, 1H), 7.61 (d, J=7.8 Hz, 1H), 7.49 (d, J=8.0 Hz, 1H), 7.24 (t, J=8.0 Hz, 1H), 3.98 (s, 4H), 3.93 (s, 3H), 3.71 (s, 3H), 2.84 (d, J=4.4 Hz, 3H), 2.13 (t, J=7.8 Hz, 2H).

Example 31

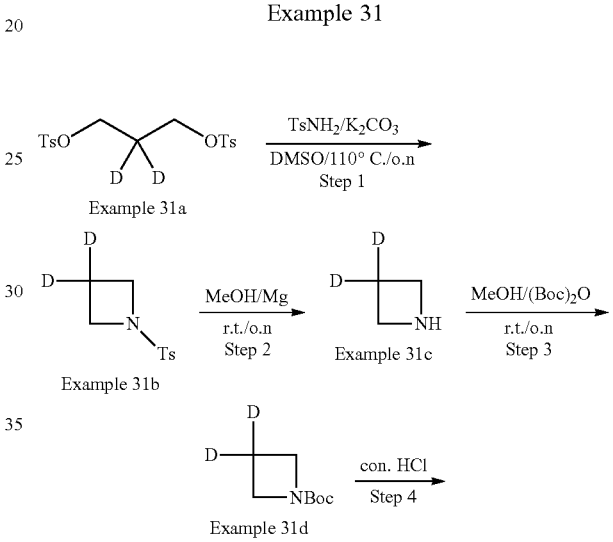

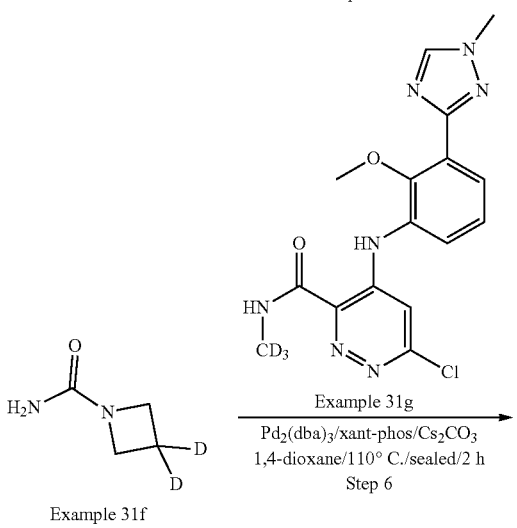

-continued

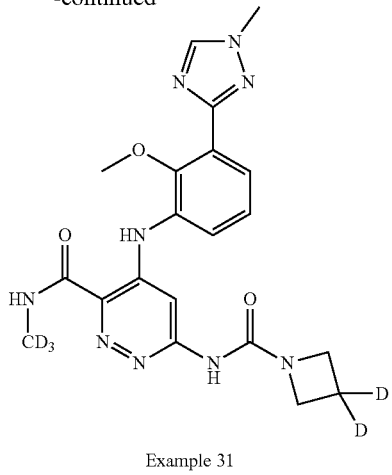

Example 31

Step 1: Example 31b

A solution of Example 31a (2.0 g, 5.4 mmol), TsNH$_2$ (1.1 g, 6.52 mmol), K$_2$CO$_3$ (1.1 g, 6.52 mmol) in MeOH (5 mL) was stirred at r.t. for 10 min, and then Example 31b (1.86 g, 13.6 mmol) in dry DMSO (20 mL) was added, which was stirred at 110° C. for o.n. When completed, the reaction was cooled to r.t., diluted by EtOAc, washed by water, and dried over Na$_2$SO$_4$. The organic layer was concentrated and purified by silica gel column (Petroleum ether/EtOAc=4/1) to give Example 031b (600 mg, 52.1% yield) as a white solid. LCMS [M+1]$^+$=214.1. $^1$H NMR (400 MHz, Chloroform-d) δ 7.73 (d, J=7.8 Hz, 1H), 7.37 (d, J=7.8 Hz, 1H), 3.93 (d, J=6.6 Hz, 4H), 3.76 (d, J=7.4 Hz, 2H), 2.46 (s, 3H).

Step 2: Example 31c

A solution of Mg (676 mg, 28 mmol) in MeOH (5 mL) was stirred at r.t. for 10 min, then Example 31b (600 mg, 2.8 mmol) in MeOH (5 mL) was added, and the mixture reaction was stirred at r.t. for o.n. in a sealed tube. Another Mg (676 mg, 28 mmol) was added, and the mixture reaction was stirred at r.t. for another 6 h. The mixture was filtered, and the solid was washed by MeOH. The filtrate Example 31c was used directly for next step. LCMS [M+1]$^+$=61.2

Step 3: Example 31d

To a solution of Example 31c (crude in MeOH) was added (Boc)$_2$O (940 mg, 5.6 mmol), which was stirred at r.t. for o.n. The mixture was filtered, and the solid was washed by MeOH. The organic layer was added additional (Boc)$_2$O (940 mg, 5.6 mmol), which was stirred at r.t. for another 4 h. After reaction was completed, the mixture was concentrated and purified by silica gel column (Petroleum Ether/EtOAc=5/1) to give Example 031d (500 mg, crude, containing (Boc)$_2$O) as a white solid. LCMS [M+1−56]$^+$=104.1. $^1$H NMR (400 MHz, Chloroform-d) 3.93 (d, J=6.6 Hz, 4H), 1.43 (s, 9H).

Step 4: Example 31e

A solution of Example 31d (500 mg, 3.1 mmol) in con. HCl (1 mL) was stirred at r.t for 0.5 h. After reaction was completed, the mixture was concentrated to give Example 31e (200 mg, 67.9% yield) as a white solid, which was used for next step without further purification. LCMS [M+1]$^+$=60.2.

Step 5: Example 31f

To a solution of Example 31c (200 mg, 3.3 mmol) and DIEA (3.3 g, 33 mmol) in 1,4-dioxane (5 mL) was added Example 31e (230 mg, 1.67 mmol), which was stirred at r.t. for o.n. After reaction was completed, the mixture was concentrated, and directly purified by silica gel column (DCM/MeOH=10/1) to give the desired product Example 31f (230 mg, crude, containing DIEA, 67.6% yield) as colorless oil. LCMS [M]$^+$=103.2

Step 6: Example 31

To a solution of Example 31f (200 mg, ~50% purity, 0.5 mmol) and Example 31g (188 mg, 0.5 mmol) in 1,4-dioxane (5 mL) were added Pd$_2$(dba)$_3$ (45 mg, 0.05 mmol), XantPhos (30 mg, 0.05 mmol) and Cs$_2$CO$_3$ (489 mg, 1.5 mmol). The mixture was degassed by nitrogen for 3 times, sealed, and stirred at 110° C. for 2 h. When completed, the reaction was cooled to r.t. and filtered. The filtrate was purified directly by prep-HPLC to give the desired product Example 31 (2.2 mg, 1% yield) as a white solid. LCMS [M+1]$^+$=442.2. $^1$H NMR (400 MHz, DMSO-d$_6$) δ 10.90 (s, 1H), 9.60 (s, 1H), 9.00 (s, 1H), 8.54 (s, 1H), 8.00 (s, 1H), 7.61 (d, J=7.8 Hz, 1H), 7.49 (d, J=8.0 Hz, 1H), 7.24 (t, J=8.0 Hz, 1H), 3.97 (s, 4H), 3.93 (s, 3H), 3.71 (s, 3H).

Example 32

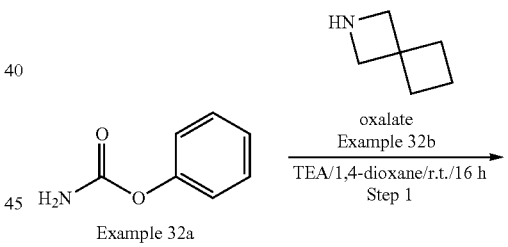

Example 32a  →  Example 32b (oxalate)  TEA/1,4-dioxane/r.t./16 h  Step 1

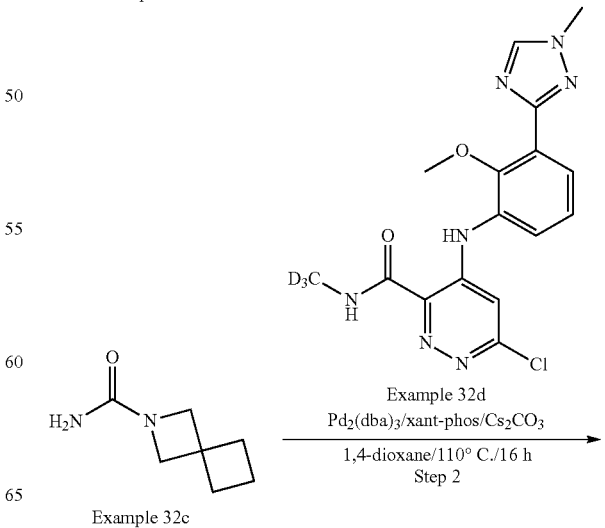

Example 32c → Example 32d  Pd$_2$(dba)$_3$/xant-phos/Cs$_2$CO$_3$  1,4-dioxane/110° C./16 h  Step 2

-continued

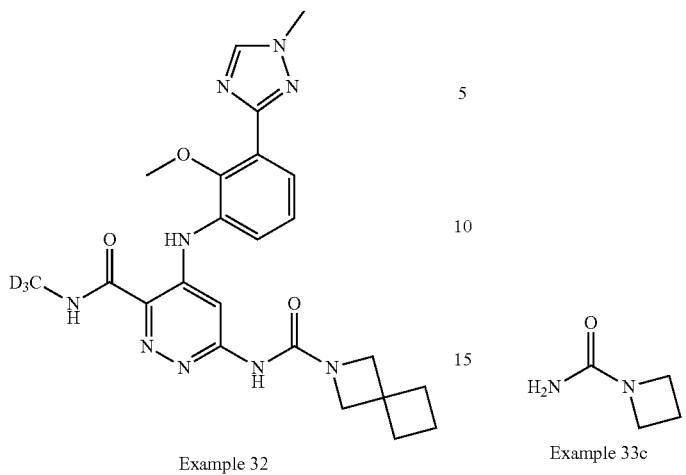

Example 32

Step 1: Example 32c

To a solution of Example 32a (300 mg, 2.19 mmol) in 1,4-dioxane (5 mL) were treated with Example 32b (623 mg, 3.28 mmol) and TEA (664 mg, 6.57 mmol). The mixture was stirred at r.t. for 16 h. After completion, the mixture was concentrated, and the residue was suspended in DCM (5 mL) and sonicated. The resulting solid was collected via filtration, and dried to afford the desired product Example 32c (226 mg, 73.9% yield) as a white solid.

LCMS [M+1]⁺=141.0

Step 2: Example 32

To a solution of Example 32d (60 mg, 0.16 mmol) and Example 32c (26.7 mg, 0.19 mmol) in 1,4-dioxane (0.6 mL) were added Pd$_2$(dba)$_3$ (14.6 mg, 0.016 mmol), XantPhos (18.4 mg, 0.032 mmol) and Cs$_2$CO$_3$ (104 mg, 0.32 mmol). The mixture was degassed by nitrogen for 3 times and stirred at 110° C. for 16 h in a sealed tube. When completed, the reaction was cooled to r.t. and filtered. The filtrate was purified directly by prep-HPLC to give the desired product Example 32 (6.6 mg, 8.7% yield) as a white solid. LCMS [M+1]⁺=481.0. ¹H NMR (400 MHz, DMSO-d$_6$) δ 10.87 (s, 1H), 9.61 (s, 1H), 8.99 (s, 1H), 8.55 (s, 1H), 7.97 (s, 1H), 7.61 (d, J=7.8 Hz, 1H), 7.48 (d, J=8.0 Hz, 1H), 7.24 (t, J=8.0 Hz, 1H), 3.93 (s, 7H), 3.69 (s, 3H), 2.08 (t, J=7.5 Hz, 4H), 1.80-1.67 (m, 2H).

Example 33

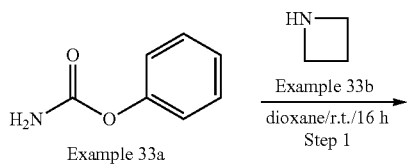

Example 33a        Example 33b dioxane/r.t./16 h
Step 1

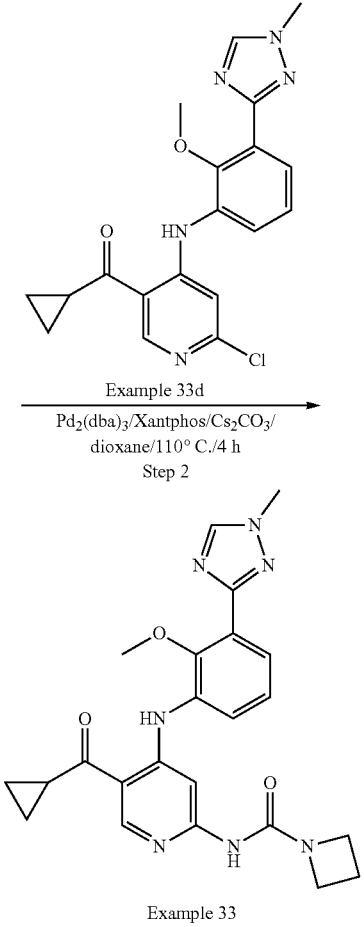

Step 1: Example 33c

To a solution of Example 33a (500 mg, 3.65 mmol, 1.0 eq) in dioxane (6 ml) was added Example 33b (624 mg, 10.95 mmol, 3.0 eq). The reaction solution was stirred for 16 h at r.t. and concentrated. The residue was treated with DCM. The resulting solid was collected by filtration to afford Example 33c (190 mg, 52% yield) as a white solid. ¹H NMR (300 MHz, DMSO-d$_6$) δ 5.72 (brs, 2H), 3.76 (t, J=7.6 Hz, 4H), 2.14-2.04 (m, 2H).

Step 2: Example 33

To a solution of Example 33d (100 mg, 0.26 mmol, 1.0 eq) and Example 33c (78.0 mg, 0.78 mmol, 3.0 eq) in dioxane (4 mL) were added Xantphos (30.1 mg, 0.05 mmol, 0.2 eq), Cs$_2$CO$_3$ (169.5 mg, 0.52 mmol, 2.0 eq) and Pd$_2$(dba)$_3$·CHCl$_3$ (26.9 mg, 0.03 mmol, 0.1 eq). The reaction mixture was stirred at 110° C. for 4 h under N$_2$ protection. The solid was filtered out and filtrate was concentrated, and the residue was purified by prep-TLC (DCM/MeOH=15/1) to afford the Example 33 (43.3 mg, 37% yield) as an off-white solid. LCMS [M+1]⁺=448.2. ¹H NMR (300 MHz, DMSO-d$_6$) δ 11.00 (s, 1H), 9.20 (s, 1H), 9.05 (s, 1H), 8.56 (s, 1H), 7.91 (s, 1H), 7.62 (dd, J=7.8, 1.6 Hz, 1H), 7.53 (dd, J=8.0, 1.6 Hz, 1H), 7.25 (t, J=7.8 Hz, 1H), 4.00-3.70 (m, 7H), 3.70 (s, 3H), 3.01-2.91 (m, 1H), 2.19-2.09 (m, 2H), 1.12-0.99 (m, 4H).

Example 34
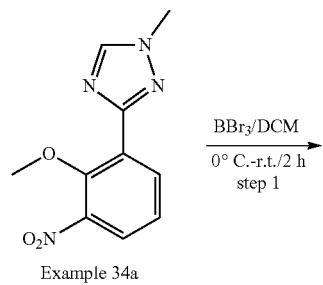
Example 34a
BBr₃/DCM
0° C.-r.t./2 h
step 1
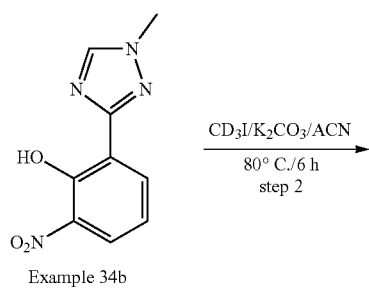
Example 34b
CD₃I/K₂CO₃/ACN
80° C./6 h
step 2
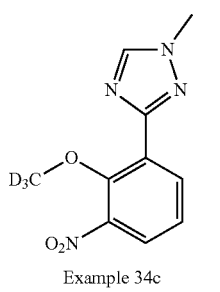
Example 34c
Pd/C/H₂/MeOH
r.t./48 h
step 3
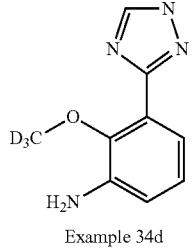
Example 34d
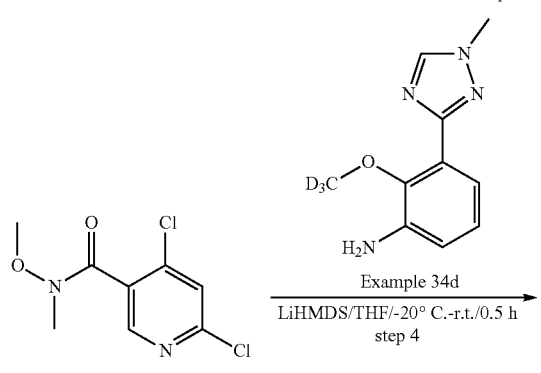
Example 34e + Example 34d
LiHMDS/THF/−20° C.-r.t./0.5 h
step 4
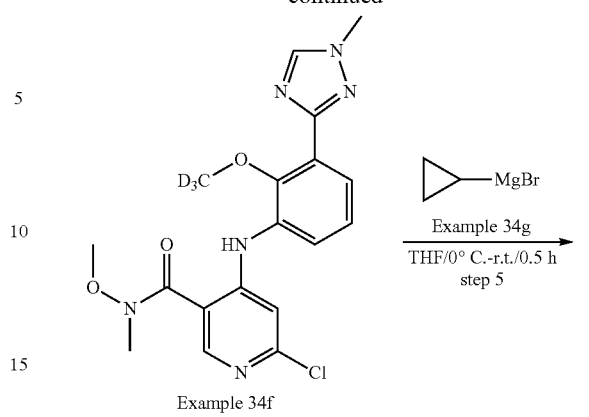
Example 34f
CyclopropylMgBr
Example 34g
THF/0° C.-r.t./0.5 h
step 5
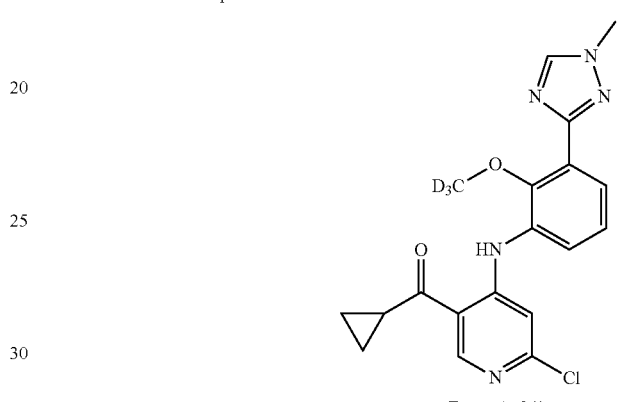
Example 34h
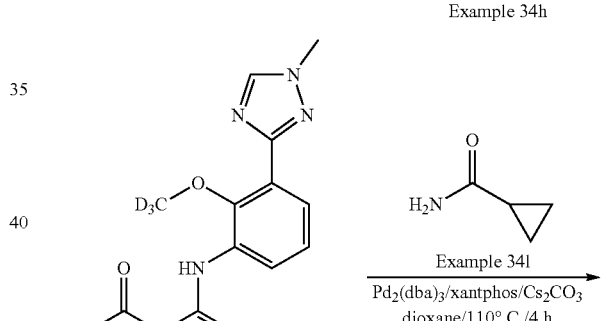
Example 34h + cyclopropanecarboxamide
Example 34I
Pd₂(dba)₃/xantphos/Cs₂CO₃
dioxane/110° C./4 h
step 6
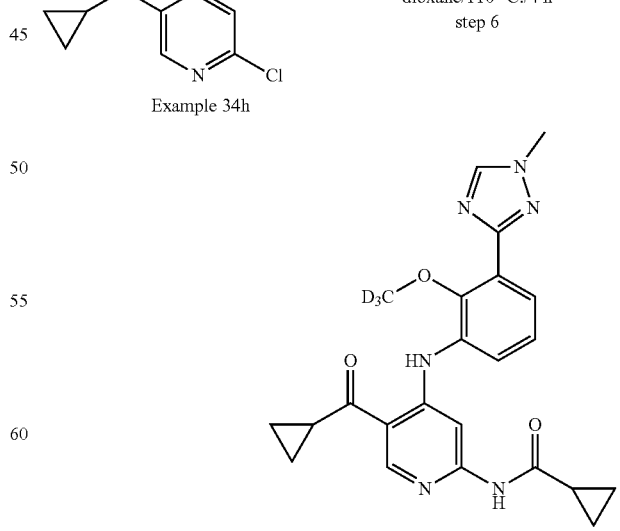
Example 34

Step 1: Example 34b

To a solution of Example 34a (10.0 g, 42.7 mmol, 1.0 eq) in DCM (100 mL) was added BBr₃ (11.8 g, 46.9 mmol, 1.1 eq) dropwise at 0° C. The mixture was stirred for 2 h at r.t. The mixture was quenched with MeOH (12 mL), washed with brine (50 mL*3), dried over Na₂SO₄, and concentrated to afford the product Example 34b (9.2 g, 98% yield) as an orange solid. LCMS [M+1]⁺=221.2.

Step 2: Example 34c

To a solution of Example 34b (9.2 g, 41.8 mmol, 1.0 eq) in ACN (184 mL) were added K₂CO₃ (11.6 g, 83.6 mmol, 2.0 eq) and CD₃I (7.3 g, 50.2 mmol, 1.2 eq). The reaction mixture was stirred for 6 h at 80° C. After the reaction was completed, the reaction mixture was concentrated and purified by silica gel chromatography (Petroleum Ether/EtOAc=2/1) to afford the product Example 34c (3.9 g, 39% yield) as an orange solid. LCMS [M+1]⁺=238.2.

Step 3: Example 34d

To a solution of Example 34c (3.9 g, 16.4 mmol, 1.0 eq) in MeOH (78 mL) was added Pd/C (780 mg) under N₂ protection. The suspension was degassed under vacuum and purged with H₂ three times. The reaction mixture was stirred at r.t. for 48 h under H₂ balloon. The solid was filtered out, and the filtrate was concentrated. The residue was purified by silica gel chromatography (Petroleum Ether/EtOAc=1/1) to afford the product Example 34d (1.9 g, 56% yield) as an off-white solid. LCMS [M+1]⁺=208.2.

Step 4: Example 34f

To a solution of Example 34e (450 mg, 1.91 mmol, 1.0 eq) and Example 34d (396 mg, 1.91 mmol, 1.0 eq) in dry THF (15 mL) was added LiHMDS (3.8 mL, 1 M in THF, 2.0 eq) dropwise at ~20° C. under N₂ protection. The reaction mixture was stirred for 0.5 h at r.t., and then the silica was added to the mixture and concentrated. The residue was purified by silica gel chromatography (DCM/MeOH=20/1) to afford the product Example 34f (450 mg, 58% yield) as a yellow solid. LCMS [M+1]⁺=406.2.

Step 5: Example 34h

To a solution of Example 34f (200 mg, 0.49 mmol, 1.0 eq) in THF (4 mL) was added Example 34g (3.0 mL, 1.0 M in THF, 6.0 eq) dropwise at 0° C. under N₂ protection. The mixture was stirred for 0.5 h at r.t. The reaction was poured into saturated aqueous NH₄Cl (10 mL) and extracted with EtOAc (15 mL*3). The combined organic layer was washed with brine, dried over Na₂SO₄, and concentrated. The crude product was purified by silica gel chromatography (DCM/MeOH=20/1) to afford the product Example 34h (160 mg, 84% yield) as a yellow solid. LCMS [M+1]⁺=387.1.

Step 6: Example 34

To a solution of Example 34h (100 mg, 0.26 mmol, 1.0 eq) in dioxane (4 mL) were added Cs₂CO₃ (169 mg, 0.52 mmol, 2.0 eq), Example 34I (66 mg, 0.77 mmol, 3.0 eq), Xantphos (30 mg, 0.05 mmol, 0.2 eq) and Pd₂(dba)₃·CHCl₃ (27 mg, 0.03 mmol, 0.1 eq). The reaction mixture was stirred for 4 h at 110° C. under N₂ protection. After cooled to room temperature, the solvent was removed, and the crude product was purified by prep-TLC (DCM/MeOH=15/1) to afford the product Example 34 (30.9 mg, 27% yield) as a yellow solid. LCMS [M+1]⁺=436.2. ¹H NMR (300 MHz, DMSO-d₆) δ 11.01 (s, 1H), 10.93 (s, 1H), 9.13 (s, 1H), 8.56 (s, 1H), 8.04 (s, 1H), 7.64 (d, J=7.6 Hz, 1H), 7.52 (d, J=7.8 Hz, 1H), 7.26 (t, J=7.8 Hz, 1H), 3.95 (s, 3H), 3.05-2.90 (m, 1H), 2.05-2.00 (m, 1H), 1.14-1.03 (m, 4H), 0.81 (d, J=6.4 Hz, 4H).

Example 35

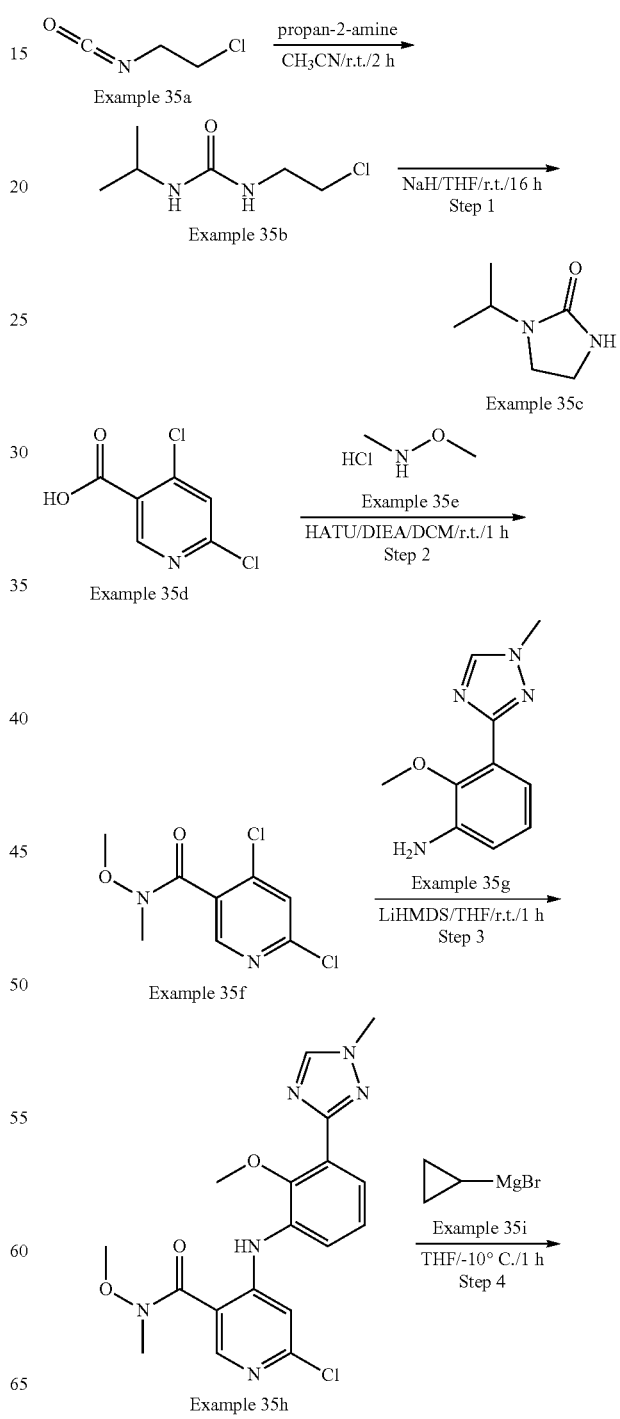

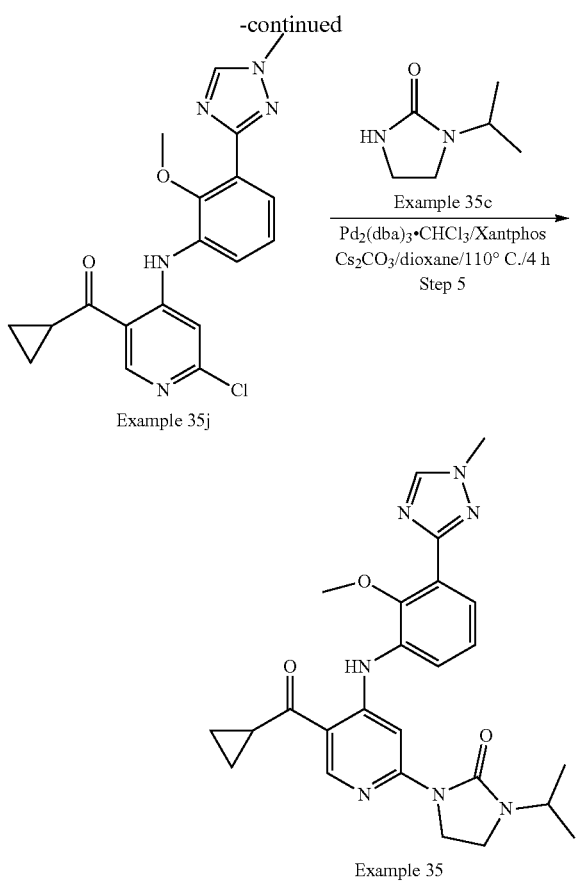

Example 35j

Example 35

Step 1: Example 35c

To a solution of Example 35a (10.0 g, 94.79 mmol, 1.0 eq) in $CH_3CN$ (50 mL) was added propan-2-amine (5.59 g, 94.79 mmol, 1.0 eq) at 0° C. The reaction solution was stirred for 2 h at room temperature. The resulting solid was collected by filtration to afford Example 35b (8.07 g) as a white solid. The solid was dissolved in THF (150 mL), followed by NaH (5.83 g, 60% in mineral oil, 145.8 mmol, 3.0 eq) in portions at 0° C. The mixture was stirred for 16 h at room temperature. The reaction was quenched with $H_2O$ and extracted with EtOAc. The combined organic layer was washed with brine, dried by $Na_2SO_4$ and concentrated. The crude product was purified by silica gel chromatography (DCM/MeOH=30/1) to give the desired product Example 35c (3.50 g, 29% yield) as a white solid. $^1$H NMR (300 MHz, $CDCl_3$-d) δ 5.07 (s, 1H), 4.21-4.06 (m, 1H), 3.38 (s, 4H), 1.13 (d, J=6.6 Hz, 6H).

Step 2: Example 35f

To a solution of Example 35d (10.0 g, 52.08 mmol, 1.0 eq) in DCM (200 mL) were added DIEA (33.59 g, 260.4 mmol, 5.0 eq) and HATU (23.75 g, 62.50 mmol, 1.2 eq). After stirred for 30 min, Example 35e (6.09 g, 62.50 mmol, 1.2 eq) was added to the solution. The reaction solution was stirred for 1 h at room temperature. After the reaction was completed, the solvent was removed and the crude was purified by silica gel chromatography (Petroleum Ether/EtOAc=3/1) to give the desired product Example 35f (11.5 g, 94.0% yield) as a yellow solid. LCMS $[M+1]^+$=235.0.

Step 3: Example 35h

To a solution of Example 35f (5.0 g, 21.28 mmol, 1.0 eq) and Example 35g (4.36 g, 21.28 mmol, 1.0 eq) in THF (100 mL) was added LiHMDS (42.55 mL, 1 M in THF, 2.0 eq) dropwise at −15° C. under $N_2$. The reaction solution was stirred for 1 h at r.t. And then the silica was added to the mixture and concentrated. The residue was purified by silica gel chromatography (DCM/MeOH=50/1) to give the desired product Example 35h (4.02 g, 46.9% yield) as a yellow solid. LCMS $[M+1]^+$=403.2.

Step 4: Example 35j

To a solution of Example 35h (2.0 g, 4.98 mmol, 1.0 eq) in THF (100 mL) was added Example 35i (39.80 mL, 39.80 mmol, 1 M, 8.0 eq) dropwise at ~10° C. under $N_2$. The reaction solution was stirred for 1 h at r.t. The reaction solution was quenched with saturated aqueous $NH_4Cl$ and extracted with EtOAc. The combined organic layer was washed with brine, dried by $Na_2SO_4$ and concentrated. The crude product was purified by silica gel chromatography (DCM/MeOH=20/1) to give the desired product Example 35j (1.90 g, 99.7% yield) as a yellow solid. LCMS $[M+1]^+$ =384.2.

Step 5: Example 35

To the solution of Example 35j (100 mg, 0.26 mmol, 1.0 eq) in dioxane (3 mL) were added Example 70c (100 mg, 0.78 mmol, 3.0 eq), $Cs_2CO_3$ (170 mg, 0.52 mmol, 2.0 eq), Xantphos (15 mg, 0.026 mmol, 0.1 eq) and $Pd_2(dba)_3CHCl_3$ (27 mg, 0.026 mmol, 0.1 eq). The reaction solution was stirred for 4 h at 110° C. under $N_2$. The reaction solution was filtered and the filtrate was concentrated. The crude product was purified by Prep-TLC (DCM/MeOH=15/1) to give the desired product Example 35 (31.3 mg, 25.3% yield) as an off white solid. LCMS $[M+1]^+$=476.3. $^1$H NMR (300 MHz, DMSO-$d_6$) δ 10.93 (s, 1H), 9.14 (s, 1H), 8.56 (s, 1H), 8.17 (s, 1H), 7.62 (dd, J=7.8, 1.8 Hz, 1H), 7.56 (dd, J=8.4 Hz, 1.6 Hz, 1H), 7.26 (t, J=7.8 Hz, 1H), 4.12-3.99 (m, 3H), 3.95 (s, 3H), 3.70 (s, 3H), 3.41 (t, J=8.0 Hz, 2H), 3.04-2.91 (m, 1H), 1.17-1.06 (m, 8H), 1.06-0.98 (m, 2H).

Example 36

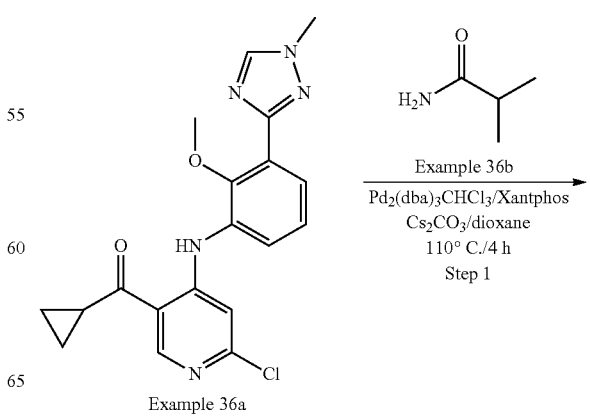

Example 36a

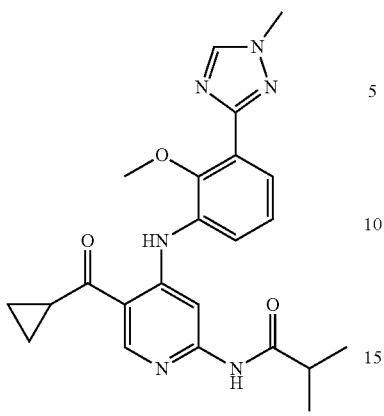

Example 36

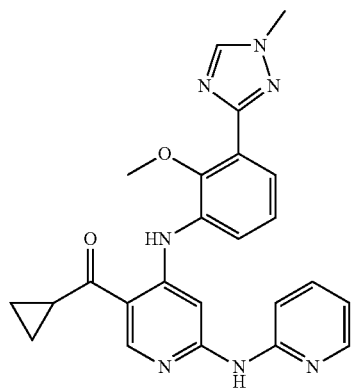

Example 37

To a solution of Example 36a (70 mg, 0.18 mmol, 1.0 eq) in dioxane (2 mL) were added Example 36b (48 mg, 0.55 mmol, 3.0 eq), $Cs_2CO_3$ (119 mg, 0.37 mmol, 2.0 eq), Xantphos (11 mg, 0.018 mmol, 0.1 eq) and $Pd_2(dba)_3 \cdot CHCl_3$ (19 mg, 0.018 mmol, 0.1 eq). The reaction solution was stirred for 4 h at 110° C. under $N_2$. The reaction solution was filtered and the filtrate was concentrated. The crude product was purified by prep-TLC (DCM/MeOH=15/1) to give the desired product Example 36 (30.9 mg, 39.0% yield) as an off-white solid.

LCMS [M+1]$^+$=435.2. $^1$H NMR (300 MHz, DMSO-d$_6$) δ 11.02 (s, 1H), 10.56 (s, 1H), 9.12 (s, 1H), 8.56 (s, 1H), 8.08 (s, 1H), 7.66 (dd, J=7.8, 1.5 Hz, 1H), 7.56 (dd, J=7.8, 1.5 Hz, 1H), 7.29 (t, J=7.4 Hz, 1H), 3.95 (s, 3H), 3.70 (s, 3H), 3.06-2.94 (m, 1H), 2.83-2.69 (m, 1H), 1.15-1.08 (m, 2H), 1.08-0.98 (m, 8H).

Example 37

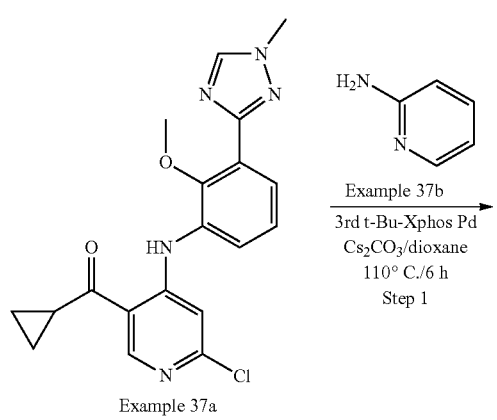

Example 37a

Example 37b

3rd t-Bu-Xphos Pd
Cs$_2$CO$_3$/dioxane
110° C./6 h
Step 1

To a solution of Example 37a (100 mg, 0.26 mmol, 1.0 eq) in dioxane (3 mL) were added Example 37b (49 mg, 0.52 mmol, 3.0 eq), $Cs_2CO_3$ (170 mg, 0.52 mmol, 2.0 eq), and 3$^{rd}$ t-Bu-Xphos Pd (23 mg, 0.026 mmol, 0.1 eq). The reaction solution was stirred for 6 h at 110° C. under $N_2$. The reaction solution was filtered and the filtrate was concentrated. The crude product was purified by Prep-TLC (DCM/MeOH=15/1) to give the desired product Example 37 (21.0 mg, 18.3% yield) as a light yellow solid. LCMS [M+1]$^+$=442.2. $^1$H NMR (300 MHz, DMSO-d$_6$) δ 11.08 (s, 1H), 9.98 (s, 1H), 9.10 (s, 1H), 8.56 (s, 1H), 8.19 (d, J=4.8 Hz, 1H), 8.01 (s, 1H), 7.69 (t, J=8.0 Hz, 2H), 7.60 (t, J=8.0 Hz, 2H), 7.31 (t, J=8.0 Hz, 1H), 6.96-6.88 (m, 1H), 3.96 (s, 3H), 3.72 (s, 3H), 3.04-2.91 (m, 1H), 1.14-0.94 (m, 4H).

Example 38

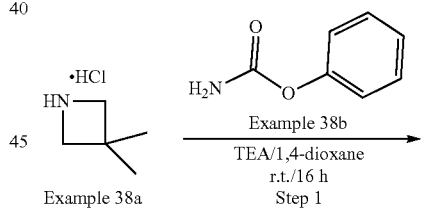

Example 38a    Example 38b

TEA/1,4-dioxane
r.t./16 h
Step 1

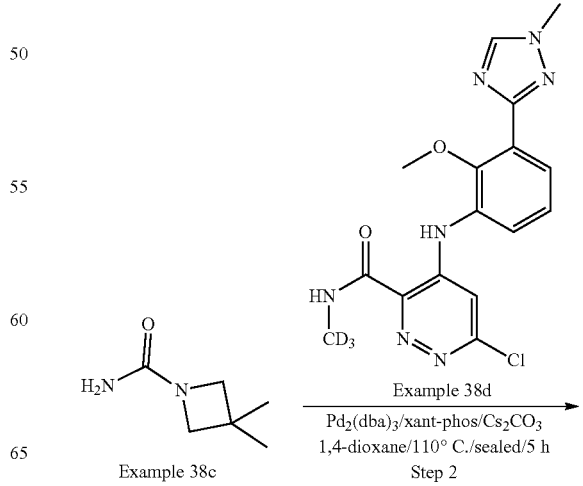

Example 38c    Example 38d

Pd$_2$(dba)$_3$/xant-phos/Cs$_2$CO$_3$
1,4-dioxane/110° C./sealed/5 h
Step 2

Example 105

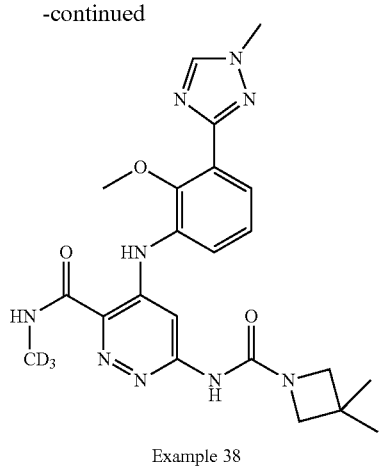

Example 38

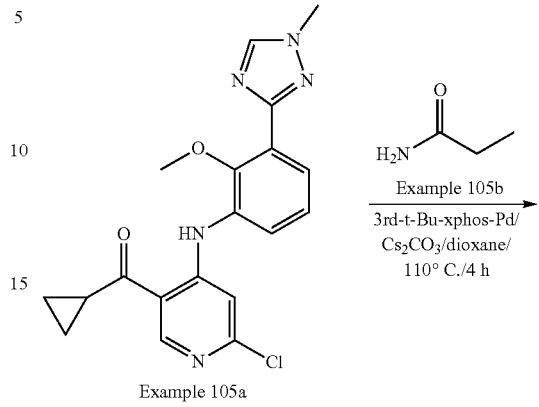

Example 105a

Step 1: Example 38c

A solution of Example 38b (1.13 g, 8.2 mmol) in 1,4-dioxane (10 mL) were treated with Example 38a (1.0 g, 8.2 mmol) and TEA (2.5 g, 24.7 mmol). The mixture was stirred at r.t. for 16 h. After the reaction was completed, the solution was concentrated, and the residue was suspended in a mixed solution (Petroleum Ether/EtOAc=1/1, 10 mL), and sonicated. The resulting solid was collected via filtration, dried to afford the desired product Example 38c (1.0 g, 94.3% yield) as a white solid, which contained some TEA·HCl. LCMS [M+1]$^+$=129.0

Step 2: Example 38

To a solution of Example 38d (250 mg, 0.66 mmol) and Example 38c (127 mg, 0.99 mmol) in 1,4-dioxane (4 mL) were added Pd$_2$(dba)$_3$ (60 mg, 0.068 mmol), Xantphos (77.5 mg, 0.13 mmol) and Cs$_2$CO$_3$ (433 mg, 1.32 mmol). The mixture was sealed, degassed by nitrogen for 3 times and stirred at 110° C. for 16 h. When completed, the reaction was cooled to r.t. and filtered. The filtrate was purified directly by prep-HPLC to give the desired product Example 38 (116 mg, 37.4% yield) as a yellow solid. LCMS [M+1]$^+$=469.0. $^1$H NMR (400 MHz, DMSO-d$_6$) δ 10.91 (s, 1H), 9.58 (s, 1H), 8.99 (s, 1H), 8.54 (s, 1H), 8.02 (s, 1H), 7.62 (d, J=7.7 Hz, 1H), 7.49 (d, J=7.8 Hz, 1H), 7.24 (t, J=7.9 Hz, 1H), 3.93 (s, 3H), 3.72 (s, 3H), 3.66 (s, 4H), 1.17 (s, 6H).

Examples 89-104 were synthesized as described for examples 1-88.

To a solution of Example 105a (100 mg, 0.26 mmol, 1.0 eq), Example 105b (57.0 mg, 0.78 mmol, 3.0 eq) in dioxane (3 mL) were added Cs$_2$CO$_3$ (169.5 mg, 0.52 mmol, 2.0 eq) and 3rd-t-Bu-xphos-Pd (26.7 mg, 0.03 mmol, 0.1 eq). The reaction mixture was stirred at 110° C. for 4 h under N$_2$ protection. The solid was filtered out and filtrate was concentrated. The residue was purified by Prep-TLC (DCM/MeOH=15/1) to afford Example 105 (36.1 mg, 33% yield) as a yellow solid. LCMS [M+1]$^+$=421.3. $^1$H NMR (300 MHz, DMSO-d6) δ 11.02 (s, 1H), 10.56 (s, 1H), 9.12 (s, 1H), 8.57 (s, 1H), 8.07 (s, 1H), 7.66 (dd, J=7.8, 1.5 Hz, 1H), 7.55 (dd, J=7.8, 1.5 Hz, 1H), 7.28 (t, J=7.8 Hz, 1H), 3.95 (s, 3H), 3.70 (s, 3H), 3.06-2.93 (m, 1H), 2.39 (q, J=7.5 Hz, 2H), 1.16-0.96 (m, 7H).

Example 106

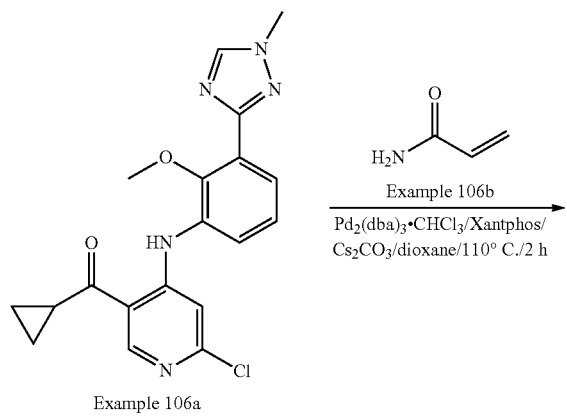

Example 107

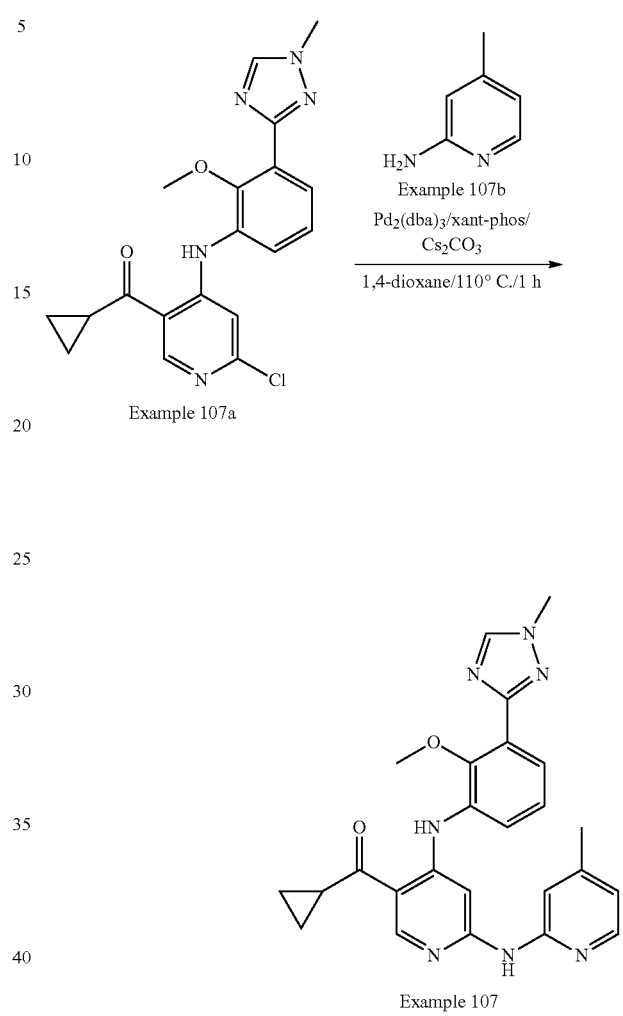

To a solution of Example 106a (50 mg, 0.13 mmol, 1.0 eq,) and Example 106b (13.9 mg, 0.20 mmol, 1.5 eq) in dioxane (3 mL) were added Cs$_2$CO$_3$ (84.9 mg, 0.26 mmol, 2.0 eq), Pd$_2$(dba)$_3$·CHCl$_3$ (13.5 mg, 0.013 mmol, 0.1 eq) and Xantphos (15.1 mg, 0.026 mmol, 0.2 eq). The reaction mixture was stirred for 2 h at 110° C. under N$_2$ protection. The mixture was filtered and the filtrate was concentrated in vacuo. The crude product was purified by pre-HPLC (DCM/MeOH=25/1) to afford the desired product Example 106 (5.9 mg, 10.8% yield) as a white solid. LCMS [M+1]$^+$ =419.3. $^1$H NMR (300 MHz, DMSO-d$_6$) δ 11.04 (s, 1H), 10.86 (s, 1H), 9.15 (s, 1H), 8.57 (s, 1H), 8.17 (s, 1H), 7.67 (dd, J=7.8, 1.5 Hz, 1H), 7.59-7.56 (m, 1H), 7.29 (t, J=7.8 Hz, 1H), 6.61 (dd, J=16.8, 10.2 Hz, 1H), 6.28 (dd, J=16.8, 1.8 Hz, 1H), 5.81 (d, J=11.7 Hz, 1H), 3.96 (s, 3H), 3.71 (s, 3H), 3.05-2.95 (m, 1H), 1.15-0.95 (m, 4H).

To a solution of Example 107a (110 mg, 0.29 mmol) and Example 107b (93 mg, 0.86 mmol) in 1,4-dioxane (2 mL) were added Pd$_2$(dba)$_3$ (26 mg, 0.029 mmol), Xantphos (33 mg, 0.057 mmol) and Cs$_2$CO$_3$ (187 mg, 0.57 mmol). The mixture was degassed by nitrogen for 3 times and stirred at 110° C. for 1 h. When completed, the reaction was cooled to r.t., diluted with MeOH (5 mL) and filtered. The filtrate was purified directly by Prep-HPLC to give the desired product Example 107 (24 mg, 18.5% yield) as a yellow solid. LCMS [M+1]$^+$=456.0. $^1$H NMR (400 MHz, DMSO-d$_6$) δ 11.04 (s, 1H), 9.88 (s, 1H), 9.07 (s, 1H), 8.55 (s, 1H), 8.03 (d, J=5.1 Hz, 1H), 7.97 (s, 1H), 7.66 (d, J=8.1 Hz, 1H), 7.57 (d, J=7.8 Hz, 1H), 7.39 (s, 1H), 7.27 (t, J=8.0 Hz, 1H), 6.74 (d, J=4.9 Hz, 1H), 3.93 (s, 3H), 3.69 (s, 3H), 2.94 (s, 1H), 2.24 (s, 3H), 1.05 (s, 2H), 0.99 (d, J=7.6 Hz, 2H).

Example 108

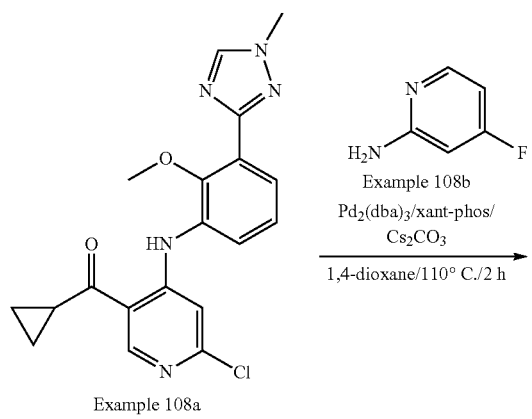

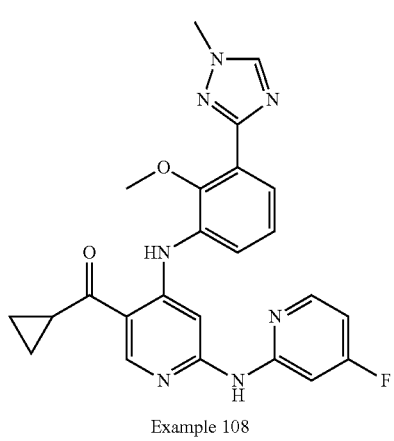

To a solution of Example 108a (100 mg, 0.26 mmol) and Example 108b (44 mg, 0.39 mmol) in 1,4-dioxane (2 mL) were added Pd$_2$(dba)$_3$ (24 mg, 0.026 mmol), Xantphos (30 mg, 0.052 mmol) and Cs$_2$CO$_3$ (170 mg, 0.52 mmol). The mixture was degassed by nitrogen for 3 times and stirred at 110° C. for 2 h. When completed, the reaction was cooled to r.t, diluted with MeOH (5 mL) and filtered. The filtrate was purified directly by Prep-HPLC to give the desired product Example 108 (18 mg, 15.1% yield) as a white solid. LCMS [M+1]$^+$=460.0. $^1$H NMR (400 MHz, DMSO-d$_6$) δ 11.01 (s, 1H), 10.15 (s, 1H), 9.11 (s, 1H), 8.54 (s, 1H), 8.20 (t, J=7.5 Hz, 1H), 7.69 (s, 1H), 7.63 (q, J=8.2, 5.8 Hz, 3H), 7.28 (t, J=8.0 Hz, 1H), 6.83 (s, 1H), 3.93 (s, 3H), 3.69 (s, 3H), 2.95 (s, 1H), 1.07 (s, 2H), 1.00 (d, J=7.4 Hz, 2H).

Example 109

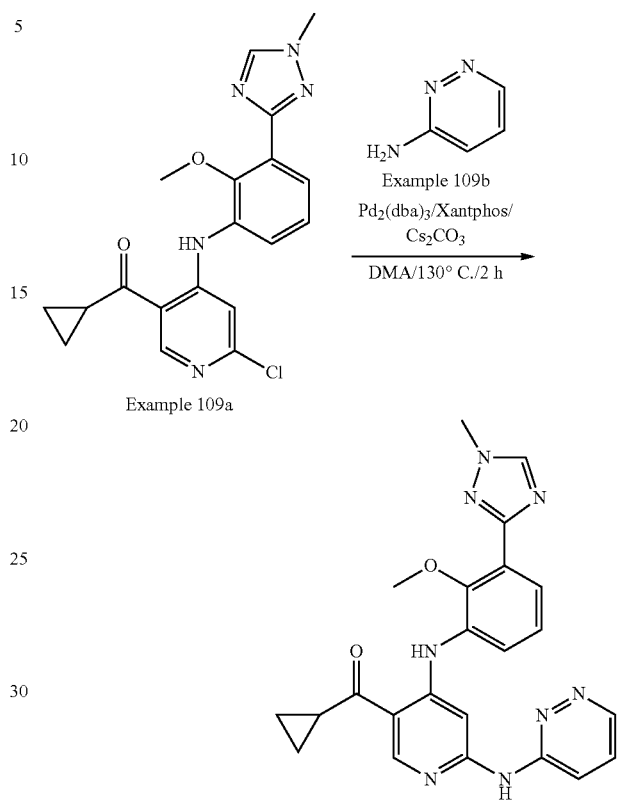

To a solution of Example 109a (100 mg, 0.26 mmol) and Example 109b (30 mg, 0.31 mmol) in DMA (2.5 mL) were added Pd$_2$(dba)$_3$ (24 mg, 0.026 mmol), xantphos (30 mg, 0.052 mmol) and Cs$_2$CO$_3$ (340 mg, 1.04 mmol). The mixture was degassed by nitrogen for 3 times and stirred at 130° C. for 2 h. When completed, the reaction was cooled to r.t., diluted with MeOH (5 mL) and filtered. The filtrate was purified directly by Prep-HPLC to give the desired product Example 109 (25 mg, 21.7% yield) as a white solid. LCMS [M+1]$^+$=443.0. $^1$H NMR (400 MHz, DMSO-d$_6$) δ 11.04 (s, 1H), 10.34 (s, 1H), 9.10 (s, 1H), 8.77 (d, J=4.4 Hz, 1H), 8.56 (s, 1H), 8.07 (d, J=9.1 Hz, 1H), 7.72 (s, 1H), 7.62 (dd, J=12.0, 8.1 Hz, 2H), 7.55 (dd, J=9.2, 4.5 Hz, 1H), 7.24 (t, J=7.9 Hz, 1H), 3.93 (s, 3H), 3.70 (s, 3H), 2.95 (t, J=7.4 Hz, 1H), 1.06 (d, J=4.1 Hz, 2H), 1.00 (d, J=7.4 Hz, 2H).

Example 110

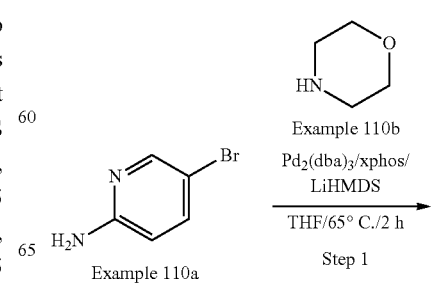

Step 1

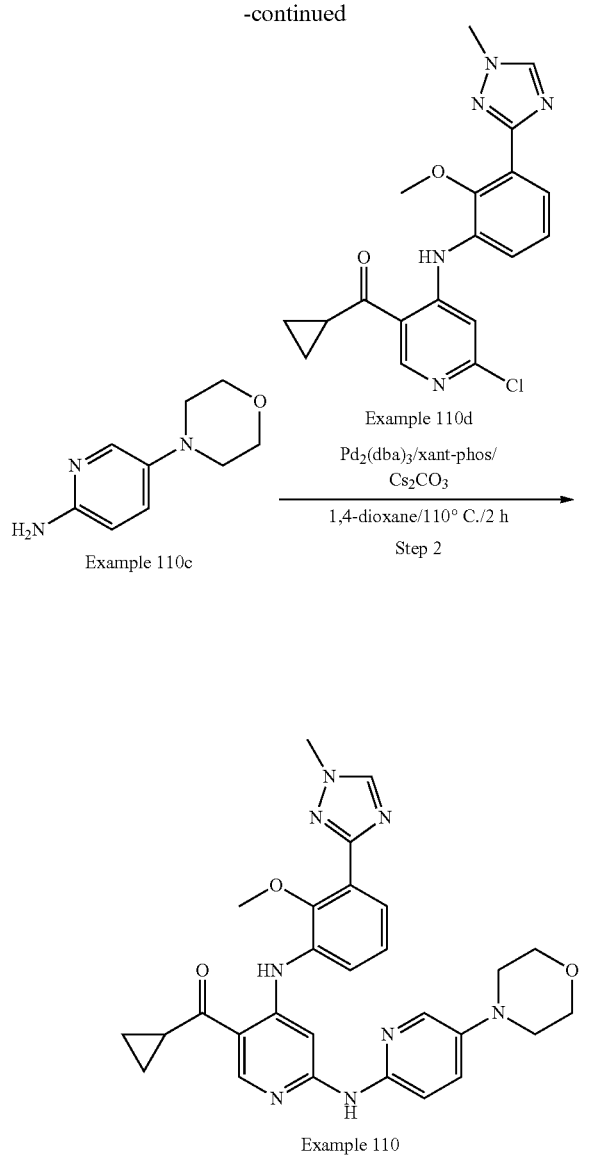

Step 1: Example 110c

To a stirred solution of Example 110a (1.0 g, 5.78 mmol), xphos (551 mg, 1.16 mmol), Pd$_2$(dba)$_3$ (530 mg, 0.58 mmol) and Example 110b (2.5 g, 28.9 mmol) in THF (12 mL) was added LiHMDS (32 mL, 1.0 M in THF) and the resulting reaction was heated to 65° C. and stirring continued for 2 h. The reaction was poured into water (100 mL) and extracted with EtOAc (150 mL*2) and DCM (150 mL*2). The combined organic layers were dried over Na$_2$SO$_4$, filtered and concentrated to give a residue which was purified by flash chromatography on a 40 g silica gel column (PE/EtOAc=0/100) to give the desired product Example 110c (900 mg, 87.4% yield) as a brown solid. LCMS [M+1]$^+$=180.0

Step 2: Example 110

To a solution of Example 110c (70 mg, 0.39 mmol) and Example 110d (100 mg, 0.26 mmol) in 1,4-dioxane (2 mL) were added Pd$_2$(dba)$_3$ (24 mg, 0.026 mmol), xantphos (30 mg, 0.052 mmol) and Cs$_2$CO$_3$ (170 mg, 0.52 mmol). The mixture was degassed by nitrogen for 3 times and stirred at 110° C. for 2 h. When completed, the reaction was cooled to r.t., diluted with MeOH (5 mL) and filtered. The filtrate was purified directly by Prep-HPLC to give the desired product Example 110 (22 mg, 16.1% yield) as a yellow solid. LCMS [M+1]$^+$=527.0. $^1$H NMR (400 MHz, DMSO-d$_6$) δ 11.06 (s, 1H), 9.74 (s, 1H), 9.04 (s, 1H), 8.54 (s, 1H), 7.85 (d, J=3.0 Hz, 1H), 7.79 (s, 1H), 7.65 (d, J=8.1 Hz, 1H), 7.57 (d, J=7.9 Hz, 1H), 7.50 (d, J=9.1 Hz, 1H), 7.39 (dd, J=9.1, 3.0 Hz, 1H), 7.29 (t, J=8.0 Hz, 1H), 3.93 (s, 3H), 3.72 (t, J=4.5 Hz, 4H), 3.69 (s, 3H), 3.04 (t, J=4.7 Hz, 4H), 2.92 (s, 1H), 1.04 (d, J=4.9 Hz, 2H), 0.97 (d, J=7.8 Hz, 2H).

Example 111

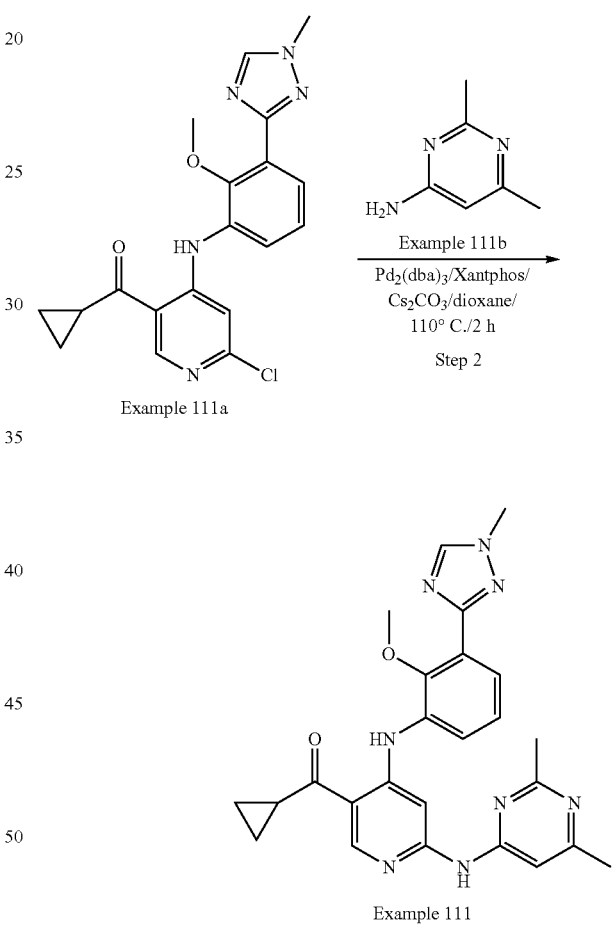

A solution of Example 111a (100 mg, 0.26 mmol), Example 111b (96 mg, 0.76 mmol), Pd$_2$(dba)$_3$ (24 mg, 0.026 mmol), Xantphos (8 mg, 0.013 mmol) and Cs$_2$CO$_3$ (170 mg, 0.52 mmol) in dioxane (3 mL) was heated to 110° C. for 2 h in Ar atmosphere. This mixture was filtered and directly purified by prep-HPLC to afford Example 111 (37 mg, 30.1% yield) as a yellow solid. LCMS [M+1]+=471.3. $^1$H NMR (400 MHz, DMSO-d$_6$) δ 11.07 (s, 1H), 10.21 (s, 1H), 9.10 (s, 1H), 8.54 (s, 1H), 8.14 (s, 1H), 7.64 (dd, J=13.6, 7.9 Hz, 2H), 7.27 (t, J=7.9 Hz, 1H), 7.08 (s, 1H), 3.92 (s, 3H), 3.69 (s, 3H), 3.01-2.92 (m, 1H), 2.34 (s, 3H), 2.27 (s, 3H), 1.11-0.96 (m, 4H).

Example 112

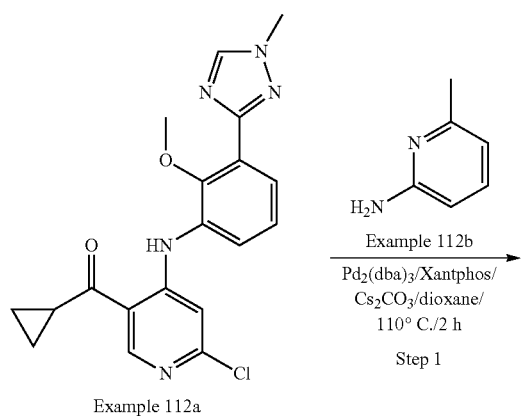

Example 112a

Example 112b

Pd$_2$(dba)$_3$/Xantphos/
Cs$_2$CO$_3$/dioxane/
110° C./2 h

Step 1

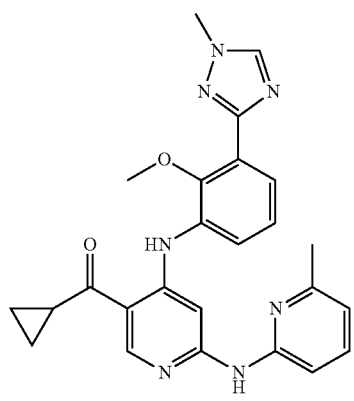

Example 112

A solution of Example 112a (100 mg, 0.26 mmol,), Example 112b (80 mg, 0.78 mmol), Pd$_2$(dba)$_3$ (24 mg, 0.026 mmol), Xantphos (8 mg, 0.013 mmol) and Cs$_2$CO$_3$ (170 mg, 0.52 mmol) in dioxane (3 mL) was heated to 110° C. for 2 h in Ar atmosphere. This mixture was filtered and directly purified by prep-HPLC to afford Example 112 (34 mg, 28.6% yield) as a yellow solid. LCMS [M+1]+=456.2. $^1$H NMR (400 MHz, DMSO-d$_6$) δ 11.12 (s, 1H), 9.91 (s, 1H), 9.06 (s, 1H), 8.53 (s, 1H), 8.25 (s, 1H), 7.68 (d, J=8.0 Hz, 1H), 7.60 (d, J=7.8 Hz, 1H), 7.52 (t, J=7.8 Hz, 1H), 7.26 (t, J=7.9 Hz, 1H), 7.15 (d, J=8.3 Hz, 1H), 6.73 (d, J=7.3 Hz, 1H), 3.92 (s, 3H), 3.69 (s, 3H), 2.98-2.89 (m, 1H), 2.28 (s, 3H), 1.09-0.94 (m, 4H).

Example 113

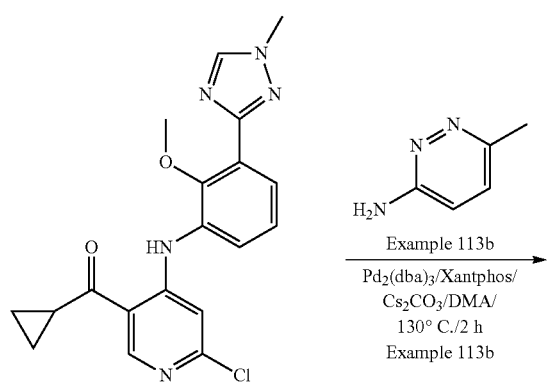

Example 113a

Example 113b

Pd$_2$(dba)$_3$/Xantphos/
Cs$_2$CO$_3$/DMA/
130° C./2 h

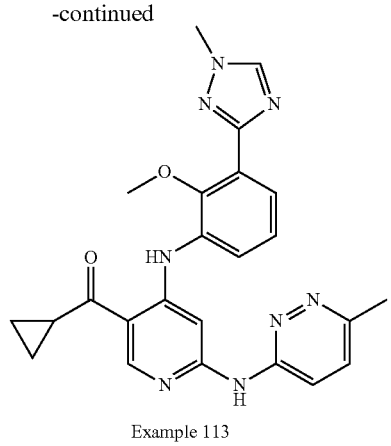

Example 113

A solution of Example 113a (100 mg, 0.26 mmol,), Example 113b (30 mg, 0.26 mmol), Pd$_2$(dba)$_3$ (24 mg, 0.026 mmol), Xantphos (8 mg, 0.013 mmol) and Cs$_2$CO$_3$ (170 mg, 0.52 mmol) in DMA (3 mL) was heated to 130°-C for 2 h in Ar atmosphere. This mixture was filtered and directly purified by prep-HPLC to afford Example 113 (13 mg, 10.9% yield) as a yellow solid. LCMS [M+1]+=457.2. $^1$H NMR (400 MHz, DMSO-d$_6$) δ 11.04 (s, 1H), 10.21 (s, 1H), 9.09 (s, 1H), 8.54 (s, 1H), 7.97 (d, J=9.1 Hz, 1H), 7.62 (dd, J=15.5, 8.4 Hz, 3H), 7.43 (d, J=9.2 Hz, 1H), 7.25 (t, J=8.0 Hz, 1H), 3.93 (s, 3H), 3.70 (s, 3H), 2.94 (t, J=5.6 Hz, 1H), 1.09-0.96 (m, 4H).

Example 114

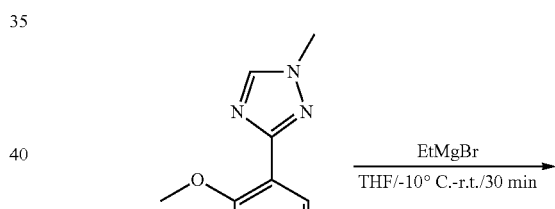

Example 114a

EtMgBr
THF/-10° C.-r.t./30 min

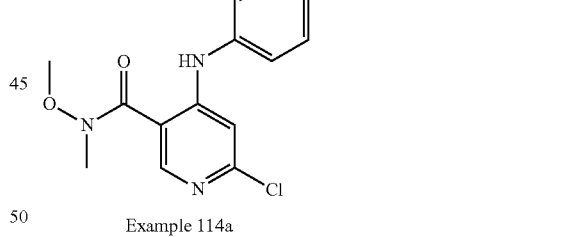

Example 114b

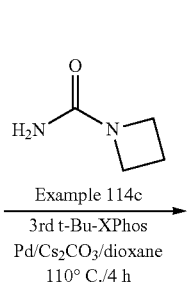

Example 114c

3rd t-Bu-XPhos
Pd/Cs$_2$CO$_3$/dioxane
110° C./4 h step 2

-continued

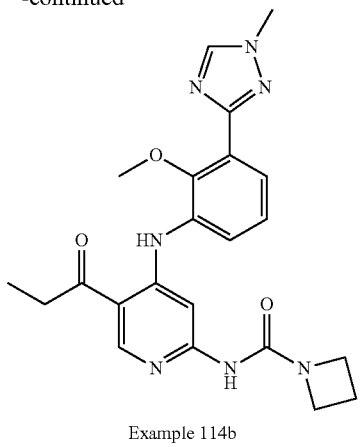

Example 114b

Example 115

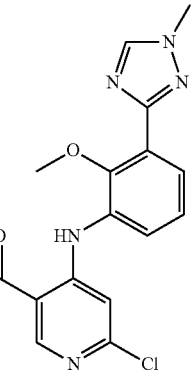

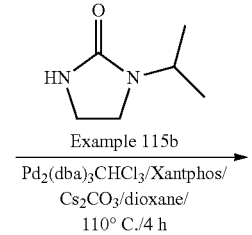

Example 115b

Pd₂(dba)₃CHCl₃/Xantphos/
Cs₂CO₃/dioxane/
110° C./4 h

Example 115a

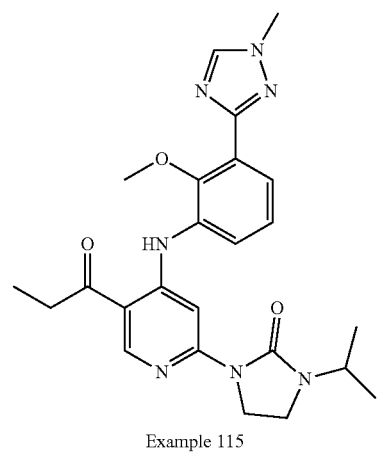

Example 115

Step 1: Example 114b

To a solution of Example 114a (500 mg, 1.24 mmol, 1.0 eq) in THF (15 mL) was added EtMgBr (9.93 mL, 1.0 M in THF, 9.93 mmol, 5.0 eq) dropwise at ~10° C. The reaction solution was stirred for 30 min at r.t. The reaction solution was poured into saturated aqueous of NH₄Cl (20 mL) at 0° C., extracted with EtOAc (20 mL*3), the combined organic layers were washed with brine (20 mL), dried over Na₂SO₄ and concentrated. The residue was purified by silica gel flash column chromatography, eluted with DCM/MeOH (10/1) to afford desired product Example 114b (367 mg, 79.5% yield) as a yellow solid. LCMS [M+1]⁺=372.3.

Step 2: Example 114

To a solution of Example 114b (100 mg, 0.27 mmol, 1.0 eq) in dioxane (5 mL) were added Example 114c (81 mg, 0.81 mmol, 3.0 eq), Cs₂CO₃ (175 mg, 0.54 mmol, 2.0 eq), and 3$^{rd}$ t-Bu-Xphos Pd (24 mg, 0.027 mmol, 0.1 eq). The reaction was stirred for 4 h at 110° C. under N₂. The mixture was filtered and the filtrate was concentrated. The crude product was purified by Prep-TLC (DCM/MeOH=15/1) to give the desired product Example 114 (43.7 mg, 37.3% yield) as a yellow solid. LCMS [M+1]⁺=436.3. ¹H NMR (300 MHz, DMSO-d₆) δ 11.03 (s, 1H), 9.16 (s, 1H), 8.81 (s, 1H), 8.57 (s, 1H), 7.90 (s, 1H), 7.63 (dd, J=7.8, 1.5 Hz, 1H), 7.54 (dd, J=7.8, 1.5 Hz, 1H), 7.26 (t, J=8.1 Hz, 1H), 4.03-3.92 (m, 7H), 3.73 (s, 3H), 3.10 (q, J=7.2 Hz, 2H), 2.21-2.08 (m, 2H), 1.13 (t, J=7.2 Hz, 3H).

To a solution of Example 115a (100 mg, 0.27 mmol, 1.0 eq) in dioxane (5 mL) were added Example 115b (103 mg, 0.81 mmol, 3.0 eq), Cs₂CO₃ (175 mg, 0.54 mmol, 2.0 eq), Xantphos (31 mg, 0.054 mmol, 0.2 eq) and Pd₂(dba)₃CHCl₃ (28 mg, 0.027 mmol, 0.1 eq). The reaction mixture was stirred for 4 h at 110° C. under N₂. The mixture was filtered and the filtrate was concentrated. The crude product was purified by Prep-TLC (DCM/MeOH=15/1) to give the desired product Example 115 (40.3 mg, 32.3% yield) as a light yellow solid. LCMS [M+1]⁺=464.3. ¹H NMR (300 MHz, DMSO-d₆) δ 10.96 (s, 1H), 8.89 (s, 1H), 8.56 (s, 1H), 8.15 (s, 1H), 7.62 (dd, J=7.8, 1.5 Hz, 1H), 7.56 (dd, J=7.8, 1.5 Hz, 1H), 7.26 (t, J=7.8 Hz, 1H), 4.09-3.96 (m 3H), 3.95 (s, 3H), 3.72 (s, 3H), 3.39 (t, J=8.1 Hz, 2H), 3.10 (q, J=7.2 Hz, 2H), 1.19-1.03 (m, 9H).

Example 116

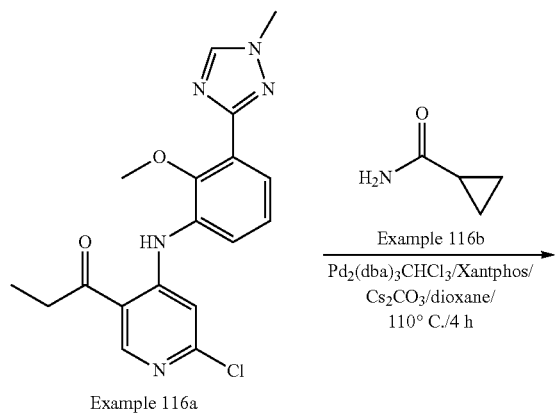

To a solution of Example 116a (100 mg, 0.27 mmol, 1.0 eq) in dioxane (5 mL) were added Example 116b (69 mg, 0.81 mmol, 3.0 eq), $Cs_2CO_3$ (175 mg, 0.54 mmol, 2.0 eq), Xantphos (31 mg, 0.054 mmol, 0.2 eq) and $Pd_2(dba)_3CHCl_3$ (28 mg, 0.027 mmol, 0.1 eq). The reaction solution was stirred for 4 h at 110° C. under $N_2$. The reaction solution was filtered and the filtrate was concentrated. The crude product was purified by Prep-TLC (DCM/MeOH=15/1) to give the desired product Example 116 (40.7 mg, 36.0% yield) as a light yellow solid. LCMS [M+1]$^+$=421.3. $^1$H NMR (300 MHz, DMSO-d$_6$) δ 11.04 (s, 1H), 10.90 (s, 1H), 8.88 (s, 1H), 8.56 (s, 1H), 8.00 (s, 1H), 7.65 (dd, J=7.8, 1.5 Hz, 1H), 7.52 (dd, J=7.8, 1.5 Hz, 1H), 7.26 (t, J=7.8 Hz, 1H), 3.95 (s, 3H), 3.71 (s, 3H), 3.12 (q, J=7.2 Hz, 2H), 2.07-1.96 (m, 1H), 1.13 (t, J=7.2 Hz, 3H), 0.79 (d, J=6.0 Hz, 4H).

Example 117

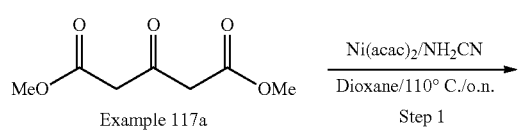

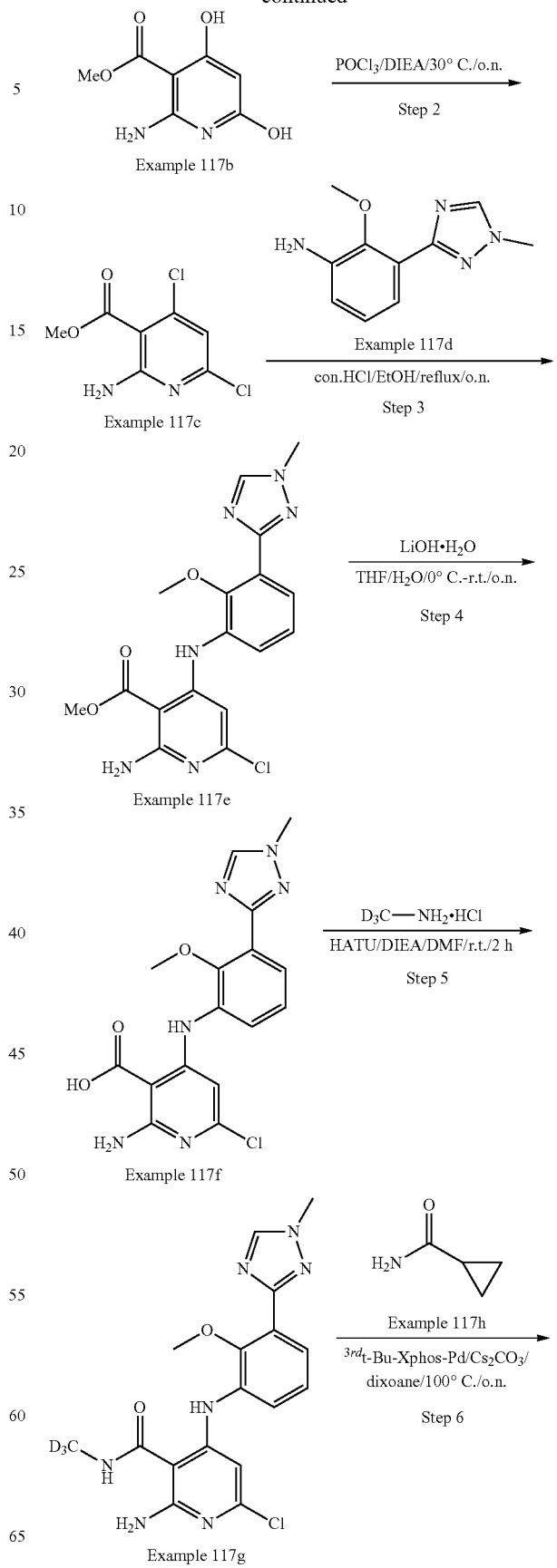

-continued

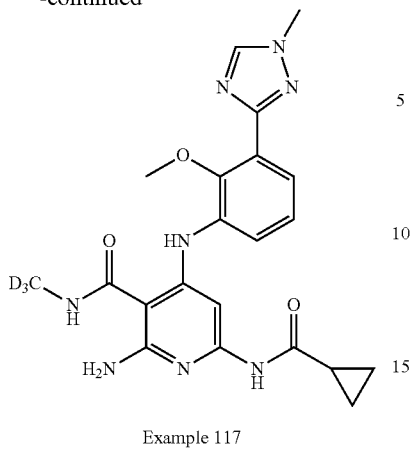

Example 117

Step 1: Example 117b

To a solution of dimethyl 3-oxopentanedioate (5.0 g, 28.7 mmol) and Ni(acac)$_2$ (738 mg, 2.87 mmol) in dioxane (30 mL) was added NH$_2$—CN (3.6 g, 86.2 mmol). The mixture was stirred at 110° C. for o.n. The reaction was cooled to r.t. The mixture was filtered and the filter cake was collected, washed with MeOH (20 mL) and concentrated in vacuo to give the desired product Example 117b (3.0 g, 56.6% yield) as a yellow solid. LCMS [M+1]$^+$=185.0

Step 2: Example 117c

To a solution of Example 117b (2.5 g, 13.58 mmol) in POCl$_3$ (15 mL) was added DIEA (2 mL) at 0° C., which was heated to 30° C. and stirred for o.n. The reaction was concentrated in vacuo. H$_2$O (15 mL) and MeOH (3 mL) were added at 0° C., which was stirred at r.t. for 1 h. The mixture was filtered and the filtrate cake was collected by filtration to give Example 117c (1.5 g, 50.1% yield) as a yellow solid. LCMS [M+1]$^+$=221.0

Step 3: Example 117e

To a solution of Example 117c (1.2 g, 5.42 mmol) and Example 117d (1.21 g, 5.96 mmol) in EtOH (30 mL) was added conc. HCl (5 mL) and the solution was heated to reflux for o.n. The reaction was concentrated in vacuo. The residue was dissolved in EtOAc (100 mL) and H$_2$O (50 mL), and the pH was adjusted to ~8 with sat. NaHCO$_3$. The organic layer was separated and concentrated. The residue was purified by silica gel chromatography (DCM/MeOH=30/1) to afford the product Example 117e (700 mg, 33.1% yield) as a yellow solid. LCMS [M+1]$^+$=389.11.

Step 4: Example 117f

To a solution of Example 117e (690 mg, 1.78 mmol) in THF (30 mL) and H$_2$O (10 mL) cooled at 0° C. was added LiOH·H$_2$O (112 mg, 2.67 mmol) and the solution was stirred at r.t. for o.n. The reaction was concentrated in vacuo. The residue was dissolved in H$_2$O (50 mL), adjusted pH ~4 with HCl (2 mol/L), and extracted with EtOAc (100 mL). The organic layer was concentrated to afford the crude product Example 117f (750 mg, 100% crude yield) as a yellow solid. LCMS [M+1]$^+$=375.2

Step 5: Example 117g

To a solution of Example 117f (500 mg, 1.33 mmol) in DMF (10 mL) were added DIEA (515 mg, 3.99 mmol), HATU (610 mg, 1.60 mmol) and CD$_3$—NH$_2$·HCl (110 mg, 1.59 mmol) and the solution was stirred at r.t. for 2 h. The reaction was diluted with EtOAc (50 mL), washed with brine (10 mL*3), dried over Na$_2$SO$_4$, and concentrated in vacuo. The residue was purified by silica gel chromatography (DCM/MeOH=30/1) to afford the product Example 117g (510 mg, 98% yield) as a light yellow solid. LCMS [M+1]$^+$=391.0

Step 6: Example 117

To a mixture of Example 117g (500 mg, 1.278 mmol), Example 117h (33 mg, 1.917 mmol) and Cs$_2$CO$_3$ (167 mg, 2.55 mmol) in dioxane (5 mL) was added 3rd t-Bu-Xphos-Pd (22.5 mg, 0.128 mmol). The mixture was degassed with N$_2$ three times, then heated to 100° C. and stirred for overnight. The reaction was concentrated in vacuo. The residue was further purified by prep-HPLC to give the desired product Example 117 (60 mg, 54.2% yield) as a white solid. LCMS [M+1]$^+$=440.1. $^1$H NMR (300 MHz, DMSO-d$_6$) δ 9.29 (s, 1H), 8.56 (s, 1H), 8.43 (s, 1H), 7.74 (d, J=6.8 Hz, 1H), 7.39 (d, J=7.6 Hz, 1H), 7.29 (t, J=7.8 Hz, 1H), 3.94 (s, 3H), 3.70 (s, 3H), 1.65-1.80 (m, 1H), 0.8-0.94 (m, 4H).

Example 118

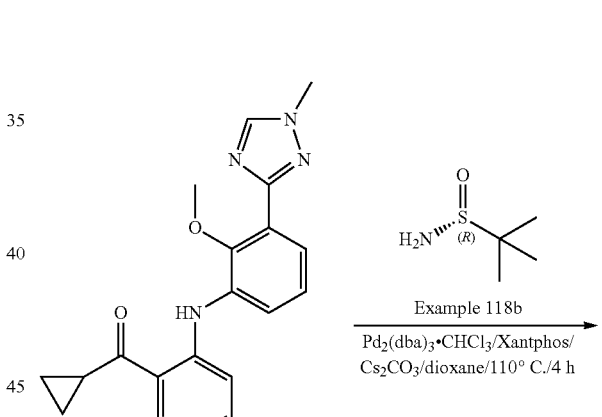

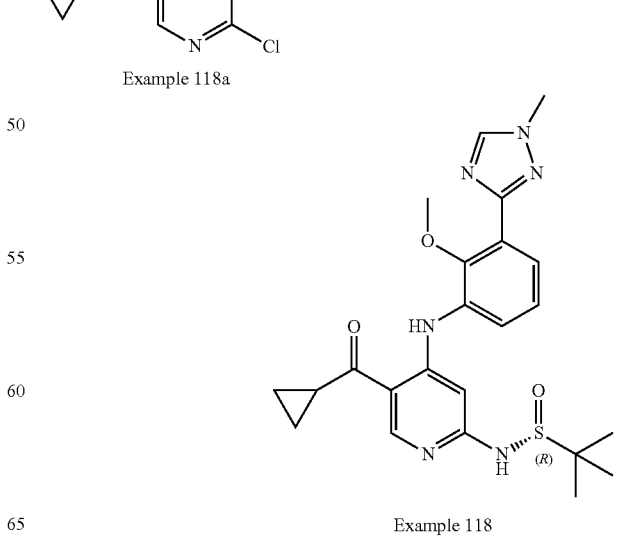

Example 118

To the solution of Example 118a (100 mg, 0.26 mmol, 1.0 eq) in dioxane (5 mL) were added Example 118b (95 mg, 0.78 mmol, 3.0 eq), $Cs_2CO_3$ (170 mg, 0.52 mmol, 2.0 eq), Xantphos (15 mg, 0.026 mmol, 0.1 eq) and $Pd_2(dba)_3 \cdot CHCl_3$ (27 mg, 0.026 mmol, 0.1 eq). The reaction solution was stirred for 4 h at 110° C. under $N_2$. The reaction solution was filtered and the filtrate was concentrated. The crude product was purified by Prep-TLC (DCM/MeOH=15/1) to afford the desired product Example 118 (21.9 mg, 17.9% yield) as a light yellow solid. LCMS $[M+1]^+$=469.3. $^1$H NMR (300 MHz, DMSO-$d_6$) δ 10.94 (s, 1H), 9.04 (s, 1H), 8.59 (s, 1H), 7.69 (dd, J=7.8, 1.8 Hz, 1H), 7.52 (dd, J=7.8, 1.5 Hz, 1H), 7.30 (t, J=7.8 Hz, 1H), 6.64 (s, 1H), 3.95 (s, 3H), 3.69 (s, 3H), 3.00-2.89 (m, 1H), 1.22 (s, 9H), 1.13-1.00 (m, 4H).

Example 119

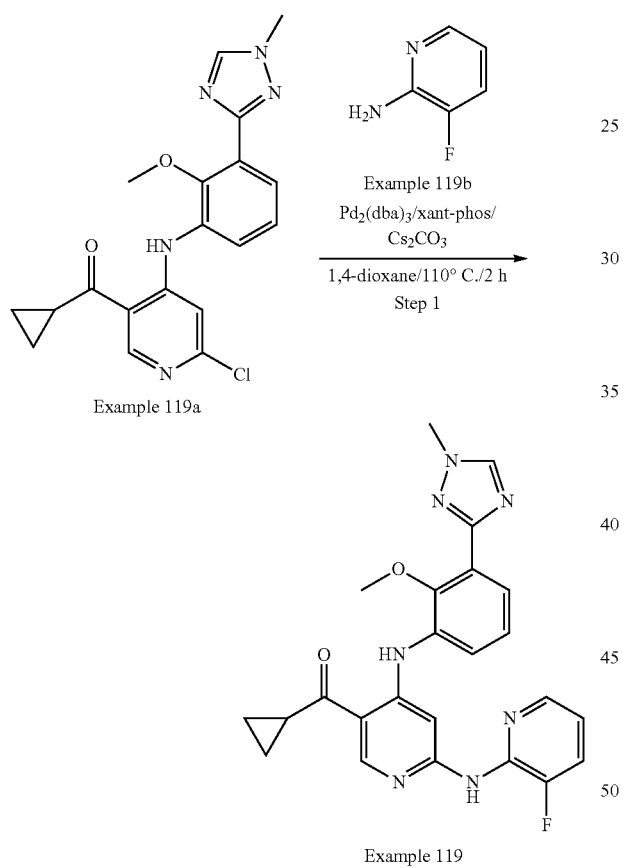

Step 1: Example 119

To a solution of Example 119a (100 mg, 0.26 mmol) and Example 119b (44 mg, 0.39 mmol) in 1,4-dioxane (2 mL) were added $Pd_2(dba)_3$ (24 mg, 0.026 mmol), xantphos (30 mg, 0.052 mmol) and $Cs_2CO_3$ (170 mg, 0.52 mmol). The mixture was degassed by nitrogen for 3 times and stirred at 110° C. for 2 h. When completed, the reaction was cooled to r.t., diluted with MeOH (5 mL) and filtered. The filtrate was purified directly by Prep-HPLC to give the desired product Example 119 (19.7 mg, 16.6% yield) as a yellow solid. LCMS $[M+1]^+$=460.0. $^1$H NMR (400 MHz, DMSO-$d_6$) δ 11.05 (s, 1H), 9.40 (s, 1H), 9.06 (s, 1H), 8.54 (s, 1H), 8.05 (d, J=4.6 Hz, 1H), 7.92 (s, 1H), 7.65 (q, J=8.1, 5.8 Hz, 2H), 7.59 (d, J=7.8 Hz, 1H), 7.29 (t, J=8.0 Hz, 1H), 7.04 (dt, J=8.0, 3.9 Hz, 1H), 3.93 (s, 3H), 3.69 (s, 3H), 2.95 (dt, J=8.1, 3.7 Hz, 1H), 1.07 (t, J=3.7 Hz, 2H), 0.99 (dd, J=7.9, 4.5 Hz, 2H).

Example 120

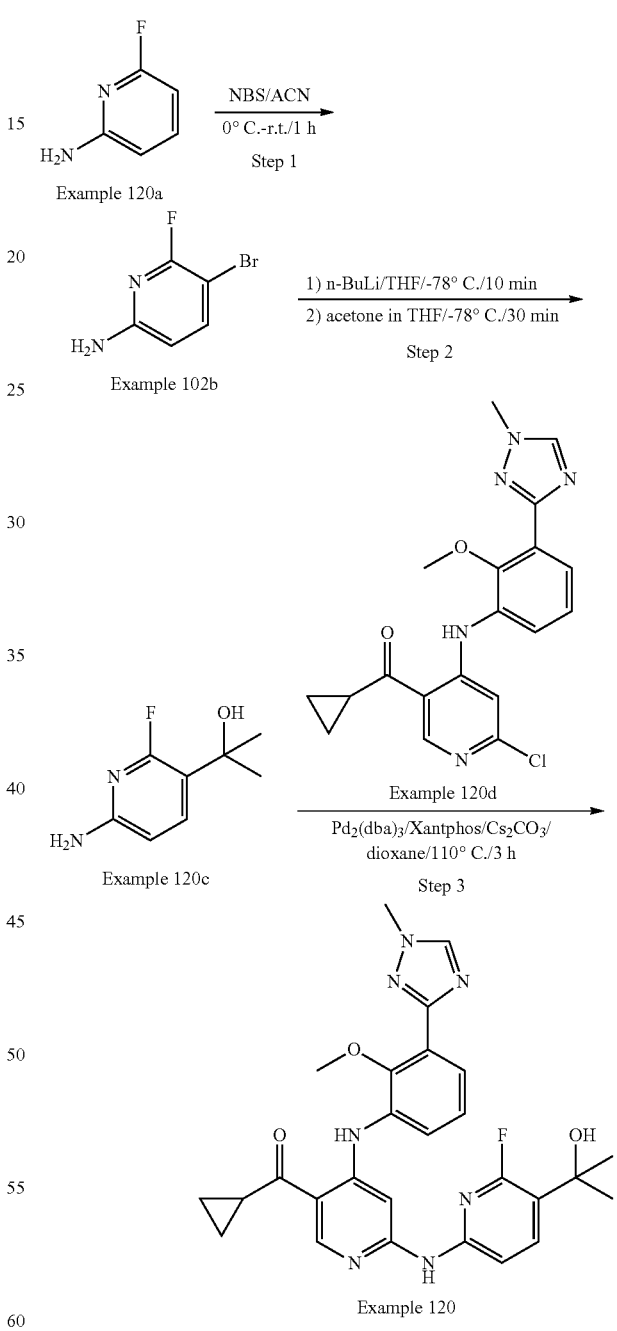

Step 1: Example 120b

To a solution of Example 120a (5.37 g, 47.9 mmol, 1.0 eq) in ACN (250 mL) was added NBS (6.2 g, 52.7 mmol, 1.1 eq) at 0° C. under $N_2$ protection. The reaction solution was stirred at r.t. for 1 h, and then the mixture was concentrated. The residue was purified by silica gel flash column chromatography (Petroleum Ether/EtOAc=5/1) to afford the product Example 120b (6.8 g, 75% yield) as a white solid. LCMS [M+1]$^+$=190.2.

Step 2: Example 120c

To a solution of Example 120b (6.0 g, 31.4 mmol, 1.0 eq) in dry THF (150 mL) was added n-BuLi (44 mL, 2.5 M in THF, 110 mmol, 3.5 eq) dropwise at ~78° C. under N$_2$ protection. The mixture was stirred for 5 min at the same temperature. Acetone (18.2 g, 314 mmol, 10.0 eq) in THF (50 mL) was added dropwise at ~78° C. under N$_2$ protection. The mixture was warmed to r.t. and stirred for 30 min. The reaction was poured into saturated aqueous NH$_4$Cl (100 mL) and extracted with EtOAc (200 mL*2). The combined organic layers were washed with brine, dried over anhydrous Na$_2$SO$_4$, and concentrated. The crude product was purified by silica gel flash column chromatography (Petroleum Ether/EtOAc=5/1) to afford the product Example 120c (3.5 g, 65% yield) as a green solid. LCMS [M+1]$^+$=171.2.

Step 3: Example 120

To a solution of Example 120d (100 mg, 0.26 mmol, 1.0 eq,) in dioxane (3 mL) were added Cs$_2$CO$_3$ (169 mg, 0.52 mmol, 2.0 eq), Example 120c (132 mg, 0.77 mmol, 3.0 eq), Xantphos (29 mg, 0.05 mmol, 0.2 eq) and Pd$_2$(dba)$_3$·CHCl$_3$ (31 mg, 0.03 mmol, 0.1 eq). The reaction mixture was stirred for 3 h at 110° C. under N$_2$ protection. After cooled to room temperature, the solvent was removed, the crude product was purified by Prep-TLC (DCM/MeOH=15/1) to afford the product Example 120 (48.4 mg, 36% yield) as an off-white solid. LCMS [M+1]$^+$=518.4. $^1$H NMR (300 MHz, DMSO-d$_6$) δ 11.11 (s, 1H), 10.14 (s, 1H), 9.11 (s, 1H), 8.56 (s, 1H), 7.97 (dd, J=10.8, 8.4 Hz, 1H), 7.80 (s, 1H), 7.73 (dd, J=7.8, 1.5 Hz, 1H), 7.62 (dd, J=7.8, 1.8 Hz, 1H), 7.49 (dd, J=8.1, 1.8 Hz, 1H), 7.27 (t, J=7.8 Hz, 1H), 5.26 (s, 1H), 3.95 (s, 3H), 3.72 (s, 3H), 3.05-2.90 (m, 1H), 1.46 (s, 6H), 1.16-0.94 (m, 4H).

Example 121

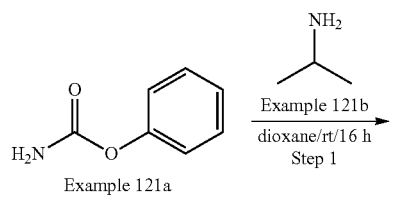

Step 1: Example 121c

To a solution of Example 121a (200 mg, 1.5 mmol, 1.0 eq) in dioxane (3 mL) was added Example 121b (265.5 mg, 4.5 mmol, 3.0 eq). The reaction solution was stirred for 16 h at r.t. and concentrated to dryness. The residue was suspended in DCM and sonicated. The resulting solid was collected by filtration to afford Example 121c (57 mg, 37% yield) as a white solid.

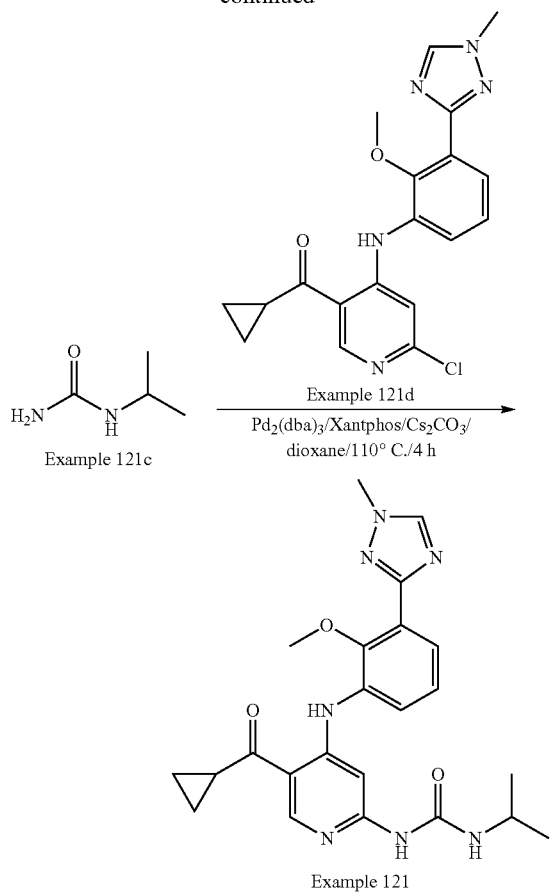

Step 2: Example 121

To a solution of Example 121d (60 mg, 0.16 mmol, 1.0 eq,) and Example 121c (49 mg, 0.48 mmol, 3.0 eq) in dioxane (2 mL) were added Cs$_2$CO$_3$ (104.3 mg, 0.32 mmol, 2.0 eq), Xantphos (17.4 mg, 0.03 mmol, 0.2 eq) and Pd$_2$(dba)$_3$·CHCl$_3$ (20.7 mg, 0.02 mmol, 0.1 eq). The reaction mixture was stirred at 110° C. for 4 h under N$_2$ protection. After cooled to room temperature, the solvent was removed, and the crude product was purified by Prep-TLC (DCM/MeOH=15/1) to afford the product Example 121 (40.1 mg, 56% yield) as a yellow solid. LCMS [M+1]$^+$=450.4. $^1$H NMR (300 MHz, DMSO-d$_6$) δ 10.97 (s, 1H), 9.13 (s, 1H), 9.05 (s, 1H), 8.56 (s, 1H), 7.76 (d, J=7.5 Hz, 1H), 7.63 (dd, J=7.8, 1.5 Hz, 1H), 7.53 (dd, J=7.8, 1.5 Hz, 1H), 7.39 (s, 1H), 7.26 (t, J=7.8 Hz, 1H), 3.95 (s, 3H), 3.86-3.73 (m, 1H), 3.70 (s, 3H), 3.00-2.88 (m, 1H), 1.16-0.95 (m, 10H).

Example 122

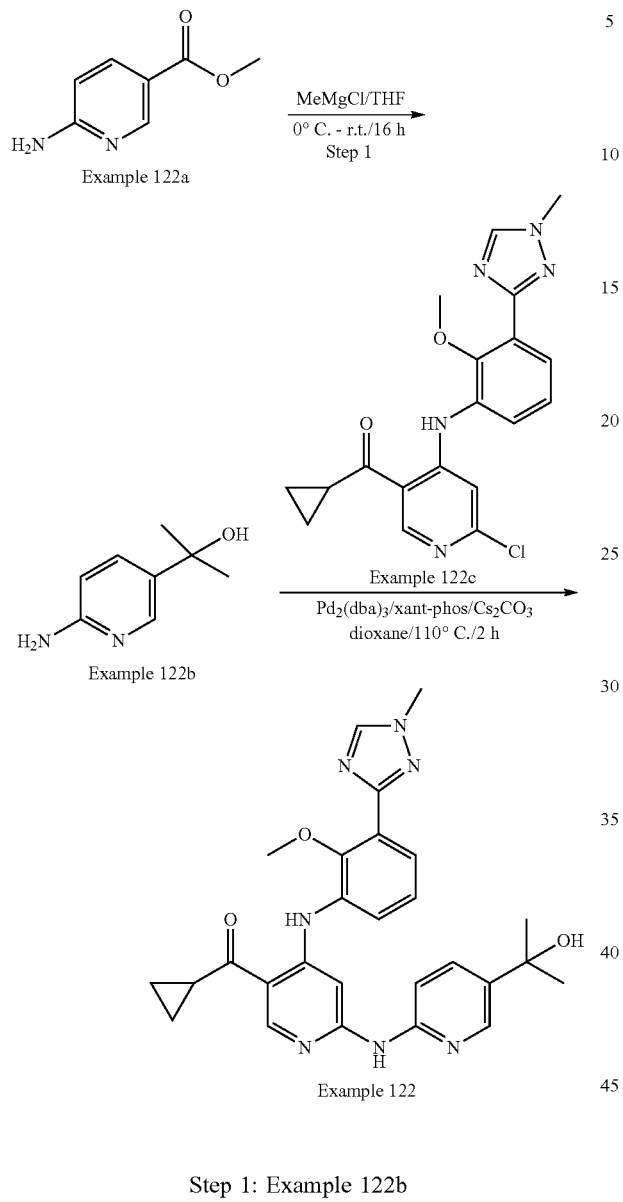

Step 1: Example 122b

To a solution of Example 122a (700 mg, 4.61 mmol) in THF (65 mL) was added MeMgCl (15 mL, 45 mmol) at 0° C. under argon protection. The reaction mixture was allowed to warm to room temperature and stirred for 16 h. Then the mixture was quenched by aq. NH$_4$C$_1$, extracted with EA (50 mL*2). The combined organic phase was washed by water, brine and dried over anhydrous Na$_2$SO$_4$. The solvent was removed under reduced pressure to give Example 122b (600 mg, 85.7% yield) as brown oil, which was used for the next step directly.

Step 1: Example 122

To a solution of Example 122c (100 mg, 0.26 mmol,) and Example 122b (59 mg, 0.39 mmol) in 1, 4-dioxane (2.5 mL) were added Pd$_2$(dba)$_3$ (24 mg, 0.026 mmol), Xantphos (30 mg, 0.052 mmol) and Cs$_2$CO$_3$ (170 mg, 0.52 mmol). The mixture was degassed by nitrogen for 3 times and stirred at 110° C. for 2 h. When completed, the reaction was cooled to r.t., diluted with MeOH (5 mL) and filtered. The filtrate was purified directly by Prep-TLC (DCM/MeOH=15/1) to give the desired product Example 122 (16 mg, 11.5% yield) as a yellow solid. LCMS [M+1]$^+$=500.0. $^1$H NMR (400 MHz, DMSO-d$_6$) δ 11.05 (s, 1H), 9.90 (s, 1H), 9.06 (s, 1H), 8.54 (s, 1H), 8.25 (s, 1H), 7.95 (s, 1H), 7.72 (d, J=8.8 Hz, 1H), 7.67 (d, J=8.0 Hz, 1H), 7.59 (d, J=8.0 Hz, 1H), 7.50 (d, J=8.8 Hz, 1H), 7.28 (t, J=8.0 Hz, 1H), 3.93 (s, 3H), 3.70 (s, 3H), 2.94 (s, 1H), 1.40 (s, 6H), 1.05 (s, 2H), 0.98 (d, J=7.7 Hz, 2H).

Example 123

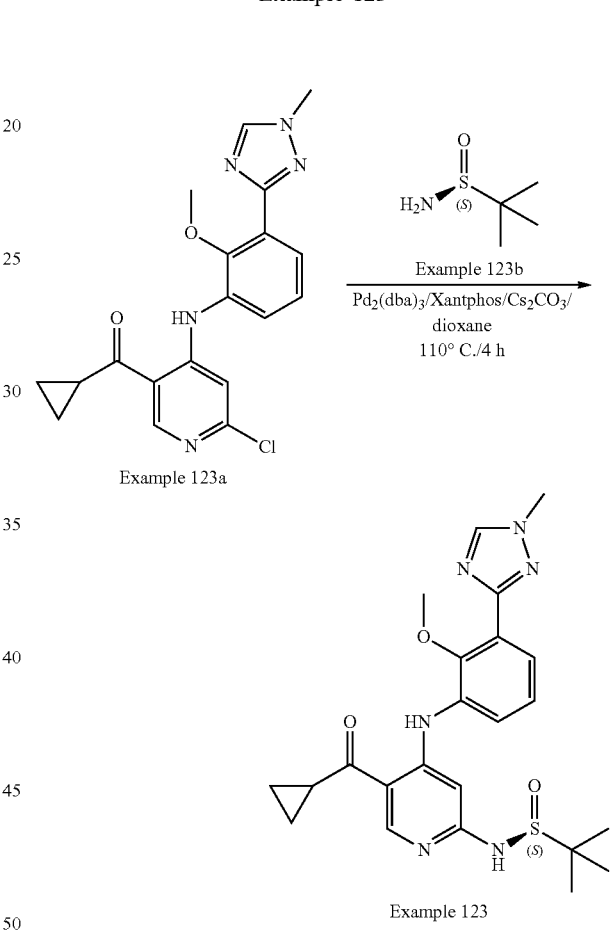

To the solution of Example 123a (100 mg, 0.26 mmol, 1.0 eq) in dioxane (5 mL) were added Example 123b (95 mg, 0.78 mmol, 3.0 eq), Cs$_2$CO$_3$ (170 mg, 0.52 mmol, 2.0 eq), Xantphos (15 mg, 0.026 mmol, 0.1 eq) and Pd$_2$(dba)$_3$·CHCl$_3$ (27 mg, 0.026 mmol, 0.1 eq). The reaction mixture was stirred for 4 h at 110° C. under N$_2$. The reaction solution was filtered and the filtrate was concentrated. The crude product was purified by Prep-TLC (DCM/MeOH=15/1) to afford the desired product Example 123 (26.1 mg, 21.4% yield) as a light yellow solid. LCMS [M+1]$^+$=469.3. $^1$H NMR (300 MHz, DMSO-d$_6$) δ 10.89 (s, 1H), 9.05 (s, 1H), 8.91 (brs, 1H), 8.56 (s, 1H), 7.67 (dd, J=7.8, 1.5 Hz, 1H), 7.52 (dd, J=8.1, 1.8 Hz, 1H), 7.29 (t, J=8.1 Hz, 1H), 6.64 (s, 1H), 3.95 (s, 3H), 3.69 (s, 3H), 3.00-2.88 (m, 1H), 1.22 (s, 9H), 1.12-0.99 (m, 4H).

Example 124

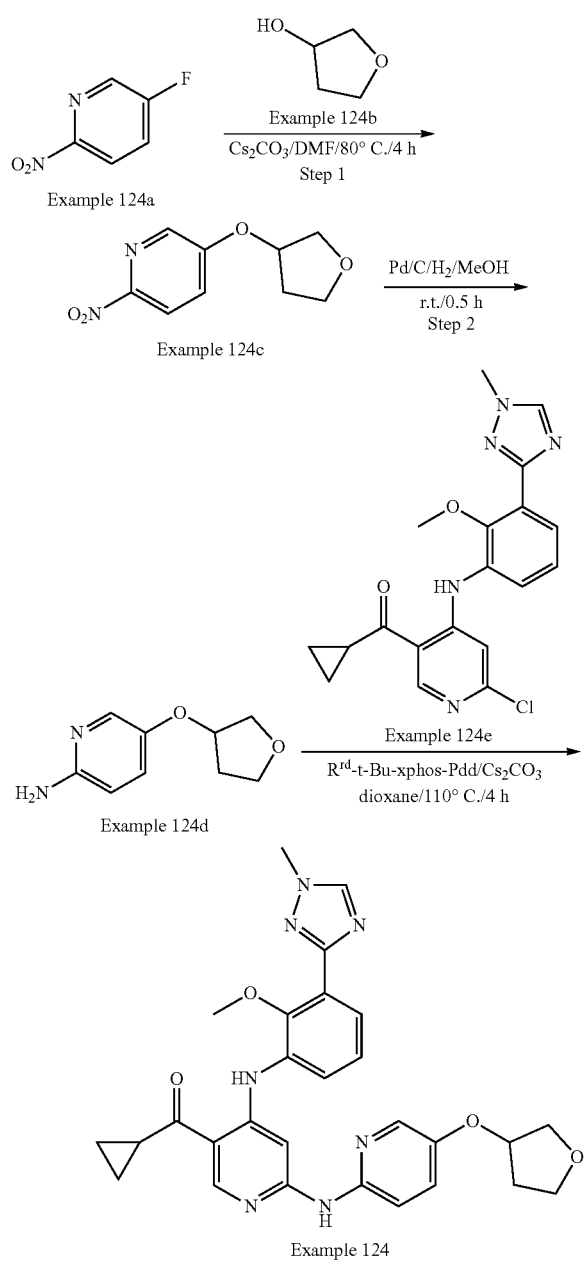 [SMILES: O=[N+]([O-])c1ccc(F)cn1 ; OC1CCOC1 ; O=[N+]([O-])c1ccc(OC2CCOC2)cn1 ; COc1c(Nc2cc(Cl)ncc2C(=O)C2CC2)cccc1-c1ncn(C)n1 ; Nc1ccc(OC2CCOC2)cn1 ; COc1c(Nc2cc(Nc3ccc(OC4CCOC4)cn3)ncc2C(=O)C2CC2)cccc1-c1ncn(C)n1]

Step 1: Example 124c

To a solution of Example 124b (465 mg, 5.28 mmol, 1.5 eq) in DMF (10 mL) was added $Cs_2CO_3$ (2.3 g, 7.04 mmol, 2.0 eq). The reaction mixture was stirred for 10 min at r.t., followed by addition of Example 124a (500 mg, 3.52 mmol, 1.0 eq) in DMF (3 mL). The mixture was stirred for 4 h at 80° C. After cooled to room temperature, the mixture was poured into $H_2O$ (25 mL) and extracted with EtOAc (50 mL*2). The combined organic layers were washed with brine, dried over $Na_2SO_4$ and concentrated. The residue was purified by silica gel flash column chromatography, eluted with Petroleum Ether/EtOAc (1/1) to afford the product Example 124c (250 mg, 32% yield) as a yellow solid. LCMS $[M+1]^+=211.2$.

Step 2: Example 124d

To a solution of Example 124c (250 mg, 1.19 mmol, 1.0 eq) in MeOH (30 mL) was added Pd/C (25 mg) under $N_2$ protection. The suspension was degassed under vacuum and purged with $H_2$ three times, and the reaction mixture was stirred at r.t. for 0.5 h under $H_2$ balloon. The solid was filtered out, and the filtrate was concentrated to afford the product Example 124d (230 mg, crude, yield: quant.) as yellow oil. LCMS $[M+1]^+=181.2$.

Step 3: Example 124

To a solution of Example 124e (100 mg, 0.26 mmol, 1.0 eq,) in dioxane (3 mL) were added $Cs_2CO_3$ (169.5 mg, 0.52 mmol, 2.0 eq), Example 124d (93.7 mg, 0.52 mmol, 2.0 eq) and $3^{rd}$-t-Bu-xphos-Pd (26.7 mg, 0.03 mmol, 0.1 eq). The reaction mixture was stirred for 4 h at 110° C. under $N_2$ protection. After cooled to room temperature, the solvent was removed, and the crude product was purified by Prep-TLC (DCM/MeOH=15/1) to afford the product Example 124 (37.0 mg, 27% yield) as a yellow solid. LCMS $[M+1]^+=528.3$. $^1$H NMR (300 MHz, DMSO-$d_6$) δ 11.06 (s, 1H), 9.87 (s, 1H), 9.07 (s, 1H), 8.56 (s, 1H), 7.90 (d, J=3.0 Hz, 1H), 7.76 (s, 1H), 7.67 (dd, J=7.8, 1.5 Hz, 1H), 7.63-7.55 (m, 2H), 7.40 (dd, J=9.0, 3.0 Hz, 1H), 7.32 (t, J=7.8 Hz, 1H), 5.08-4.99 (m, 1H), 3.95 (s, 3H), 3.91-3.75 (m, 4H), 3.72 (s, 3H), 3.00-2.88 (m, 1H), 2.29-2.05 (m, 1H), 2.03-1.89 (m, 1H), 1.15-0.91 (m, 4H).

Example 125

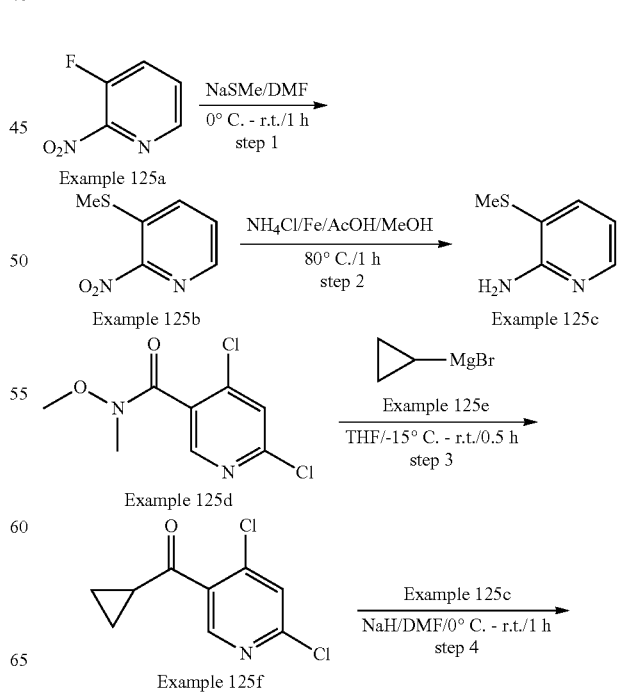

-continued

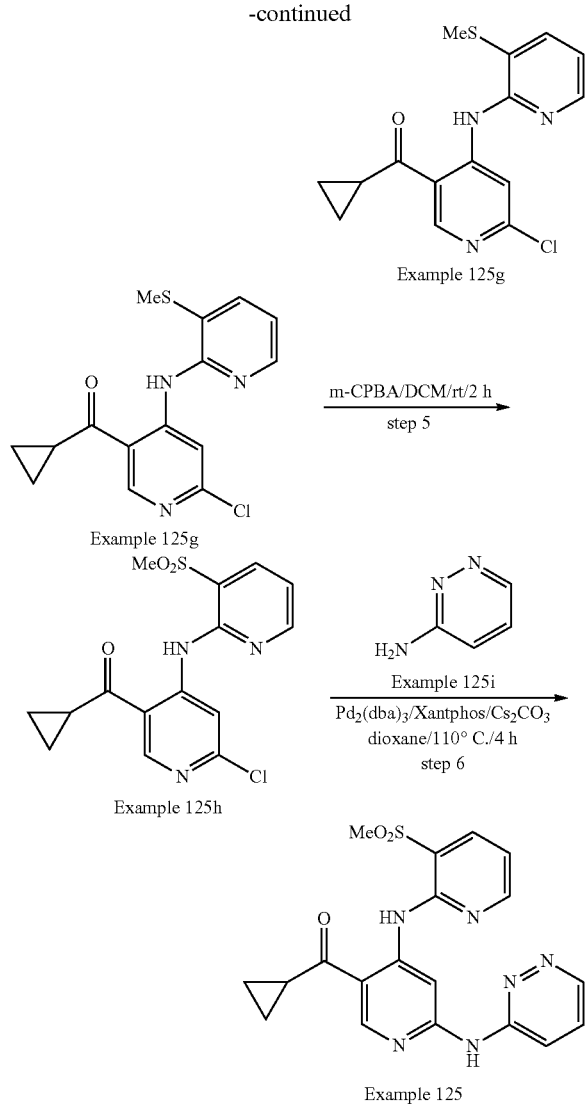

Step 1: Example 125b

To a solution of Example 125a (5.0 g, 35.2 mmol, 1.0 eq) in DMF (50 mL) was added NaSMe (18.5 g, 20% in water, 53 mmol, 1.5 eq) dropwise at 0° C. The reaction mixture was stirred for 1 h at r.t. The reaction was diluted with EtOAc (100 mL) and washed with brine. The organic layer was dried over $Na_2SO_4$ and concentrated. The residue was purified by silica gel flash column chromatography, eluted with Petroleum Ether/EtOAc (2/1) to afford the product Example 125b (4.9 g, 82% yield) as a yellow solid. LCMS [M+1]$^+$=171.2.

Step 2: Example 125c

To a solution of Example 125b (4.8 g, 28 mmol, 1.0 eq) in MeOH (100 mL) were added Fe powder (7.9 g, 141 mmol, 5.0 eq), $NH_4Cl$ (7.5 g, 141 mmol, 5.0 eq) and AcOH (3 mL). The reaction mixture was stirred for 1 h at 80° C. The reaction mixture was basified with $K_2CO_3$ (pH=7-8). The solid was filtered out, and the filtrate was concentrated. The crude product was purified by silica gel flash column chromatography, eluted with Petroleum Ether/EtOAc (2/1) to afford the product Example 125c (3.6 g, 92% yield) as red oil.

LCMS [M+1]$^+$=141.2.

Step 3: Example 125f

To a solution of Example 125d (5.0 g, 21 mmol, 1.0 eq) in dry THF (50 mL) was added Example 125e (105 mL, 1.0 M in THF, 105 mmol, 5.0 eq) dropwise at ~15° C. under $N_2$ protection. The mixture was stirred for 0.5 h at r.t. The mixture was poured into saturated aqueous of $NH_4Cl$ (100 mL) and extracted with EtOAc (150 mL*2). The combined organic layers were washed with brine, dried over $Na_2SO_4$ and concentrated. The residue was purified by silica gel flash column chromatography, eluted with Petroleum Ether/EtOAc (10/1) to afford the product Example 125f (2.8 g, 62% yield) as yellow oil. LCMS [M+1]$^+$=216.2

Step 4: Example 125g

To a solution of Example 125c (500 mg, 3.57 mmol, 1.0 eq) in DMF (10 mL), was added NaH (1.43 g, 60% in mineral oil, 35.7 mmol, 10.0 eq) in portions at 0° C. After addition, the reaction was stirred for 30 min at 0° C., followed by addition of Example 125f (768 mg, 3.57 mmol, 1.0 eq) in DMF. The reaction mixture was stirred for 1 h at r.t. The reaction solution was poured into water, extracted with EtOAc (50 mL*2), and the combined organic layer dried over $Na_2SO_4$ and concentrated. The crude product was purified by silica gel flash column chromatography, eluted with Petroleum Ether/EtOAc (3/1) to afford the product Example 125g (370 mg, 32% yield) as a yellow solid. LCMS [M+1]$^+$=320.1

Step 5: Example 125h

To a solution of Example 125g (200 mg, 0.627 mmol, 1.0 eq) in DCM (4 mL) was added m-CPBA (434 mg, 2.51 mmol, 4.0 eq) at 0° C. The reaction mixture was stirred for 1 h at r.t. The reaction was diluted with DCM (50 mL), washed with NaOH aqueous solution (1M), $Na_2SO_3$ aqueous solution and brine. The organic layer was dried over $Na_2SO_4$ and concentrated. The residue was purified by silica gel flash column chromatography, eluted with Petroleum Ether/EtOAc (1/1) to afford the product Example 125h (60 mg, 27% yield) as a yellow solid. LCMS [M+1]$^+$=352.2.

Step 6: Example 125

To a solution of Example 125h (50 mg, 0.142 mmol, 1.0 eq) in dioxane (2 mL) were added $Cs_2CO_3$ (93 mg, 0.285 mmol, 2.0 eq), Example 125i (27 mg, 0.285 mmol, 2.0 eq), Xantphos (17 mg, 0.028 mmol, 0.2 eq) and $Pd_2(dba)_3$·$CHCl_3$ (15 mg, 0.014 mmol, 0.1 eq). The reaction mixture was stirred for 4 h at 110° C. under $N_2$ protection. After cooled to room temperature, the solvent was removed, and the crude product was purified by Prep-TLC (DCM/MeOH=15/1) to afford the product Example 125 (17 mg, 29% yield) as a yellow solid. LCMS [M+1]$^+$=411.2. $^1$H NMR (300 MHz, DMSO-$d_6$) δ 11.83 (s, 1H), 10.54 (s, 1H), 9.18 (s, 1H), 8.86-8.78 (m, 2H), 8.62 (dd, J=4.8, 2.1 Hz, 1H), 8.28 (dd, J=7.8, 2.1 Hz, 1H), 8.17 (dd, J=9.3, 1.5 Hz, 1H), 7.61 (dd, J=9.3, 4.8 Hz, 1H), 7.33 (dd, J=7.8, 4.8 Hz, 1H), 3.31 (s, 3H), 3.03-2.90 (m, 1H), 1.16-0.99 (m, 4H).

Example 126

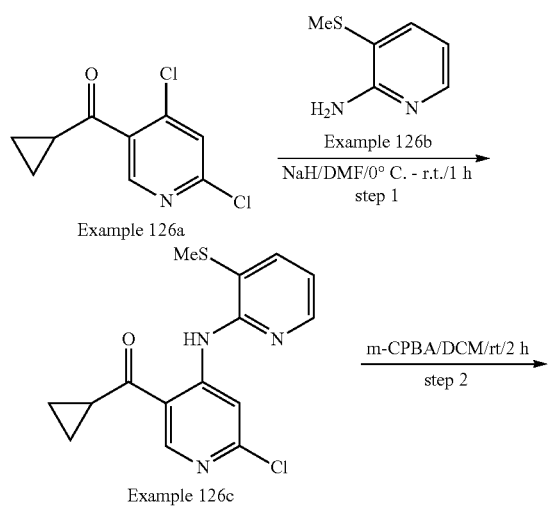

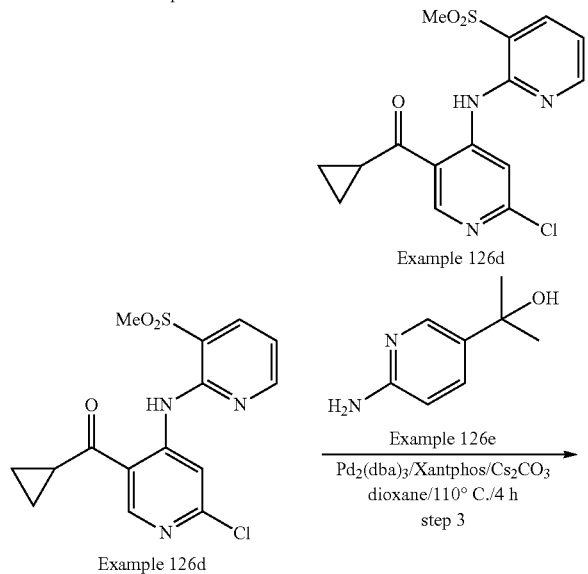

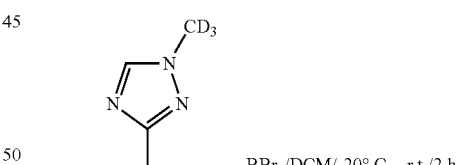

Step 1: Example 126c

To a solution of Example 126a (1.54 g, 7.1 mmol, 1.0 eq) in DMF (20 mL), was added NaH (2.86 g, 60% in mineral oil, 71 mmol, 10.0 eq) in portions at 0° C. Example 126b (1.0 g, 7.1 mmol, 1.0 eq) in DMF was added to the solution. The reaction mixture was stirred for 1 h at r.t. The reaction was poured into water (100 mL), extracted with EtOAc (100 mL*3), and the combined organic layers were dried over Na$_2$SO$_4$ and concentrated. The crude product was purified by silica gel flash column chromatography, eluted with Petroleum Ether/EtOAc (3/1) to afford the product Example 126c (570 mg, 25% yield) as a yellow solid. LCMS [M+1]$^+$=320.1

Step 2: Example 126d

To a solution of Example 126c (740 mg, 2.32 mmol, 1.0 eq) in DCM (8 mL) was added m-CPBA (1.61 g, 9.28 mmol, 4.0 eq) at 0° C. The reaction mixture was stirred for 2 h at r.t. The reaction was diluted with DCM (20 mL), washed with NaOH aqueous solution (1M), Na$_2$SO$_3$ aqueous solution and brine. The organic layer was dried over Na$_2$SO$_4$, and concentrated. The residue was purified by silica gel flash column chromatography, eluted with Petroleum Ether/EtOAc (1/1) to afford the product Example 126d (470 mg, 57% yield) as a yellow solid. LCMS [M+1]$^+$=352.2.

Step 3: Example 126

To a solution of Example 126d (100 mg, 0.285 mmol, 1.0 eq) in dioxane (2 mL) were added Cs$_2$CO$_3$ (186 mg, 0.57 mmol, 2.0 eq), Example 126e (87 mg, 0.57 mmol, 2.0 eq), BINAP (36 mg, 0.057 mmol, 0.2 eq) and Pd$_2$(dba)$_3$·CHCl$_3$ (30 mg, 0.028 mmol, 0.1 eq). The reaction mixture was stirred for 4 h at 110° C. under N$_2$ protection. After cooled to room temperature, the solvent was removed, and the crude product was purified by Prep-TLC (DCM/MeOH=15/1) to afford the product Example 126 (12 mg, 9% yield) as an off-white solid. LCMS [M+1]$^+$=468.1. $^1$H NMR (300 MHz, DMSO-d$_6$) δ11.84 (s, 1H), 10.04 (s, 1H), 9.14 (s, 1H), 8.95 (s, 1H), 8.69-8.63 (m, 1H), 8.35 (dd, J=2.7, 0.9 Hz, 1H), 8.26 (dd, J=7.8, 2.4 Hz, 1H), 7.78 (dd, J=8.7, 2.4 Hz, 1H), 7.68 (d, J=8.7 Hz, 1H), 7.32 (dd, J=7.8, 4.8 Hz, 1H), 5.09 (s, 1H), 3.31 (s, 3H), 3.01-2.88 (m, 1H), 1.45 (s, 6H), 1.12-0.97 (m, 4H).

Example 127

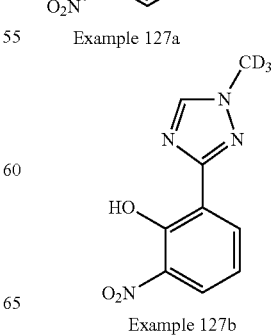

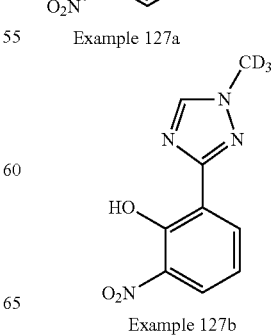

-continued

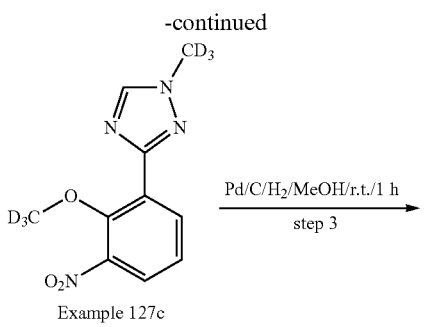

Example 127c

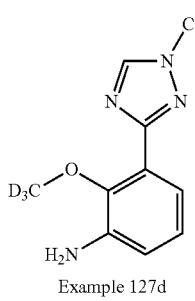

Example 127d

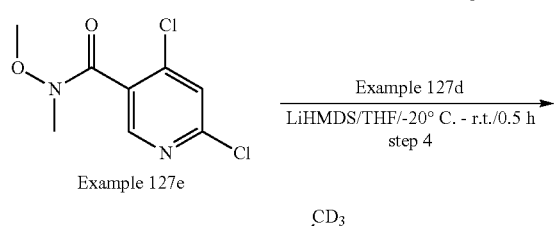

Example 127e

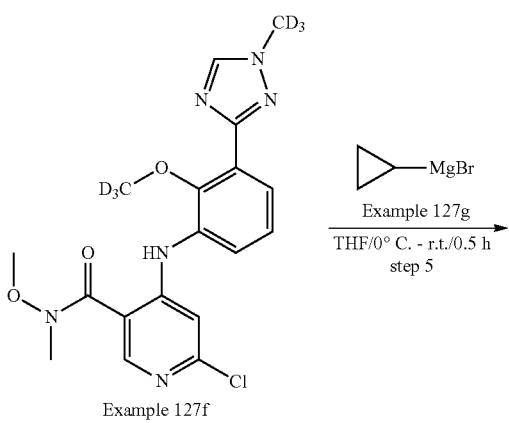

Example 127f

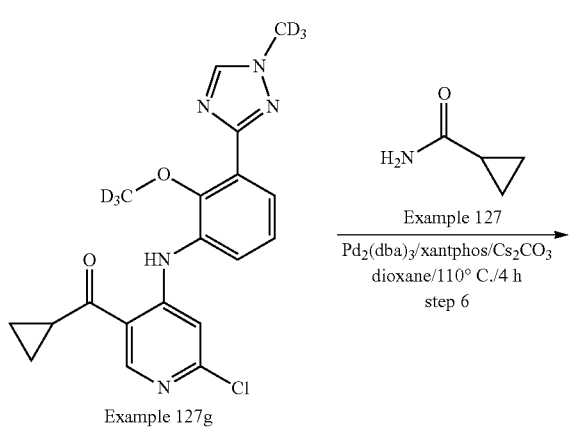

Example 127g

-continued

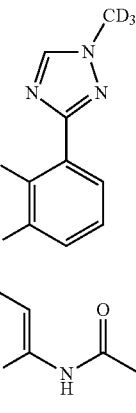

Example 127

Step 1: Example 127b

To a solution of Example 127a (550 mg, 2.32 mmol, 1.0 eq) in DCM (10 mL) was added BBr$_3$ (1.15 g, 4.64 mmol, 2.0 eq) at ~20° C. The reaction mixture was stirred for 2 h at r.t. It was quenched with NaHCO$_3$ aqueous solution (10 mL), extracted with DCM (20 mL*3). The combined organic layer was washed with brine, dried over Na$_2$SO$_4$ and concentrated to afford the product Example 127b (500 mg, crude, 96% yield) as a brown solid. LCMS [M+1]$^+$=224.3.

Step 2: Example 127c

To a mixture of Example 127b (500 mg, 2.24 mmol, 1.0 eq) and K$_2$CO$_3$ (927 mg, 6.72 mmol, 3.0 eq) in ACN (10 mL) was added CD$_3$I (487.2 mg, 3.36 mmol, 1.5 eq). The reaction mixture was stirred for 6 h at 80° C. After cooled to room temperature, the solvent was removed. The crude product was purified by silica gel flash column chromatography eluted with PE/EtOAc (1/3) to afford the product Example 127c (200 mg, 37% yield) as a yellow solid. LCMS [M+1]$^+$=241.2.

Step 3: Example 127d

To a solution of Example 127c (200 mg, 0.84 mmol, 1.0 eq) in MeOH (20 mL) was added Pd/C (20 mg) under N$_2$ protection, the suspension was degassed under vacuum and purged with H$_2$ three times, the reaction mixture was stirred at r.t. for 1 h under H$_2$ balloon. The solid was filtered out, the filtrate was concentrated to afford the product Example 127d (160 mg, 90% yield) as a yellow solid. LCMS [M+1]$^+$=211.2.

Step 4: Example 127f

To a solution of Example 127e (170 mg, 0.72 mmol, 1.0 eq) and Example 127d (151.2 mg, 0.72 mmol, 1.0 eq) in dry THF (6 mL) was added LiHMDS (1.4 mL, 1 M in THF, 1.44 mmol, 2.0 eq) dropwise at ~20° C. under N$_2$ protection. The reaction mixture was stirred for 0.5 h at r.t., and then the silica was added to the mixture and concentrated. The residue was purified by silica gel flash column chromatography eluted with DCM/MeOH (20/1) to afford the product Example 127f (45 mg, 15% yield) as a yellow solid. LCMS [M+1]$^+$=409.4.

Step 5: Example 127h

To a solution of Example 127f (45 mg, 0.11 mmol, 1.0 eq) in THF (3 mL) was added Example 127g (0.9 mL, 1.0 M in THF, 0.88 mmol, 8.0 eq) dropwise at 0° C. under $N_2$ protection. The mixture was stirred for 0.5 h at r.t. The reaction was poured into saturated aqueous of $NH_4Cl$ (10 mL) and extracted with EtOAc (15 mL×3). The combined organic layer was washed with brine, dried over $Na_2SO_4$, and concentrated. The crude product was purified by Prep-TLC (DCM/MeOH=15/1) to afford the product Example 127f (40 mg, 93% yield) as a yellow solid. LCMS $[M+1]^+=390.3$.

Step 6: Example 127

To a solution of Example 127f (40 mg, 0.10 mmol, 1.0 eq) in dioxane (3 mL) were added $Cs_2CO_3$ (65.2 mg, 0.20 mmol, 2.0 eq), Example 127I (26.2 mg, 0.30 mmol, 3.0 eq), Xantphos (11.6 mg, 0.02 mmol, 0.2 eq) and $Pd_2(dba)_3 \cdot CHCl_3$ (10.4 mg, 0.01 mmol, 0.1 eq). The reaction mixture was stirred for 4 h at 110° C. under $N_2$ protection. After cooled to room temperature, the solvent was removed, the crude product was purified by Prep-TLC (DCM/MeOH=15/1) to afford the product Example 127 (3.1 mg, 7% yield) as a yellow solid. LCMS $[M+1]^+=439.3$. $^1$H NMR (300 MHz, DMSO-$d_6$) δ 11.01 (s, 1H), 10.93 (s, 1H), 9.13 (s, 1H), 8.56 (s, 1H), 8.04 (s, 1H), 7.64 (dd, J=7.8, 1.5 Hz, 1H), 7.52 (dd, J=8.1, 1.8 Hz, 1H), 7.26 (t, J=7.8 Hz, 1H), 3.08-2.90 (m, 1H), 2.11-1.93 (m, 1H), 1.18-0.98 (m, 4H), 0.81 (d, J=6.0 Hz, 4H).

Example 128

To a solution of Example 128 (100 mg, 0.26 mmol, 1.0 eq) in dioxane (5 mL) were added Example 128b (95 mg, 0.78 mmol, 3.0 eq), $Cs_2CO_3$ (170 mg, 0.52 mmol, 2.0 eq), Xantphos (15 mg, 0.026 mmol, 0.1 eq) and $Pd_2(dba)_3 \cdot CHCl_3$ (27 mg, 0.026 mmol, 0.1 eq). The reaction mixture was stirred for 4 h at 110° C. under $N_2$. The reaction solution was filtered and the filtrate was concentrated. The crude product was purified by Prep-TLC (DCM/MeOH=15/1) to give 32.0 mg crude product (90% purity) and further purified by Prep-TLC (DCM/MeOH=15/1) to afford the desired product Example 128 (12.1 mg, 9.9% yield) as a yellow solid. LCMS $[M+1]^+=469.3$. $^1$H NMR (300 MHz, DMSO-$d_6$) δ 10.89 (s, 1H), 9.04 (s, 1H), 8.91 (brs, 1H), 8.56 (s, 1H), 7.67 (dd, J=7.8, 1.5 Hz, 1H), 7.53 (d, J=6.6 Hz, 1H), 7.29 (t, J=7.8 Hz, 1H), 6.64 (s, 1H), 3.95 (s, 3H), 3.69 (s, 3H), 3.00-2.88 (m, 1H), 1.22 (s, 9H), 1.12-0.99 (m, 4H).

Example 129

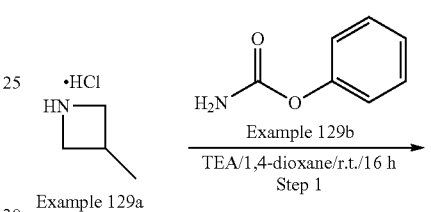

Example 129a

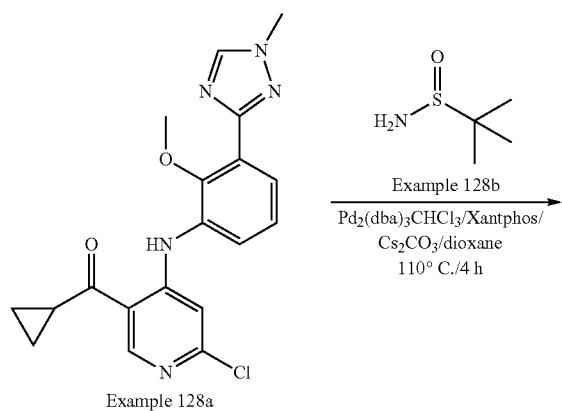

Example 128a

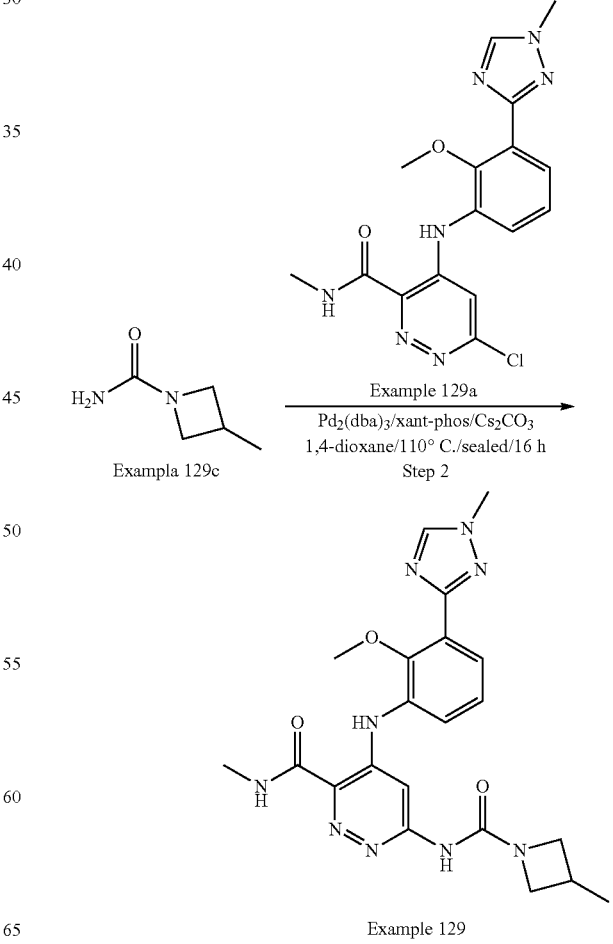

Example 128

Example 129

Step 1: Example 129c

A solution of Example 129b (300 mg, 2.19 mmol) in 1,4-dioxane (5 mL) was treated with Example 129a (353 mg, 3.28 mmol) and TEA (664 mg, 6.57 mmol). The mixture was stirred at r.t. for 16 hrs. After reaction completed, the solvent was concentrated, the residue was suspended in DCM (5 mL), sonicated and the resulting solid was collected via filtration, dried to afford the desired product Example 129c (253 mg, crude) as a white solid. LCMS [M+1]$^+$=115.0.

Step 2: Example 129

To a solution of Example 129a (80 mg, 0.21 mmol) and Example 129c (29.3 mg, 0.26 mmol) in 1,4-dioxane (2 mL) were added Pd$_2$(dba)$_3$ (19.6 mg, 0.021 mmol), XantPhos (24.7 mg, 0.042 mmol) and Cs$_2$CO$_3$ (140 mg, 0.43 mmol). The mixture was sealed, degassed by nitrogen for 3 times and stirred at 110° C. for 16 h. When completed, the reaction was cooled to r.t. and filtered. The filtrate was purified directly by Prep-HPLC to give the desired product Example 129 (21.8 mg, 22.7% yield) as a white solid. LCMS [M+1]$^+$=452.0. $^1$H NMR (400 MHz, DMSO-d$_6$) δ 10.89 (s, 1H), 9.59 (s, 1H), 9.02 (d, J=5.3 Hz, 1H), 8.54 (s, 1H), 8.00 (s, 1H), 7.62 (d, J=7.8 Hz, 1H), 7.49 (d, J=7.9 Hz, 1H), 7.24 (t, J=8.0 Hz, 1H), 4.09 (s, 2H), 3.93 (s, 3H), 3.71 (s, 3H), 3.54 (s, 2H), 2.84 (d, J=4.4 Hz, 3H), 2.59 (d, J=8.4 Hz, 1H), 1.15 (d, J=6.7 Hz, 3H).

Example 130

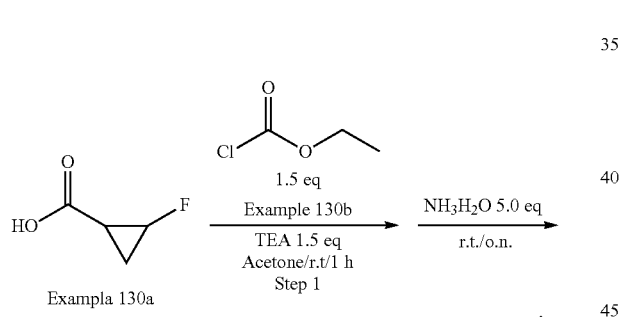

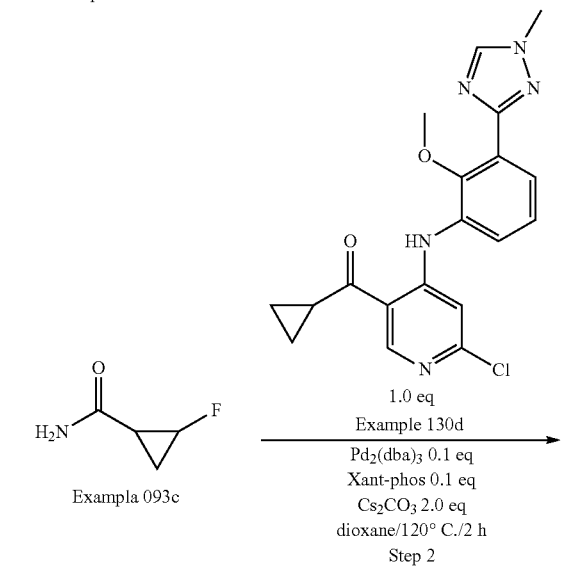

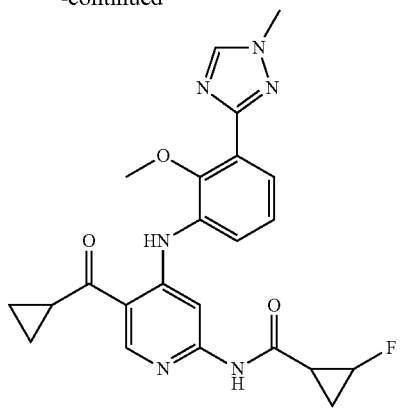

Example 130

Step 1: Example 130c

To a solution of Example 130a (200 mg, 1.92 mmol) in acetone (4 mL) was added TEA (291 mg, 2.88 mmol) at 0-5° C., and then Example 130b (311 mg, 2.88 mmol) was added dropwise. The mixture was stirred at room temperature for 1 h under N$_2$. The white solid was filtered off. To the filtration was added NH$_3$—H$_2$O (5 eq.). The reaction mixture was stirred at room temperature overnight. The mixture was concentrated. The residue was cooled and added Petroleum ether/EtOAc=1/1 (3 mL). The solid was collected by filtered and dried to give Example 130c (17 mg, 8% yield) as a white solid.

Step 2: Example 130

To a solution of Example 130d (63 mg, 0.16 mmol) in dioxane (1.5 mL) were added Example 130c (17 mg, 0.16 mmol), Pd$_2$(dba)$_3$ (15 mg, 0.016 mmol), Xantphos (10 mg, 0.016 mmol) and Cs$_2$CO$_3$ (108 mg, 0.33 mmol). The mixture was sealed and heated to 120° C. for 2 h. The mixture was filtrated and concentrated under reduced pressure. The residue was purified by Prep-HPLC to give Example 130 (8.7 mg, 12% yield) as a yellow solid. LCMS [M+1]$^+$=451.1. $^1$H NMR (400 MHz, Chloroform-d) δ 11.12 (s, 1H), 8.90 (s, 1H), 8.22-8.03 (m, 3H), 7.75 (d, J=7.8 Hz, 1H), 7.59 (d, J=7.9 Hz, 1H), 7.25-7.22 (m, 1H), 4.78 (d, J=65.0 Hz, 1H), 3.99 (s, 3H), 3.77 (s, 3H), 2.66-2.57 (m, 1H), 1.94-1.76 (m, 2H), 1.27-1.17 (m, 3H), 1.07-1.0 (m, 2H).

Example 131

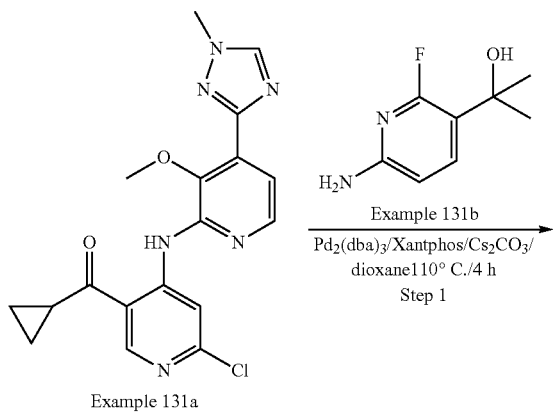

Example 131a

Example 132

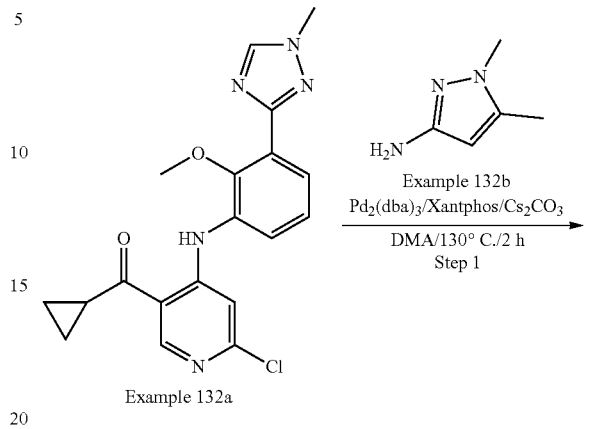

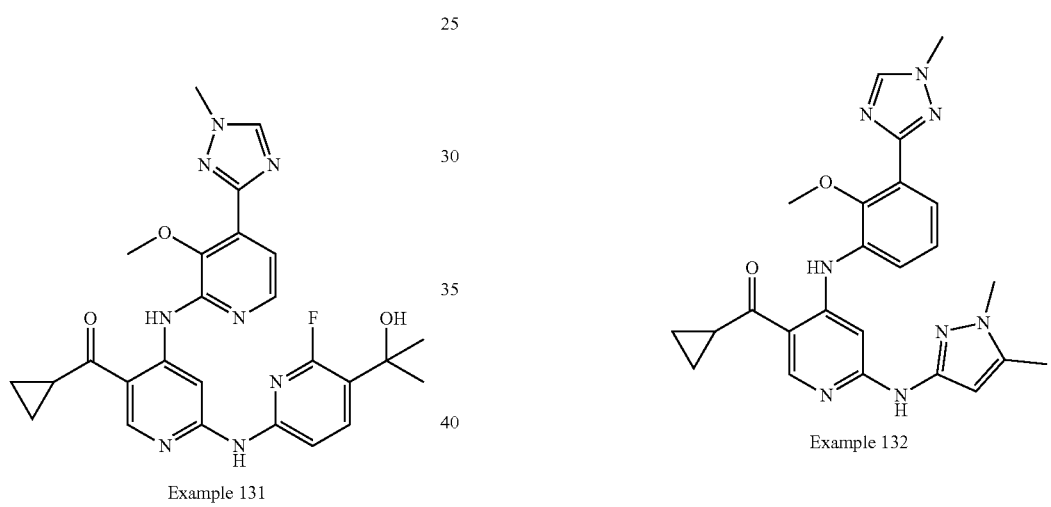

To a solution of Example 131a (40 mg, 0.104 mmol, 1.0 eq) and Example 131b (35.4 mg, 0.208 mmol, 2.0 eq) in dioxane (3 mL) were added Xantphos (12.0 mg, 0.02 mmol, 0.2 eq), Cs$_2$CO$_3$ (67.8 mg, 0.208 mmol, 2.0 eq) and Pd$_2$(dba)$_3$·CHCl$_3$ (10.4 mg, 0.01 mmol, 0.1 eq). The reaction mixture was stirred at 110° C. for 4 h under N$_2$ protection. After cooled to room temperature, the solvent was removed, and the crude product was purified by Prep-TLC (DCM/MeOH=15/1) to afford the product Example 131 (7.4 mg, 14% yield) as a yellow solid. LCMS [M+1]$^+$=519.4.

$^1$H NMR (300 MHz, DMSO-d$_6$) δ 12.33 (s, 1H), 10.27 (s, 1H), 9.54 (s, 1H), 9.18 (s, 1H), 8.66 (s, 1H), 8.17 (d, J=5.1 Hz, 1H), 8.05-7.95 (m, 1H), 7.58 (d, J=8.1 Hz, 1H), 7.50 (d, J=5.1 Hz, 1H), 5.30 (s, 1H), 4.00 (s, 3H), 3.88 (s, 3H), 3.08-2.93 (m, 1H), 1.50 (s, 6H), 1.16-0.98 (m, 4H).

To a solution of Example 132a (100 mg, 0.26 mmol) and Example 132b (43 mg, 0.39 mmol) in DMA (2.5 mL) were added Pd$_2$(dba)$_3$ (24 mg, 0.026 mmol), Xantphos (30 mg, 0.052 mmol) and Cs$_2$CO$_3$ (340 mg, 1.04 mmol). The mixture was degassed by nitrogen for 3 times and stirred at 130° C. for 2 h. When completed, the reaction was cooled to r.t., diluted with MeOH (5 mL) and filtered. The filtrate was purified directly by Prep-HPLC to give the desired product Example 132 (1.3 mg, 3.5% yield) as a white solid. LCMS [M+1]$^+$=459.0. $^1$H NMR (400 MHz, DMSO-d$_6$) δ 11.07 (s, 1H), 9.49 (s, 1H), 8.97 (s, 1H), 8.53 (s, 1H), 8.30 (s, OH), 7.65 (d, J=8.0 Hz, 1H), 7.56 (d, J=8.0 Hz, 1H), 7.27 (t, J=7.9 Hz, 1H), 5.90 (s, 1H), 3.92 (s, 3H), 3.68 (s, 3H), 3.57 (s, 3H), 2.88 (s, 1H), 2.17 (s, 3H), 1.03 (s, 2H), 0.95 (d, J=7.7 Hz, 2H).

Example 133

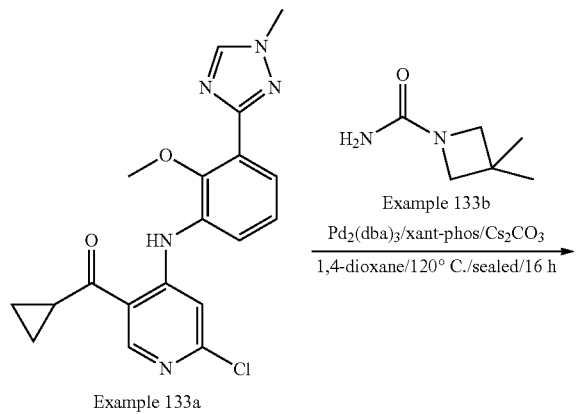

Example 134

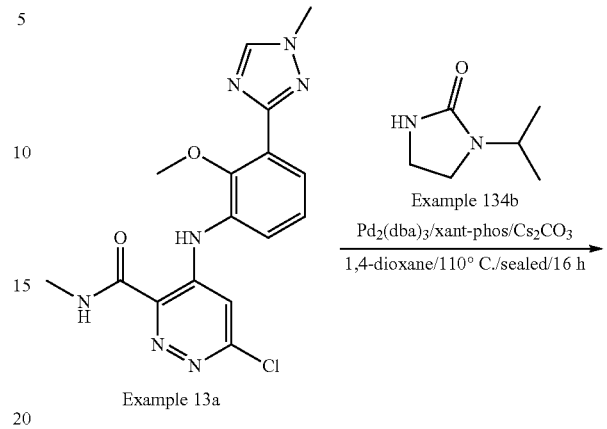

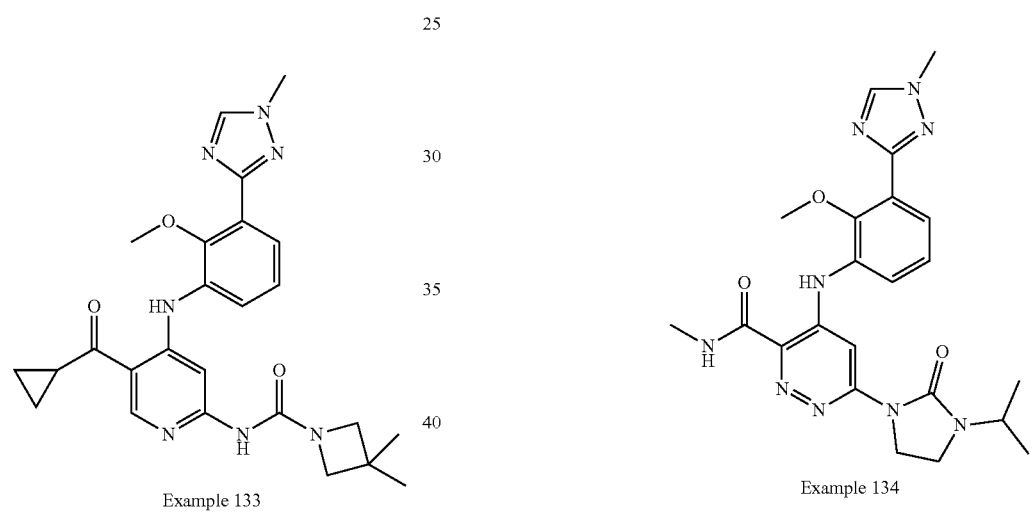

To a solution of Example 133a (180 mg, 0.47 mmol,) and Example 133b (180 mg, 1.41 mmol) in 1,4-dioxane (2 mL) were added $Pd_2(dba)_3$ (43 mg, 0.047 mmol), xantphos (54 mg, 0.094 mmol) and $Cs_2CO_3$ (306 mg, 0.94 mmol). The mixture was degassed by nitrogen for 3 times, sealed and stirred at 120° C. for 16 h. When completed, the reaction was cooled to r.t., diluted with MeOH (5 mL) and filtered. The filtrate was purified directly by Prep-HPLC to give the desired product Example 133 (67.3 mg, 30.3% yield) as a white solid. LCMS $[M+1]^+=476.0$. $^1$H NMR (400 MHz, DMSO-$d_6$) δ 10.98 (s, 1H), 9.19 (s, 1H), 9.02 (s, 1H), 8.54 (s, 1H), 7.90 (s, 1H), 7.60 (d, J=7.8 Hz, 1H), 7.51 (d, J=8.0 Hz, 1H), 7.23 (t, J=8.0 Hz, 1H), 3.93 (s, 3H), 3.67 (s, 3H), 3.64 (s, 4H), 2.94 (s, 1H), 1.18 (s, 6H), 1.06 (d, J=4.5 Hz, 2H), 1.00 (d, J=7.8 Hz, 2H).

To a solution of Example 134a (130 mg, 0.35 mmol) and Example 134b (67 mg, 0.52 mmol) in 1,4-dioxane (4 mL) were added $Pd_2(dba)_3$ (32 mg, 0.035 mmol), XantPhos (40 mg, 0.070 mmol) and $Cs_2CO_3$ (227 mg, 0.70 mmol). The mixture was sealed, degassed by nitrogen for 3 times and stirred at 110° C. for 16 h. When completed, the reaction was cooled to r.t. and filtered. The filtrate was purified directly by Prep-HPLC to give the desired product Example 134 (34 mg, 21.0% yield) as a yellow solid. LCMS $[M+1]^+=466.0$. $^1$H NMR (400 MHz, DMSO-$d_6$) δ 10.86 (s, 1H), 9.17 (d, J=5.3 Hz, 1H), 8.55 (s, 1H), 8.27 (s, 1H), 7.62 (d, J=7.8 Hz, 1H), 7.51 (d, J=7.9 Hz, 1H), 7.25 (t, J=7.9 Hz, 1H), 4.06 (t, J=8.2 Hz, 2H), 4.02 (s, 1H), 3.93 (s, 3H), 3.71 (s, 3H), 3.44 (t, J=8.1 Hz, 2H), 2.83 (d, J=4.6 Hz, 3H), 1.09 (d, J=6.7 Hz, 6H).

Example 135

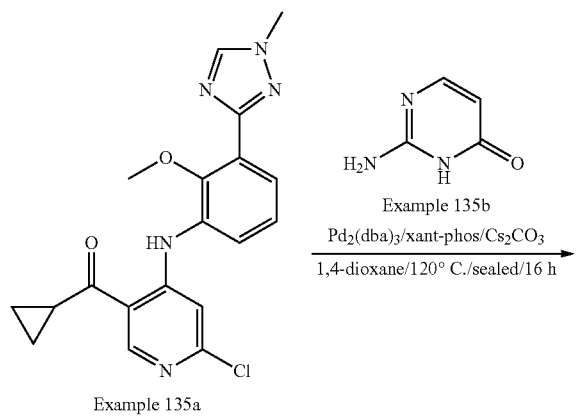

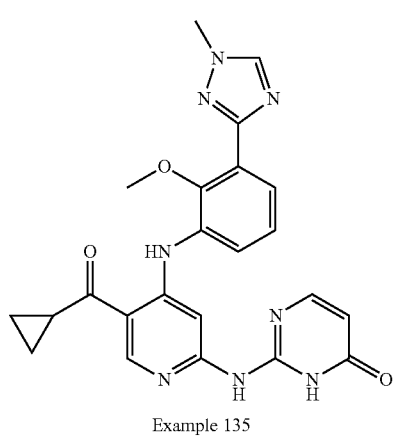

To a solution of Example 135a (100 mg, 0.26 mmol,) and Example 135b (43 mg, 0.39 mmol) in 1,4-dioxane (2 mL) were added Pd$_2$(dba)$_3$ (24 mg, 0.026 mmol), xantphos (30 mg, 0.052 mmol) and Cs$_2$CO$_3$ (170 mg, 0.52 mmol). The mixture was degassed by nitrogen for 3 times and stirred at 120° C. for 16 h. When completed, the reaction was cooled to r.t, diluted with MeOH (5 mL) and filtered. The filtrate was purified directly by Prep-HPLC to give the desired product Example 135 (41.8 mg, 35.1% yield) as a white solid (contain 0.43 FA salt by $^1$H NMR). LCMS [M+1]$^+$=459.0. $^1$H NMR (400 MHz, DMSO-d$_6$) δ 13.32 (s, 1H), 10.96 (s, 1H), 9.20 (s, 1H), 8.54 (s, 1H), 7.72 (d, J=6.6 Hz, 1H), 7.66 (d, J=7.8 Hz, 1H), 7.53 (d, J=7.9 Hz, 1H), 7.27 (t, J=8.0 Hz, 1H), 6.99 (s, 1H), 5.84 (d, J=6.6 Hz, 1H), 3.93 (s, 3H), 3.68 (s, 3H), 2.98 (d, J=7.1 Hz, 1H), 1.09 (d, J=4.3 Hz, 2H), 1.03 (dd, J=9.6, 5.4 Hz, 2H).

Example 136

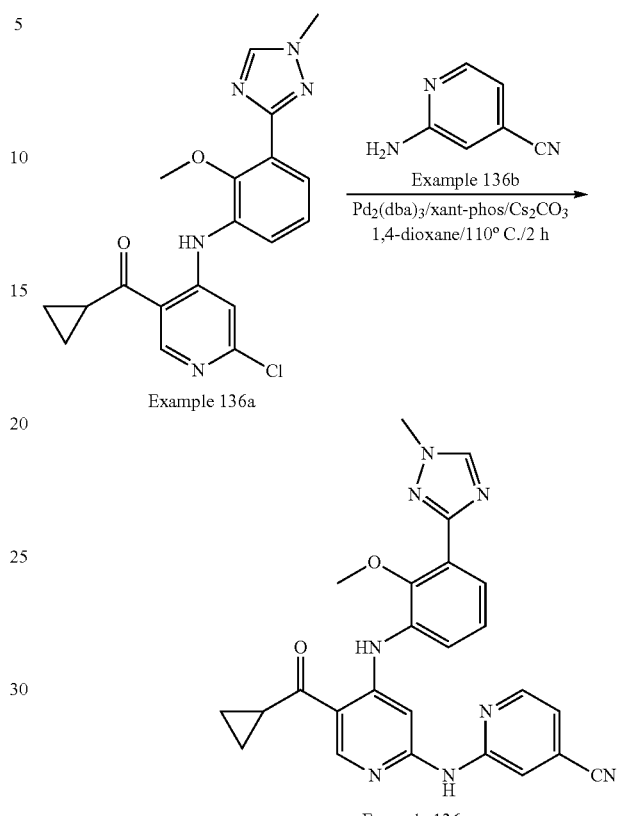

To a solution of Example 136a (100 mg, 0.26 mmol,) and Example 136b (37 mg, 0.31 mmol) in 1,4-dioxane (1 mL) were added Pd$_2$(dba)$_3$ (24 mg, 0.026 mmol), XantPhos (30 mg, 0.052 mmol) and Cs$_2$CO$_3$ (170 mg, 0.52 mmol). The mixture was degassed by nitrogen for 3 times and stirred at 110° C. for 2 h. When completed, the reaction was cooled to r.t., diluted with MeOH (5 mL) and filtered. The filtrate was purified directly by Prep-HPLC to give the desired product Example 136 (4.5 mg, 3.7% yield) as a white solid. LCMS [M+1]$^+$=467.2. $^1$H NMR (400 MHz, DMSO-d$_6$) δ 11.00 (s, 1H), 10.34 (s, 1H), 9.16 (s, 1H), 8.54 (s, 1H), 8.40 (d, J=8.0 Hz, 1H), 8.21 (s, 1H), 7.63-7.60 (m, 3H), 7.31-7.27 (m, 2H), 3.93 (s, 3H), 3.69 (s, 3H), 2.97 (br, 1H), 1.07-1.00 (m, 4H).

Example 137

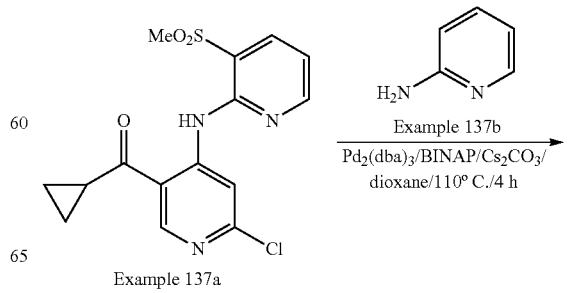

-continued

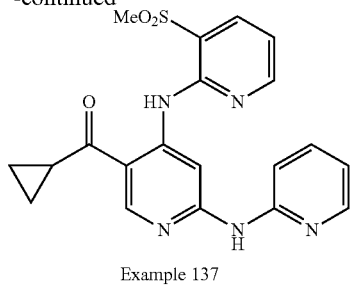

Example 137

To a solution of Example 137a (60 mg, 0.171 mmol, 1.0 eq) in dioxane (2 mL) were added Cs$_2$CO$_3$ (111 mg, 0.342 mmol, 2.0 eq), Example 137b (32 mg, 0.342 mmol, 2.0 eq), BINAP (21.3 mg, 0.034 mmol, 0.2 eq) and Pd$_2$(dba)$_3$·CHCl$_3$ (17.7 mg, 0.017 mmol, 0.1 eq). The reaction mixture was stirred for 4 h at 110° C. under N$_2$ protection. After cooled to room temperature, the solvent was removed, and the crude product was purified by Prep-TLC (DCM/MeOH=30/1) to afford the product Example 137 (8 mg, 11% yield) as an off-white solid. LCMS [M+1]$^+$=410.2. H NMR (300 MHz, DMSO-d$_6$) δ 11.85 (s, 1H), 10.11 (s, 1H), 9.16 (s, 1H), 9.03 (s, 1H), 8.66 (dd, J=4.8, 1.8 Hz, 1H), 8.30-8.22 (m, 2H), 7.76-7.68 (m, 2H), 7.31 (dd, J=7.8, 4.8 Hz, 1H), 6.99-6.91 (m, 1H), 3.12, (m, 3H), 3.01-2.89 (m, 1H), 1.12-0.97 (m, 4H).

Example 138

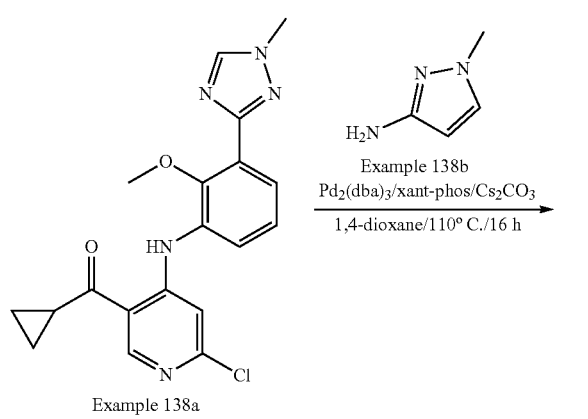

Example 138

To a solution of Example 138a (277 mg, 0.72 mmol) and Example 138b (84 mg, 0.87 mmol) in 1,4-dioxane (4 mL) were added Pd$_2$(dba)$_3$ (66 mg, 0.072 mmol), Xantphos (83 mg, 0.14 mmol) and Cs$_2$CO$_3$ (470 mg, 1.44 mmol). The mixture was degassed by nitrogen for 3 times and stirred at 110° C. for 16 h. When completed, the reaction was cooled to r.t., diluted with MeOH (5 mL) and filtered. The filtrate was purified directly by Prep-HPLC to give the desired product Example 138 (21 mg, 6.6% yield) as a yellow solid. LCMS [M+1]$^+$=445.0. $^1$H NMR (400 MHz, DMSO-d$_6$) δ 11.06 (s, 1H), 9.60 (s, 1H), 8.99 (s, 1H), 8.54 (s, 1H), 7.65 (d, J=8.0 Hz, 1H), 7.56 (d, J=8.1 Hz, 1H), 7.51 (s, 2H), 7.27 (t, J=7.9 Hz, 1H), 6.08 (s, 1H), 3.92 (s, 3H), 3.69 (d, J=4.7 Hz, 6H), 2.89 (s, 1H), 1.03 (s, 2H), 0.95 (s, 2H).

Example 139

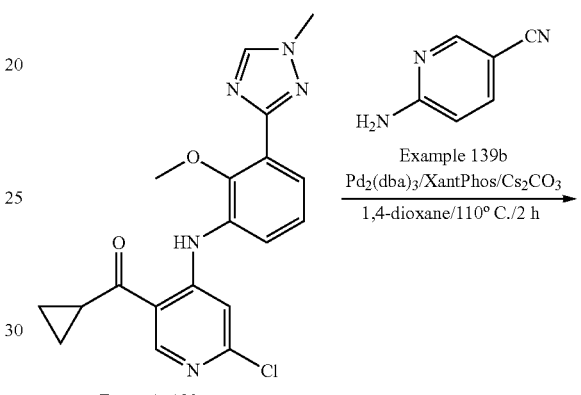

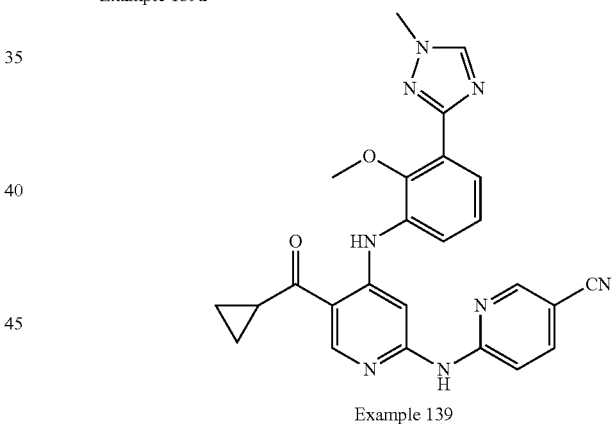

Example 139

To a solution of Example 139a (100 mg, 0.26 mmol) and Example 139b (37 mg, 0.31 mmol) in 1,4-dioxane (1 mL) were added Pd$_2$(dba)$_3$ (24 mg, 0.026 mmol), XantPhos (30 mg, 0.052 mmol) and Cs$_2$CO$_3$ (170 mg, 0.52 mmol). The mixture was degassed by nitrogen for 3 times and stirred at 110° C. for 2 h. When completed, the reaction was cooled to r.t., diluted with MeOH (5 mL) and filtered. The filtrate was purified directly by Prep-TLC (MeOH/DCM=1/15) to give the desired product Example 139 (14.6 mg, 12.1% yield) as a white solid. LCMS [M+1]$^+$=467.2. $^1$H NMR (400 MHz, DMSO-d) δ 11.04 (s, 1H), 10.53 (s, 1H), 9.13 (s, 1H), 8.61 (s, 1H), 8.54 (s, 1H), 8.07 (d, J=12.0 Hz, 1H), 7.83-7.79 (m, 2H), 7.62 (t, J=8.0 Hz, 2H), 7.33 (t, J=8.0 Hz, 1H), 3.93 (s, 3H), 3.69 (s, 3H), 2.97 (br, 1H), 1.21-1.01 (m, 4H).

Example 140

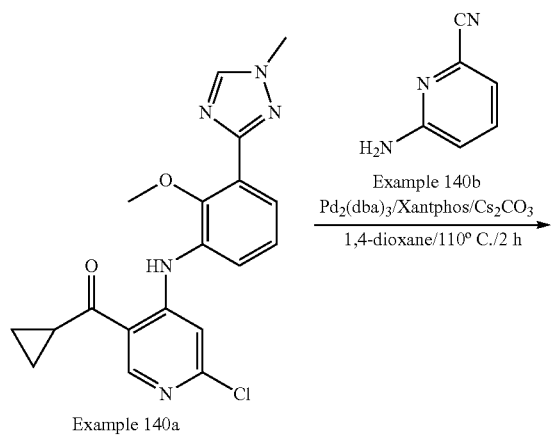

Example 141

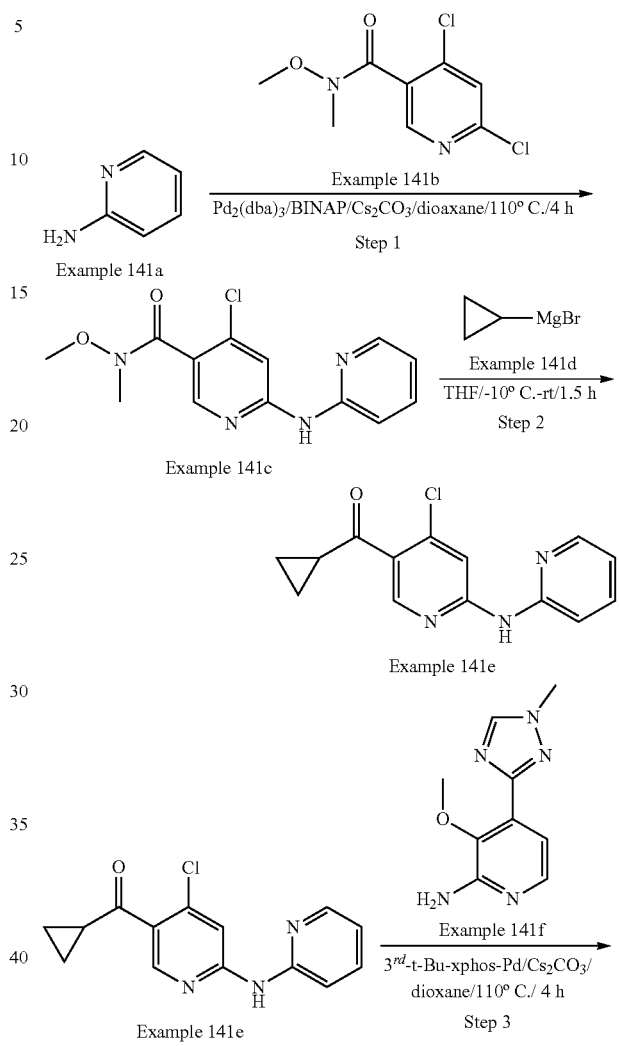

To a solution of Example 140a (100 mg, 0.26 mmol,) and Example 140b (37 mg, 0.31 mmol) in 1,4-dioxane (1 mL) were added Pd$_2$(dba)$_3$ (24 mg, 0.026 mmol), Xantphos (30 mg, 0.052 mmol) and Cs$_2$CO$_3$ (170 mg, 0.52 mmol). The mixture was degassed by nitrogen for 3 times and stirred at 110° C. for 2 h. When completed, the reaction was cooled to r.t., diluted with MeOH (5 mL) and filtered. The filtrate was purified directly by Prep-TLC (DCM/MeOH=15/1) to give the desired product Example 140 (12.2 mg, 10.1% yield) as a white solid. LCMS [M+1]$^+$=467.2. $^1$H NMR (400 MHz, DMSO-d) δ 11.24 (s, 1H), 10.42 (s, 1H), 9.12 (s, 1H), 8.54 (s, 1H), 7.98 (s, 1H), 7.87 (t, J=8.0 Hz, 1H), 7.78 (d, J=8.0 Hz, 1H), 7.72 (d, J=8.0 Hz, 1H), 7.58 (d, J=8.0 Hz, 1H), 7.52 (d, J=8.0 Hz, 1H), 7.35 (t, J=8.0 Hz, 1H), 3.93 (s, 3H), 3.70 (s, 3H), 2.96 (br, 1H), 1.21-1.00 (m, 4H).

Step 1: Example 141c

To a solution of Example 141a (182 mg, 1.94 mmol, 1.0 eq) in dioxane (10 mL) were added Cs$_2$CO$_3$ (1.25 g, 3.87 mmol, 2.0 eq), Example 141b (500 mg, 2.32 mmol, 1.2 eq), BINAP (240 mg, 0.387 mmol, 0.2 eq) and Pd$_2$(dba)$_3$·CHCl$_3$ (199 mg, 0.194 mmol, 0.1 eq). The reaction mixture was stirred for 4 h at 110° C. under $N_2$ protection. The solvent was concentrated, and the crude product was purified by silica gel flash column chromatography, eluted with (DCM/MeOH=30/1) to afford the product Example 141c (490 mg, 72% yield) as a yellow solid. LCMS $[M+1]^+=293.1$.

Step 2: Example 141e

To a solution of Example 141c (490 mg, 1.678 mmol, 1.0 eq) in THF (10 mL) was added Example 141d (25.17 mL, 1.0 M in THF, 25.17 mmol, 15.0 eq) dropwise at 0° C. under $N_2$ protection. The mixture was stirred for 1.5 h at r.t. After the reaction was completed, the mixture was poured into saturated aqueous of $NH_4Cl$ (20 mL) and extracted with EtOAc (50 mL*2). The combined organic layers were washed with brine, dried over $Na_2SO_4$ and concentrated. The residue was purified by silica gel flash column chromatography, eluted with DCM/MeOH=(30/1) to afford the product Example 141e (170 mg, 37% yield) as a yellow solid. LCMS $[M+1]^+=274.1$.

Step 3: Example 141

To a solution of Example 141e (60 mg, 0.22 mmol, 1.0 eq) in dioxane (2 mL) were added $Cs_2CO_3$ (143 mg, 0.44 mmol, 2.0 eq), Example 141f (90 mg, 0.44 mmol, 2.0 eq), 3rd-t-Bu-xphos-Pd (39 mg, 0.044 mmol, 0.2 eq). The reaction mixture was stirred for 4 h at 110° C. under $N_2$ protection. After cooled to room temperature, the solvent was removed, the crude product was purified by Prep-TLC (DCM/MeOH=20/1) to afford the product Example 141 (29 mg, 29% yield) as a yellow solid. LCMS $[M+1]^+=443.3$. $^1H$ NMR (300 MHz, DMSO-$d_6$) δ 12.31 (s, 1H), 10.10 (s, 1H), 9.51 (s, 1H), 9.17 (s, 1H), 8.66 (s, 1H), 8.35-8.32 (m, 1H), 8.19 (d, J=5.1 Hz, 1H), 7.82-7.64 (m, 2H), 7.48 (d, J=5.1 Hz, 1H), 7.02-6.92 (m, 1H), 4.00 (s, 3H), 3.88 (s, 3H), 3.06-2.95 (m, 1H), 1.67-0.97 (m, 4H).

Example 142

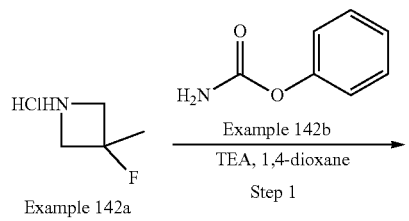

Step 1: Example 142c

A mixture of Example 142a (250 mg, 2.0 mmol), Example 142b (276 mg, 2.0 mmol) and TEA (610 mg, 6.0 mmol) in 1,4-dioxane (2 mL) was stirred at room temperature overnight. The reaction was filtered to give the desired product Example 142c (350 mg, 51.4% yield) as a white solid. LCMS $[M+1]^+=133.1$. $^1H$ NMR (400 MHz, DMSO-$d_6$) δ 5.97 (s, 2H), 3.88-3.75 (m, 4H), 3.69 (s, 3H), 1.51 (d, J=24.0 Hz, 3H).

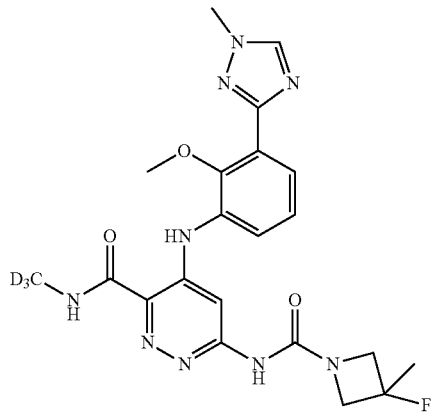

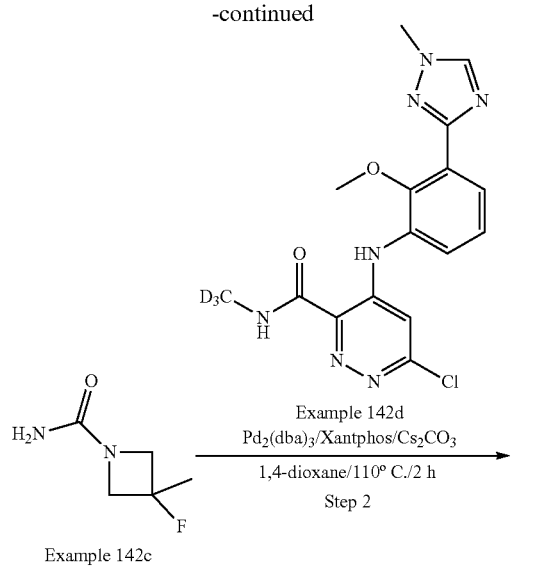

Step 2: Example 142

To a solution of Example 142c (40 mg, 0.31 mmol) and Example 142d (96 mg, 0.25 mmol) in 1,4-dioxane (1 mL) were added $Pd_2(dba)_3$ (23 mg, 0.025 mmol), Xantphos (29 mg, 0.051 mmol) and $Cs_2CO_3$ (166 mg, 0.51 mmol). The mixture was degassed by nitrogen for 3 times and stirred at 110° C. for 2 h. When completed, the reaction was cooled to r.t., diluted with MeOH (5 mL) and filtered. The filtrate was purified directly by Prep-HPLC to give the desired product Example 142 (46.7 mg, 38.9% yield) as a yellow solid. LCMS $[M+1]^+=473.2$. $^1H$ NMR (400 MHz, DMSO-$d_6$) δ 10.90 (s, 1H), 9.89 (s, 1H), 9.01 (s, 1H), 8.54 (s, 1H), 7.99 (s, 1H), 7.62 (d, J=8.0 Hz, 1H), 7.49 (d, J=8.0 Hz, 1H), 7.25

(t, J=8.0 Hz, 1H), 4.13-4.01 (m, 4H), 3.93 (s, 3H), 3.71 (s, 3H), 1.54 (d, J=24.0 Hz, 3H).

Example 143

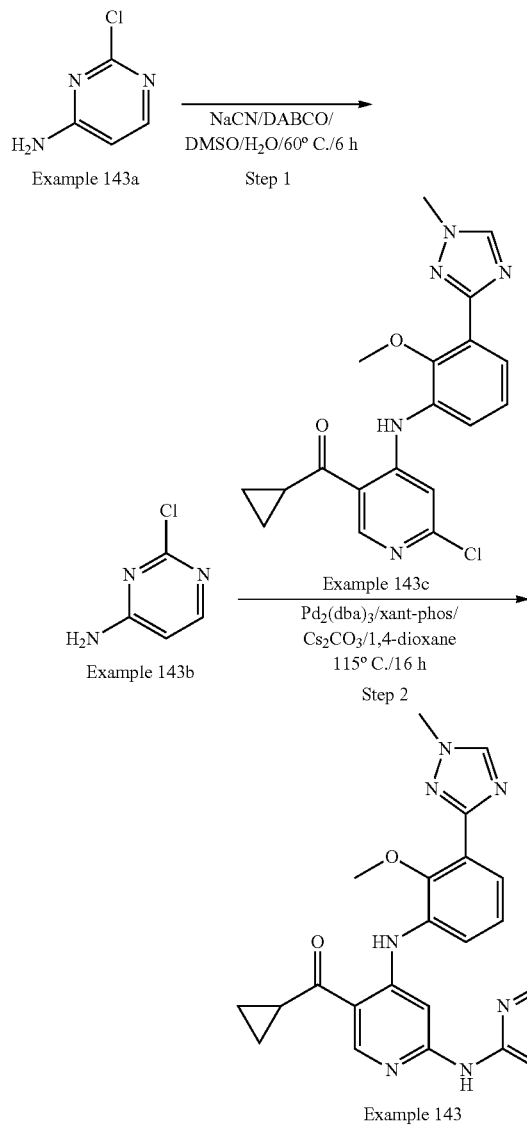

Step 1: Example 143b

A solution of Example 143a (2.0 g, 15.5 mmol) in DMSO/H₂O (20 mL/20 mL) were treated with NaCN (1.52 g, 31.0 mmol) and DABCO (1.74 g, 15.5 mmol). The mixture was stirred at 60° C. for 6 h. After reaction completed, the solvent was extracted by DCM (50 mL) and concentrated to give crude product, which was purified directly by Prep-HPLC to give the desired product Example 143b (500 mg, 26.8% yield) as a white solid. LCMS [M+1]⁺=121.0

Step 2: Example 143

To a solution of Example 143b (60 mg, 0.5 mmol) and Example 143c (191 mg, 0.5 mmol,) in dioxane (5 mL) were added Pd₂(dba)₃ (50 mg, 0.05 mmol), Xantphos (30 mg, 0.05 mmol) and Cs₂CO₃ (224.5 mg, 0.75 mmol). The mixture was degassed by nitrogen for 3 times and stirred at 110° C. for overnight. When completed, the reaction was cooled to r.t., diluted with MeOH (5 mL) and filtered. The filtrate was purified directly by Prep-HPLC to give the desired product Example 143 (7.4 mg, 3.2% yield) as a off white solid. LCMS [M+1]⁺=468.2. ¹H NMR (400 MHz, DMSO-d₆) δ 11.14 (s, 1H), 10.90 (s, 1H), 9.16 (s, 1H), 8.60-8.51 (m, 2H), 7.85 (s, 1H), 7.76 (s, 1H), 7.67 (d, J=7.9 Hz, 1H), 7.62 (d, J=7.9 Hz, 1H), 7.34 (d, J=8.0 Hz, 1H), 3.93 (s, 3H), 3.69 (s, 3H), 2.98 (s, 1H), 1.21 (s, 1H), 1.09 (s, 2H), 1.04 (d, J=7.0 Hz, 2H).

Example 144

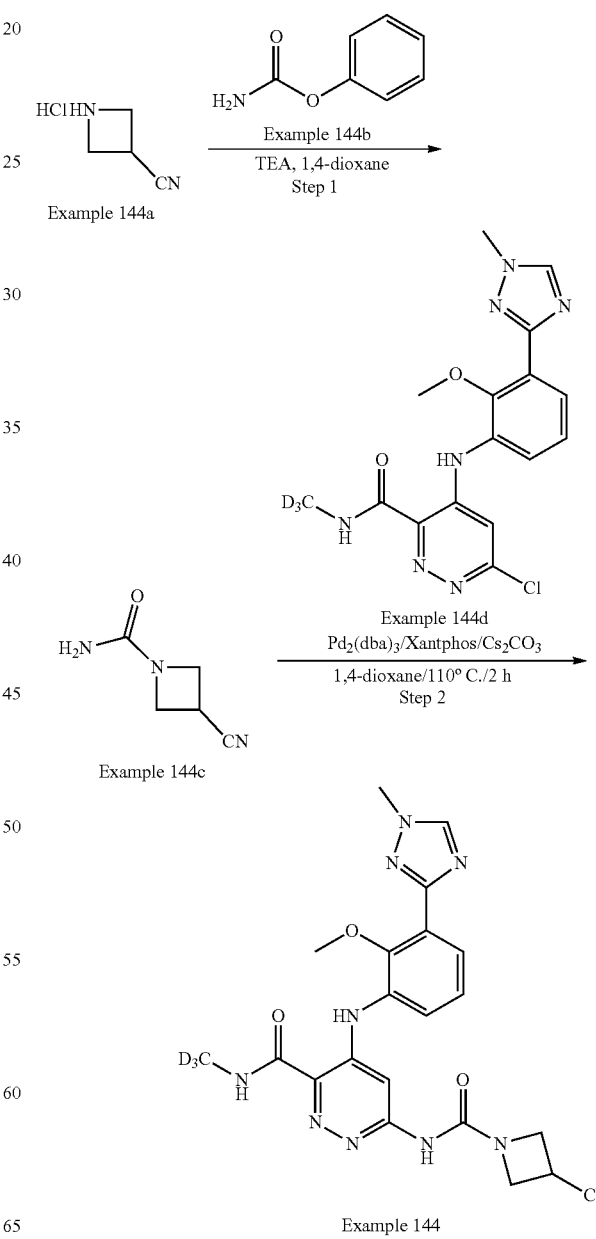

Step 1: Example 144c

A mixture of Example 144a (250 mg, 2.1 mmol), Example 144b (288 mg, 2.1 mmol) and TEA (637 mg, 6.3 mmol) in 1,4-dioxane (2 mL) was stirred at room temperature overnight. The reaction was filtered to give the desired product Example 144c (200 mg, 76.3% yield) as a white solid. $^1$H NMR (400 MHz, DMSO-$d_6$) δ 6.04 (s, 2H), 4.03 (t, J=8.0 Hz, 2H), 3.86 (t, J=8.0 Hz, 2H), 3.67-3.62 (m, 1H).

Step 2: Example 144

To a solution of Example 144c (66 mg, 0.53 mmol) and Example 144d (100 mg, 0.27 mmol) in 1,4-dioxane (2 mL) were added Pd$_2$(dba)$_3$ (24 mg, 0.027 mmol), Xantphos (31 mg, 0.053 mmol) and Cs$_2$CO$_3$ (173 mg, 0.53 mmol). The mixture was degassed by nitrogen for 3 times and stirred at 110° C. overnight. When completed, the reaction was cooled to r.t., diluted with CH$_3$CN (5 mL) and filtered. The filtrate was purified directly by Prep-HPLC to give the desired product Example 144 (61.3 mg, 49.7% yield) as a yellow solid. LCMS [M+1]$^+$=466.2. $^1$H NMR (400 MHz, DMSO-$d_6$) δ 10.91 (s, 1H), 9.96 (s, 1H), 9.02 (s, 1H), 8.54 (s, 1H), 7.96 (s, 1H), 7.62 (d, J=8.0 Hz, 1H), 7.48 (d, J=8.0 Hz, 1H), 7.25 (t, J=8.0 Hz, 1H), 4.27 (t, J=8.0 Hz, 2H), 4.13 (t, J=8.0 Hz, 1H), 3.93 (s, 3H), 3.75-3.67 (m, 4H).

Example 145

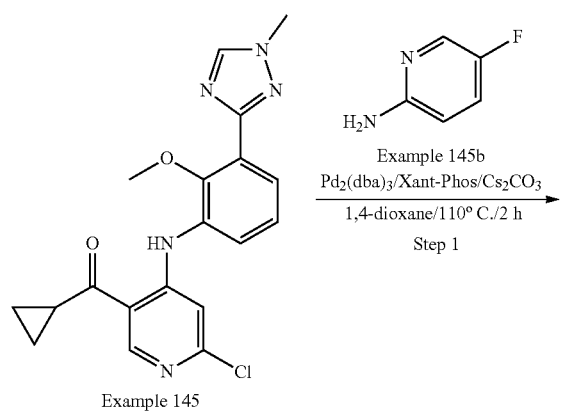

To a solution of Example 145a (100 mg, 0.26 mmol) and Example 145b (98 mg, 0.78 mmol) in 1,4-dioxane (2 mL) were added Pd$_2$(dba)$_3$ (24 mg, 0.026 mmol), Xantphos (30 mg, 0.052 mmol) and Cs$_2$CO$_3$ (170 mg, 0.52 mmol). The mixture was degassed by nitrogen for 3 times and stirred at 110° C. for 2 h. When completed, the reaction was cooled to r.t., diluted with MeOH (5 mL) and filtered. The filtrate was purified directly by Prep-HPLC to give the desired product Example 145 (32 mg, 26.0% yield) as a white solid. LCMS [M+1]$^+$=474.0. $^1$H NMR (400 MHz, DMSO-$d_6$) δ 11.03 (s, 1H), 9.92 (s, 1H), 9.08 (s, 1H), 8.54 (s, 1H), 8.05 (s, 1H), 7.71 (s, 1H), 7.63 (d, J=8.0 Hz, 1H), 7.58 (d, J=8.3 Hz, 2H), 7.29 (t, J=7.9 Hz, 1H), 3.93 (s, 3H), 3.69 (s, 3H), 2.94 (s, 1H), 2.23 (s, 3H), 1.05 (s, 2H), 0.99 (d, J=7.6 Hz, 2H).

Example 146

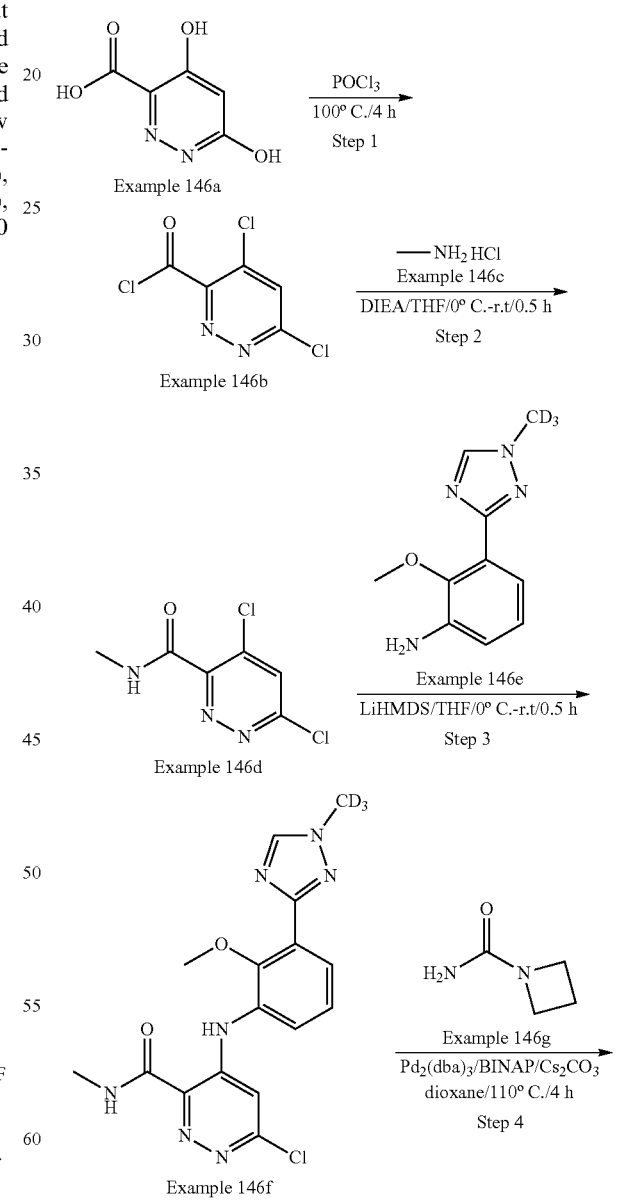

9.05 (d, J=4.8 Hz, 1H), 8.57 (s, 1H), 8.03 (s, 1H), 7.64 (dd, J=7.8, 1.8 Hz, 1H), 7.52 (dd, J=8.1, 1.8 Hz, 1H), 7.27 (t, J=7.8 Hz, 1H), 4.01 (t, J=7.8 Hz, 4H), 3.74 (s, 3H), 2.87 (d, J=4.8 Hz, 3H), 2.23-2.08 (m, 2H).

Example 147

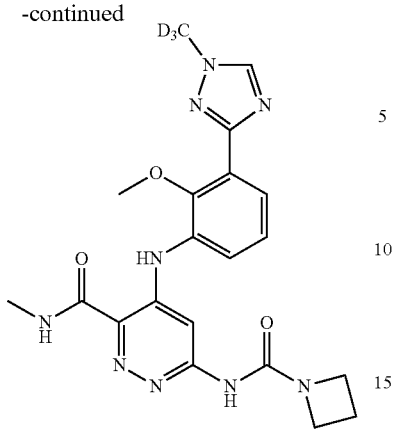

Example 146

Step 1: Example 146b

The solution of Example 146a (3.0 g, 19.2 mmol, 1.0 eq) in POCl₃ (30 mL) was stirred for 4 h at 100° C. After the reaction completed, it was concentrated under vacuo to give crude product (3.0 g, crude) which was used to next step without further purification.

Step 2: Example 146d

To a solution of Example 146c (1.96 g, 28.4 mmol, 2.0 eq) and DIEA (14.7 g, 113.6 mmol, 8.0 eq) in THF (30 mL) was added a solution of Example 146b (3.0 g, crude) in DCM (20 mL) dropwise at 0° C. The reaction solution was stirred for 30 min at r.t. The reaction solution was diluted with EtOAc (100 mL), washed with brine (50 mL*3), dried over Na₂SO₄ and concentrated. The residue was purified by silica gel flash column chromatography, eluted with Petroleum Ether/EtOAc=(3/1) to afford the product Example 146d (400 mg, 14% yield) as a yellow solid. LCMS [M+1]⁺=206.2.

Step 3: Example 146f

To a solution of Example 146d (400 mg, 1.94 mmol, 1.0 eq) and Example 146e (402 mg, 1.94 mmol, 1.0 eq) in dry THF (15 mL) was added LiHMDS (3.88 mL, 1M in THF, 3.88 mmol, 2.0 eq) dropwise at 0° C. under N₂ protection. The reaction mixture was stirred for 0.5 h at r.t. Then the silica was added to the mixture and concentrated. The residue was purified by silica gel flash column chromatography, eluted with DCM/MeOH=(20/1) to afford the product Example 146f (310 mg, 42% yield) as a yellow solid. LCMS [M+1]⁺=377.3.

Step 4: Example 146

To a solution of Example 146f (290 mg, 0.77 mmol, 1.0 eq) in dioxane (5 mL) were added Cs₂CO₃ (502.0 mg, 1.54 mmol, 2.0 eq), Example 146g (231 mg, 2.31 mmol, 3.0 eq) and BINAP (95.9 mg, 0.15 mmol, 0.2 eq) and Pd₂(dba)₃CHCl₃ (82.8 mg, 0.08 mmol, 0.1 eq). The reaction mixture was stirred for 4 h at 110° C. under N₂ protection. After cooled to room temperature, the solvent was removed, and the crude product was purified by Prep-TLC (DCM/MeOH=15/1) to afford the product Example 146 (80.5 mg, 24% yield) as an off-white solid. LCMS [M+1]=441.3. ¹H NMR (300 MHz, DMSO-d₆) δ 10.92 (s, 1H), 9.61 (s, 1H),

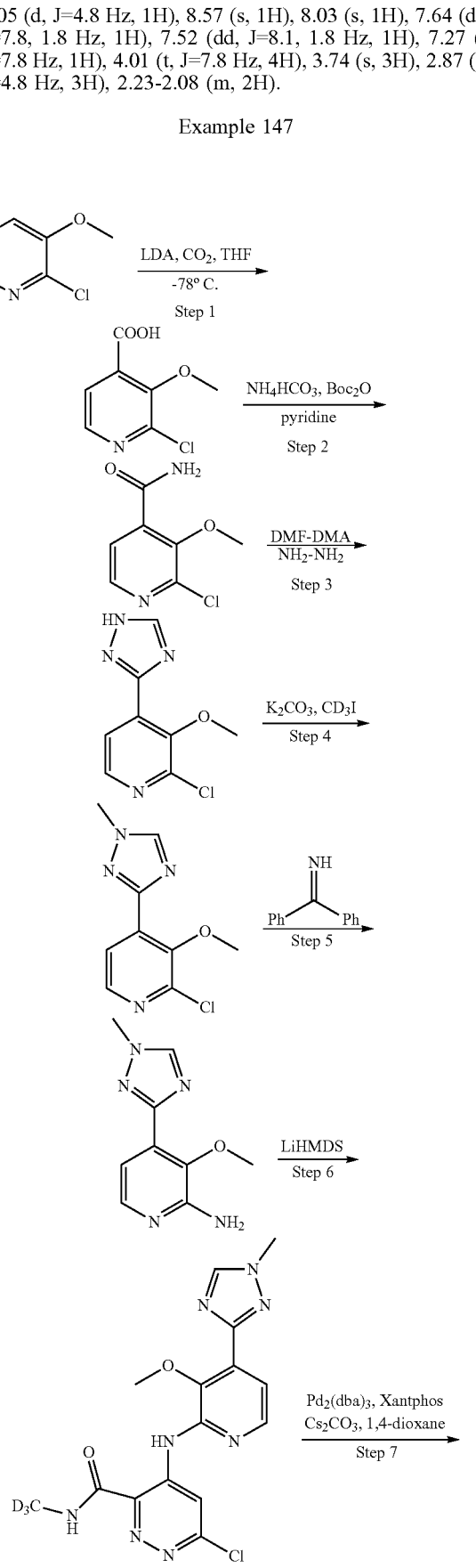

361
-continued

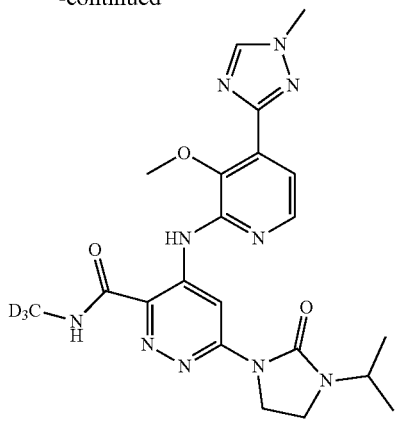

Step 1: 2-chloro-3-methoxyisonicotinic acid

To a solution of 2-chloro-3-methoxypyridine (50 g, 0.348 mol) in THF (500 mL) at −78° C. was added LDA (1.0 M in THF, 418 mL, 0.418 mmol) dropwise. After addition, the mixture was stirred at −78° C. for 30 minutes, then dry ice was added to the reaction during 30 minutes. The reaction was quenched with 5% w/v aqueous NaOH (200 mL) and the aqueous layer was washed with EtOAc (200 mL×2). The organic fractions were discarded and the pH of the aqueous layer was adjusted to 2 with a 6 M aqueous HCl solution. The aqueous layer was extracted with EtOAc (30 mL×3) and the combined organic fractions dried by $Na_2SO_4$, filtered and concentrated to give the desired compound as a yellow solid (35 g, 53.8%).

Step 2: 2-chloro-3-methoxyisonicotinamide

To a solution of 2-chloro-3-methoxyisonicotinic acid (37 g, 0.197 mol), $Boc_2O$ (49.84 mL, 0.217 mol) and pyridine (19.14 mL, 0.239 mol) in DCM (600 mL) at 0° C. was added $NH_4HCO_3$ (78.0 g, 0.985 mol). After the addition was complete, the ice bath was removed and the reaction mixture was allowed to warm to rt. After stirring at room temperature for overnight, the reaction mixture was concentrated on the rotovap to remove some of the DCM, and filtered to collect the liquid. The filtrate washed with $H_2O$ (100 mL×2). The combined organic layers were washed by brine (100 mL), dried over $Na_2SO_4$, filtered and concentrated under reduced pressure to afford the crude product which was purified by column chromatography (DCM/MeOH=20/1) to give the title compound as a brown solid (24.0 g, Yield: 65.3%). LM-MS: m/z=187.6[M+H]⁺

Step 3: 2-chloro-3-methoxy-4-(1H-1,2,4-triazol-3-yl)pyridine 2-chloro-3-methoxyisonicotinamide (24 g, 0.129 mol) was slurried in dimethyl formamide dimethyl acetal (173 mL, 1.29 mol) and the mixture was heated to 95° C. giving a clear, pale yellow solution. After heating for 1 h, the reaction was cooled and was concentrated on the rotovap and the resulting yellow oil was azeotroped twice with 1,2-dichloroethane (40 mL portions) to ensure complete removal of any residual dimethyl formamide dimethyl acetal. The crude oil thus obtained was immediately dissolved in 50 mL of ethanol and was immediately used in the following step.

In a separate flask was prepared a mixture of ethanol (500 mL) and acetic acid (AcOH, 130 mL) and the resulting solution was cooled in an ice bath. Once cooled, hydrazine hydrate 64 mL, 1.29 mol) was added dropwise. At this time, the solution containing the crude dimethyl formamide dimethyl acetal adduct as prepared above was transferred dropwise over 15 min by cannula into the previously prepared well-stirred ice-cold mixture containing the hydrazine. During the addition, a pale yellow solid formed in the solution. After the addition was completed, the resulting cloudy yellow mixture was allowed to warm to room temperature and stirred for overnight. The reaction mixture at this time was concentrated on the rotovap to remove some of the ethanol, diluted with additional water and filtered to collect the solid. The solid was washed with additional portions of water, air dried in the funnel then under vacuum to afford 24 g (88%) of a pale yellow solid as the desired product. LM-MS: m/z=211.6 [M+H]⁺

Step 4: 2-chloro-3-methoxy-4-(1-methyl-1H-1, 2, 4-triazol-3-yl) pyridine

To a solution of 2-chloro-3-methoxy-4-(1H-1, 2, 4-triazol-3-yl) pyridine (9.00 g, 42.7 mmol) in DMF (80 mL) was treated with potassium carbonate (17.7 g, 128.1 mmol). After cooling the resulting mixture in an ice bath, a solution of iodomethane (8.1 g, 57.6 mmol) in DMF (5 mL) was slowly added dropwise by syringe over 2 min. After the addition was complete, the ice bath was removed and the reaction mixture was allowed to warm to rt. After stirring at room temperature for overnight, LCMS analysis indicated complete and clean conversion to the regioisomeric mixture of products in ~3:1 ratio, respectively. The reaction was cooled in an ice bath and was diluted with water (~50 mL) and the solution was extracted with EtOAc (3×40 mL) and the combined extracts were washed with 10% aq. LiCl (2×20 mL), water (20 mL) then brine (20 mL), concentrated and purified by column chromatography (PE/EA=5/1) to afford the title compound (5.0 g, 52%) of the major isomer as a pale yellow solid. LM-MS: m/z=225.6[M+H]⁺

Step 5: 3-methoxy-4-(1-methyl-1H-1,2,4-triazol-3-yl)pyridin-2-amine

To a solution of 2-chloro-3-methoxy-4-(1-methyl-1H-1,2,4-triazol-3-yl) pyridine (5 g, 22.3 mmol), diphenylmethanimine (6.01 g, 33.45 mmol), Sodium tert-butoxide (3.2 g, 33.45 mmol) and DPEphos (2.4 g, 4.46 mmol) in 1,4-dioxane (100 mL) was added $Pd_2(dba)_3$ (2.0 g, 2.23 mmol). The mixture degassed by $N_2$ for 3 times and heated to 100° C. for 1 hrs. When reaction completed, filtered, filtrate was removed in vacuo, added DCM 50 mL, 2M HCl 50 ml stirring at room temperature for 20 min, the aqueous layer was washed with DCM (20 mL×2). the pH of the aqueous layer was adjusted to 9 with 5% w/v aqueous NaOH, The aqueous layer was extracted with DCM (50 mL×6) and the combined organic fractions dried ($Na_2SO_4$), filtered and concentrated and chromatography (DCM/MeOH=20/1) to give the title compound as a white solid. (2.6 g, 56.8%)

Step 6: 6-chloro-4-((3-methoxy-4-(1-methyl-1H-1,2,4-triazol-3-yl)pyridin-2-yl)amino)-N-(methyl-d₃) pyridazine-3-carboxamide To a solution of 4,6-dichloro-N-(trideuteriomethyl) pyridazine-3-carboxamide (3.97 g, 19.0 mmol) and 3-methoxy-4-(1-methyl-1,2,4-triazol-3-yl)pyridin-2-amine (3.00 g, 14.6 mmol) in THF (50 mL) under N₂ was added LiHMDS (1 M, 43.80 mL, 43.80 mmol) at 0° C. resulting a mild exotherm. The reaction was stirred at r.t. When completed, the reaction mixture was cooled to 0° C., quenched by adding satd. NH₄Cl (aq.), diluted with water (100 mL) and extracted by EtOAc (50 mL×3). The combined organic layers were washed by brine (50 mL), dried over Na₂SO₄, filtered and concentrated under reduced pressure to afford the crude product which was purified by column chromatography (DCM/EtOAc=3/1) to give the title compound as a yellow solid (2.70 g, 48.9%).

Step 7: 6-(3-isopropyl-2-oxo-imidazolidin-1-yl)-4-[[3-methoxy-4-(1-methyl-1,2,4-triazol-3-yl)-2-pyridyl]amino]-N-(trideuteriomethyl)pyridazine-3-carboxamide To a solution of 6-chloro-4-((3-methoxy-4-(1-methyl-1H-1,2,4-triazol-3-yl)pyridin-2-yl)amino)-N-(methyl-d3) pyridazine-3-carboxamide (3.6 g, 9.5 mmol) and 1-isopropylimidazolidin-2-one (2.4 g, 19 mmol) in 1,4-dioxane (30 mL) was added cesium carbonate (6.2 g, 19 mmol), Pd₂(dba)₃ (2.6 g, 2.9 mmol), and Xantphos (3.3 g, 5.7 mmol). The mixture degassed by N₂ for 3 times and heated to 120° C. for 4 hrs. When reaction completed, filtered, filtrate was removed in vacuo, chromatography (PE/EtOAc=50/50 then DCM/MeOH=97/3) to give the desired product T241 as a yellow solid (0.55 g, 12%). ¹H NMR (400 MHz, CDCl₃): δ 12.20 (s, 1H), 10.16 (s, 1H), 8.28 (d, 1H), 8.22 (s, 1H), 8.14 (s, 1H), 7.51 (d, 1H), 4.43-4.32 (m, 1H), 4.23 (t, 2H), 4.03 (s, 3H), 4.00 (s, 3H), 3.51 (t, 2H), 1.23 (d, 6H). LM-MS: m/z=470.3 [M+H]⁺

Example 148

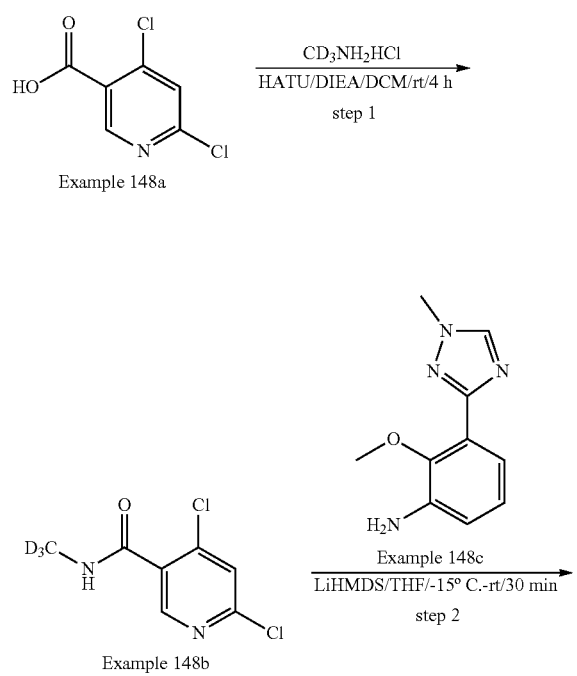

Step 1: Example 148b

To a solution of Example 148a (1.0 g, 5.21 mmol, 1.0 eq) in DCM (15 mL) were added CD₃NH₂·HCl (438 mg, 6.25 mmol, 1.2 eq), DIEA (3.36 g, 26.04 mmol, 5.0 eq) and HATU (2.37 g, 6.25 mmol, 1.2 eq). The reaction mixture was stirred for 4 h at r.t. The solvent was removed, and the residue was purified by silica gel flash column chromatography, eluted with PE/EtOAc (1/1) to afford the product Example 148b (670 mg, 61.8% yield) as an off white solid. LCMS [M+1]⁺=208.2.

Step 2: Example 148d

To a solution of Example 148b (200 mg, 0.96 mmol, 1.0 eq) and Example 148c (196 mg, 0.96 mmol, 1.0 eq) in dry THF (5 mL) was added LiHMDS (1.92 mL, 1 M in THF, 1.92 mmol, 2.0 eq) dropwise at ~15° C. The reaction solution was stirred at r.t. for 30 min. After the reaction was completed, the solvent was removed, the residue was purified by silica gel flash column chromatography, eluted with DCM/MeOH (20/1) to afford the product Example 148d (212 mg, 58.7% yield) as a yellow solid. LCMS [M+1]$^+$=376.3

Step 3: Example 148

To a solution of Example 148d (100 mg, 0.27 mmol, 1.0 eq) in dioxane (3 mL) were added Cs$_2$CO$_3$ (260 mg, 0.80 mmol, 3.0 eq), Example 148e (102 mg, 0.80 mmol, 3.0 eq) and 3$^{rd}$ Brettphos catalyst (48 mg, 0.05 mmol, 0.2 eq). The reaction mixture was stirred for 6 h at 120° C. under N$_2$. The mixture was filtered and the filtrate was concentrated. The crude product was purified by Prep-TLC (DCM/MeOH=15/1) to afford the product Example 148 (26.1 mg, 21.0% yield) as a light yellow solid. LCMS [M+1]$^+$=468.4. $^1$H NMR (300 MHz, DMSO-d$_6$) δ 10.66 (s, 1H), 8.96 (s, 1H), 8.55 (s, 1H), 8.52 (s, 1H), 8.46 (s, 1H), 7.94 (s, 1H), 7.56-7.48 (m, 2H), 7.22 (t, J=7.8 Hz, 1H), 3.95 (s, 3H), 3.74 (s, 3H), 3.65 (s, 4H), 1.21 (s, 6H).

Example 149

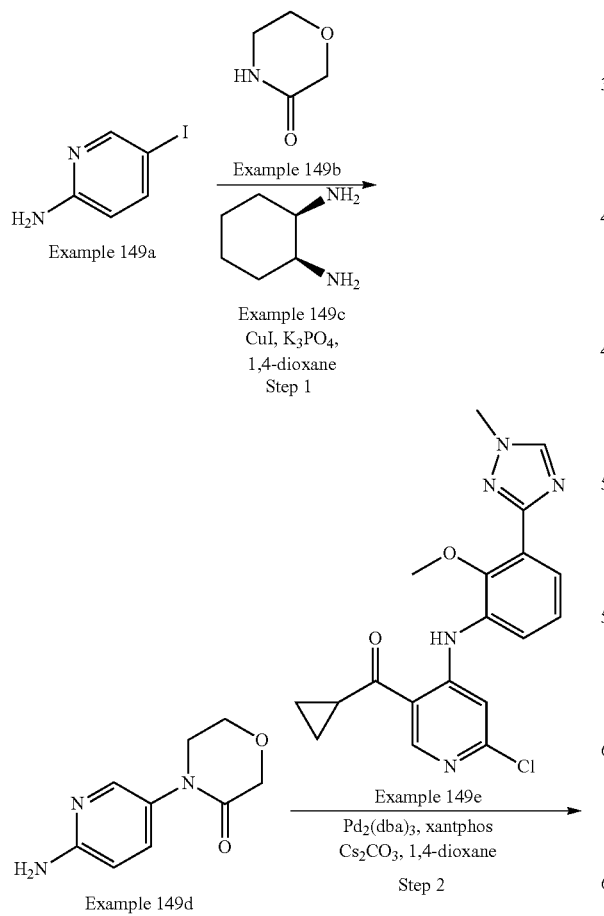

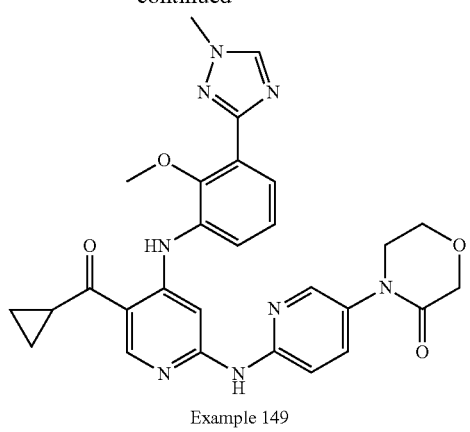

Example 149

Step 1: Example 149c

A solution of Example 149a (200 mg, 0.90 mmol), Example 149b (95 mg, 0.91 mmol), Example 149c (26 mg, 0.18 mmol), CuI (18 mg, 0.09 mmol) and K$_3$PO$_4$ (380 mg, 1.82 mmol) in 1,4-dioxane (5 mL) was stirred at 110° C. overnight. The reaction was diluted with CH$_3$CN (5 mL), filtered and concentrated to give the crude product Example 149d (210 mg, quant.) as black oil. $^1$H NMR (400 MHz, DMSO-d$_6$) δ 7.85 (br, 1H), 7.33 (d, J=8.0 Hz, 1H), 6.43 (d, J=8.0 Hz, 1H), 5.98 (s, 2H), 4.13 (s, 2H), 3.91 (t, J=4.0 Hz, 2H), 3.61 (t, J=4.0 Hz, 2H).

Step 2: Example 149

To a solution of Example 149d (210 mg, 0.90 mmol) and Example 149e (200 mg, 0.52 mmol,) in 1,4-dioxane (5 mL) were added Pd$_2$(dba)$_3$ (48 mg, 0.05 mmol), XantPhos (60 mg, 0.10 mmol) and Cs$_2$CO$_3$ (340 mg, 1.04 mmol). The mixture was degassed by nitrogen for 3 times and stirred at 110° C. overnight. When completed, the reaction was cooled to r.t., diluted with MeOH (5 mL) and filtered. The filtrate was purified directly by Prep-HPLC to give the desired product Example 149 (11.5 mg, 4.1% yield) as an off-white solid. LCMS [M+1]$^+$=541.3. $^1$H NMR (400 MHz, DMSO-d$_6$) δ 11.05 (s, 1H), 10.08 (s, 1H), 9.09 (s, 1H), 8.54 (s, 1H), 8.20 (s, 1H), 7.91 (s, 1H), 7.72-7.58 (m, 4H), 7.29 (t, J=8.0 Hz, 1H), 4.19 (s, 2H), 3.96 (t, J=4.0 Hz, 2H), 3.93 (s, 3H), 3.72-3.70 (m, 5H), 2.95 (br, 1H), 1.06-0.97 (m, 4H).

Example 150

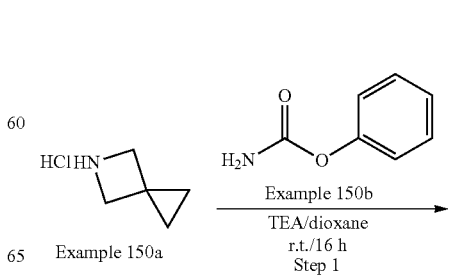

367

-continued

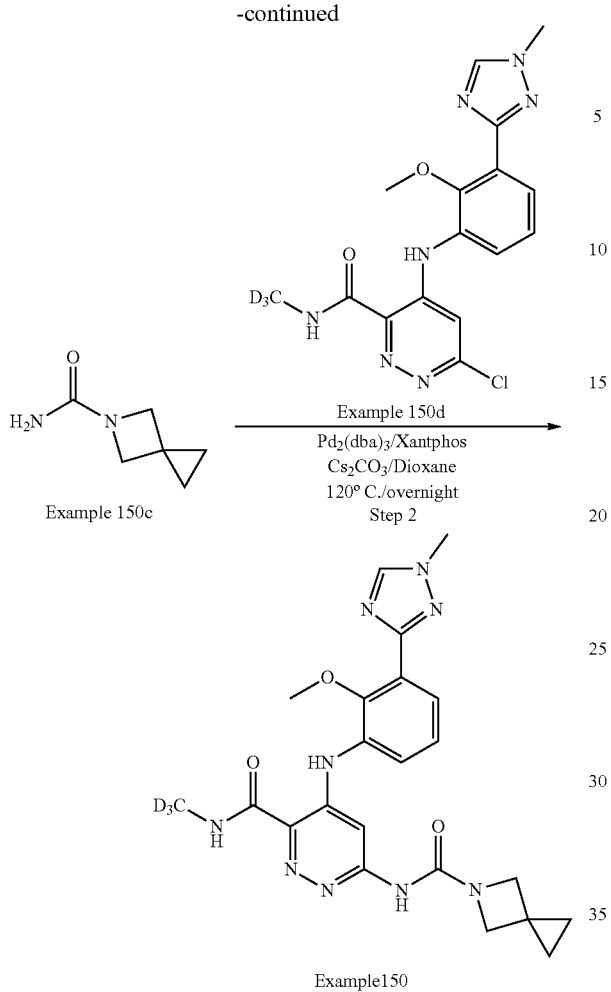

Example 150c

Example150

Step 1: Example 150c

To a solution of Example 150a (240 mg, 2.0 mmol) in dioxane (4 mL) were added Example 150b (411 mg, 3.0 mmol) and TEA (606 mg, 6.0 mmol). The reaction mixture was stirred at room temperature overnight. The mixture was concentrated, and the residue was triturated with Petroleum ether/EtOAc=1/1 (5 mL). The solid was collected by filtered and dried to give Example 150c (120 mg, 47.5% yield) as a white solid. LCMS [M+1]$^+$=127.1

Step 2: Example 150

To a solution of Example 150d (100 mg, 0.27 mmol) in dioxane (3 mL) were added Example 150c (50 mg, 0.4 mmol), Pd$_2$(dba)$_3$ (25 mg, 0.027 mmol), Xantphos (16 mg, 0.027 mmol) and Cs$_2$CO$_3$ (176 mg, 0.26 mmol). The mixture was sealed and heated to 120° C. for overnight. The mixture was filtrated and concentrated under reduced pressure. The residue was purified by Prep-HPLC to give Example 150 (47 mg, 37.3% yield) as a yellow solid. LCMS [M+1]$^+$=467.2. $^1$H NMR (400 MHz, Chloroform-d) δ 10.94 (s, 1H), 8.14-8.02 (m, 3H), 7.76 (d, J=7.7 Hz, 1H), 7.53 (d, J=7.2 Hz, 1H), 7.26 (s, 1H), 7.14 (s, 1H), 4.15 (s, 3H), 3.99 (s, 3H), 3.81 (s, 3H), 0.69 (br, 4H).

368

Example 151

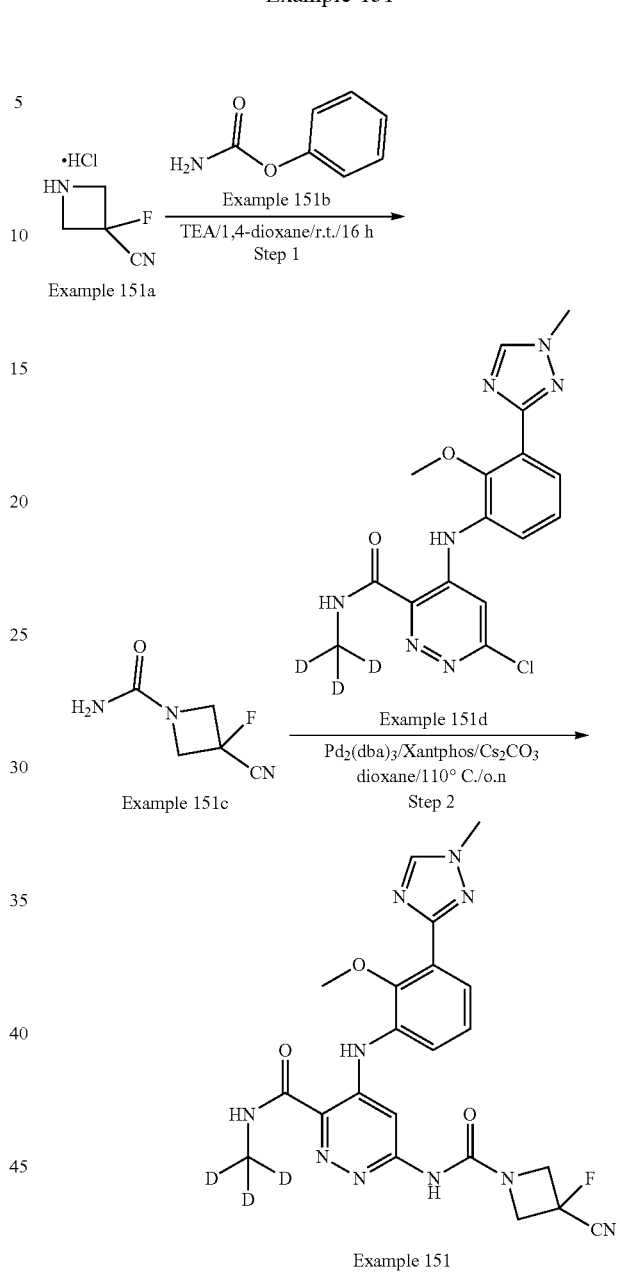

Step 1: Example 151c

A solution of Example 151a (200 mg, 1.1 mmol) in 1,4-dioxane (35 mL) were treated with Example 151b (274 mg, 2.0 mmol) and TEA (300 mg, 3.0 mmol). The mixture was stirred at r.t. for 16 h. After reaction completed, the solvent was concentrated, and the residue was suspended in DCM (5 mL), and sonicated. The resulting solid was collected via filtration, and dried to afford the desired crude product Example 151c (300 mg, crude, 190.7% yield) as a white solid.

Step 2: Example 151

To a solution of Example 151d (94 mg, 0.25 mmol) and Example 151c (150 mg crude, 1.0 mmol) in dioxane (5 mL)

were added Pd$_2$(dba)$_3$ (91 mg, 0.1 mmol), Xantphos (59 mg, 0.1 mmol) and Cs$_2$CO$_3$ (652 mg, 2.0 mmol). The mixture was degassed by nitrogen for 3 times and stirred at 110° C. for overnight. When completed, the reaction was cooled to r.t., diluted with MeOH (5 mL) and filtered. The filtrate was purified directly by Prep-HPLC to give the desired product Example 151 (3.7 mg, 0.7% yield) as an off white solid. LCMS [M+1]$^+$=484.2. $^1$H NMR (400 MHz, Chloroform-d) δ 11.12 (s, 1H), 8.11 (s, 1H), 7.97-7.83 (m, 3H), 7.51-7.44 (m, 1H), 4.71-4.61 (m, 2H), 4.52 (dd, J=21.4, 10.8 Hz, 2H), 4.01 (s, 3H), 3.80 (s, 3H).

Example 152

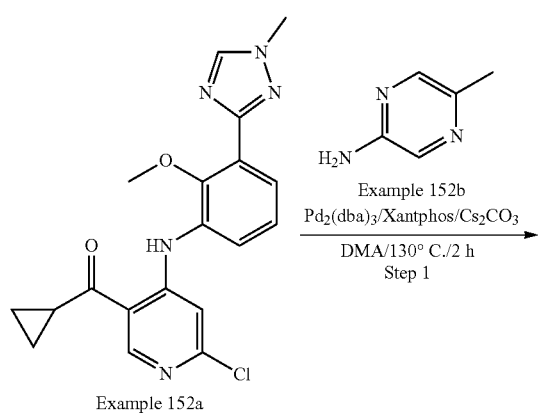

Example 152a

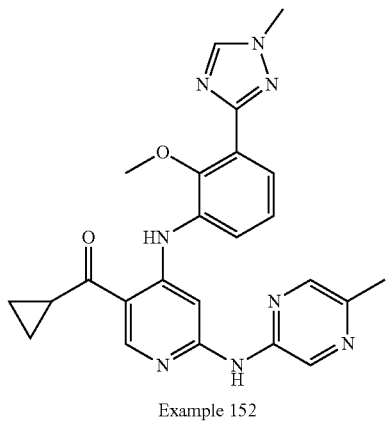

Example 152

To a solution of Example 152a (100 mg, 0.26 mmol,) and Example 152b (45 mg, 0.41 mmol) in DMA (2.5 mL) were added Pd$_2$(dba)$_3$ (24 mg, 0.026 mmol), Xantphos (30 mg, 0.052 mmol) and Cs$_2$CO$_3$ (340 mg, 1.04 mmol). The mixture was degassed by nitrogen for 3 times and stirred at 130° C. for 2 h. When completed, the reaction was cooled to r.t., diluted with MeOH (5 mL) and filtered. The filtrate was purified directly by Prep-HPLC to give the desired product Example 152 (10.0 mg, 8.4% yield) as a white solid. LCMS [M+1]$^+$=457.2. $^1$H NMR (400 MHz, DMSO-d$_6$) δ 11.03 (s, 1H), 10.12 (s, 1H), 9.10 (s, 1H), 8.88 (s, 1H), 8.54 (d, J=3.4 Hz, 1H), 8.08 (s, 1H), 7.69 (s, 1H), 7.62 (d, J=9.3 Hz, 2H), 7.29 (t, J=7.7 Hz, 1H), 3.93 (s, 3H), 3.69 (s, 3H), 2.96 (s, 1H), 2.37 (d, J=3.4 Hz, 3H), 1.06 (s, 2H), 0.99 (s, 2H).

Example 153

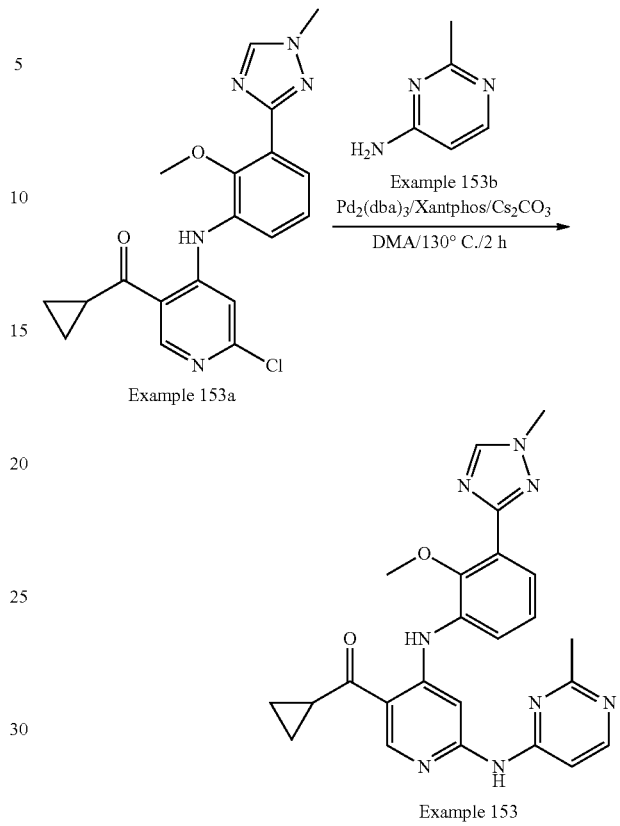

Example 153

To a solution of Example 153a (100 mg, 0.26 mmol,) and Example 153b (45 mg, 0.41 mmol) in DMA (2.5 mL) were added Pd$_2$(dba)$_3$ (24 mg, 0.026 mmol), Xantphos (30 mg, 0.052 mmol) and Cs$_2$CO$_3$ (340 mg, 1.04 mmol). The mixture was degassed by nitrogen for 3 times and stirred at 130° C. for 2 h. When completed, the reaction was cooled to r.t., diluted with MeOH (5 mL) and filtered. The filtrate was purified directly by Prep-HPLC to give the desired product Example 153 (20.0 mg, 17.1% yield) as a white solid. LCMS [M+1]$^+$=457.2. $^1$H NMR (400 MHz, DMSO-d$_6$) δ 11.07 (s, 1H), 10.31 (s, 1H), 9.11 (s, 1H), 8.54 (s, 1H), 8.30 (s, 1H), 8.15 (s, 1H), 7.65 (t, J=9.6 Hz, 2H), 7.29 (d, J=7.9 Hz, 1H), 7.23 (s, 1H), 3.93 (s, 3H), 3.69 (s, 3H), 2.97 (s, 1H), 2.37 (s, 3H), 1.08 (s, 2H), 1.02 (s, 2H).

Example 154

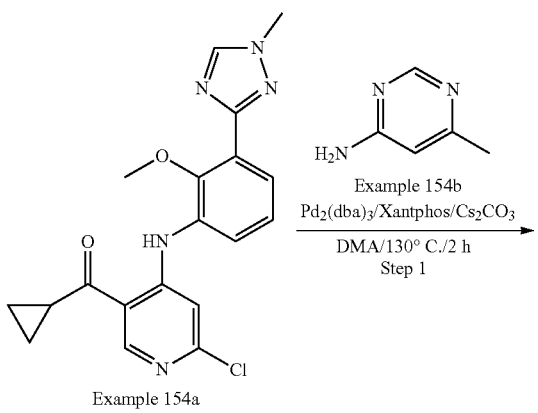

Example 154a

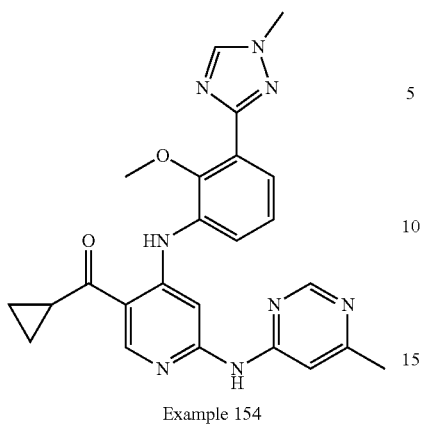

Example 154

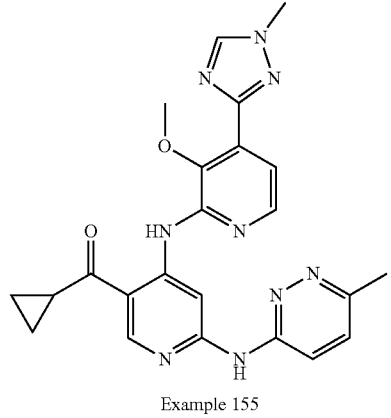

Example 155

To a solution of Example 154a (100 mg, 0.26 mmol,) and Example 154b (45 mg, 0.39 mmol) in DMA (2.5 mL) were added Pd$_2$(dba)$_3$ (24 mg, 0.026 mmol), Xantphos (30 mg, 0.052 mmol) and Cs$_2$CO$_3$ (340 mg, 1.04 mmol). The mixture was degassed by nitrogen for 3 times and stirred at 130° C. for 2 h. When completed, the reaction was cooled to r.t., diluted with MeOH (5 mL) and filtered. The filtrate was purified directly by Prep-HPLC to give the desired product Example 154 (40.0 mg, 34.2% yield) as a white solid. LCMS [M+1]$^+$=457.2. $^1$H NMR (400 MHz, DMSO-d$_6$) δ 11.03 (s, 1H), 10.27 (s, 1H), 9.14 (s, 1H), 8.55 (s, 2H), 7.78 (s, 1H), 7.65-7.57 (m, 3H), 7.30 (d, J=7.9 Hz, 1H), 3.93 (s, 3H), 3.69 (s, 3H), 2.97 (s, 1H), 2.34 (s, 3H), 1.07 (s, 2H), 1.01 (s 2H).

Example 155

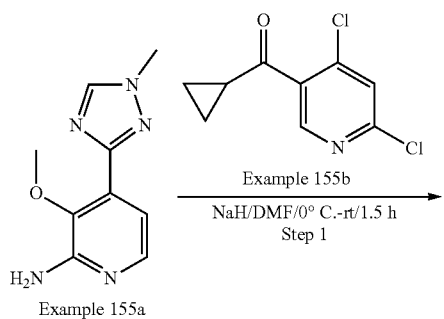

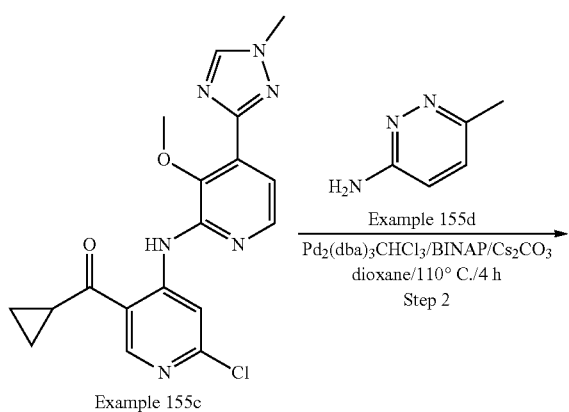

Step 1: Example 155c

To a solution of Example 155a (120 mg, 0.585 mmol, 1.0 eq) in DMF (10 mL), was added NaH (234 mg, 60% in mineral oil, 5.85 mmol, 10.0 eq) in portions at 0° C. After Example 155b (188.8 mg, 0.878 mmol, 1.5 eq) in DMF was added to the mixture, and the reaction mixture was stirred for 1.5 h at r.t. The reaction solution was poured into water (50 mL), extracted with EtOAc (50 mL*3), and the combined organic layers were dried over Na$_2$SO$_4$ and concentrated. The crude product was purified by silica gel flash column chromatography, eluted with DCM/MeOH (20/1) to afford the product Example 155c (24 mg, 11% yield) as a yellow solid. LCMS [M+1]$^+$=385.1.

Step 2: Example 155

To a solution of Example 155c (18 mg, 0.047 mmol, 1.0 eq) in dioxane (2 mL) were added Cs$_2$CO$_3$ (30.1 mg, 0.094 mmol, 2.0 eq), Example 155d (10.2 mg, 0.094 mmol, 2.0 eq), BINAP (5.8 mg, 0.009 mmol, 0.2 eq) and Pd$_2$(dba)$_3$·CHCl$_3$ (4.9 mg, 0.005 mmol, 0.1 eq). The reaction mixture was stirred for 4 h at 110° C. under N$_2$ protection. After cooled to room temperature, the solvent was removed, and the crude product was purified by Prep-TLC (DCM/MeOH=20/1) to afford the product Example 155 (8.6 mg, 41% yield) as a yellow solid. LCMS [M+1]$^+$=458.3. $^1$H NMR (300 MHz, DMSO-d$_6$) δ 12.28 (s, 1H), 10.46 (s, 1H), 9.16 (d, J=7.2 Hz, 2H), 8.66 (s, 1H), 8.20-8.11 (m, 2H), 7.54-7.46 (m, 2H), 4.00 (s, 3H), 3.88 (s, 3H), 3.05-2.93 (m, 1H), 2.56 (s, 3H), 1.17-0.99 (m, 4H).

Example 156

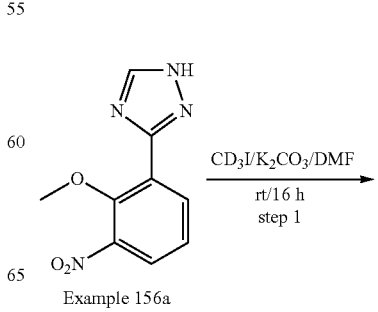

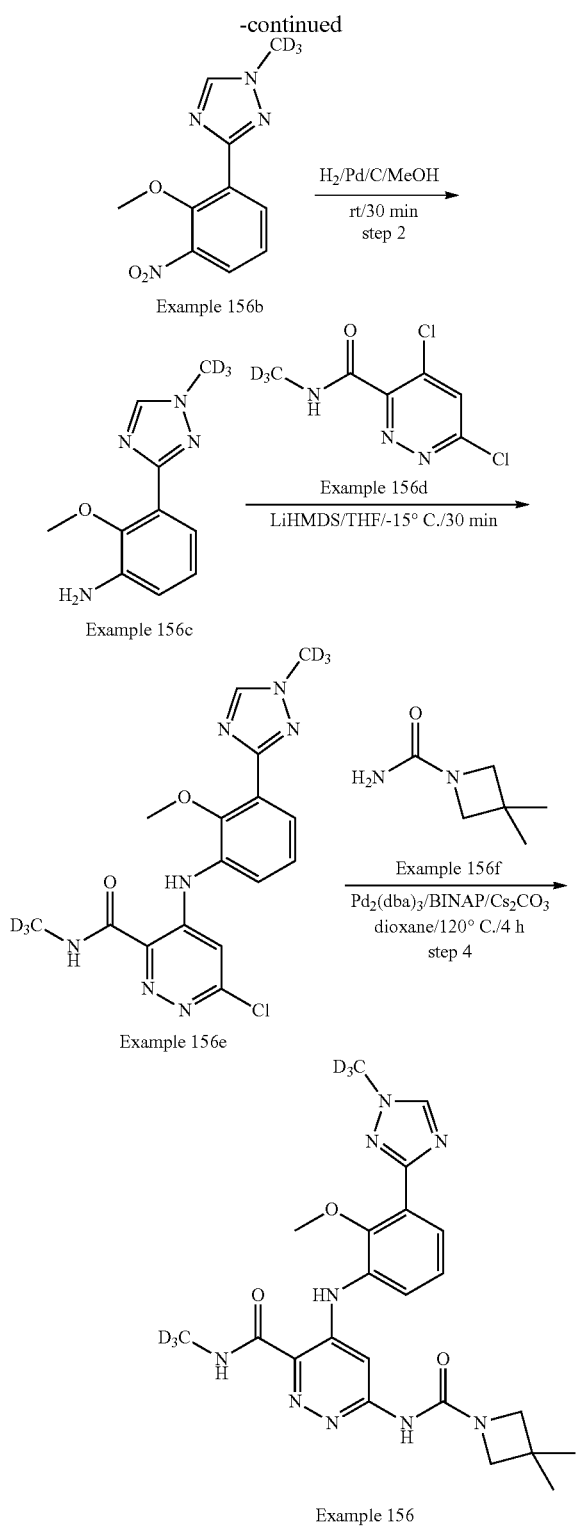

layer dried over Na$_2$SO$_4$ and concentrated. The residue was purified by silica gel flash column chromatography, eluted with Petroleum Ether/EtOAc (1/1) to afford the product Example 156b (1.58 g, 29.3% yield) as a yellow solid. LCMS [M+1]$^+$=238.2.

Step 2: Example 156c

To a solution of Example 156b (500 mg, 2.11 mmol, 1.0 eq) in MeOH (10 mL) was added Pd/C (200 mg) in portions under N$_2$ protection, the suspension was degassed under vacuum and purged with H$_2$ three times, the reaction mixture was stirred for 30 min at r.t. under H$_2$ balloon. The solid was filtered out, the filtrate was concentrated to afford the product Example 156c (425 mg, crude, 97.3% yield) as a gray solid. LCMS [M+1]$^+$=208.2.

Step 3: Example 156e

To a solution of Example 156c (425 mg, 2.05 mmol, 1.0 eq) and Example 156d (429 mg, 2.05 mmol, 1.0 eq) in dry THF (15 mL) was added LiHMDS (4.11 mL, 1 M in THF, 4.11 mmol, 2.0 eq) dropwise at ~15° C. The reaction solution was stirred at ~15° C. for 30 min. After the reaction was completed, the reaction solution was concentrated. The residue was purified by silica gel flash column chromatography, eluted with Petroleum Ether/EtOAc (1/2) to afford the product Example 156e (170 mg, 27.8% yield) as a yellow solid. LCMS [M+1]$^+$=380.3.

Step 4: Example 156

To a solution of Example 156e (100 mg, 0.26 mmol, 1.0 eq) in dioxane (3 mL) were added Example 156f (102 mg, 0.79 mmol, 3.0 eq), Cs$_2$CO$_3$ (257 mg, 0.79 mmol, 3.0 eq), BINAP (66 mg, 0.11 mmol, 0.4 eq) and Pd$_2$(dba)$_3$CHCl3 (54 mg, 0.05 mmol, 0.2 eq). The reaction solution was stirred for 4 h at 120° C. under N$_2$. The mixture was filtered and the filtrate was concentrated. The crude product was purified by Prep-TLC (DCM/MeOH=15/1) to give the desired product Example 156 (18.0 mg, 28.2% yield) as a white solid. LCMS [M+1]$^+$=472.3. $^1$H NMR (400 MHz, DMSO-d$_6$) δ 10.89 (s, 1H), 9.60 (s, 1H), 8.99 (s, 1H), 8.54 (s, 1H), 8.01 (s, 1H), 7.62 (d, J=8.1 Hz, 1H), 7.49 (d, J=7.8 Hz, 1H), 7.24 (t, J=8.1 Hz, 1H), 3.71 (s, 2H), 3.67 (s, 2H), 1.19 (s, 6H).

Example 157

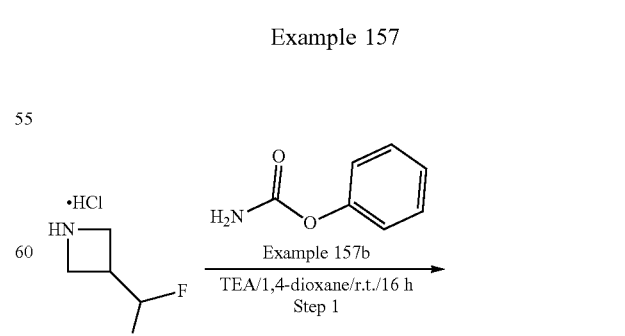

Step 1: Example 156b

To a solution of Example 156a (5.0 g, 22.73 mmol, 1.0 eq) in DMF (100 mL) were added K$_2$CO$_3$ (9.41 g, 68.18 mmol, 3.0 eq) and CD$_3$I (6.60 g, 45.45 mmol, 2.0 eq) at 0° C. The reaction mixture was stirred for 16 h at r.t. The reaction was diluted with EtOAc and washed with brine. The organic

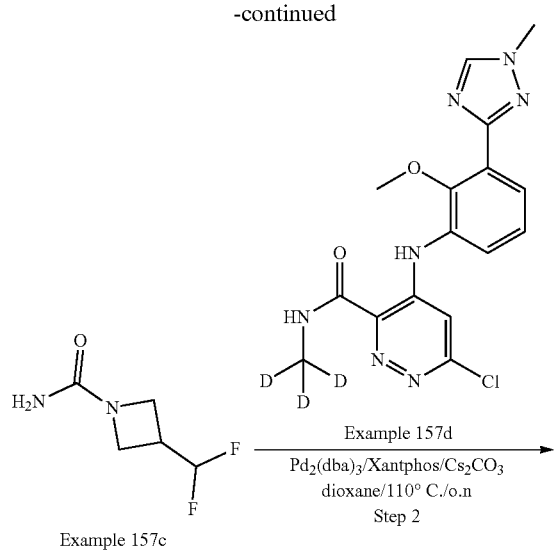

Example 157c

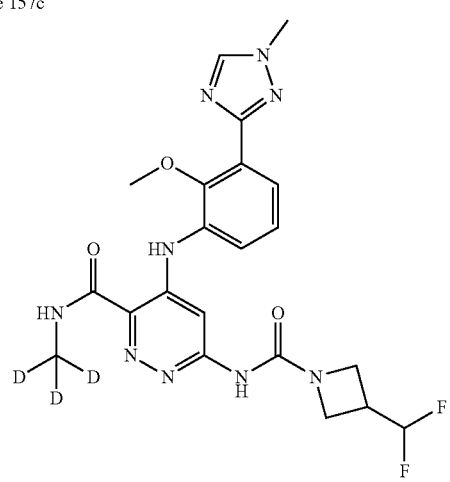

Example 157

Step 1: Example 157c

A solution of Example 157a (200 mg, 1.4 mmol) in 1,4-dioxane (3 mL) were treated with Example 157b (374 mg, 2.8 mmol) and TEA (420 mg, 4.2 mmol). The mixture was stirred at r.t. for 16 h. After reaction completed, the solvent was concentrated, and the residue was suspended in DCM (5 mL), and sonicated. The resulting solid was collected via filtration, and dried to afford the desired product Example 157c (130 mg, 62% yield) as a white solid. LCMS [M+1]$^+$=151.0

Step 2: Example 157

To a solution of Example 157d (157 mg, 0.42 mmol) and Example 157c (300 mg, 2.1 mmol) in dioxane (5 mL) were added Pd$_2$(dba)$_3$ (91 mg, 0.1 mmol), Xantphos (59 mg, 0.1 mmol) and Cs$_2$CO$_3$ (325.8 mg, 1.0 mmol). The mixture was degassed by nitrogen for 3 times and stirred at 110° C. for overnight. When completed, the reaction was cooled to r.t., diluted with MeOH (5 mL) and filtered. The filtrate was purified directly by Prep-HPLC to give the desired product Example 157 (14.8 mg, 7.2% yield) as a off white solid. LCMS [M+1]$^+$=491.2. $^1$H NMR (400 MHz, DMSO-d$_6$) δ 10.90 (s, 1H), 9.84 (s, 1H), 9.01 (s, 1H), 8.54 (s, 1H), 7.98 (s, 1H), 7.62 (d, J=7.7 Hz, 1H), 7.48 (d, J=7.8 Hz, 1H), 7.26 (d, J=8.1 Hz, 1H), 6.16-6.44 (t, 1H), 4.09 (s, 2H), 3.93 (s, 5H), 3.71 (s, 3H), 3.06 (s, 1H).

Example 158

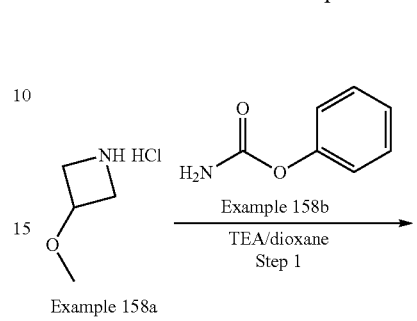

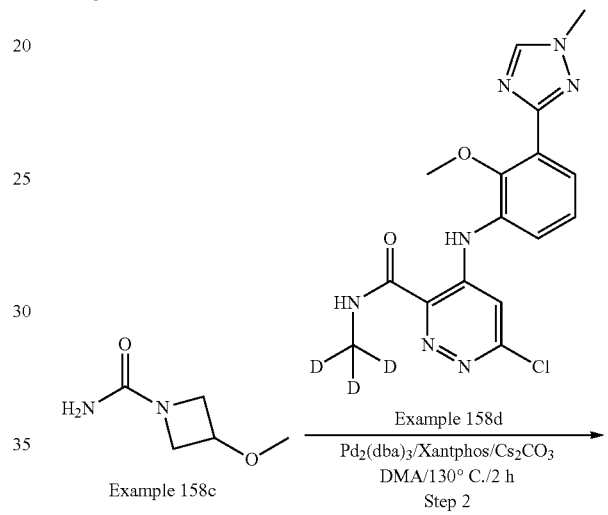

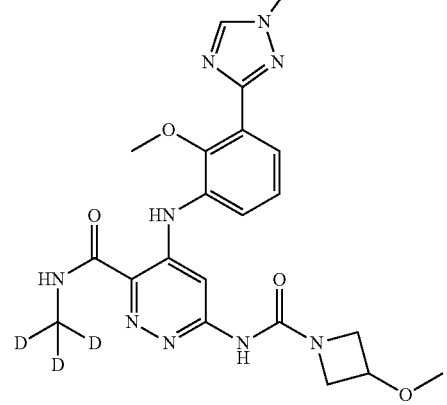

Example 158

Step 1: Example 158c

To a solution of Example 158a (200 mg, 2.29 mmol) in dioxane (5 mL) were added Example 158b (400 mg, 2.91 mmol), and TEA (795 mg, 7.87 mmol). The reaction mixture was stirred at room temperature overnight. Then the mixture was diluted with EtOAc, washed by water, brine, and dried over anhydrous Na$_2$SO$_4$. The solution was concentrated to afford crude Example 158c (170 mg, 57.2% yield) and used directly for next step.

Step 2: Example 158

To a solution of Example 158d (100 mg, 0.26 mmol) and Example 158c (120 mg, 0.92 mmol) in DMA (2.5 mL) were added Pd$_2$(dba)$_3$ (24 mg, 0.026 mmol), Xantphos (30 mg, 0.052 mmol) and Cs$_2$CO$_3$ (340 mg, 1.04 mmol). The mixture was degassed by nitrogen for 3 times and stirred at 130° C. for 2 h. When completed, the reaction was cooled to r.t., diluted with MeOH (5 mL) and filtered. The filtrate was purified directly by Prep-HPLC to give the desired product Example 158 (14.0 mg, 13.1% yield) as a white solid. LCMS [M+1]$^+$=471.3. $^1$H NMR (400 MHz, DMSO-d$_6$) δ 10.90 (s, 1H), 9.74 (s, 1H), 9.01 (s, 1H), 8.54 (s, 1H), 7.99 (s, 1H), 7.62 (d, J=7.6 Hz, 1H), 7.49 (d, J=7.9 Hz, 1H), 7.25 (d, J=8.1 Hz, 1H), 4.16 (d, J=11.1 Hz, 4H), 3.93 (s, 3H), 3.79 (s, 2H), 3.71 (s, 3H), 3.18 (s, 3H).

Example 159

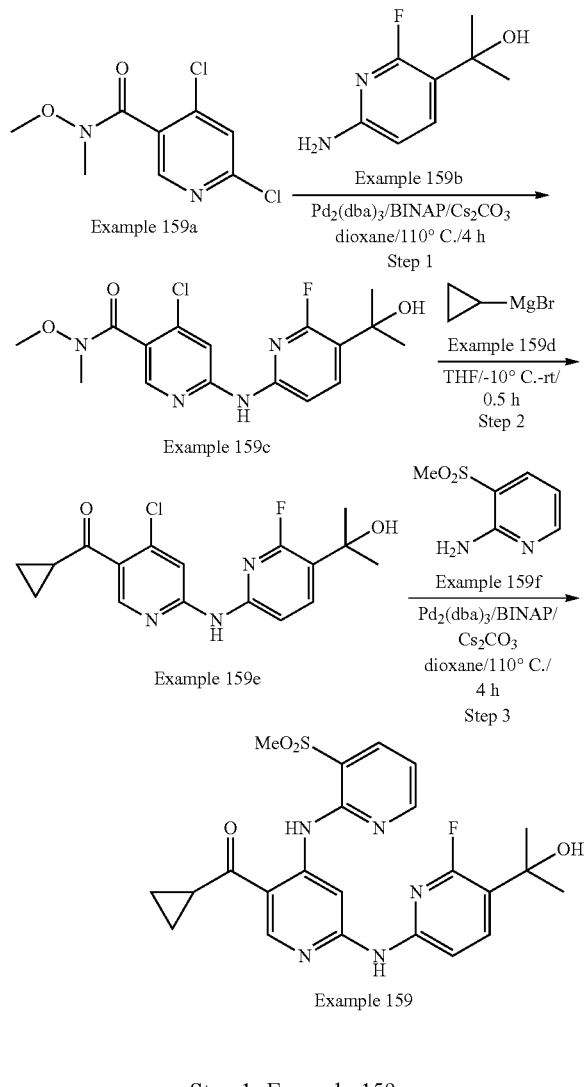

Step 1: Example 159c

To a solution of Example 159a (1.0 g, 4.2 mmol, 1.0 eq) in dioxane (15 mL) were added Cs$_2$CO$_3$ (2.7 g, 8.4 mmol, 2.0 eq), Example 159b (861.8 mg, 5.04 mmol, 1.2 eq), BINAP (523.3 mg, 0.84 mmol, 0.2 eq) and Pd$_2$(dba)$_3$·CHCl$_3$ (434.7 mg, 0.42 mmol, 0.1 eq). The reaction mixture was stirred for 4 h at 110° C. under N$_2$ protection. After cooled to room temperature, the solvent was removed. The crude product was purified by silica gel flash column chromatography (DCM/MeOH=20/1) to afford the product Example 159c (1.0 g, 67% yield) as a yellow solid. LCMS [M+1]$^+$=369.3.

Step 2: Example 159e

To a solution of Example 159c (1.0 g, 2.7 mmol, 1.0 eq) in THF (10 mL) was added Example 159d (40.5 mL, 1.0 M in THF, 40.5 mmol, 15.0 eq) dropwise at 0° C. under N$_2$ protection. The mixture was stirred for 0.5 h at r.t. The reaction was poured into saturated aqueous of NH$_4$Cl (70 mL) and extracted with EtOAc (100 mL*3). The combined organic layer was washed with brine, dried over Na$_2$SO$_4$, and concentrated. The crude product was purified by silica gel flash column chromatography (DCM/MeOH=20/1) to afford the product Example 159e (640 mg, 68% yield) as a yellow solid. LCMS [M+1]$^+$=350.2.

Step 3: Example 159

To a solution of Example 159e (300 mg, 0.86 mmol, 1.0 eq) in dioxane (5 mL) were added Cs$_2$CO$_3$ (560 mg, 1.72 mmol, 2.0 eq), Example 159f (176 mg, 1.0 mmol, 1.2 eq), BINAP (107.2 mg, 0.172 mmol, 0.2 eq) and Pd$_2$(dba)$_3$·CHCl$_3$ (89 mg, 0.086 mmol, 0.1 eq). The reaction mixture was stirred for 4 h at 110° C. under N$_2$ protection. After cooled to room temperature, the solvent was removed. The crude product was purified by silica gel flash column chromatography (DCM/MeOH=20/1) to give 270 mg crude product (90% purity) and further purified by Prep-TLC (DCM/MeOH=20/1) to afford the product Example 159 (120 mg, 32% yield) as an off-white solid. LCMS [M+1]$^+$=486.4. $^1$H NMR (300 MHz, DMSO-d$_6$) δ 11.89 (s, 1H), 10.28 (s, 1H), 9.17 (s, 1H), 9.02 (s, 1H), 8.64 (dd, J=4.8, 1.8 Hz, 1H), 8.27 (dd, J=7.8, 1.8 Hz, 1H), 7.99 (dd, J=10.8, 8.4 Hz, 1H), 7.58 (dd, J=8.1, 2.1 Hz, 1H), 7.34 (dd, J=7.8, 4.8 Hz, 1H), 5.28 (s, 1H), 3.30 (s, 3H), 3.01-2.86 (m, 1H), 1.49 (s, 6H), 1.14-0.97 (m, 4H).

Example 160

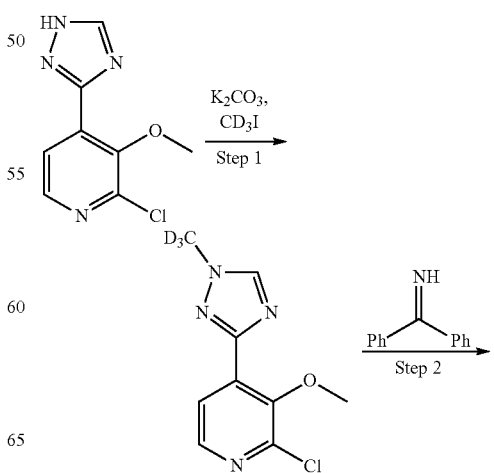

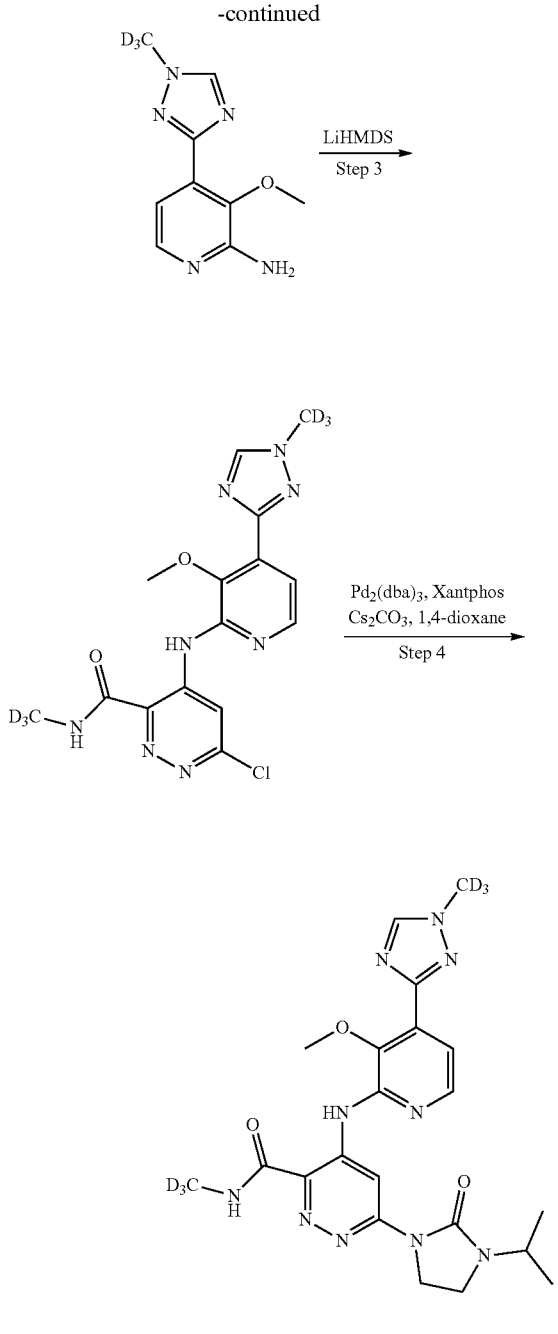

Step 1: 2-chloro-3-methoxy-4-[1-(trideuteriomethyl)-1,2,4-triazol-3-yl]pyridine To a solution of 2-chloro-3-methoxy-4-(1H-1,2,4-triazol-3-yl)pyridine (10.00 g, 47.5 mmol) in DMF (50 mL) was treated with potassium carbonate (13.1 g, 95.0 mmol). a solution of trideuterioiodomethane (8.26 g, 57.0 mmol) in DMF (5 mL) was slowly added dropwise by syringe over 2 min. The reaction was stirring at room temperature for 4 h, The reaction was cooled in an ice bath and was diluted with water (50 mL) and the solution was extracted with EtOAc (3×50 mL) and the combined extracts were washed water (50 mL) then brine (50 mL), dried over Na₂SO₄, filtered and concentrated under reduced pressure to afford the crude product which was purified by column chromatography (PE/EtOAc=3/1) to give the title compound as a yellow solid (8.0 g, 74%).

Step 2: 3-methoxy-4-[1-(trideuteriomethyl)-1,2,4-triazol-3-yl]pyridin-2-amine To a solution of 2-chloro-3-methoxy-4-(1-methyl-1H-1,2,4-triazol-3-yl) pyridine (8.0 g, 35.1 mmol), diphenylmethanimine (7.64 g, 42.2 mmol), Sodium tert-butoxide (6.75 g, 70.3 mmol) and DPEphos (1.88 g, 3.51 mmol) in 1,4-dioxane (100 mL) was added Pd₂(dba)₃ (3.22 g, 3.51 mmol). The mixture degassed by N₂ for 3 times and heated to 100° C. for 1 hr. When the reaction completed, filtered, filtrate was removed in vacuo, Added DCM 50 mL, 2N HCl 50 mL stirring at room temperature for 20 min, the aqueous layer was washed with DCM (20 mL×2). the pH of the aqueous layer was adjusted to 9 with 5% w/v aqueous NaOH, The aqueous layer was extracted with DCM (50 mL×6) and the combined organic fractions dried (Na₂SO₄), filtered and concentrated and chromatography (DCM/MeOH=20/1) to give the title compound as a white solid. (3.2 g, 43.7%)

Step 3: 6-chloro-4-[[3-methoxy-4-(1-methyl-1,2,4-triazol-3-yl)-2-pyridyl]amino]-N-(trideuteriomethyl)pyridazine-3-carboxamide To a solution of 4,6-dichloro-N-(trideuteriomethyl)pyridazine-3-carboxamide (4.18 g, 20.0 mmol) and 3-methoxy-4-[1-(trideuteriomethyl)-1,2,4-triazol-3-yl]pyridin-2-amine (3.20 g, 15.4 mmol) in THF (50 mL) under N₂ was added LiHMDS (1 M, 46.2 mL, 46.2 mmol) at 0° C. resulting a mild exotherm. The reaction was stirred at r.t. When completed, The reaction mixture was cooled to 0° C., quenched by adding satd. NH₄Cl (aq.), diluted with water (100 mL) and extracted by EtOAc (50 mL×3). The combined organic layers were washed by brine (50 mL), dried over Na₂SO₄, filtered and concentrated under reduced pressure to afford the crude product which was purified by column chromatography (DCM/EtOAc=3/1) to give the title compound as a yellow solid (2.70 g, 46.1%).

Step 4: 6-(3-isopropyl-2-oxo-imidazolidin-1-yl)-4-[[3-methoxy-4-[1-(trideuteriomethyl)-1,2,4-triazol-3-yl]-2-pyridyl]amino]-N-(trideuteriomethyl)pyridazine-3-carboxamide To a solution of 6-chloro-4-[[3-methoxy-4-(1-methyl-1,2,4-triazol-3-yl)-2-pyridyl]amino]-N-(trideuteriomethyl)pyridazine-3-carboxamide (2.8 g, 7.4 mmol) and 1-isopropylimidazolidin-2-one (1.9 g, 15 mmol) in 1,4-dioxane (30 mL) was added cesium carbonate (4.8 g, 15 mmol), Pd₂(dba)₃ (2.0 g, 2.2 mmol), and Xantphos (2.6 g, 4.4 mmol). The mixture degassed by N₂ for 3 times and heated to 120° C. for 4 hrs. When reaction completed, filtered, filtrate was removed in vacuo, chromatography (PE/EtOAc=50/50 then DCM/MeOH=97/3) to give the desired product T 311 as a yellow solid (0.58 g, 17%). $^1$H NMR (400 MHz, CDCl₃) δ 12.20 (s, 1H), 10.16 (s, 1H), 8.28 (d, 1H), 8.22 (s, 1H), 8.14 (s, 1H), 7.51 (d, 1H), 4.43-4.32 (m, 1H), 4.23 (t, 2H), 4.00 (s, 3H), 3.51 (t, 2H), 1.23 (d, 6H). LM-MS: m/z=473.3 [M+H]$^+$

Example 161

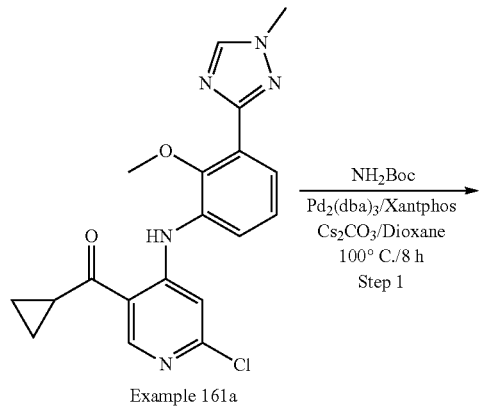

Example 161a

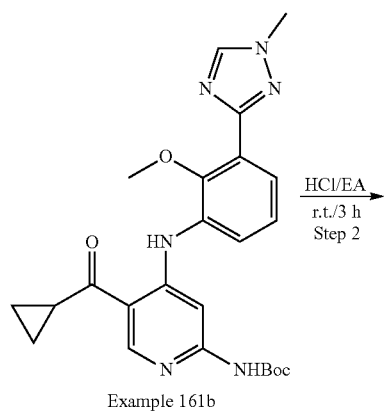

Example 161b

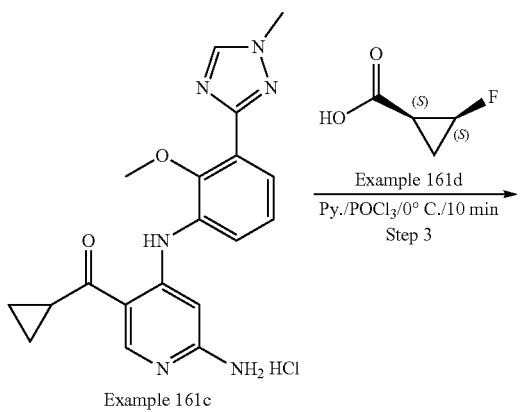

Example 161c

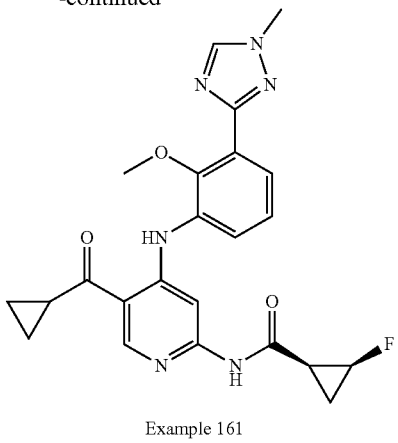

Example 161

Step 1: Example 161b

To a solution of Example 161a (383 mg, 1.0 mmol,) in dioxane (10 mL) were added NH₂Boc (176 mg, 1.5 mmol), Pd₂(dba)₃ (91 mg, 0.1 mmol), Xantphos (60 mg, 0.1 mmol) and Cs₂CO₃ (652 mg, 2.0 mmol). The mixture was sealed and heated to 100° C. for 8 h. The mixture was cooled to room temperature, diluted by EtOAc, washed by water, dried over anhydrous Na₂SO₄, and then concentrated under reduced pressure. The residue was purified by silica gel flash column chromatography, eluted with DCM/MeOH (10/1) to afford the product Example 161b (401 mg, 86.4% yield) as a yellow solid. LCMS [M+1]⁺=465.2.

Step 2: Example 161c

A solution of Example 169b (401 mg, 0.86 mmol) in HCl/EtOAc (2 mL) was stirred at room temperature for 3 h. Then the mixture was concentrated, and used at next step directly.

Step 3: Example 161

To a solution of Example 161c (40 mg, 0.1 mmol) and Example 161d (10.4 mg, 0.1 mmol) in pyridine (3 mL) was added POCl3 (77 mg, 0.5 mmol) at 0° C. The reaction mixture was stirred at 0° C. for 10 min. Then water (5 mL) was added dropwise, and the mixture was extracted with DCM (6 mL). The organic phase was dried over anhydrous Na₂SO₄, concentrated under reduced pressure. The residue was purified by Prep-HPLC to give Example 161 (12.1 mg, 26.9% yield) as a white solid. LCMS [M+1]⁺=451.2. ¹H NMR (400 MHz, DMSO-d₆) δ 11.01 (s, 1H), 10.95 (s, 1H), 9.11 (s, 1H), 8.53 (s, 1H), 8.00 (s, 1H), 7.63 (d, J=7.8 Hz, 1H), 7.51 (d, J=7.8 Hz, 1H), 7.25 (t, J=7.9 Hz, 1H), 4.97 (s, 1H), 4.80 (s, 1H), 3.92 (s, 3H), 3.67 (s, 3H), 2.98 (s, 1H), 2.19 (s, 1H), 1.58 (d, J=23.5 Hz, 1H), 1.21 (s, 2H), 1.10-1.00 (m, 4H).

Example 162

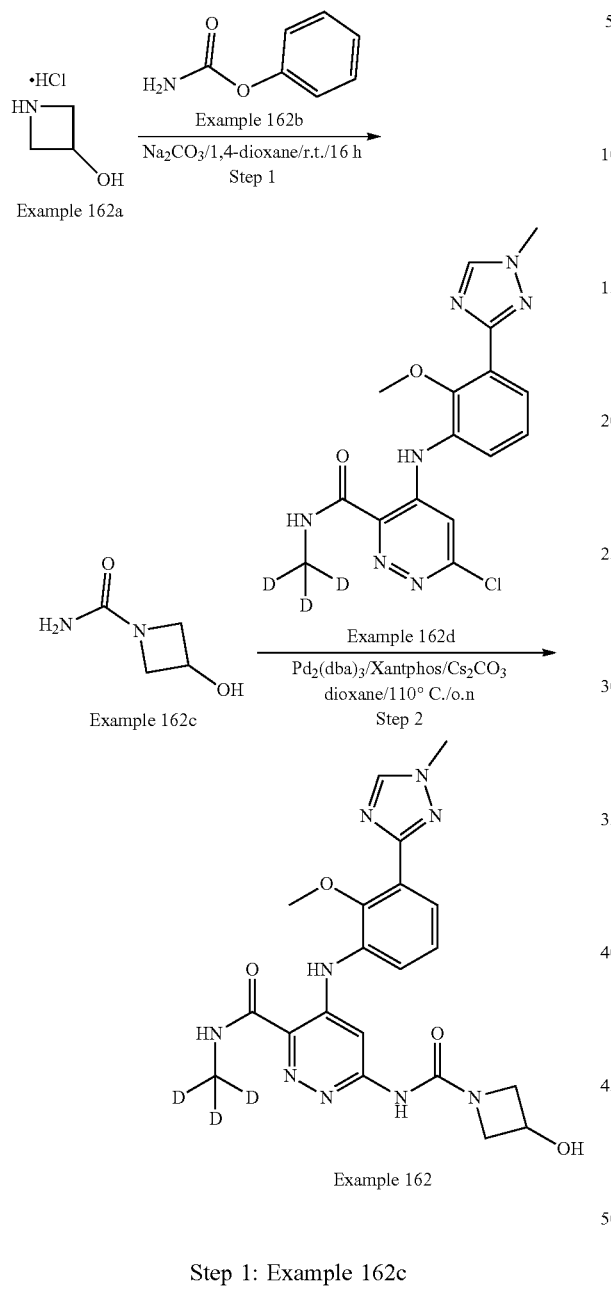

0.05 mmol) and $Cs_2CO_3$ (163 mg, 0.5 mmol). The mixture was degassed by nitrogen for 3 times and stirred at 110° C. for overnight. When completed, the reaction was cooled to r.t., diluted with MeOH (5 mL) and filtered. The filtrate was purified directly by Prep-HPLC to give the desired product Example 162 (2.7 mg, yield: 11.8%) as a off white solid. LCMS $[M+1]^+=457.2$. $^1$H NMR (400 MHz, DMSO-$d_6$) δ 10.90 (s, 1H), 9.67 (s, 1H), 9.00 (s, 1H), 8.54 (s, 1H), 8.00 (s, 1H), 7.62 (d, J=7.6 Hz, 1H), 7.49 (d, J=7.8 Hz, 1H), 7.25 (d, J=8.4 Hz, 1H), 5.62 (d, J=6.2 Hz, 1H), 4.38 (s, 1H), 4.17 (s, 2H), 3.93 (s, 3H), 3.76-3.69 (m, 5H).

Example 163

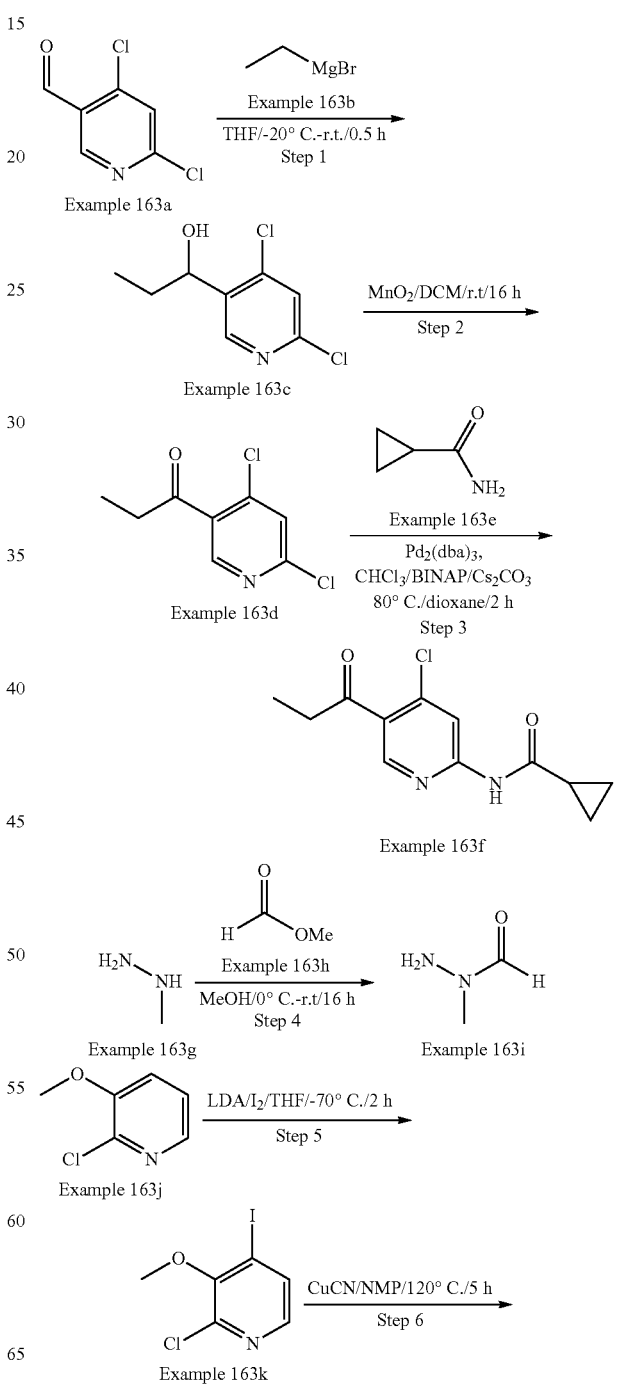

Step 1: Example 162c

A solution of Example 162a (800 mg, 17.34 mmol) in 1,4-dioxane (35 mL) was treated with Example 162b (1.0 g, 7.34 mmol) and $Na_2CO_3$ (1.2 g, 11.1 mmol). The mixture was stirred at r.t. for 16 h. After reaction completed, the solvent was concentrated, the residue was suspended in DCM (5 mL), sonicated and the resulting solid was collected via filtration, dried to afford the desired product Example 162c (300 mg, 35.3% yield) as a white solid.

Step 2: Example 162

To a solution of Example 162d (58 mg, 0.5 mmol) and Example 162c (94 mg, 0.25 mmol) in dioxane (3 mL) were added $Pd_2(dba)_3$ (46 mg, 0.05 mmol), Xantphos (30 mg,

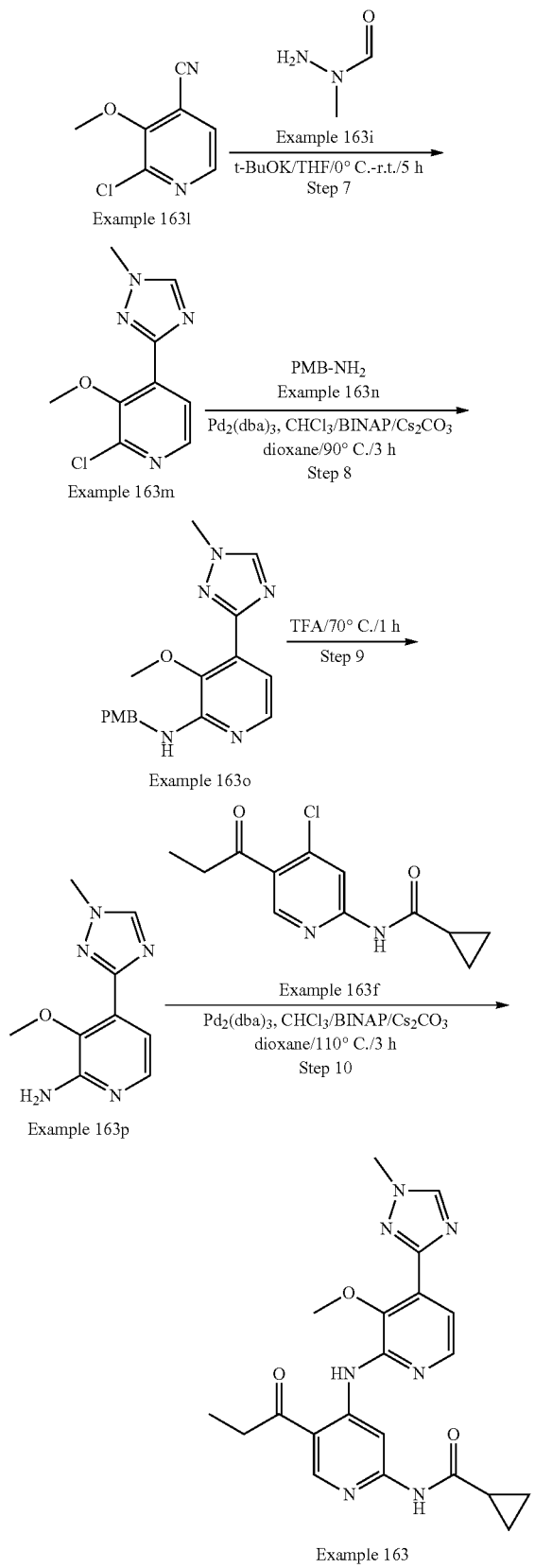

Step 1: Example 163c

To a solution of Example 163a (7.5 g, 43.0 mmol, 1.0 eq) in THF (100 mL) was added Example 163b (21.4 mL, 3.0 M in THF, 64.2 mmol, 1.5 eq) dropwise at ~20° C. under $N_2$ protection. The mixture was stirred at r.t. for 0.5 h. The reaction was quenched with saturated aqueous of $NH_4Cl$ (80 mL) and extracted with EtOAc (150 mL*2). The combined organic layers were washed with brine, dried over $Na_2SO_4$ and concentrated. The residue was purified by silica gel flash column chromatography (Petroleum Ether/EtOAc=5/1) to afford the product Example 163c (4.0 g, 45.8% yield) as yellow oil. LCMS [M+1]=206.1.

Step 2: Example 163d

To a solution of Example 163c (3.8 g, 18.0 mmol, 1.0 eq) in DCM (100 mL) was added $MnO_2$ (40.1 g, 450 mmol, 25.0 eq), and the reaction mixture was stirred at r.t. for 16 h. The reaction mixture was filtered and the filtrate was concentrated. The crude product was purified by silica gel flash column chromatography (Petroleum Ether/EtOAc=10/1) to afford the product Example 163d (2.5 g, 66.5% yield) as an off-white solid. LCMS $[M+1]^+$=204.1.

Step 3: Example 163f

To a solution of Example 163d (100 mg, 0.49 mmol, 1.0 eq) in dioxane (2.0 mL) were added $Cs_2CO_3$ (320 mg, 0.98 mmol, 2.0 eq), Example 163e (41.9 mg, 0.49 mmol, 1.0 eq), BINAP (61.3 mg, 0.098 mmol, 0.2 eq) and $Pd_2(dba)_3·CHCl_3$ (50.9 mg, 0.049 mmol, 0.1 eq). The reaction mixture was stirred for 2 h at 80° C. under $N_2$ protection. After cooling to r.t., the solvent was concentrated under vacuum. The residue was purified by silica gel flash column chromatography (Petroleum Ether/EtOAc=3/1) to afford the product Example 163f (60 mg, 48.4% yield) as a yellow solid. LCMS $[M+1]^+$=253.2.

Step 4: Example 163i

To a solution of Example 163g (28.0 g, 243.4 mmol, 1.0 eq) in MeOH (400 mL) at 0° C. (ice-water bath) was added Example 163h (16.0 g, 267.7 mmol, 1.1 eq) dropwise. After addition, the reaction was stirred at r.t. for 16 h. The solution was concentrated in vacuum and then swapped with THF (80 mL*4) to remove the MeOH residue. After removal of solvent by evaporation, Example 163i (15.0 g, 83.8% yield) was obtained as yellow oil.

Step 5: Example 163k

To a solution of Example 163j (40.0 g, 279.7 mmol, 1.0 eq) in dry THF (400 mL) was added LDA (181.8 mL, 2 M in THF, 363.6 mmol, 1.3 eq) at ~70° C. dropwise, which was stirred for additional 40 min at the same temperature after addition. $I_2$ (92.3 g, 363.6 mmol, 1.3 eq) in THF (100 mL) was added to the solution dropwise. After addition, the reaction was warmed to r.t. and stirred for 2 h. The mixture was quenched with saturated aqueous of $NH_4Cl$ (200 mL), extracted with EtOAc (200 mL*3). The combined organic layers were washed with brine, dried over $Na_2SO_4$ and concentrated in vacuum. The residue was purified by silica gel flash column chromatography (Petroleum Ether/EtOAc=80/1) to afford the desired product Example 163k (20.0 g, 26.6% yield) as a white solid. LCMS $[M+1]^+$=270.1.

Step 6: Example 163l

To a solution of Example 163k (15.0 g, 55.6 mmol, 1.0 eq) in NMP (50 mL) was added CuCN (9.9 g, 111.2 mmol, 2.0 eq), and the mixture was stirred for 5 h at 120° C. After cooling to room temperature, the mixture was diluted with EtOAc (200 mL) and filtered. The filtrate was washed with brine (50 mL*3), dried over Na$_2$SO$_4$ and concentrated in vacuum. The residue was purified by silica gel flash column chromatography (Petroleum Ether/EtOAc=50/1) to afford the desired product Example 163l (7.5 g, 80.1% yield) as a yellow solid. LCMS [M+1]$^+$=169.2.

Step 7: Example 163m

To a solution of Example 163l (5.0 g, 29.8 mmol, 1.0 eq) and Example 163i (4.4 g, 59.6 mmol, 2.0 eq) in THF (150 mL) was added t-BuOK (7.3 g, 65.6 mmol, 2.2 eq) in portions at 0° C. After addition, the mixture was warmed to r.t. and stirred for 5 h. The mixture was concentrated in vacuum. The residue was purified by silica gel flash column chromatography (Petroleum Ether/EtOAc=1/1) to afford the product Example 163m (2.6 g, 42.7% yield) as a white solid. LCMS [M+1]$^+$=225.2.

Step 8: Example 163o

To a solution of Example 163m (1.1 g, 4.9 mmol, 1.0 eq) in dioxane (20 mL) were added Cs$_2$CO$_3$ (3.26 g, 9.8 mmol, 2.0 eq), Example 163n (1.37 g, 5.39 mmol, 1.1 eq), BINAP (623 mg, 0.98 mmol, 0.2 eq) and Pd$_2$(dba)$_3$·CHCl$_3$ (517 mg, 0.49 mmol, 0.1 eq). The reaction mixture was stirred for 3 h at 90° C. under N$_2$ protection. After the reaction was completed, the solvent was removed, and the residue was purified by silica gel flash column chromatography (DCM/MeOH=20/1) to afford the product Example 163o (1.4 g, 89.3% yield) as a yellow solid. LCMS [M+1]$^+$=326.3.

Step 9: Example 163p

A solution of Example 163o (1.4 g, 4.29 mmol, 1.0 eq) in TFA (20 mL) was stirred for 1 h at 70° C. After the reaction was completed, it was concentrated in vacuum. The residue was dissolved in MeOH (20 mL) and basified with NaHCO$_3$ (910 mg, 8.58 mmol, 2.0 eq). The solid was filtered out, and the filtrate was concentrated in vacuum. The residue was purified by silica gel flash column chromatography (DCM/MeOH=20/1) to afford the product Example 163p (750 mg, 84.9% yield) as a light gray solid. [M+1]$^+$=206.2.

Step 10: Example 163

To a solution of Example 163f (22 mg, 0.11 mmol, 1.0 eq) and Example 163p (30 mg, 0.12 mmol, 0.9 eq) in dioxane (2 mL) were added Cs$_2$CO$_3$ (77.3 mg, 0.22 mmol, 2.0 eq), Pd$_2$(dba)$_3$·CHCl$_3$ (12.3 mg, 0.011 mmol, 0.1 eq) and BINAP (15.0 mg, 0.022 mmol, 0.2 eq). The reaction mixture was stirred for 3 h at 110° C. under N$_2$ protection. The reaction solution was filtered and the filtrate was concentrated in vacuo. The crude product was purified by Prep-TLC (DCM/MeOH=30/1) to afford the desired product Example 163 (13.8 mg, 27.6% yield) as a light yellow solid. LCMS [M+1]$^+$=422.3. $^1$H NMR (300 MHz, DMSO-d$_6$) δ 12.36 (s, 1H), 10.91 (s, 1H), 9.71 (s, 1H), 8.96 (s, 1H), 8.67 (s, 1H), 8.14 (d, J=5.4 Hz, 1H), 7.50 (d, J=5.1 Hz, 1H), 4.00 (s, 3H), 3.92 (s, 3H), 3.16 (q, J=7.2 Hz, 2H), 2.12-2.04 (m, 1H), 1.15 (t, J=7.2 Hz, 3H), 0.89-0.82 (m, 4H).

Example 164

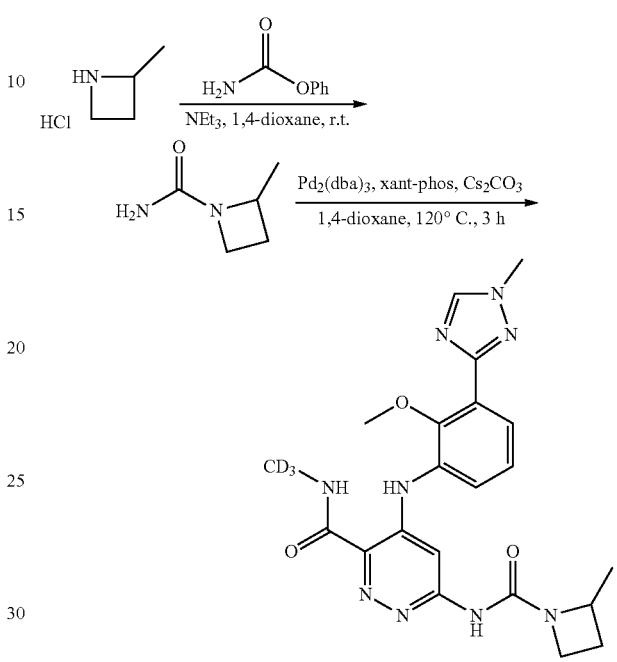

Step 1: 2-methylazetidine-1-carboxamide

To a solution of 2-methylazetidine hydrochloride (120 mg, 1.12 mmol), phenyl carbamate (184 mg, 1.34 mmol) in 1,4-dioxane (20 mL) was added NEt$_3$ (0.5 mL, 3.36 mmol) and stirred at r.t. for 16 hrs. After reaction completed, the solvent was concentrated, the residue was suspended in DCM (5 mL), sonicated and the resulting solid was collected via filtration, dried to afford the desired product (150 mg, 89%) as a white solid. LM-MS: m/z=115.1 [M+H]+

Step 2: 4-((2-methoxy-3-(1-methyl-1H-1,2,4-triazol-3-yl)phenyl)amino)-N-(methyl-d3)-6-(2-methylazetidine-1-carboxamido)pyridazine-3-carboxamide To a solution of 6-chloro-4-((2-methoxy-3-(1-methyl-1H-1,2,4-triazol-3-yl) phenyl)amino)-N-(methyl-d3)pyridazine-3-carboxamide (244.7 mg, 0.65 mmol) and 2-methylazetidine-1-carboxamide (150 mg, 1.0 mmol) in 1,4-dioxane (10 mL) was added Pd$_2$(dba)$_3$ (60 mg, 0.065 mmol), XantPhos (75 mg, 0.13 mmol) and Cs$_2$CO$_3$ (635 mg, 1.95 mmol). The mixture was sealed, degassed by nitrogen for 3 times and stirred at 120° C. for 4 hrs. When completed, the reaction was cooled to r.t. and filtered. The filtrate was purified directly by prep-HPLC to give the racemic product (125 mg, yield: 42%) as a white solid. LM-MS: m/z=455.3[M+H]$^+$ The racemic compound was separated by SFC, and got enantiomer A (49.5 mg, R.T.: 3.008 min). $^1$H NMR (400 MHz, CDCl$_3$) δ 11.19 (s, 1H), 8.15 (s, 1H), 8.10 (s, 1H), 7.93 (s, 1H), 7.82 (dd, 1H), 7.53 (dd, 1H), 7.31-7.24 (m, 2H), 4.53 (dd, 1H), 4.17-4.01 (m, 2H), 4.00 (s, 3H), 3.82 (s, 3H), 2.53-2.36 (m, 1H), 1.98-1.83 (m, 1H), 1.50 (d, 3H). ee %=100%; LM-MS: m/z=455.3[M+H]+ enantiomer B (49.9 mg, R.T.: 4.240 min). ¹H NMR (400 MHz, CDCl₃) δ 11.13 (s, 1H), 8.13 (s, 1H), 8.09 (s, 1H), 7.96 (s, 1H), 7.80 (dd, 1H), 7.53 (d, 1H), 7.32-7.21 (m, 2H), 4.52 (dd, 1H), 4.14-4.02 (m, 2H), 4.00 (s, 3H), 3.82 (s, 3H), 2.57-2.35 (m, 1H), 2.05-1.81 (m, 1H), 1.50 (d, 3H). ee %=100%; LM-MS: m/z=455.3 [M+H]+

Example 165

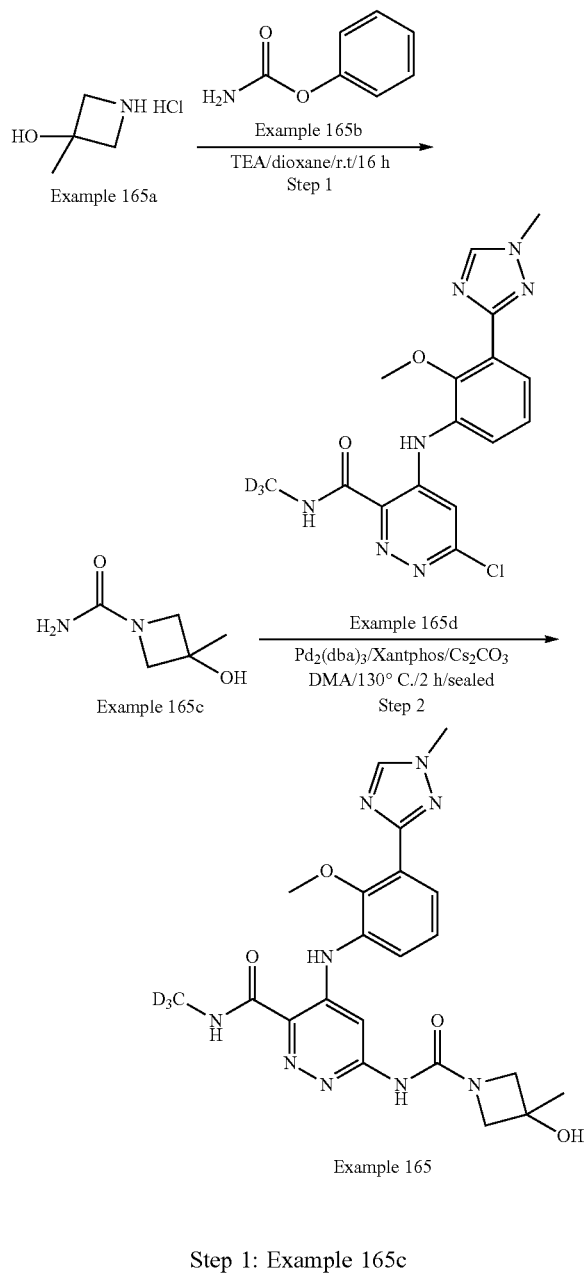

Step 1: Example 165c

To a solution of Example 165a (270 mg, 3.1 mmol) in dioxane (5 mL) were added Example 165b (500 mg, 3.64 mmol), and TEA (795 mg, 7.87 mmol). The reaction mixture was stirred at room temperature overnight. Then the mixture was diluted with EtOAc, washed by water, brine, and dried over anhydrous Na₂SO₄. The solution was concentrated to afford crude Example 165c (200 mg, 49.6% yield) and used directly for next step.

Step 2: Example 165

To a solution of Example 165d (100 mg, 0.26 mmol) and Example 165c (120 mg, 0.92 mmol) in DMA (2.5 mL) were added Pd₂(dba)₃ (24 mg, 0.026 mmol), xantphos (30 mg, 0.052 mmol) and Cs₂CO₃ (340 mg, 1.04 mmol). The mixture was degassed by nitrogen for 3 times and stirred at 130° C. for 2 h. When completed, the reaction was cooled to r.t., diluted with MeOH (5 mL) and filtered. The filtrate was purified directly by Prep-HPLC to give the desired product Example 165 (46.0 mg, 37.6% yield) as a white solid. LCMS [M+1]+=471.50. ¹H NMR (400 MHz, DMSO-d₆) δ 10.89 (s, 1H), 9.67 (s, 1H), 8.99 (s, 1H), 8.54 (s, 1H), 8.01 (s, 1H), 7.62 (d, J=7.9 Hz, 1H), 7.48 (d, J=7.9 Hz, 1H), 7.24 (s, 1H), 5.54 (s, 1H), 3.93 (s, 3H), 3.83 (br, 4H), 3.71 (s, 3H), 1.33 (s, 3H).

Example 166

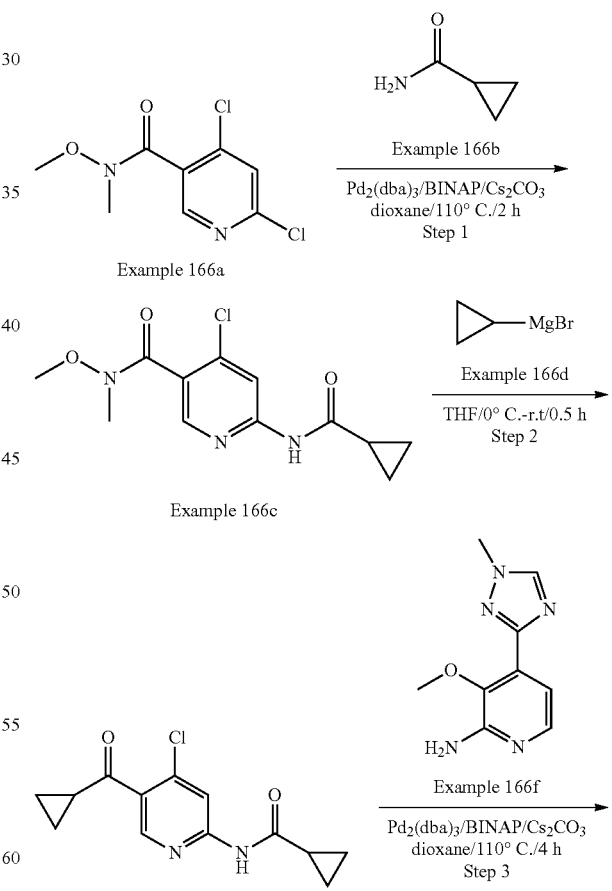

7.49 (d, J=5.1 Hz, 1H), 3.99 (s, 3H), 3.86 (s, 3H), 3.11-2.96 (m, 1H), 2.15-2.04 (m, 1H), 1.19-1.03 (m, 4H), 0.92-0.80 (m, 4H).

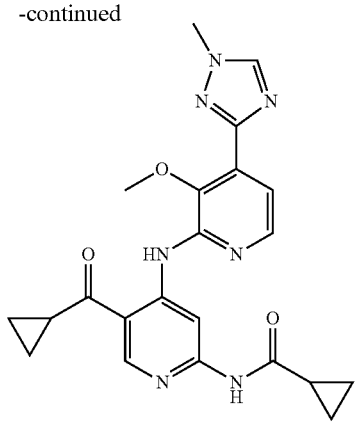

Example 166

Step 1: Example 166c

To a solution of Example 166a (2.0 g, 8.0 mmol, 1.0 eq) in dioxane (20 mL) were added $Cs_2CO_3$ (5.2 g, 16 mmol, 2.0 eq), Example 166b (1.36 g, 16 mmol, 2.0 eq), BINAP (997 mg, 1.6 mmol, 0.2 eq) and $Pd_2(dba)_3 \cdot CHCl_3$ (800 mg, 0.8 mmol, 0.1 eq). The reaction mixture was stirred for 2 h at 110° C. under $N_2$ protection. After cooled to room temperature, the solvent was removed. The crude product was purified by silica gel flash column chromatography (Petroleum Ether/EtOAc=1/1) to afford the product Example 166c (1.9 g, 86% yield) as yellow oil. LCMS [M+1]$^+$=284.2.

Step 2: Example 166e

To a solution of Example 166c (1.9 g, 7.0 mmol, 1.0 eq) in THF (20 mL) was added Example 166d (210 mL, 1.0 M in THF, 210 mmol, 30.0 eq) dropwise at 0° C. under $N_2$ protection. The mixture was stirred for 0.5 h at r.t. The reaction was poured into saturated aqueous of $NH_4Cl$ (200 mL) and extracted with EtOAc (150 mL*3). The combined organic layer were washed with brine, dried over $Na_2SO_4$ and concentrated. The crude product was purified by silica gel flash column chromatography (Petroleum Ether/EtOAc=2/1) to afford the product Example 166e (850 mg, 47% yield) as a yellow solid. LCMS [M+1]$^+$=265.2.

Step 3: Example 166

To a solution of Example 166e (650 mg, 2.33 mmol, 1.2 eq) in dioxane (10 mL) were added $Cs_2CO_3$ (1.3 g, 3.88 mmol, 2.0 eq), Example 166f (400 mg, 1.94 mmol, 1.0 eq), BINAP (241.7 mg, 0.388 mmol, 0.2 eq) and $Pd_2(dba)_3 \cdot CHCl_3$ (200.8 mg, 0.194 mmol, 0.1 eq). The reaction mixture was stirred for 4 h at 110° C. under $N_2$ protection. After cooled to room temperature, the solvent was removed. The crude product was purified by silica gel flash column chromatography (DCM/MeOH=20/1) to obtained 580 mg crude product (90% purity), which was further purified by Prep-HPLC (Prep-C18, 5 µM XBridge column, 19×150 mm, Waters; gradient elution of 35% MeCN in water to 55% MeCN in water over a 7 min period, where the aqueous phase contains 10 mM $NH_4HCO_3$+0.5% ammonia) to afford the product Example 166 (401.4 mg, 48% yield) as a white solid. LCMS [M+1]$^+$=434.4. $^1$H NMR (300 MHz, DMSO-d$_6$) δ 12.30 (s, 1H), 10.94 (s, 1H), 9.70 (s, 1H), 9.21 (s, 1H), 8.66 (s, 1H), 8.13 (d, J=5.1 Hz, 1H),

Example 169

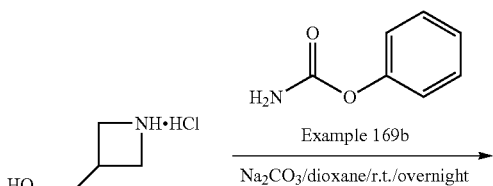

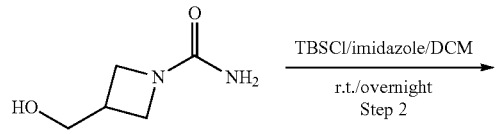

Example 169d

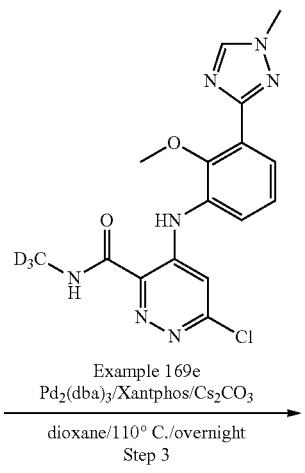

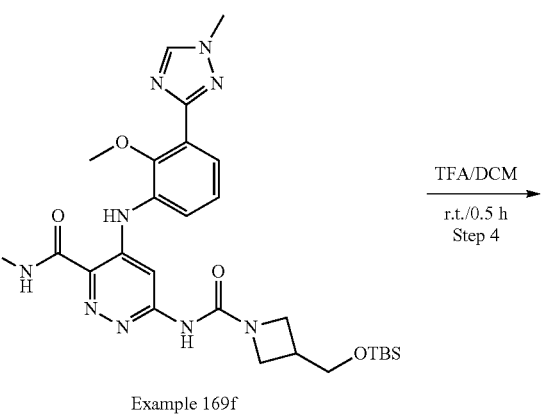

Example 169f

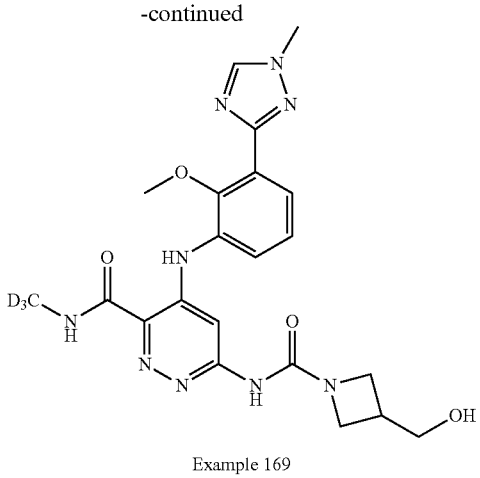

Example 169

Step 1: Example 169c

To a solution of Example 169a (123 mg, 1.0 mmol) and Example 169b (206 mg, 1.5 mmol) in dioxane (3 mL) was added $Na_2CO_3$ (212 mg, 2.0 mmol). The reaction mixture was stirred at r.t. overnight. The mixture was filtrated, the solid was washed by DCM, and the combined filtrate was used directly at next step.

Step 2: Example 169d

To a solution of Example 169c was added imidazole (350 mg, 5.0 mmol) in portions, followed by addition of TBSCl (300 mg, 2.0 mmol). The reaction mixture was stirred at room temperature overnight. The mixture was concentrated, and the crude product was purified by silica gel flash column chromatography, eluted with (DCM/MeOH=30/1) to afford the product Example 169d (60 mg, 24.5% yield) as a white solid.

Step 3: Example 169f

To a solution of Example 169d (60 mg, 0.26 mmol) in dioxane (5 mL) were added Example 169e (100 mg, 0.26 mmol), $Pd_2(dba)_3$ (24 mg, 0.027 mmol), Xantphos (16 mg, 0.027 mmol) and $Cs_2CO_3$ (130 mg, 0.40 mmol). The mixture was sealed and heated to 110° C. for overnight. The mixture was filtrated and concentrated under reduced pressure to give crude Example 169f (190 mg, quant.).

Step 4: Example 169

To a solution of Example 169f (130 mg, crude, 0.22 mmol) in DCM (4 mL) was added TFA (1 mL). The mixture was stirred at r.t. for 30 min. The mixture was concentrated under reduced pressure, and the residue was purified by Prep-HPLC (Prep-C18, 5 μM XBridge column, 19×150 mm, Waters; gradient elution of 35% MeCN in water to 55% MeCN in water over a 7 min period, where the aqueous phase contains 10 mM $NH_4HCO_3$+0.5% ammonia) to give Example 169 (2 mg, 1.9% yield over 2 steps) as a white solid. LCMS [M+1]$^+$=471.2. $^1$H NMR (300 MHz, CDCl$_3$) δ 10.94 (s, 1H), 8.11-8.03 (m, 3H), 7.77 (d, J=8.0 Hz, 1H), 7.51 (d, J=8.0 Hz, 1H), 4.14 (br, 2H), 4.00 (s, 3H), 3.90 (s, 2H), 3.80 (s, 5H), 2.83 (br, 1H), 1.25 (s, 1H).

Example 171

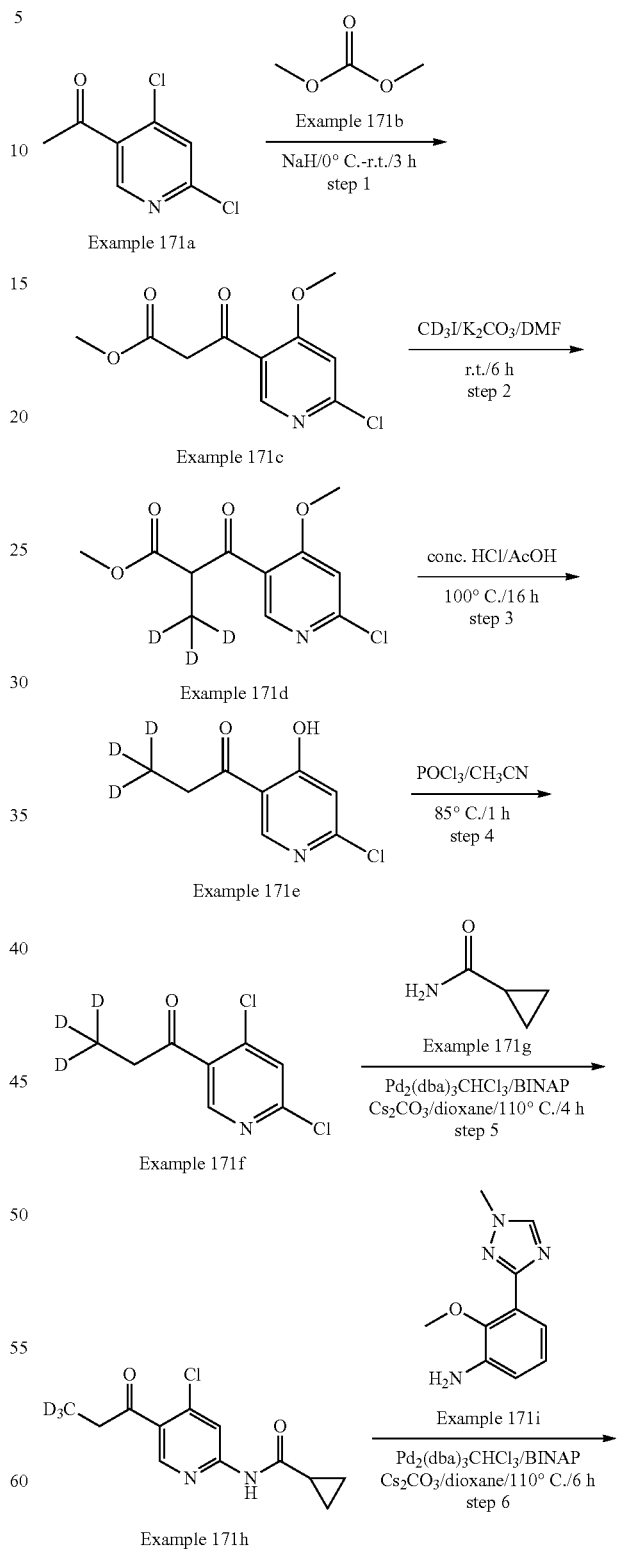

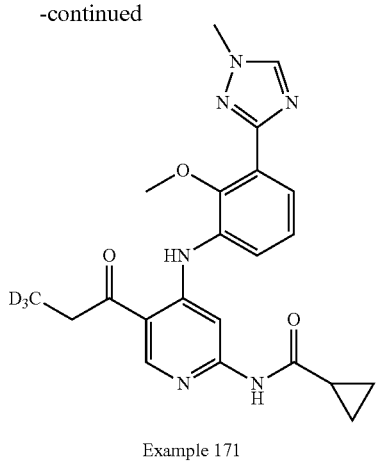

Example 171

Step 1: Example 171c

To a solution of Example 171a (5.0 g, 26.3 mmol, 1.0 eq) in Example 171b (50 mL) was added NaH (3.15 g, 60% in mineral oil, 78.9 mmol, 3.0 eq) in portions at 0° C. The reaction mixture was stirred at r.t. for 3 h. The reaction mixture was diluted with EtOAc (100 mL), quenched with 2 N aqueous HCl (15 mL), washed with brine (50 mL), dried over $Na_2SO_4$ and concentrated. The crude product was purified by silica gel flash column chromatography (Petroleum Ether/EtOAc=3/1) to give the desired product Example 171c (4.1 g, 64.0% yield) as a light yellow solid. LCMS $[M+1]^+$=244.2.

Step 2: Example 171d

To a solution of Example 171c (4.1 g, 16.80 mmol, 1.0 eq) and $K_2CO_3$ (2.55 g, 18.48 mmol, 1.1 eq) in DMF (50 mL) was added $CD_3I$ (2.68 g, 18.48 mmol, 1.1 eq) at 0° C. The reaction mixture was stirred at r.t. for 6 h. The mixture was diluted with EtOAc (100 mL) and washed with brine (50 mL*3). The organic layer was dried by $Na_2SO_4$ and concentrated. The crude product was purified by silica gel flash column chromatography (Petroleum ether/EtOAc=3/1) to give the desired product Example 171d (2.83 g, 64.5% yield) as colorless oil. LCMS $[M+1]^+$=261.1.

Step 3: Example 171e

To a solution of Example 171d (2.83 g, 10.84 mmol, 1.0 eq) in AcOH (20 mL) was added conc. HCl (40 mL). The reaction solution was heated at 100° C. for 16 h. After cooled to r.t., the mixture was concentrated, diluted with $H_2O$ (20 mL) and extracted with EtOAc (30 mL*3). The combined organic layer was washed with brine (50 mL), dried by $Na_2SO_4$ and concentrated. The crude product was purified by silica gel flash column chromatography (Petroleum ether/EtOAc=3/1) to give the desired product Example 171e (1.12 g, 54.7% yield) as a white solid. LCMS $[M+1]^+$=189.2.

Step 4: Example 171f

To a solution of Example 171e (1.12 g, 5.94 mmol, 1.0 eq) in $CH_3CN$ (15 mL) was added $POCl_3$ (2 mL). The reaction solution was heated at 85° C. for 1 h. After cooled to r.t., the mixture was concentrated and diluted with EtOAc (5 mL). The solution was added to a mixed solution of EtOAc (20 mL) and saturated aqueous $NaHCO_3$ (20 mL). After separation, the aqueous layer was extracted with EtOAc (20 mL*3). The combined organic layer was washed with brine (20 mL), dried by $Na_2SO_4$ and concentrated. The crude product was purified by silica gel flash column chromatography (Petroleum ether/EtOAc=8/1) to give the desired product Example 171f (1.05 g, 85.4% yield) as a white solid. LCMS $[M+1]^+$=207.1.

Step 5: Example 171h

To a solution of Example 171f (100 mg, 0.48 mmol, 1.0 eq) in dioxane (4 mL) were added Example 171g (37 mg, 0.43 mmol, 0.9 eq), $Cs_2CO_3$ (315 mg, 0.97 mmol, 2.0 eq), BINAP (30 mg, 0.048 mmol, 0.1 eq) and $Pd_2(dba)_3 \cdot CHCl_3$ (50 mg, 0.048 mmol, 0.1 eq). The reaction mixture was stirred for 4 h at 110° C. under $N_2$. The mixture was filtered and the filtrate was concentrated. The crude product was purified by prep-TLC (Petroleum ether/EtOAc=3/1) to give the desired product Example 171h (40.0 mg, 32.4% yield) as a light yellow solid. LCMS $[M+1]^+$=256.3.

Step 6: Example 171

To a solution of Example 171h (40 mg, 0.16 mmol, 1.0 eq) in dioxane (3 mL) were added Example 171i (29 mg, 0.14 mol, 0.9 eq), $Cs_2CO_3$ (102 mg, 0.31 mmol, 2.0 eq), BINAP (10 mg, 0.016 mmol, 0.1 eq) and $Pd_2(dba)_3 \cdot CHCl_3$ (16 mg, 0.016 mmol, 0.1 eq). The reaction solution was stirred for 6 h at 110° C. under $N_2$. The reaction mixture was filtered and the filtrate was concentrated. The crude product was purified by prep-TLC (DCM/MeOH=20/1) to give the desired product Example 171 (8.2 mg, 12.3% yield) as an off-white solid. LCMS $[M+1]^+$=424.3. $^1$H NMR (300 MHz, DMSO-$d_6$) δ 11.05 (s, 1H), 10.90 (s, 1H), 8.89 (s, 1H), 8.57 (s, 1H), 8.03 (s, 1H), 7.65 (dd, J=7.8, 1.8 Hz, 1H), 7.53 (dd, J=7.8, 1.8 Hz, 1H), 7.26 (d, J=7.8 Hz, 1H), 3.96 (s, 3H), 3.72 (s, 3H), 3.11 (s, 2H), 2.07-1.96 (m, 1H), 0.79 (d, J=6.0 Hz, 4H).

Example 172

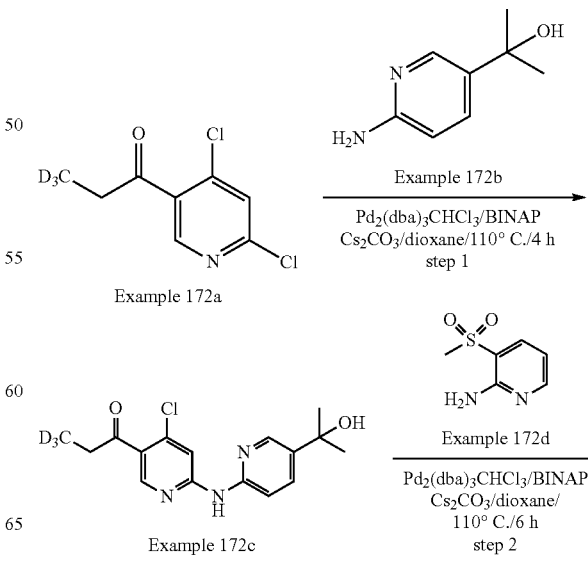

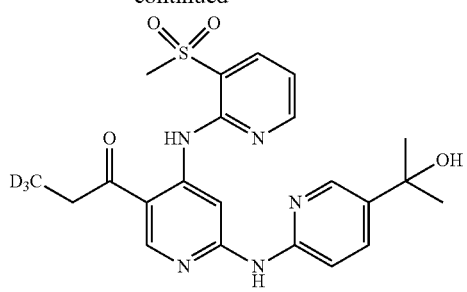

Example 172

Step 1: Example 172c

To a solution of Example 172a (150 mg, 0.72 mmol, 1.0 eq) in dioxane (5 mL) were added Example 172b (88 mg, 0.58 mmol, 0.8 eq), Cs$_2$CO$_3$ (472 mg, 1.45 mmol, 2.0 eq), BINAP (45 mg, 0.072 mmol, 0.1 eq) and Pd$_2$(dba)$_3$CHCl$_3$ (75 mg, 0.072 mmol, 0.1 eq). The reaction mixture was stirred for 4 h at 110° C. under N$_2$. The mixture was filtered and the filtrate was concentrated. The crude product was purified by prep-TLC (Petroleum Ether/EtOAc=1/1) to give the desired product Example 172c (62 mg, 26.5% yield) as a yellow solid. LCMS [M+1]$^+$=323.3.

Step 2: Example 172

To a solution of Example 172c (62 mg, 0.19 mmol, 1.0 eq) in dioxane (5 mL) were added Example 172d (33 mg, 0.19 mol, 1.0 eq), Cs$_2$CO$_3$ (126 mg, 0.39 mmol, 2.0 eq), BINAP (24 mg, 0.039 mmol, 0.2 eq) and Pd$_2$(dba)$_3$CHCl$_3$ (20 mg, 0.019 mmol, 0.1 eq). The reaction mixture was stirred for 6 h at 110° C. under N$_2$. The mixture was filtered and the filtrate was concentrated. The crude product was purified by prep-TLC (DCM/MeOH=20/1) to give the desired product Example 172 (16.1 mg, 18.3% yield) as a white solid. LCMS [M+1]$^+$=459.3. $^1$H NMR (300 MHz, DMSO-d$_6$) δ 11.96 (s, 1H), 10.02 (s, 1H), 8.95 (s, 1H), 8.92 (s, 1H), 8.67 (dd, J=4.8, 2.1 Hz, 1H), 8.34 (d, J=2.4 Hz, 1H), 8.28 (dd, J=7.8, 2.1 Hz, 1H), 7.78 (dd, J=8.7, 2.4 Hz, 1H), 7.68 (d, J=8.7 Hz, 1H), 7.33 (dd, J=7.8, 4.8 Hz, 1H), 5.07 (s, 1H), 3.34 (s, 3H), 3.08 (s, 2H), 1.45 (s, 6H).

Example 173

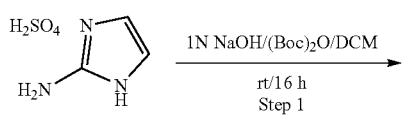

Example 173a

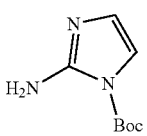

Example 173b

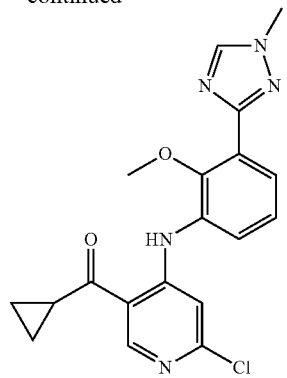

Example 173c

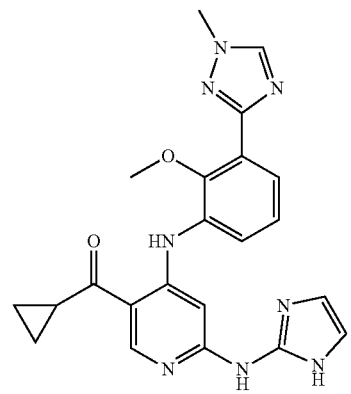

Example 173

Step 1: Example 173b

To a solution of Example 173a (1.0 g, 3.7 mmol, 1.0 eq) in NaOH aqueous solution (11.1 mL, 1M, 11.1 mmol, 3.0 eq) was added (Boc)$_2$O (1.29 g, 5.92 mmol, 1.6 eq) in DCM (11.1 mL). The reaction mixture was stirred for 16 h at r.t. Upon completion of the reaction, two phases were separated. The organic layer was washed with water (10 mL), dried over Na$_2$SO$_4$ and concentrated. The residue was purified by silica gel flash column chromatography, eluted with Petroleum Ether/EtOAc (1/1) to afford the product Example 173b (505 mg, 74% yield) as a yellow solid. LCMS [M+1]$^+$=184.2.

Step 2: Example 173

To a solution of Example 173c (150 mg, 0.39 mmol, 1.0 eq,) in dioxane (5 mL) were added Cs$_2$CO$_3$ (254.3 mg, 0.78 mmol, 2.0 eq), Example 173b (143.5 mg, 0.78 mmol, 2.0 eq), BINAP (48.6 mg, 0.078 mmol, 0.2 eq) and Pd$_2$(dba)$_3$·CHCl$_3$ (40.4 mg, 0.039 mmol, 0.1 eq). The reaction mixture was stirred for 3 h at 110° C. under N$_2$ protection. After cooled to room temperature, the solvent was removed. The crude product was purified by Prep-TLC (DCM/MeOH=10/1) to afford the crude product 42 mg (90% purity), which was purified by Prep-HPLC (Prep-C18, 5 μM XBridge column, 19×150 mm, Waters; gradient elution of 35% MeCN in water to 55% MeCN in water over a 7 min period, where the aqueous phase contains 10 mM NH₄HCO₃+0.5% ammonia) to afford the product to afford the product Example 173 (14.2 mg, 8% yield) as a white solid. LCMS [M+1]⁺=431.3. ¹H NMR (300 MHz, DMSO-d₆) δ 11.48 (br, 1H), 10.97 (s, 1H), 10.22 (br, 1H), 9.04 (s, 1H), 8.56 (s, 1H), 7.66-7.52 (m, 2H), 7.26 (t, J=7.8 Hz, 1H), 7.01 (br, 1H), 6.74 (br, 2H), 3.95 (s, 3H), 3.72 (s, 3H), 2.97-2.81 (m, 1H), 1.18-0.93 (m, 4H).

Example 174

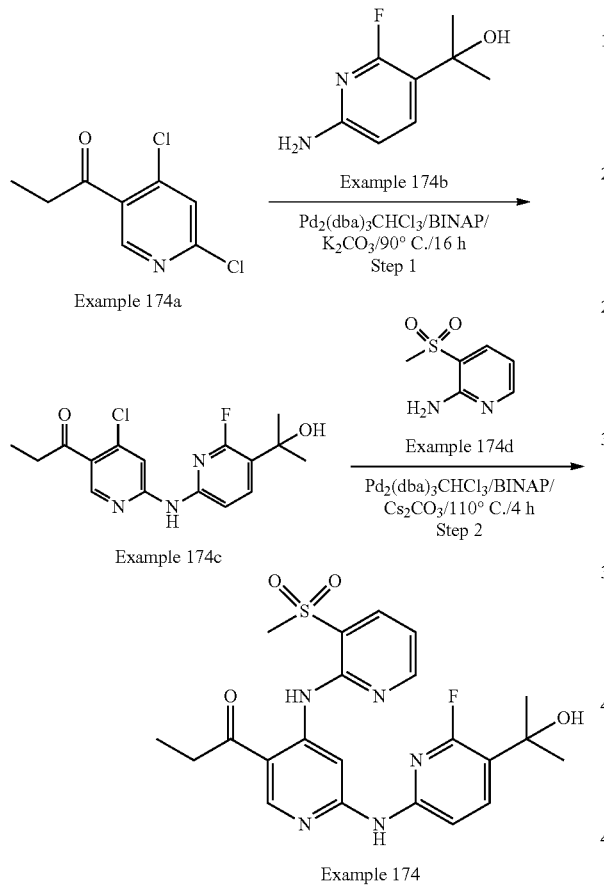

Step 1: Example 174c

To a solution of Example 174a (500 mg, 2.45 mmol) in dioxane (20 mL) were added Example 174b (417 mg, 2.45 mmol), K₂CO₃ (676 mg, 4.9 mmol), BINAP (304 mg, 0.49 mmol) and Pd₂(dba)₃CHCl₃ (252 mg, 0.25 mmol). The reaction mixture was stirred at 90° C. for 16 h under N₂. The reaction mixture was concentrated and the crude was purified by silica gel flash column chromatography (Petroleum Ether/EtOAc=2/1) to afford the product Example 174c (170 mg, 20.5% yield) as a yellow solid. LCMS [M+1]⁺=338.2.

Step 2: Example 174

To a mixture of Example 174c (170 mg, 0.5 mmol) in dioxane (5 mL) were added Example 174d (86 mg, 0.5 mmol), Cs₂CO₃ (326 mg, 1.0 mmol), BINAP (125 mg, 0.1 mmol) and Pd₂(dba)₃CHCl₃ (51 mg, 0.05 mmol). The reaction mixture was stirred at 110° C. for 4 h under N₂. The reaction mixture was concentrated and the residue was purified by Prep-TLC (DCM/EtOAc=1/2) to afford the product Example 174 (66.6 mg, 28.0% yield) as a white solid. LCMS [M+1]⁺=474.3. ¹H NMR (300 MHz, DMSO-d₆) δ12.00 (s, 1H), 10.25 (s, 1H), 9.02 (s, 1H), 8.95 (s, 1H), 8.66 (dd, J=4.8, 2.1 Hz, 1H), 8.29 (dd, J=7.8, 2.1 Hz, 1H), 7.99 (dd, J=10.8, 8.1 Hz, 1H), 7.60 (dd, J=8.4, 1.8 Hz, 1H), 7.35 (dd, J=7.8, 1.5 Hz, 1H), 5.29 (s, 1H), 3.34 (s, 3H), 3.11 (q, J=7.2 Hz, 2H), 1.48 (s, 6H), 1.13 (t, J=7.2 Hz, 3H).

Example 175

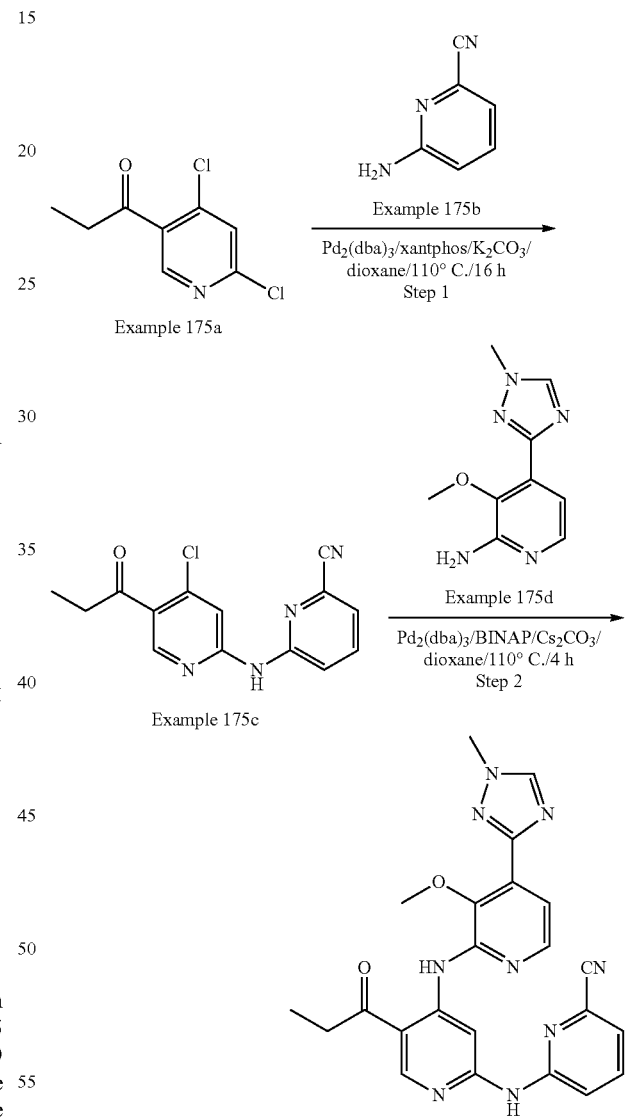

Step 1: Example 175c

To a solution of Example 175a (500 mg, 2.46 mmol, 1.0 eq) in dioxane (10 mL) were added K₂CO₃ (680 mg, 4.93 mmol, 2.0 eq), Example 175b (293 mg, 2.46 mmol, 1.0 eq), Xantphos (285 mg, 0.493 mmol, 0.2 eq) and Pd₂(dba)₃·CHCl₃ (255 mg, 0.246 mmol, 0.1 eq). The reaction mixture was stirred for 16 h at 110° C. under N₂ protection. After the reaction was completed, the solvent was concentrated, and the crude product was purified by silica gel flash column chromatography, eluted with (DCM/MeOH=30/1) to afford the product Example 175c (380 mg, 53.8% yield) as a yellow solid. LCMS [M+1]⁺=287.1.

Step 2: Example 175

To a solution of Example 175c (300 mg, 1.05 mmol, 1.0 eq) in dioxane (6 mL) were added Cs₂CO₃ (683.9 mg, 2.10 mmol, 2.0 eq), Example 175d (193.5 mg, 0.94 mmol, 0.9 eq), BINAP (130.7 mg, 0.21 mmol, 0.2 eq) and Pd₂(dba)₃·CHCl₃ (108.5 mg, 0.105 mmol, 0.1 eq). The reaction mixture was stirred for 4 h at 110° C. under N₂ protection. After cooled to room temperature, the solvent was removed. The crude product was purified by silica gel flash column chromatography, eluted with (DCM/MeOH=20/1) to afford the product 160 mg (crude, 80% purity), which was further purified by Prep-HPLC (Prep-C18, 5 µM XBridge column, 19×150 mm, Waters; gradient elution of 35% MeCN in water to 55% MeCN in water over a 7 min period, where the aqueous phase contains 10 mM NH₄HCO₃+0.5% ammonia) to afford the product Example 175 (58.3 mg, 12.2% yield) as a yellow solid. LCMS [M+1]+=456.3. ¹H NMR (300 MHz, DMSO-d₆) δ 12.49 (s, 1H), 10.53 (s, 1H), 9.78 (s, 1H), 8.96 (s, 1H), 8.68 (s, 1H), 8.36 (d, J=5.4 Hz, 1H), 7.92 (t, J=8.1 Hz, 1H), 7.82 (d, J=8.4 Hz, 1H), 7.59 (d, J=7.2 Hz, 1H), 7.50 (d, J=5.1 Hz, 1H), 4.01 (s, 3H), 3.94 (s, 3H), 3.17 (q, J=7.2 Hz, 2H), 1.17 (t, J=7.2 Hz, 3H).

Example 176

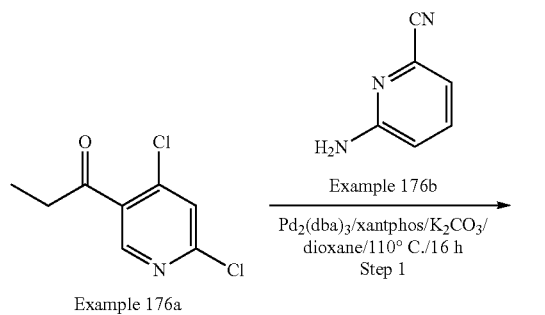

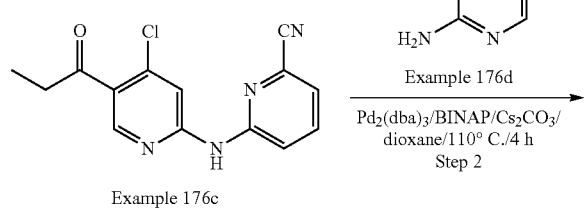

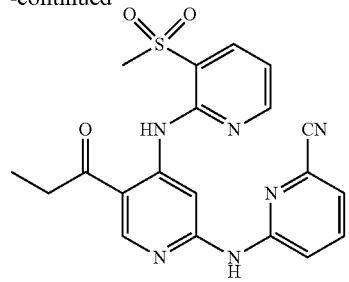

Example 176

Step 1: Example 176c

To a solution of Example 176a (500 mg, 2.46 mmol, 1.0 eq) in dioxane (10 mL) were added K₂CO₃ (680 mg, 4.93 mmol, 2.0 eq), Example 176b (293 mg, 2.46 mmol, 1.0 eq), Xantphos (285 mg, 0.493 mmol, 0.2 eq) and Pd₂(dba)₃·CHCl₃ (255 mg, 0.246 mmol, 0.1 eq). The reaction mixture was stirred for 16 h at 110° C. under N₂ protection. The solvent was concentrated. The crude product was purified by silica gel flash column chromatography, eluted with (DCM/MeOH=30/1) to afford the product Example 176c (310 mg, 44% yield) as a yellow solid. LCMS [M+1]⁺=287.1.

Step 2: Example 176

To a solution of Example 176c (310 mg, 1.084 mmol, 1.0 eq) in dioxane (6 mL) were added Cs₂CO₃ (683.9 mg, 2.168 mmol, 2.0 eq), Example 176d (167.8 mg, 0.975 mmol, 0.9 eq), BINAP (130.7 mg, 0.217 mmol, 0.2 eq) and Pd₂(dba)₃·CHCl₃ (112.2 mg, 0.108 mmol, 0.1 eq). The reaction mixture was stirred for 4 h at 110° C. under N₂ protection. After cooled to room temperature, the solvent was removed. The crude product was purified by silica gel flash column chromatography, eluted with (DCM/MeOH=15/1) to afford the crude product 120 mg (80% purity) and further purified by Prep-HPLC to afford the product Example 176 (61.1 mg, 13% yield) as an off-white solid. LCMS [M+1]⁺=423.2. ¹H NMR (300 MHz, DMSO-d₆) δ 12.06 (s, 1H), 10.54 (s, 1H), 9.19 (s, 1H), 8.97 (s, 1H), 8.77 (dd, J=4.8, 2.1 Hz, 1H), 8.30 (dd, J=7.8, 1.8 Hz, 1H), 7.97-7.84 (m, 2H), 7.57 (dd, J=6.6, 1.5 Hz, 1H), 7.34 (dd, J=7.8, 4.8 Hz, 1H), 3.36 (s, 3H), 3.14 (q, J=7.2 Hz, 2H), 1.13 (t, J=7.2 Hz, 3H).

Example 177

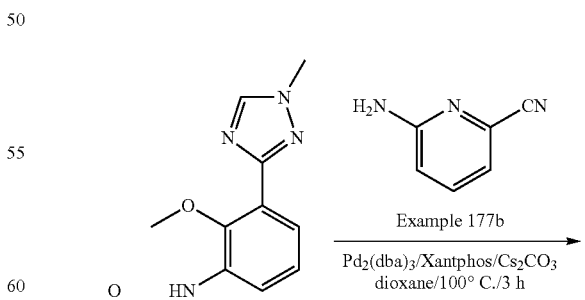

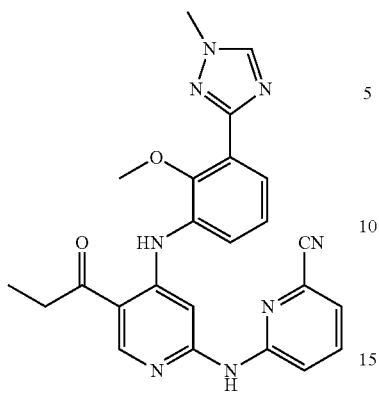

Example 177

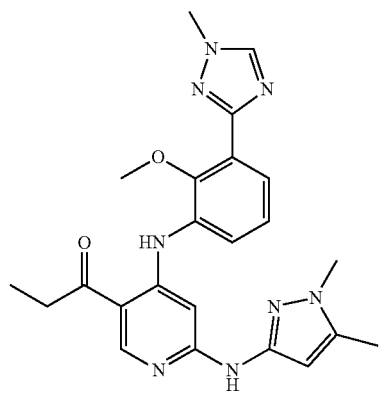

Example 178

To a solution of Example 177a (371 mg, 1.0 mmol) and Example 177b (119 mg, 1.0 mmol) in dioxane (10 mL) were added Pd$_2$(dba)$_3$ (91.5 mg, 0.1 mmol), Xantphos (59.5 mg, 0.1 mmol) and Cs$_2$CO$_3$ (489 mg, 1.5 mmol). The mixture was degassed by nitrogen for 3 times and stirred at 100° C. for 3 h. When completed, the reaction was cooled to r.t., diluted with MeOH (5 mL) and filtered. The filtrate was purified directly by Prep-HPLC to give the desired product Example 177 (154.2 mg, 33.9% yield) as a pale yellow solid. LCMS [M+1]$^+$=455.2. $^1$H NMR (400 MHz, DMSO-d$_6$) δ 11.27 (s, 1H), 10.37 (s, 1H), 8.85 (s, 1H), 8.54 (s, 1H), 7.96 (s, 1H), 7.84 (t, J=7.8 Hz, 1H), 7.74 (dd, J=17.3, 8.3 Hz, 2H), 7.58 (d, J=7.7 Hz, 1H), 7.50 (d, J=7.2 Hz, 1H), 7.34 (d, J=8.6 Hz, 1H), 3.93 (s, 3H), 3.73 (s, 3H), 3.09 (t, J=7.0 Hz, 2H), 1.11 (t, J=6.9 Hz, 3H).

To a solution of Example 178a (371 mg, 1.0 mmol) and Example 178b (111 mg, 1.0 mmol) in dioxane (10 mL) were added Pd$_2$(dba)$_3$ (91.5 mg, 0.1 mmol), Xantphos (59.5 mg, 0.1 mmol) and Cs$_2$CO$_3$ (489 mg, 1.5 mmol). The mixture was degassed by nitrogen for 3 times and stirred at 110° C. for 3 h. When completed, the reaction was cooled to r.t, diluted with MeOH (5 mL) and filtered. The filtrate was purified directly by Prep-HPLC to give the desired product Example 178 (8.4 mg, 1.9% yield) as a pale yellow solid. LCMS [M+1]$^+$=447.2. $^1$H NMR (400 MHz, DMSO-d$_6$) δ 11.09 (s, 1H), 9.45 (s, 1H), 8.73 (s, 1H), 8.54 (s, 1H), 7.66 (d, J=7.4 Hz, 1H), 7.57 (d, J=7.8 Hz, 2H), 7.27 (t, J=7.9 Hz, 1H), 5.90 (s, 1H), 3.93 (s, 3H), 3.72 (s, 3H), 3.57 (s, 3H), 3.04-2.97 (m, 2H), 2.17 (s, 3H), 1.12-1.08 (m, 3H).

Example 179

Example 178

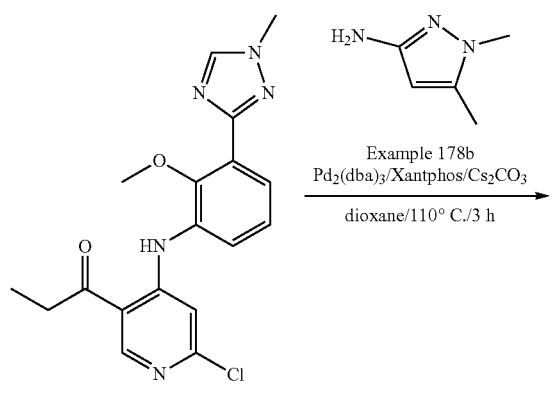

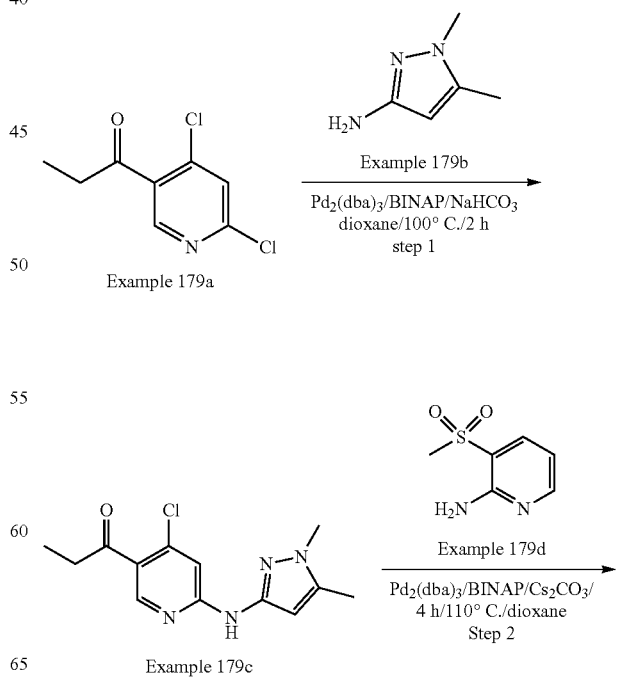

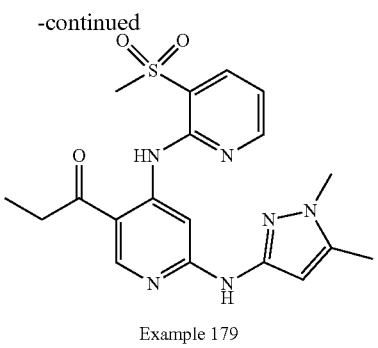

Example 179

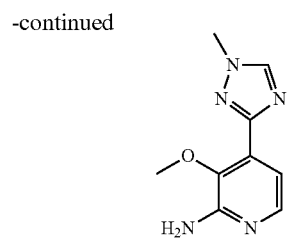

Example 180c

Step 1: Example 179c

To a solution of Example 179a (650 mg, 3.19 mmol, 1.0 eq) in dioxane (10 mL) were added NaHCO$_3$ (548.7 mg, 6.38 mmol, 2.0 eq), Example 179b (354.1 mg, 0.319 mmol, 1.0 eq), BINAP (398.7 mg, 0.638 mmol, 0.2 eq) and Pd$_2$(dba)$_3$·CHCl$_3$ (331.2 mg, 0.319 mmol, 0.1 eq). The reaction mixture was stirred for 2 h at 100° C. under N$_2$ protection. After cooled to room temperature, the solvent was removed, and the crude product was purified by silica gel flash column chromatography (Petroleum Ether/EtOAc=2/1) to afford the product Example 179c (250 mg, 28% yield) as a yellow solid. LCMS [M+1]$^+$=279.2.

Step 2: Example 179

To a solution of Example 179c (250 mg, 0.899 mmol, 1.0 eq) in dioxane (5 mL) were added Cs$_2$CO$_3$ (586 mg, 1.80 mmol, 2.0 eq), Example 179d (139 mg, 0.809 mmol, 0.9 eq), BINAP (112 mg, 0.180 mmol, 0.2 eq) and Pd$_2$(dba)$_3$·CHCl$_3$ (90 mg, 0.087 mmol, 0.1 eq). The reaction mixture was stirred for 4 h at 110° C. under N$_2$ protection. After cooled to room temperature, the solvent was removed. The crude product was purified by silica gel flash column chromatography, eluted with DCM/MeOH (20/1) to afford the crude product 140 mg (90% purity) and further purified by Prep-HPLC to afford the product Example 179 (84.6 mg, 23% yield) as an off-white solid. LCMS [M+1]$^+$=415.3. $^1$H NMR (300 MHz, DMSO-d$_6$) δ 11.98 (s, 1H), 9.64 (s, 1H), 8.83 (s, 1H), 8.65 (dd, J=4.8, 1.8 Hz, 1H), 8.53 (brs, 1H), 8.27 (dd, J=7.8, 2.1 Hz, 1H), 7.31 (dd, J=7.8, 4.8 Hz, 1H), 6.11 (s, 1H), 3.64 (s, 3H), 3.33 (s, 3H), 3.06 (q, J=7.2 Hz, 2H), 2.24 (s, 3H), 1.11 (t, J=7.2 Hz, 3H).

Example 180

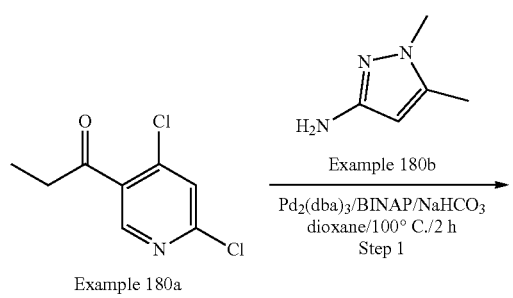

Example 180

Step 1: Example 180c

To a solution of Example 180a (1.0 g, 4.9 mmol, 1.0 eq) in dioxane (20 mL) were added NaHCO$_3$ (842.8 mg, 9.8 mmol, 2.0 eq), Example 180b (543.9 mg, 4.9 mmol, 1.0 eq), BINAP (610.5 mg, 0.98 mmol, 0.2 eq) and Pd$_2$(dba)$_3$·CHCl$_3$ (507.2 mg, 0.49 mmol, 0.1 eq). The reaction mixture was stirred for 2 h at 100° C. under N$_2$ protection. After cooled to room temperature, the solvent was removed, and the crude product was purified by silica gel flash column chromatography (Petroleum Ether/EtOAc=2/1) to afford the product Example 180c (380 mg, 28% yield) as a yellow solid. LCMS [M+1]$^+$=279.2.

Step 2: Example 180

To a solution of Example 180c (340 mg, 1.22 mmol, 1.0 eq) in dioxane (5 mL) were added Cs$_2$CO$_3$ (795.4 mg, 2.44 mmol, 2.0 eq), Example 180d (226.6 mg, 0.32 mmol, 1.1 eq), BINAP (152.0 mg, 0.24 mmol, 0.2 eq) and Pd$_2$(dba)$_3$·CHCl$_3$ (126.3 mg, 0.12 mmol, 0.1 eq). The reaction mixture was stirred for 4 h at 110° C. under N$_2$ protection. After cooled to room temperature, the solvent was removed. The crude product was purified by silica gel flash column chromatography (DCM/MeOH=20/1) to afford the crude product (220 mg) and further purified by Prep-HPLC (Prep-C18, 5 μM XBridge column, 19×150 mm, Waters; gradient elution of 35% MeCN in water to 55% MeCN in water over a 7 min period, where the aqueous phase contains 10 mM NH$_4$HCO$_3$+0.5% ammonia) to afford the product Example 180 (61.9 mg, 11% yield) as a white solid. LCMS [M+1]$^+$=448.3. $^1$H NMR (300 MHz, DMSO-d$_6$) δ 12.38 (s, 1H), 9.61 (s, 1H), 9.00 (s, 1H), 8.83 (s, 1H), 8.67 (s, 1H), 8.16 (d, J=5.4 Hz, 1H), 7.47 (d, J=5.1 Hz, 1H), 6.13 (s, 1H), 4.01 (s, 3H), 3.92 (s, 3H), 3.68 (s, 3H), 3.08 (q, J=7.2 Hz, 2H), 2.26 (s, 3H), 1.15 (t, J=7.2 Hz, 3H).

Example 181

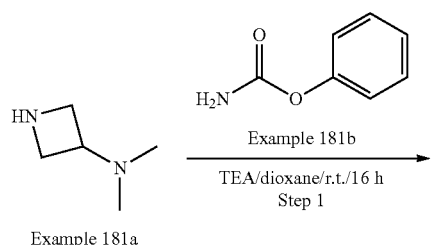

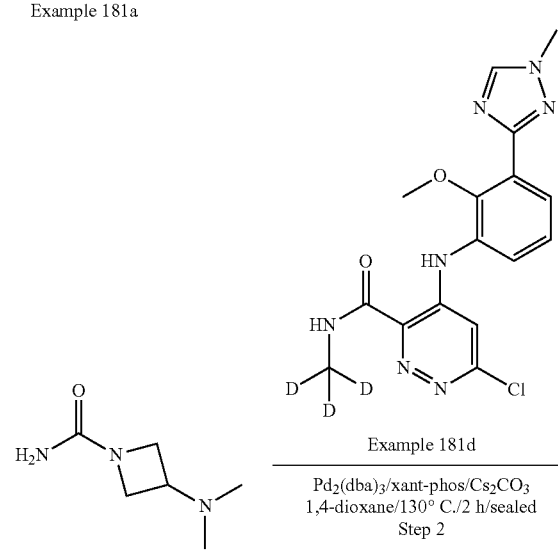

Step 1: Example 181c

To a solution of Example 181a (1 g, 10.0 mmol) in dioxane (15 mL) were added Example 181b (2 g, 14.6 mmol), and TEA (2 g, 19.8 mmol). The reaction mixture was stirred at room temperature for 16 h. Then the mixture was diluted with EtOAc, washed by water, brine, and dried over anhydrous $Na_2SO_4$. The solution was concentrated to afford crude residue, which was purified by silica gel flash column chromatography (Petroleum Ether/EtOAc=1/1) to afford the product Example 181c (1 g, 69.8% yield) as a white solid.

Step 2: Example 181

To a solution of Example 181d (100 mg, 0.26 mmol) and Example 181c (38.3 mg, 0.26 mmol) in DMA (2.5 mL) were added $Pd_2(dba)_3$ (24 mg, 0.026 mmol), Xantphos (15.6 mg, 0.026 mmol) and $Cs_2CO_3$ (172 mg, 0.53 mmol). The mixture was degassed by nitrogen for 3 times and stirred at 130° C. for 2 h. When completed, the reaction was cooled to r.t., diluted with MeOH (5 mL) and filtered. The filtrate was purified directly by Prep-HPLC to give the desired product Example 181 (24.3 mg, 18.9% yield) as a off white solid. LCMS [M+1]$^+$=484.3. $^1$H NMR (400 MHz, Chloroform-d) δ 11.33 (s, 1H), 10.08 (s, 1H), 9.43 (s, 1H), 8.96 (s, 1H), 8.41 (s, 1H), 8.04 (d, J=7.8 Hz, 1H), 7.91 (d, J=7.8 Hz, 1H), 7.66 (t, J=7.9 Hz, 1H), 4.41 (s, 2H), 4.35 (s, 3H), 4.18 (s, 2H), 4.13 (s, 3H), 3.40 (d, J=9.1 Hz, 1H), 2.91 (s, 6H).

Example 182

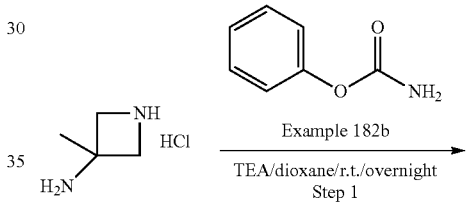

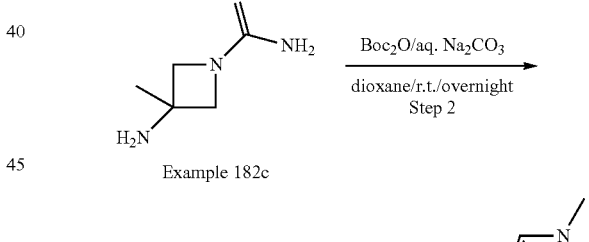

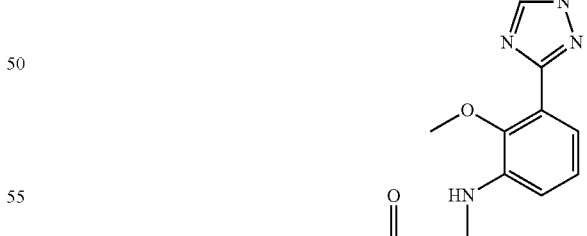

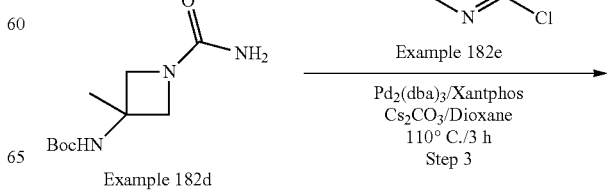

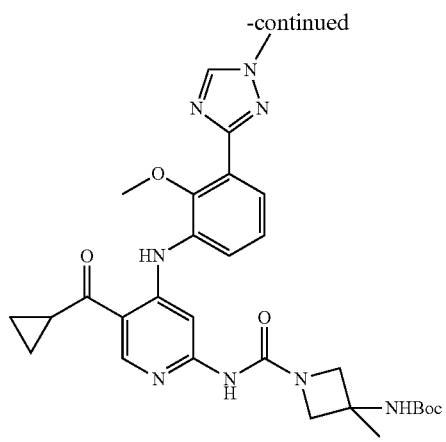

Example 182f

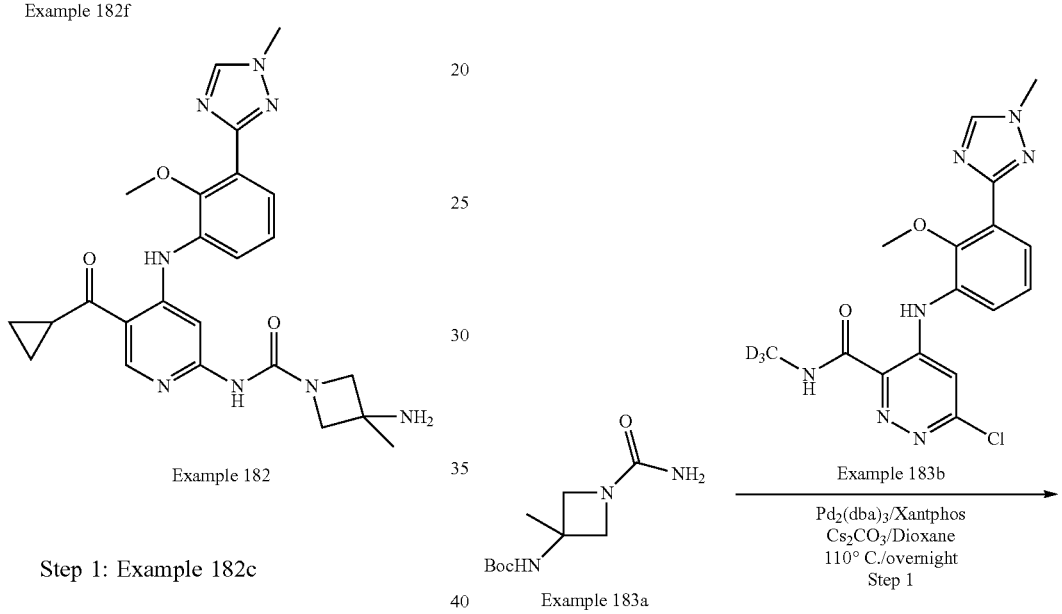

Example 182

Step 1: Example 182c

To a solution of Example 182a (400 mg, 2.65 mmol) in dioxane (5 mL) were added Example 182b (365 mg, 2.56 mmol), and TEA (795 mg, 7.87 mmol). The reaction mixture was stirred at room temperature overnight. Then the mixture was used directly in the next step.

Step 2: Example 182d

To a solution of Example 182c in dioxane was added Boc$_2$O (687 mg, 3.18 mmol), followed by addition of Na$_2$CO$_3$ (687 mg in 5 mL of H$_2$O). The mixture was stirred at room temperature overnight. Then the mixture was extracted by EtOAc, dried over anhydrous Na$_2$SO$_4$, concentrated, and purified by silica gel flash column chromatography, eluted with DCM/MeOH (10/1) to afford the product Example 182d (170 mg, 27.8% yield) as a white solid.

Step 3: Example 182f

To a solution of Example 182e (75 mg, 0.2 mmol,) in dioxane (5 mL) were added Example 182d (46 mg, 0.2 mmol), Pd$_2$(dba)$_3$ (18 mg, 0.02 mmol), Xantphos (13 mg, 0.02 mmol) and Cs$_2$CO$_3$ (130 mg, 0.4 mmol). The mixture was sealed and heated to 110° C. for 3 h. The mixture was filtrated and concentrated under reduced pressure to give crude Example 182f (200 mg, quant.) which was used for the next step directly without purification.

Step 4: Example 182

To a solution of Example 182f (200 mg, crude 0.2 mmol) in DCM (5 mL) was added TFA (2 mL). The mixture was stirred at room temperature for 2 h. then the mixture was concentrated, and purified by Prep-HPLC to give Example 182 (15.7 mg, 9.5% yield) as a white solid. LCMS [M+1]*=477.2. $^1$H NMR (400 MHz, DMSO-d$_6$) δ 10.99 (s, 1H), 9.73 (s, 1H), 9.05 (s, 1H), 8.54 (s, 1H), 8.33 (s, 2H), 7.74-7.62 (m, 2H), 7.48 (d, J=7.8 Hz, 1H), 7.25 (t, J=7.8 Hz, 1H), 4.04 (d, J=9.3 Hz, 2H), 3.92 (s, 4H), 3.67 (s, 3H), 3.53 (d, J=7.6 Hz, 2H), 2.93 (s, 1H), 1.48 (s, 3H), 1.15-0.99 (m, 4H).

Example 183

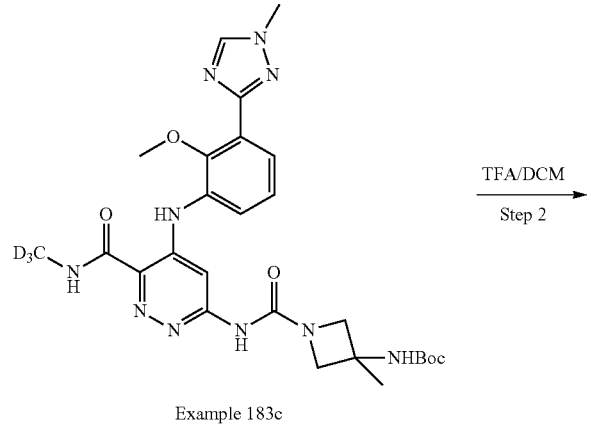

Example 183c

411

-continued

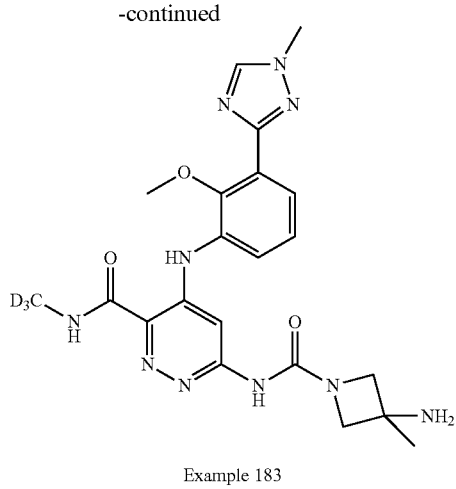

Example 183

Step 1: Example 183c

To a solution of Example 183a (61 mg, 0.27 mmol) in dioxane (5 mL) were added Example 183b (100 mg, 0.27 mmol), Pd$_2$(dba)$_3$ (24 mg, 0.027 mmol), Xantphos (16 mg, 0.027 mmol) and Cs$_2$CO$_3$ (173 mg, 0.53 mmol). The mixture was sealed and heated to 110° C. for overnight. The mixture was filtrated and concentrated under reduced pressure to give crude Example 183c (170 mg), which was used for the next step directly without purification.

Step 2: Example 183

To a solution of Example 183c (170 mg, crude 0.27 mmol) in DCM (5 mL) was added TFA (2 mL). The mixture was stirred at room temperature for 2 h. Then the mixture was concentrated, and purified by Prep-HPLC to give Example 183 (14.6 mg, 10.4% yield) as a yellow solid. LCMS [M+1]$^+$=470.2. $^1$H NMR (400 MHz, Methanol-d$_4$) δ 8.48 (s, 1H), 7.86 (s, 1H), 7.69 (d, J=7.9 Hz, 1H), 7.58 (d, J=8.0 Hz, 1H), 7.29 (t, J=8.2 Hz, 1H), 4.19-4.11 (m, 4H), 4.02 (s, 3H), 3.73 (s, 3H), 1.64 (s, 3H).

Example 184

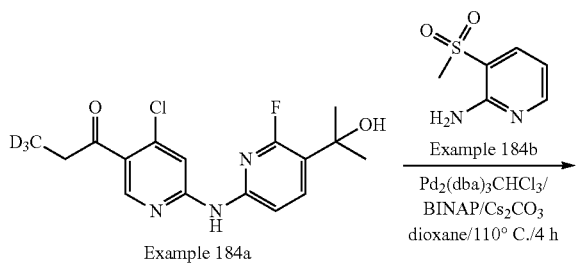

412

-continued

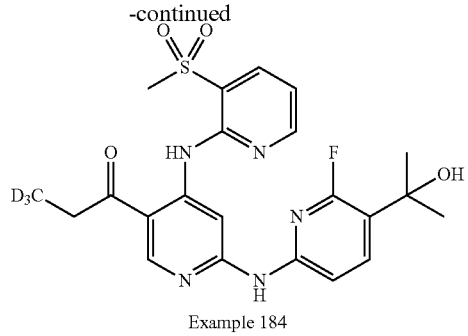

Example 184

To a solution of Example 184a (50 mg, 0.15 mmol, 1.0 eq) in dioxane (2 mL) were added Example 184b (25 mg, 0.15 mmol, 1.0 eq), Cs$_2$CO$_3$ (96 mg, 0.29 mmol, 2.0 eq), BINAP (18 mg, 0.029 mmol, 0.2 eq) and Pd$_2$(dba)$_3$CHCl$_3$ (15 mg, 0.015 mmol, 0.1 eq). The reaction mixture was stirred for 4 h at 110° C. under N$_2$. The solid was filtered out and the filtrate was concentrated. The crude product was purified by Prep-TLC (DCM/MeOH=20/1) to give the desired product Example 184 (23.5 mg, 33.6% yield) as a light yellow solid. LCMS [M+1]$^+$=477.3. $^1$H NMR (300 MHz, DMSO-d$_6$) δ 12.00 (s, 1H), 10.25 (s, 1H), 9.02 (s, 1H), 8.95 (s, 1H), 8.66 (dd, J=4.8, 2.1 Hz, 1H), 8.29 (dd, J=7.8, 1.8 Hz, 1H), 7.99 (dd, J=10.8, 8.4 Hz, 1H), 7.62 (d, J=7.8 Hz, 1H), 7.35 (dd, J=7.8, 4.5 Hz, 1H), 5.29 (s, 1H), 3.34 (s, 3H), 3.09 (s, 2H), 1.48 (s, 6H).

Example 185

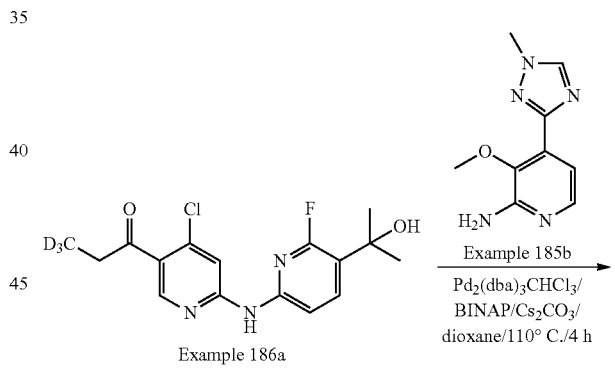

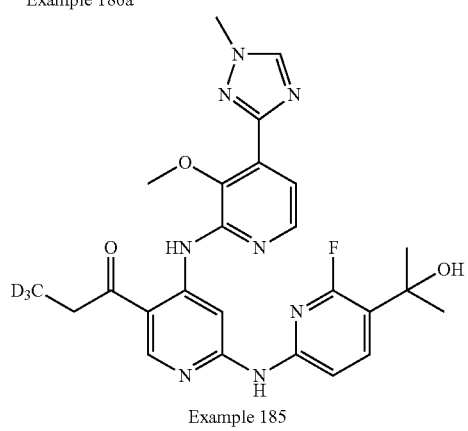

Example 185

To a solution of Example 185a (50 mg, 0.15 mmol, 1.0 eq) in dioxane (2 mL) were added Example 185b (30 mg, 0.15 mmol, 1.0 eq), Cs₂CO₃ (96 mg, 0.29 mmol, 2.0 eq), BINAP (18 mg, 0.029 mmol, 0.2 eq) and Pd₂(dba)₃CHCl₃ (15 mg, 0.015 mmol, 0.1 eq). The reaction solution was stirred for 4 h at 110° C. under N₂. The mixture was filtered and the filtrate was concentrated. The crude product was purified by prep-TLC (DCM/MeOH=20/1) to give the desired product Example 185 (35.0 mg, 46.8% yield) as a light yellow solid. LCMS [M+1]⁺=510.4. ¹H NMR (300 MHz, DMSO-d₆) δ 12.38 (s, 1H), 10.25 (s, 1H), 9.53 (s, 1H), 8.94 (s, 1H), 8.68 (s, 1H), 8.18 (d, J=5.1 Hz, 1H), 8.00 (dd, J=10.8, 8.4 Hz, 1H), 7.59 (d, J=8.1 Hz, 1H), 7.52 (d, J=5.1 Hz, 1H), 5.29 (s, 1H), 4.01 (s, 3H), 3.93 (s, 3H), 3.11 (s, 2H), 1.50 (s, 6H).

Example 188

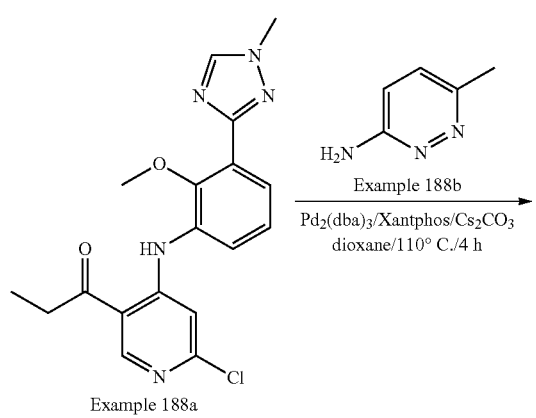

To a solution of Example 188a (100 mg, 0.27 mmol) and Example 188b (30 mg, 0.27 mmol) in dioxane (10 mL) were added Pd₂(dba)₃ (24.6 mg, 0.027 mmol), Xantphos (16 mg, 0.027 mmol) and Cs₂CO₃ (131 mg, 0.40 mmol). The mixture was degassed by nitrogen for 3 times and stirred at 110° C. for 4 h. When completed, the reaction was cooled to r.t, diluted with EtOAc (5 mL) and filtered. The filtrate was purified directly by Prep-HPLC to give the desired product Example 188 (27.5 mg, 22.4% yield) as a pale yellow solid. LCMS [M+1]⁺=445.2. ¹H NMR (400 MHz, DMSO-d₆) δ 11.07 (s, 1H), 10.19 (s, 1H), 8.85 (s, 1H), 8.55 (s, 1H), 7.97 (d, J=9.2 Hz, 1H), 7.67-7.61 (m, 3H), 7.43 (d, J=9.2 Hz, 1H), 7.25 (t, J=8.0 Hz, 1H), 3.94 (s, 3H), 3.73 (s, 3H), 3.08 (q, J=7.6 Hz, 2H), 1.11 (t, J=7.1 Hz, 3H).

Example 189

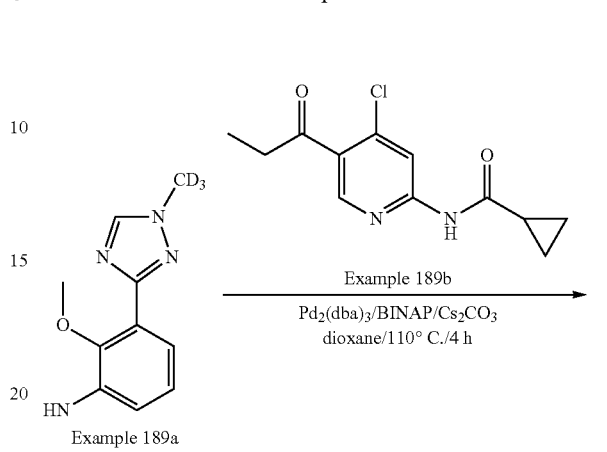

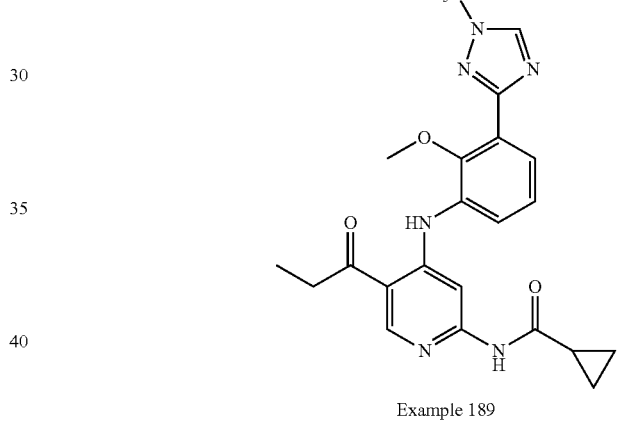

To a solution of Example 189b (869 mg, 3.45 mmol, 1.1 eq) in dioxane (100 mL) were added Example 189a (650 mg, 3.14 mmol, 1.0 eq), Cs₂CO₃ (2.04 g, 6.27 mmol, 2.0 eq), BINAP (391 mg, 0.63 mmol, 0.2 eq) and Pd₂(dba)₃CHCl₃ (325 mg, 0.31 mmol, 0.1 eq). The reaction solution was stirred for 4 h at 110° C. under N₂. The solvent was concentrated, and the residue was purified by silica gel flash column chromatography, eluted with DCM/MeOH (v/v=25/1) to give the desired product Example 189 (1.1 g, crude, 85% purity) as a yellow solid and further purified by reverse phase preparative MPLC to give the desired product Example 189 (512.6 mg, 38.6% yield) as a white solid. LCMS [M+1]⁺=424.4. ¹H NMR (300 MHz, DMSO-d₆) δ 11.05 (s, 1H), 10.90 (s, 1H), 8.89 (s, 1H), 8.56 (s, 1H), 8.04 (s, 1H), 7.65 (dd, J=7.8, 1.8 Hz, 1H), 7.53 (dd, J=8.1, 1.5 Hz, 1H), 7.26 (t, J=7.8 Hz, 1H), 3.72 (s, 3H), 3.13 (q, J=7.2 Hz, 2H), 2.10-1.94 (m, 1H), 1.13 (t, J=7.2 Hz, 3H), 0.79 (d, J=6.0 Hz, 4H).

Example 190

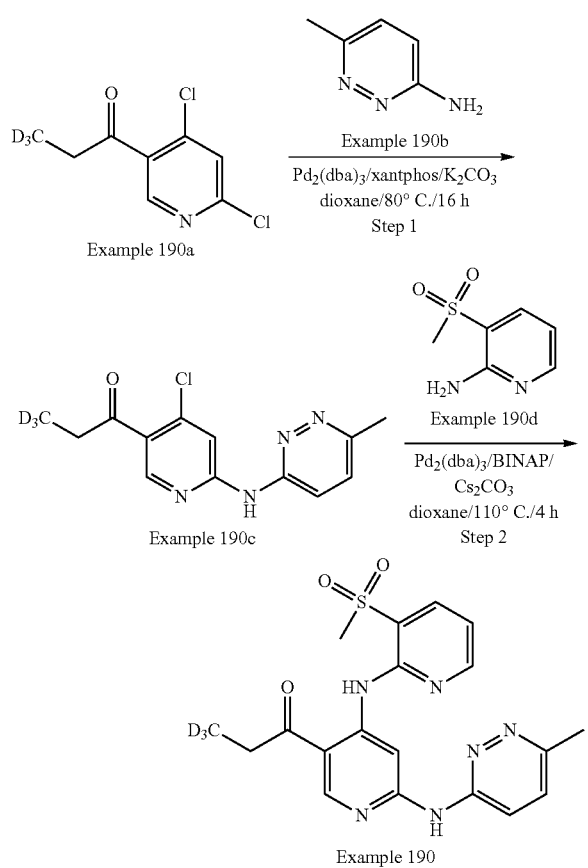

Step 1: Example 190c

To a solution of Example 190a (150 mg, 0.73 mmol, 1.0 eq) and Example 190b (79 mg, 0.73 mmol, 1.0 eq) in dioxane (3 mL) were added K$_2$CO$_3$ (201 mg, 1.46 mmol, 2.0 eq), Pd$_2$(dba)$_3$·CHCl$_3$ (75 mg, 0.073 mmol, 0.1 eq) and BINAP (15.0 mg, 0.15 mmol, 0.2 eq). The reaction mixture was stirred for 16 h at 80° C. under N$_2$ protection. The reaction solution was filtered and the filtrate was concentrated in vacuum. The crude product was purified by silica gel flash column chromatography (Petroleum Ether/EtOAc=1/1) to afford the desired product Example 190c (65 mg, 32.0% yield) as a yellow solid. LCMS [M+1]$^+$=280.2.

Step 2: Example 190

To a solution of Example 190c (60 mg, 0.22 mmol, 1.0 eq) in dioxane (3 mL) and Example 190d (37 mg, 0.22 mmol, 1.0 eq) were added Cs$_2$CO$_3$ (139.7 mg, 0.44 mmol, 2.0 eq), Pd$_2$(dba)$_3$·CHCl$_3$ (22.2 mg, 0.022 mmol, 0.1 eq) and BINAP (25 mg, 0.044 mmol, 0.2 eq). The reaction mixture was stirred for 4 h at 110° C. under N$_2$ protection. The mixture was filtered and the filtrate was concentrated in vacuum. The crude product was purified by prep-TLC (DCM/MeOH=30/1) to afford the desired product Example 190 (9.2 mg, 10.3% yield) as a light yellow solid. LCMS [M+1]$^+$=416.3. $^1$H NMR (300 MHz, DMSO-d$_6$) δ 11.94 (s, 1H), 10.41 (s, 1H), 8.94 (s, 1H), 8.73 (s, 1H), 8.67-8.59 (m, 1H), 8.29 (d, J=8.1 Hz, 1H), 8.09 (d, J=9.0 Hz, 1H), 7.49 (d, J=9.0 Hz, 1H), 7.34 (dd, J=7.8, 4.8 Hz, 1H), 3.35 (s, 3H), 3.09 (s, 2H), 2.54 (s, 3H).

Example 191

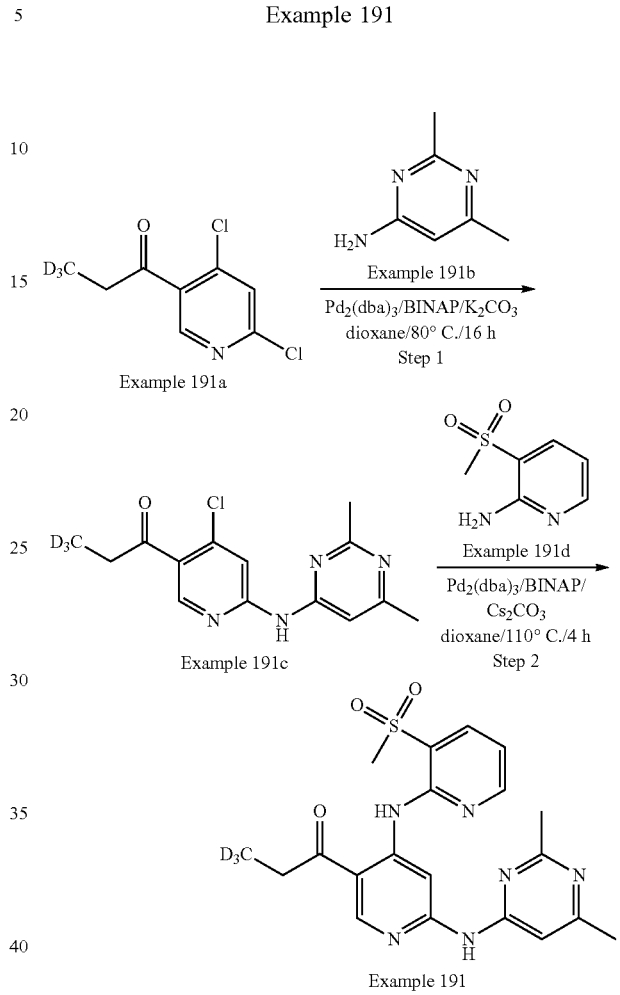

Step 1: Example 191c

To a solution of Example 191a (150 mg, 0.73 mmol, 1.0 eq) and Example 191b (89.5 mg, 0.73 mmol, 1.0 eq) in dioxane (10 mL) were added K$_2$CO$_3$ (201 mg, 1.46 mmol, 2.0 eq), Pd$_2$(dba)$_3$·CHCl$_3$ (75.3 mg, 0.073 mmol, 0.1 eq) and BINAP (90.6 mg, 0.15 mmol, 0.2 eq). The reaction mixture was stirred for 16 h at 80° C. under N$_2$ protection. The mixture was filtered and the filtrate was concentrated in vacuum. The crude product was purified by silica gel flash column chromatography (DCM/MeOH=40/1) to afford the desired product Example 191c (60 mg, 28.4% yield) as a yellow solid. LCMS [M+1]$^+$=294.2.

Step 2: Example 191

To a solution of Example 191c (60 mg, 0.22 mmol, 1.0 eq) and Example 191d (35 mg, 0.22 mmol, 1.0 eq) in dioxane (3 mL) were added Cs$_2$CO$_3$ (132 mg, 0.44 mmol, 2.0 eq), Pd$_2$(dba)$_3$·CHCl$_3$ (21 mg, 0.022 mmol, 0.1 eq) and BINAP (25.4 mg, 0.044 mmol, 0.2 eq). The reaction mixture was stirred for 4 h at 110° C. under N$_2$ protection. The mixture was filtered and the filtrate was concentrated in vacuum. The crude product was purified by prep-TLC (DCM/MeOH=30/1) to afford the desired product Example 191 (19.2 mg, 22.3% yield) as a light yellow solid. LCMS [M+1]$^+$=430.3. $^1$H NMR (300 MHz, DMSO-d$_6$) δ 11.97 (s, 1H), 10.35 (s, 1H), 9.07 (s, 1H), 8.98 (s, 1H), 8.68 (dd, J=4.8, 1.8 Hz, 1H), 8.30 (dd, J=7.8, 1.8 Hz, 1H), 7.43-7.30 (m, 2H), 3.35 (s, 3H), 3.11 (s, 2H), 2.44 (s, 3H), 2.33 (s, 3H).

Example 193

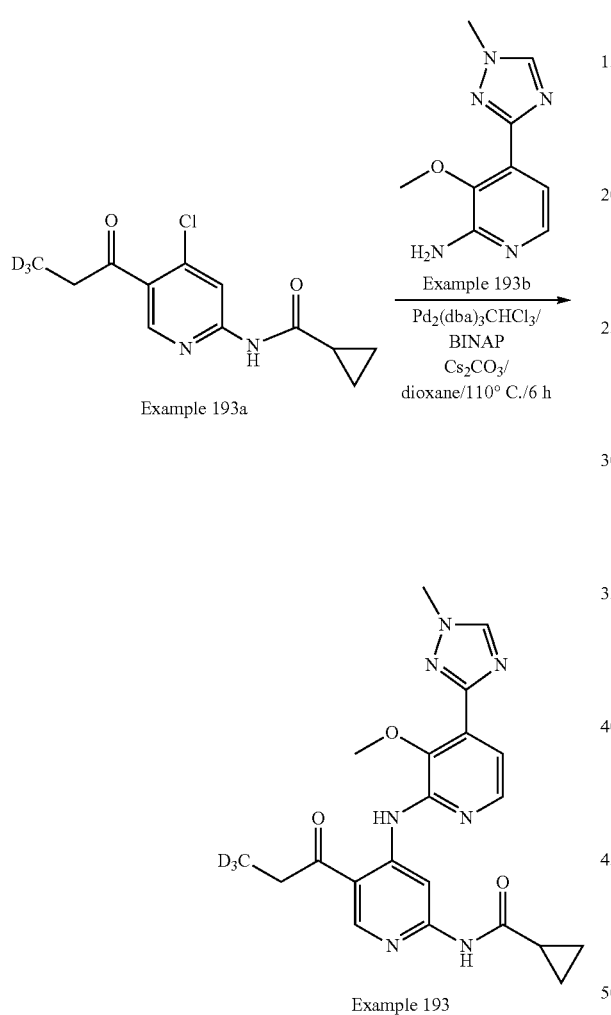

Example 193

To a solution of Example 193a (750 mg, 2.93 mmol, 1.0 eq) in dioxane (25 mL) were added Example 193b (900 mg, 4.39 mmol, 1.5 eq), Cs$_2$CO$_3$ (1.91 g, 5.86 mmol, 2.0 eq), BINAP (365 mg, 0.59 mmol, 0.2 eq) and Pd$_2$(dba)$_3$CHCl$_3$ (303 mg, 0.29 mmol, 0.1 eq). The reaction solution was stirred for 6 h at 110° C. under N$_2$. The reaction solution was concentrated and the residue was purified by silica gel flash column chromatography, eluted with DCM/MeOH (v/v=20/1) to give the desired product Example 193 (411.8 mg, 33.1% yield) as a light yellow solid. LCMS [M+1]$^+$=425.3. $^1$H NMR (300 MHz, DMSO-d$_6$) δ 12.36 (s, 1H), 10.91 (s, 1H), 9.71 (s, 1H), 8.96 (s, 1H), 8.67 (s, 1H), 8.14 (d, J=5.1 Hz, 1H), 7.50 (d, J=5.1 Hz, 1H), 4.00 (s, 3H), 3.92 (s, 3H), 3.14 (s, 2H), 2.13-2.01 (m, 1H), 0.91-0.79 (m, 4H).

Example 195

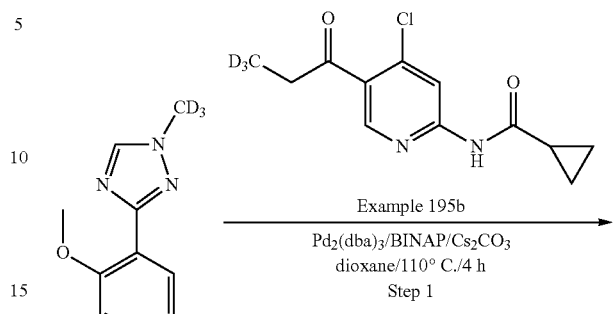

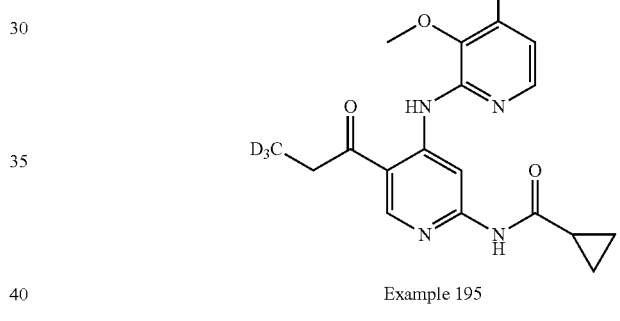

Example 195

To a solution of Example 195b (700 mg, 2.73 mmol, 1.0 eq) in dioxane (20 mL) were added Cs$_2$CO$_3$ (1.8 g, 5.46 mmol, 2.0 eq), Example 195a (847.6 mg, 4.09 mmol, 1.5 eq), BINAP (340.2 mg, 0.55 mmol, 0.2 eq) and Pd$_2$(dba)$_3$·CHCl$_3$ (279.5 mg, 0.27 mmol, 0.1 eq). The reaction mixture was stirred for 4 h at 110° C. under N$_2$ protection. After cooled to room temperature, the solvent was removed. The crude product was purified by silica gel flash column chromatography (DCM/MeOH=20/1) to afford the crude product 1.2 g, which was further purified by Prep-HPLC (Prep-C18, 5 μM XBridge column, 19×150 mm, Waters; gradient elution of 35% MeCN in water to 55% MeCN in water over a 7 min period, where the aqueous phase contains 10 mM NH$_4$HCO$_3$+0.5% ammonia) to afford the product Example 195 (401.9 mg, 35% yield) as an off-white solid. LCMS [M+1]$^+$=427.3. $^1$H NMR (300 MHz, DMSO-d$_6$) δ 11.05 (s, 1H), 10.89 (s, 1H), 8.89 (s, 1H), 8.56 (s, 1H), 8.03 (s, 1H), 7.65 (dd, J=7.8, 1.5 Hz, 1H), 7.53 (dd, J=7.8, 1.5 Hz, 1H), 7.26 (t, J=7.8 Hz, 1H), 3.72 (s, 3H), 3.11 (s, 2H), 2.08-1.95 (m, 1H), 0.79 (d, J=6.3 Hz, 4H).

Example 196

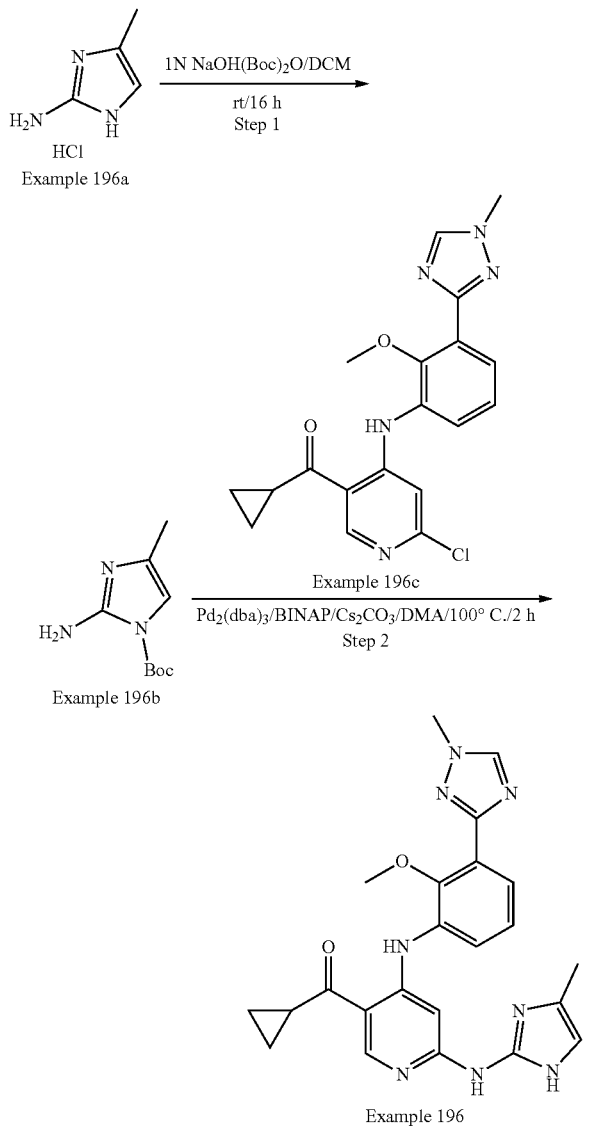

Step 1: Example 196b

To a solution of Example 196a (100 mg, 0.75 mmol, 1.0 eq) in 1MNaOH aqueous solution (2.25 mL, 2.25 mmol, 3.0 eq) was added a solution of (Boc)₂O (261.6 mg, 1.2 mmol, 1.6 eq) in DCM (5 mL). The reaction mixture was stirred for 16 h at r.t. Upon completion of the reaction, two phases were separated. The organic layer was washed with water (5 mL), dried over Na₂SO₄ and concentrated. The crude product was purified by Prep-TLC (DCM/MeOH=20/1) to afford the product Example 196b (78 mg, 53% yield) as yellow oil. LCMS [M+1]⁺=198.2.

Step 2: Example 196

To a solution of Example 196c (50 mg, 0.13 mmol, 1.0 eq,) in DMA (2 mL) were added Cs₂CO₃ (84.8 mg, 0.26 mmol, 2.0 eq), Example 196b (51 mg, 0.26 mmol, 2.0 eq), BINAP (16.2 mg, 0.03 mmol, 0.2 eq) and Pd₂(dba)₃·CHCl₃ (13.5 mg, 0.01 mmol, 0.1 eq). The reaction mixture was stirred for 2 h at 110° C. under N₂ protection. After cooled to room temperature, the reaction was diluted with EtOAc (20 mL), washed with brine, dried over Na₂SO₄ and concentrated. The crude product was purified by Prep-TLC (DCM/MeOH=10/1) to afford the product Example 196 (9.1 mg, 16% yield) as a yellow solid. LCMS [M+1]⁺=445.3. ¹H NMR (300 MHz, DMSO-d₆) δ 11.10 (br, 1H), 10.98 (s, 1H), 10.03 (brs, 1H), 9.04 (s, 1H), 8.56 (s, 1H), 7.61 (d, J=8.1 Hz, 2H), 7.26 (t, J=7.8 Hz, 1H), 7.08 (brs, 1H), 6.45 (brs, 1H), 3.95 (s, 3H), 3.71 (s, 3H), 2.95-2.81 (m, 1H), 2.09 (s, 3H), 1.12-0.96 (m, 4H).

Example 198

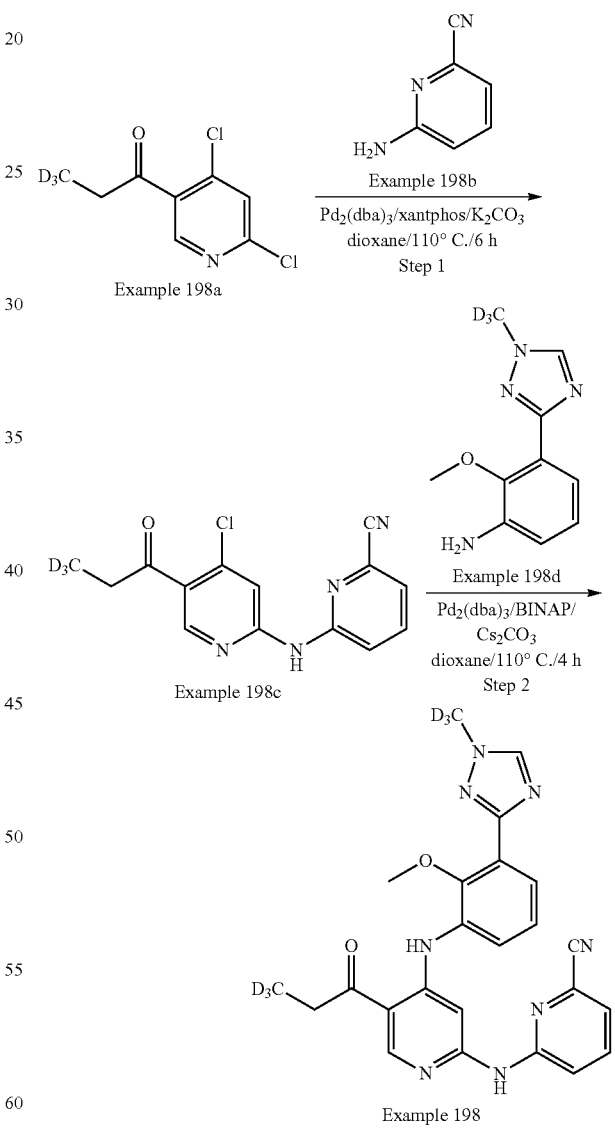

Step 1: Example 198

To a solution of Example 198a (200 mg, 0.97 mmol, 1.0 eq) in dioxane (5 mL) were added K₂CO₃ (267.7 mg, 1.94 mmol, 2.0 eq), Example 198b (115.4 mg, 0.97 mmol, 1.0 eq) and Xantphos (112.3 mg, 0.194 mmol, 0.2 eq) and Pd$_2$(dba)$_3$·CHCl$_3$ (100.4 mg, 0.097 mmol, 0.1 eq). The reaction mixture was stirred for 6 h at 110° C. under N$_2$ protection. After cooled to room temperature, the solvent was removed. The crude product was purified by silica gel flash column chromatography (DCM/MeOH=20/1) to afford the product Example 198c (120 mg, 43% yield) as a yellow solid.

LCMS [M+1]$^+$=290.2

Step 2: Example 198

To a solution of Example 198c (60 mg, 0.21 mmol, 1.0 eq) in dioxane (3 mL) were added Cs$_2$CO$_3$ (136.9 mg, 0.42 mmol, 2.0 eq), Example 198d (65.2 mg, 0.32 mmol, 1.5 eq), BINAP (26.2 mg, 0.042 mmol, 0.2 eq) and Pd$_2$(dba)$_3$·CHCl$_3$ (21.7 mg, 0.021 mmol, 0.1 eq). The reaction mixture was stirred for 4 h at 110° C. under N$_2$ protection. After cooled to room temperature, the solvent was removed. The crude product was purified by Prep-TLC (DCM/MeOH=15/1) to afford the product 60 mg crude product, which was further purified by Prep-HPLC (Prep-C18, 5 μM XBridge column, 19×150 mm, Waters; gradient elution of 35% MeCN in water to 55% MeCN in water over a 7 min period, where the aqueous phase contains 10 mM NH$_4$HCO$_3$+0.5% ammonia) to afford the product Example 198 (15.4 mg, 16% yield) as an off-white solid. LCMS [M+1]$^+$=461.3. $^1$H NMR (300 MHz, DMSO-d$_6$) δ 11.29 (s, 1H), 10.40 (brs, 1H), 8.90 (s, 1H), 8.57 (s, 1H), 7.99 (s, 1H), 7.92-7.86 (m, 1H), 7.85-7.71 (m, 2H), 7.62 (dd, J=8.1, 1.8 Hz, 1H), 7.54 (d, J=7.2 Hz, 1H), 7.38 (t, J=7.8 Hz, 1H), 3.76 (s, 3H), 3.10 (s, 2H).

Example 199

To a solution of Example 199a (60 mg, 0.204 mmol, 1.2 eq) in dioxane (3 mL) were added Cs$_2$CO$_3$ (110.8 mg, 0.34 mmol, 2.0 eq), Example 199b (35 mg, 0.17 mmol, 1.0 eq), BINAP (21.2 mg, 0.034 mmol, 0.2 eq) and Pd$_2$(dba)$_3$CHCl3 (17.6 mg, 0.017 mmol, 0.1 eq). The reaction mixture was stirred for 4 h at 110° C. under N$_2$ protection. After cooled to room temperature, the solvent was removed. The crude product was purified by Prep-TLC (DCM/MeOH=15/1) to afford the product Example 199 (19.3 mg, 24% yield) a yellow solid. LCMS [M+1]$^+$=462.3. $^1$H NMR (300 MHz, DMSO-d$_6$) δ 12.48 (s, 1H), 10.52 (s, 1H), 9.78 (s, 1H), 8.96 (s, 1H), 8.67 (s, 1H), 8.36 (d, J=5.1 Hz, 1H), 7.92 (t, J=8.1 Hz, 1H), 7.82 (d, J=8.4 Hz, 1H), 7.59 (d, J=6.9 Hz, 1H), 7.50 (d, J=5.4 Hz, 1H), 3.94 (s, 3H), 3.13 (s, 2H).

Example 200

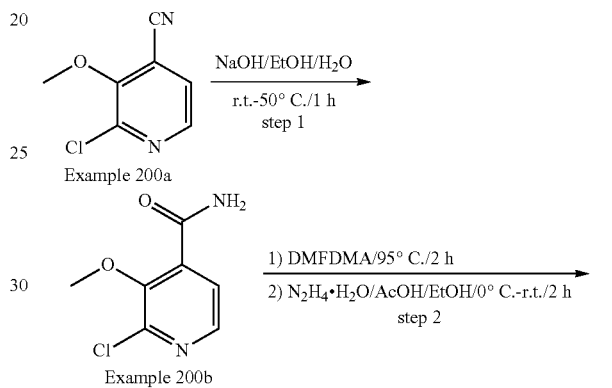

Example 200a

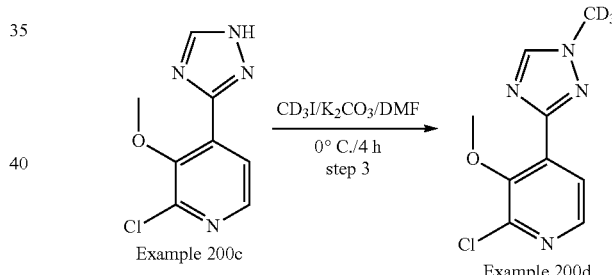

Example 200b

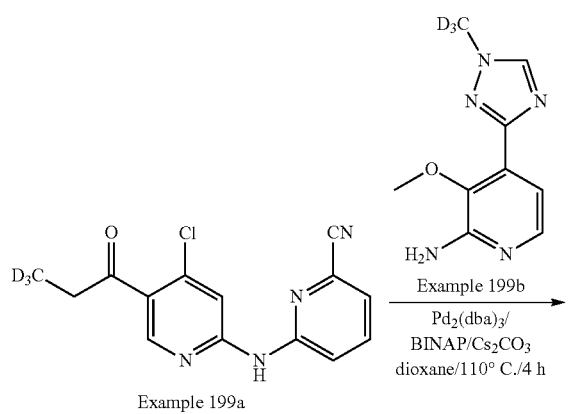

Example 199a

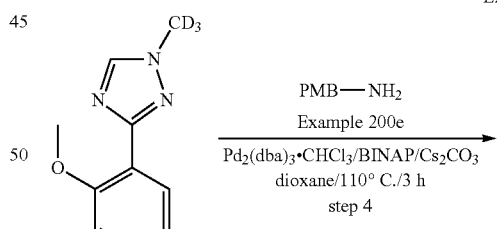

Example 200c

Example 200d

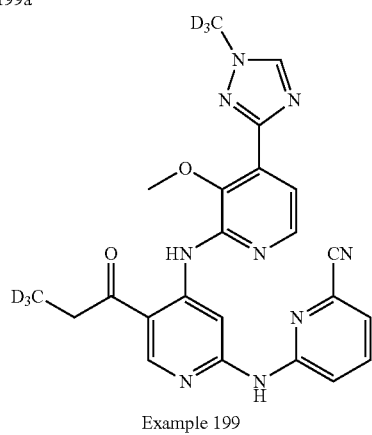

Example 199

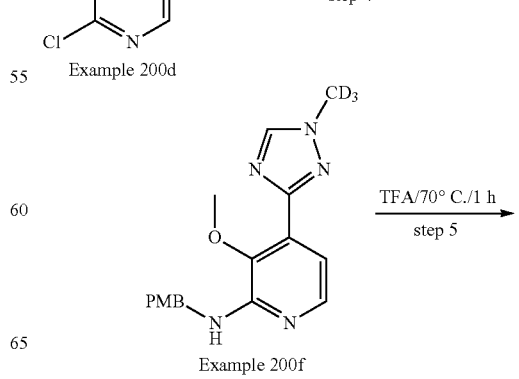

Example 200d

Example 200f

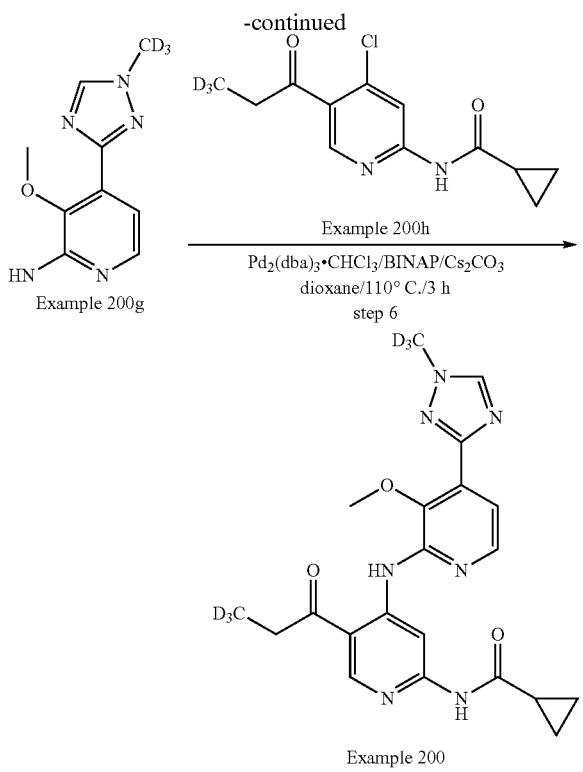

Step 1: Example 200b

To a solution of Example 200a (3.2 g, 18.93 mmol, 1.0 eq) in EtOH (20 mL) and H$_2$O (4 mL) was added NaOH (908 mg, 22.72 mmol, 1.2 eq) at r.t. The mixture was stirred for 1 h at 50° C. After the reaction was completed, the solvent was removed. The crude product was purified by silica gel flash column chromatography (Petroleum Ether/EtOAc=20/1) to afford the product Example 200b (1.2 g, 33.9% yield) as a white solid. LCMS [M+1]$^+$=187.2.

Step 2: Example 200c

A solution of Example 200b (1.2 g, 6.45 mmol, 1.0 eq) in DMF-DMA (3.07 g, 25.8 mmol, 4.0 eq) was stirred for 2 h at 95° C. After the reaction completed, it was concentrated under vacuum. The residue was dissolved in AcOH (5 mL) and EtOH (20 mL), and N$_2$H$_4$·H$_2$O (3.2 g, 80% in water, 51.6 mmol, 8.0 eq) was added dropwise at 0° C. The reaction mixture was stirred for 2 h at r.t. After completion, the mixture was concentrated in vacuo. The crude product was purified by silica gel flash column chromatography (DCM/MeOH=20/1) to afford the product Example 200c (600 mg, 44.4% yield) as a white solid. LCMS [M+1]$^+$=211.2.

Step 3: Example 200d

To a solution of Example 200c (600 mg, 2.86 mmol, 1.0 eq) in DMF (10 mL) were added K$_2$CO$_3$ (789 mg, 5.72 mmol, 2.0 eq) and CD$_3$I (621 mg, 4.29 mmol, 1.5 eq) at 0° C. The reaction mixture was stirred for 4 h at r.t. The reaction was diluted with EtOAc and washed with brine. The organic layer was dried over Na$_2$SO$_4$ and concentrated. The residue was purified by silica gel flash column chromatography, eluted with Petroleum Ether/EtOAc (v/v=1/3) to afford the product Example 200d (550 mg, 84.8% yield) as a yellow solid. LCMS [M+1]$^+$=228.2.

Step 4: Example 200f

To a solution of Example 200d (550 mg, 2.42 mmol, 1.0 eq) in dioxane (10 mL) were added Cs$_2$CO$_3$ (1.57 g, 4.84 mmol, 2.0 eq), Example 200e (399 mg, 2.9 mmol, 1.2 eq), BINAP (302 mg, 0.48 mmol, 0.2 eq) and Pd$_2$(dba)$_3$·CHCl$_3$ (251 mg, 0.24 mmol, 0.1 eq). The reaction mixture was stirred for 3 h at 110° C. under N$_2$ protection. After the reaction was completed, the solvent was removed, and the residue was purified by silica gel flash column chromatography (DCM/MeOH=20/1) to afford the product Example 200f (505 mg, 63.5% yield) as a yellow solid. LCMS [M+1]$^+$=329.3.

Step 5: Example 200g

The solution of Example 200f (505 mg, 1.54 mmol, 1.0 eq) in TFA (20 mL) was stirred for 1 h at 70° C. After the reaction was completed, it was concentrated in vacuum. The residue was dissolved in MeOH (20 mL) and basified with NaHCO$_3$ (910 mg, 8.58 mmol, 2.0 eq). The solid was filtered out, and the filtrate was concentrated in vacuum. The residue was purified by silica gel flash column chromatography (DCM/MeOH=20/1) to afford the product Example 200g (180 mg, 56.3% yield) as a light gray solid. [M+1]$^+$=209.4.

Step 6: Example 200

To a solution of Example 200g (40 mg, 0.19 mmol, 1.0 eq) and Example 200h (59.1 mg, 0.23 mmol, 1.2 eq) in dioxane (2 mL) were added Cs$_2$CO$_3$ (125 mg, 0.38 mmol, 2.0 eq), Pd$_2$(dba)$_3$·CHCl$_3$ (19.9 mg, 0.019 mmol, 0.1 eq) and BINAP (23.9 mg, 0.038 mmol, 0.2 eq). The reaction mixture was stirred for 3 h at 110° C. under N$_2$ protection. The mixture was filtered and the filtrate was concentrated in vacuum. The crude product was purified by prep-TLC (DCM/MeOH=30/1) to afford the desired product Example 200 (19.6 mg, 23.9% yield) as a light yellow solid. LCMS [M+1]$^+$=428.3. $^1$H NMR (300 MHz, DMSO-d$_6$) δ 12.36 (s, 1H), 10.90 (s, 1H), 9.71 (s, 1H), 8.96 (s, 1H), 8.67 (s, 1H), 8.14 (d, J=5.1 Hz, 1H), 7.50 (d, J=5.1 Hz, 1H), 3.92 (s, 3H), 3.14 (s, 2H), 2.06-2.08 (m, 1H), 0.83-0.88 (m, 4H).

Example 201

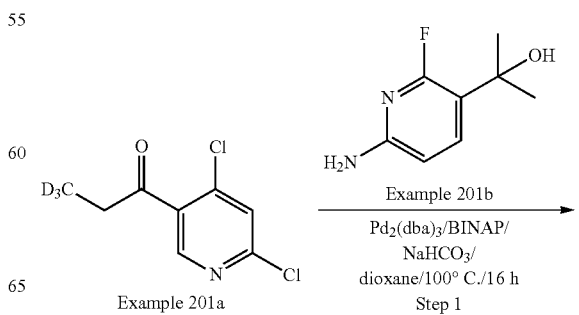

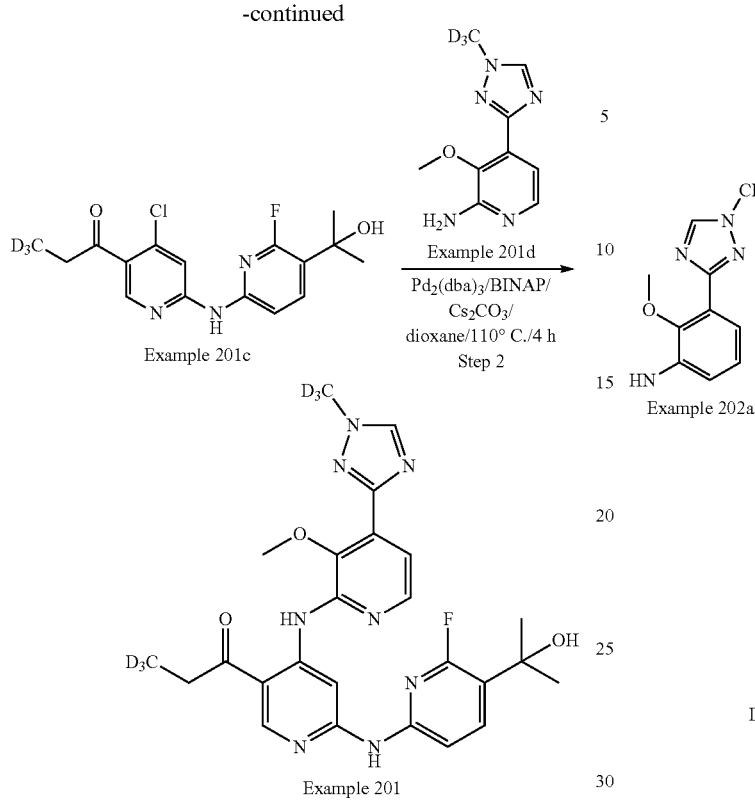

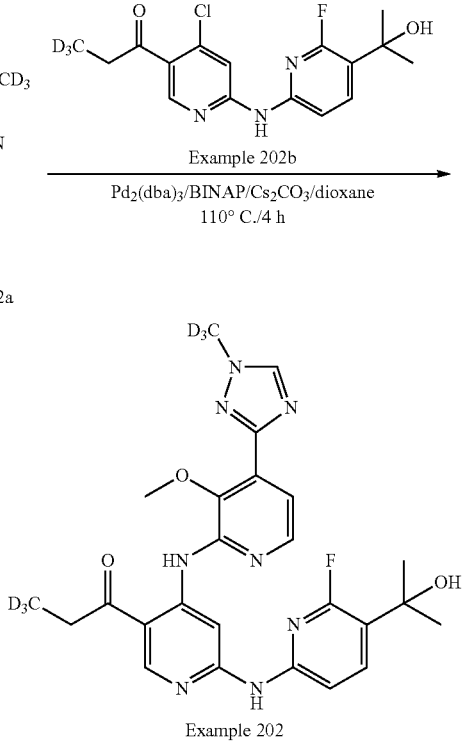

Step 1: Example 201c

To a solution of Example 201a (1.7 g, 8.21 mmol, 1.0 eq) and Example 201b (1.39 g, 8.21 mmol, 1.0 eq) in dioxane (25 mL) were added NaHCO$_3$ (1.38 g, 16.4 mmol, 2.0 eq), Pd$_2$(dba)$_3$·CHCl$_3$ (850 mg, 0.82 mmol, 0.1 eq) and BINAP (15.0 mg, 1.64 mmol, 0.2 eq). The reaction mixture was stirred for 16 h at 100° C. under N$_2$ protection. The mixture was filtered and the filtrate was concentrated in vacuum. The crude product was purified by silica gel flash column chromatography (Petroleum Ether/EtOAc=1/1) to afford the desired product Example 201c (1.01 g, 36.2% yield) as a light brown solid. LCMS [M+1]$^+$=341.3.

Step 2: Example 201

To a solution of Example 201c (78.7 mg, 0.23 mmol, 1.2 eq) and Example 201d (40 mg, 0.19 mmol, 1.0 eq) in dioxane (2 mL) were added Cs$_2$CO$_3$ (125 mg, 0.38 mmol, 2.0 eq), Pd$_2$(dba)$_3$·CHCl$_3$ (19.9 mg, 0.019 mmol, 0.1 eq) and BINAP (23.9 mg, 0.038 mmol, 0.2 eq). The reaction mixture was stirred for 4 h at 110° C. under N$_2$ protection. The mixture was filtered and the filtrate was concentrated in vacuum. The crude product was purified by prep-TLC (DCM/MeOH=30/1) to afford the desired product Example 201 (18.9 mg, 19.3% yield) as a light yellow solid. LCMS [M+1]$^1$=513.4. $^1$H NMR (300 MHz, DMSO-d$_6$) δ 12.38 (s, 1H), 10.24 (s, 1H), 9.53 (s, 1H), 8.94 (s, 1H), 8.67 (s, 1H), 8.18 (d, J=5.4 Hz, 1H), 8.00 (dd, J=10.8, 8.4 Hz, 1H), 7.60 (dd, J=8.4, 1.8 Hz, 1H), 7.51 (d, J=5.1 Hz, 1H), 5.29 (s, 1H), 3.93 (s, 3H), 3.11 (s, 2H), 1.50 (s, 6H).

Example 202

To a solution of Example 202b (750 mg, 2.20 mmol, 1.0 eq) in dioxane (25 mL) were added Example 202a (546 mg, 2.64 mmol, 1.2 eq), Cs$_2$CO$_3$ (1.43 g, 4.40 mmol, 2.0 eq), BINAP (274 mg, 0.44 mmol, 0.2 eq) and Pd$_2$(dba)$_3$CHCl$_3$ (228 mg, 0.22 mmol, 0.1 eq). The reaction mixture was stirred for 4 h at 110° C. under N$_2$. The solvent was concentrated; the residue was purified by silica gel flash column chromatography, eluted with DCM/MeOH (v/v=20/1) to give the desired product Example 202 (401.3 mg, 35.67% yield) as a light yellow solid. LCMS [M+1]$^+$=512.4. $^1$H NMR (300 MHz, DMSO-d$_6$) δ 11.15 (s, 1H), 10.11 (s, 1H), 8.87 (s, 1H), 8.57 (s, 1H), 7.96 (dd, J=10.8, 8.4 Hz, 1H), 7.79 (s, 1H), 7.73 (dd, J=8.4, 1.5 Hz, 2H), 7.63 (dd, J=7.8, 1.8 Hz, 1H), 7.49 (dd, J=8.1, 1.8 Hz, 1H), 7.28 (t, J=7.8 Hz, 1H), 5.26 (s, 1H), 3.76 (s, 3H), 3.08 (s, 2H), 1.46 (s, 6H).

Example 203

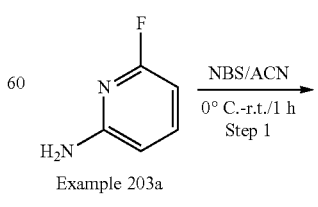

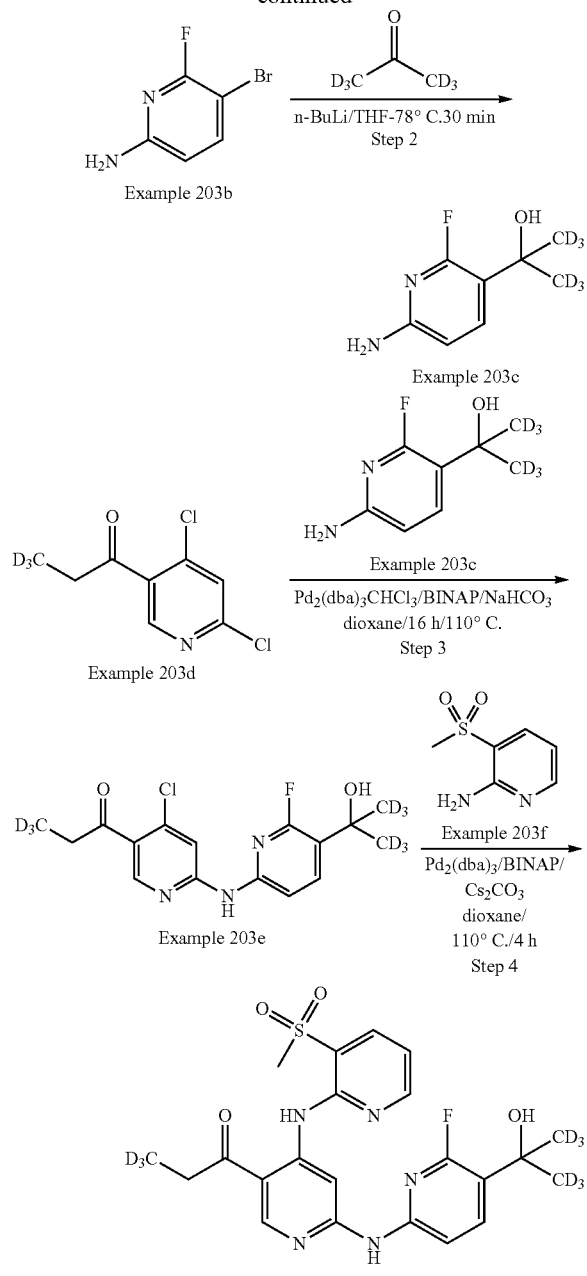

in hexane, 184.21 mmol, 3.5 eq) dropwise at ~78° C. under $N_2$. The reaction was stirred for 30 min at the same temperature; A solution of Acetone-$d_6$ (16.84 g, 263.16 mmol, 5.0 eq) in THF (30 mL) was added dropwise at ~78° C. The reaction mixture was stirred for 30 min at r.t. and then quenched with saturated aqueous of $NH_4Cl$ (200 mL) and extracted with EtOAc (300 mL*3). The combined organic layers were washed with brine (500 mL), dried over $Na_2SO_4$ and concentrated. The residue was purified by silica gel flash column chromatography eluted with Petroleum Ether/ EtOAc (1/1) to give the desired product Example 203c (5.9 g, 64.0% yield) as a yellow solid. LCMS [M+1]$^+$=177.2.

Step 3: Example 203e

To a solution of Example 203d (2.0 g, 9.66 mmol, 1.0 eq) in dioxane (50 mL) were added Example 203c (1.71 g, 9.66 mol, 1.0 eq), $NaHCO_3$ (1.62 g, 19.32 mmol, 2.0 eq), BINAP (1.2 g, 1.93 mmol, 0.2 eq) and $Pd_2(dba)_3CHCl_3$ (1.0 g, 0.97 mmol, 0.1 eq). The reaction mixture was stirred for 16 h at 100° C. under $N_2$. The solvent was concentrated and the residue was purified by silica gel flash column chromatography eluted with Petroleum Ether/EtOAc (1/1) to give the desired product Example 203e (960 mg, 28.7% yield) as a yellow solid. LCMS [M+1]$^+$=347.3.

Step 4: Example 203

To a solution of Example 203e (860 mg, 2.48 mmol, 1.0 eq) in dioxane (40 mL) were added Example 203f (512 mg, 2.97 mol, 1.2 eq), $Cs_2CO_3$ (1.62 g, 4.96 mmol, 2.0 eq), BINAP (309 mg, 0.50 mmol, 0.2 eq) and $Pd_2(dba)_3CHCl_3$ (257 mg, 0.25 mmol, 0.1 eq). The reaction mixture was stirred for 4 h at 110° C. under $N_2$. The solvent was concentrated and the residue was purified by silica gel flash column chromatography eluted with DCM/MeOH (20/1) to give the desired product Example 203 (425.0 mg, 35.5% yield) as an off white solid. LCMS [M+1]$^+$=483.3. $^1$H NMR (300 MHz, DMSO-$d_6$) δ 12.00 (s, 1H), 10.24 (s, 1H), 9.02 (s, 1H), 8.94 (s, 1H), 8.66 (dd, J=4.8, 1.8 Hz, 1H), 8.29 (dd, J=7.8, 1.8 Hz, 1H), 7.99 (dd, J=10.8, 8.1 Hz, 1H), 7.60 (dd, J=8.4, 2.1 Hz, 1H), 7.35 (dd, J=7.8, 4.8 Hz, 1H), 5.25 (s, 1H), 3.34 (s, 3H), 3.09 (s, 2H).

Example A. TYK2 JH2 Domain Binding Assay

DiscoverX's KINOMEscan™ is a popular platform for kinase profiling, frequently used in academic and industry witnessed by publications, therefore we selected this platform as a primary cell-free screening assay to determine the relative binding potency and guide chemistry SAR.

Developed by DiscoverX, KINOMEscan™ employs proprietary active-site dependent competition binding assays to determine how compounds bind to kinases. KINOMEscan™ is based on a competition binding assay that quantitatively measures the ability of a compound to compete with an immobilized, active site directed ligand. The assay is performed by combining three components: DNA-tagged kinase; immobilized ligand; and a test compound. The ability of the test compound to compete with the immobilized ligand is measured via quantitative PCR of the DNA tag.

Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05%

Step 1: Example 203b

To a solution of Example 203a (50.0 g, 0.446 mol, 1.0 eq) in ACN (1000 mL) was added NBS (87.0 g, 0.491 mol, 1.1 eq) at 0° C. under $N_2$ protection. The reaction solution was stirred for 1 h at r.t. The solvent was concentrated under vacuum. The residue was purified by silica gel flash column chromatography (Petroleum Ether/EtOAc=5/1) to afford the product Example 203b (68.1 g, 80.3% yield) as a white solid. LCMS [M+1]$^+$=191.2.

Step 2: Example 203c

To a solution of Example 211b (10.0 g, 52.63 mmol, 1.0 eq) in THF (200 mL) was added n-BuLi (73.68 mL, 2.5 M Tween 20, 1 mM DTT) to remove unbound ligand and to reduce non-specific binding. Binding reactions were assembled by combining TYK2 (JH2domain-pseudokinase), liganded affinity beads, and test compounds in 1x binding buffer (20% SeaBlock, 0.17x PBS, 0.05% Tween 20, 6 mM DTT). Test compounds were prepared as 111X stocks in 100% DMSO. All test compounds were shipped to DiscoverX in DMSO with concentration of 10 mM. Kds were determined using an 11-point 3-fold compound dilution series with three DMSO control points. Each compound was tested in duplicate. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 ml. The assay plates were incubated at room temperature with shaking for 1 hour and the affinity beads were washed with wash buffer (lx PBS, 0.05% Tween 20). The beads were then re-suspended in elution buffer (lx PBS, 0.05% Tween 20, 0.5 µM non-biotinylated affinity ligand) and incubated at room temperature with shaking for 30 minutes. The kinase concentration in the eluates was measured by qPCR.

The amount of kinase measured by qPCR (Signal; y-axis) is plotted against the corresponding compound concentration in nM in log 10 scale (x-axis). Binding constants (Kds) were calculated with a standard dose-response curve using the Hill equation:

$$\text{Response} = \text{Background} + \frac{\text{Signal} - \text{Background}}{1 + (Kd^{\text{Hill Slope}}/\text{Dose}^{\text{Hill Slope}})}$$

The Hill Slope was set to -1.

Curves were fitted using a non-linear least square fit with the Levenberg-Marquardt algorithm.

The results are shown in table 1.

TABLE 1

| Ex. | TYK2 (JH2 domain) binding Kd (nM) | Ex. | TYK2 (JH2 domain) binding Kd (nM) | Ex. | TYK2 (JH2 domain) binding Kd (nM) |
|---|---|---|---|---|---|
| 1 | A | 42 | B | 82 | A |
| 2 | A | 43 | C | 83 | A |
| 3 | C | 44 | B | 84 | A |
| 4 | A | 45 | A | 85 | A |
| 5 | A | 46 | A | 86 | A |
| 6 | A | 47 | A | 87 | A |
| 7 | A | 48 | A | 88 | A |
| 8 | A | 49 | A | 89 | A |
| 9 | A | 50 | A | 90 | A |
| 10 | A | 51 | A | 91 | A |
| 11 | A | 52 | A | 92 | A |
| 12 | A | 53 | A | 93 | A |
| 13 | A | 54 | A | 94 | A |
| 14 | A | 55 | B | 95 | A |
| 15 | A | 56 | B | 96 | A |
| 16 | A | 57 | B | 97 | A |
| 17 | A | 58 | C | 98 | A |
| 18 | A | 59 | B | 99 | A |
| 19 | A | 60 | B | 100 | A |
| 20 | A | 61 | B | 101 | A |
| 21 | A | 62 | C | 102 | A |
| 22 | A | 63 | A | 103 | A |
| 23 | A | 64 | A | 104 | C |
| 24 | B | 65 | C | 116 | A |
| 25 | A | 66 | B | 108 | A |
| 26 | A | 67 | A | 118 | D |
| 27 | A | 68 | A | 123 | D |
| 28 | A | 69 | A | 126 | A |
| 29 | A | 70 | B | 127 | A |
| 30 | A | 71 | A | 145 | A |
| 32 | A | 72 | A | 147 | A |
| 33 | A | 73 | C | 159 | A |
| 34 | A | 74 | A | 163 | A |
| 35 | A | 75 | A | 166 | A |
| 36 | A | 76 | B | 195 | A |
| 37 | A | 77 | B | 200 | A |
| 38 | A | 78 | A | 198 | A |
| 39 | C | 79 | A | 199 | A |
| 40 | A | 80 | A | 202 | A |
| 41 | B | 81 | A | 201 | A |

A is less or equal than 1 nM;
B is more than 1 nM and less or equal than 5 nM;
C is more than 5 nM and less or equal than 10 nM;
D is more than 10 nM.

Example B: IL-12 Induced pSTAT4 in Human PBMC

Fresh Human PBMCs were resuspended in RPMI 1640 medium with 10% FBS. Cells were seeded in a round bottom 96-well plate at the concentration of 200,000 cells/well. A 10-point dilution series of test compound (top dose 10 uM, 1:5 dilution) was added to the well using the liquid dispenser (Tecan D300e) and incubated for 1 hour at 37 C. Then human IL-12 recombinant protein (R&D Systems) was added to the well at the final concentration of 10 ng/ml and incubated for 15 minutes at 37 C. Cell lysates were prepared and analyzed by Phospho STAT4 (Tyr693) Kit (Meso Scale Discovery) following manufacturer's protocol.

For calculation of the inhibition rate, the relative pSTAT4 signal of each well=pSTAT4 signal of each well–the average pSTAT4 signal of baseline.

The inhibition %=(the average pSTAT4 signal of IL-12 treatment wells–the relative of pSTAT4 signal in each compound containing well)/the average pSTAT4 signal of IL-12 treatment wells*100%

The curve was plotted as the inhibition % (y-axis) vs. compounds concentration (x-axis) and was fitted with log (inhibitor) vs. normalized response—Variable slope by GraphPad Prism7.0.

Control is BMS-986165:

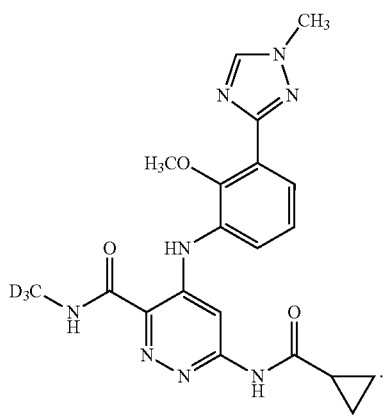 [SMILES: [2H]C([2H])([2H])NC(=O)c1nnc(NC(=O)C2CC2)cc1Nc1cccc(-c2ncn(C)n2)c1OC]

The results are shown in table 2.

TABLE 2

| Ex. | Suppression of IL12-induced p-STAT4 in human PBMC | |
|---|---|---|
| | p-STAT4 IC$_{50}$ (nM) | Relative IC$_{50}$ to control |
| 1 | + | 17.4 |
| 2 | + | 10.1 |
| 3 | ++ | 146.6 |
| 4 | + | 15.6 |
| 5 | + | 20.8 |
| 6 | + | 4.4 |
| 7 | ++ | 59.8 |
| 8 | + | 13.7 |
| 9 | + | 22.9 |
| 10 | + | 6.4 |
| 11 | + | 3.6 |
| 12 | + | 4.5 |
| 13 | + | 2.9 |
| 14 | + | 2 |
| 15 | + | 2.7 |
| 16 | + | 3.4 |
| 17 | + | 7.8 |
| 18 | + | 5.4 |
| 19 | + | 3 |
| 20 | + | 3.6 |
| 21 | + | 4.3 |
| 22 | + | 3.4 |
| 23 | ++ | 51.9 |
| 24 | ++ | 32.4 |
| 25 | ++ | 32.5 |
| 26 | + | 11 |
| 27 | + | 3 |
| 28 | + | 3.3 |
| 29 | + | 10.2 |
| 30 | + | 1.7 |
| 31 | + | 4.7 |
| 32 | + | 9.3 |
| 33 | + | 10.6 |
| 34 | + | 6.4 |
| 36 | + | 44.9 |
| 37 | + | 2 |
| 39 | ++ | 45.4 |
| 40 | ++ | 46.9 |
| 41 | +++ | 468.6 |
| 42 | ++ | 147.9 |
| 43 | ++++ | >3039 |
| 44 | ++ | 77 |
| 47 | + | 10.6 |
| 48 | + | 2.6 |
| 49 | + | 5.1 |
| 50 | + | 21.8 |
| 51 | + | 4.1 |
| 52 | + | 5.6 |
| 54 | + | 3.1 |
| 55 | ++ | 260.4 |
| 56 | ++ | 53.8 |
| 57 | +++ | 208.9 |
| 59 | +++ | 188.6 |
| 60 | ++++ | >196.1 |
| 61 | +++ | 224.8 |
| 62 | +++ | 630.4 |
| 63 | ++ | 202.1 |
| 64 | ++ | 143.1 |
| 67 | + | 17.3 |
| 68 | + | 10.2 |
| 69 | + | 6.7 |
| 71 | ++ | 28.5 |
| 72 | + | 9.1 |
| 74 | + | 13.6 |
| 77 | ++ | 52.7 |
| 78 | + | 58.9 |
| 79 | ++ | 10.6 |
| 80 | + | 3.7 |
| 82 | + | 4.3 |
| 84 | + | 6 |
| 85 | ++ | 613.9 |
| 86 | + | 9.7 |
| 87 | + | 18.7 |
| 88 | + | 6 |
| 89 | + | 8 |
| 91 | + | 8.3 |
| 94 | + | 16.1 |
| 95 | + | 18 |
| 96 | + | 18.7 |
| 98 | + | 24.2 |
| 99 | + | 9.2 |
| 100 | + | 19.7 |
| 103 | + | 10.8 |

+ is less or equal than 100 nM;
++ is more than 100 nM and less or equal than 1 μM;
+++ is more than 1 μM and less or equal than 10 μM;
++++ is more than 10 μM.

Example C: INFα Induced pSTAT3 or pSTAT5 in Human PBMC

Fresh Human PBMCs were resuspended in RPMI 1640 medium with 10% FBS. Cells were seeded in a round bottom 96-well plate at the concentration of 200,000 cells/well. A 10-point dilution series of test compound (top dose 10 uM, 1:5 dilution) was added to the well using the liquid dispenser (Tecan D300e) and incubated for 1 hour at 37 C. Then human INFα recombinant protein (R&D Systems) was added to the well at the final concentration of 5000 units/ml and incubated for 15 minutes at 37 C. Cell lysates were prepared and analyzed by Phospho STAT3 (Tyr705) cellular kit (Cisbio) or Phospho STAT5 (Tyr693) Kit (Meso Scale Discovery) following manufacturer's protocol.

For calculation of the inhibition rate, the relative pSTAT signal of each well=pSTAT signal of each well–the average pSTAT signal of baseline.

The inhibition % (the average pSTAT signal of INFα treatment wells–the relative of pSTAT signal in each compound containing well)/the average pSTAT signal of INFα treatment wells*100%

The curve was plotted as the inhibition % (y-axis) vs. compounds concentration (x-axis) and was fitted with log (inhibitor) vs. normalized response—Variable slope by GraphPad Prism7.0.

The results are shown in table 3.

TABLE 3

| Ex. | p-STAT3 IC$_{50}$ (nM) | p-STAT5 IC$_{50}$ (nM) | Relative IC$_{50}$ to control |
|---|---|---|---|
| 1 | B | | 6.4 |
| 2 | B | | 2.7 |
| 3 | C | | >61.7 |
| 4 | B | | 19.0 |
| 5 | B | | 13.9 |
| 6 | | A | 10.6 |
| 7 | B | | 18.7 |
| 8 | A | | 8.0 |
| 9 | B | | 21.7 |
| 10 | | A | 14.9 |
| 11 | | A | 6.3 |
| 12 | A | | 7.4 |
| 13 | A | | 2.2 |

TABLE 3-continued

| Ex. | p-STAT3 IC$_{50}$ (nM) | p-STAT5 IC$_{50}$ (nM) | Relative IC$_{50}$ to control |
|---|---|---|---|
| 14 | | A | 1.9 |
| 15 | | A | 5.0 |
| 16 | | A | 4.8 |
| 23 | B | | 6.6 |
| 24 | B | | 14.2 |
| 25 | B | | 8.4 |
| 26 | B | | 10.5 |
| 27 | | A | 1.5 |
| 28 | | A | 7.8 |
| 37 | | A | 2.2 |
| 38 | | A | 4.1 |
| 39 | B | | 14.6 |
| 40 | B | | 14.2 |
| 41 | C | | 575.0 |
| 42 | C | | 224.3 |
| 43 | C | | 135.5 |
| 44 | C | | 374.8 |
| 49 | | A | 6.5 |
| 51 | | A | 12.8 |
| 54 | | A | 9.3 |
| 55 | B | | 15.5 |
| 56 | C | | 89.5 |
| 57 | C | | 230.5 |
| 59 | C | | 122.2 |
| 60 | D | | >61.7 |
| 61 | C | | 113.5 |
| 62 | C | | 544.7 |
| 63 | B | | 79.9 |
| 64 | B | | 91.6 |
| 67 | B | | 9.4 |
| 68 | A | | 4.5 |
| 69 | A | | 8.5 |
| 71 | B | | 10.0 |
| 72 | B | | 15.7 |
| 74 | A | | 7.0 |
| 77 | C | | 145.8 |
| 79 | B | | 49.7 |
| 80 | A | | 3.7 |
| 82 | A | | 5.6 |
| 84 | A | | 5.2 |
| 86 | B | | 17.0 |
| 87 | B | | 28.6 |
| 89 | | A | 5.4 |
| 107 | | A | 5.3 |
| 108 | | A | 2.9 |
| 109 | | A | 5.5 |
| 110 | | A | 1.5 |
| 111 | | A | 1.4 |
| 112 | | A | 1.8 |
| 113 | | A | 2.2 |
| 114 | | A | 4.7 |
| 115 | | A | 53.8 |
| 116 | | A | 2.8 |
| 119 | | A | 14.1 |
| 120 | | A | 1.1 |
| 121 | | A | 9.1 |
| 122 | | A | 2.7 |
| 124 | | A | 3.1 |
| 125 | | A | 14.4 |
| 126 | | A | 4.8 |
| 127 | | A | 10.7 |
| 128 | | C | >1000 |
| 129 | | A | 9.6 |
| 130 | | A | 9.3 |
| 131 | | A | 2.1 |
| 132 | | A | 4.3 |
| 133 | | A | 18.8 |
| 135 | | C | >1000 |
| 136 | | A | 3.3 |
| 137 | | A | 6.1 |
| 138 | | A | 20.8 |
| 139 | | A | 2.3 |
| 140 | | A | 0.8 |
| 141 | | A | 3.2 |
| 142 | | A | 4 |
| 143 | | A | 3.8 |
| 144 | | A | 24.2 |
| 145 | | A | 2.5 |
| 147 | | A | 5.8 |
| 148 | | A | 3 |
| 149 | | A | 2.6 |
| 150 | | A | 9.7 |
| 151 | | A | 16.3 |
| 152 | | A | 2.8 |
| 153 | | A | 4.8 |
| 154 | | A | 3.0 |
| 155 | | A | 3.8 |
| 156 | | A | 4.4 |
| 157 | | A | 9.5 |
| 158 | | A | 7.2 |
| 159 | | A | 1.6 |
| 160 | | A | 5.5 |
| 161 | | A | 6.1 |
| 163 | | A | 1.7 |
| 164 | | A | 3.9 |
| 165 | | B | 206 |
| 166 | | A | 3.0 |
| 169 | | A | 49.3 |
| 171 | | A | 1.2 |
| 172 | | A | 1.7 |
| 173 | | B | 113.7 |
| 174 | | A | 0.8 |
| 175 | | A | 0.3 |
| 176 | | A | 1.8 |
| 177 | | A | 0.4 |
| 178 | | A | 1.2 |
| 179 | | A | 5.8 |
| 180 | | A | 1.3 |
| 184 | | A | 0.8 |
| 185 | | A | 0.3 |
| 188 | | A | 0.6 |
| 189 | | A | 0.8 |
| 190 | | A | 6.3 |
| 191 | | A | 5.4 |
| 193 | | A | 1.4 |
| 195 | | A | 1.6 |
| 196 | | B | 784 |
| 198 | | A | 0.3 |
| 199 | | A | 0.2 |
| 200 | | A | 1.9 |
| 201 | | A | 0.2 |
| 202 | | A | 0.3 |
| 203 | | A | 0.7 |

A is less or equal than 100 nM;
B is more than 100 nM and less or equal than 1 μM;
C is more than 1 μM and less or equal than 10 μM;
D is more than 10 μM.

Example D: JAK1 JH2 and JAK2 JH1 Domain Binding Assay

Similar to the method for TYK2 JH2 binding described above, JAK1 JH2 and JAK2 JH1 domain binding assay was performed using DiscoverX's KINOMEscan™, but with change of kinase domain. These assays were performed to compare the binding selectivity of test compounds to JAK1 JH2 and JAK2 JH1 domain. The results are shown in table 4.

TABLE 4

| Ex. | JAK1 (JH2 domain) binding Kd (nM) | JAK2 (JH1 domain) binding Kd (nM) |
|---|---|---|
| control | A | C |
| 147 | A | D |
| 38 | A | C |
| 116 | A | C |
| 166 | A | C |

TABLE 4-continued

| Ex. | JAK1 (JH2 domain) binding Kd (nM) | JAK2 (JH1 domain) binding Kd (nM) |
|---|---|---|
| 159 | A | C |
| 163 | A | B |
| 195 | A | C |
| 200 | A | C |
| 198 | A | D |
| 199 | A | D |
| 202 | A | B |
| 201 | A | B |

A is less or equal than 100 nM;
B is more than 100 nM and less or equal than 1 μM;
C is more than 1 μM and less or equal than 10 μM;
D is more than 10 μM.

TABLE 5

| Ex. | GM-CSF-induced pSTAT5 IC$_{50}$ (nM) | IL-2-induced pSTAT5 IC$_{50}$ (nM) |
|---|---|---|
| control | C | B |
| 195 | C | C |
| 200 | D | C |
| 198 | C | B |
| 199 | C | B |
| 202 | B | B |
| 201 | B | B |
| 203 | C | B |

A is less or equal than 100 nM;
B is more than 100 nM and less or equal than 1 μM;
C is more than 1 μM and less or equal than 10 μM;
D is more than 10 μM.

Example E: GM-CSF-Induced pSTAT5 and IL-2-Induced pSTAT5 in Human PBMC in Human PBMC Similar to the method for IL-12 induced pSTAT4 in human PBMC described above, these assays were performed to check if test compounds have cross-activity to JAK1. JAK2 and JAK3 pathways in human PBMC. The procedure is as described with change of stimuli to 10 ng/ml of GM-CSF or 20 ng/ml of IL-2. The data are shown in Table 5.

Example F: Pharmacokenetic Studies

The pharmacokinetics of test compounds were evaluated in male C57BL/6 mice, Sprague Dawley rats, Beagle dogs, and cynomolgus monkeys when administered via oral gavage and IV injection. The formulation for each test compound is summarized in the table 6. The animals were fasted overnight before administration. Plasma samples were collected predose and at 0.5, 1, 3, 6, 9, 12, and 24 hours postdose. The samples were analyzed by LC/MS/MS and the concentration of test compound at each timepoint was determined by linear regression. Pharmacokinetic parameters were calculated from the plasma concentrations using Pheonix WinNonlin. The PK results were summarized in the tables 7-10.

TABLE 6

Drug formulations used for each test compound in different species

| Ex. | Route of administration | Mouse | Rat | Dog | Monkey |
|---|---|---|---|---|---|
| control | Oral | A | A | A | A |
|  | IV | B | B | B | B |
| 195 | Oral | A | A | A | A |
|  | IV | C | B | B | B |
| 200 | Oral | A | A | A | A |
|  | IV | C | B | B | B |
| 198 | Oral |  | A | D | D |
|  | IV |  | B | C | C |
| 199 | Oral |  | A | D |  |
|  | IV |  | B | C |  |
| 202 | Oral | D | A | A |  |
|  | IV | C | B | B |  |
| 201 | Oral |  | A | D | D |
|  | IV |  | B | C | C |
| 203 | Oral |  |  |  | D |
|  | IV |  |  |  | C |

Formulation A: 0.5% methylcellulose
Formulation B: 5% DMSO/5% Solutol/90% saline
Formulation C: 10% DMSO + 10% Solutol + 80% (20% SBE-β-CD)
Formulation D: 10% DMSO + 10% HS-15 + 40% PEG400 + 40% (30% SBE-β-CD)

TABLE 7

Pharmacokinetic parameters of test compounds in C57BL/6 mice.

| Ex. | Route of administration and dose | $C_0$ or $C_{max}$ (ng/mL) | AUC (h · ng · mL$^{-1}$) | $T_{1/2}$ (h) | $T_{max}$ (h) | F % | CL (mL· kg-1 · min-1) | Vdss (L/kg) |
|---|---|---|---|---|---|---|---|---|
| control | Oral (10 mg/kg) | 4699 | 8871 | 2.96 | 0.25 | 86.7 | | |
| | I.V. (2 mg/kg) | 3220 | 2045 | 2.19 | | | 15.6 | 1.56 |
| 195 | Oral (10 mg/kg) | 4295 | 16678 | 2.110 | 0.500 | 41.7 | | |
| | I.V. (2 mg/kg) | 2950 | 7994 | 2.46 | | | 4.16 | 0.688 |
| 200 | Oral (10 mg/kg) | 4193 | 19295 | 2.010 | 0.250 | 85.1 | | |
| | I.V. (2 mg/kg) | 2391 | 4475 | 4.62 | | | 7.35 | 1.5 |
| 202 | Oral (10 mg/kg) | 1899 | 6395 | 3.27 | 0.500 | 66.6 | | |
| | I.V. (2 mg/kg) | 3343 | 1911 | 0.97 | | | 17.3 | 0.785 |

TABLE 8

Pharmacokinetic parameters of test compounds in Sprague Dawley rats.

| Ex. | Route of administration & dose | $C_0$ or $C_{max}$ (ng/mL) | AUC (h · ng · mL$^{-1}$) | $T_{1/2}$ (h) | $T_{max}$ (h) | F % | CL (mL· kg-1 · min-1) | Vdss (L/kg) |
|---|---|---|---|---|---|---|---|---|
| control | Oral (5 mg/kg) | 792 ± 260 | 3197 ± 600 | 2.93 ± 1.27 | 1.0 ± 0.8 | 32.6 ± 5.4 | | |
| | I.V. (1 mg/kg) | 1743 ± 276 | 1966 ± 166 | 2.42 ± 1.7 | | | 8.41 ± 0.7 | 0.933 ± 0.12 |
| 195 | Oral (5 mg/kg) | 1255 ± 226 | 7444 ± 1396 | 2.37 ± 0.32 | 1.67 ± 0.58 | 46.7 ± 8.8 | | |
| | I.V. (1 mg/kg) | 2153 ± 123 | 3188 ± 603 | 2.14 ± 0.12 | | | 4.96 ± 0.91 | 0.824 ± 0.11 |
| 200 | Oral (5 mg/kg) | 948 ± 43 | 3657 ± 684 | 4.22 ± 3.6 | 1.00 | 42.7 ± 8.0 | | |
| | I.V. (1 mg/kg) | 1033 ± 47 | 1714 ± 19 | 1.58 ± 0.21 | | | 9.42 ± 0.022 | 1.24 ± 0.065 |
| 198 | Oral (5 mg/kg) | 261 ± 35 | 1187 ± 53 | 2.85 ± 2.8 | 1.00 ± 0.87 | 16.9 ± 0.76 | | |
| | I.V. (1 mg/kg) | 1202 ± 7 | 1405 ± 290 | 1.22 ± 0.12 | | | 11.8 ± 0.22 | 1.10 ± 0.065 |
| 199 | Oral (5 mg/kg) | 140 ± 32 | 650 ± 34 | 1.66 ± 0.37 | 1.33 ± 0.58 | 18.4 ± 1.0 | | |
| | I.V. (1 mg/kg) | 414 ± 56 | 705 ± 140 | 1.74 ± 0.20 | | | 23.3 ± 4.9 | 3.27 ± 0.87 |
| 202 | Oral (5 mg/kg) | 50.1 ± 11 | 210 ± 60 | 1.29 ± 0.24 | 4 00 ± 2.0 | 8.35 ± 2.4 | | |
| | I.V. (1 mg/kg) | 1975 ± 101 | 504 ± 58 | 0.323 ± 0.035 | | | 33.1 ± 4.0 | 0.653 ± 0.03 |
| 201 | Oral (5 mg/kg) | 185 ± 138 | 499 ± 502 | 1.14 ± 0.2 | 0 42 ± 0.14 | 18.7 ± 18.9 | | |
| | I.V. (1 mg/kg) | 1186 ± 116 | 533 ± 225 | 0.759 ± 0.60 | | | 34.3 ± 12 | 1.31 ± 0.42 |

TABLE 9

Pharmacokinetic parameters of test compounds in Beagle dogs

| Ex. | Route of administration & dose | $C_0$ or $C_{max}$ (ng/mL) | AUC (h · ng · mL$^{-1}$) | $T_{1/2}$ (h) | $T_{max}$ (h) | F % | CL (mL· kg-1 · min-1) | Vdss (L/kg) |
|---|---|---|---|---|---|---|---|---|
| control | Oral (2 mg/kg) | 222 ± 46 | 1312 ± 579 | 6.21 ± 2.9 | 1.67 ± 0.58 | 35.5 ± 15 | | |
| | I.V. (1 mg/kg) | 559 ± 34 | 1902 ± 349 | 4.43 ± 0.87 | | | 8.85 ± 1.7 | 2.27 ± 0.23 |

TABLE 9-continued

Pharmacokinetic parameters of test compounds in Beagle dogs

| Ex. | Route of administration & dose | $C_0$ or $C_{max}$ (ng/mL) | AUC (h · ng · mL$^{-1}$) | $T_{1/2}$ (h) | $T_{max}$ (h) | F % | CL (mL · kg-1 · min−1) | Vdss (L/kg) |
|---|---|---|---|---|---|---|---|---|
| 195 | Oral (2 mg/kg) | 285 ± 285 | 1517 ± 1334 | 5.73 ± 2.02 | 1.33 ± 0.58 | 26.2 ± 23.0 | | |
| | I.V. (1 mg/kg) | 185 ± 8.4 | 2899 ± 453 | 6.69 ± 0.39 | | | 5.31 ± 0.93 | 3.04 ± 0.27 |
| 200 | Oral (2 mg/kg) | 247 ± 17 | 2619 ± 258 | 8.51 ± 1.6 | 1.33 ± 0 | 82.9 ± 8.2 | | |
| | I.V. (0.5 mg/kg) | 29.7 ± 14 | 790 ± 196 | 11.5 ± 1.6 | | | 8.17 ± 2.6 | 8.37 ± 1.39 |
| 198 | Oral (2 mg/kg) | 68.8 ± 18 | 253 ± 48 | 1.42 ± 0.24 | 1.67 ± 0.58 | 54.0 ± 10 | | |
| | I.V. (1 mg/kg) | 182 ± 47.6 | 234 ± 94 | 4 29 ± 1.25 | | | 68.6 ± 28 | 23.1 ± 4.59 |
| 199 | Oral (2 mg/kg) | 23.4 ± 4 | 67.6 ± 25 | 1.36 ± 0.05 | 1.33 ± 0.6 | 10.7 ± 3.9 | | |
| | I.V. (1 mg/kg) | 334 ± 96 | 315 ± 188 | 1.78 ± 0.59 | | | 63.2 ± 30 | 5.62 ± 1.13 |
| 202 | Oral (2 mg/kg) | 156 ± 53 | 555 ± 154 | 1.59 ± 0.15 | 1.00 | 55.0 ± 15 | | |
| | I.V. (1 mg/kg) | 469 ± 255 | 504 ± 49 | 1.74 ± 0.28 | | | 32.7 ± 3.1 | 4.21 ± 0.19 |
| 201 | Oral (2 mg/kg) | 103 ± 28 | 442 ± 81 | 5.05 ± 0.47 | 2.0 ± 0 | 38.5 ± 7.1 | | |
| | I.V. (1 mg/kg) | 458 ± 336 | 575 ± 158 | 4 54 ± 1.26 | | | 29.3 ± 8.01 | 7.41 ± 2.64 |

TABLE 10

Pharmacokinetic parameters of test compounds in cynomolgus monkeys (NA: no detectable)

| Ex. | Route of administration & dose | $C_0$ or $C_{max}$ (ng/mL) | AUC (h · ng · mL$^{-1}$) | $T_{1/2}$ (h) | $T_{max}$ (h) | F % | CL (mL · kg-1 · min−1) | Vdss (L/kg) |
|---|---|---|---|---|---|---|---|---|
| control | Oral (2 mg/kg) | 247 ± 136 | 3192 ± 1629 | 10.6 ± 3.8 | 5.33 ± 1.2 | 27.8 ± 14 | | |
| | I.V. (1 mg/kg) | 1417 ± 264 | 5739 ± 1168 | 7.54 ± 1.6 | | | 2.79 ± 0.74 | 1.20 ± 0.042 |
| 195 | Oral (2 mg/kg) | 663 ± 497 | 5420 ± 3250 | 5.80 ± 0.73 | 4.0 ± 0 | 16.6 ± 9.95 | | |
| | I.V. (1 mg/kg) | 1286 ± 106 | 16326 ± 664 | 7.65 ± 0.56 | | | 0.898 ± 0.04 | 0.624 ± 0.03 |
| 200 | Oral (2 mg/kg) | 384 ± 22 | 4060 ± 251 | 8.60 ± 0.73 | 2.0 ± 0 | 27.7 ± 1.7 | | |
| | I.V. (1 mg/kg) | 677 ± 81 | 7316 ± 202 | 9.35 ± 1.57 | | | 1.87 ± 0.21 | 1.45 ± 0.18 |
| 198 | Oral (2 mg/kg) | 246 ± 124 | 1228 ± 435 | 1.28 ± 0.18 | 4 ± 0 | 59.4 ± 21.1 | | |
| | I.V. (1 mg/kg) | 667 ± 82 | 1034 ± 159 | 1.45 ± 0.22 | | | 16.1 ± 2.4 | 1.94 ± 0.03 |
| 201 | Oral (2 mg/kg) | 13.9 ± 2 | 67.9 ± 21 | 3.08 ± 0.66 | 2.33 ± 1.5 | 4.67 ± 1.5 | 23.2 ± 4.3 | 1.47 ± 0.1 |
| | I.V. (1 mg/kg) | 849 ± 50 | 726 ± 134 | 1.81 ± 0.76 | | | | |
| 203 | Oral (2 mg/kg) | NA | NA | NA | NA | NA | | |
| | I.V. (1 mg/kg) | 787 ± 61 | 595 ± 48 | 0.951 ± 0.22 | | | 27.6 ± 1.9 | 0.931 ± 0.01 |

Example E: Pharmaceutical Compositions

Example E1: Parenteral Composition

To prepare a parenteral pharmaceutical composition suitable for administration by injection, 100 mg of a water-soluble salt of a compound described herein is dissolved in DMSO and then mixed with 10 mL of 0.9% sterile saline. The mixture is incorporated into a dosage unit form suitable for administration by injection.

Example E2: Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

Example E3: Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

The examples and embodiments described herein are for illustrative purposes only and in some embodiments, various modifications or changes are to be included within the purview of disclosure and scope of the appended claims.

What is claimed is:

1. A compound of Formula (I):

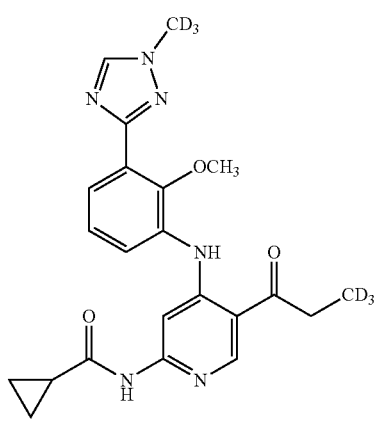

(I)

wherein the compound of Formula (I) is prepared by a process comprising the following steps:

(1) reducing a compound of the following formula:

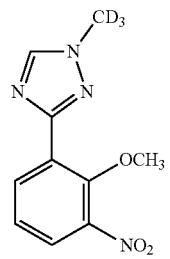 [SMILES: [2H]C([2H])([2H])n1cnc(-c2cccc([N+](=O)[O-])c2OC)n1]

in the presence of $H_2$ and a palladium catalyst, to provide a compound of the following formula:

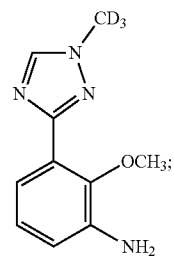

and (2) coupling the compound provided in step (1) above with a compound of Formula (II):

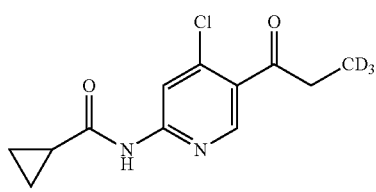

(II)

in the presence of a palladium catalyst, to provide the compound of Formula (I):

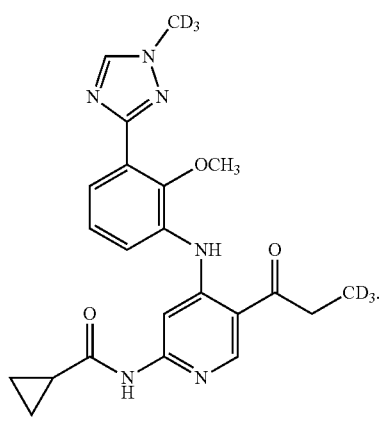

(I)

2. A process for preparing a compound of Formula (I):

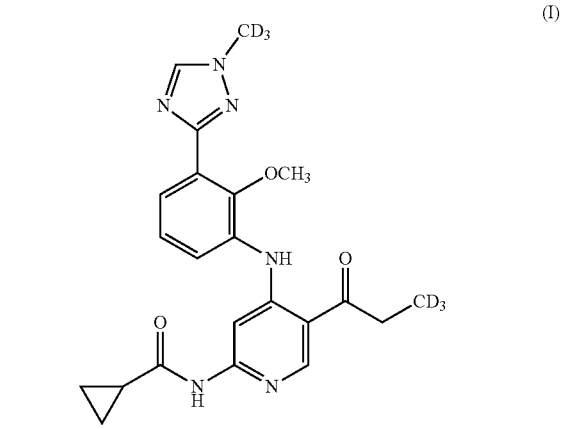 [SMILES: [2H]C([2H])([2H])CC(=O)c1cnc(NC(=O)C2CC2)cc1Nc1cccc(-c2ncn(C([2H])([2H])[2H])n2)c1OC]

(I)

wherein the process comprises the following steps:

(1) reducing a compound of the following formula:

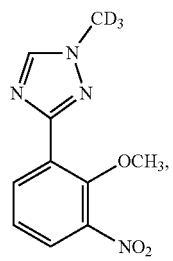

in the presence of H₂ and a palladium catalyst, to provide a compound of the following formula:

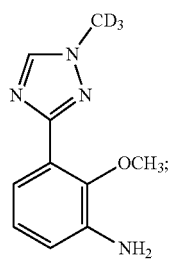 [SMILES: [2H]C([2H])([2H])n1cnc(-c2cccc(N)c2OC)n1]

and (2) coupling the compound provided in step (1) above with a compound of Formula (II):

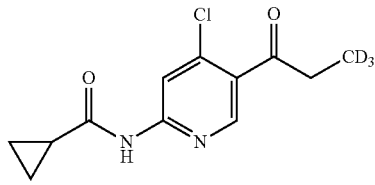

in the presence of a palladium catalyst, to provide the compound of Formula (I):

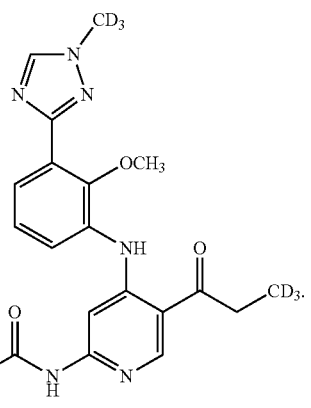

3. The process of claim 2, wherein reducing comprises hydrogenating in the presence of Pd—C.

4. The process of claim 2, wherein coupling comprises palladium-catalyzed cross coupling with Pd₂(dba)₂.

5. A compound:

6. A compound:

* * * * *